United States Patent
Yu et al.

(10) Patent No.: US 10,759,816 B2
(45) Date of Patent: Sep. 1, 2020

(54) HETEROCYCLIC COMPOUNDS AS RSV INHIBITORS

(71) Applicant: Enanta Pharmaceuticals, Inc., Watertown, MA (US)

(72) Inventors: Jianming Yu, Plainsboro, NJ (US); Brian C. Shook, Holliston, MA (US); Thomas P. Blaisdell, Brighton, MA (US); In Jong Kim, Lexington, MA (US); Joseph Panarese, Malden, MA (US); Kevin McGrath, Brighton, MA (US); Solymar Negretti-Emmanuelli, Watertown, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/100,721

(22) Filed: Aug. 10, 2018

(65) Prior Publication Data
US 2019/0040084 A1     Feb. 7, 2019

Related U.S. Application Data

(63) Continuation of application No. 15/405,526, filed on Jan. 13, 2017, now abandoned.

(60) Provisional application No. 62/279,320, filed on Jan. 15, 2016.

(51) Int. Cl.
| | |
|---|---|
| C07D 519/00 | (2006.01) |
| C07D 495/04 | (2006.01) |
| C07D 491/048 | (2006.01) |
| C07D 513/04 | (2006.01) |
| C07D 498/04 | (2006.01) |
| C07D 401/06 | (2006.01) |
| C07D 401/14 | (2006.01) |
| C07D 487/04 | (2006.01) |
| A61K 31/55 | (2006.01) |
| A61K 31/551 | (2006.01) |
| A61K 31/553 | (2006.01) |
| A61K 31/554 | (2006.01) |
| A61K 45/06 | (2006.01) |

(52) U.S. Cl.
CPC ............ *C07D 519/00* (2013.01); *A61K 31/55* (2013.01); *A61K 31/551* (2013.01); *A61K 31/553* (2013.01); *A61K 31/554* (2013.01); *A61K 45/06* (2013.01); *C07D 401/06* (2013.01); *C07D 401/14* (2013.01); *C07D 487/04* (2013.01); *C07D 491/048* (2013.01); *C07D 495/04* (2013.01); *C07D 498/04* (2013.01); *C07D 513/04* (2013.01)

(58) Field of Classification Search
CPC .................................................. C07D 519/00
See application file for complete search history.

(56) References Cited

U.S. PATENT DOCUMENTS

| | | |
|---|---|---|
| 4,010,153 A | 3/1977 | Kajfez et al. |
| 4,511,510 A | 4/1985 | Mauri |
| 5,571,809 A | 11/1996 | Hargrave et al. |
| 5,637,697 A | 6/1997 | Finch et al. |
| 5,681,833 A | 10/1997 | Castro et al. |
| 7,582,624 B2 | 9/2009 | Carter et al. |
| 9,732,098 B2 | 8/2017 | Hunt et al. |
| 9,957,281 B2 | 5/2018 | Shook et al. |
| 2006/0040923 A1 | 2/2006 | Carter et al. |
| 2006/0083741 A1 | 4/2006 | Hoffman et al. |
| 2007/0142403 A1 | 6/2007 | Powell et al. |

(Continued)

FOREIGN PATENT DOCUMENTS

| | | |
|---|---|---|
| EP | 0703222 A1 | 3/1996 |
| WO | 9308175 A1 | 4/1993 |

(Continued)

OTHER PUBLICATIONS

Setoi, et al. Document No. 131:116236, retrieved from STN; entered in STN on Aug. 6, 1999.*

(Continued)

*Primary Examiner* — Shawquia Jackson
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

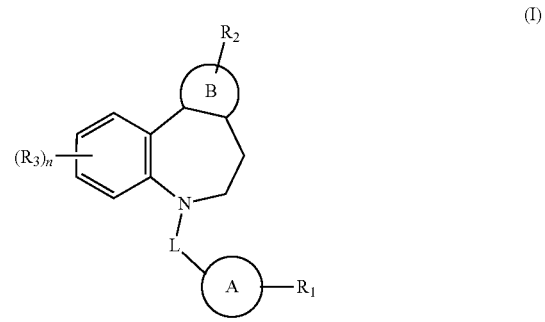

which inhibit Respiratory Syncytial Virus (RSV). The present invention further relates to pharmaceutical compositions comprising the aforementioned compounds for administration to a subject suffering from RSV infection. The invention also relates to methods of treating an RSV infection in a subject by administering a pharmaceutical composition comprising the compounds of the present invention.

20 Claims, No Drawings

(56) References Cited

U.S. PATENT DOCUMENTS

| | | |
|---|---|---|
| 2007/0185094 A1 | 8/2007 | Lattmann et al. |
| 2007/0185096 A1 | 8/2007 | Powell et al. |
| 2007/0293482 A1 | 12/2007 | Dowdell et al. |
| 2008/0139536 A1 | 6/2008 | Dowdell et al. |
| 2009/0274655 A1 | 11/2009 | Grimes et al. |
| 2010/0015063 A1 | 1/2010 | Carter et al. |
| 2012/0196846 A1 | 8/2012 | Mackman et al. |
| 2014/0038947 A1 | 2/2014 | Glick et al. |
| 2014/0100365 A1 | 4/2014 | Gavai et al. |
| 2015/0065504 A1 | 3/2015 | Wang et al. |
| 2015/0299210 A1 | 10/2015 | Bailey et al. |
| 2017/0022221 A1 | 1/2017 | Blaisdell et al. |
| 2017/0226127 A1 | 8/2017 | Estrada et al. |
| 2017/0226129 A1 | 8/2017 | Yu et al. |
| 2017/0305935 A1 | 10/2017 | Hunt et al. |
| 2017/0355717 A1 | 12/2017 | Hunt et al. |
| 2018/0193352 A1 | 7/2018 | Shook et al. |
| 2018/0237425 A1 | 8/2018 | Kim et al. |
| 2018/0258102 A1 | 9/2018 | Shook et al. |
| 2018/0354912 A1 | 12/2018 | Or et al. |
| 2019/0002478 A1 | 1/2019 | Kim et al. |
| 2019/0002479 A1 | 1/2019 | Kim et al. |

FOREIGN PATENT DOCUMENTS

| | | |
|---|---|---|
| WO | 2006081389 A1 | 8/2006 |
| WO | 2011005842 A1 | 1/2011 |
| WO | 2011151651 A1 | 12/2011 |
| WO | 2014047369 A1 | 3/2014 |
| WO | 2014125444 A1 | 8/2014 |
| WO | 2014184350 A1 | 11/2014 |
| WO | 2016055792 A1 | 4/2016 |
| WO | 2016097761 A1 | 6/2016 |
| WO | 2016166546 A1 | 10/2016 |
| WO | 2017123884 A1 | 7/2017 |
| WO | 2017175000 A1 | 10/2017 |

OTHER PUBLICATIONS

Kim, In Jong, et al., U.S. Appl. No. 16/023,363, filed Jun. 29, 2018.
Kim, In Jong, et al., U.S. Appl. No. 16/023,422, filed Jun. 29, 2018.
Mayo Clinic Staff, Respiratory syncytial virus (RSV) [online], retrieved from from internet on Jun. 25, 2017.; URL http://www.mayoclinic.org/diseases-condiitons/respiratory-syncytial-virus/basics/prevention.
Albright, et al., (Document No. 129:54301) retrieved from STN; entered in STN on Jun. 17, 1998.
Albright, et al., (Document No. 130:153583) retrieved from STN; entered in STN on Feb. 16, 1999.
Andrzej, et al., (Document No. 144:274313) retrieved from STN; entered in STN on Mar. 3, 2006.
Carter, M. C. et al., "1,4-Benzodiazepines as Inhibitors of Respiratory Syncytial Virus", Journal of Medicinal Chemistry, vol. 49, Mar. 9, 2006, 2311-2319.
Heeney, et al., (Document No. 153:359062) retrieved from STN; entered in STN on Sep. 2, 2010.
Henderson, E. A. et al., "1,4-Benzodiazepines as Inhibitors of Respiratory Syncytial Virus. The Identification of a Clinical Candidate", Journal of Medicinal Chemistry, vol. 50, Mar. 7, 2007, 1685-1692.
Lee, et al., (Document No. 140:69941) retrieved from STN; entered in STN on Jul. 8, 2003.
Peesapati, et al., (Document No. 120:244848) retrieved from STN; entered in STN on May 14, 1994.
Wang, et al., (Document No. 160:385666) retrieved from STN; entered in STN on Feb. 27, 2014.
Xiong, et al., (Document No. 160:101182) retrieved from STN; entered in STN on Nov. 12, 2013.
Xiong, H., "Discovery of a Potent Respiratory Syncytial Virus RNA Polymerase Inhibitor", Bioorganic & Medicinal Chemistry Letters, 23, 2013, 6789-6793.
Zheng, et al., (Document No. 161 :399872) retrieved from STN; entered in STN on Jul. 23, 2014.
PUBCHEM-CID: 10595203, p. 3, Fig, Oct. 25, 2006, 1-9.
Aquino, Christopher J. et al., "Discovery of 1,5-Benzodiazepines with Peripheral Cholecystokinin (CCK-A) Receptor Agonist Activity. 1. Optimization of the Agonist "Trigger"", J. Med. Chem. 1996, 39, 1996, 562-569.
Chapman, Joanna et al., "RSV604, a Novel Inhibitor of Respiratory Syncytial Virus Replication", Antimicrobial Agents and Chemotherapy, vol. 51, No. 9, 2007, 3346-3353.
Fordyce, et al., "Discovery of novel benzothienoazepine derivatives as potent inhibitors of respiratory syncytial virus", Bioorganic & Medicinal Chemistry Letters, 27, 2017, 2201-2206.
Offel, M. et al., "Synthesis of Substituted 3-Anilino-5-phenyl-1,3-dihydro-2H-I, 4-benzodiazepine-2-ones and their Evaluation as Cholecystokinin-Ligands", Archiv Der Pharmazie, vol. 339, No. 4, Apr. 1, 2006, 163-173.

\* cited by examiner

HETEROCYCLIC COMPOUNDS AS RSV INHIBITORS

RELATED APPLICATION

This application is a continuation of U.S. application Ser. No. 15/405,526, filed Jan. 13, 2017, which claims the benefit of U.S. Provisional Application No. 62/279,320, filed on Jan. 15, 2016. The entire teachings of the above applications are incorporated herein by reference.

TECHNICAL FIELD

The present invention relates generally to compounds and pharmaceutical compositions useful as Respiratory Syncytial Virus (RSV) inhibitors.

BACKGROUND OF THE INVENTION

Human respiratory syncytial virus (HRSV) is a negative-sense, single stranded, RNA paramyxovirus (K M. Empey, et al., *Rev. Anti-Infective Agents,* 2010, 50 (1 May), 1258-1267). RSV is the leading cause of acute lower respiratory tract infections (ALRI) and affects patients of all ages. The symptoms in adults are usually not severe and are typically analogous to a mild cold. However, in infants and toddlers the virus can cause lower respiratory tract infections including bronchiolitis or pneumonia with many of them requiring hospitalization. Nearly all children have been infected by age 3. There are known high-risk groups that infection with RSV is more likely to progress into the ALRI. Premature infants and/or infants suffering from lung or cardiac disease are at the highest risk to develop ALRI. Additional high-risk groups include the elderly, adults with chronic heart and/or lung disease, stem cell transplant patients and the immunosuppressed.

Currently, there is no vaccine available to prevent HRSV infection. Palivizumab is a monoclonal antibody that is used prophylactically to prevent HRSV infection in high risk infants, e.g. premature infants, and infants with cardiac and/or lung disease. The high cost of palivizumab treatment limits its use for general purposes. Ribavirin has also been used to treat HRSV infections but its effectiveness is limited. There is a major medical need for new and effective HRSV treatments that can be used generally by all population types and ages.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, and *J. Med Chem.* 2015, 58, 1630-1643. Examples of other N-protein inhibitors for treatment of HRSV have been disclosed in the following publications: WO 2004/026843, *J. Med Chem.* 2006, 49, 2311-2319, and *J. Med. Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med. Chem. Lett.* 2013, 23, 6789-6793. Examples of nucleosides/polymerase inhibitors have been disclosed in the following publications: WO 2013/242525 and *J. Med. Chem.* 2015, 58, 1862-1878.

There is a need for the development of effective treatments for HRSV. The present invention has identified these novel compounds and their inhibitory activity against HRSV. The invention includes methods to prepare the compounds as well as methods of using these compounds to treat disease.

SUMMARY OF THE INVENTION

The present invention provides compounds represented by Formula (I), or pharmaceutically acceptable salts, stereoisomer, solvate, hydrate or combination thereof that can be used to treat or prevent viral (particularly HRSV) infection:

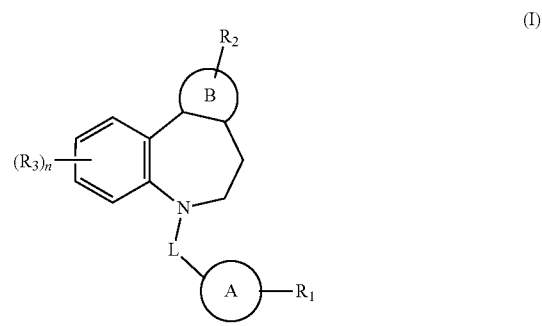

wherein:
A is selected from the group consisting of:
  1) Optionally substituted —$C_3$-$C_{12}$ cycloalkyl;
  2) Optionally substituted —$C_3$-$C_{12}$ cycloalkenyl;
  3) Optionally substituted 3- to 12-membered heterocycloalkyl;
  4) Optionally substituted aryl; and
  5) Optionally substituted heteroaryl;
L is —$CH_2$—, —CO—, or —$SO_2$—;
B is optionally substituted aryl or optionally substituted heteroaryl;
$R_1$ is selected from the group consisting of:
  1) Absent;
  2) Optionally substituted —$C_1$-$C_8$ alkoxy;
  3) Optionally substituted —$C_1$-$C_8$ alkyl;
  4) Optionally substituted —$C_2$-$C_8$ alkenyl;
  5) Optionally substituted —$C_2$-$C_8$ alkynyl;
  6) Optionally substituted —$C_3$-$C_{12}$ cycloalkyl;
  7) Optionally substituted —$C_3$-$C_{12}$ cycloalkenyl;
  8) Optionally substituted 3- to 12-membered heterocycloalkyl;
  9) Optionally substituted aryl;
  10) Optionally substituted heteroaryl;
  11) —C(O)$R_{12}$;
  12) —C(O)N$R_{13}R_{14}$;
  13) —C(O)N$R_{11}$S(O)$_2R_{12}$;
  14) —S(O)$_2$N$R_{13}R_{14}$;
  15) —N$R_{13}R_{14}$;
  16) —N$R_{11}$S(O)$_2R_{12}$;
  17) —N$R_{11}$C(O)$R_{12}$;
  18) —N$R_{11}$C(O)N$R_{13}R_{14}$; and
  19) —N$R_{11}$C(O)NHS(O)$_2R_{12}$;
  provided that when A is substituted or unsubstituted 1,4-phenylene, $R_1$ is not —N$R_{11}$C(O)$R_{12}$, wherein $R_{12}$ is optionally substituted aryl or optionally substituted heteroaryl;
  preferably, $R_1$ is not absent;
$R_2$ is selected from the group consisting of:
  1) Optionally substituted —$C_1$-$C_8$ alkoxy;
  2) Optionally substituted —$C_1$-$C_8$ alkyl;

3) Optionally substituted —$C_2$-$C_8$ alkenyl;
4) Optionally substituted —$C_2$-$C_8$ alkynyl;
5) Optionally substituted —$C_3$-$C_{12}$ cycloalkyl;
6) Optionally substituted —$C_3$-$C_{12}$ cycloalkenyl;
7) Optionally substituted 3- to 12-membered heterocycloalkyl;
8) —C(O)$R_{12}$;
9) —C(O)N$R_{13}R_{14}$;
10) —C(O)N$R_{11}$S(O)$_2R_{12}$;
11) —S(O)$_2$N$R_{13}R_{14}$;
12) —N$R_{13}R_{14}$;
13) —N$R_{11}$S(O)$_2R_{12}$;
14) —N$R_{11}$C(O)$R_{12}$;
15) —N$R_{11}$C(O)N$R_{13}R_{14}$; and
16) —N$R_{11}$C(O)NHS(O)$_2R_{12}$;
  preferably $R_2$ is —C(O)$R_{12}$, —C(O)N$R_{13}R_{14}$, —C(O)N$R_{11}$S(O)$_2R_{12}$, —S(O)$_2$N$R_{13}R_{14}$, —N$R_{13}R_{14}$, —N$R_{11}$S(O)$_2R_{12}$, —N$R_{11}$C(O)$R_{12}$, —N$R_{11}$C(O)N$R_{13}R_{14}$, or —N$R_{11}$C(O)NHS(O)$_2R_{12}$;

Each $R_3$ is the same or different and independently selected from halogen, hydroxyl, protected hydroxyl, cyano, amino, protected amino, nitro, optionally substituted —$C_1$-$C_8$ alkyl, optionally substituted —$C_1$-$C_8$ alkoxy, and optionally substituted —$C_1$-$C_8$ alkyl-O—$C_1$-$C_8$ alkoxy;

$R_{12}$ at each occurrence is independently selected from the group consisting of:
  1) Hydrogen;
  2) Halogen;
  3) Hydroxyl;
  4) Optionally substituted —$C_1$-$C_8$ alkoxy;
  5) Optionally substituted —$C_1$-$C_8$ alkyl;
  6) Optionally substituted —$C_2$-$C_8$ alkenyl;
  7) Optionally substituted —$C_2$-$C_8$ alkynyl;
  8) Optionally substituted —$C_3$-$C_8$ cycloalkyl;
  9) Optionally substituted —$C_3$-$C_8$ cycloalkenyl;
  10) Optionally substituted 3- to 8-membered heterocycloalkyl;
  11) Optionally substituted aryl;
  12) Optionally substituted arylalkyl;
  13) Optionally substituted heteroaryl; and
  14) Optionally substituted heteroarylalkyl;

$R_{11}$, $R_{13}$ and $R_{14}$ are each independently selected from hydrogen, optionally substituted —$C_1$-$C_8$-alkyl, optionally substituted —$C_2$-$C_8$-alkenyl, optionally substituted —$C_2$-$C_8$-alkynyl; optionally substituted —$C_3$-$C_8$-cycloalkyl, optionally substituted 3- to 8-membered heterocyclic, optionally substituted aryl, optionally substituted arylalkyl, optionally substituted heteroaryl, and optionally substituted heteroarylalkyl; alternatively, $R_{13}$ and $R_{14}$ are taken together with the nitrogen atom they attached to form a 3- to 12-membered heterocyclic ring;

and n is 0, 1, 2, 3 or 4; preferably n is 0, 1, 2 or 3; more preferably n is 0, 1 or 2; and most preferably n is 0 or 1 or n is 0.

Each preferred group stated above can be taken in combination with one, any or all other preferred groups.

DETAILED DESCRIPTION OF THE INVENTION

In one embodiment of the present invention is a compound represented by Formula (I) as described above, or a pharmaceutically acceptable salt, hydrate, solvate, ester or prodrug thereof.

In certain embodiments, the present invention relates to compounds of Formula (I), and pharmaceutically acceptable salts thereof, wherein L is —CO—.

In certain embodiments, the present invention relates to compounds of Formula (I), and pharmaceutically acceptable salts thereof, wherein A is optionally substituted aryl; preferably A is optionally substituted phenyl. The optional substituents are preferably independently selected from, but not limited to, halogen, —CN, —OH, —$NH_2$, —$NO_2$, —$CH_3$, —$CF_3$, —$OCH_3$, —$OCF_3$, —$SO_2CH_3$, —$CH_2$N($CH_3$)$_2$, and —C(O)$CH_3$. In preferred embodiments, there are 0 to 2 substituents and, more preferably, 0 or 1 substituent.

In certain embodiments, the present invention relates to compounds of Formula (I), and pharmaceutically acceptable salts thereof, wherein A is optionally substituted heteroaryl, preferably A is optionally substituted pyridinyl; preferably the optional substituents are independently selected from, but not limited to, halogen, —CN, —OH, —$NH_2$, —$NO_2$, —$CH_3$, —$CF_3$, —$OCH_3$, —$OCF_3$, —$SO_2CH_3$, —$CH_2$N($CH_3$)$_2$, and —C(O)$CH_3$. The number of substituents is 0 to k, where k is the total number of CH and NH groups in A when unsubstituted. In certain embodiments, there are 0 to 3 substituents. In preferred embodiments, there are 0 to 2 substituents and, more preferably, 0 or 1 substituent.

In certain embodiments, the present invention relates to compounds of Formula (I), and pharmaceutically acceptable salts thereof, wherein A is optionally substituted 3- to 10-membered heterocyclyl.

In one embodiment, the present invention relates to compounds of Formula (I), and pharmaceutically acceptable salts thereof, wherein A is derived from one of the following by removal of two hydrogen atoms:

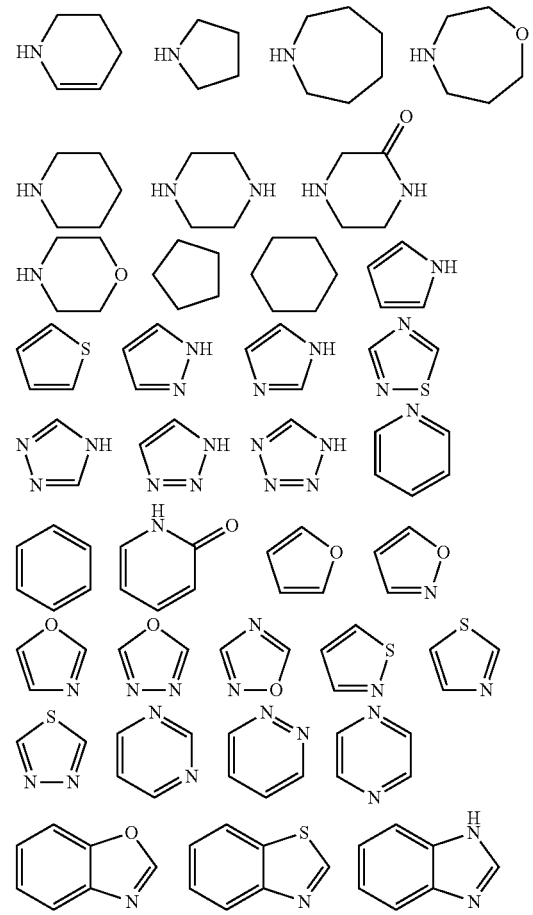

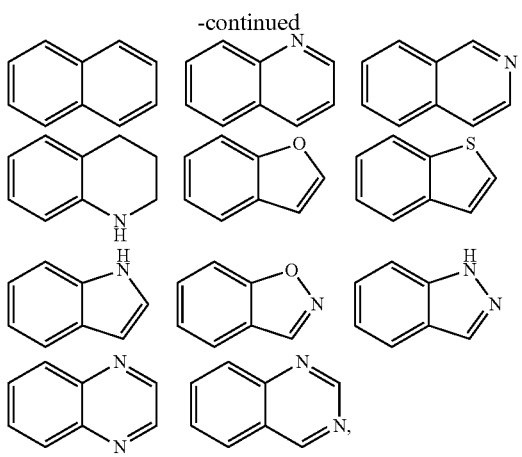

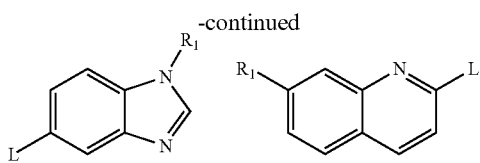

wherein each of the above is optionally substituted when possible. In this embodiment, A is attached to L and $R_1$ via any available ring atoms. In the 5/6 fused rings, A is preferably attached to $R_1$ via an available atom in the 5-membered ring.

In certain embodiments, A is selected from the groups shown below, each of which can be optionally substituted. In groups with the labels "L" and "$R_1$", these indicate respectively the points of attachment to elements L and $R_1$ of Formula I.

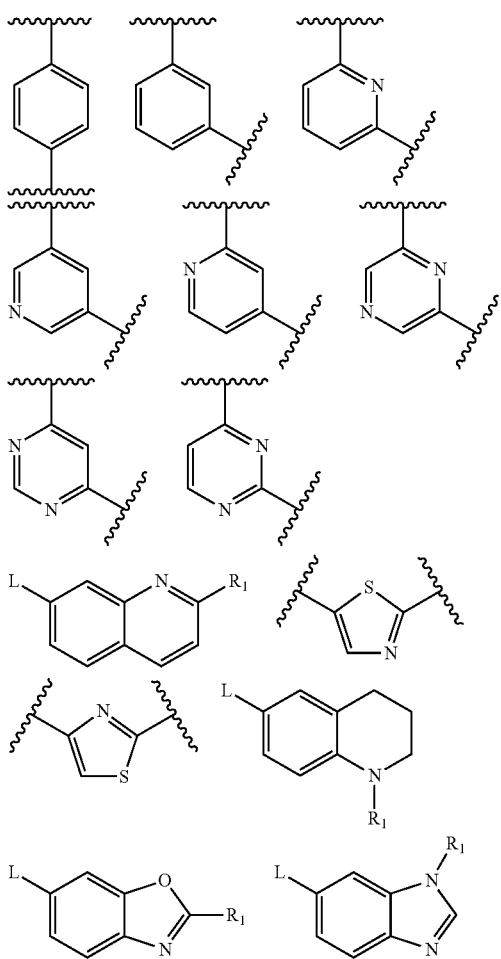

In certain embodiments, the present invention relates to compounds of Formula (I), and pharmaceutically acceptable salts thereof, wherein B is optionally substituted aryl, preferably B is optionally substituted phenyl.

In certain embodiments, the present invention relates to compounds of Formula (I), and pharmaceutically acceptable salts thereof, wherein B is optionally substituted heteroaryl, preferably B is optionally substituted 5-membered heteroaryl or 6-membered heteroaryl. In certain embodiments, B is a six-membered nitrogen-containing heteroaryl group, such as a pyrido, pyrimido, pyridazo or pyrazo group.

In one embodiment, B is a optionally substituted 5-membered sulfur and/or nitrogen containing heteroaryl group; preferably, B is a optionally substituted 5-membered sulfur containing heteroaryl group, such as a thieno, thiazolo, isothiazolo, 1,2,4-thiadiazolo or 1,3,4-thiadiazolo group.

In certain embodiments, the present invention relates to compounds of Formula (I), and pharmaceutically acceptable salts thereof, where

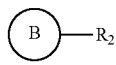

is selected from, but is not limited to, the groups set forth below, where the two indicated valences are the points of attachment to the 4- and 5-positions of azepanyl in Formula (I). Each of these groups is optionally additionally substituted when possible:

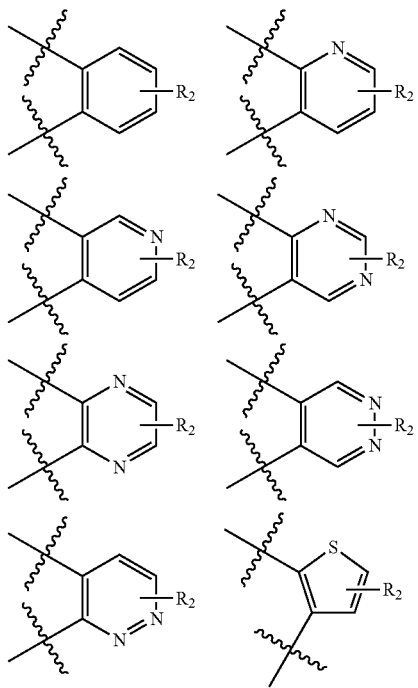

-continued

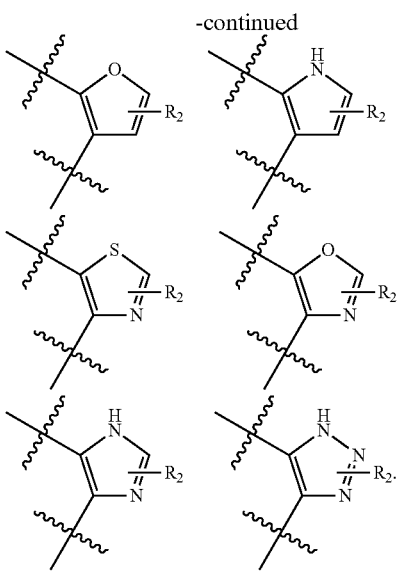

In certain embodiments,

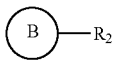

is selected from the groups below, where "4" and "5" indicate respectively the point of attachment to the 4- and 5-positions of the benzoazepine ring system:

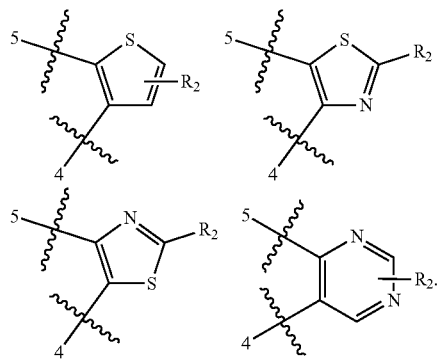

In certain embodiments, the present invention relates to compounds of Formula (I), and pharmaceutically acceptable salts thereof, wherein $R_1$ is optionally substituted aryl, preferably A is optionally substituted phenyl.

In certain embodiments, the present invention relates to compounds of Formula (I), and pharmaceutically acceptable salts thereof, wherein $R_1$ is optionally substituted heteroaryl, preferably $R_1$ is optionally substituted 5-membered heteroaryl or 6-membered heteroaryl, more preferably $R_1$ is optionally substituted pyridinyl.

In certain embodiments, the present invention relates to compounds of Formula (I), and pharmaceutically acceptable salts thereof, wherein $R_1$ is —$NR_{13}R_{14}$, wherein $R_{13}$ and $R_{14}$ are previously defined.

In certain embodiments, the present invention relates to compounds of Formula (I), and pharmaceutically acceptable salts thereof, wherein $R_1$ is —$NR_{13}R_{14}$, wherein $R_{13}$ and $R_{14}$ are taken together with the nitrogen atom they are attached to to form an optionally substituted 3- to 10- or 3- to 12-membered heterocyclic.

In one embodiment, the present invention relates to compounds of Formula (I), or a pharmaceutically acceptable salt thereof, wherein $R_1$ is derived from one of the groups below by removal of one hydrogen atom, wherein each of these groups is optionally substituted:

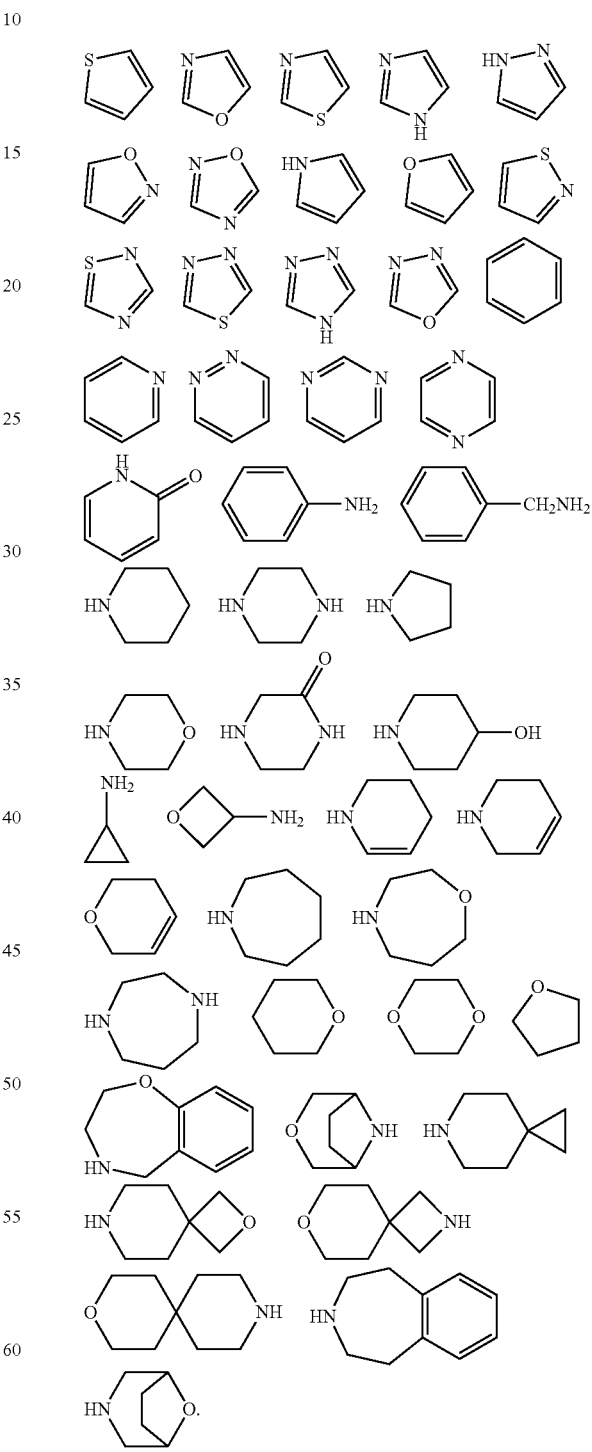

In certain embodiments, $R_1$ is selected from the groups shown below, each of which can be optionally substituted:

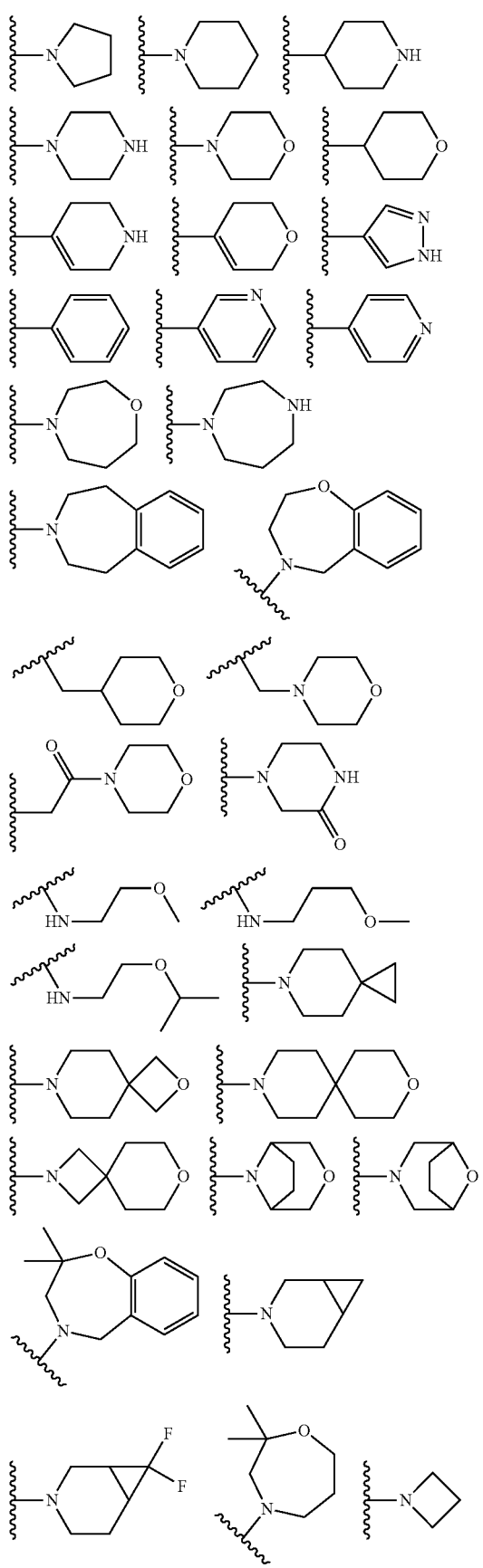

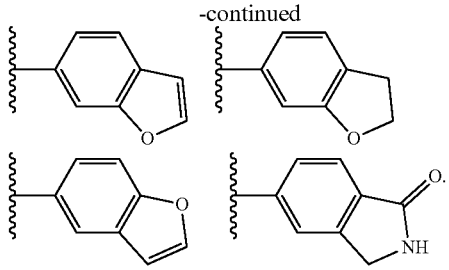

In certain embodiments, the present invention relates to compounds of Formula (I), and pharmaceutically acceptable salts thereof, wherein $R_2$ is —C(O)NR$_{13}$R$_{14}$, wherein $R_{13}$ and $R_{14}$ are previously defined.

In certain embodiments, the present invention relates to compounds of Formula (I), and pharmaceutically acceptable salts thereof, wherein $R_2$ is —C(O)NR$_{13}$R$_{14}$, wherein $R_{13}$ and $R_{14}$ are taken together with the nitrogen atom they are attached to form an optionally substituted 3- to 10-membered heterocyclic.

In certain embodiments of the compounds of the invention, $R_2$ is —C(O)NR$_{13}$R$_{14}$, where $R_{13}$ and $R_{14}$ are as defined above. Preferably, $R_{13}$ is hydrogen or $C_1$-$C_6$-alkyl and $R_{14}$ is optionally substituted $C_1$-$C_6$-alkyl or $C_3$-$C_8$-cycloalkyl. In certain embodiments, $R_{13}$ is hydrogen or methyl and $R_{14}$ is methyl, cyclopropyl, cyclopropylmethyl or 2-methoxyethyl. In one embodiment, $R_{13}$ is hydrogen and $R_{14}$ is methyl, cyclopropyl, cyclopropylmethyl or 2-methoxyethyl. In another embodiment $R_{13}$ and $R_{14}$ are both methyl. In particularly preferred embodiments, $R_{13}$ is hydrogen and $R_{14}$ is cyclopropyl.

In certain embodiments, the present invention relates to compounds of Formula (I), and pharmaceutically acceptable salts thereof, wherein $R_2$ is —NR$_{13}$R$_{14}$, wherein $R_{13}$ and $R_{14}$ are previously defined. In certain embodiments, the present invention relates to compounds of Formula (I), and pharmaceutically acceptable salts thereof, wherein $R_2$ is —NR$_{13}$R$_{14}$, and $R_{13}$ and $R_{14}$ are taken together with the nitrogen atom they are attached to form an optionally substituted 3- to 10- or 3- to 12-membered heterocyclic.

In certain embodiments, the present invention relates to compounds of Formula (I), and pharmaceutically acceptable salts thereof, wherein $R_2$ is —NR$_{11}$S(O)$_2$R$_{12}$, —NR$_{11}$C(O)R$_{12}$, or —NR$_{11}$C(O)NR$_{13}$R$_{14}$, wherein $R_{11}$, $R_{12}$, $R_{13}$ and $R_{14}$ are previously defined.

In certain embodiments, the present invention relates to compounds of Formula (I), and pharmaceutically acceptable salts thereof, wherein $R_3$ is halogen, —CN, optionally substituted alkyl, or optionally substituted —C$_1$-C$_8$-alkoxy, for examples, —CH$_3$, —OCH$_3$, —CF$_3$, or —OCF$_3$.

In certain embodiments, n is 0 to 3, 0 to 2, 1 or 0. More preferably, n is 0.

In certain embodiments, the present invention relates to compounds of Formula (I), and pharmaceutically acceptable salts thereof, wherein L is —CO—; A is optionally substituted aryl; B is optionally substituted heteroaryl; $R_2$ is —C(O)R$_{12}$, —C(O)NR$_{13}$R$_{14}$, —C(O)NR$_{11}$S(O)$_2$R$_{12}$, —S(O)$_2$NR$_{13}$R$_{14}$, —NR$_{13}$R$_{14}$, —NR$_{11}$S(O)$_2$R$_{12}$, —NR$_{11}$C(O)R$_{12}$, —NR$_{11}$C(O)NR$_{13}$R$_{14}$, or —NR$_{11}$C(O)NHS(O)$_2$R$_{12}$; n is 0 to 2.

In certain embodiments, the present invention relates to compounds of Formula (I), and pharmaceutically acceptable salts thereof, wherein L is —CO—; A is optionally substituted heteroaryl; B is optionally substituted heteroaryl; $R_2$ is —C(O)R$_{12}$, —C(O)NR$_{13}$R$_{14}$, —C(O)NR$_{11}$S(O)$_2$R$_{12}$, —S(O)$_2$NR$_{13}$R$_{14}$, —NR$_{13}$R$_{14}$, —NR$_{11}$S(O)$_2$R$_{12}$, —NR$_{11}$C(O)R$_{12}$, —NR$_{11}$C(O)NR$_{13}$R$_{14}$, or —NR$_{11}$C(O)NHS(O)$_2$R$_{12}$; and n is 0 to 2.

In certain embodiments, the present invention relates to compounds of Formula (I), and pharmaceutically acceptable salts thereof, wherein L is —CO—; A is optionally substituted heteroaryl; B is optionally substituted heteroaryl; R$_2$ is —C(O)NR$_{13}$R$_{14}$; and n is 0 to 2.

In another embodiment of the invention is a compound represented by Formulas (IIa), (IIb), or (IIc) or a pharmaceutically acceptable salt thereof:

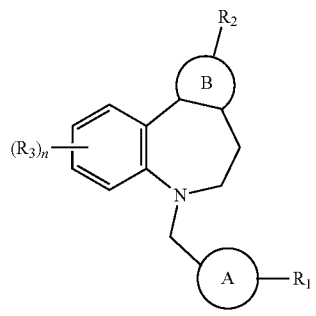
(IIa)

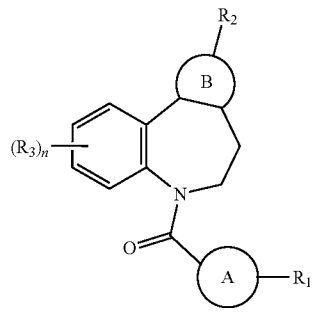
(IIb)

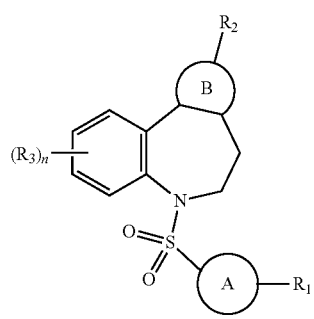
(IIc)

wherein A, B, R$_1$, R$_2$, R$_3$, and n are as previously defined.

In another embodiment of the invention is a compound represented by one of Formulas (IIIa)–(IIIh), or a pharmaceutically acceptable salt thereof:

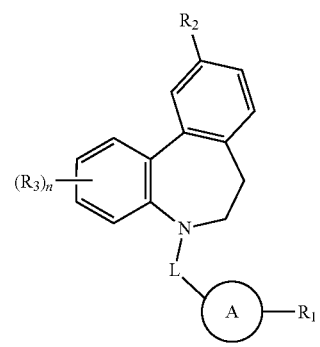
(IIIa)

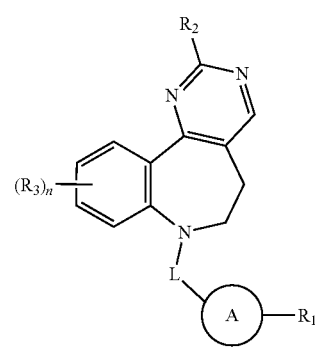
(IIIb)

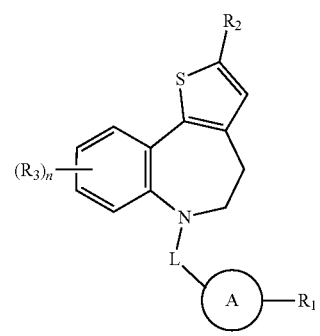
(IIIc)

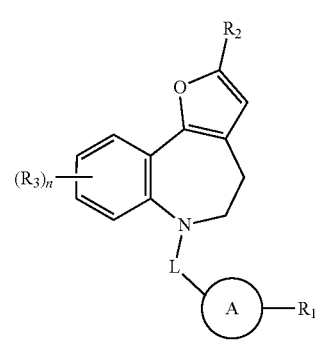
(IIId)

(IIIe)
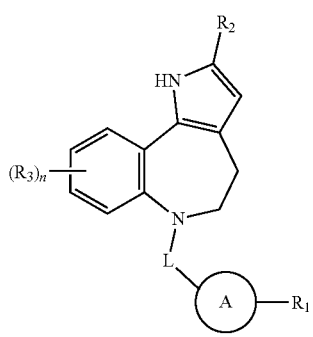
(IIIf)
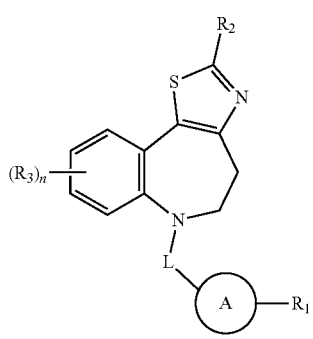
(IIIg)
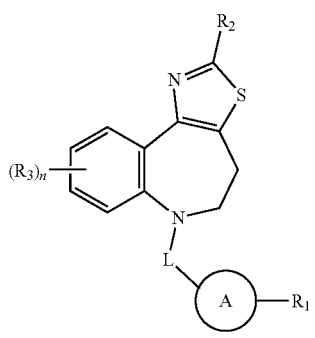
(IIIh)
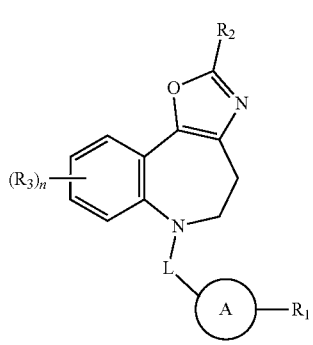
wherein $R_1$, $R_2$, $R_3$, A, L and n are as previously defined.
In another embodiment of the invention is a compound represented by one of Formulas (IIIa-1)~(IIIh-1), or a pharmaceutically acceptable salt thereof:
(IIIa-1)
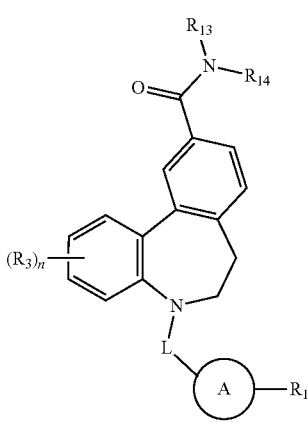
(IIIb-1)
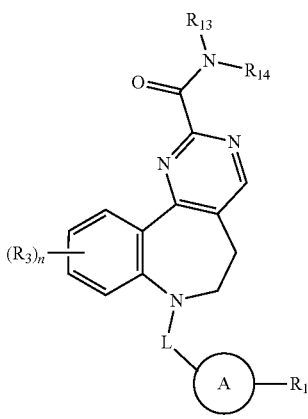
(IIIc-1)
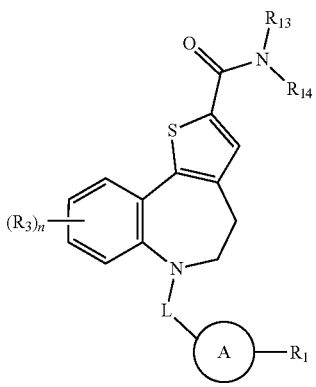
(IIId-1)
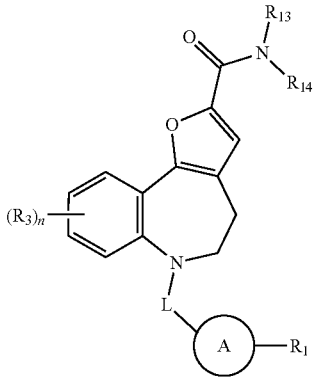

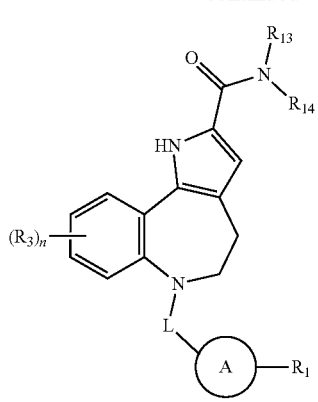
(IIIe-1)

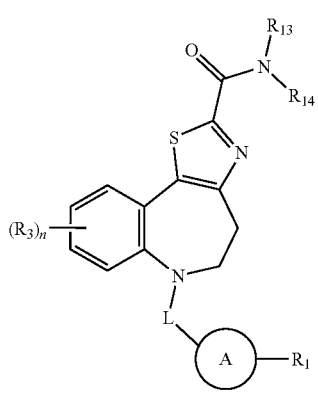
(IIIf-1)

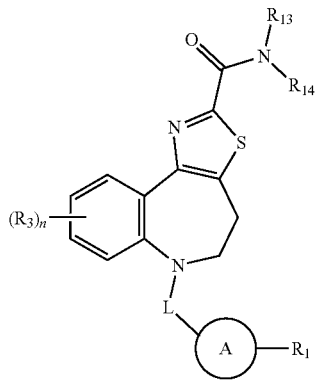
(IIIg-1)

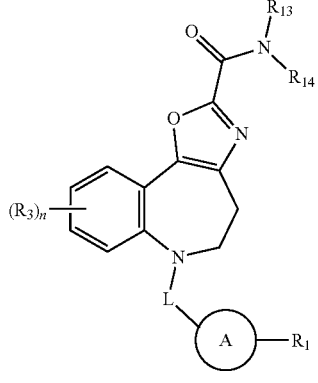
(IIIh-1)

wherein $R_{13}$, $R_{14}$, $R_1$, $R_3$, A, L and n are as previously defined; preferably n is 0 or 1. In certain embodiments, $R_{13}$ is hydrogen or optionally substituted $—C_1-C_6$ alkyl; $R_{14}$ is hydrogen, optionally substituted $—C_1-C_6$ alkyl or derived from one of the following by removal of a hydrogen atom from one carbon atom, each of which is optionally substituted:

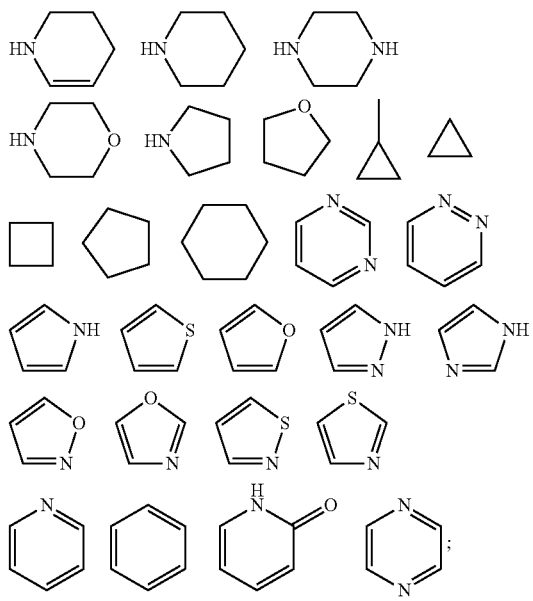

alternatively $R_{13}$ and $R_{14}$ are taken together with the nitrogen atom to which they are attached to form an optionally substituted 3- to 12-membered heterocyclic. In one embodiment, $R_{13}$ is hydrogen and $R_{14}$ is methyl, cyclopropyl, cyclopropylmethyl or 2-methoxyethyl. In another embodiment $R_{13}$ and $R_{14}$ are both methyl. In particularly preferred embodiments, $R_{13}$ is hydrogen and $R_{14}$ is cyclopropyl. In particularly preferred embodiments, $R_{13}$ is hydrogen and $R_{14}$ is

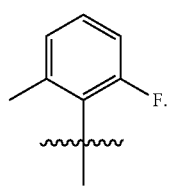 [SMILES: *c1c(C)cccc1F]

In certain embodiments $R_1$ is a group derived from one of the following by removal of one hydrogen atom, and $R_1$ is optionally substituted:

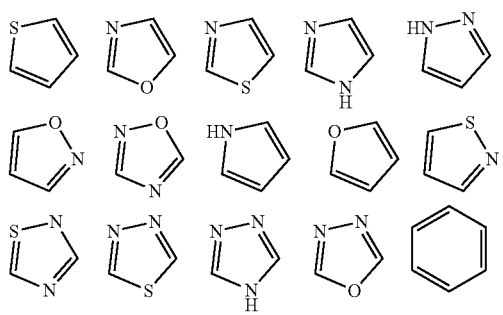

-continued

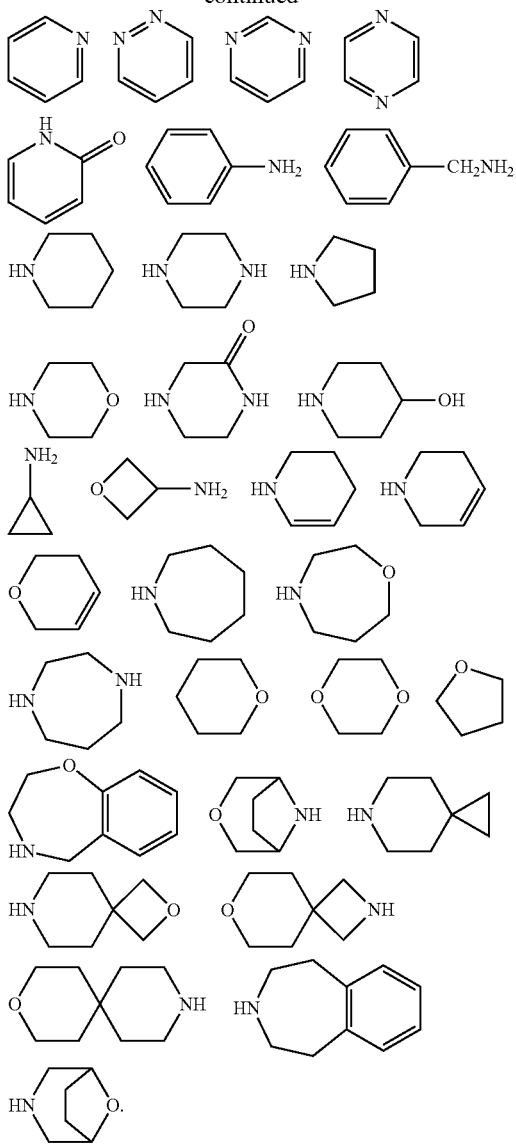

In another embodiment of the invention is a compound represented by one of Formulas (IVa)~(IVd), or a pharmaceutically acceptable salt thereof:

(IVa)

-continued

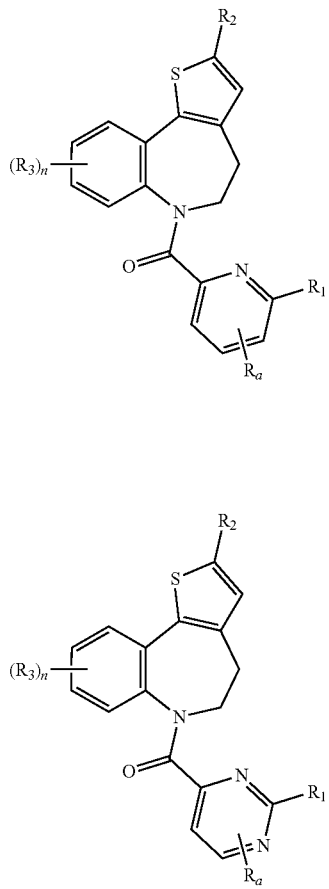

(IVb)

(IVc)

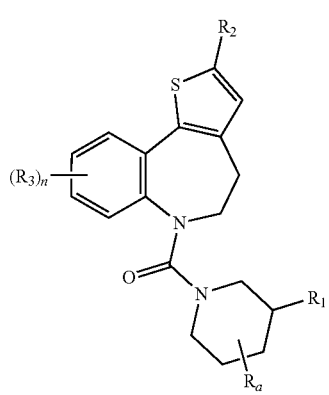

(IVd)

wherein $R_1$, $R_2$, and $R_3$ are previously defined; n is 1, 2 or 0; $R_a$ is hydrogen, halogen, optionally substituted alkyl, optionally substituted alkoxy, or —CN. preferably, $R_2$ is —C(O)$R_{12}$, —C(O)N$R_{13}R_{14}$, —C(O)N$R_{11}$S(O)$_2R_{12}$, —S(O)$_2$N$R_{13}R_{14}$, —N$R_{13}R_{14}$, —N$R_{11}$S(O)$_2R_{12}$, —N$R_{11}$C(O)$R_{12}$, —N$R_{11}$C(O)N$R_{13}R_{14}$, or —N$R_{11}$C(O)NHS(O)$_2R_{12}$, wherein $R_{11}$, $R_{12}$, $R_{13}$, and $R_{14}$ are previously defined.

In another embodiment of the invention is a compound represented by one of Formulas (Va)~(Vd), or a pharmaceutically acceptable salt thereof:

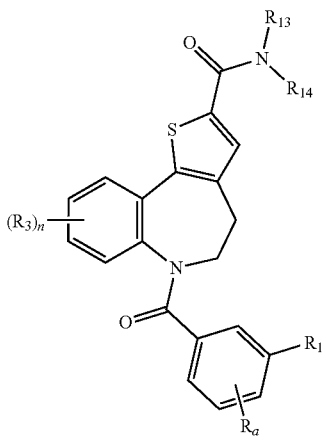
(Va)

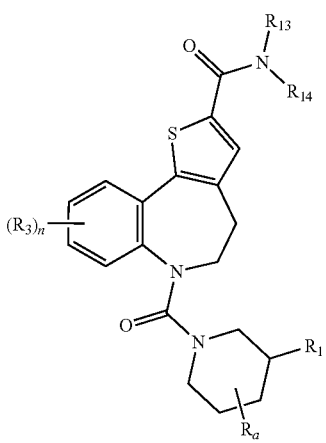
(Vd)

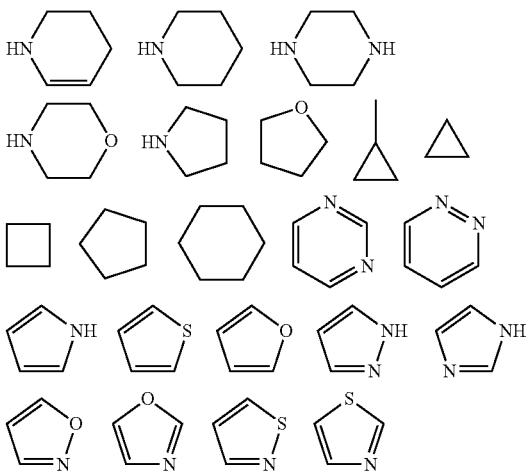

wherein $R_1$, $R_3$, $R_{13}$, and $R_{14}$ are previously defined; n is 1, 2 or 0, preferably n is 0 or 1; $R_a$ is hydrogen, halogen, optionally substituted alkyl, optionally substituted alkoxy, or —CN. In certain embodiments, $R_{13}$ is hydrogen or optionally substituted —$C_1$-$C_6$ alkyl; $R_{14}$ is hydrogen, optionally substituted —$C_1$-$C_6$ alkyl or derived from one of the following by removal of a hydrogen atom from one carbon atom, each of which is optionally substituted:

alternatively $R_{13}$ and $R_{14}$ are taken together with the nitrogen atom to which they are attached to form an optionally substituted 3- to 10- or 3 to 12-membered heterocyclic. In one embodiment, $R_{13}$ is hydrogen and $R_{14}$ is methyl, cyclopropyl, cyclopropylmethyl or 2-methoxyethyl. In another embodiment $R_{13}$ and $R_{14}$ are both methyl. In particularly preferred embodiments, $R_{13}$ is hydrogen and $R_{14}$ is cyclopropyl. In particularly preferred embodiments, $R_{13}$ is hydrogen and $R_{14}$ is

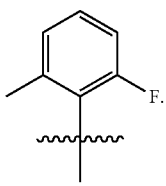 [SMILES: *c1c(C)cccc1F]
In certain embodiments $R_1$ is a group derived from one of the following by removal of one hydrogen atom, and $R_1$ is optionally substituted:
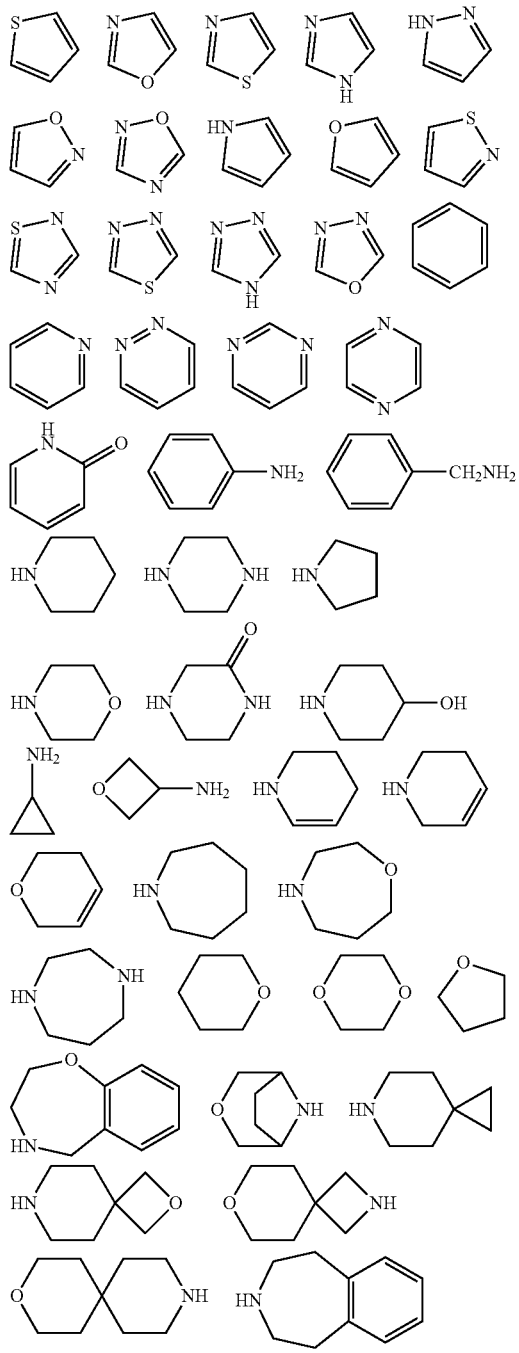
In another embodiment the invention provides a compound represented by one of Formulas (VIa)~(VIh), or a pharmaceutically acceptable salt thereof
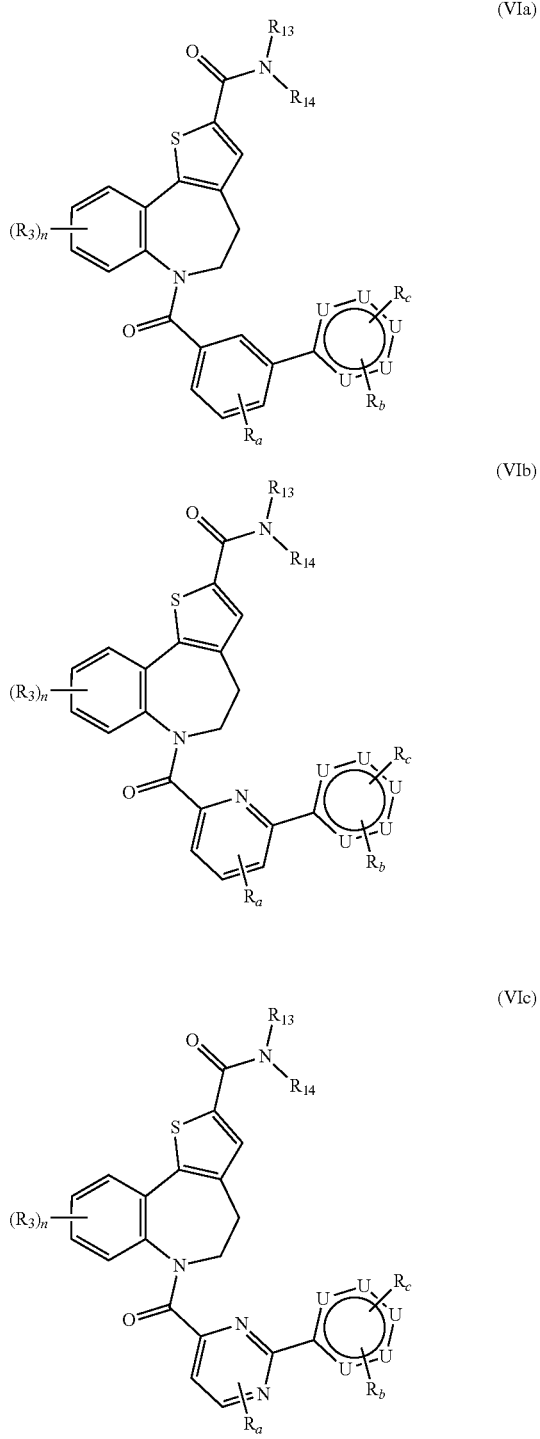

-continued

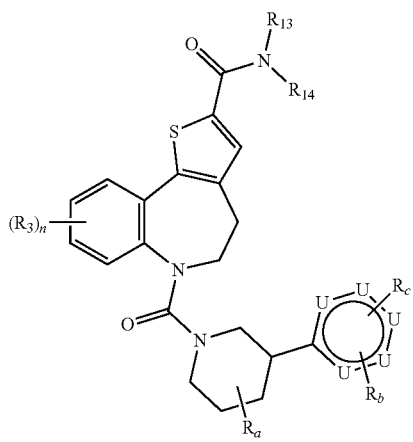
(VId)

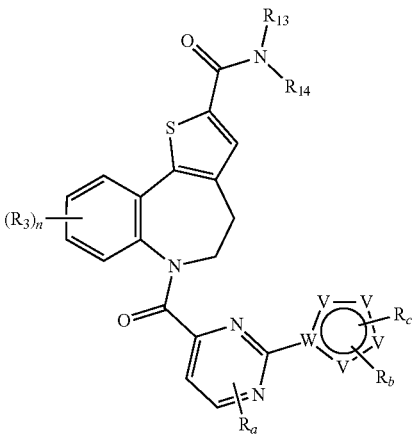
(VIg)

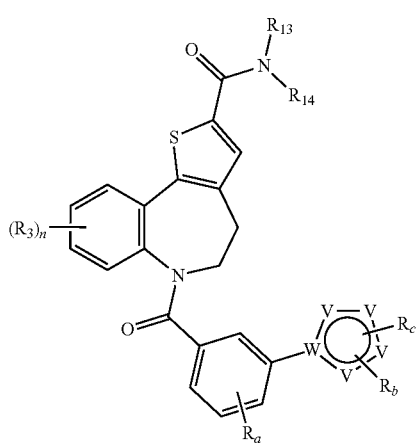
(VIe)

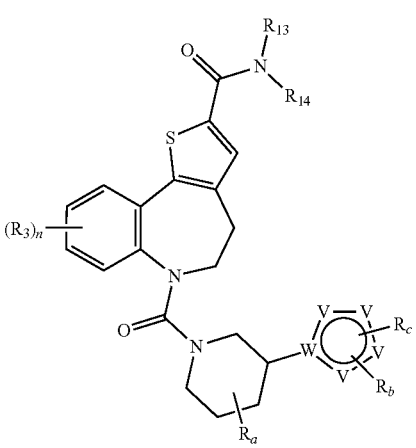
(VIh)

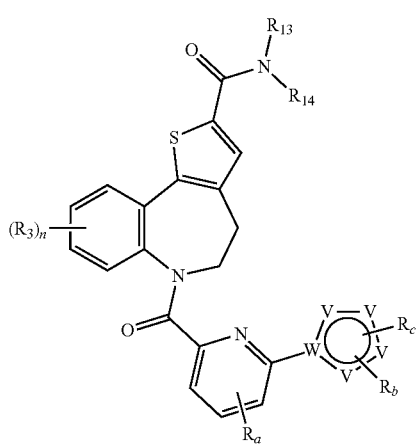
(VIf)

wherein $R_1$, $R_3$, $R_{13}$, and $R_{14}$ are previously defined; n is 1, 2 or 0, preferably n is 0 or 1; each U is the same or different and independently selected from N, C and CH; W is C or N; each V is the same or different and independently selected form N, NH, O, S, C and CH; $R_a$ and $R_b$ are each independently selected from hydrogen, halogen, optionally substituted —$C_1$-$C_6$ alkyl, optionally substituted —$C_1$-$C_6$ alkoxy, or —CN; in certain embodiments, $R_{13}$ is hydrogen, optionally substituted —$C_1$-$C_6$ alkyl; $R_{14}$ is hydrogen, optionally substituted —$C_1$-$C_6$ alkyl, or is derived from one of the following by removal of one hydrogen atom and the said hydrogen atom is not from —NH, each of which is optionally substituted:

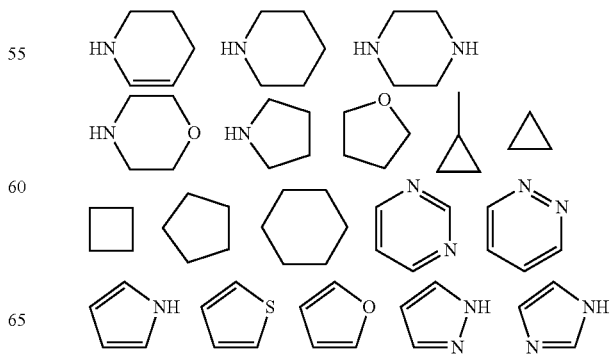

alternatively $R_{13}$ and $R_{14}$ are taken together with the nitrogen atom to which they are attached to form an optionally substituted 3- to 10- or 3- to 12-membered heterocyclic; In one embodiment, $R_{13}$ is hydrogen and $R_{14}$ is methyl, cyclopropyl, cyclopropylmethyl or 2-methoxyethyl. In another embodiment $R_{13}$ and $R_{14}$ are both methyl. In particularly preferred embodiments, $R_{13}$ is hydrogen and $R_{14}$ is cyclopropyl. In particularly preferred embodiments, $R_{13}$ is hydrogen and $R_{14}$ is In certain embodiments, $R_c$ is hydrogen, optionally substituted alkyl, optionally substituted heterocycloalkyl, optionally substituted heterocycloalkenyl, optionally substituted heterocycloalkyl-X— or optionally substituted heterocycloalkenyl-X—, where X is O or NH. In certain embodiments, $R_c$ is a group selected from one of the following by removal of one hydrogen atom, and $R_c$ is optionally substituted:

Representative compounds of the present invention include compounds 1-527 compiled in Table 1 and pharmaceutically acceptable salts thereof:

TABLE 1

| Entry | Compound |
|---|---|
| 1 | |
| 2 | |

TABLE 1-continued
| Entry | Compound |
|---|---|
| 3 | 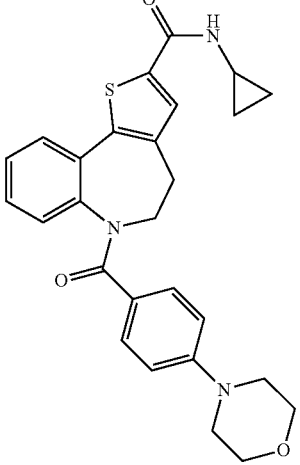 |
| 4 | 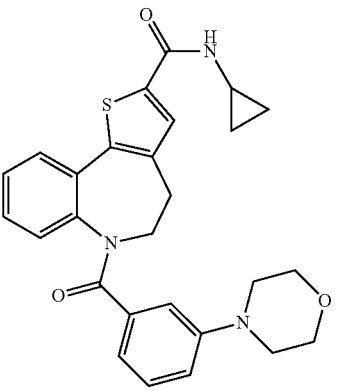 [SMILES: O=C(NC1CC1)c1cc2c(s1)-c1ccccc1N(C(=O)c1cccc(N3CCOCC3)c1)CC2] |
| 5 | 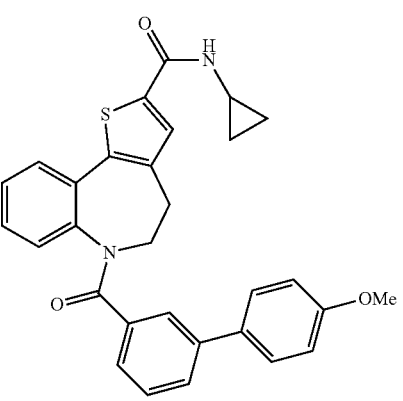 [SMILES: COc1ccc(-c2cccc(C(=O)N3CCc4cc(C(=O)NC5CC5)sc4-c4ccccc43)c2)cc1] |
| 6 | 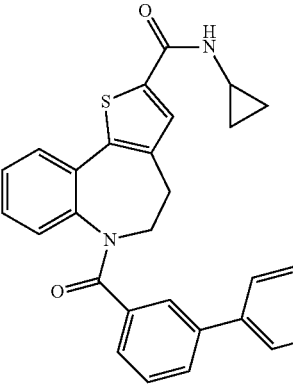 |
| 7 | 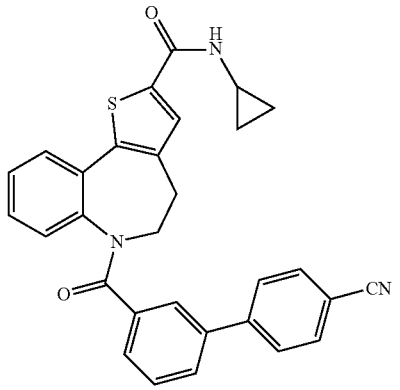 [SMILES: N#Cc1ccc(-c2cccc(C(=O)N3CCc4cc(C(=O)NC5CC5)sc4-c4ccccc43)c2)cc1] |
| 8 | 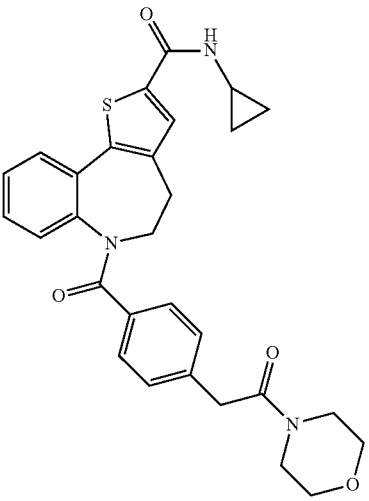 [SMILES: O=C(NC1CC1)c1cc2c(s1)-c1ccccc1N(C(=O)c1ccc(CC(=O)N3CCOCC3)cc1)CC2] |

TABLE 1-continued
| Entry | Compound |
|---|---|
| 9 | 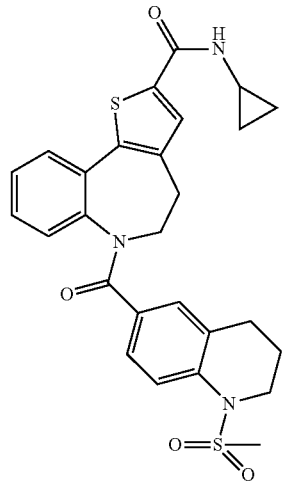 [SMILES: CS(=O)(=O)N1CCCc2cc(C(=O)N3CCc4cc(C(=O)NC5CC5)sc4-c4ccccc43)ccc21] |
| 10 | 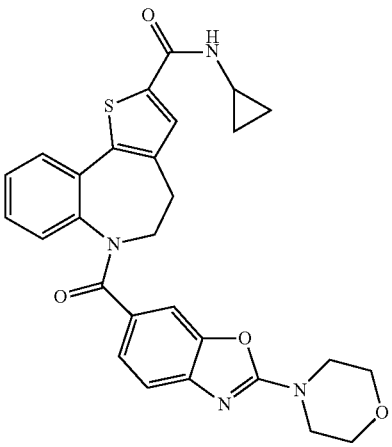 [SMILES: O=C(NC1CC1)c1cc2c(s1)-c1ccccc1N(C(=O)c1ccc3nc(N4CCOCC4)oc3c1)CC2] |
| 11 | 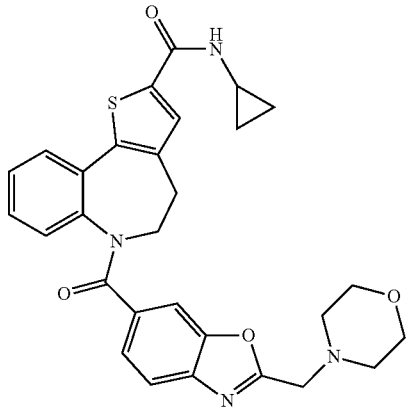 [SMILES: O=C(NC1CC1)c1cc2c(s1)-c1ccccc1N(C(=O)c1ccc3nc(CN4CCOCC4)oc3c1)CC2] |
| 12 | 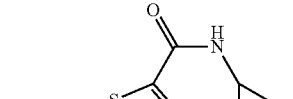 |
| 13 | 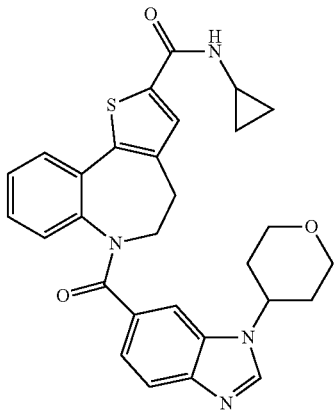 [SMILES: O=C(NC1CC1)c1cc2c(s1)-c1ccccc1N(C(=O)c1ccc3ncn(C4CCOCC4)c3c1)CC2] |
| 14 | 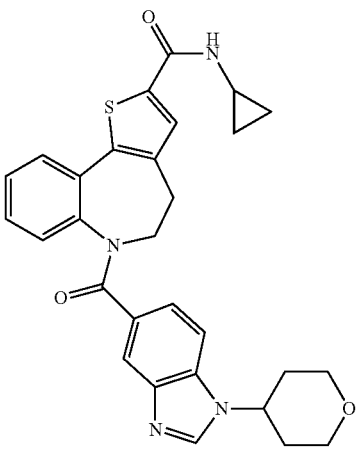 [SMILES: O=C(NC1CC1)c1cc2c(s1)-c1ccccc1N(C(=O)c1ccc3c(c1)ncn3C1CCOCC1)CC2] |

TABLE 1-continued
| Entry | Compound |
|---|---|
| 15 | 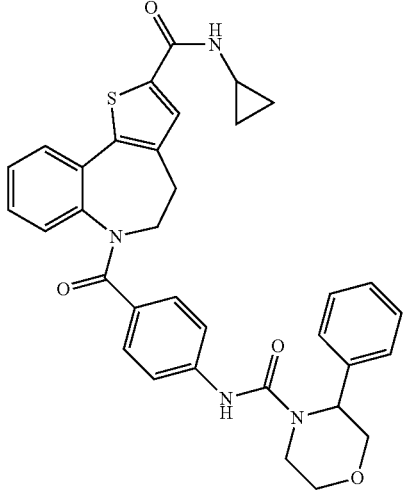 [SMILES: O=C(NC1CC1)c1cc2c(s1)-c1ccccc1N(C(=O)c1ccc(NC(=O)N3CCOCC3c3ccccc3)cc1)CC2] |
| 16 | 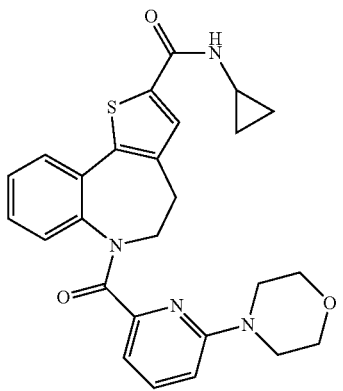 [SMILES: O=C(NC1CC1)c1cc2c(s1)-c1ccccc1N(C(=O)c1cccc(N3CCOCC3)n1)CC2] |
| 17 | 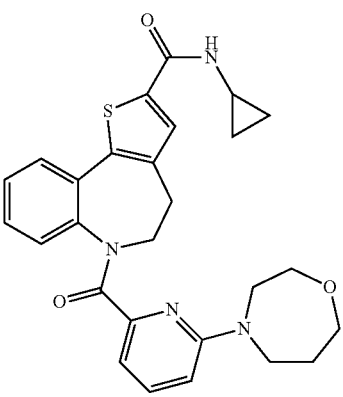 [SMILES: O=C(NC1CC1)c1cc2c(s1)-c1ccccc1N(C(=O)c1cccc(N3CCCOCC3)n1)CC2] |
| 18 | 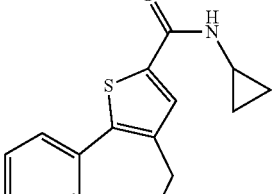 |
| 19 | 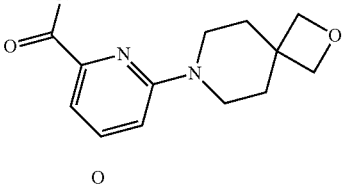 |
| 20 | 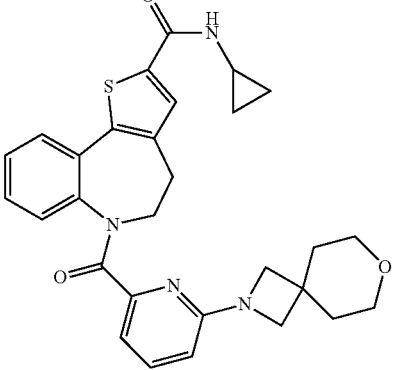 |
| 21 | 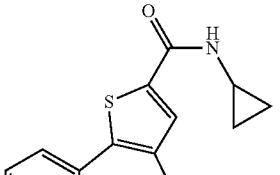 |

TABLE 1-continued
| Entry | Compound |
|---|---|
| 22 | 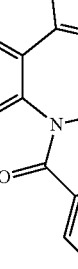 |
| 23 | 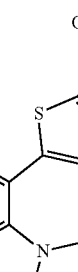 |
| 24 |  |
| 25 | 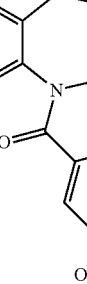 |
| 26 | 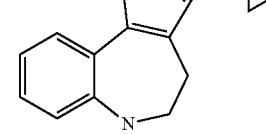 |
| 27 | 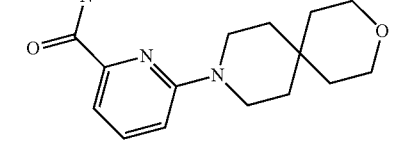 |
| 28 | 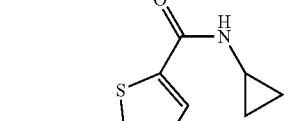 |
| 29 |  |

TABLE 1-continued
| Entry | Compound |
|---|---|
| 30 | 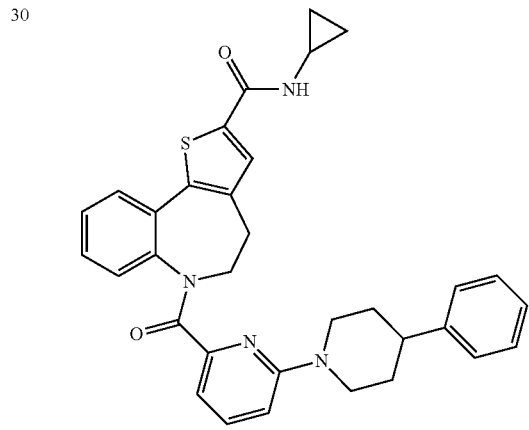 |
| 31 | 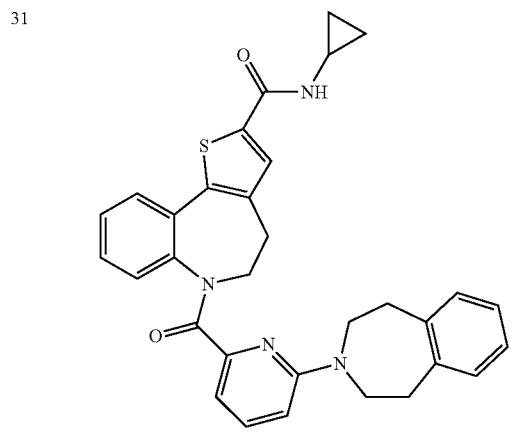 |
| 32 | 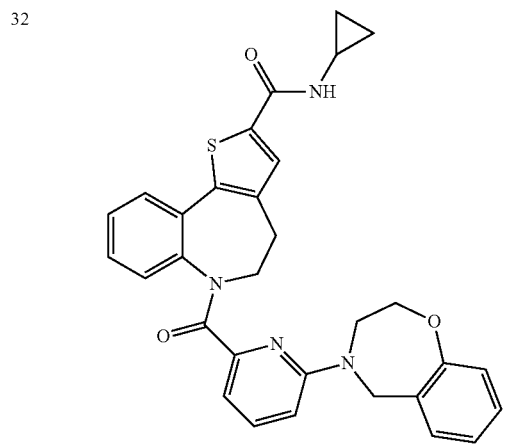 |
| 33 | 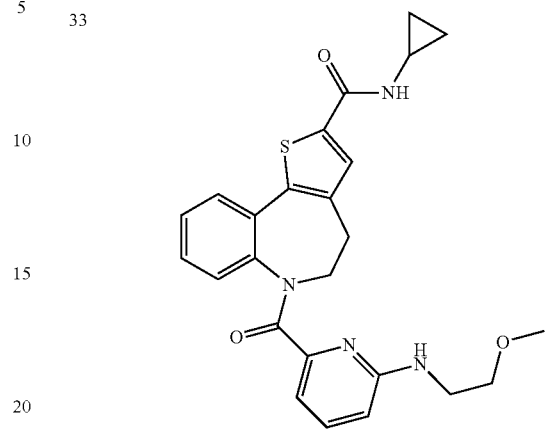 |
| 34 | 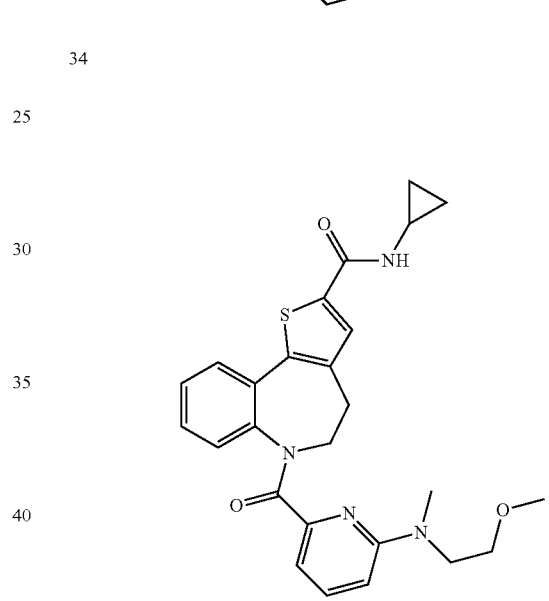 |
| 35 | 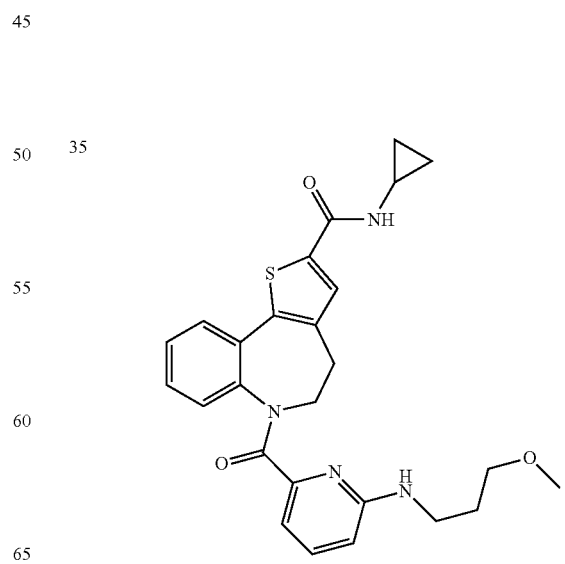 |

TABLE 1-continued
| Entry | Compound |
|---|---|
| 36 | |
| 37 | |
| 38 | |
| 39 | |
| 40 | |
| 41 | |
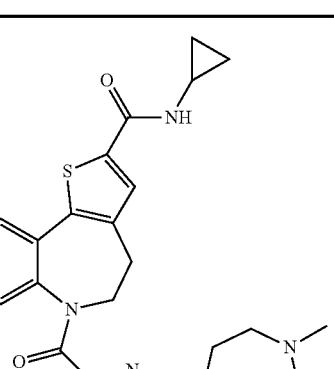

TABLE 1-continued
| Entry | Compound |
|---|---|
| 42 | 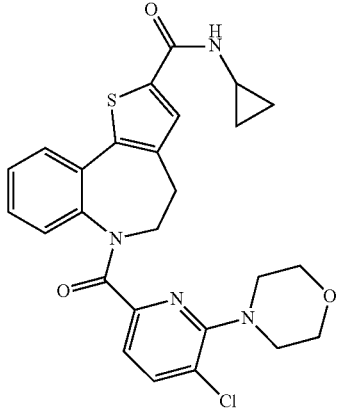 [SMILES: O=C(NC1CC1)c1cc2c(s1)-c1ccccc1N(C(=O)c1ccc(Cl)c(N3CCOCC3)n1)CC2] |
| 43 | 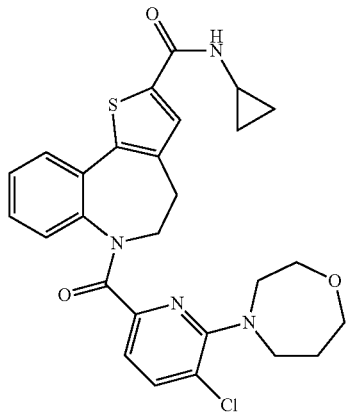 [SMILES: O=C(NC1CC1)c1cc2c(s1)-c1ccccc1N(C(=O)c1ccc(Cl)c(N3CCCOCC3)n1)CC2] |
| 44 | 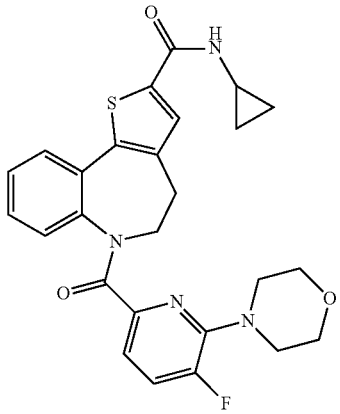 [SMILES: O=C(NC1CC1)c1cc2c(s1)-c1ccccc1N(C(=O)c1ccc(F)c(N3CCOCC3)n1)CC2] |
| 45 | 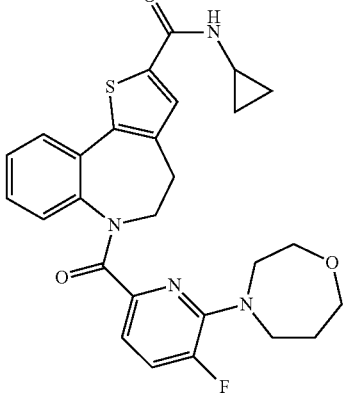 |
| 46 | 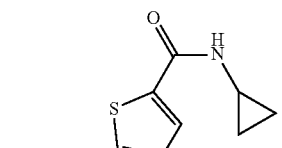 |
| 47 | 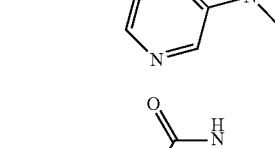 |
| 48 | 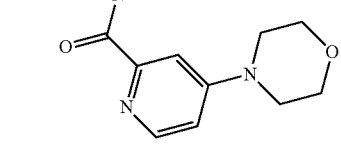 |

TABLE 1-continued
| Entry | Compound |
|---|---|
| 49 |  |
| 50 |  |
| 51 | 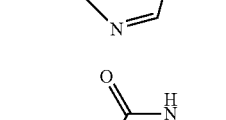 |
| 52 | 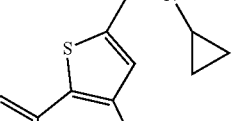 |
| 53 | 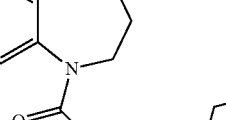 |
| 54 | 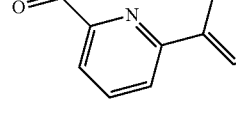 |
| 55 | 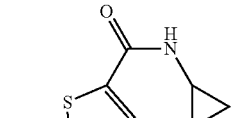 |
| 56 | 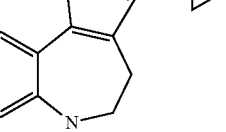 |

TABLE 1-continued

| Entry | Compound |
|---|---|
| 57 | |
| 58 | |
| 59 | |
| 60 | |
| 61 | |
| 62 | |
| 63 | |
| 64 | |

TABLE 1-continued

| Entry | Compound |
|---|---|
| 65 | (structure) |
| 66 | (structure) |
| 67 | (structure) |
| 68 | (structure) |
| 69 | (structure) |
| 70 | (structure) |
| 71 | (structure) |
| 72 | (structure) |

TABLE 1-continued
| Entry | Compound |
|---|---|
| 73 | 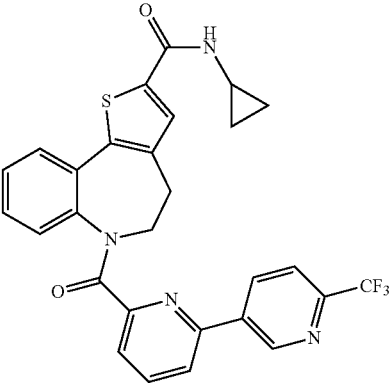 [SMILES: O=C(NC1CC1)c1cc2c(s1)-c1ccccc1N(C(=O)c1cccc(-c3ccc(C(F)(F)F)nc3)n1)CC2] |
| 74 | 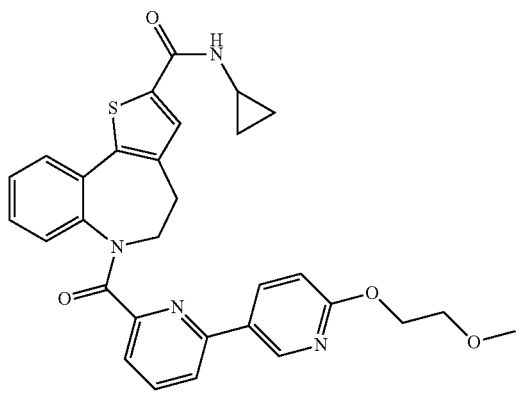 [SMILES: COCCOc1ccc(-c2cccc(C(=O)N3CCc4cc(C(=O)NC5CC5)sc4-c4ccccc43)n2)cn1] |
| 75 | 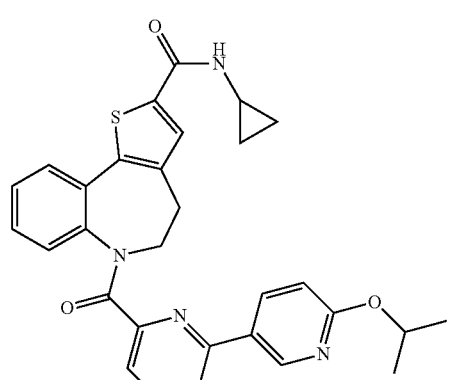 |
| 76 | 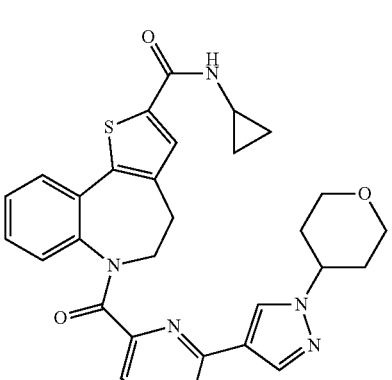 |
| 77 | 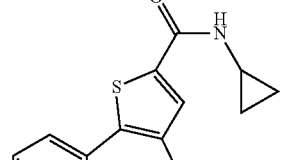 |
| 78 | 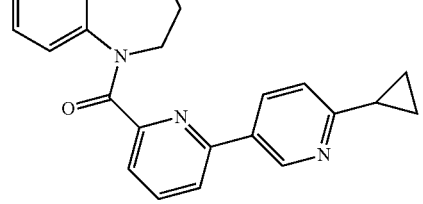 |
| 79 | 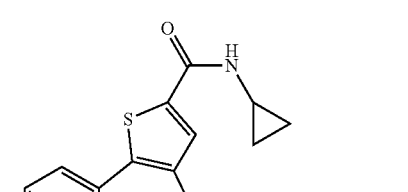 |
| 80 | 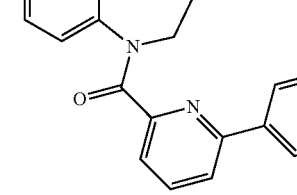 |

TABLE 1-continued
| Entry | Compound |
|---|---|
| 81 | 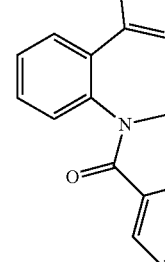 |
| 82 | |
| 83 | |
| 84 | |
| 85 | 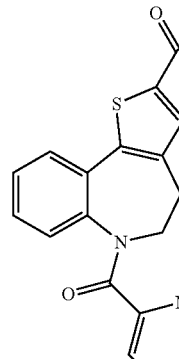 |
| 86 | |
| 87 | |

TABLE 1-continued
| Entry | Compound |
|---|---|
| 88 | 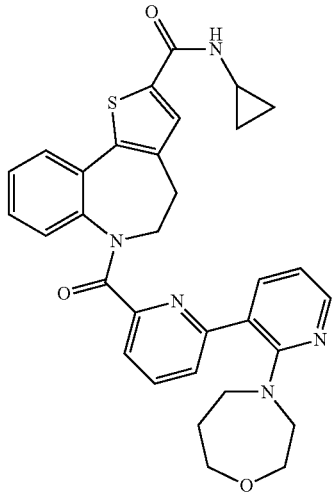 [SMILES: O=C(NC1CC1)c1cc2c(s1)-c1ccccc1N(C(=O)c1cccc(-c3cccnc3N3CCCOCC3)n1)CC2] |
| 89 | 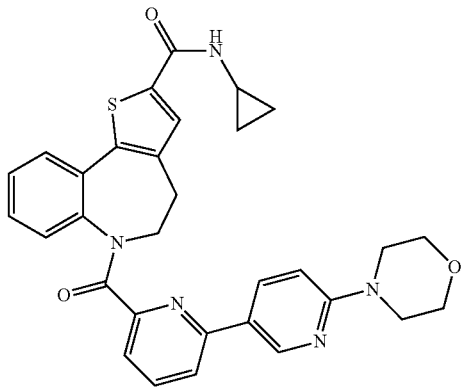 [SMILES: O=C(NC1CC1)c1cc2c(s1)-c1ccccc1N(C(=O)c1cccc(-c3ccc(N4CCOCC4)nc3)n1)CC2] |
| 90 | 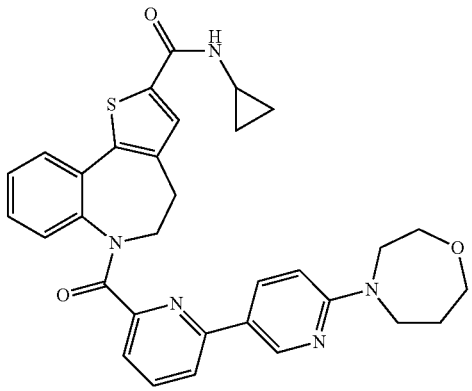 [SMILES: O=C(NC1CC1)c1cc2c(s1)-c1ccccc1N(C(=O)c1cccc(-c3ccc(N4CCCOCC4)nc3)n1)CC2] |
| 91 | 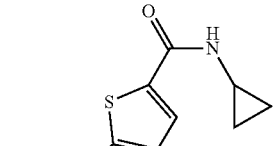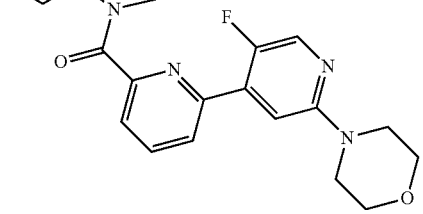 |
| 92 | 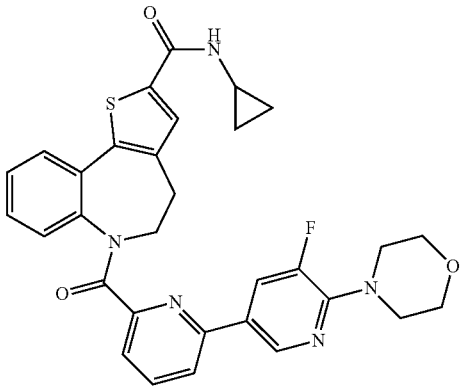 [SMILES: O=C(NC1CC1)c1cc2c(s1)-c1ccccc1N(C(=O)c1cccc(-c3cnc(N4CCOCC4)c(F)c3)n1)CC2]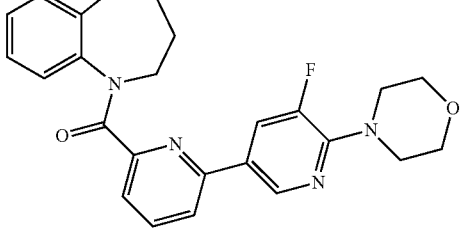 |
| 93 | 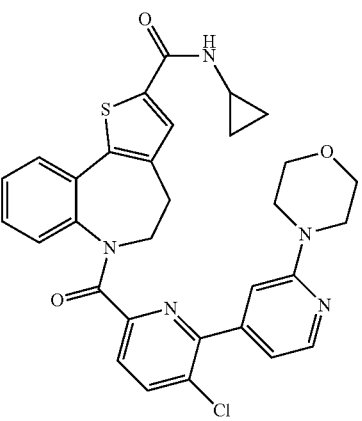 [SMILES: O=C(NC1CC1)c1cc2c(s1)-c1ccccc1N(C(=O)c1ccc(Cl)c(-c3ccnc(N4CCOCC4)c3)n1)CC2] |

TABLE 1-continued

| Entry | Compound |
|---|---|
| 94 | |
| 95 | |
| 96 | |
| 97 | |
| 98 | |
| 99 | |
| 100 | |
| 101 | |

TABLE 1-continued
| Entry | Compound |
|---|---|
| 102 | 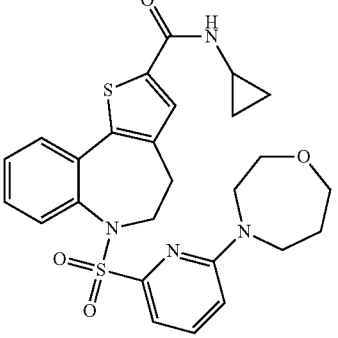 |
| 103 | 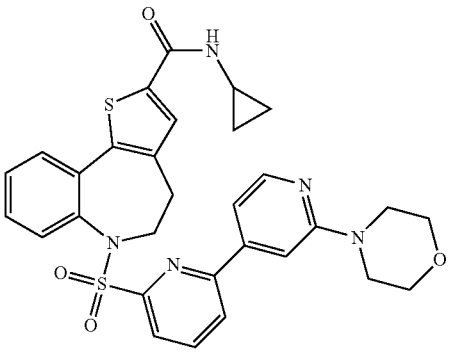 [SMILES: O=C(NC1CC1)c1cc2c(s1)-c1ccccc1N(S(=O)(=O)c1cccc(-c3ccnc(N4CCOCC4)c3)n1)CC2] |
| 104 | 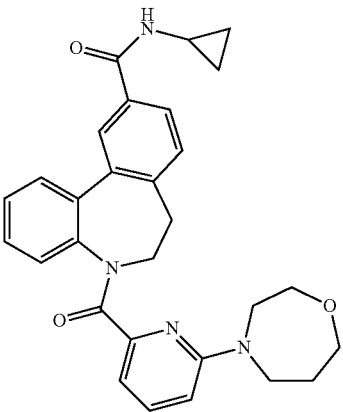 [SMILES: O=C(NC1CC1)c1ccc2c(c1)-c1ccccc1N(C(=O)c1cccc(N3CCCOCC3)n1)CC2] |
| 105 | 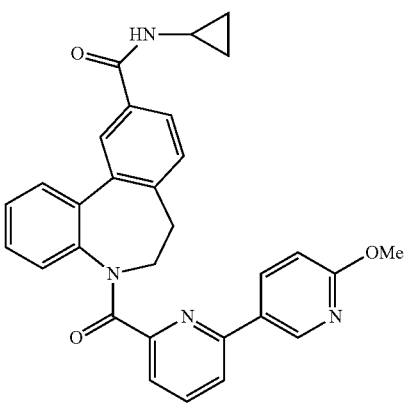 [SMILES: COc1ccc(-c2cccc(C(=O)N3CCc4ccc(C(=O)NC5CC5)cc4-c4ccccc43)n2)cn1] |
| 106 | 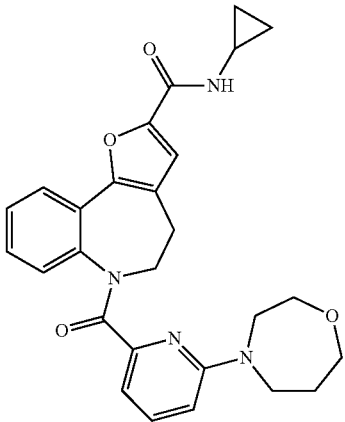 [SMILES: O=C(NC1CC1)c1cc2c(o1)-c1ccccc1N(C(=O)c1cccc(N3CCCOCC3)n1)CC2] |
| 107 | 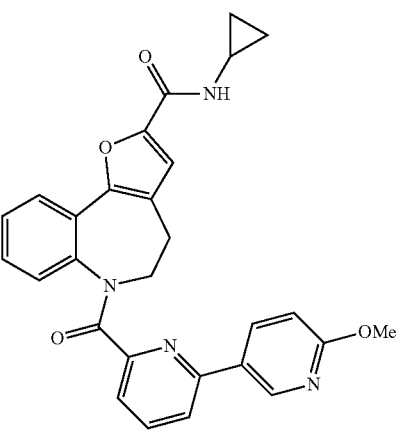 [SMILES: COc1ccc(-c2cccc(C(=O)N3CCc4cc(C(=O)NC5CC5)oc4-c4ccccc43)n2)cn1] |
| 108 | 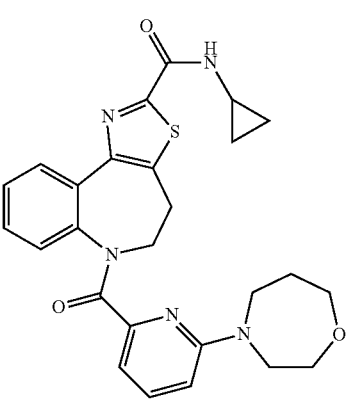 [SMILES: O=C(NC1CC1)c1nc2c(s1)CCN(C(=O)c1cccc(N3CCCOCC3)n1)c1ccccc1-2] |

TABLE 1-continued

| Entry | Compound |
|---|---|
| 109 | |
| 110 | |
| 111 | |
| 112 | |
| 113 | |
| 114 | |

TABLE 1-continued

| Entry | Compound |
|---|---|
| 115 | (structure) |
| 116 | (structure) |
| 117 | (structure) |
| 118 | (structure) |
| 119 | (structure) |
| 120 | (structure) |

TABLE 1-continued

| Entry | Compound |
|---|---|
| 121 | (structure) |
| 122 | (structure) |
| 123 | (structure) |
| 124 | (structure) |
| 125 | (structure) |
| 126 | (structure) |

TABLE 1-continued
| Entry | Compound |
|---|---|
| 127 | 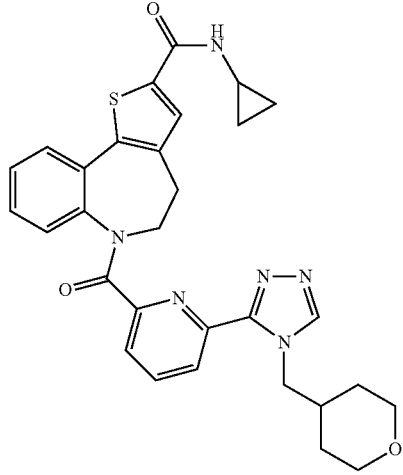 [SMILES: O=C(NC1CC1)c1cc2c(s1)-c1ccccc1N(C(=O)c1cccc(-c3nncn3CC3CCOCC3)n1)CC2] |
| 128 | 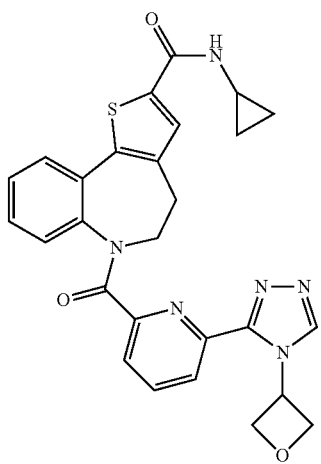 [SMILES: O=C(NC1CC1)c1cc2c(s1)-c1ccccc1N(C(=O)c1cccc(-c3nncn3C3COC3)n1)CC2] |
| 129 | 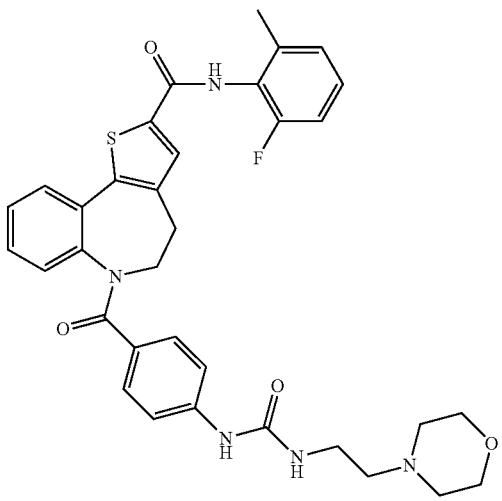 [SMILES: Cc1cccc(F)c1NC(=O)c1cc2c(s1)-c1ccccc1N(C(=O)c1ccc(NC(=O)NCCN3CCOCC3)cc1)CC2] |
TABLE 1-continued
| Entry | Compound |
|---|---|
| 130 | 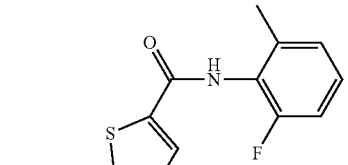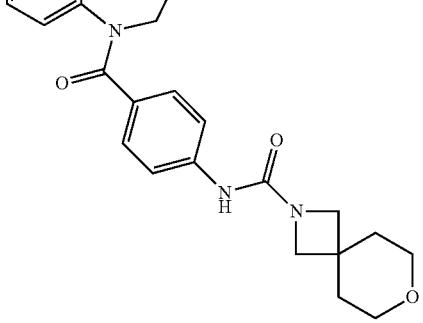 |
| 131 | 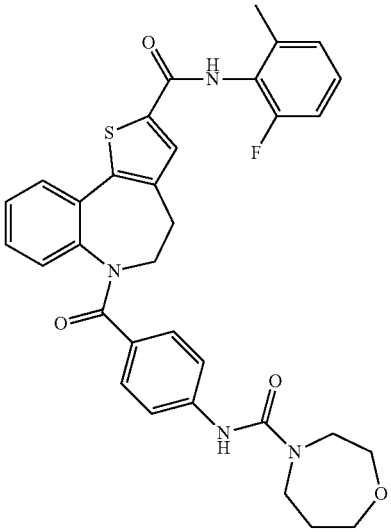 [SMILES: Cc1cccc(F)c1NC(=O)c1cc2c(s1)-c1ccccc1N(C(=O)c1ccc(NC(=O)N3CCCOCC3)cc1)CC2] |

TABLE 1-continued

| Entry | Compound |
|---|---|
| 132 | |
| 133 | |
| 134 | |
| 135 | |

TABLE 1-continued
| Entry | Compound |
|---|---|
| 136 | 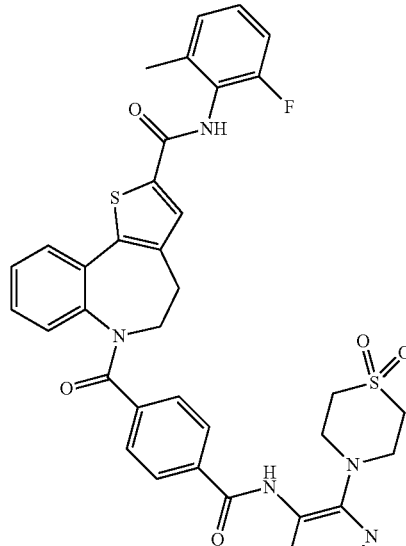 |
| 137 | |
| 138 | |
| 139 | |

TABLE 1-continued
| Entry | Compound |
|---|---|
| 140 | 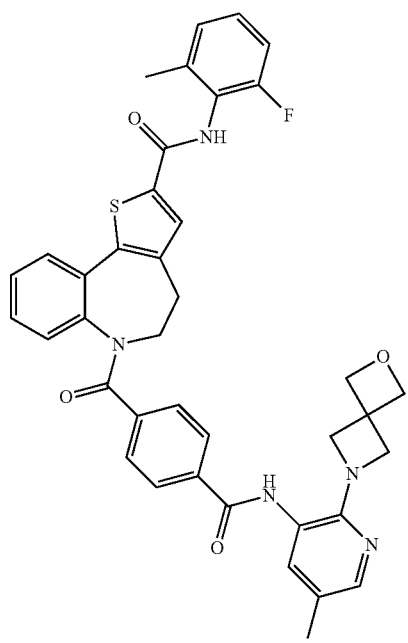 [SMILES: Cc1cnc(N2CC3(COC3)C2)c(NC(=O)c2ccc(C(=O)N3CCc4cc(C(=O)Nc5c(C)cccc5F)sc4-c4ccccc43)cc2)c1] |
| 141 | 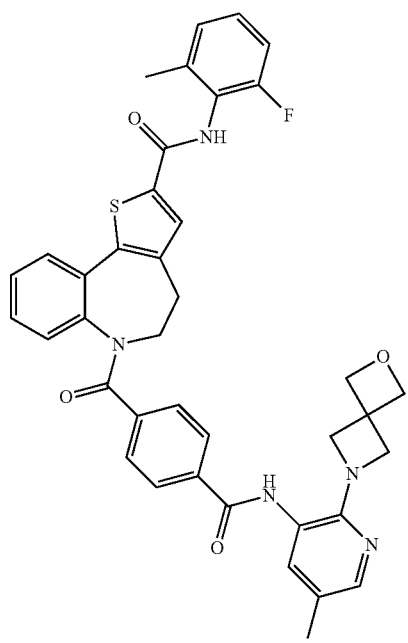 [SMILES: Cc1cnc(N2CC3(COC3)C2)c(NC(=O)c2ccc(C(=O)N3CCc4cc(C(=O)Nc5c(C)cccc5F)sc4-c4ccccc43)cc2)c1] |
TABLE 1-continued
| Entry | Compound |
|---|---|
| 142 | 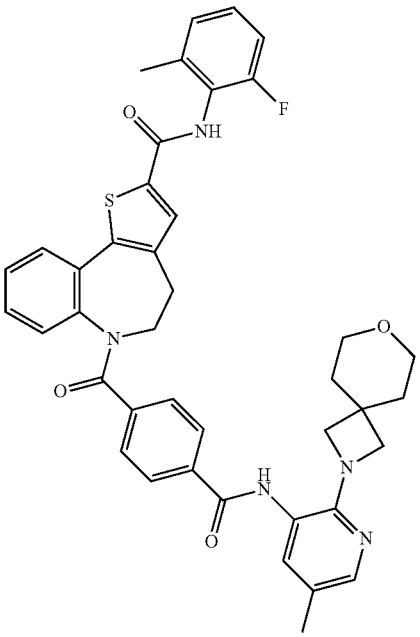 [SMILES: Cc1cnc(N2CC3(CCOCC3)C2)c(NC(=O)c2ccc(C(=O)N3CCc4cc(C(=O)Nc5c(C)cccc5F)sc4-c4ccccc43)cc2)c1] |
| 143 | 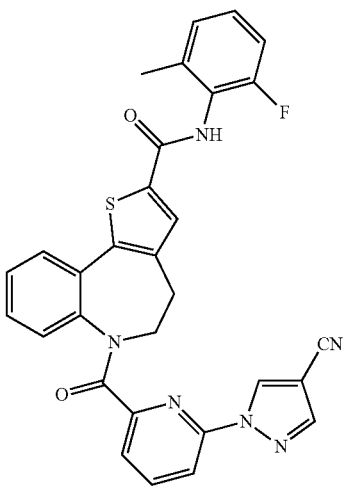 [SMILES: Cc1cccc(F)c1NC(=O)c1cc2c(s1)-c1ccccc1N(C(=O)c1cccc(-n3cc(C#N)cn3)n1)CC2] |
| 144 | 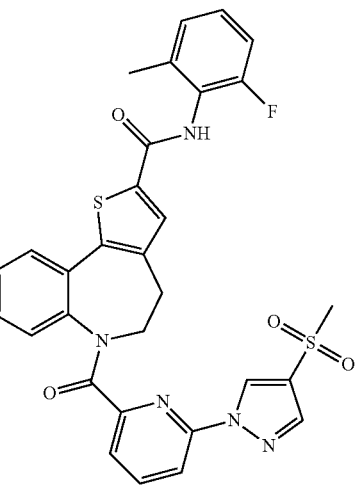 |

TABLE 1-continued

| Entry | Compound |
|---|---|
| 145 | (structure) |
| 146 | (structure) |
| 147 | (structure) |
| 148 | (structure) |
| 149 | (structure) |
| 150 | (structure) |

TABLE 1-continued
| Entry | Compound |
|---|---|
| 151 | |
| 152 | |
| 153 | |
| 154 | |
| 155 | |
| 156 | |
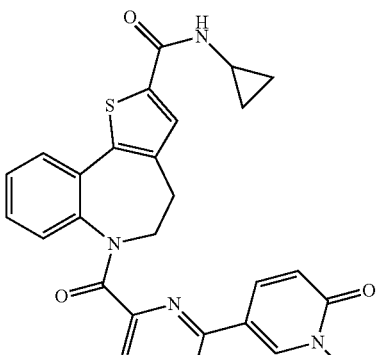

TABLE 1-continued
| Entry | Compound |
|---|---|
| 157 | 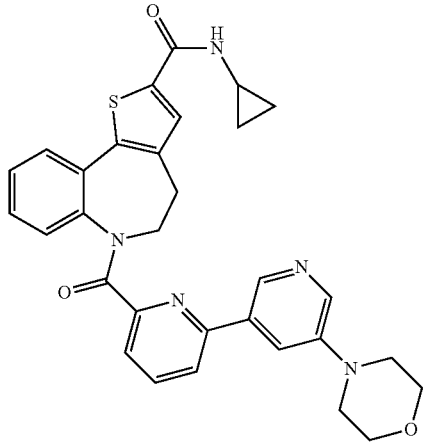 [SMILES: O=C(NC1CC1)c1cc2c(s1)-c1ccccc1N(C(=O)c1cccc(-c3cncc(N4CCOCC4)c3)n1)CC2] |
| 158 | |
| 159 | |
| 160 | |
| 161 | |
| 162 | |

TABLE 1-continued
| Entry | Compound |
|---|---|
| 163 | 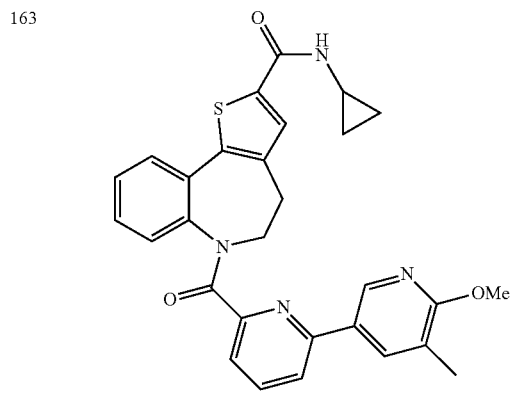 |
| 164 | 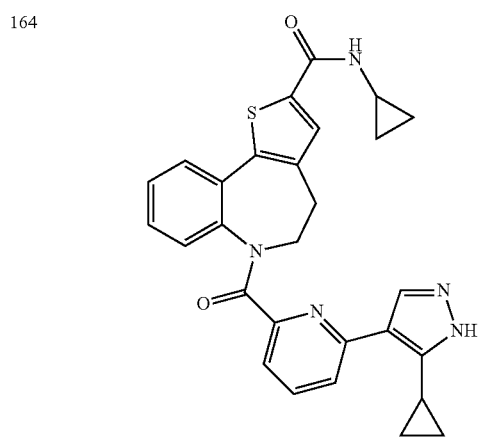 |
| 165 | 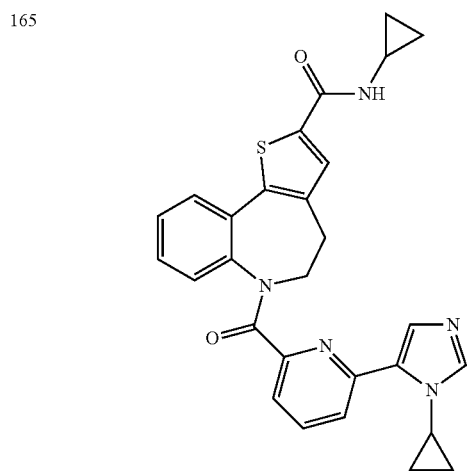 |
| 166 | 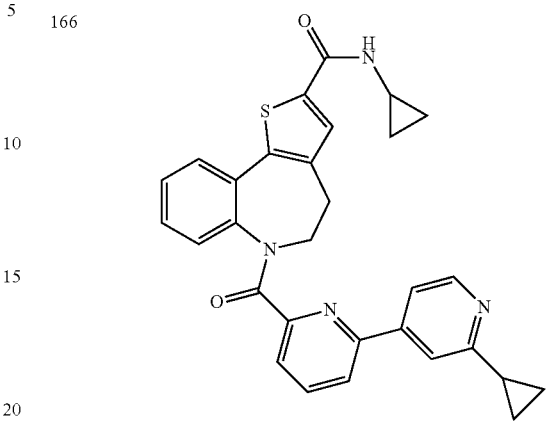 |
| 167 | 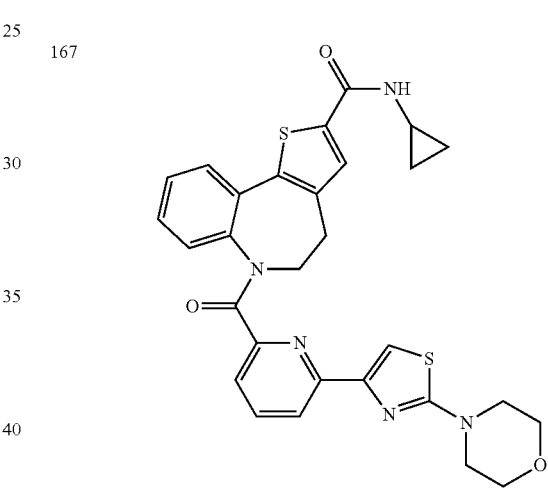 |
| 168 | 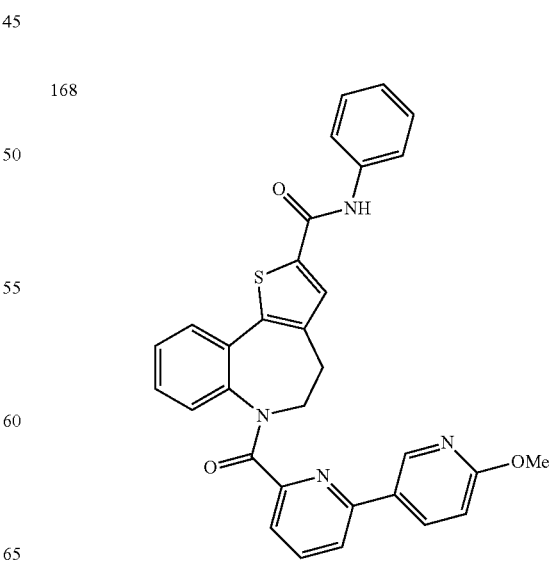 |

TABLE 1-continued

| Entry | Compound |
|---|---|
| 169 | |
| 170 | |
| 171 | |
| 172 | |
| 173 | |
| 174 | |

TABLE 1-continued

| Entry | Compound |
|---|---|
| 175 | |
| 176 | |
| 177 | |
| 178 | |
| 179 | |
| 180 | |

TABLE 1-continued

| Entry | Compound |
|---|---|
| 181 | |
| 182 | |
| 183 | |
| 184 | |
| 185 | |
| 186 | |

TABLE 1-continued
| Entry | Compound |
|---|---|
| 187 | 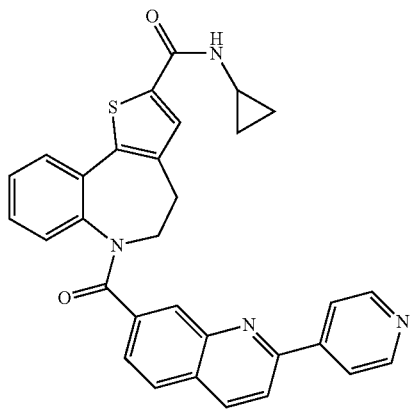 [SMILES: O=C(NC1CC1)c1cc2c(s1)-c1ccccc1N(C(=O)c1ccc3ccc(-c4ccncc4)nc3c1)CC2] |
| 188 | 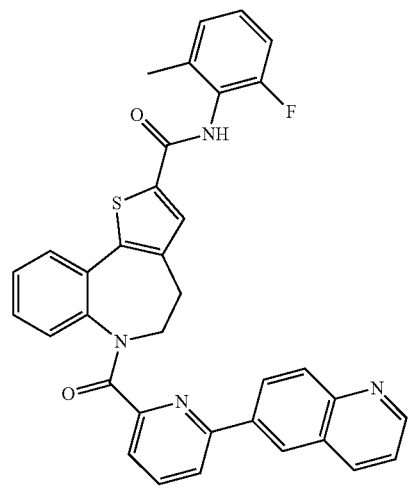 [SMILES: Cc1cccc(F)c1NC(=O)c1cc2c(s1)-c1ccccc1N(C(=O)c1cccc(-c3ccc4ncccc4c3)n1)CC2] |
| 189 | 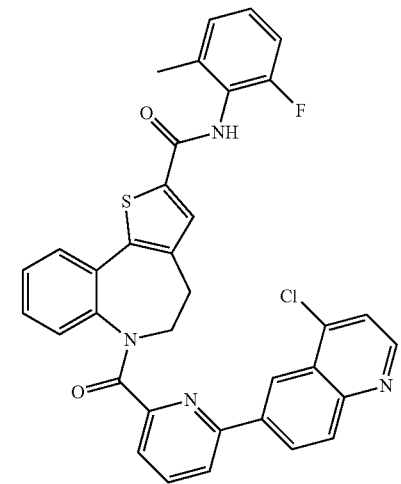 [SMILES: Cc1cccc(F)c1NC(=O)c1cc2c(s1)-c1ccccc1N(C(=O)c1cccc(-c3ccc4nccc(Cl)c4c3)n1)CC2] |
| 190 | 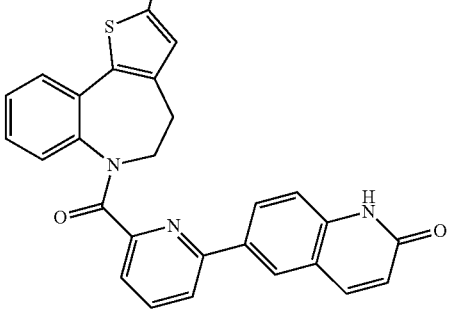 |
| 191 | 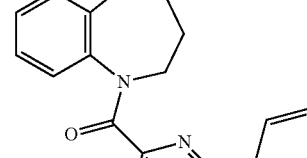 |
| 192 | 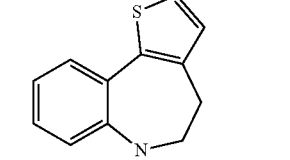 |

US 10,759,816 B2
TABLE 1-continued
| Entry | Compound |
|---|---|
| 193 | 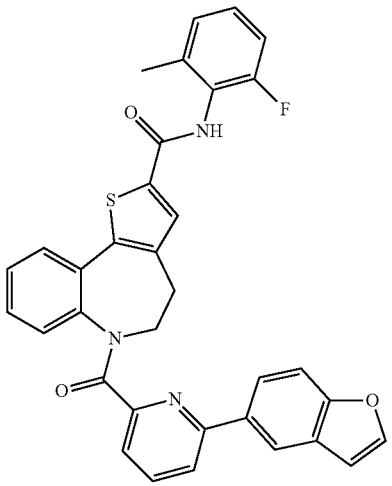 [SMILES: Cc1cccc(F)c1NC(=O)c1cc2c(s1)-c1ccccc1N(C(=O)c1cccc(-c3ccc4occc4c3)n1)CC2] |
| 194 | 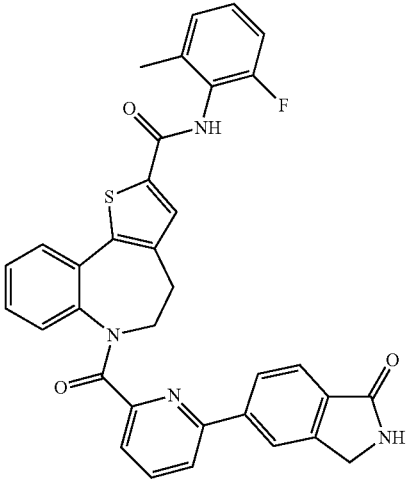 [SMILES: Cc1cccc(F)c1NC(=O)c1cc2c(s1)-c1ccccc1N(C(=O)c1cccc(-c3ccc4c(c3)CNC4=O)n1)CC2] |
| 195 | 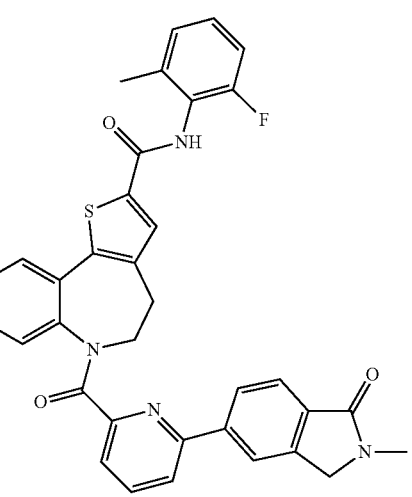 |
| 196 | 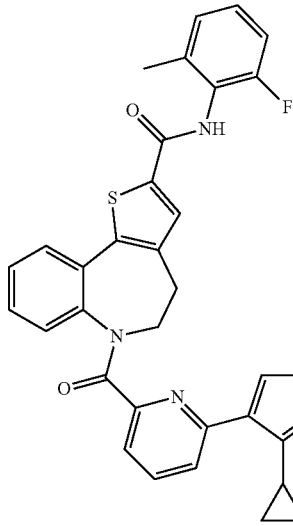 |
| 197 | 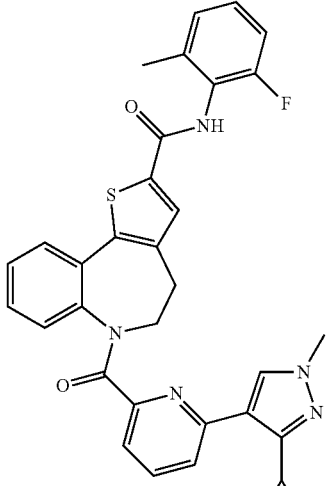 |
| 198 | 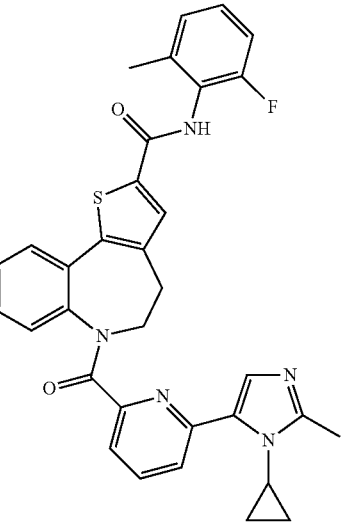 |

TABLE 1-continued
| Entry | Compound |
|---|---|
| 199 | 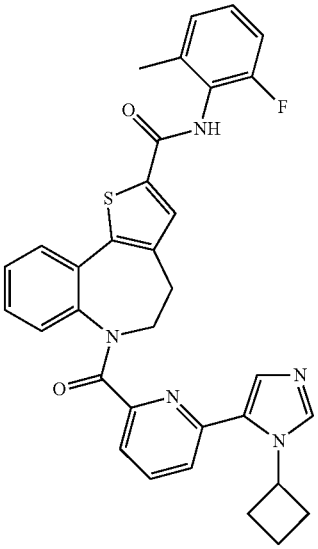 [SMILES: Cc1cccc(F)c1NC(=O)c1cc2c(s1)-c1ccccc1N(C(=O)c1cccc(-c3cncn3C3CCC3)n1)CC2] |
| 200 | 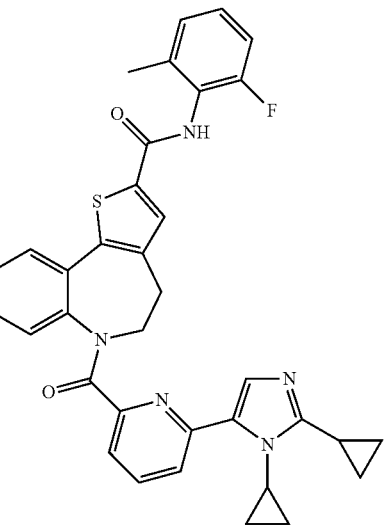 |
| 201 | 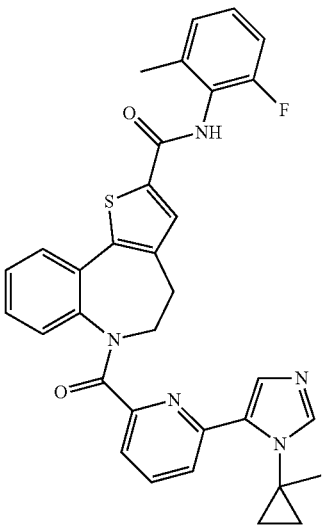 [SMILES: Cc1cccc(F)c1NC(=O)c1cc2c(s1)-c1ccccc1N(C(=O)c1cccc(-c3cncn3C3(C)CC3)n1)CC2] |
| 202 |  |
| 203 | 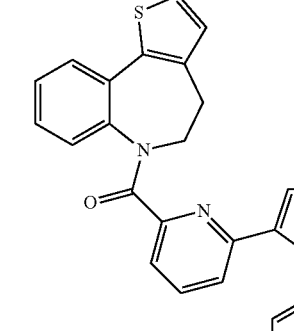 |

TABLE 1-continued

| Entry | Compound |
|---|---|
| 204 | |
| 205 | |
| 206 | |
| 207 | |
| 208 | |

TABLE 1-continued
| Entry | Compound |
|---|---|
| 209 | 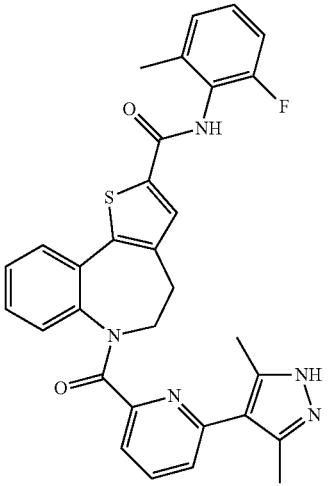 [SMILES: Cc1cccc(F)c1NC(=O)c1cc2c(s1)-c1ccccc1N(C(=O)c1cccc(-c3c(C)n[nH]c3C)n1)CC2] |
| 210 | 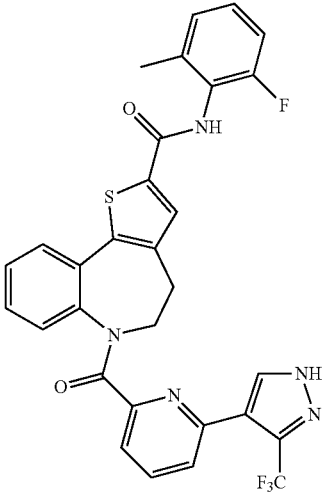 [SMILES: Cc1cccc(F)c1NC(=O)c1cc2c(s1)-c1ccccc1N(C(=O)c1cccc(-c3c[nH]nc3C(F)(F)F)n1)CC2] |
| 211 | 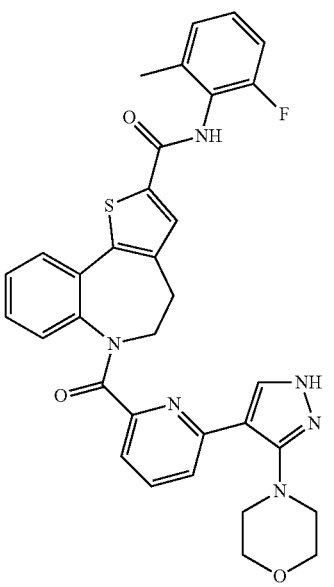 [SMILES: Cc1cccc(F)c1NC(=O)c1cc2c(s1)-c1ccccc1N(C(=O)c1cccc(-c3c[nH]nc3N3CCOCC3)n1)CC2] |
| 212 | 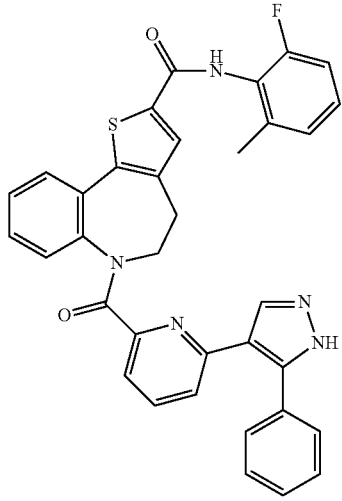 [SMILES: Cc1cccc(F)c1NC(=O)c1cc2c(s1)-c1ccccc1N(C(=O)c1cccc(-c3cn[nH]c3-c3ccccc3)n1)CC2] |
| 213 | 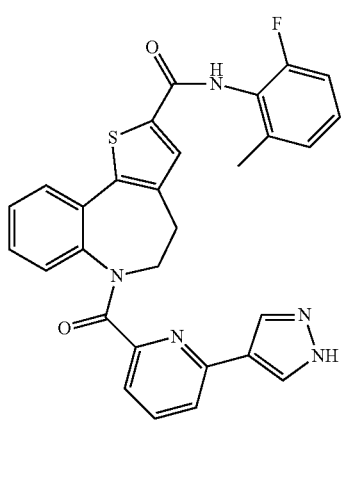 [SMILES: Cc1cccc(F)c1NC(=O)c1cc2c(s1)-c1ccccc1N(C(=O)c1cccc(-c3cn[nH]c3)n1)CC2] |
| 214 | 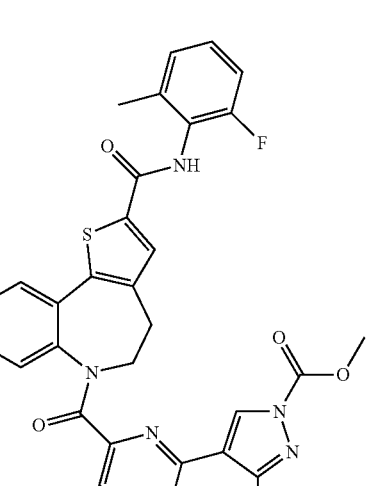 |

TABLE 1-continued

| Entry | Compound |
|---|---|
| 215 | |
| 216 | |
| 217 | |
| 218 | |
| 219 | |
| 220 | |

TABLE 1-continued
| Entry | Compound |
|---|---|
| 221 | 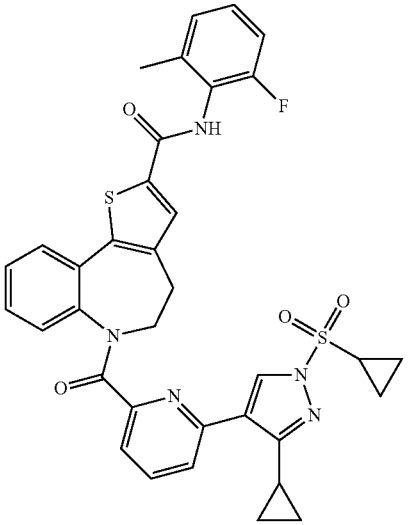 [SMILES: Cc1cccc(F)c1NC(=O)c1cc2c(s1)-c1ccccc1N(C(=O)c1cccc(-c3cn(S(=O)(=O)C4CC4)nc3C3CC3)n1)CC2] |
| 222 | 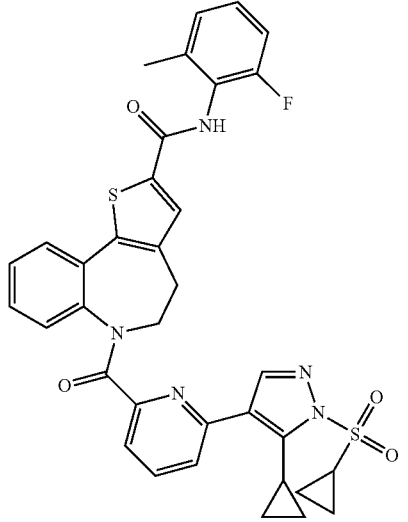 [SMILES: Cc1cccc(F)c1NC(=O)c1cc2c(s1)-c1ccccc1N(C(=O)c1cccc(-c3cnn(S(=O)(=O)C4CC4)c3C3CC3)n1)CC2] |
| 223 | 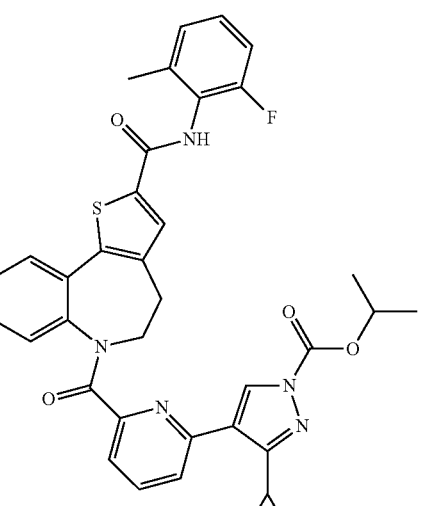 |
| 224 | 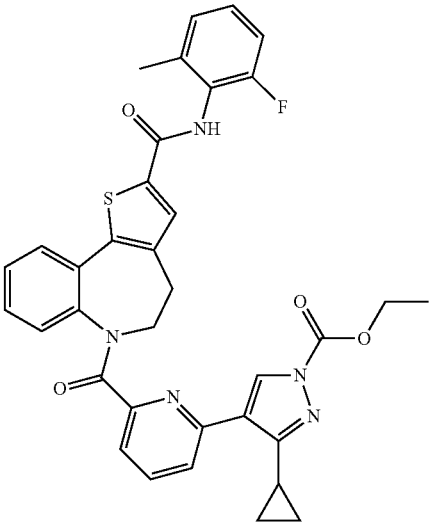 [SMILES: CCOC(=O)n1cc(-c2cccc(C(=O)N3CCc4cc(C(=O)Nc5c(C)cccc5F)sc4-c4ccccc43)n2)c(C2CC2)n1] |
| 225 | 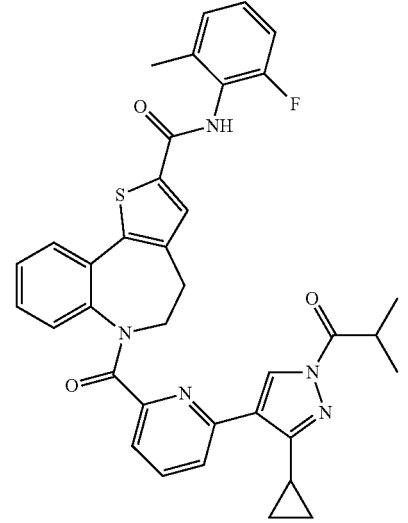 [SMILES: Cc1cccc(F)c1NC(=O)c1cc2c(s1)-c1ccccc1N(C(=O)c1cccc(-c3cn(C(=O)C(C)C)nc3C3CC3)n1)CC2] |
| 226 | 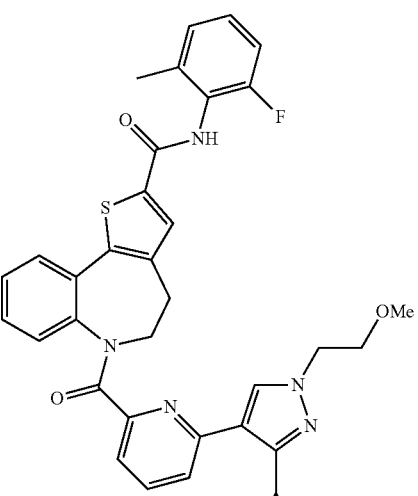 |

TABLE 1-continued

| Entry | Compound |
|---|---|
| 227 | |
| 228 | |
| 229 | |
| 230 | |
| 231 | |
| 232 | |

TABLE 1-continued

| Entry | Compound |
|---|---|
| 233 | |
| 234 | |
| 235 | |
| 236 | |
| 237 | |
| 238 | |

TABLE 1-continued

| Entry | Compound |
|---|---|
| 239 | |
| 240 | |
| 241 | |
| 242 | |
| 243 | |
| 244 | |

TABLE 1-continued

| Entry | Compound |
|---|---|
| 245 | |
| 246 | |
| 247 | |
| 248 | |
| 249 | |
| 250 | |

TABLE 1-continued
| Entry | Compound |
|---|---|
| 251 | 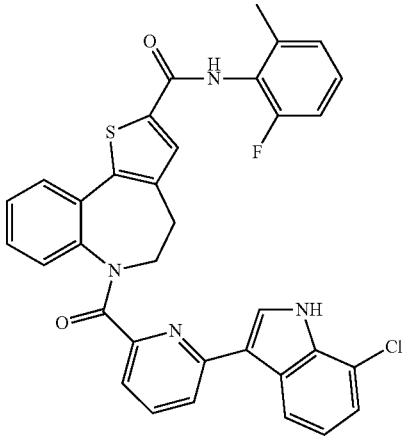 [SMILES: Cc1cccc(F)c1NC(=O)c1cc2c(s1)-c1ccccc1N(C(=O)c1cccc(-c3c[nH]c4c(Cl)cccc34)n1)CC2] |
| 252 | 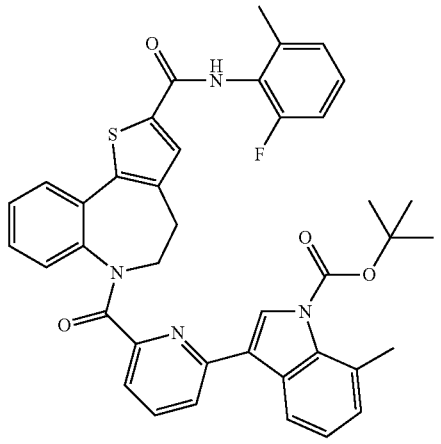 [SMILES: Cc1cccc(F)c1NC(=O)c1cc2c(s1)-c1ccccc1N(C(=O)c1cccc(-c3cn(C(=O)OC(C)(C)C)c4c(C)cccc34)n1)CC2] |
| 253 | 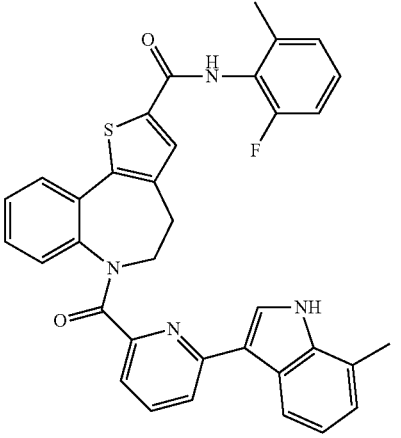 [SMILES: Cc1cccc(F)c1NC(=O)c1cc2c(s1)-c1ccccc1N(C(=O)c1cccc(-c3c[nH]c4c(C)cccc34)n1)CC2] |
| 254 | 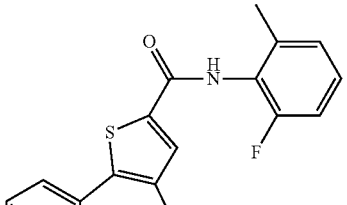 |
| 255 | 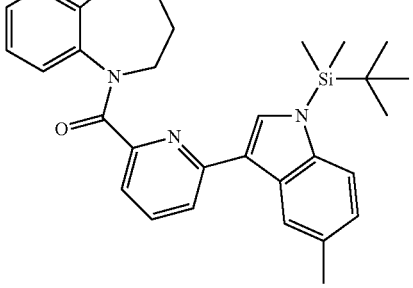 |
| 256 |  |

TABLE 1-continued

| Entry | Compound |
|---|---|
| 257 | (structure) |
| 258 | (structure) |
| 259 | (structure) |
| 260 | (structure) |
| 261 | (structure) |
| 262 | (structure) |

TABLE 1-continued
| Entry | Compound |
|---|---|
| 263 | 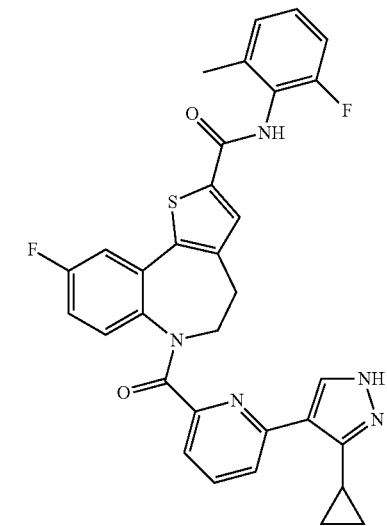 [SMILES: Cc1cccc(F)c1NC(=O)c1cc2c(s1)-c1cc(F)ccc1N(C(=O)c1cccc(-c3c[nH]nc3C3CC3)n1)CC2] |
| 264 | 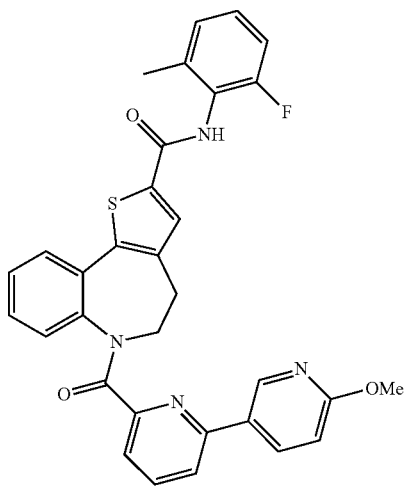 [SMILES: COc1ccc(-c2cccc(C(=O)N3CCc4cc(C(=O)Nc5c(C)cccc5F)sc4-c4ccccc43)n2)cn1] |
| 265 | 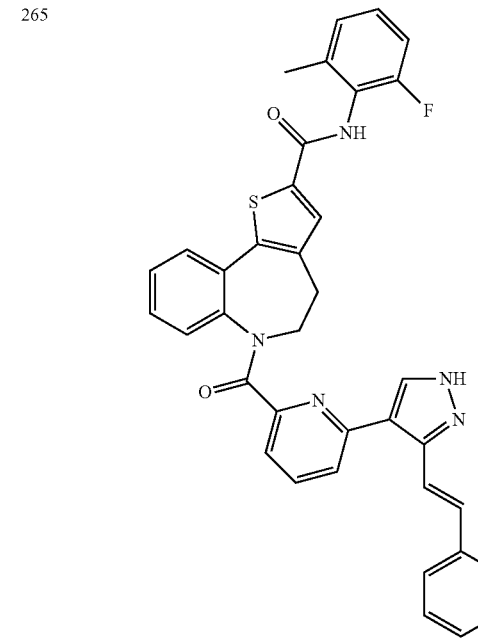 |
| 266 | 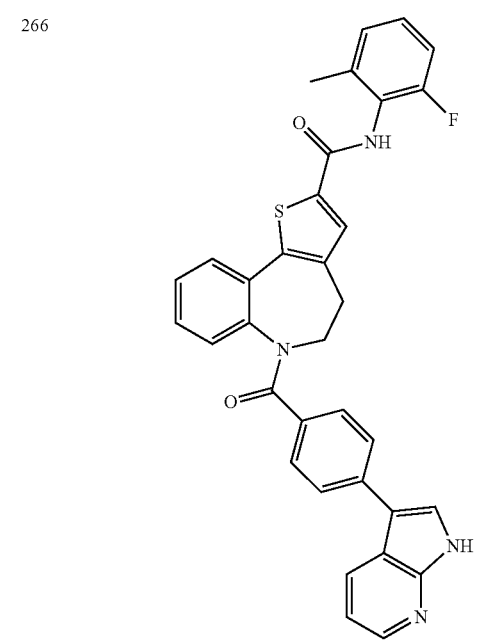 |

TABLE 1-continued
| Entry | Compound |
|---|---|
| 267 | 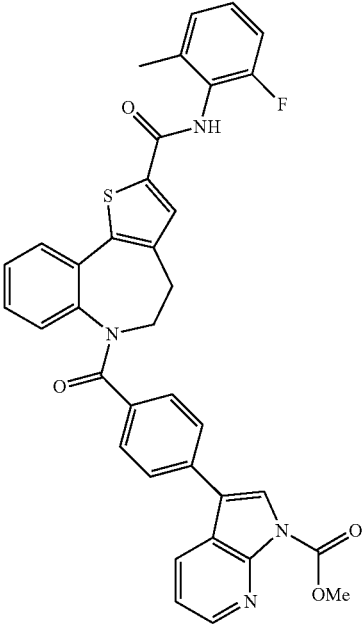 [SMILES: COC(=O)n1cc(-c2ccc(C(=O)N3CCc4cc(C(=O)Nc5c(C)cccc5F)sc4-c4ccccc43)cc2)c2cccnc21] |
| 268 | 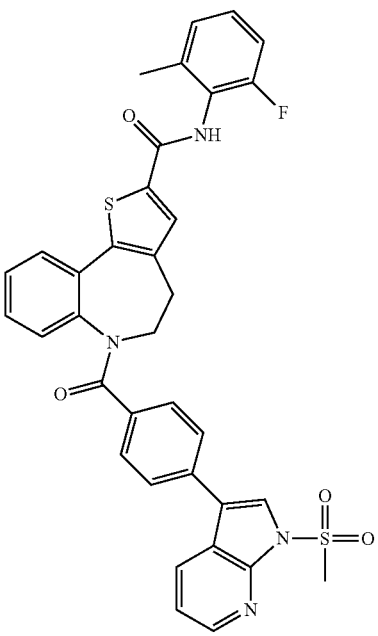 [SMILES: Cc1cccc(F)c1NC(=O)c1cc2c(s1)-c1ccccc1N(C(=O)c1ccc(-c3cn(S(C)(=O)=O)c4ncccc34)cc1)CC2] |
| 269 | 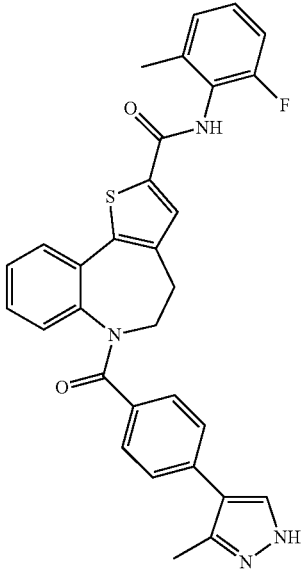 [SMILES: Cc1cccc(F)c1NC(=O)c1cc2c(s1)-c1ccccc1N(C(=O)c1ccc(-c3c[nH]nc3C)cc1)CC2] |
| 270 | 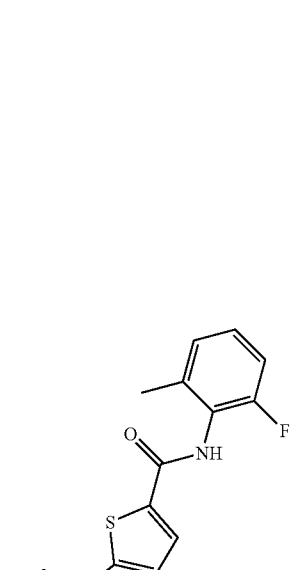 |

TABLE 1-continued

| Entry | Compound |
|---|---|
| 271 | |
| 272 | |
| 273 | |
| 274 | |
| 275 | |

TABLE 1-continued
| Entry | Compound |
|---|---|
| 276 | 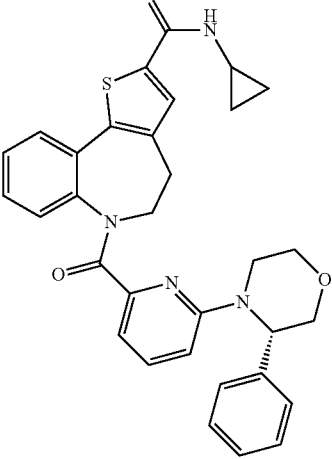 |
| 277 | 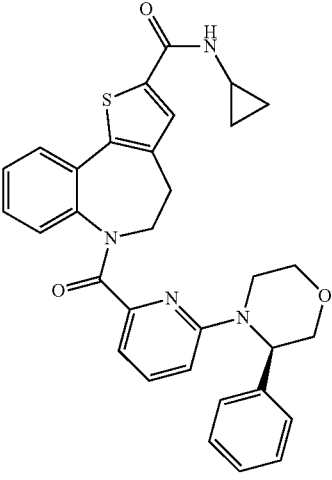 [SMILES: O=C(NC1CC1)c1cc2c(s1)-c1ccccc1N(C(=O)c1cccc(N3CCOC[C@H]3c3ccccc3)n1)CC2] |
| 278 | 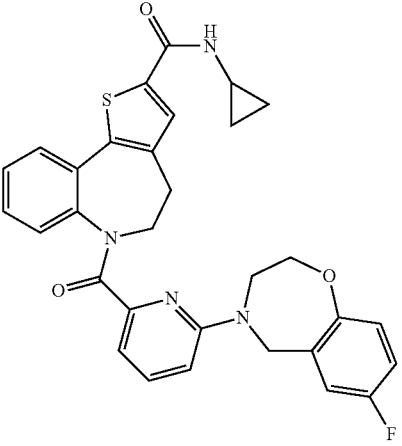 [SMILES: O=C(NC1CC1)c1cc2c(s1)-c1ccccc1N(C(=O)c1cccc(N3CCOc4ccc(F)cc4C3)n1)CC2] |
| 279 | 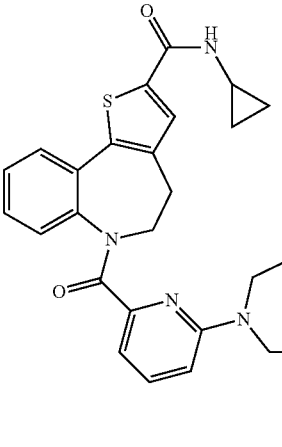 |
| 280 | 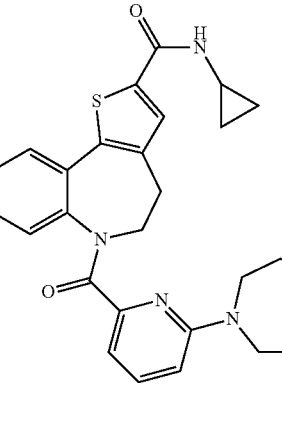 |
| 281 | 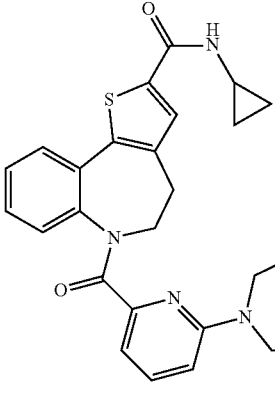 |

TABLE 1-continued
| Entry | Compound |
|---|---|
| 282 | 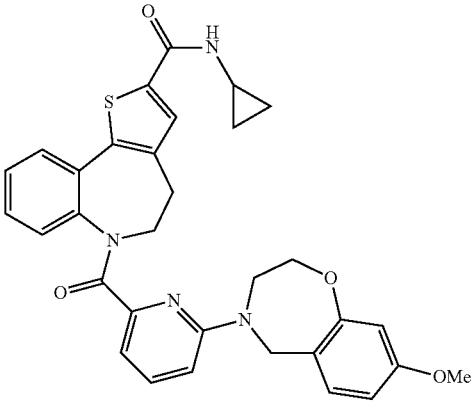 [SMILES: COc1ccc2c(c1)OCCN(c1cccc(C(=O)N3CCc4cc(C(=O)NC5CC5)sc4-c4ccccc43)n1)C2] |
| 283 | 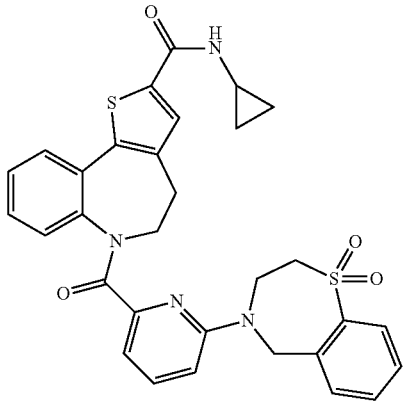 [SMILES: O=C(NC1CC1)c1cc2c(s1)-c1ccccc1N(C(=O)c1cccc(N3CCS(=O)(=O)c4ccccc4C3)n1)CC2] |
| 284 | 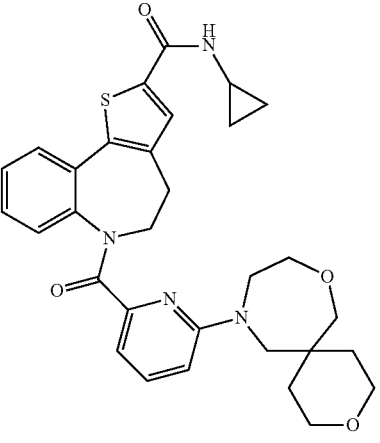 [SMILES: O=C(NC1CC1)c1cc2c(s1)-c1ccccc1N(C(=O)c1cccc(N3CCOCC4(CCOCC4)C3)n1)CC2] |
| 285 | 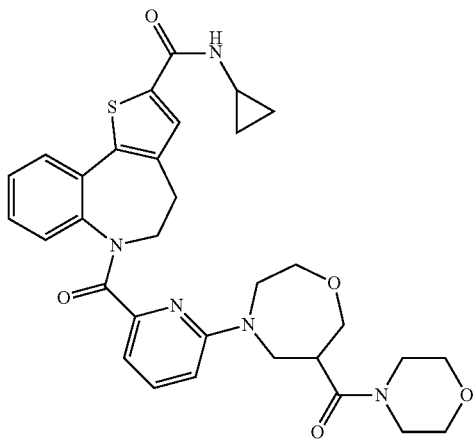 [SMILES: O=C(NC1CC1)c1cc2c(s1)-c1ccccc1N(C(=O)c1cccc(N3CCOCC(C(=O)N4CCOCC4)C3)n1)CC2] |
| 286 | 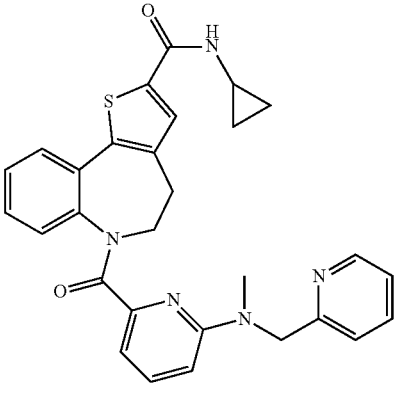 [SMILES: CN(Cc1ccccn1)c1cccc(C(=O)N2CCc3cc(C(=O)NC4CC4)sc3-c3ccccc32)n1] |
| 287 | 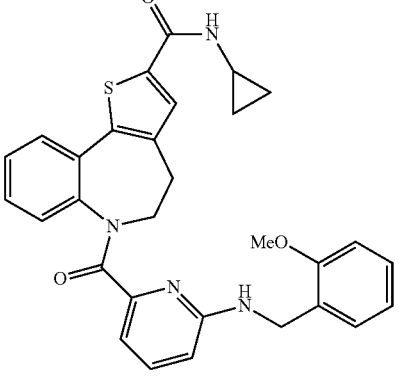 |
| 288 | 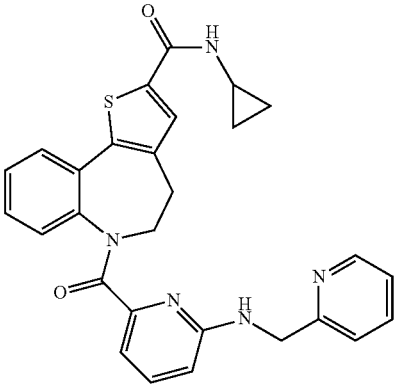 [SMILES: O=C(NC1CC1)c1cc2c(s1)-c1ccccc1N(C(=O)c1cccc(NCc3ccccn3)n1)CC2] |

TABLE 1-continued
| Entry | Compound |
|---|---|
| 289 | 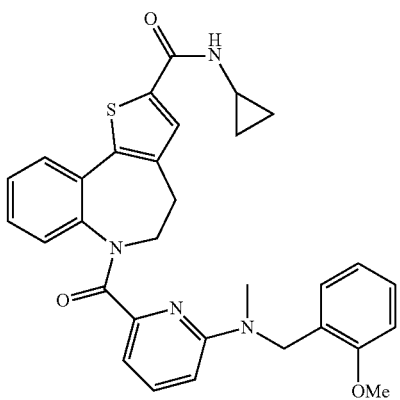 [SMILES: COc1ccccc1CN(C)c1cccc(C(=O)N2CCc3cc(C(=O)NC4CC4)sc3-c3ccccc32)n1] |
| 290 | 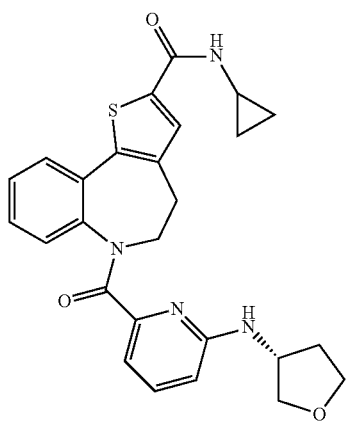 [SMILES: O=C(NC1CC1)c1cc2c(s1)-c1ccccc1N(C(=O)c1cccc(N[C@@H]3CCOC3)n1)CC2] |
| 291 | 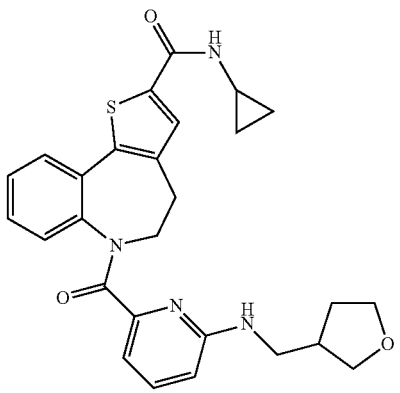 [SMILES: O=C(NC1CC1)c1cc2c(s1)-c1ccccc1N(C(=O)c1cccc(NCC3CCOC3)n1)CC2] |
TABLE 1-continued
| Entry | Compound |
|---|---|
| 292 | 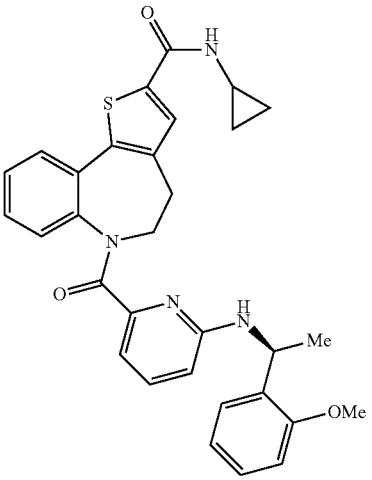 [SMILES: COc1ccccc1[C@H](C)Nc1cccc(C(=O)N2CCc3cc(C(=O)NC4CC4)sc3-c3ccccc32)n1] |
| 293 | 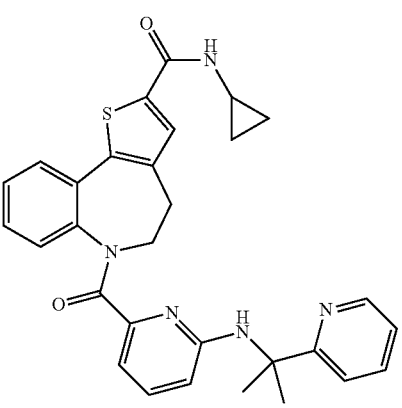 [SMILES: CC(C)(Nc1cccc(C(=O)N2CCc3cc(C(=O)NC4CC4)sc3-c3ccccc32)n1)c1ccccn1] |
| 294 | 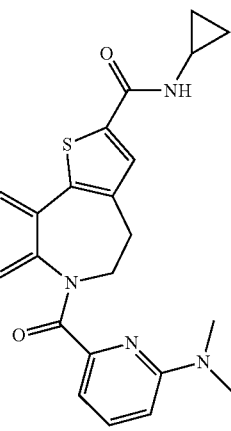 |

TABLE 1-continued
| Entry | Compound |
|---|---|
| 295 | |
| 296 | |
| 297 | |
| 298 | |
| 299 | |
| 300 | |
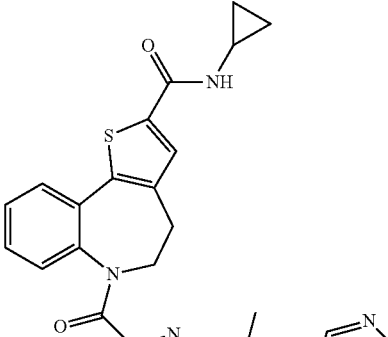

TABLE 1-continued

| Entry | Compound |
|---|---|
| 301 | |
| 302 | |
| 303 | |
| 304 | |
| 305 | |
| 306 | |

TABLE 1-continued
| Entry | Compound |
|---|---|
| 307 | 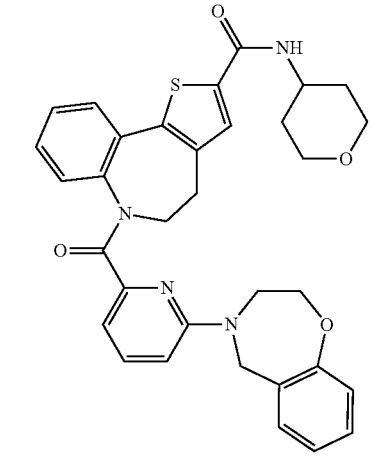 [SMILES: O=C(NC1CCOCC1)c1cc2c(s1)-c1ccccc1N(C(=O)c1cccc(N3CCOc4ccccc4C3)n1)CC2] |
| 308 | 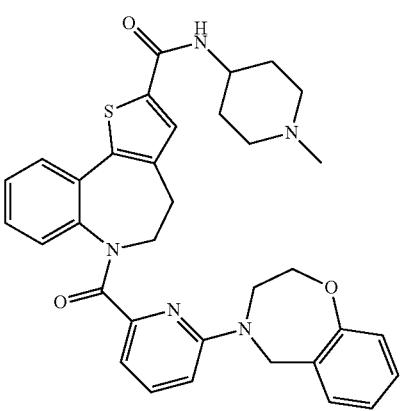 [SMILES: CN1CCC(NC(=O)c2cc3c(s2)-c2ccccc2N(C(=O)c2cccc(N4CCOc5ccccc5C4)n2)CC3)CC1] |
| 309 | 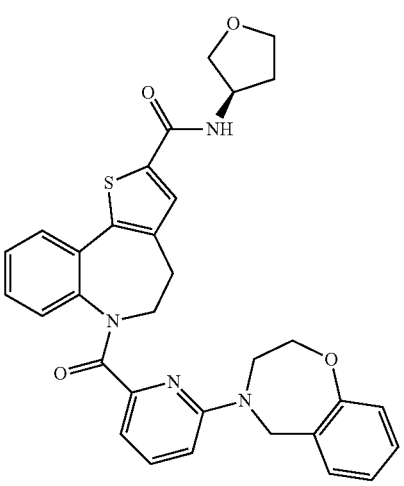 [SMILES: O=C(N[C@@H]1CCOC1)c1cc2c(s1)-c1ccccc1N(C(=O)c1cccc(N3CCOc4ccccc4C3)n1)CC2] |
TABLE 1-continued
| Entry | Compound |
|---|---|
| 310 | |
| 311 | |
| 312 | |

TABLE 1-continued

| Entry | Compound |
|---|---|
| 313 | (structure) |
| 314 | (structure) |
| 315 | (structure) |
| 316 | (structure) |
| 317 | (structure) |
| 318 | (structure) |

TABLE 1-continued
| Entry | Compound |
|---|---|
| 319 | 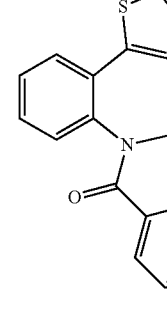 |
| 320 | |
| 321 | |
| 322 |  |
| 323 | |
| 324 |  |

TABLE 1-continued

| Entry | Compound |
|---|---|
| 325 | |
| 326 | |
| 327 | |
| 328 | |
| 329 | |
| 330 | |

TABLE 1-continued

| Entry | Compound |
|---|---|
| 331 | |
| 332 | |
| 333 | |
| 334 | |
| 335 | |
| 336 | |

TABLE 1-continued

| Entry | Compound |
|---|---|
| 337 | (structure) |
| 338 | (structure) |
| 339 | (structure) |
| 340 | (structure) |
| 341 | (structure) |
| 342 | (structure) |

TABLE 1-continued

| Entry | Compound |
|---|---|
| 343 | (structure) |
| 344 | (structure) |
| 345 | (structure) |
| 346 | (structure) |
| 347 | (structure) |
| 348 | (structure) |

TABLE 1-continued
| Entry | Compound |
|---|---|
| 349 | |
| 350 | |
| 351 | |
| 352 | |
| 353 | |
| 354 | |
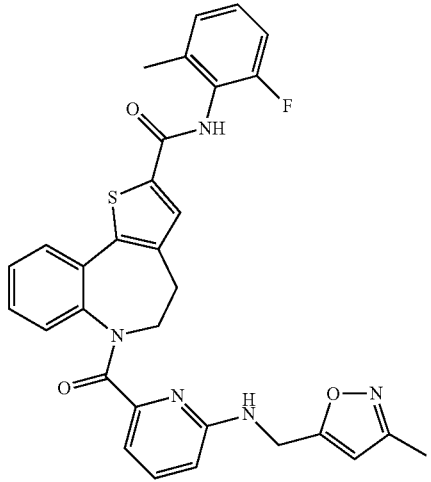 [SMILES: Cc1cc(CNc2cccc(C(=O)N3CCc4cc(C(=O)Nc5c(C)cccc5F)sc4-c4ccccc43)n2)on1]
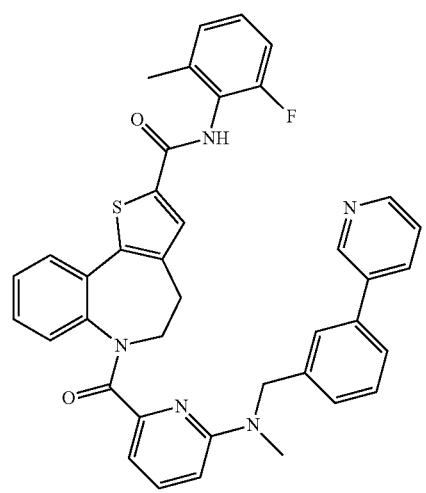 [SMILES: Cc1cccc(F)c1NC(=O)c1cc2c(s1)-c1ccccc1N(C(=O)c1cccc(N(C)Cc3cccc(-c4cccnc4)c3)n1)CC2]

US 10,759,816 B2
TABLE 1-continued
| Entry | Compound |
|---|---|
| 355 | 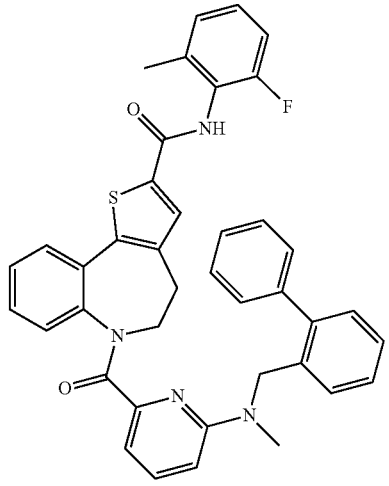 [SMILES: Cc1cccc(F)c1NC(=O)c1cc2c(s1)-c1ccccc1N(C(=O)c1cccc(N(C)Cc3ccccc3-c3ccccc3)n1)CC2] |
| 356 | 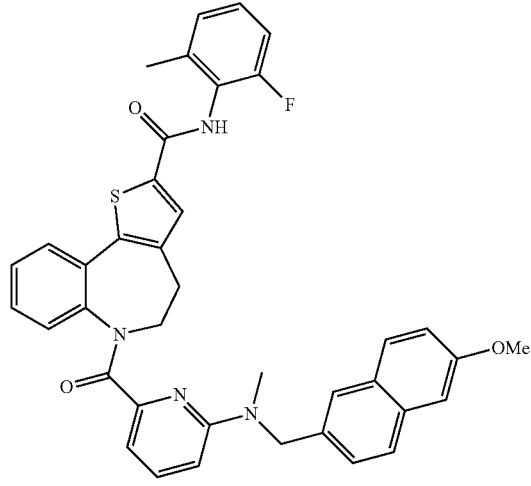 [SMILES: COc1ccc2cc(CN(C)c3cccc(C(=O)N4CCc5cc(C(=O)Nc6c(C)cccc6F)sc5-c5ccccc54)n3)ccc2c1] |
| 357 | 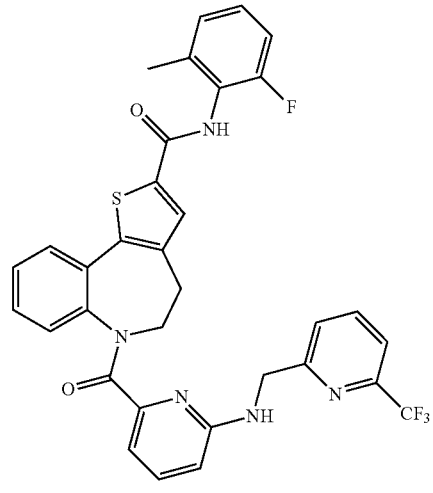 [SMILES: Cc1cccc(F)c1NC(=O)c1cc2c(s1)-c1ccccc1N(C(=O)c1cccc(NCc3cccc(C(F)(F)F)n3)n1)CC2] |
TABLE 1-continued
| Entry | Compound |
|---|---|
| 358 | 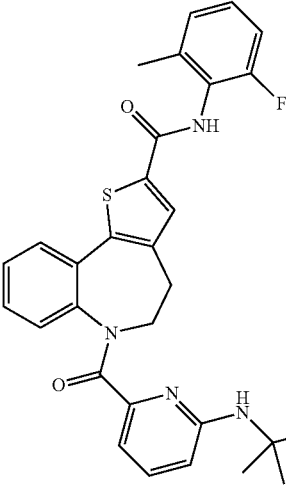 |
| 359 | 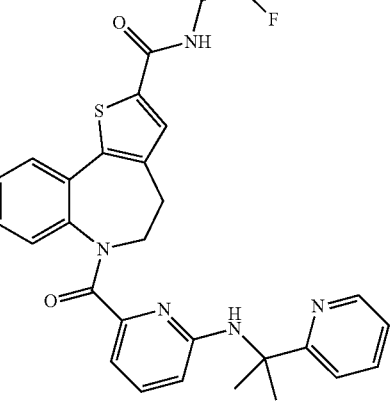 |
| 360 | 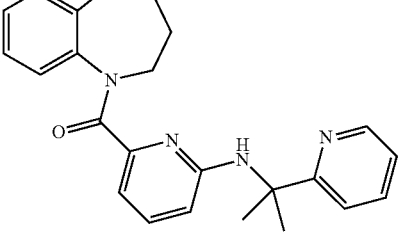 |

TABLE 1-continued

| Entry | Compound |
|---|---|
| 361 | |
| 362 | |
| 363 | |
| 364 | |
| 365 | |
| 366 | |

TABLE 1-continued
| Entry | Compound |
|---|---|
| 367 | 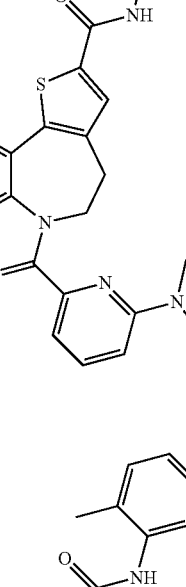 |
| 368 | |
| 369 | |
| 370 | 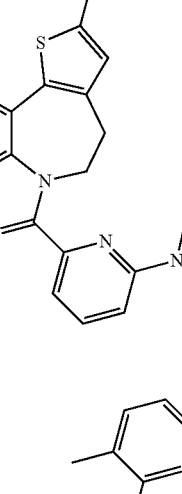 |
| 371 | |
| 372 | |

TABLE 1-continued

| Entry | Compound |
|---|---|
| 373 | (structure) |
| 374 | (structure) |
| 375 | (structure) |
| 376 | (structure) |
| 377 | (structure) |
| 378 | (structure) |

TABLE 1-continued

| Entry | Compound |
|---|---|
| 379 | |
| 380 | |
| 381 | |
| 382 | |
| 383 | |
| 384 | |

TABLE 1-continued
| Entry | Compound |
|---|---|
| 385 | 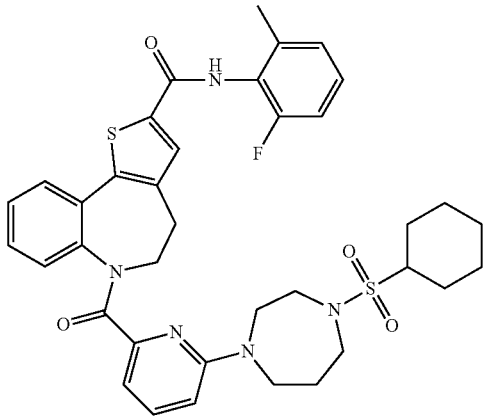 [SMILES: Cc1cccc(F)c1NC(=O)c1cc2c(s1)-c1ccccc1N(C(=O)c1cccc(N3CCCN(S(=O)(=O)C4CCCCC4)CC3)n1)CC2] |
| 386 | 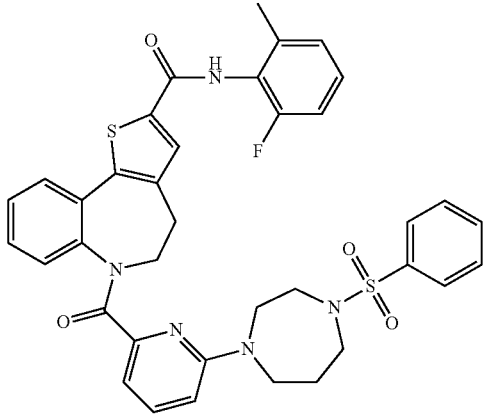 [SMILES: Cc1cccc(F)c1NC(=O)c1cc2c(s1)-c1ccccc1N(C(=O)c1cccc(N3CCCN(S(=O)(=O)c4ccccc4)CC3)n1)CC2] |
| 387 | 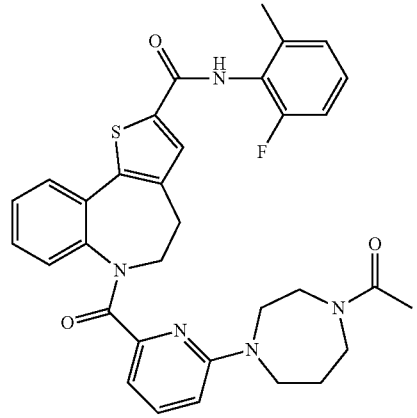 [SMILES: CC(=O)N1CCCN(c2cccc(C(=O)N3CCc4cc(C(=O)Nc5c(C)cccc5F)sc4-c4ccccc43)n2)CC1] |ора
TABLE 1-continued
| Entry | Compound |
|---|---|
| 388 | 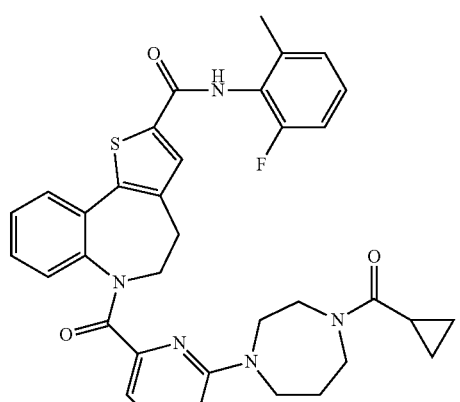 |
| 389 | 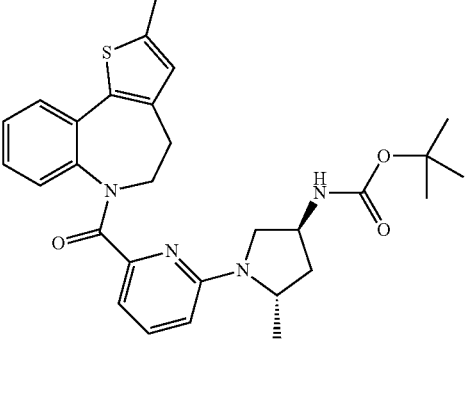 |
| 390 | 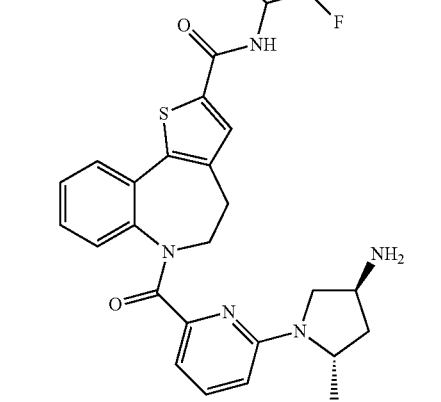 |

TABLE 1-continued

| Entry | Compound |
|---|---|
| 391 | |
| 392 | |
| 393 | |
| 394 | |
| 395 | |
| 396 | |

TABLE 1-continued
| Entry | Compound |
|---|---|
| 397 | 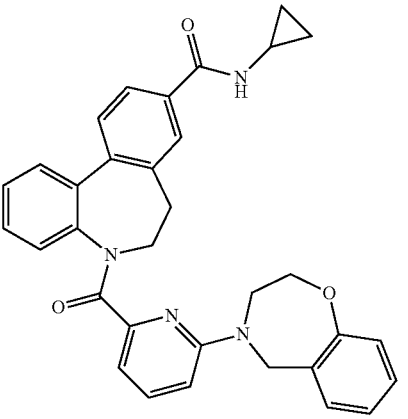 [SMILES: O=C(NC1CC1)c1ccc2c(c1)CCN(C(=O)c1cccc(N3CCOc4ccccc4C3)n1)c1ccccc1-2] |
| 398 | 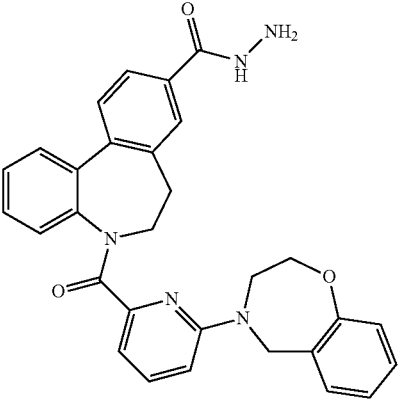 [SMILES: NNC(=O)c1ccc2c(c1)CCN(C(=O)c1cccc(N3CCOc4ccccc4C3)n1)c1ccccc1-2] |
| 399 | 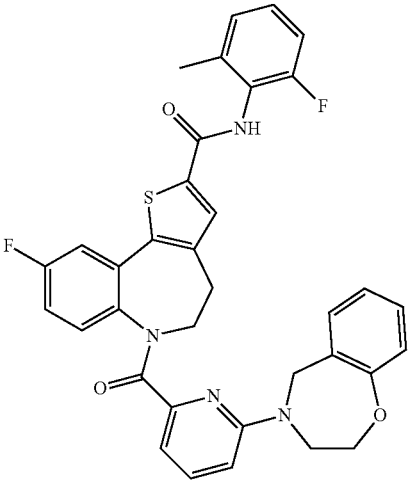 [SMILES: Cc1cccc(F)c1NC(=O)c1cc2c(s1)-c1cc(F)ccc1N(C(=O)c1cccc(N3CCOc4ccccc4C3)n1)CC2] |
| 400 | 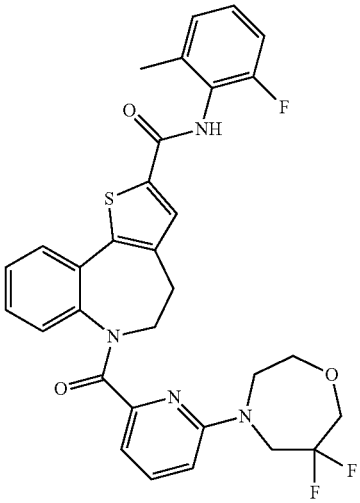 [SMILES: Cc1cccc(F)c1NC(=O)c1cc2c(s1)-c1ccccc1N(C(=O)c1cccc(N3CCOCC(F)(F)C3)n1)CC2] |
| 401 | 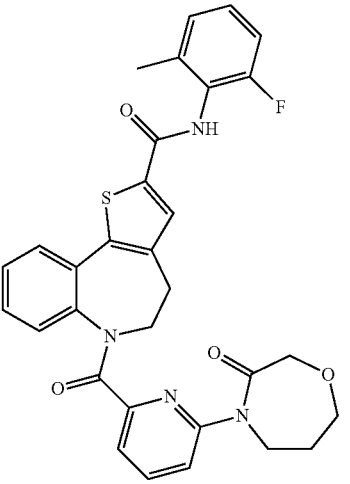 [SMILES: Cc1cccc(F)c1NC(=O)c1cc2c(s1)-c1ccccc1N(C(=O)c1cccc(N3CCCOCC3=O)n1)CC2] |
| 402 | 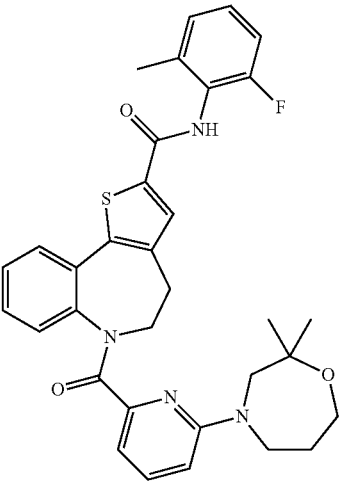 [SMILES: Cc1cccc(F)c1NC(=O)c1cc2c(s1)-c1ccccc1N(C(=O)c1cccc(N3CCCOC(C)(C)C3)n1)CC2] |

TABLE 1-continued

| Entry | Compound |
|---|---|
| 403 | (structure) |
| 404 | (structure) |
| 405 | (structure) |
| 406 | (structure) |
| 407 | (structure) |
| 408 | (structure) |

TABLE 1-continued
| Entry | Compound |
|---|---|
| 409 | 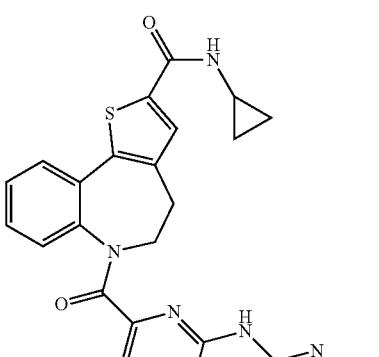 |
| 410 | |
| 411 | |
| 412 | |
| 413 | |
| 414 | |

TABLE 1-continued
| Entry | Compound |
|---|---|
| 415 | 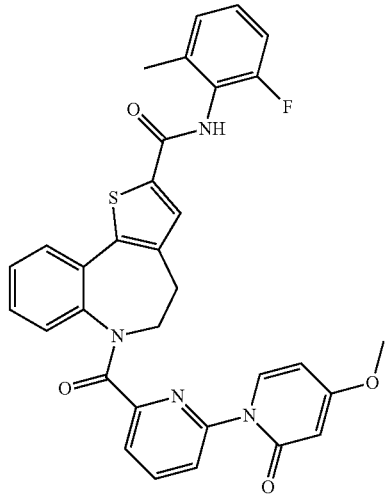 [SMILES: COc1ccn(-c2cccc(C(=O)N3CCc4cc(C(=O)Nc5c(C)cccc5F)sc4-c4ccccc43)n2)c(=O)c1] |
| 416 | 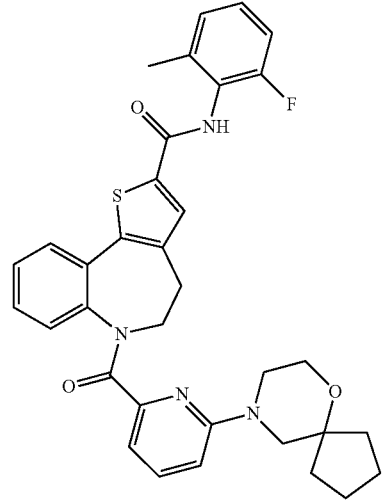 [SMILES: Cc1cccc(F)c1NC(=O)c1cc2c(s1)-c1ccccc1N(C(=O)c1cccc(N3CCOC4(CCCC4)C3)n1)CC2] |
| 417 | 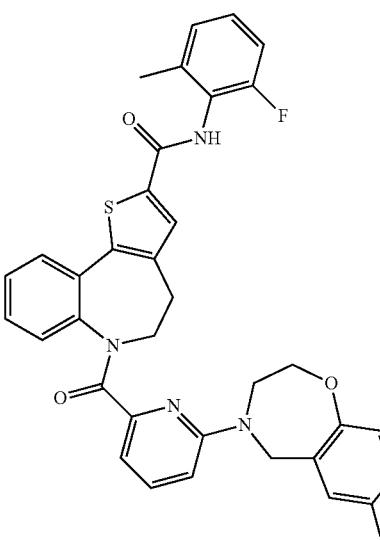 |
| 418 | 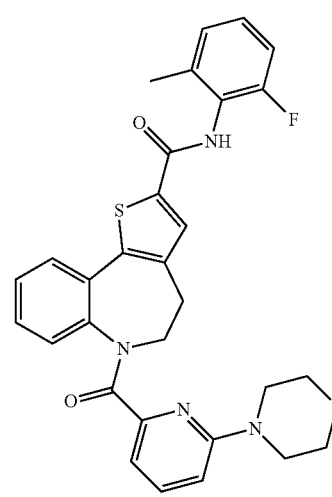 |
| 419 | 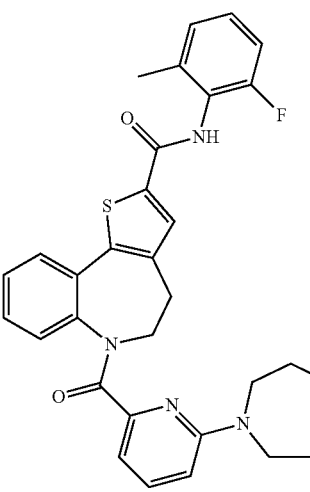 |
| 420 | 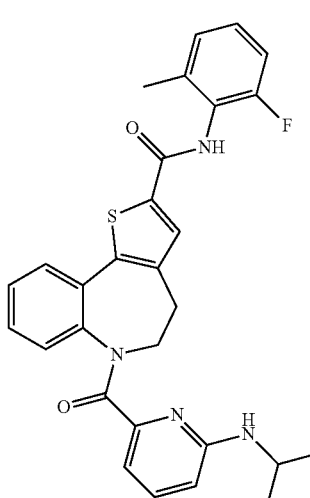 |

TABLE 1-continued

| Entry | Compound |
|---|---|
| 421 | (structure) |
| 422 | (structure) |
| 423 | (structure) |
| 424 | (structure) |
| 425 | (structure) |

TABLE 1-continued

| Entry | Compound |
|---|---|
| 426 | |
| 427 | |
| 428 | |
| 429 | |
| 430 | |
| 431 | |

TABLE 1-continued
| Entry | Compound |
|---|---|
| 432 | 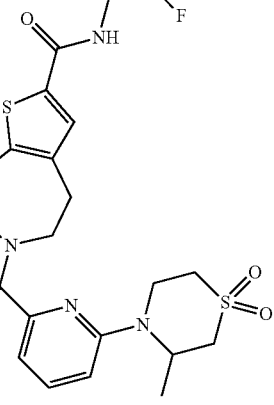 |
| 433 | |
| 434 | |️
| 435 | 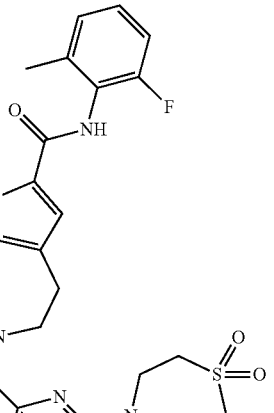 |
| 436 | |
| 437 | |

TABLE 1-continued

| Entry | Compound |
|---|---|
| 438 | |
| 439 | |
| 440 | |
| 441 | |
| 442 | |
| 443 | |

TABLE 1-continued

| Entry | Compound |
|---|---|
| 444 | (structure) |
| 445 | (structure) |
| 446 | (structure) |
| 447 | (structure) |
| 448 | (structure) |
| 449 | (structure) |

TABLE 1-continued

| Entry | Compound |
|---|---|
| 450 | |
| 451 | |
| 452 | |
| 453 | |
| 454 | |
| 455 | |

TABLE 1-continued

| Entry | Compound |
|---|---|
| 456 | |
| 457 | |
| 458 | |
| 459 | |
| 460 | |
| 461 | |

TABLE 1-continued

| Entry | Compound |
|---|---|
| 462 | |
| 463 | |
| 464 | |
| 465 | |
| 466 | |
| 467 | |

TABLE 1-continued

| Entry | Compound |
|---|---|
| 468 | (structure) |
| 469 | (structure) |
| 470 | (structure) |
| 471 | (structure) |
| 472 | (structure) |
| 473 | (structure) |

TABLE 1-continued

| Entry | Compound |
|---|---|
| 474 | |
| 475 | |
| 476 | |
| 477 | |
| 478 | |
| 479 | |

TABLE 1-continued

| Entry | Compound |
|---|---|
| 480 | |
| 481 | |
| 482 | |
| 483 | |
| 484 | |

TABLE 1-continued

| Entry | Compound |
|---|---|
| 485 | (structure) |
| 486 | (structure) |
| 487 | (structure) |
| 488 | (structure) |
| 489 | (structure) |

TABLE 1-continued
| Entry | Compound |
|---|---|
| 490 | 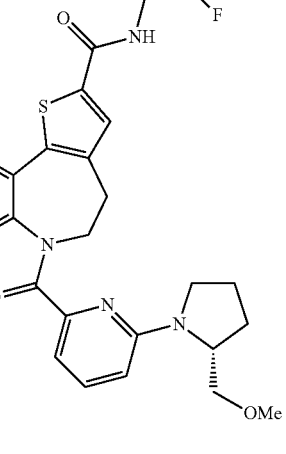 |
| 491 | 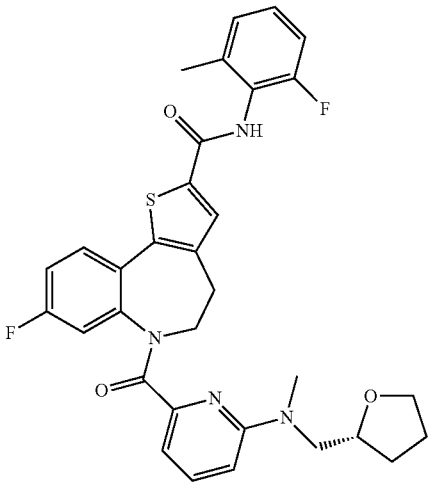 [SMILES: Cc1cccc(F)c1NC(=O)c1cc2c(s1)-c1ccc(F)cc1N(C(=O)c1cccc(N(C)C[C@H]3CCCO3)n1)CC2] |
| 492 | 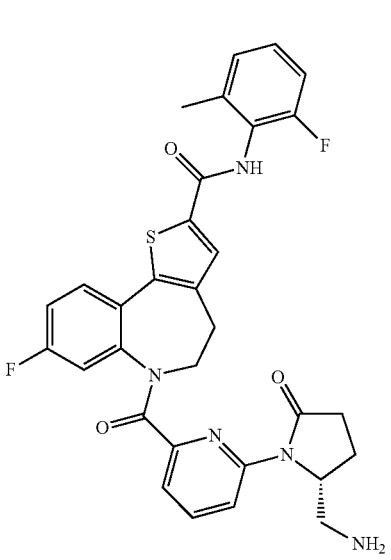 [SMILES: Cc1cccc(F)c1NC(=O)c1cc2c(s1)-c1ccc(F)cc1N(C(=O)c1cccc(N3C(=O)CC[C@@H]3CN)n1)CC2] |
| 493 | 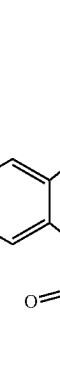 |
| 494 | 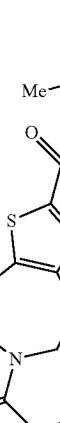 |
| 495 | 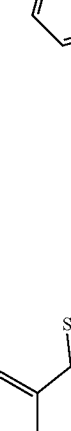 |

TABLE 1-continued

| Entry | Compound |
|---|---|
| 496 | (structure) |
| 497 | (structure) |
| 498 | (structure) |
| 499 | (structure) |
| 500 | (structure) |

TABLE 1-continued

| Entry | Compound |
|---|---|
| 501 | |
| 502 | |
| 503 | |
| 504 | |
| 505 | |
| 506 | |

TABLE 1-continued

| Entry | Compound |
|---|---|
| 507 | (structure) |
| 508 | (structure) |
| 509 | (structure) |
| 510 | (structure) |
| 511 | (structure) |
| 512 | (structure) |

| Entry | Compound |
|---|---|
| 513 | |
| 514 | |
| 515 | |
| 516 | |
| 517 | |
| 518 | |

TABLE 1-continued

| Entry | Compound |
|---|---|
| 519 | (structure) |
| 520 | (structure) |
| 521 | (structure) |
| 522 | (structure) |
| 523 | (structure) |
| 524 | (structure) |

TABLE 1-continued

| Entry | Compound |
|---|---|
| 525 | (structure) |
| 526 | (structure) |
| 527 | (structure) |

It will be appreciated that the description of the present invention herein should be construed in congruity with the laws and principles of chemical bonding. In some instances it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV activities and for treating RSV infection in a subject in need thereof. The method comprises administering to the subject a therapeutically effective amount of a compound of formula (I).

The present invention also provides the use of a compound of formula (I) for the preparation of a medicament for the prevention or treatment of RSV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV and influenza infections. The present invention thus also relates to a product containing a compound of formula (I), or a pharmaceutically acceptable salt thereof, and an anti-influenza compound for simultaneous, separate or sequential use in the treatment of concomitant RSV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebuliser containing a medicament which comprises (a) a benzodiazepine derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluent or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral centre include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl", as used herein, refers to a saturated, monovalent straight- or branched-chain hydrocarbon radicals. Preferred alkyl radicals include $C_1$-$C_6$ alkyl and $C_1$-$C_8$ alkyl radicals. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl groups include, but are not limited to, methyl, ethyl, propyl, isopropyl, n-butyl, tert-butyl, neopentyl, n-hexyl, heptyl, and octyl radicals.

The term "alkenyl" as used herein, refers to straight- or branched-chain hydrocarbon radicals having at least one carbon-carbon double bond by the removal of a single hydrogen atom. Preferred alkenyl groups include $C_2$-$C_6$ alkenyl and $C_2$-$C_8$ alkenyl groups. Alkenyl groups include, but are not limited to, for example, ethenyl, propenyl, butenyl, 1-methyl-2-buten-1-yl, heptenyl, octenyl and the like.

The term "alkynyl" as used herein, refers to straight- or branched-chain hydrocarbon radicals having at least one carbon-carbon triple bond by the removal of a single hydrogen atom. Preferred alkynyl radicals include $C_2$-$C_6$ alkynyl and $C_2$-$C_8$ alkynyl radicals. Representative alkynyl radicals include, but are not limited to, for example, ethynyl, 1-propynyl, 1-butynyl, heptynyl, octynyl and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

The term "alkynylene" refers to an alkynyl group from which an additional hydrogen atom has been removed to form a diradical group. Alkynylene groups include, but are not limited to, for example, ethynylene, propynylene, butynylene, 1-methyl-2-butyn-1-ylene, heptenylene, octynylene, and the like.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. Where a carbocycle group is a divalent moiety linking two other elements in a depicted chemical structure, the carbocycle group can be attached to the two other elements through any two substitutable ring atoms. A $C_4$-$C_6$ carbocycle has 4-6 ring atoms.

The term "cycloalkyl", as used herein, refers to a monocyclic or polycyclic saturated carbocyclic ring compound, and the carbon atoms may be optionally oxo-substituted. A polycyclic cycloalkenyl can comprise fused rings. Preferred cycloalkyl groups include $C_3$-$C_8$ cycloalkyl and $C_3$-$C_{12}$ cycloalkyl groups. Examples of $C_3$-$C_8$-cycloalkyl include, but are not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl.

The term "cycloalkenyl", as used herein, refers to monocyclic or polycyclic carbocyclic ring compound having at least one carbon-carbon double bond and the carbon atoms may be optionally oxo-substituted. A polycyclic cycloalkenyl can comprise fused rings, covalently attached rings or a combination thereof. Preferred cycloalkenyl groups include $C_3$-$C_8$ cycloalkenyl and $C_3$-$C_{12}$ cycloalkenyl groups. Examples of $C_3$-$C_8$-cycloalkenyl include, but are not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "heterocycloalkyl" and "heterocyclic" can be used interchangeably and refer to a non-aromatic 3-12-membered ring or a bi- or tri-cyclic group fused, spiro or bridged system, where: (i) each ring contains between one and three heteroatoms independently selected from oxygen, sulfur and nitrogen, (ii) each 5-membered ring has 0 to 1 double bonds and each 6-, 7-, 8-, 9-, 10, 11-, or 12-membered ring has 0 to 2 double bonds, (iii) the nitrogen and sulfur heteroatoms may optionally be oxidized, (iv) the nitrogen heteroatom may optionally be quaternized, (v) any of the above rings may be fused to a benzene ring, and (vi) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted to give substituted heterocyclic. Heteroaryl or heterocyclic groups can be C-attached or N-attached (where possible).

The term "aryl," as used herein, refers to a mono- or polycyclic carbocyclic ring system comprising at least one aromatic ring, including, but not limited to, phenyl, naphthyl, tetrahydronaphthyl, indanyl, indenyl and the like. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Preferred heteroaryl groups are monocyclic or bicyclic. Heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. A polycyclic heteroaryl can comprise fused rings, covalently attached rings or a combination thereof.

In accordance with the invention, aromatic groups can be substituted or unsubstituted.

The term "arylalkyl," as used herein, refers to functional group wherein an alkylene chain is attached to an aryl group. Examples include, but are not limited to, benzyl, phenethyl and the like. The term "substituted arylalkyl" means an arylalkyl functional group in which the aryl group is substituted. Similarly, the term "heteroarylalkyl" means a functional group wherein an alkylene chain is attached to a heteroaryl group. Examples include, but are not limited to, pyridinylmethyl, pyrimidinylethyl and the like. The term "substituted heteroarylalkyl" means a heteroarylalkyl functional group in which the heteroaryl group is substituted.

The term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_6$) alkoxy.

The term "halo" or "halogen" alone or as part of another substituent, as used herein, refers to a fluorine, chlorine, bromine, or iodine atom. Preferred halogens are fluorine, chlorine and bromine.

The term "hydrogen" includes hydrogen and deuterium. In addition, the recitation of an atom includes other isotopes of that atom so long as the resulting compound is pharmaceutically acceptable.

The term "substituted" as used herein, refers to independent replacement of one, two, three or more of the hydrogen atoms thereon with substituents including, but not limited to, deuterium, tritium, —F, —Cl, —Br, —I, —OH, protected hydroxy, —NO$_2$, —CN, —NH$_2$, —N$_3$, protected amino, alkoxy, thioalkoxy, oxo, thioxo, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)— heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)— heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)— heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH— heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH— C$_1$-C$_{12}$-alkyl, —SO$_2$NH—C$_2$-C$_{12}$-alkenyl, —SO$_2$NH— C$_2$-C$_{12}$-alkynyl, —SO$_2$NH—C$_3$-C$_{12}$-cycloalkyl, —SO$_2$NH— aryl, —SO$_2$NH— heteroaryl, —SO$_2$NH— heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, methylthiomethyl, or -L'-R', wherein L' is C$_1$-C$_6$alkylene, C$_2$-C$_6$alkenylene or C$_2$-C$_6$alkynylene, and R' is aryl, heteroaryl, heterocyclic, C$_3$-C$_{12}$cycloalkyl or C$_3$-C$_{12}$cycloalkenyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, NH$_2$, C(O), S(O)$_2$, C(O)O, C(O)NH, OC(O)O, OC(O)NH, OC(O)NH$_2$, S(O)$_2$NH, S(O)$_2$NH$_2$, NHC(O)NH$_2$, NHC(O)C(O)NH, NHS(O)$_2$NH, NHS(O)$_2$NH$_2$, C(O)NHS(O)$_2$, C(O)NHS(O)$_2$NH or C(O)NHS(O)$_2$NH$_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "alicyclic," as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo [2.2.1] heptyl, and bicyclo [2.2.2] octyl. Such alicyclic groups may be further substituted.

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethyl silyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$Hs), and trimethylsilyl (TMS or —Si(CH$_3$)$_3$), and the like.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques, which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

In certain embodiments, the invention provides pharmaceutically acceptable esters of the compounds disclosed herein. As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

In certain embodiments, the invention provides pharmaceutically acceptable prodrugs of the compounds disclosed herein. The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound. For example, a compound of formula I wherein $R_1$ is an amino acid residue can also be esterified, for example at a hydroxyl group of the sugar residue, to form a compound with two groups that can be removed in vivo to yield the active compound.

The term "treating", as used herein, means relieving, lessening, reducing, eliminating, modulating, or ameliorating, i.e. causing regression of the disease state or condition. Treating can also include inhibiting, i.e. arresting the development, of a existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc. "Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
BME for 2-mercaptoethanol;
BOP for benzotriazol-1-yloxy-tris(dimethylamino)phosphonium hexafluorophosphate;
BTC for bis(trichloromethyl)carbonate; triphosgene;
BzCl for benzoyl chloride;
CDI for carbonyldiimidazole;
COD for cyclooctadiene;
DABCO for 1,4-diazabicyclo[2.2.2]octane;
DAST for diethylaminosulfur trifluoride;
DABCYL for 6-(N-4'-carboxy-4-(dimethylamino)azobenzene)-aminohexyl-; 1-O-(2-cyanoethyl)-(N,N-diisopropyl)-phosphoramidite;
DBU for 1,8-Diazabicycloundec-7-ene;
DCC for N,N'-dicyclohexylcarbodiimide;
DCM for dichloromethane;
DIAD for diisopropyl azodicarboxylate;
DIBAL-H for diisobutylaluminum hydride;
DIPEA for diisopropyl ethylamine;
DMAP for N,N-dimethylaminopyridine;
DME for ethylene glycol dimethyl ether;

DMEM for Dulbecco's Modified Eagles Media;
DMF for N,N-dimethyl formamide;
DMSO for dimethylsulfoxide;
DSC for N,N'-disuccinimidyl carbonate;
DUPHOS for

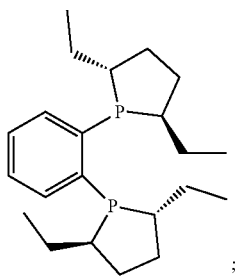 [SMILES: CC[C@@H]1CC[C@@H](CC)P1c1ccccc1P1[C@H](CC)CC[C@H]1CC]

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
EtOH for ethyl alcohol;
HATU for O (7-Azabenzotriazole-1-yl)-N,N,N',N'-tetramethyluronium hexafluorophosphate;
HCl for hydrochloric acid;
Hoveyda's Cat. for Dichloro(o-isopropoxyphenylmethylene) (tricyclohexylphosphine)ruthenium(II);
In for indium;
KHMDS is potassium bis(trimethylsilyl) amide;
Ms for mesyl;
NMM for N-4-methylmorpholine;
NMI for N-methylimidazole;
NMO for N-4-methylmorpholine-N-Oxide;
PyBrOP for Bromo-tri-pyrolidino-phosphonium hexafluorophosphate;
Ph for phenyl;
RCM for ring-closing metathesis;
RT for reverse transcription;
RT-PCR for reverse transcription-polymerase chain reaction;
TBME for tert-butyl methyl ether;
TCDI for 1,1'-thiocarbonyldiimidazole;
TEA for triethyl amine;
Tf$_2$O for trifluoromethanesulfonic anhydride;
TFA for trifluoroacetic acid;
THF for tetrahydrofuran;
TLC for thin layer chromatography;
(TMS)$_2$NH for hexamethyldisilazane;
TMSOTf for trimethylsilyl trifluoromethanesulfonate;
TBS for t-Butyldimethylsilyl;
TMS for trimethylsilyl;
TPAP tetrapropylammonium perruthenate;
TPP or PPh$_3$ for triphenylphosphine;
TrCl for trityl chloride;
DMTrCl for 4,4'-dimethoxytrityl chloride;
tBOC or Boc for tert-butyloxy carbonyl;
Xantphos for 4,5-Bis-diphenylphosphanyl-9,9-dimethyl-9H-xanthene; and
Zhan 1 B for

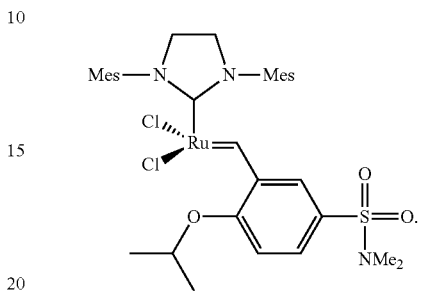

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, novel RSV analogs of the compounds of formulas 8, 10 and 11 are prepared starting from compounds 1, wherein R$_2$, R$_3$, R', R", R'" and ring A are defined as previously described. Compound 1 is reacted with TsCl in the presence of pyridine to obtain nitrogen protected intermediate 2, which is converted to aldehyde 3 when heated with POCl$_3$. Compound 3 cyclizes with either ethyl 2-mercaptoacetate, ethyl 2-hydroxyacetate or the like to provide 4 with fused thiophene or furan (X=S or O), wherein R$_2$ is as previous defined. After remove the Ts protecting group on nitrogen in 4 with H$_2$SO$_4$ or the like, the obtained compound 5 is coupled with 6, wherein L and ring A are defined as previous described, to afford 7. Compound 7 is the common intermediate that will be used in various ways to access compounds of the formula (8 or 10 or 11). Following Path 1, compound 8 could be prepared by direct amination of 7 with various amines, wherein R' and R" are as previous defined, with heated in DMSO. Following Path 2, compound 7 is coupled with various boronic esters, boronic acids, organotin reagents, organozinc reagents, organomagnesium reagents, organic silicon reagents or the like catalyzed by appropriate Pd, Ni, Cu or the like catalyst to afford compounds of formula 10. Further direct amination of 10 with various amines, when R'" is a halogen, compounds of formula 11 are prepared.

Scheme 1

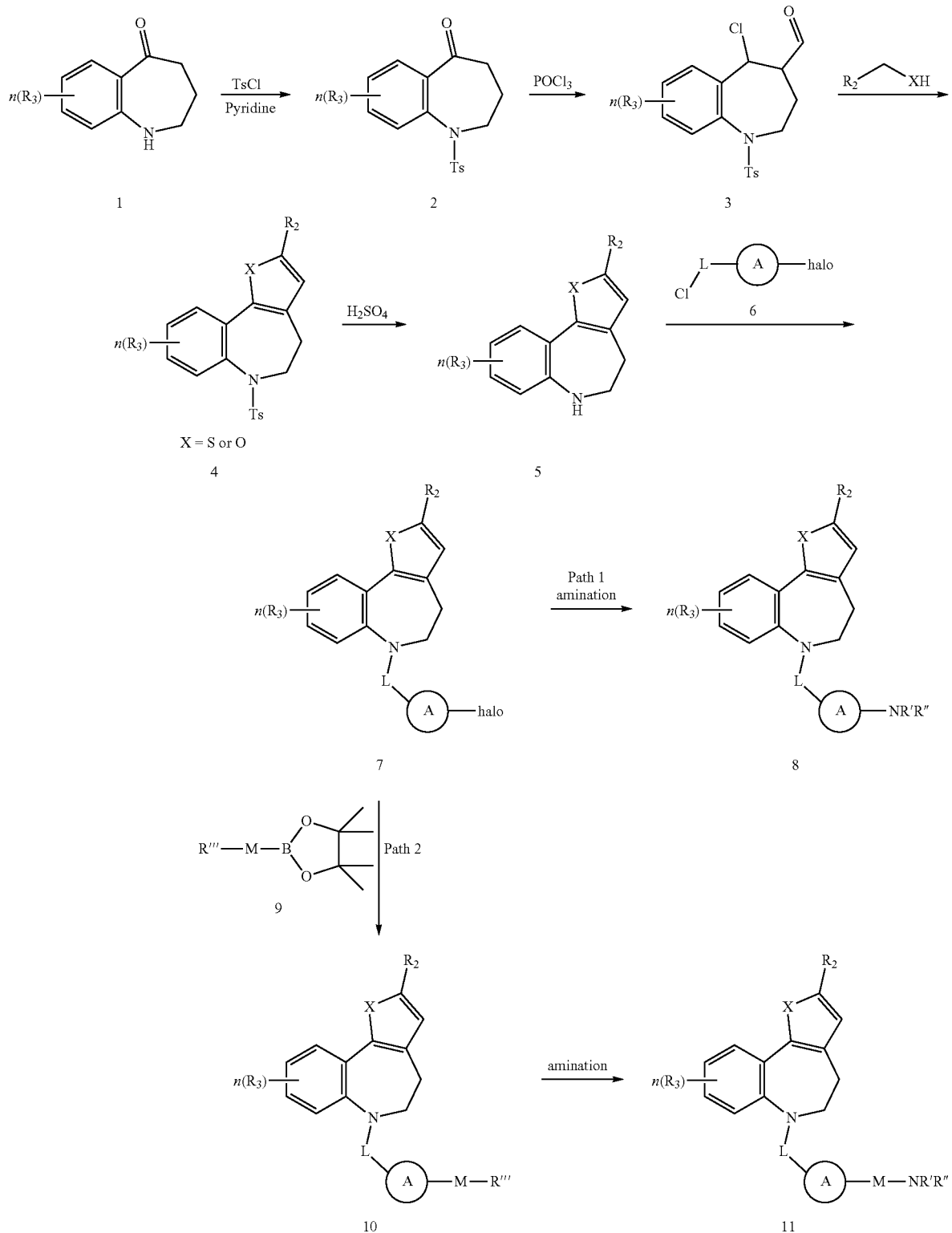

Scheme 2 illustrates methods, wherein $R_2$, $R_3$, R', R", R'", L and ring A are defined as previously described, to prepare compounds of formulas 19-21. Compound 12 is reacted with NBS in the presence of $(PhCO_2)_2$ to afford 13, which is converted to methyl ester 14 in two steps by reacting with NaCN followed by TMSCl. Compound 14 is coupled with 15 in the presence of palladium or the like catalyst to give cyclized compound 16. Amide in 16 is reduced by using BH$_3$ or the like to afford 17, which is reacted with 6 to form 18. Following the similar Path 1 and Path 2 procedures as described in Scheme 1, compounds of formulas 19-21 are prepared.
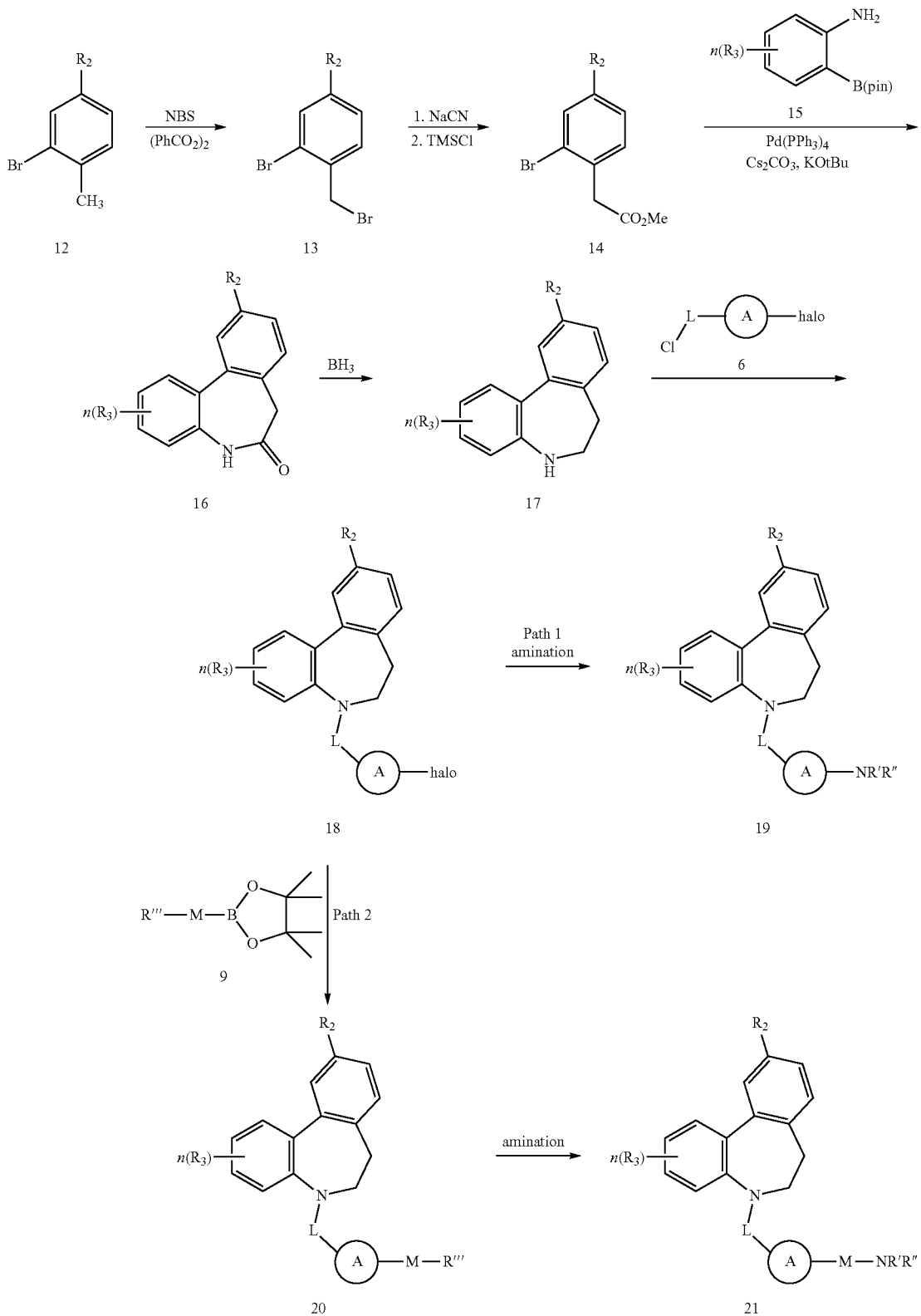

Scheme 3 illustrates methods, wherein $R_2$, $R_3$, R', R", R'", L and ring A are defined as previously described, to prepare compounds of formulas 27-29. Compound 2 is brominated with $Br_2$ or the like to afford 22, which is heated with 23 (ethyl 2-amino-2-thioxoacetate or the like) in EtOH to afford the cyclized compound 24. After removing the Ts protecting group on nitrogen in 24 with $H_2SO_4$ or the like, the obtained compound 25 is coupled with 6 to afford 26. Following the similar Path 1 and Path 2 procedures as described in Scheme 1, compounds of formulas 27-29 are prepared.

Scheme 4 illustrates methods, wherein $R_2$, $R_3$, R', R", R'", L and ring A are defined as previously described, to prepare compounds of formulas 35-37. Compound 2 is heated with DMA and DMF to afford 30, which reacts with guanidine hydrochloride in the presence of TEA to form the cyclized pyrimidine compound 31. After acylation (or alkylation) or the like, followed by the de-protection of Ts group on nitrogen with $H_2SO_4$ or the like, intermediate 33 is obtained. Following the similar Path 1 and Path 2 procedures as described in Scheme 1, compounds of formulas 35-37 are prepared.

Scheme 3

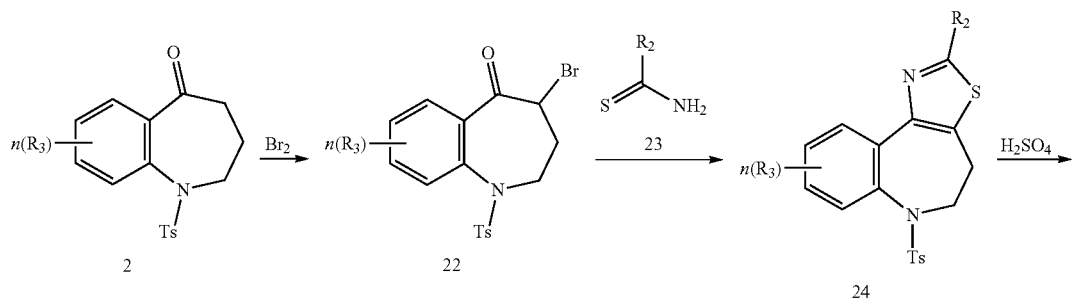

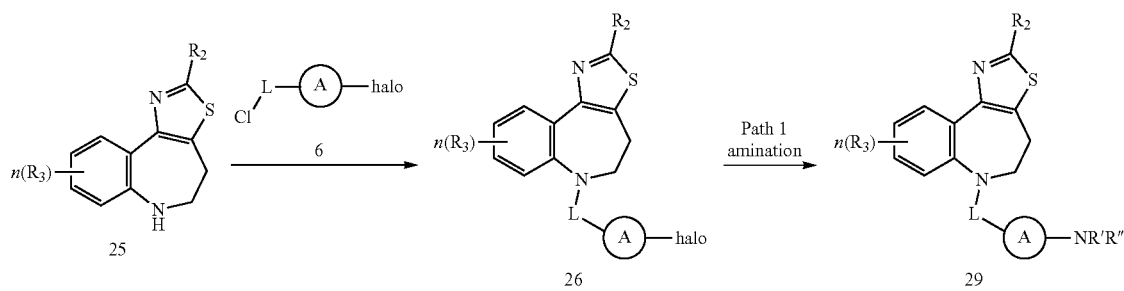

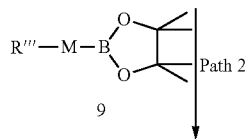

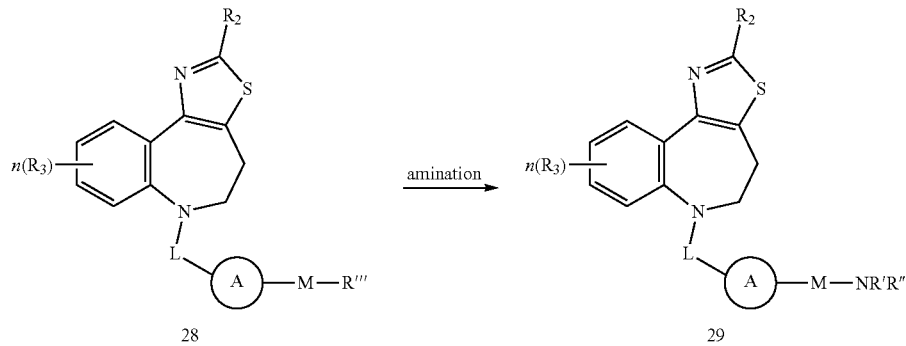

Scheme 4

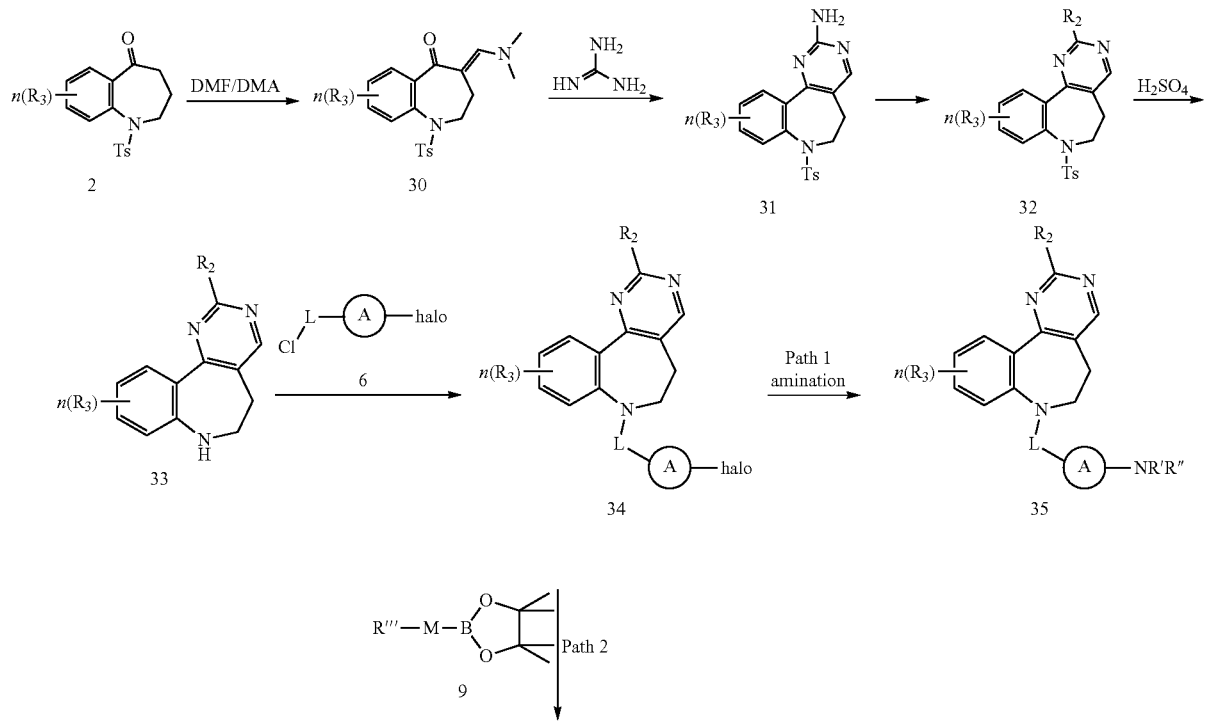

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Scheme 1

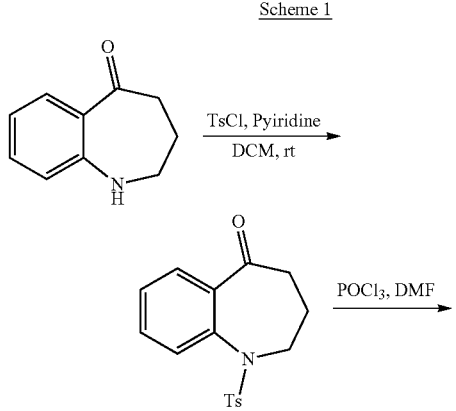

227
-continued

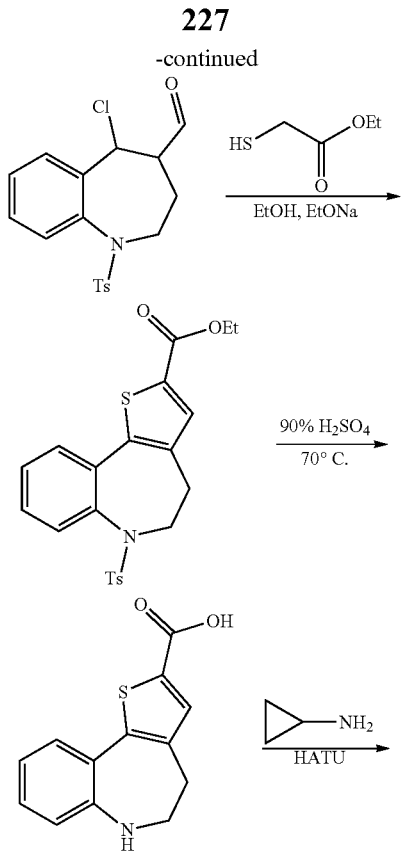

228
-continued

Example 1:

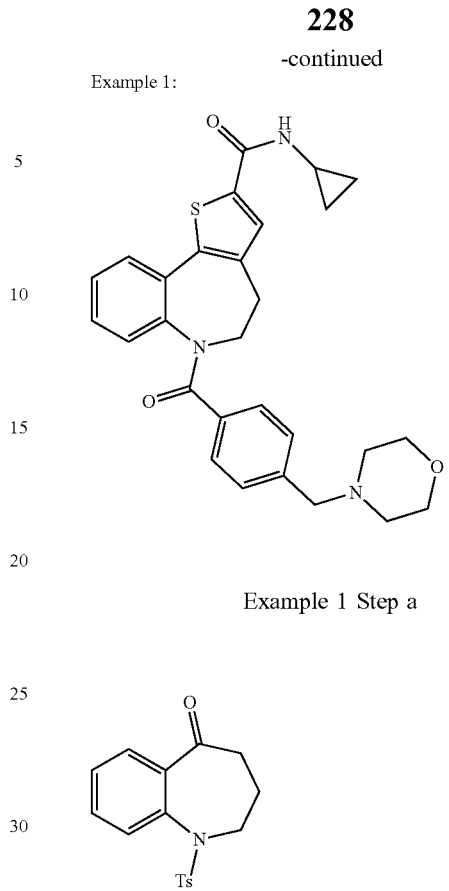

Example 1 Step a

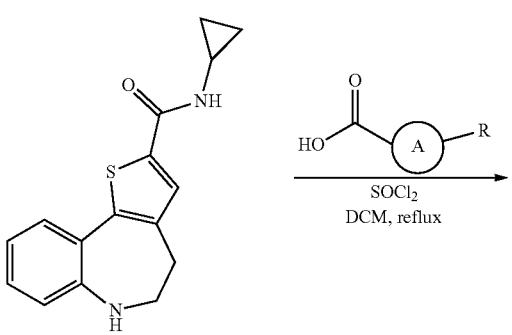

To a stirring solution of 1,2,3,4-tertahydrobenzo[b]azepine-5-one (50 g, 0.31 mol) in DCM (250 mL) was added pyridine (175 mL). The mixture was cooled with ice bath and TsCl (84 g, 0.44 mol) was added. The mixture was warmed to room temperature and stirred overnight. Water (750 mL) was added and the mixture was extracted with DCM (300 mL×3). The combined organic phase was washed with water, brine, dried over anhydrous $Na_2SO_4$ and concentrated under reduced pressure. The residue was washed with a mixed solvent (petroleum ether/EtOAc=70:1) to give the title product as a light yellowish solid (97 g, 99%). ESI MS m/z=316.05 [M+H]$^+$.

Example 1 Step b

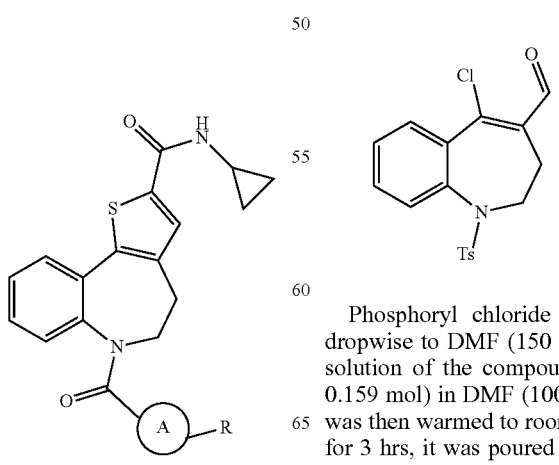

Phosphoryl chloride (44 mL, 0.475 mol) was added dropwise to DMF (150 mL) at 0° C. under $N_2$, and then a solution of the compound from Example 1 step a (50 g, 0.159 mol) in DMF (100 mL) was added. After the mixture was then warmed to room temperature and heated to 80° C. for 3 hrs, it was poured into ice cooled aqueous NaOAc (1 L) and extracted with ethyl acetate. The combined organic phase was washed with water, saturated NaHCO₃ aqueous, brine, dried over anhydrous Na₂SO₄ and concentrated under reduced pressure. The residue was washed with a mixed solvent (petroleum ether/EtOAc=30/1) to give the desired product as a yellow solid (50 g, 87%). ESI MS m/z=362.00 [M+H]⁺.

Example 1 Step c

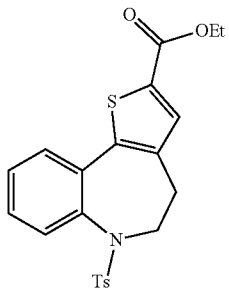 [SMILES: CCOC(=O)c1cc2c(s1)-c1ccccc1N(S(=O)(=O)c1ccc(C)cc1)CC2]

A solution of 21% EtONa/EtOH (87 mL, 0.24 mol) was added to a mixture of ethyl-2-mercaptoacetate (26 mL, 0.24 mol) in EtOH (300 mL), which was cooled down to 0° C. with ice bath under N₂. The mixture was stirred for 30 min and then the compound from Example 1 step b (42.0 g, 0.12 mol) was added. The resulted mixture was stirred at this temperature for 30 min and then refluxed for 2.5 hrs. The mixture was then cooled to room temperature and 2N HCl aqueous was added to adjust the pH to 7. The mixture was extracted with ethyl acetate (1 L×2) and the combined organic phase was washed with water, saturated NaHCO₃ aqueous, brine, dried over anhydrous Na₂SO₄ and concentrated under reduced pressure to give the desired product as a yellow solid (43 g, 84%). ESI MS m/z=428.10 [M+H]⁺.

Example 1 Step d

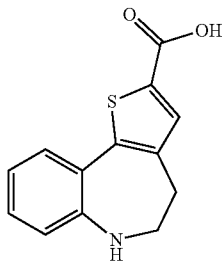 [SMILES: O=C(O)c1cc2c(s1)-c1ccccc1NCC2]

Compound from Example 1 step c (5.0 g, 11.7 mmol) was added to 90% H₂SO₄ (50 mL) at 0° C. The mixture was stirred for 10 min at this temperature and then heated to 70° C. for 2 hrs. The mixture was cooled to room temperature and then added to ice water. The precipitated solid was filtered and the filter cake was washed with water dried under vacuum to give the desired product as a gray solid (2.58 g, 90%). ESI MS m/z=246.05 [M+H]⁺.

Example 1 Step e

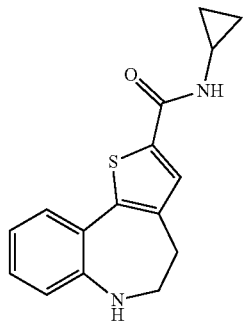 [SMILES: O=C(NC1CC1)c1cc2c(s1)-c1ccccc1NCC2]

To a stirring solution of the compound from Example 1 step d (1.0 g, 4.08 mmol) in DMF (10 mL) were added DIEA (2.0 mL, 12.2 mmol) and cyclopropanamine (0.56 mL, 8.15 mmol). Then HATU (1.86 g, 4.89 mmol) was added and the mixture was stirred at room temperature for 4 hrs. Water (10 mL) was added and the mixture was extracted with EtOAc. The combined organic phase was washed with water, brine, dried over anhydrous Na₂SO₄ and concentrated under reduced pressure. The resulted residue was purified by silica gel column chromatography to give the desired product as a yellow solid (900 mg, 77%). ESI MS m/z=295.05 [M+H]⁺.

Example 1 Step f

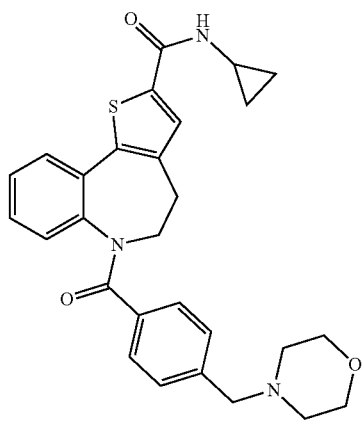 [SMILES: O=C(NC1CC1)c1cc2c(s1)-c1ccccc1N(C(=O)c1ccc(CN3CCOCC3)cc1)CC2]

To a solution of 4-(4-morpholinyl)benzoic acid (100 mg, 0.46 mmol) in DCM (5 mL) was added thionoyl chloride (1 mL), and then the resulting mixture was refluxed for 4 hrs. After removed most solvent thionoyl chloride, the residual thionoyl chloride was further removed by azeotropic drying with toluene (20 mL×2). The residue was dissolved in DCM (4 mL), and then diisopropylethylamine (0.5 mL) and compound from Example 1 step e (122 mg, 0.46 mmol) were added. The mixture was stirred at rt for 12 hrs, then diluted with DCM (20 mL) and water (5 mL). The organic layer was washed with aq. NaHCO₃ (2N, 10 mL), brine (20 mL), dried over Na₂SO₄, filtered and evaporated. The residue was purified by silica gel column chromatography to give the title compound (70 mg, 31%) as a white solid. ESI MS m/z=488.43 [M+H]⁺.

Example 2

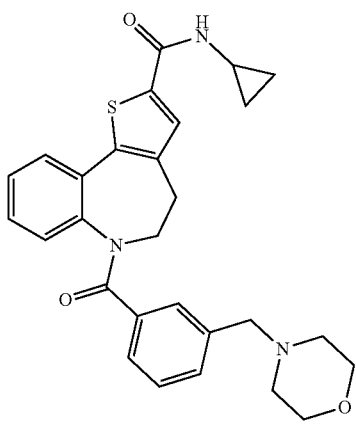 [SMILES: O=C(NC1CC1)c1cc2c(s1)-c1ccccc1N(C(=O)c1cccc(CN3CCOCC3)c1)CC2]

Example 2 was prepared using a procedure similar to that used to prepare Example 1 where 3-(4-morpholinylmethyl)benzoic acid was used in place of 4-(4-morpholinylmethyl)benzoic acid in step f. ESI MS m/z=488.43 [M+H]+.

Example 3

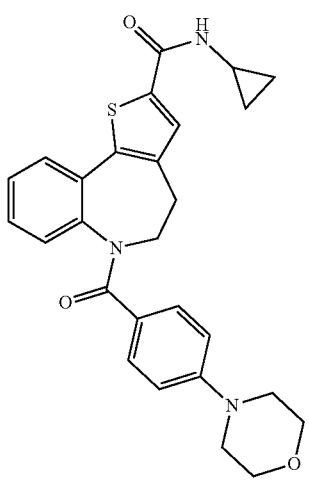 [SMILES: O=C(NC1CC1)c1cc2c(s1)-c1ccccc1N(C(=O)c1ccc(N3CCOCC3)cc1)CC2]

Example 3 was prepared using a procedure similar to that used to prepare Example 1 where 4-(4-morpholinyl)benzoic acid was used in place of 4-(4-morpholinylmethyl)benzoic acid in step f ESI MS m/z=474.18 [M+H]+.

Example 4

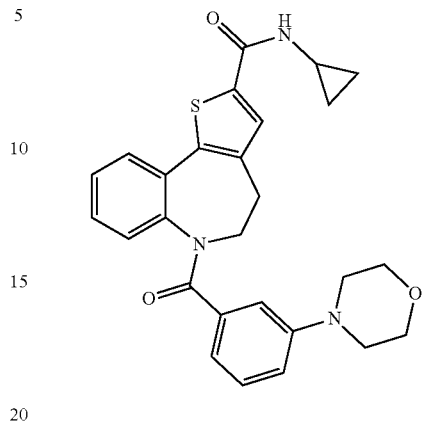

Example 4 was prepared using a procedure similar to that used to prepare Example 1 where 3-(4-morpholinyl)benzoic acid was used in place of 4-(4-morpholinylmethyl)benzoic acid in step f. ESI MS m/z=474.18 [M+H]+.

Example 5

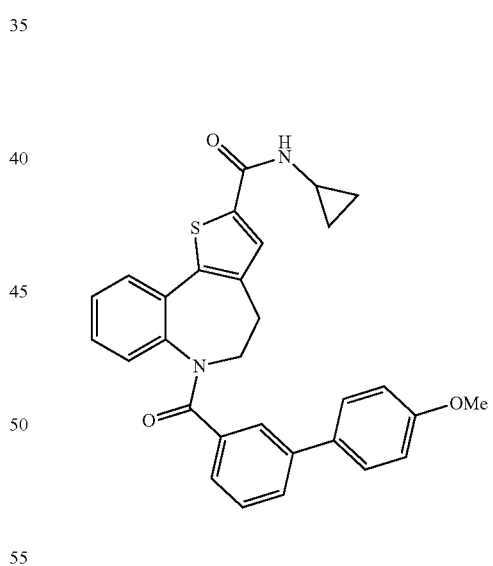

Example 5 was prepared using a procedure similar to that used to prepare Example 1 where 4'-methoxy-[1,1'-biphenyl]-3-carboxylic acid was used in place of 4-(4-morpholinylmethyl)-benzoic acid in step f. ESI MS m/z=495.17 [M+H]+.

Example 6

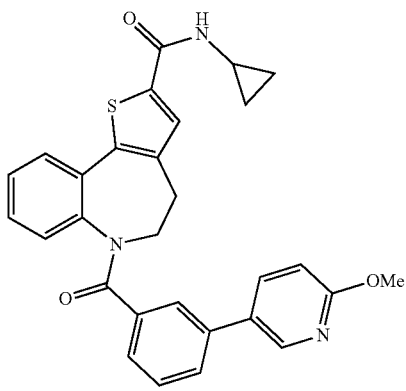 [SMILES: COc1ccc(-c2cccc(C(=O)N3CCc4cc(C(=O)NC5CC5)sc4-c4ccccc43)c2)cn1]

Example 6 was prepared using a procedure similar to that used to prepare Example 1 where 3-(6-methoxypyridin-3-yl)benzoic acid was used in place of 4-(4-morpholinylmethyl)benzoic acid in step f. ESI MS m/z=496.16 [M+H]$^+$.

Example 7

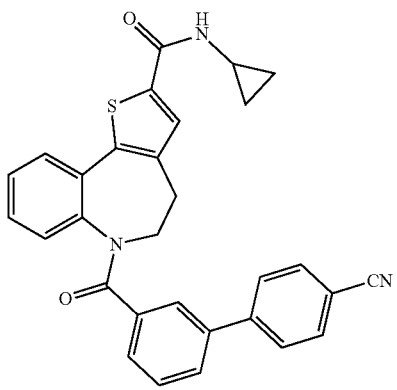 [SMILES: N#Cc1ccc(-c2cccc(C(=O)N3CCc4cc(C(=O)NC5CC5)sc4-c4ccccc43)c2)cc1]

Example 7 was prepared using a procedure similar to that used to prepare Example 1 where 4'-cyano-[1,1'-biphenyl]-3-carboxylic acid was used in place of 4-(4-morpholinylmethyl)benzoic acid in step f. ESI MS m/z=490.16 [M+H]$^+$.

Example 8

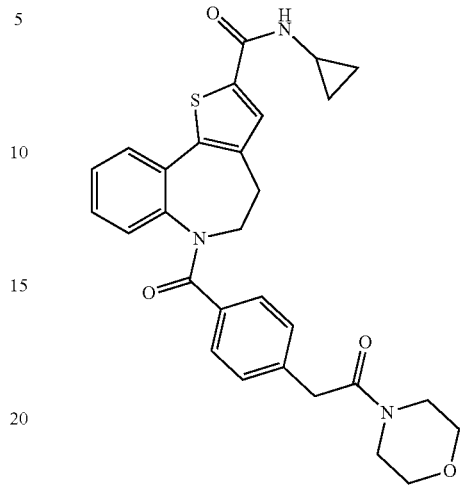

Example 8 Step a

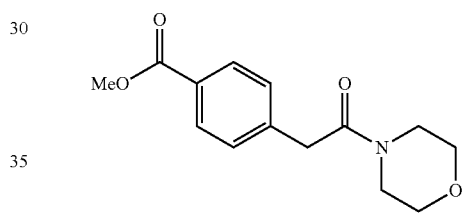

Solid HATU (540 mg, 1.4 mmol) was added to a DMF solution (6 mL) of 2-(4-(methoxycarbonyl)phenyl)acetic acid (250 mg, 1.3 mmol), morpholine (0.13 mL, 1.5 mmol), and i-Pr$_2$NEt (0.45 mL, 2.6 mmol) and the mixture was warmed to 45° C. After 4 h the mixture was diluted with EtOAc, and washed with water and brine, dried, concentrated, and purified by column chromatography to give the desired product (3414 mg) as a white solid.

Example 8 Step b

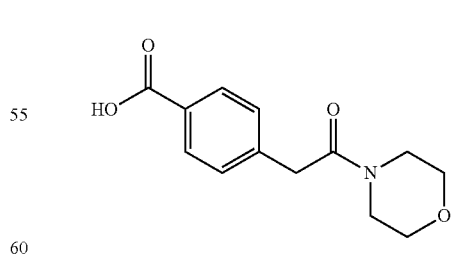

Solid LiOH.H$_2$O (69 mg, 1.6 mmol) was added to a THF/MeOH/H$_2$O solution (0.5/0.5/1 mL) of compound from Example 8 step a (344 mg, 1.3 mmol) and the mixture was stirred at rt overnight. The mixture was concentrated, suspended in water, and 2 N HCl was added dropwise (~3 mL). The resulting white precipitate was filtered off and dried under high vacuum to give the desired product (125 mg) as a white solid that was used directly without further purification.

Example 8 Step c

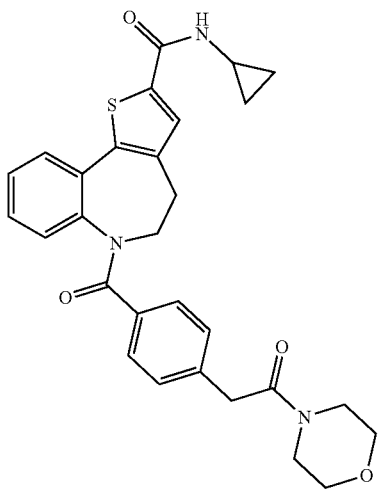 [SMILES: O=C(NC1CC1)c1cc2c(s1)-c1ccccc1N(C(=O)c1ccc(CC(=O)N3CCOCC3)cc1)CC2]

Example 8 was prepared using a procedure similar to that used to prepare Example 1 where 4-(2-morpholino-2-oxo-ethyl)benzoic acid (from Example 8 step b) was used in place of 4-(4-morpholinylmethyl)benzoic acid in step f. ESI MS m/z=516.19 [M+H]$^+$.

Example 9

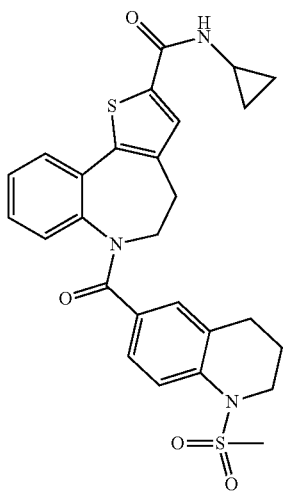 [SMILES: CS(=O)(=O)N1CCCc2cc(C(=O)N3CCc4cc(C(=O)NC5CC5)sc4-c4ccccc43)ccc21]

Example 9 was prepared using a procedure similar to that used to prepare Example 1 where 1-(methylsulfonyl)-1,2,3,4-tetrahydroquinoline-6-carboxylic acid was used in place of 4-(4-morpholinylmethyl)benzoic acid in step f. ESI MS m/z=522.15 [M+H]$^+$.

Example 10

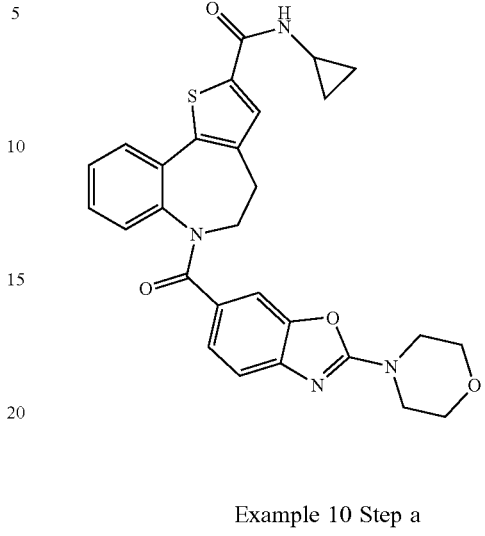

Example 10 Step a

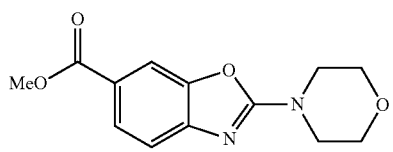

Neat morpholine (0.14 mL, 1.7 mmol) was added to a THF solution (5 mL) of methyl 2-chlorobenzo[d]oxazole-6-carboxylate (250 mg, 1.2 mmol) and Et$_3$N (0.25 mL, 1.8 mmol) and the mixture was warmed to 45° C. overnight. The mixture was diluted with EtOAc, and washed with water and brine, dried, concentrated, and purified by column chromatography to give the desired product (240 mg) as a white solid.

Example 10 Step b

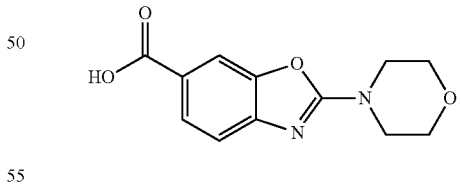

Solid LiOH.H$_2$O (77 mg, 1.8 mmol) was added to a THF/MeOH/H$_2$O solution (4/4/4 mL) of compound from Example 10 step a (240 mg, 0.9 mmol) and the mixture was stirred at rt overnight. The mixture was concentrated, suspended in water, and 2 N HCl was added dropwise (~5 mL). The resulting white precipitate was filtered off and dried under high vacuum to give the desired product (160 mg) as a white solid that was used directly without further purification.

Example 10 Step c

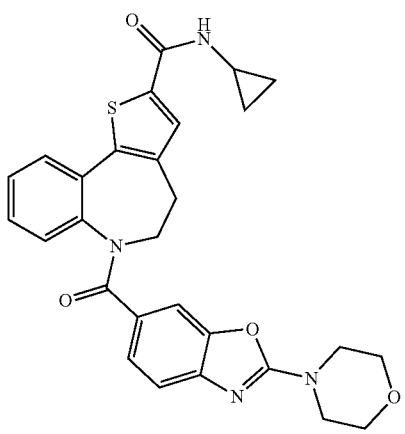 [SMILES: O=C(NC1CC1)c1cc2c(s1)-c1ccccc1N(C(=O)c1ccc3nc(N4CCOCC4)oc3c1)CC2]

Example 10 was prepared using a procedure similar to that used to prepare Example 1 where 2-morpholinobenzo[d]oxazole-6-carboxylic acid (from Example 10 step b) was used in place of 4-(4-morpholinylmethyl)-benzoic acid in step f. ESI MS m/z=515.17 [M+H]⁺.

Example 11

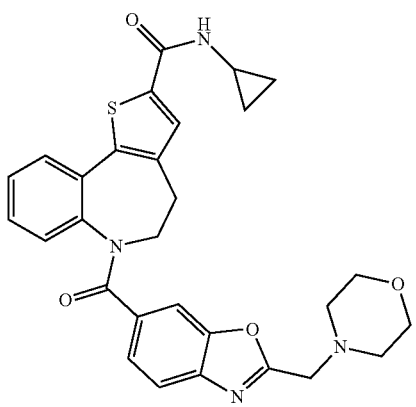 [SMILES: O=C(NC1CC1)c1cc2c(s1)-c1ccccc1N(C(=O)c1ccc3nc(CN4CCOCC4)oc3c1)CC2]

Example 11 Step a

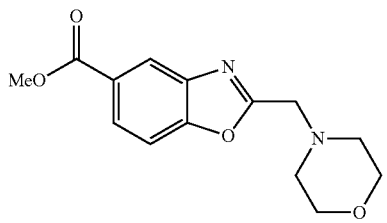 [SMILES: COC(=O)c1ccc2oc(CN3CCOCC3)nc2c1]

Neat morpholine (0.25 mL, 2.9 mmol) was added to a THF solution (5 mL) of methyl 2-(chloromethyl)benzo[d]oxazole-5-carboxylate (308 mg, 1.4 mmol) and the mixture was stirred at rt overnight. The mixture was diluted with EtOAc, and washed with water and brine, dried, concentrated, and purified by column chromatography to give the desired product (275 mg) as a white solid.

Example 11 Step b

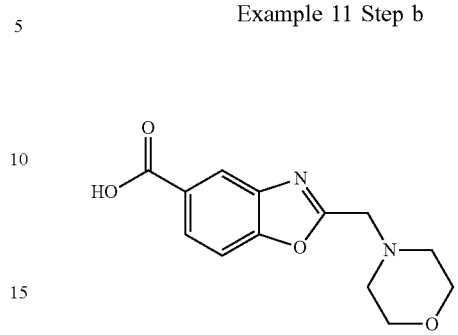

Solid LiOH.H₂O (84 mg, 2.0 mmol) was added to a THF/MeOH/H₂O solution (4/4/4 mL) of compound from Example 11 step a (275 mg, 1.0 mmol) and the mixture was stirred at rt overnight. The mixture was concentrated, suspended in water, and 2 N HCl was added dropwise (~5 mL). The resulting white precipitate was filtered off and dried under high vacuum to give the desired product (185 ng) as a white solid that was used directly without further purification.

Example 11 Step c

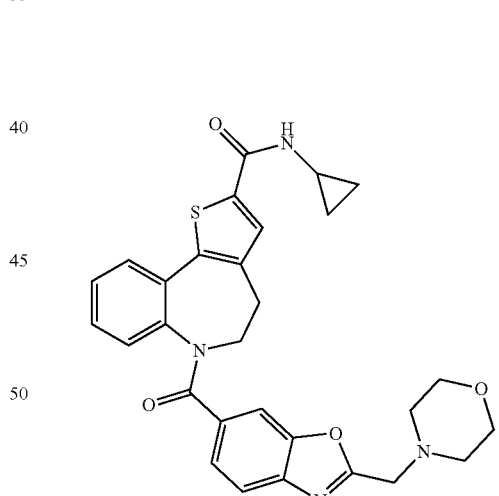

Example 11 was prepared using a procedure similar to that used to prepare Example 1 where 2-(morpholinomethyl)benzo[d]oxazole-6-carboxylic acid (from Example 11 step b) was used in place of 4-(4-morpholinyl-methyl)benzoic acid in step f. ESI MS m/z=529.18 [M+H]⁺.

Example 12

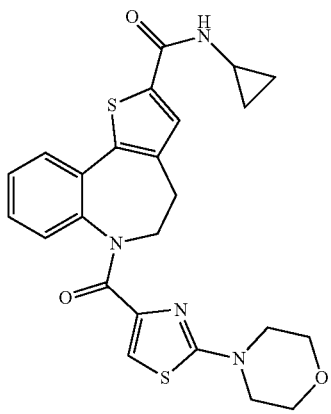 [SMILES: O=C(NC1CC1)c1cc2c(s1)-c1ccccc1N(C(=O)c1csc(N3CCOCC3)n1)CC2]

Example 12 was prepared using a procedure similar to that used to prepare Example 1 where 2-morpholinothiazole-4-carboxylic acid was used in place of 4-(4-morpholinylmethyl)benzoic acid in step f. ESI MS m/z=481.13 [M+H]+.

Example 13

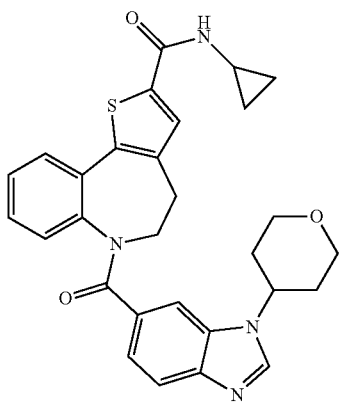 [SMILES: O=C(NC1CC1)c1cc2c(s1)-c1ccccc1N(C(=O)c1ccc3ncn(C4CCOCC4)c3c1)CC2]

Example 13 Step a

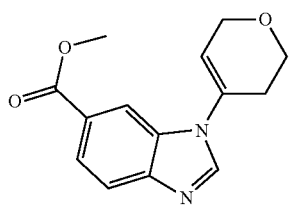

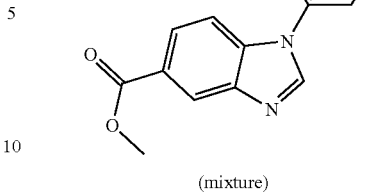

(mixture)

In a round bottom flask were added copper (II) acetate (0.35 g, 1.91 mmol) and 2,2'-bipyridine (0.32 g, 1.91 mmol) in DCM (30 mL). The mixture was heated to 70° C. To this mixture, sodium carbonate (0.82 g, 8.81 mmol) and a mixture of 6-chloro-1H-pyrrolo[3,2-c]pyridine 91.4 g, 7.66 mmol) and 3,6-dihydro-2H-pyran-4-yl-4-boronic acid (1.0 g, 8.81 mmol) in DCM 925 mL) were added. The resulting mixture turned from green to dark red color and was heated at this temperature overnight. Then second portion of copper (II) acetate (0.35 g, 1.91 mmol), 2,2'-bipyridine (0.32 g, 1.91 mmol) and 3,6-dihydro-2H-pyran-4-yl-4-boronic acid (1.0 g, 8.81 mmol) were added. The mixture was continued to stir under reflux for 20 hrs. After cooling down to rt, the reaction mixture was diluted with EtOAc (50 mL) and the organic layer was washed with brine, dried and evaporated. The residue was purified by FCC to give 0.90 g of the mixture of methyl 3-(3,6-dihydro-2H-pyran-4-yl)-3H-benzo[d]imidazole-5-carboxylate and methyl 1-cyclohexenyl-1H-benzo[d]imidazole-5-carboxylate.

Example 13 Step b

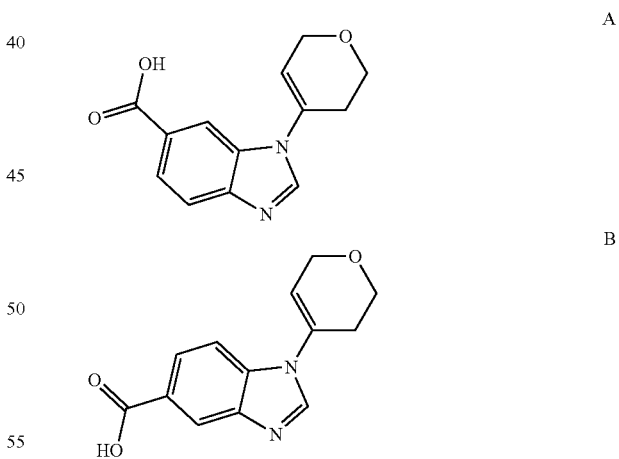

To a solution of the mixture from Example 13 step a in THF and methanol was added a solution of LiOH in water. Reaction mixture was stirred at rt for 30 min, concentrated, extracted with ethyl ether. The aqueous layer was acidified with 1 N HCl to pH ~3. The solid was collected, washed with water, dried to afford 0.74 g of a mixture of A and B. The mixture was subjected to FCC to afford 1-(3,6-dihydro-2H-pyran-4-yl)-1H-benzo[d]imidazole-6-carboxylic acid (A, 0.13 g) and 1-(3,6-dihydro-2H-pyran-4-yl)-1H-benzo[d]imidazole-5-carboxylic acid (B, 0.12 g).

Example 13 Step c

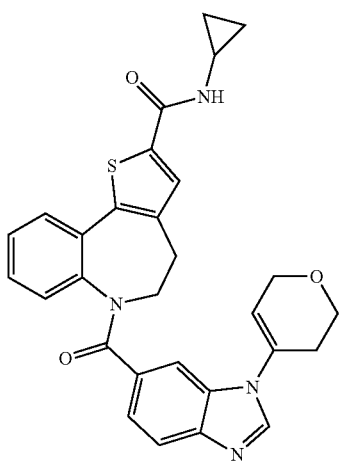 [SMILES: O=C(NC1CC1)c1cc2c(s1)-c1ccccc1N(C(=O)c1ccc3ncn(C4=CCOCC4)c3c1)CC2]

Compound was prepared using a procedure similar to that used to prepare Example 1 where 1-(3,6-dihydro-2H-pyran-4-yl)-1H-benzo[d]imidazole-6-carboxylic acid from Example 13 step b was used in place of 4-(4-morpholinyl-methyl)benzoic acid in step f. The compound was directly for the next step.

Example 13 Step d

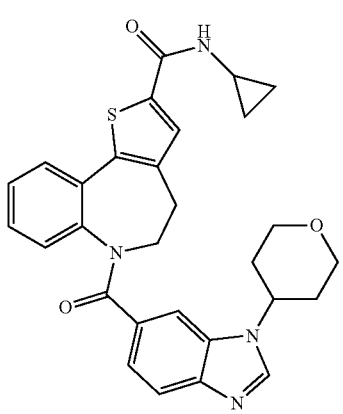 [SMILES: O=C(NC1CC1)c1cc2c(s1)-c1ccccc1N(C(=O)c1ccc3ncn(C4CCOCC4)c3c1)CC2]

Solid 10% Pd/C (40 mg) was added to a MeOH/DCM solution (2/1 mL) of compound from Example 13 step c (44 mg, 0.09 mmol) and the flask was sealed with a rubber septum. The air was evacuated under vacuum and purged with $H_2$ gas via balloon, this was repeated 3 times, and the mixture was stirred at rt overnight. After the $H_2$ was removed via vacuum, the mixture was diluted with DCM, and filtered through Celite. The Celite was washed with DCM and the filtrate was concentrated and purified via column chromatography to give the desired product (26 mg) as a white solid. ESI MS m/z=513.19 [M+H]$^+$.

Example 14

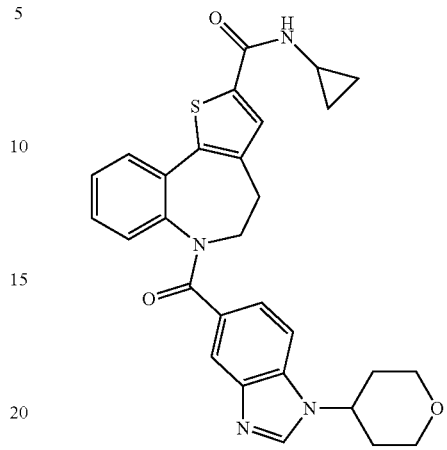

Example 14 Step a

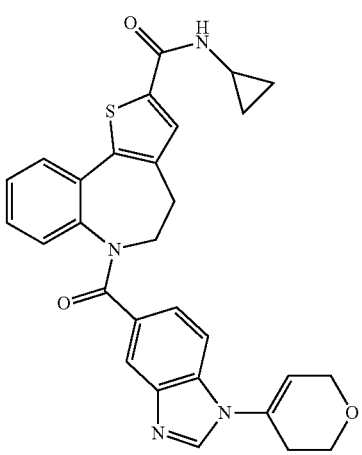 [SMILES: O=C(NC1CC1)c1cc2c(s1)-c1ccccc1N(C(=O)c1ccc3c(c1)ncn3C1=CCOCC1)CC2]

Compound was prepared using a procedure similar to that used to prepare Example 13 step c where 1-(3,6-dihydro-2H-pyran-4-yl)-1H-benzo[d]imidazole-5-carboxylic acid from Example 13 step b (B) was used in place of 1-(3,6-dihydro-2H-pyran-4-yl)-1H-benzo[d]imidazole-6-carboxylic acid from Example 13 step b (A).

Example 14 Step b

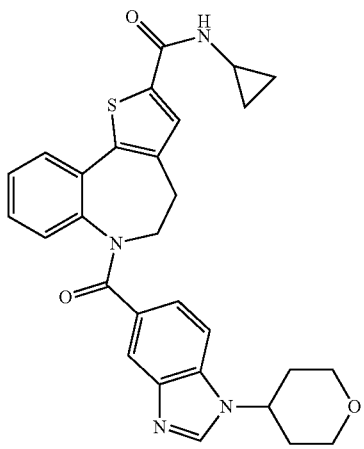 [SMILES: O=C(NC1CC1)c1cc2c(s1)-c1ccccc1N(C(=O)c1ccc3c(c1)ncn3C1CCOCC1)CC2]

Solid 10% Pd/C (30 mg) was added to a MeOH/DCM solution (2/1 mL) of compound from Example 14 step b (36 mg, 0.07 mmol) and the flask was sealed with a rubber septum. The air was evacuated under vacuum and purged with $H_2$ gas via balloon, this was repeated 3 times, and the mixture was stirred at rt overnight. After the H?2 was removed via vacuum, the mixture was diluted with DCM, and filtered through Celite. The Celite was washed with DCM and the filtrate was concentrated and purified via column chromatography to give the desired product (17 mg) as a white solid. ESI MS m/z=513.19 [M+H]$^+$.

Example 15

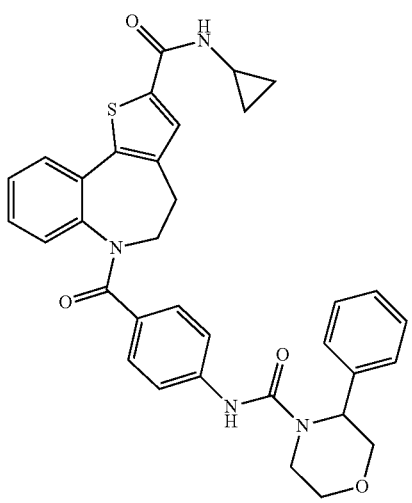 [SMILES: O=C(NC1CC1)c1cc2c(s1)-c1ccccc1N(C(=O)c1ccc(NC(=O)N3CCOCC3c3ccccc3)cc1)CC2]

Example 15 Step a

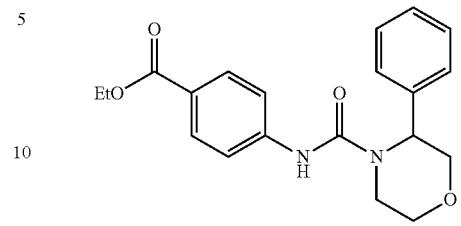

Solid 3-phenylmorpholine (250 mg, 1.5 mmol) was added to a THF solution (8 mL) of ethyl 4-isocyanatobenzoate (322 mg, 1.7 mmol) and the mixture was stirred at rt overnight. The mixture was concentrated, and purified via column chromatography to give the desired product (540 mg) as a light yellow solid.

Example 15 Step b


Solid LiOH.H$_2$O (96 mg, 2.3 mmol) was added to a THF/MeOH/H$_2$O solution (1.5/1.5/3 mL) of compound from Example 15 step a (540 mg, 1.5 mmol) and the mixture was stirred at rt overnight. The mixture was concentrated, suspended in water, and 2 N HCl was added dropwise (~3 mL). The resulting white precipitate was filtered off and dried under high vacuum to give the desired product (330 mg) as a white solid that was used directly without further purification.

Example 15 Step c

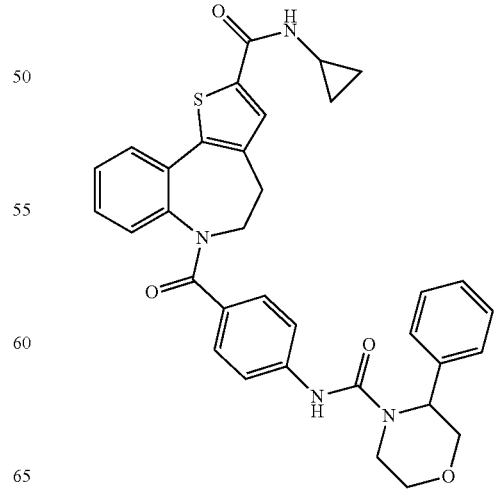

Example 15 was prepared using a procedure similar to that used to prepare Example 1 where 4-(3-phenylmorpholine-4-carboxamido)benzoic acid (from Example 15 step b) was used in place of 4-(4-morpholinyl-methyl)benzoic acid in step f. ESI MS m/z=593.22 [M+H]⁺.

Scheme 2

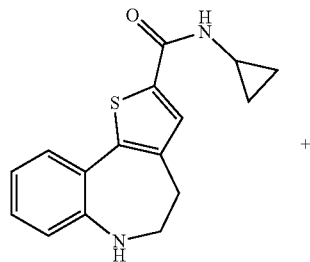

+

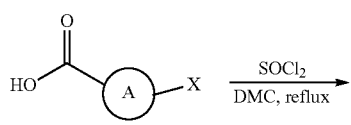

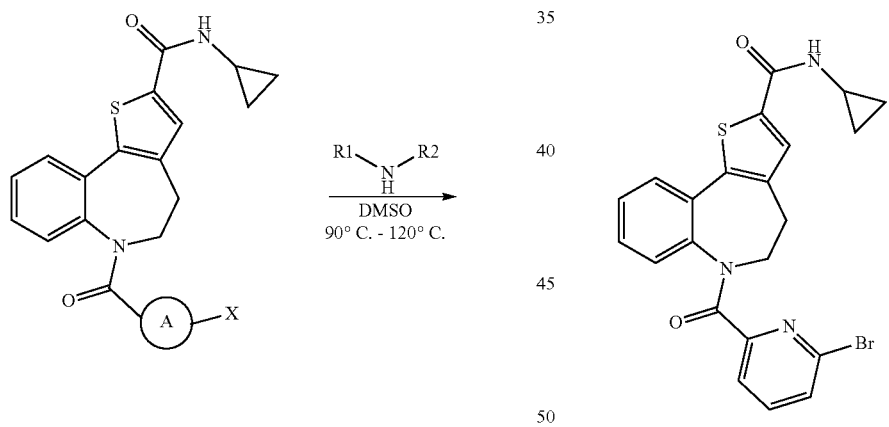

Example 16

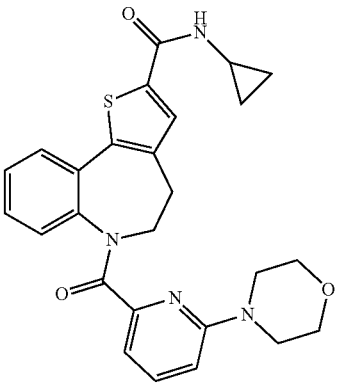 [SMILES: O=C(NC1CC1)c1cc2c(s1)-c1ccccc1N(C(=O)c1cccc(N3CCOCC3)n1)CC2]

Example 16 Step a

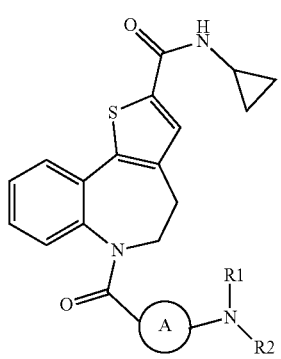

To a solution of 6-bromopicolinic acid (313 mg, 1.55 mmol) in DCM (5 mL) was added thionoyl chloride (2 mL), the resulting mixture was refluxed for 4 hrs. After removed most solvent thionoyl chloride, the residual thionoyl chloride was further removed by azeotropic drying with toluene (20 mL×2). The residue was dissolved in DCM (4 mL), and then diisopropylethylamine (2.0 mL) and amine from Example 1 step e (400 mg, 1.41 mmol) were added. The mixture was stirred at rt for 12 hrs, then diluted with DCM (20 mL) and water (5 mL). The organic layer was washed with aq. NaHCO₃ (2N, 10 mL), brine (20 mL), dried over Na₂SO₄, filtered and evaporated. The residue was purified by silica gel column chromatography to give the desired product (530 mg, 81%) as a yellow foam. ESI MS m/z=468.03 [M+H]⁺.

Example 16 Step b

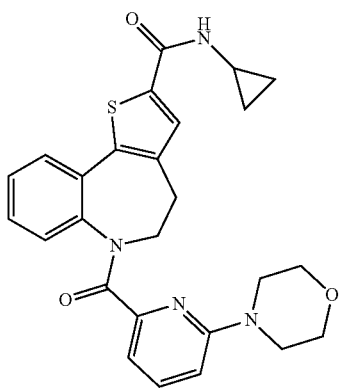 [SMILES: O=C(NC1CC1)c1cc2c(s1)-c1ccccc1N(C(=O)c1cccc(N3CCOCC3)n1)CC2]

To a solution of bromide from Example 16 step a (46.7 mg, 0.1 mmol) in DMSO (2 mL) was added morphine (0.2 mL), the resulting mixture was heated at 80° C. for 10 hrs. After diluted with EtOAc (50 mL), the solution was washed with water (20 mL×2) and brine (20 mL). The organic layer was dried over $Na_2SO_4$, filtered and evaporated. The residue was purified by silica gel column chromatography to give the title compound (20 mg, 42%) as a white solid. ESI MS m/z=475.18 $[M+H]^+$.

Example 17

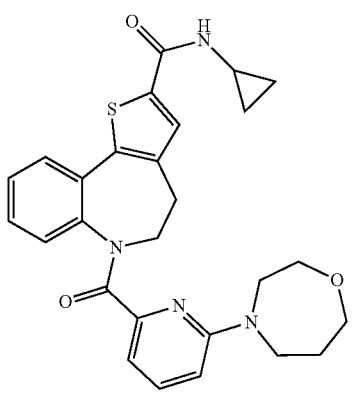 [SMILES: O=C(NC1CC1)c1cc2c(s1)-c1ccccc1N(C(=O)c1cccc(N3CCCOCC3)n1)CC2]

Example 17 was prepared using a procedure similar to that used to prepare Example 16 where 1,4-oxazepane was used in place of morpholine in step b. ESI MS m/z=489.19 $[M+H]^+$.

Example 18

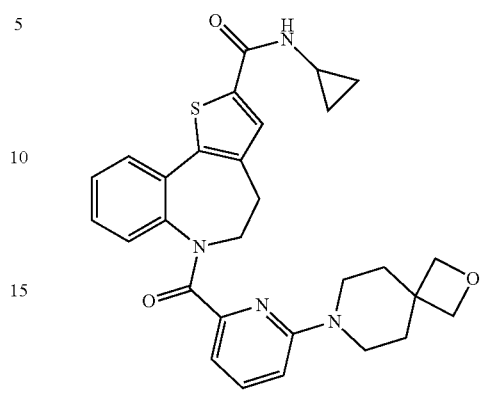

Example 18 was prepared using a procedure similar to that used to prepare Example 16 where 2-oxa-7-azaspiro[3.5]nonane was used in place of morpholine in step b. ESI MS m/z=515.21 $[M+H]^+$.

Example 19

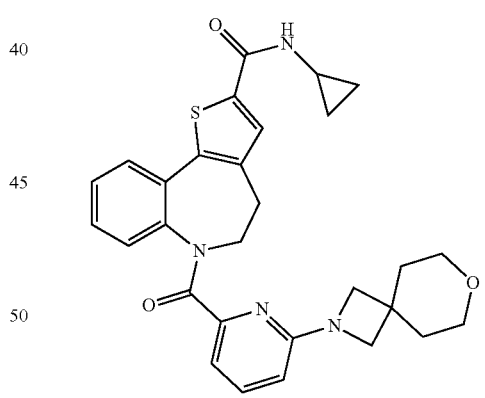

Example 19 was prepared using a procedure similar to that used to prepare Example 16 where 7-oxa-2-azaspiro[3.5]nonane was used in place of morpholine in step b. ESI MS m/z=515.21 $[M+H]^+$.

Example 20

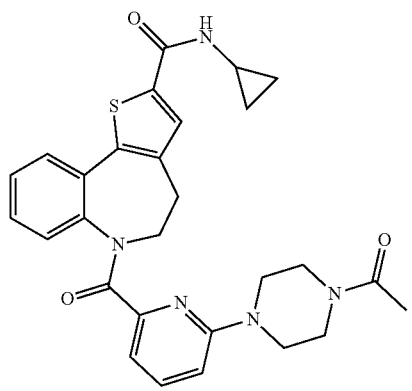 [SMILES: CC(=O)N1CCN(c2cccc(C(=O)N3CCc4cc(C(=O)NC5CC5)sc4-c4ccccc43)n2)CC1]

Example 20 was prepared using a procedure similar to that used to prepare Example 16 where 1-acetyl-piperazine was used in place of morpholine in step b. ESI MS m/z=516.20 [M+H]⁺.

Example 21

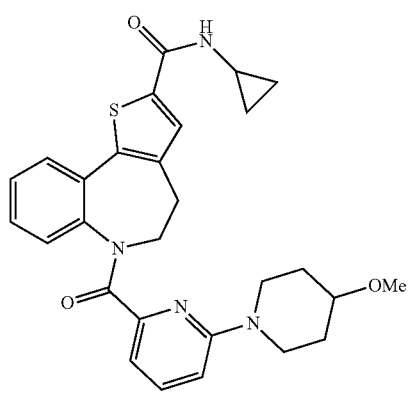 [SMILES: COC1CCN(c2cccc(C(=O)N3CCc4cc(C(=O)NC5CC5)sc4-c4ccccc43)n2)CC1]

Example 21 was prepared using a procedure similar to that used to prepare Example 16 where 4-methoxy-piperidine was used in place of morpholine in step b. ESI MS m/z=503.21 [M+H]⁺.

Example 22

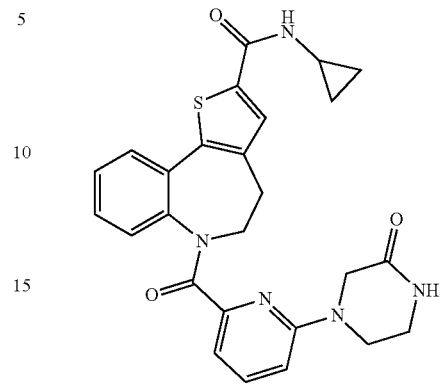

Example 22 was prepared using a procedure similar to that used to prepare Example 16 where 2-piperazinone was used in place of morpholine in step b. ESI MS m/z=488.17 [M+H]⁺.

Example 23

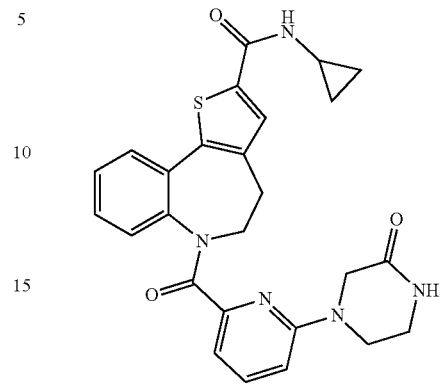

Example 23 was prepared using a procedure similar to that used to prepare Example 16 where 4,4-difluoro-piperidine was used in place of morpholine in step b. ESI MS m/z=509.18 [M+H]⁺.

Example 24

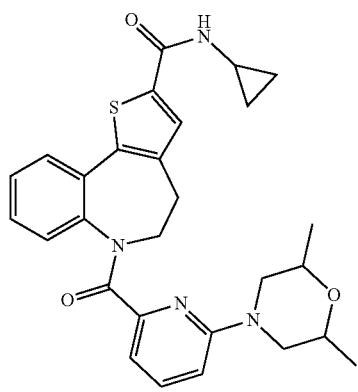 [SMILES: CC1CN(c2cccc(C(=O)N3CCc4cc(C(=O)NC5CC5)sc4-c4ccccc43)n2)CC(C)O1]

Example 24 was prepared using a procedure similar to that used to prepare Example 16 where 2,6-dimethyl-morpholine was used in place of morpholine in step b. ESI MS m/z=503.21 [M+H]$^+$.

Example 25

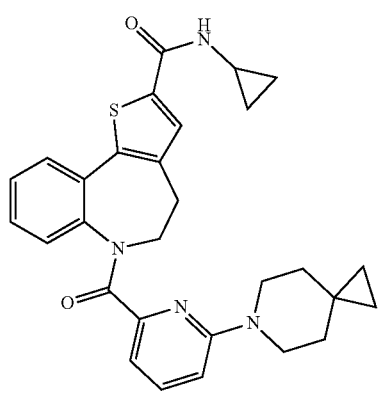 [SMILES: O=C(NC1CC1)c1cc2c(s1)-c1ccccc1N(C(=O)c1cccc(N3CCC4(CC3)CC4)n1)CC2]

Example 25 was prepared using a procedure similar to that used to prepare Example 16 where 6-azaspiro[2.5]octane was used in place of morpholine in step b. ESI MS m/z=499.21 [M+H]$^+$.

Example 26

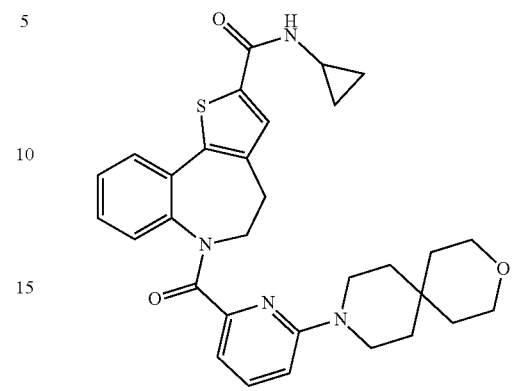

Example 26 was prepared using a procedure similar to that used to prepare Example 16 where 3-oxa-9-azaspiro[5.5]undecane was used in place of morpholine in step b. ESI MS m/z=543.24 [M+H]$^+$.

Example 27

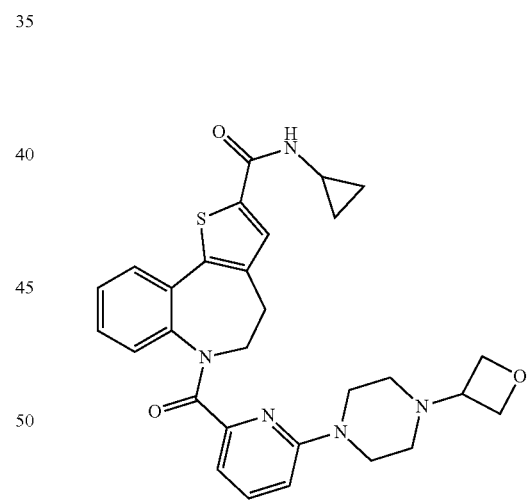

Example 27 was prepared using a procedure similar to that used to prepare Example 16 where 1-(3-oxetanyl)-piperazine was used in place of morpholine in step b. ESI MS m/z=530.22 [M+H]$^+$.

Example 28

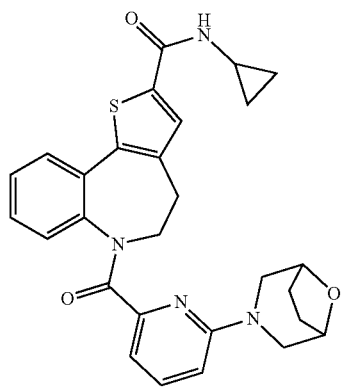 [SMILES: O=C(NC1CC1)c1cc2c(s1)-c1ccccc1N(C(=O)c1cccc(N3CC4CCC(C3)O4)n1)CC2]

Example 28 was prepared using a procedure similar to that used to prepare Example 16 where 8-oxa-3-azabicyclo[3.2.1]octane was used in place of morpholine in step b. ESI MS m/z=501.19 [M+H]$^+$.

Example 29

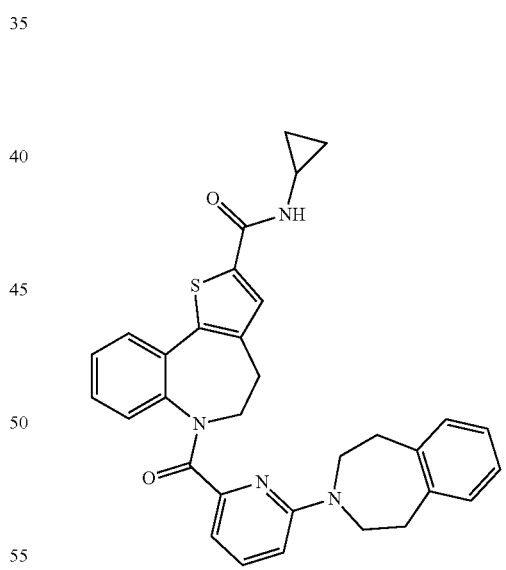

Example 29 was prepared using a procedure similar to that used to prepare Example 16 where 3-oxa-8-azabicyclo[3.2.1]octane was used in place of morpholine in step b. ESI MS m/z=501.19 [M+H]$^+$.

Example 30

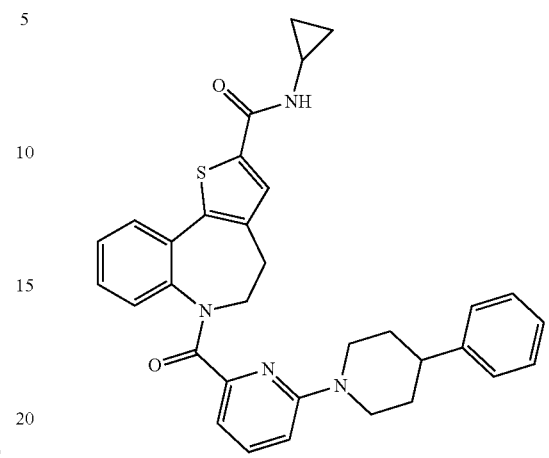

Example 30 was prepared using a procedure similar to that used to prepare Example 16 where 4-phenylpiperidine was used in place of morpholine in step b. ESI MS m/z=549.30 [M+H]$^+$.

Example 31

Example 31 was prepared using a procedure similar to that used to prepare Example 16 where 2,3,4,5-tetrahydro-1H-benzo[d]azepine was used in place of morpholine in step b. ESI MS m/z=535.40 [M+H]$^+$.

Example 32

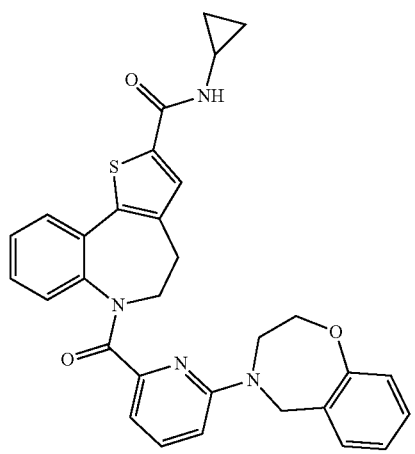 [SMILES: O=C(NC1CC1)c1cc2c(s1)-c1ccccc1N(C(=O)c1cccc(N3CCOc4ccccc4C3)n1)CC2]

Example 32 was prepared using a procedure similar to that used to prepare Example 16 where 2,3,4,5-tetrahydrobenzo[f][1,4]oxazepine was used in place of morpholine in step b. ESI MS m/z=537.25 [M+H]$^+$.

Example 33

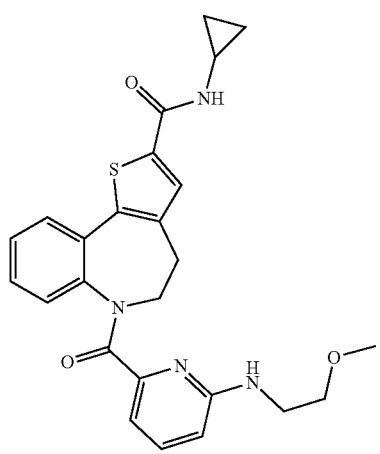 [SMILES: COCCNc1cccc(C(=O)N2CCc3cc(C(=O)NC4CC4)sc3-c3ccccc32)n1]

Example 33 was prepared using a procedure similar to that used to prepare Example 16 where 2-methoxyethan-1-amine was used in place of morpholine in step b. ESI MS m/z=463.15 [M+H]$^+$.

Example 34

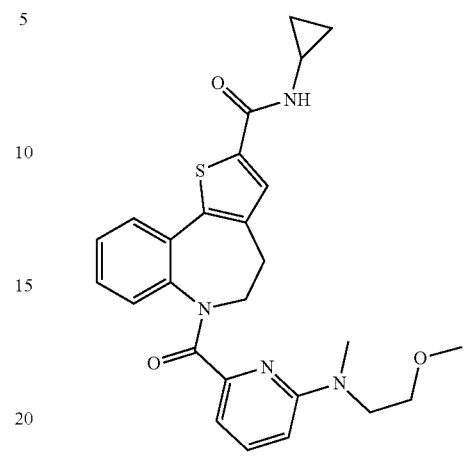

Example 34 was prepared using a procedure similar to that used to prepare Example 16 where 2-methoxy-N-methylethan-1-amine was used in place of morpholine in step b. ESI MS m/z=477.25 [M+H]$^+$.

Example 35

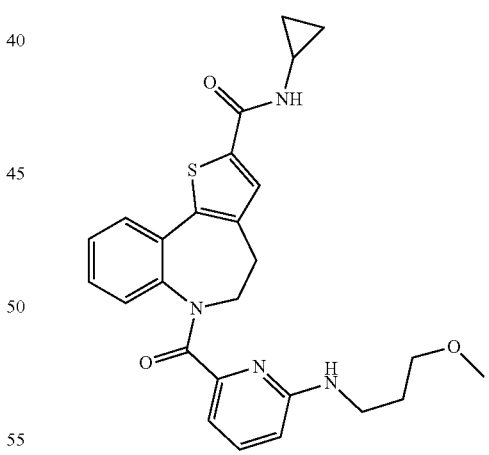

Example 35 was prepared using a procedure similar to that used to prepare Example 16 where 3-methoxypropan-1-amine was used in place of morpholine in step b. ESI MS m/z=477.15 [M+H]$^+$.

Example 36

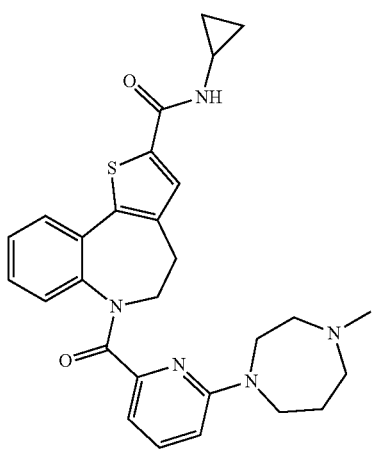 [SMILES: CN1CCCN(c2cccc(C(=O)N3CCc4cc(C(=O)NC5CC5)sc4-c4ccccc43)n2)CC1]

Example 36 was prepared using a procedure similar to that used to prepare Example 16 where 1-methyl-1,4-diazepane was used in place of morpholine in step b. ESI MS m/z=502.25 [M+H]$^+$.

Example 37

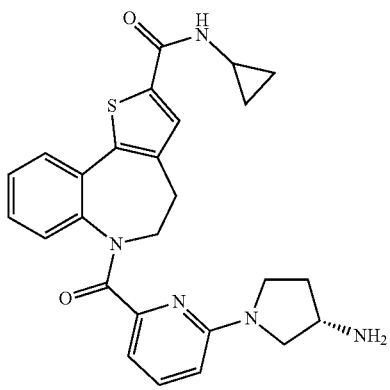 [SMILES: N[C@H]1CCN(c2cccc(C(=O)N3CCc4cc(C(=O)NC5CC5)sc4-c4ccccc43)n2)C1]

Example 37 Step a

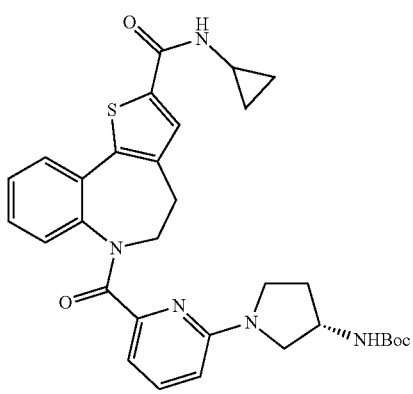 [SMILES: CC(C)(C)OC(=O)N[C@H]1CCN(c2cccc(C(=O)N3CCc4cc(C(=O)NC5CC5)sc4-c4ccccc43)n2)C1]

The desired intermediate was prepared using a procedure similar to that used to prepare Example 16 where (2S)—N-Boc-2-pyrrolidinamine was used in place of morpholine in step b. ESI MS m/z=574.24 [M+H]$^+$.

Example 37 Step b

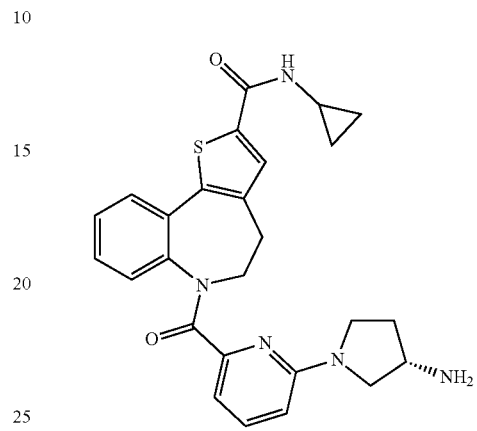

The N-Boc protected intermediate (50 mg, 0.1 mmol) obtained in Example 37 step a was dissolved in DCM (2 mL) and 4M HCl in 1,4-dioxane (2 mL) was added. The resulting mixture was stirred at rt overnight. After diluted with DCM (20 mL) and then cooled down with ice bath, the solution was neutralized to pH=10 with aq. NaOH (2N). The organic layer was washed with brine, dried over Na$_2$SO$_4$, filtered and evaporated. The residue was purified by silica gel column chromatography to give the title compound (17 mg, 36%) as a yellowish foam. ESI MS m/z=474.19 [M+H]$^+$.

Example 38

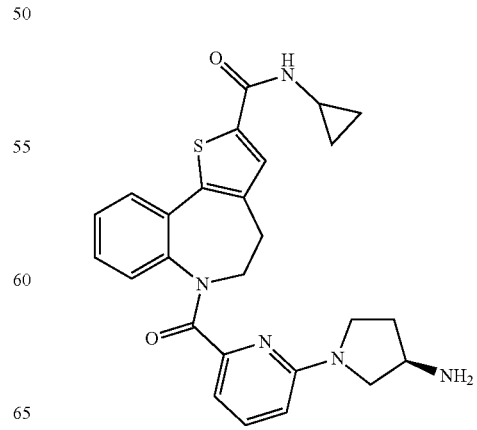

Example 38 Step a

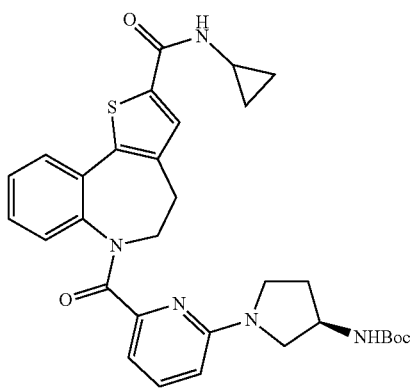 [SMILES: CC(C)(C)OC(=O)N[C@@H]1CCN(c2cccc(C(=O)N3CCc4cc(C(=O)NC5CC5)sc4-c4ccccc43)n2)C1]

The desired intermediate was prepared using a procedure similar to that used to prepare Example 16 where (2R)—N-Boc-2-pyrrolidin amine was used in place of morpholine in step b. ESI MS m/z=574.24 [M+H]$^+$.

Example 38 Step b

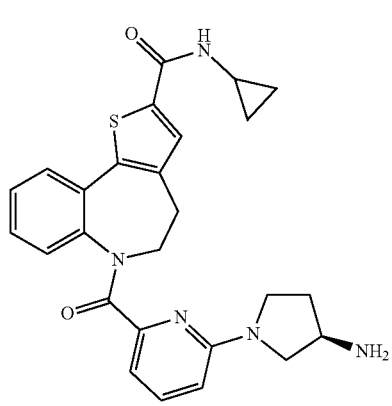 [SMILES: N[C@@H]1CCN(c2cccc(C(=O)N3CCc4cc(C(=O)NC5CC5)sc4-c4ccccc43)n2)C1]

Example 38 was prepared using a procedure similar to that used to prepare Example 37 in step b. ESI MS m/z=474.19 [M+H]$^+$.

Example 39

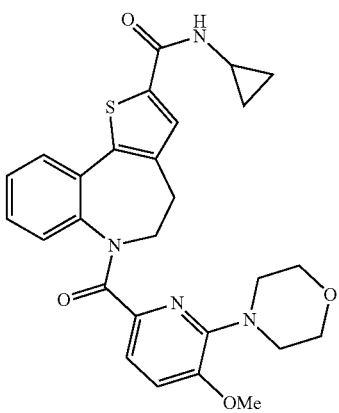 [SMILES: COc1ccc(C(=O)N2CCc3cc(C(=O)NC4CC4)sc3-c3ccccc32)nc1N1CCOCC1]

Example 39 was prepared using a procedure similar to that used to prepare Example 16 where 2-bromo-3-methoxy-pyridine-6-carboxylic acid was used in place of 6-bromopicolinic acid in step a. ESI MS m/z=505.19 [M+H]$^+$.

Example 40

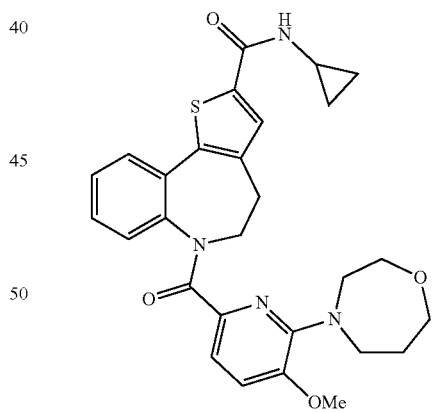

Example 40 was prepared using a procedure similar to that used to prepare Example 16 where 2-bromo-3-methoxy-pyridine-6-carboxylic acid was used in place of 6-bromopicolinic acid in step a. ESI MS m/z=519.20 [M+H]$^+$.

Example 41

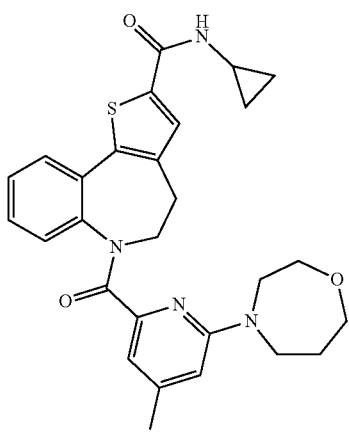 [SMILES: Cc1cc(C(=O)N2CCc3cc(C(=O)NC4CC4)sc3-c3ccccc32)nc(N2CCCOCC2)c1]

Compound 41 was prepared using a procedure similar to that used to prepare Example 16 where 6-chloro-4-methyl-picolinic acid was used in place of 6-bromopicolinic acid in step a. ESI MS m/z=490.16 [M+H]$^+$.

Example 42

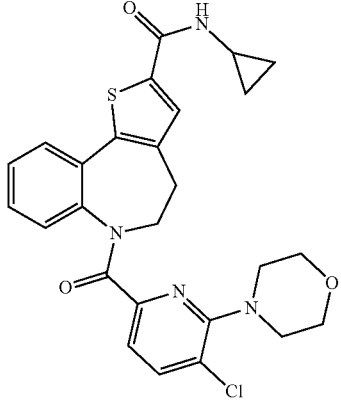 [SMILES: O=C(NC1CC1)c1cc2c(s1)-c1ccccc1N(C(=O)c1ccc(Cl)c(N3CCOCC3)n1)CC2]

Example 42 was prepared using a procedure similar to that used to prepare Example 16 where 2-bromo-3-chloro-pyridine-6-carboxylic acid was used in place of 6-bromopi-colinic acid in step a. ESI MS m/z=509.14 [M+H]$^+$.

Example 43

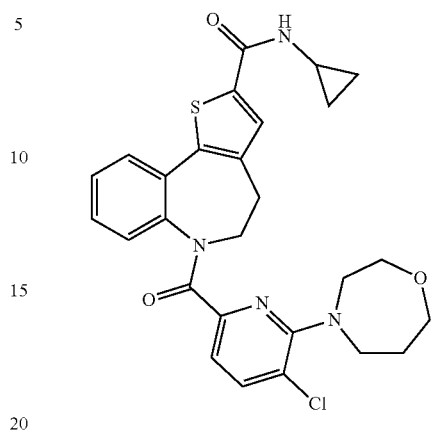

Example 43 was prepared using a procedure similar to that used to prepare Example 16 where 2-bromo-3-chloro-pyridine-6-carboxylic acid was used in place of 6-bromopi-colinic acid in step a. ESI MS m/z=523.15 [M+H]$^+$.

Example 44

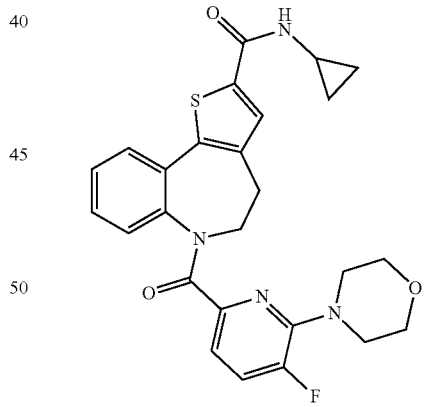

Example 44 was prepared using a procedure similar to that used to prepare Example 16 where 2-bromo-3-fluoro-pyridine-6-carboxylic acid was used in place of 6-bromopi-colinic acid in step a. ESI MS m/z=493.16 [M+H]$^+$.

Example 45

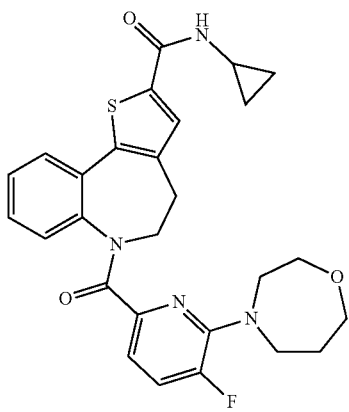 [SMILES: O=C(NC1CC1)c1cc2c(s1)-c1ccccc1N(C(=O)c1ccc(F)c(N3CCCOCC3)n1)CC2]

Example 45 was prepared using a procedure similar to that used to prepare Example 16 where 2-bromo-3-fluoro-pyridine-6-carboxylic acid was used in place of 6-bromopicolinic acid in step a. ESI MS m/z=507.18 [M+H]$^+$.

Example 46

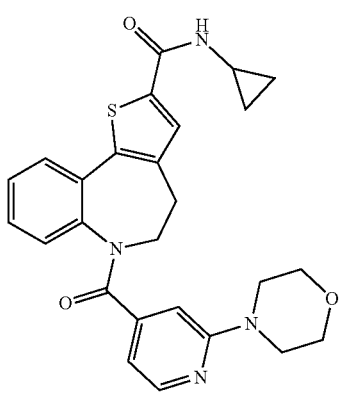 [SMILES: O=C(NC1CC1)c1cc2c(s1)-c1ccccc1N(C(=O)c1ccnc(N3CCOCC3)c1)CC2]

Example 46 was prepared using a procedure similar to that used to prepare Example 16 where 2-bromoisonicotinic acid was used in place of 6-bromopicolinic acid in step a. ESI MS m/z=475.18 [M+H]$^+$.

Example 47

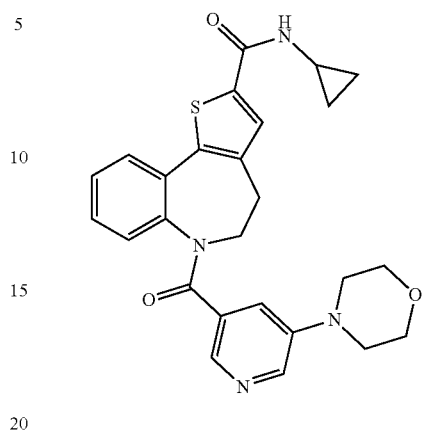

Example 47 was prepared using a procedure similar to that used to prepare Example 16 where 5-bromonicotinic acid was used in place of 6-bromopicolinic acid in step a. ESI MS m/z=475.18 [M+H]$^+$.

Example 48

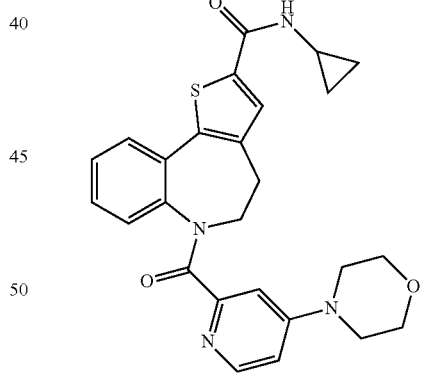

Example 48 was prepared using a procedure similar to that used to prepare Example 16 where 4-bromopicolinic acid was used in place of 6-bromopicolinic acid in step a. ESI MS m/z=475.18 [M+H]$^+$.

Example 49

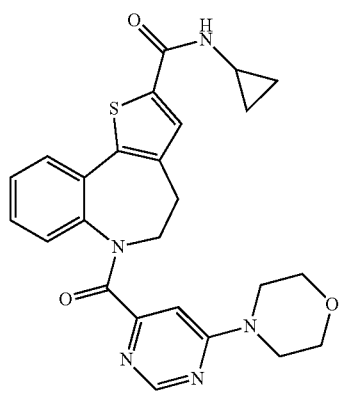

Example 49 was prepared using a procedure similar to that used to prepare Example 16 where 6-bromo-4-pyrimidinecarboxylic acid was used in place of 6-bromopicolinic acid in step a. ESI MS m/z=476.17 [M+H]$^+$.

Example 50

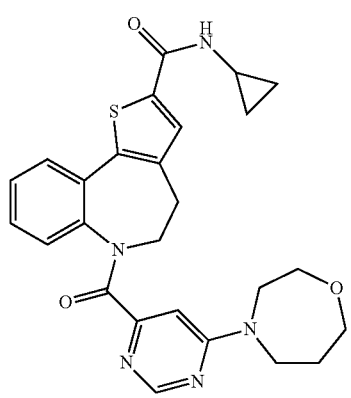 [SMILES: O=C(NC1CC1)c1cc2c(s1)-c1ccccc1N(C(=O)c1cc(N3CCCOCC3)ncn1)CC2]

Example 50 was prepared using a procedure similar to that used to prepare Example 16 where 6-bromo-4-pyrimidinecarboxylic acid was used in place of 6-bromopicolinic acid in step a. ESI MS m/z=490.18 [M+H]$^+$.

Example 51

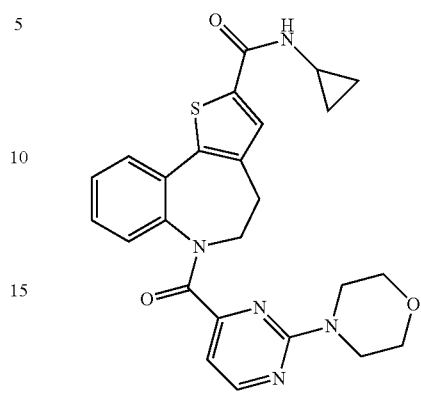

Example 51 was prepared using a procedure similar to that used to prepare Example 16 where 2-bromo-4-pyrimidinecarboxylic acid was used in place of 6-bromopicolinic acid in step a. ESI MS m/z=476.17 [M+H]$^+$.

Example 52

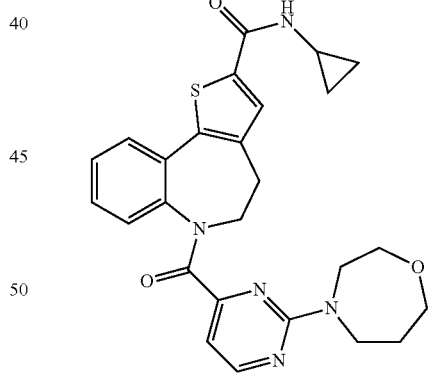

Example 52 was prepared using a procedure similar to that used to prepare Example 16 where 2-bromo-4-pyrimidinecarboxylic acid was used in place of 6-bromopicolinic acid in step a. ESI MS m/z=490.18 [M+H]$^+$.

Example 53
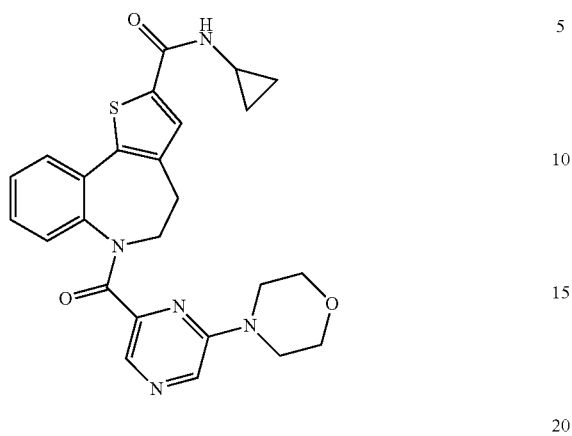
Example 53 was prepared using a procedure similar to that used to prepare Example 16 where 6-bromo-4-pyrazinecarboxylic acid was used in place of 6-bromopicolinic acid in step a. ESI MS m/z=476.17 [M+H]$^+$.
Scheme 3
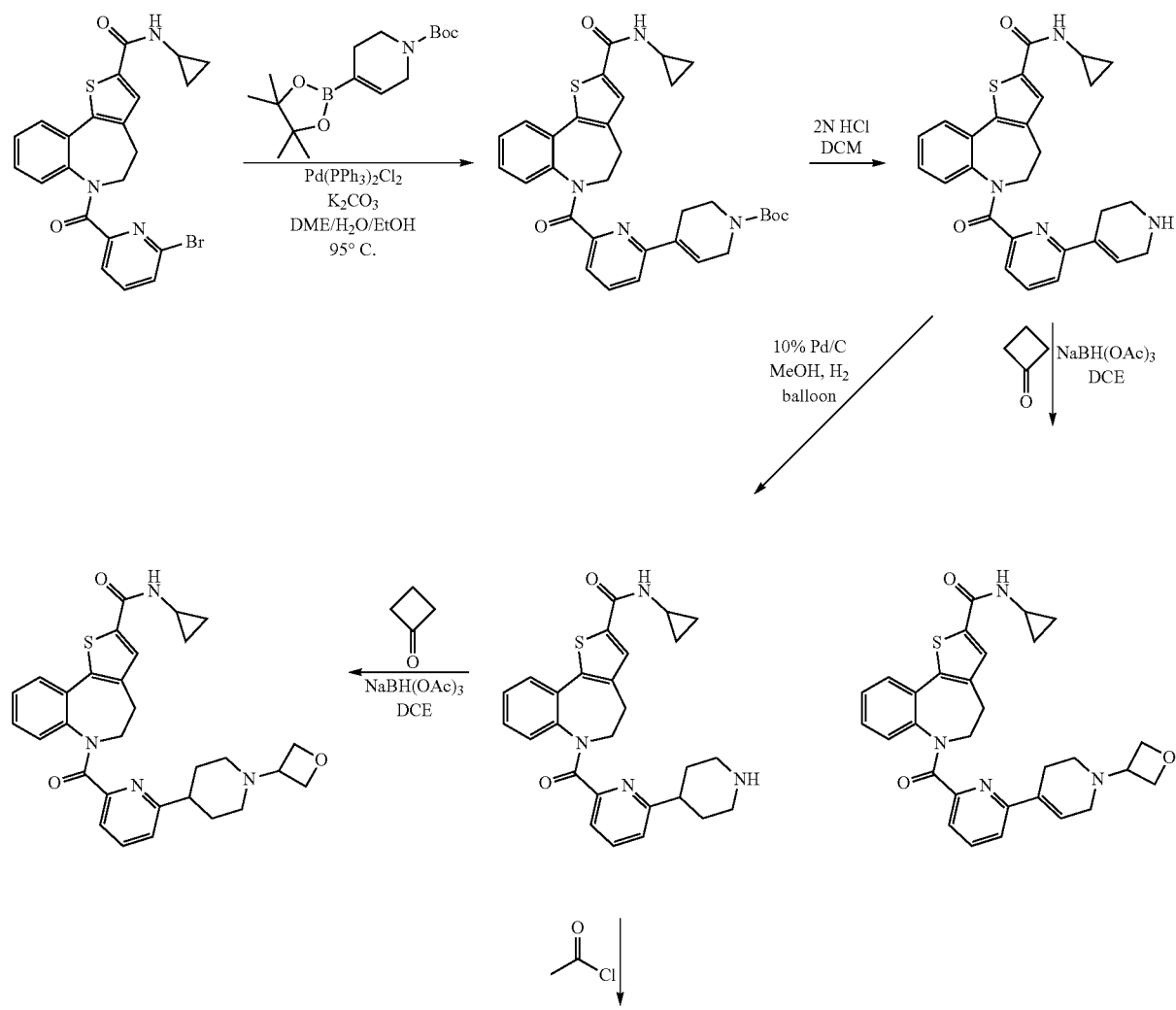

-continued

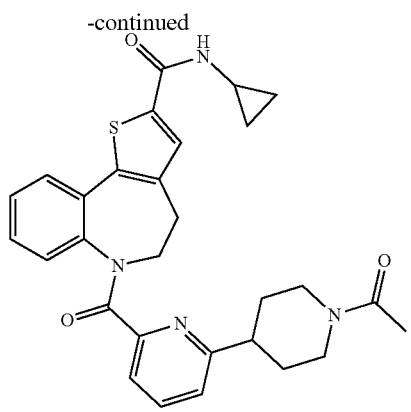

Example 54

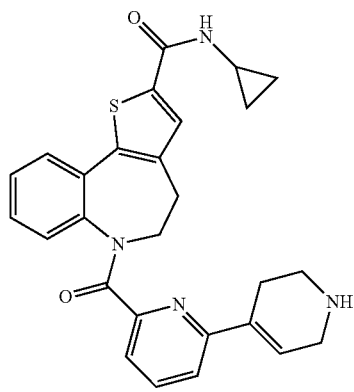 [SMILES: O=C(NC1CC1)c1cc2c(s1)-c1ccccc1N(C(=O)c1cccc(C3=CCNCC3)n1)CC2]

Example 54 Step a

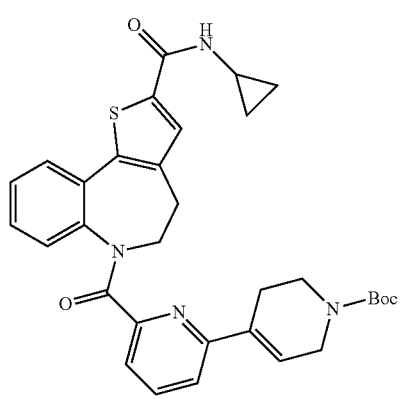 [SMILES: CC(C)(C)OC(=O)N1CC=C(c2cccc(C(=O)N3CCc4cc(C(=O)NC5CC5)sc4-c4ccccc43)n2)CC1]

To a round-bottomed flask bottomed flask was charged with bromide from Example 16 step a (210 mg, 0.45 mmol), pinacol ester (139 mg, 0.45 mmol), Pd(PPh$_3$)$_2$Cl$_2$ (32 mg, 0.045 mmol), potassium carbonate (93 mg, 0.68 mmol), and a mixture of DME/EtOH/H$_2$O (2/1/2, 15 mL). The reaction mixture was degassed and heated at 95° C. with vigorous stirring. After 8 h, the reaction mixture was cooled to room temperature and diluted with ethyl acetate (50 mL). The organic layer was washed with brine, dried over Na$_2$SO$_4$, filtered and concentrated. The residue was purified by silica gel column chromatography to give the title compound (180 mg, 70%) as a white foam. ESI MS m/z=571.23 [M+H]$^+$.

Example 54 Step b

To a solution of compound from Example 54 step a (180 mg, 2.54 mmol) in DCM (10 mL) at 0° C. was added 4 M HCl in 1,4-dioxane (4 mL). The resulting mixture was stirred at rt for 10 hrs, then neutralized with aq. NaHCO$_3$ to pH ~10. The organic layer was washed with brine, dried over Na$_2$SO$_4$, filtered and concentrated to give the title compound (120 mg, 81%) as a pale-yellow oil. ESI MS m/z=471.18 [M+H]$^+$.

Example 55

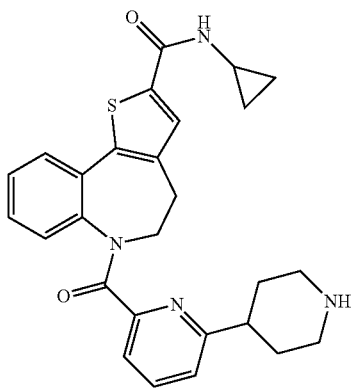 [SMILES: O=C(NC1CC1)c1cc2c(s1)-c1ccccc1N(C(=O)c1cccc(C3CCNCC3)n1)CC2]

To a solution of compound from Example 54 step b (20 mg, 0.04 mmol) in MeOH (8 mL) was added 10% Pd/C (10 mg). After degassed and refilled with $H_2$ three times, the reaction mixture was stirred at rt for 10 hrs with a $H_2$ balloon. The solution was filtered through Celite and evaporated to give the title compound (16 mg, 80%) as a pale yellow foam. ESI MS m/z=473.20 $[M+H]^+$.

Example 56

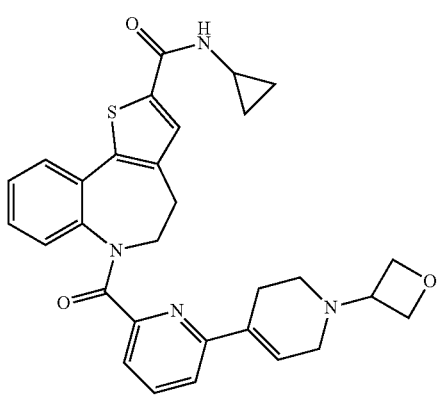 [SMILES: O=C(NC1CC1)c1cc2c(s1)-c1ccccc1N(C(=O)c1cccc(C3=CCN(C4COC4)CC3)n1)CC2]

To a solution of compound from Example 54 (100 mg, 0.21 mmol) in DCE (20 mL) were added acetic acid (3 drops), which was stirred at rt for 2 hrs. After NaBH(OAc)$_3$ (71 mg, 0.32 mmol) was added in one portion, the reaction mixture was stirred at rt for 10 hrs. The reaction was quenched with aq. NaHCO$_3$ and the organic layer was washed with brine, dried over Na$_2$SO$_4$, filtered and concentrated. The residue was purified by silica gel column chromatography to give the title compound (58 mg, 52%) as a white foam. ESI MS m/z=527.21 $[M+H]^+$.

Example 57

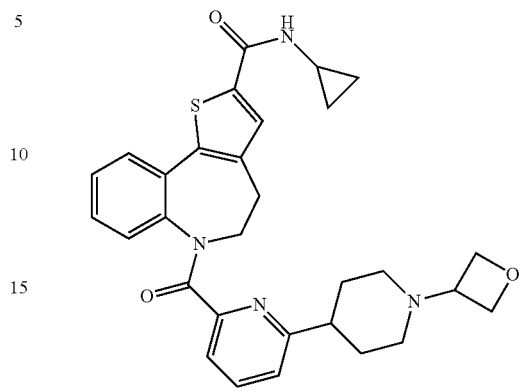

To a solution of compound from Example 56 (20 mg, 0.038 mmol) in DCM/MeOH (1:1, 8 mL) was added 10% Pd/C (10 mg). After degassed and refilled with $H_2$ three times, the reaction mixture was stirred at rt for 10 hrs with a $H_2$ balloon. The solution was filtered through Celite and evaporated to give the title compound (15 mg, 75%) as an off-white foam. ESI MS m/z=529.22 $[M+H]^+$.

Example 58

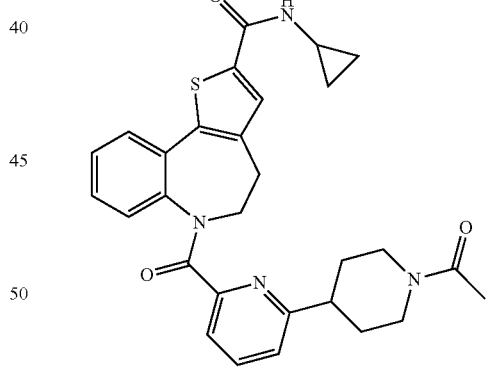

To a solution of compound from Example 55 (12 mg, 0.025 mmol) in DCM (2 mL) were added acetyl chloride (4 mg, 0.05 mmol) and triethylamine (0.1 mL), which was stirred at rt for 12 hrs. After diluted with DCM (5 mL) and neutralized with aq. NaHCO$_3$, the organic layer was washed with brine, dried over Na$_2$SO$_4$, filtered and concentrated. The residue was purified by silica gel column chromatography to give the title compound (7 mg, 54%) as a colorless oil. ESI MS m/z=515.21 $[M+H]^+$.

Scheme 4

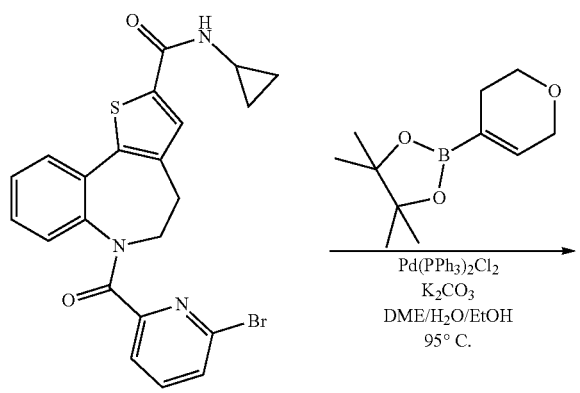

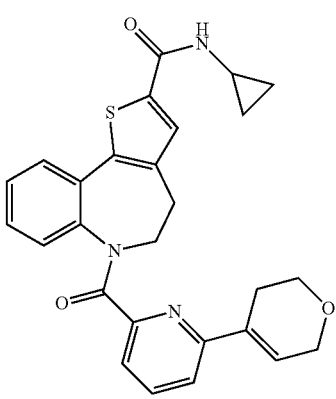 [SMILES: O=C(NC1CC1)c1cc2c(s1)-c1ccccc1N(C(=O)c1cccc(C3=CCOCC3)n1)CC2]

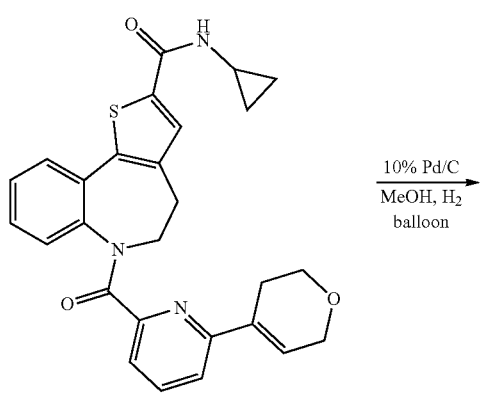

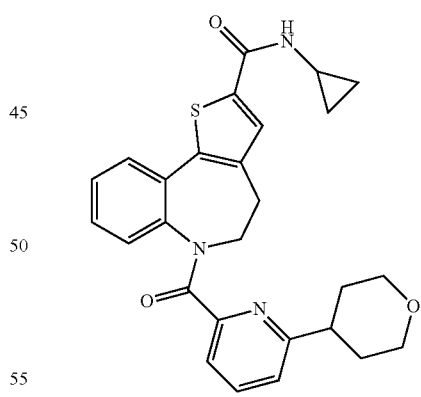

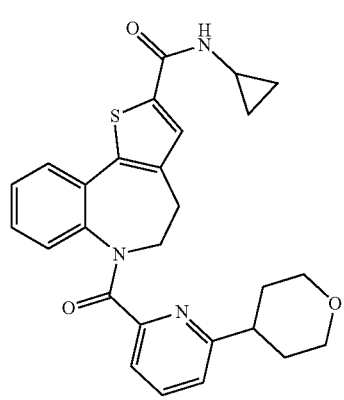

Example 59

To a round-bottomed flask bottomed flask was charged with bromide from Example 16 step a (46.7 mg, 0.10 mmol), pinacol ester (26 mg, 0.12 mmol), Pd(PPh$_3$)$_2$Cl$_2$ (7 mg, 0.01 mmol), potassium carbonate (21 mg, 0.15 mmol), and a mixture of DME/EtOH/H$_2$O (2/1/2, 5 mL). The reaction mixture was degassed and heated at 95° C. with vigorous stirring. After 6 h, the reaction mixture was cooled to room temperature and diluted with ethyl acetate (50 mL). The organic layer was washed with brine, dried over Na$_2$SO$_4$, filtered and concentrated. The residue was purified by silica gel column chromatography to give the title compound (18 mg, 36%) as a pale yellow foam. ESI MS m/z=472.16 [M+H]$^+$.

Example 60

To a solution of compound from Example 59 (12 mg, 0.025 mmol) in DCM/MeOH (1/1, 4 mL) was added 10% Pd/C (5 mg). After degassed and refilled with H$_2$ three times, the reaction mixture was stirred at rt for 10 hrs with a H$_2$ balloon. The solution was filtered through Celite and evaporated to give the title compound (8 mg, 67%) as a pale yellow foam. ESI MS m/z=474.18 [M+H]$^+$.

Scheme 5

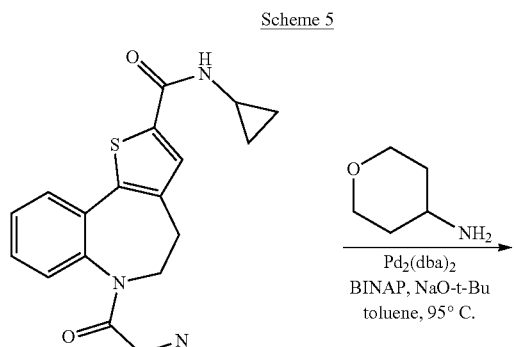

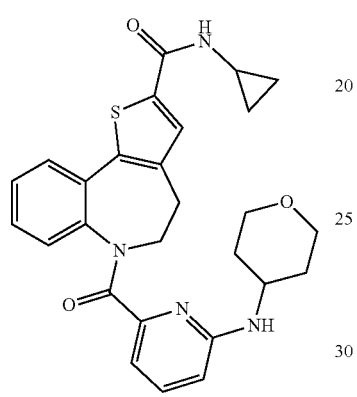

Example 61

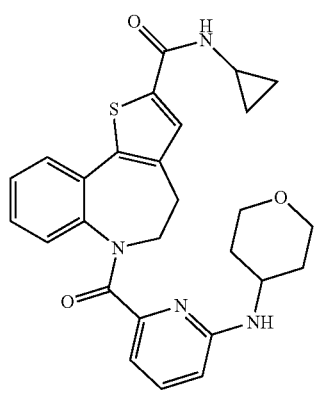 [SMILES: O=C(NC1CC1)c1cc2c(s1)-c1ccccc1N(C(=O)c1cccc(NC3CCOCC3)n1)CC2]

To a round-bottomed flask bottomed flask was charged with bromide from Example 16 step a (46.7 mg, 0.10 mmol), tetrahydro-2H-pyran-4-amine (12 mg, 0.12 mmol), Pd$_2$(dba)$_3$ (1.8 mg, 0.02 mmol), BINAP (2.4 mg, 0.04 mmol), NaO-t-Bu (13.4 mg, 0.14 mmol) in toluene (5 mL). The reaction mixture was degassed and heated at 95° C. with vigorous stirring. After 4 h, the reaction mixture was cooled to room temperature and diluted with ethyl acetate (50 mL). The organic layer was washed with brine, dried over Na$_2$SO$_4$, filtered and concentrated. The residue was purified by silica gel column chromatography to give the title compound (14 mg, 29%) as a white foam. ESI MS m/z=489.19 [M+H]$^+$.

Scheme 6

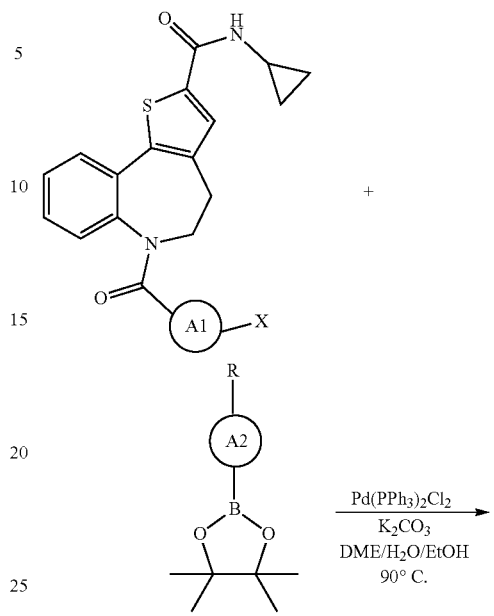

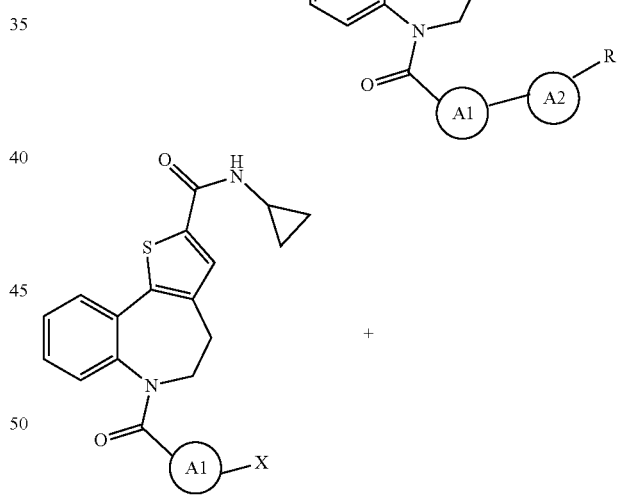

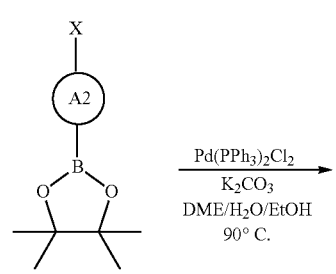

-continued

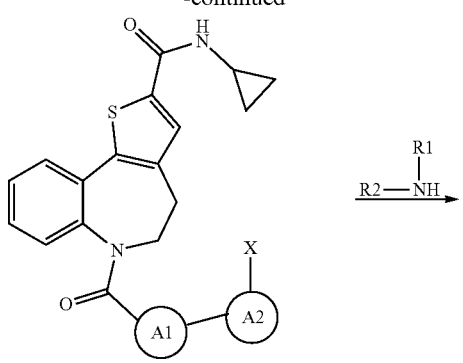

Example 63

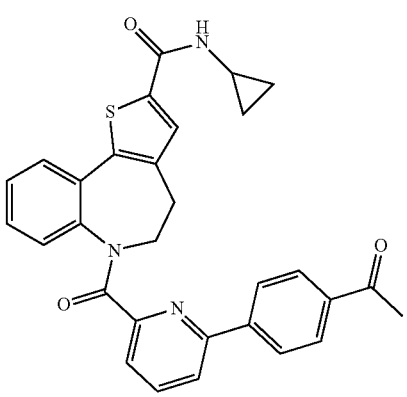

Example 63 was prepared using a procedure similar to that used to prepare Example 54 where 1-(4-(4,4,5,5-tetramethyl-1,3,2-dioxaborolan-2-yl)phenyl)ethan-1-one was used in place of 1-Boc-1,2,5,6-tetrahydropyridine-4-boronic acid pinacol ester in step a. ESI MS m/z=508.16 [M+H]$^+$.

Example 64

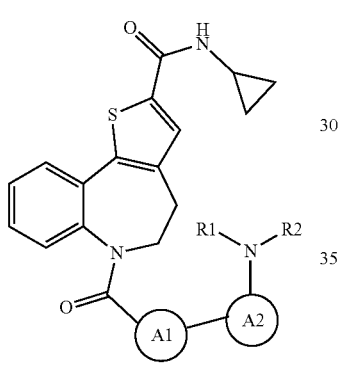

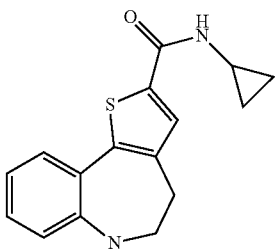

Example 62

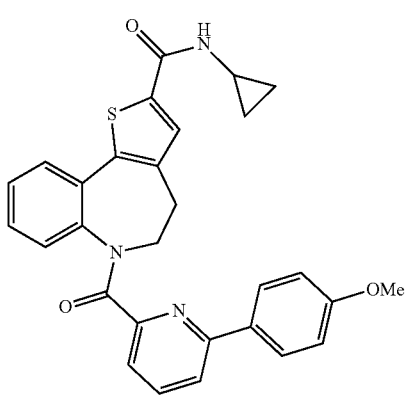 [SMILES: COc1ccc(-c2cccc(C(=O)N3CCc4cc(C(=O)NC5CC5)sc4-c4ccccc43)n2)cc1]

Example 62 was prepared using a procedure similar to that used to prepare Example 54 where 4-methoxyphenylboronic acid pinacol ester was used in place of 1-Boc-1,2,5,6-tetrahydropyridine-4-boronic acid pinacol ester in step a. ESI MS m/z=496.16 [M+H]$^+$.

Example 64 was prepared using a procedure similar to that used to prepare Example 54 where 2-(4-(4,4,4,5,5-tetramethyl-1,3,2-dioxaborolan-2-yl)phenyl)propan-2-ol was used in place of 1-Boc-1,2,5,6-tetrahydropyridine-4-boronic acid pinacol ester in step a. ESI MS m/z=524.20 [M+H]$^+$.

Example 65

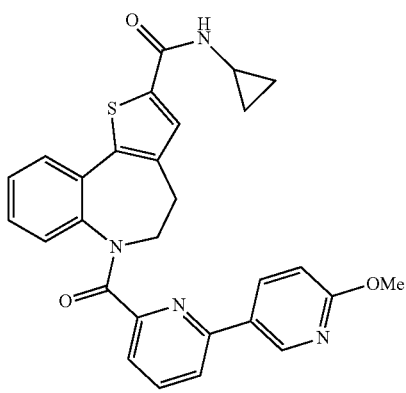 [SMILES: COc1ccc(-c2cccc(C(=O)N3CCc4cc(C(=O)NC5CC5)sc4-c4ccccc43)n2)cn1]

Example 65 was prepared using a procedure similar to that used to prepare Example 54 where 2-methoxy-5-pyridineboronic acid pinacol ester was used in place of 1-Boc-1,2,5,6-tetrahydropyridine-4-boronic acid pinacol ester in step a. ESI MS m/z=497.16 [M+H]$^+$.

Example 66

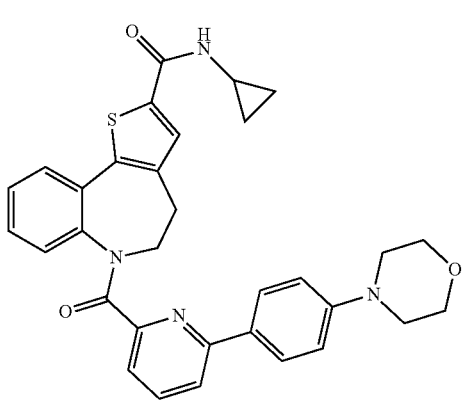 [SMILES: O=C(NC1CC1)c1cc2c(s1)-c1ccccc1N(C(=O)c1cccc(-c3ccc(N4CCOCC4)cc3)n1)CC2]

Example 66 was prepared using a procedure similar to that used to prepare Example 54 where 4-(4-(4,4,5,5-tetramethyl-1,3,2-dioxaborolan-2-yl)phenyl)morpholine was used in place of 1-Boc-1,2,5,6-tetrahydropyridine-4-boronic acid pinacol ester in step a. ESI MS m/z=551.21 [M+H]$^+$.

Example 67

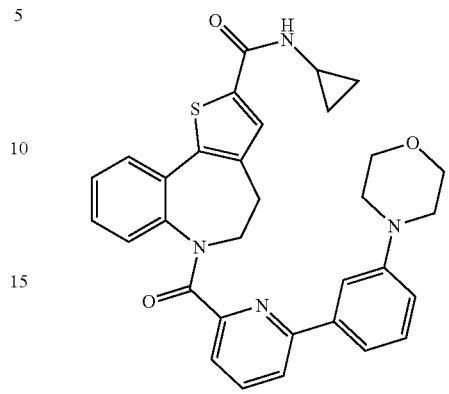

Example 67 was prepared using a procedure similar to that used to prepare Example 54 where 4-(3-(4,4,5,5-tetramethyl-1,3,2-dioxaborolan-2-yl)phenyl)morpholine was used in place of 1-Boc-1,2,5,6-tetrahydropyridine-4-boronic acid pinacol ester in step a. ESI MS m/z=551.21 [M+H]$^+$.

Example 68

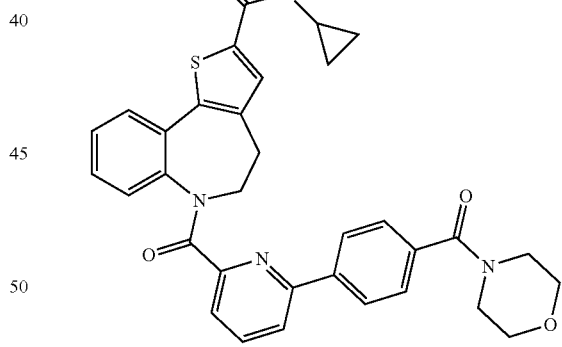

Example 68 was prepared using a procedure similar to that used to prepare Example 54 where morpholino(4-(4,4,5,5-tetramethyl-1,3,2-dioxaborolan-2-yl)phenyl)methanone was used in place of 1-Boc-1,2,5,6-tetrahydropyridine-4-boronic acid pinacol ester in step a. ESI MS m/z=579.20 [M+H]$^+$.

Example 69

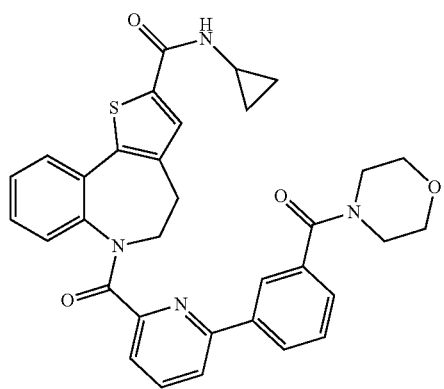 [SMILES: O=C(NC1CC1)c1cc2c(s1)-c1ccccc1N(C(=O)c1cccc(-c3cccc(C(=O)N4CCOCC4)c3)n1)CC2]

Example 69 was prepared using a procedure similar to that used to prepare Example 54 where morpholino(3-(4,4,5,5-tetramethyl-1,3,2-dioxaborolan-2-yl)phenyl)methanone was used in place of 1-Boc-1,2,5,6-tetrahydropyridine-4-boronic acid pinacol ester in step a. ESI MS m/z=579.20 [M+H]$^+$.

Example 70

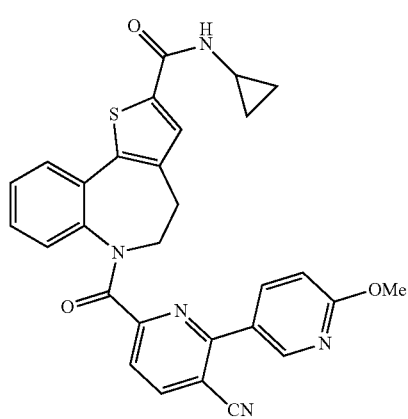 [SMILES: COc1ccc(-c2nc(C(=O)N3CCc4cc(C(=O)NC5CC5)sc4-c4ccccc43)ccc2C#N)cn1]

Example 70 was prepared using a procedure similar to that used to prepare Example 62. ESI MS m/z=522.15 [M+H]$^+$.

Example 71

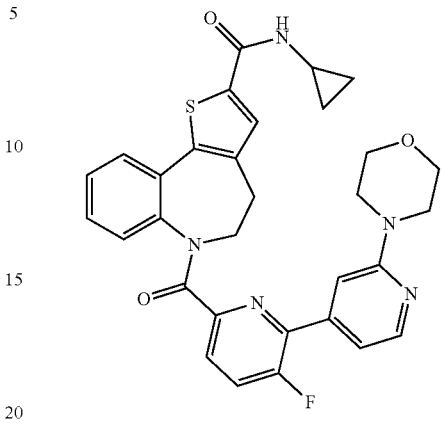

Example 71 was prepared using a procedure similar to that used to prepare Example 62. ESI MS m/z=570.19 [M+H]$^+$.

Example 72

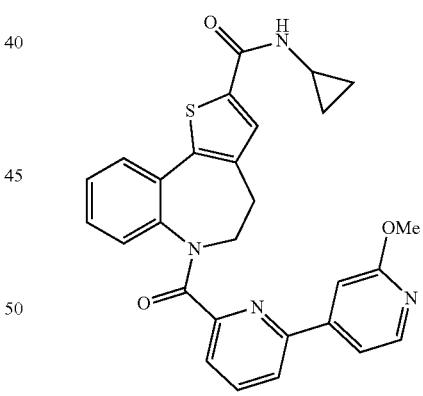

Example 72 was prepared using a procedure similar to that used to prepare Example 54 where 2-methoxy-4-pyridineboronic acid pinacol ester was used in place of 1-Boc-1,2,5,6-tetrahydropyridine-4-boronic acid pinacol ester in step a. ESI MS m/z=497.16 [M+H]$^+$.

Example 73

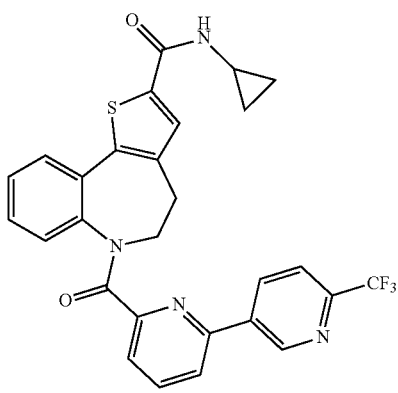 [SMILES: O=C(NC1CC1)c1cc2c(s1)-c1ccccc1N(C(=O)c1cccc(-c3ccc(C(F)(F)F)nc3)n1)CC2]

Example 73 was prepared using a procedure similar to that used to prepare Example 54 where 2-trifluoro-5-pyridineboronic acid pinacol ester was used in place of 1-Boc-1,2,5,6-tetrahydropyridine-4-boronic acid pinacol ester in step a. ESI MS m/z=535.14 [M+H]$^+$.

Example 74

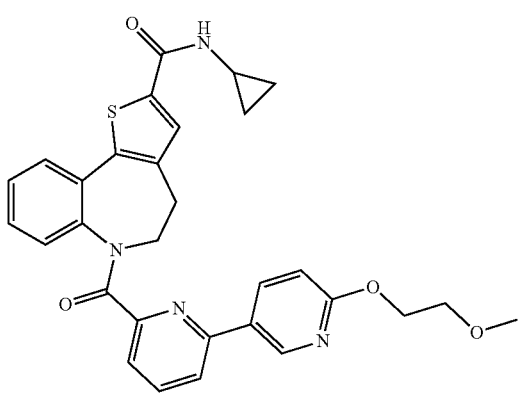 [SMILES: COCCOc1ccc(-c2cccc(C(=O)N3CCc4cc(C(=O)NC5CC5)sc4-c4ccccc43)n2)cn1]

Example 74 was prepared using a procedure similar to that used to prepare Example 54 where 2-(2-methoxyethoxy)-5-(4,4,5,5-tetra methyl-1,3,2-dioxaborolan-2-yl)pyridine was used in place of 1-Boc-1,2,5,6-tetrahydropyridine-4-boronic acid pinacol ester in step a. ESI MS m/z=541.19 [M+H]$^+$.

Example 75

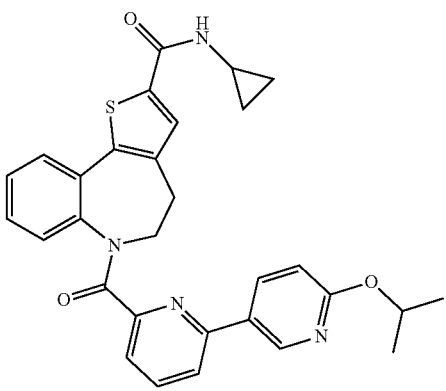 [SMILES: CC(C)Oc1ccc(-c2cccc(C(=O)N3CCc4cc(C(=O)NC5CC5)sc4-c4ccccc43)n2)cn1]

Example 75 was prepared using a procedure similar to that used to prepare Example 54 where 2-isopropoxy-5-pyridineboronic acid pinacol ester was used in place of 1-Boc-1,2,5,6-tetrahydropyridine-4-boronic acid pinacol ester in step a. ESI MS m/z=525.19 [M+H]$^+$.

Example 76

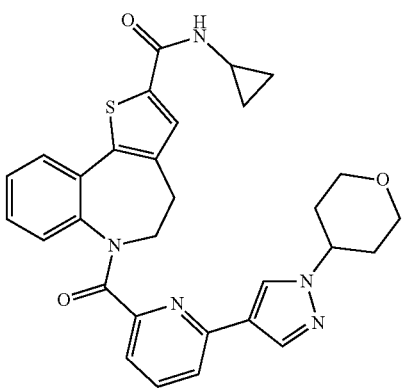 [SMILES: O=C(NC1CC1)c1cc2c(s1)-c1ccccc1N(C(=O)c1cccc(-c3cnn(C4CCOCC4)c3)n1)CC2]

Example 76 was prepared using a procedure similar to that used to prepare Example 54 where 1-(tetrahydro-2H-pyran-4-yl)-4-(4,4,5,5-tetramethyl-1,3,2-dioxaborolan-2-yl)-1H-pyrazole was used in place of 1-Boc-1,2,5,6-tetrahydropyridine-4-boronic acid pinacol ester in step a. ESI MS m/z=540.20 [M+H]$^+$.

Example 77

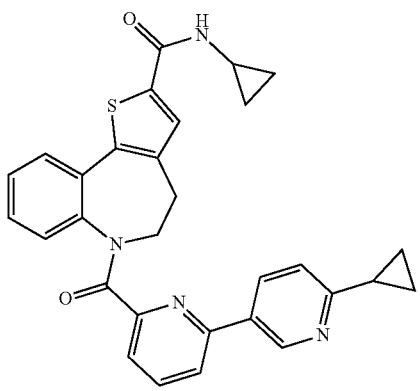 [SMILES: O=C(NC1CC1)c1cc2c(s1)-c1ccccc1N(C(=O)c1cccc(-c3ccc(C4CC4)nc3)n1)CC2]

Example 77 was prepared using a procedure similar to that used to prepare Example 54 where 2-cyclopropyl-5-pyridineboronic acid pinacol ester was used in place of 1-Boc-1,2,5,6-tetrahydropyridine-4-boronic acid pinacol ester in step a. ESI MS m/z=507.18 [M+H]+.

Example 78

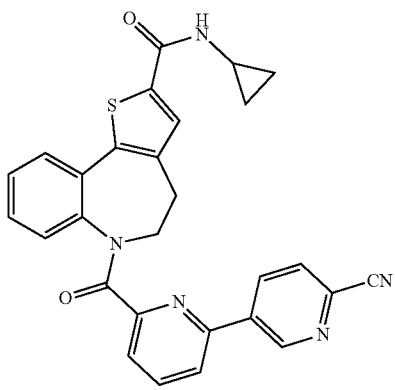

Example 78 was prepared using a procedure similar to that used to prepare Example 54 where 5-(4,4,5,5-tetramethyl-1,3,2-dioxaborolan-2-yl)-2-pyridinecarbonitrile was used in place of 1-Boc-1,2,5,6-tetrahydropyridine-4-boronic acid pinacol ester in step a. ESI MS m/z=492.30 [M+H]+.

Example 79

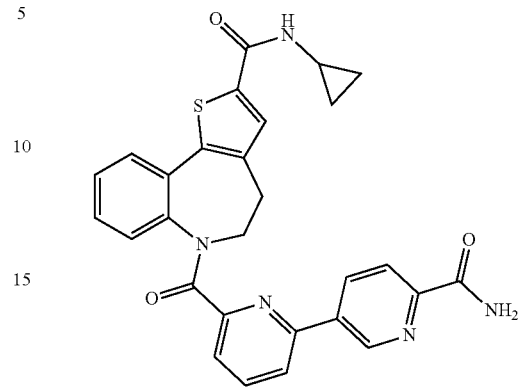

A solution of compound from Example 78 (100 mg, 0.20 mmol) in HCl (37%, 3 mL) was stirred for 1 hr at 50° C. The reaction mixture was then poured into ice water (200 mL). The resulting solution was extracted ethyl acetate and the organic layer was separated, dried and concentrated under vacuum. The obtained residue was purified by prep-HPLC to give the title compound (33.7 mg, 97%) as a white solid. ESI MS m/z=492.30 [M+H]+. 1H NMR (300 MHz, DMSO-$d_6$) δ 0.46-0.76 (m, 4H), 2.07 (s, 1H), 2.80 (tq, J=7.7, 3.9 Hz, 1H), 3.04-3.42 (m, 3H), 4.82-5.00 (m, 1H), 6.82 (dd, J=7.9, 1.3 Hz, 1H), 6.97 (td, J=7.6, 1.4 Hz, 1H), 7.20 (td, J=7.6, 1.3 Hz, 1H), 7.64 (s, 1H), 7.67-7.89 (m, 2H), 7.94-8.13 (m, 4H), 8.52 (d, J=4.1 Hz, 1H), 8.72 (dd, J=1.9, 1.1 Hz, 1H).

Example 80

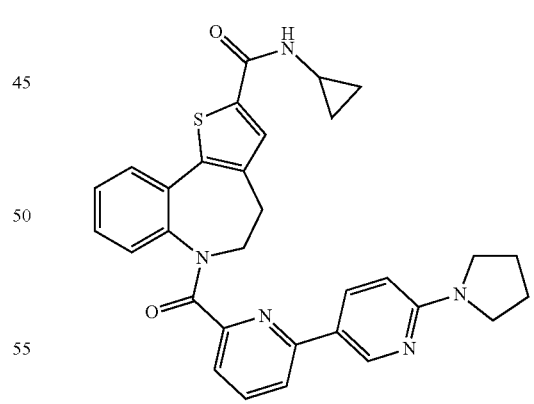

Example 80 was prepared using a procedure similar to that used to prepare Example 54 where 2-(1-pyrrolidinyl)-5-(4,4,5,5-tetramethyl-1,3,2-dioxaborolan-2-yl)pyridine was used in place of 1-Boc-1,2,5,6-tetrahydropyridine-4-boronic acid pinacol ester in step a. ESI MS m/z=536.20 [M+H]+.

Example 81

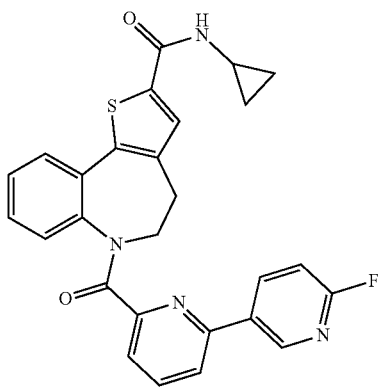 [SMILES: O=C(NC1CC1)c1cc2c(s1)-c1ccccc1N(C(=O)c1cccc(-c3ccc(F)nc3)n1)CC2]

Example 81 was prepared using a procedure similar to that used to prepare Example 54 where 2-fluoro-4-pyridineboronic acid pinacol ester was used in place of 1-Boc-1,2,5,6-tetrahydropyridine-4-boronic acid pinacol ester in step a. ESI MS m/z=485.15 [M+H]$^+$.

Example 82

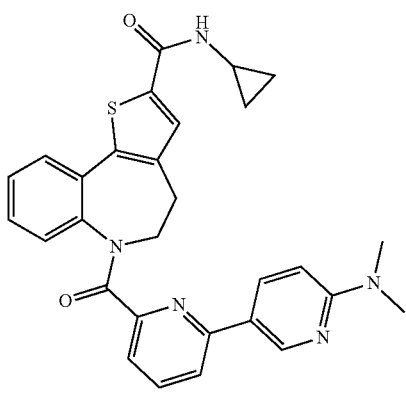 [SMILES: CN(C)c1ccc(-c2cccc(C(=O)N3CCc4cc(C(=O)NC5CC5)sc4-c4ccccc43)n2)cn1]

The compound from Example 81 (97 mg, 0.20 mmol) was added to Me$_2$NH in THF (2 mL) and K$_2$CO$_3$ (138 mg, 1.0 mmol) in DMF (4 mL). The mixture was heated by microwave reactor to 110° C. for 1 h. Then the reaction mixture was diluted with EtOAc and washed with brine. The organic layer was dried and concentrated in vacuo. The residue was purified by prep-HPLC to give the title compound as a white solid (49.2 mg, 48%). ESI MS m/z=510.20 [M+H]$^+$.

Example 83

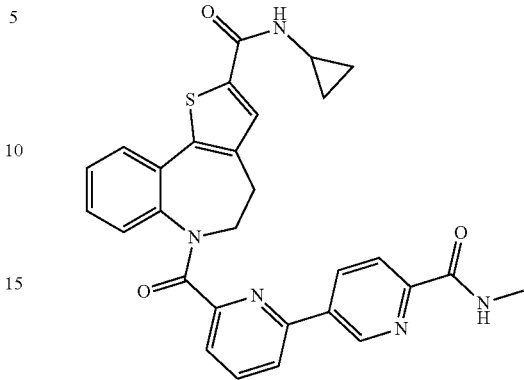

Example 83 Step a

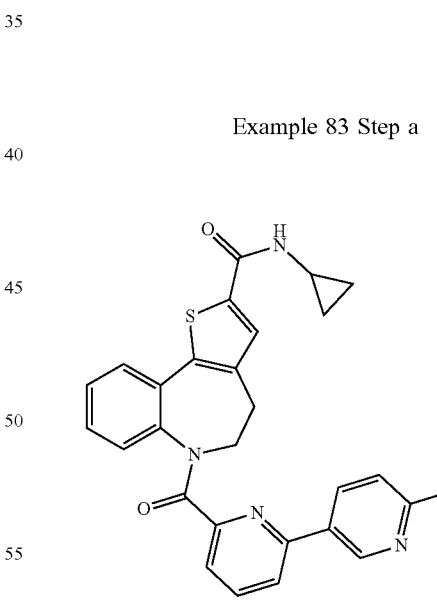

To a solution of Pd(PPh$_3$)$_2$Cl$_2$ (21.1 mg, 0.03 mmol) in EtOH/H$_2$O/DME (2/1/2, 25 mL) were added compound from Example 17 step a (140 mg, 0.3 mmol), K$_2$CO$_3$ (62.1 mg, 0.45 mmol) and [6-(methoxycarbonyl)pyridin-3-yl]boronic acid (65.2 mg, 0.36 mmol). The mixture was stirred for 2 h at 90° C. under N$_2$. Then ethyl acetate (20 mL) and H$_2$O (30 mL) were added to the mixture. The precipitate was collected by filtration to afford the product as a purple solid (102 mg, 67%). ESI MS m/z=511.10 [M+H]$^+$.

Example 83 Step b

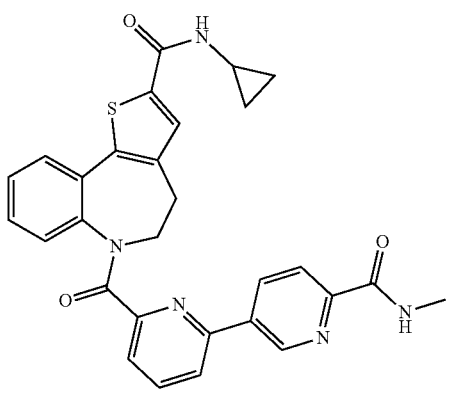 [SMILES: CNC(=O)c1ccc(-c2cccc(C(=O)N3CCc4cc(C(=O)NC5CC5)sc4-c4ccccc43)n2)cn1]

BOP (221 mg, 0.5 mmol) was added to the solution of the compound from Example 83 step a (102 mg, 0.2 mmol), MeNH$_2$ in THF (2 N, 1 mL) and DIPEA (0.5 mL) in DMF (10 mL). The mixture was stirred at rt for 1 h. Then it was poured into water (20 mL) and extracted with EtOAc (25 mL×2). The combined organic layers were dried over Na$_2$SO$_4$, filtered and concentrated. The residue was purified by prep-HPLC to afford the title compound as a white solid (56.6 mg, 54%). ESI MS m/z=524.20 [M+H]$^+$.

Example 84

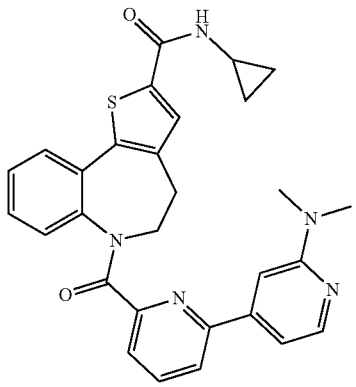 [SMILES: CN(C)c1cc(-c2cccc(C(=O)N3CCc4cc(C(=O)NC5CC5)sc4-c4ccccc43)n2)ccn1]

Example 84 Step a

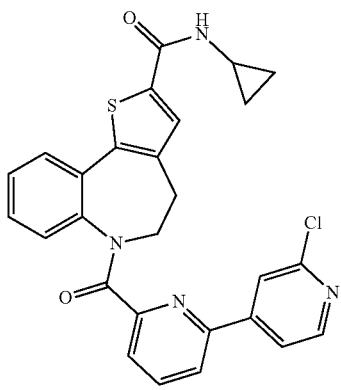 [SMILES: O=C(NC1CC1)c1cc2c(s1)-c1ccccc1N(C(=O)c1cccc(-c3ccnc(Cl)c3)n1)CC2]

A solution of the compound from Example 16 step a (940 mg, 2.0 mmol), 6-chloropyridin-3-ylboronic acid (320 mg, 2.03 mmol), K$_2$CO$_3$ (420 mg, 3.04 mmol), Pd(PPh$_3$)$_2$Cl$_2$ (150 mg, 0.2 mmol), DME (20 mL), H$_2$O (10 mL) in EtOH (20 mL) was hated at 90° C. for 1 h. The mixture was diluted with water, extracted with EtOAc. The organic phase was dried, filtered and concentrated. The residue was purified by silica gel column chromatography to give the desired compound as a yellow solid (1.12 g, 76%). ESI MS m/z=501.25 [M+H]$^+$.

Example 84 Step b

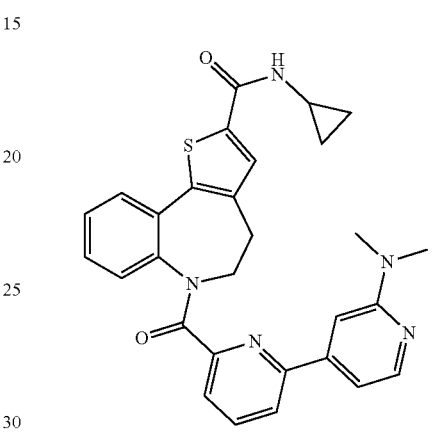

A solution of the compound from Example 84 step a (120 mg, 0.24 mmol), K$_2$CO$_3$ (200 mg, 1.45 mmol) and DMA (2 ml) in DMF (2 mL) was heated at 150° C. for 5 hrs under microwave. The mixture was purified by prep-HPLC to give the tile compound (6.8 mg, 5.6%) as a yellow solid. ESI MS m/z=510.25 [M+H]$^+$. $^1$H NMR (300 MHz, DMSO-d$_6$) δ 0.55 (d, J=3.6 Hz, 2H), 0.69 (d, J=7.2 Hz, 2H), 2.74-2.84 (m, 1H), 3.00 (s, 6H), 3.07-3.31 (m, 2H), 4.89 (s, 1H), 6.49-6.57 (m, 1H), 6.67-6.82 (m, 2H), 6.86-7.02 (m, 1H), 7.18 (t, J=7.7 Hz, 1H), 7.61-7.73 (m, 2H), 7.78 (d, J=7.7 Hz, 1H), 7.88-8.03 (m, 3H), 8.53 (d, J=4.3 Hz, 1H).

Example 85

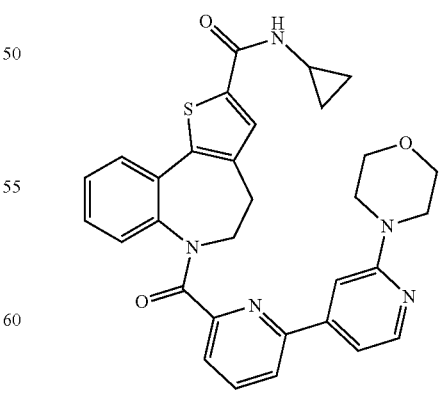

Example 85 was prepared using a procedure similar to that used to prepare Example 84. ESI MS m/z=552.20 [M+H]$^+$.

Example 86

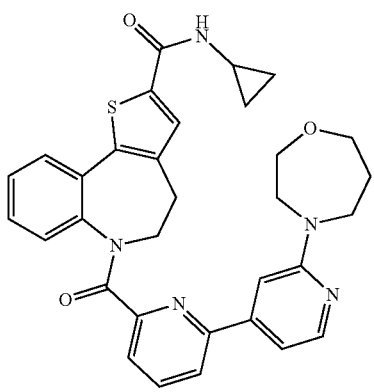 [SMILES: O=C(NC1CC1)c1cc2c(s1)-c1ccccc1N(C(=O)c1cccc(-c3ccnc(N4CCCOCC4)c3)n1)CC2]

Example 86 was prepared using a procedure similar to that used to prepare Example 84. ESI MS m/z=566.22 [M+H]⁺.

Example 87

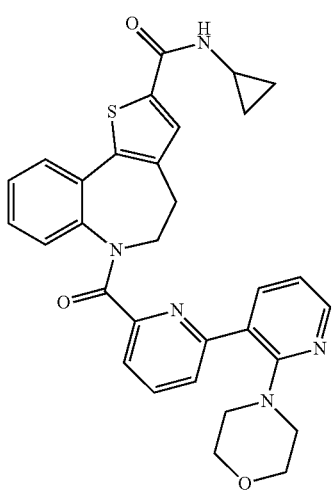 [SMILES: O=C(NC1CC1)c1cc2c(s1)-c1ccccc1N(C(=O)c1cccc(-c3cccnc3N3CCOCC3)n1)CC2]

Example 87 was prepared using a procedure similar to that used to prepare Example 84. ESI MS m/z=552.20 [M+H]⁺.

Example 88

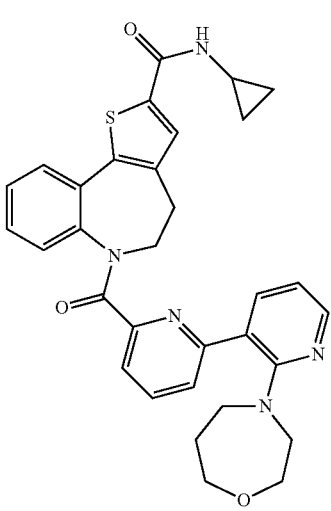 [SMILES: O=C(NC1CC1)c1cc2c(s1)-c1ccccc1N(C(=O)c1cccc(-c3cccnc3N3CCCOCC3)n1)CC2]

Example 88 was prepared using a procedure similar to that used to prepare Example 84. ESI MS m/z=566.22 [M+H]⁺.

Example 89

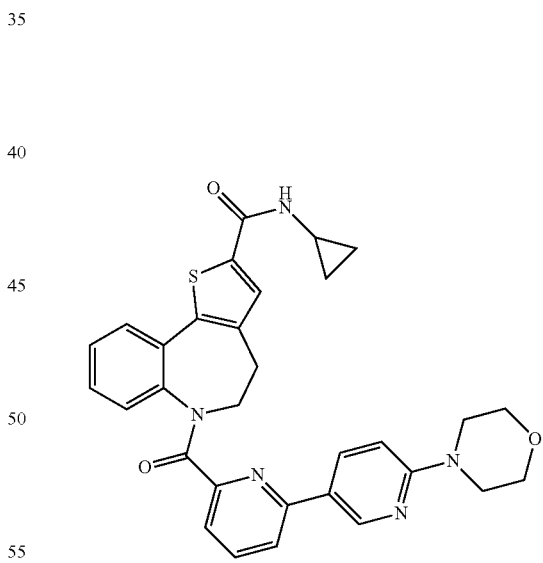

Example 89 was prepared using a procedure similar to that used to prepare Example 84. ESI MS m/z=552.20 [M+H]⁺.

Example 90

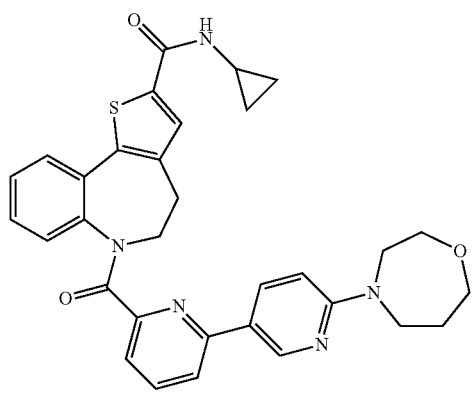 [SMILES: O=C(NC1CC1)c1cc2c(s1)-c1ccccc1N(C(=O)c1cccc(-c3ccc(N4CCCOCC4)nc3)n1)CC2]

Example 90 was prepared using a procedure similar to that used to prepare Example 84. ESI MS m/z=566.22 [M+H]+.

Example 91

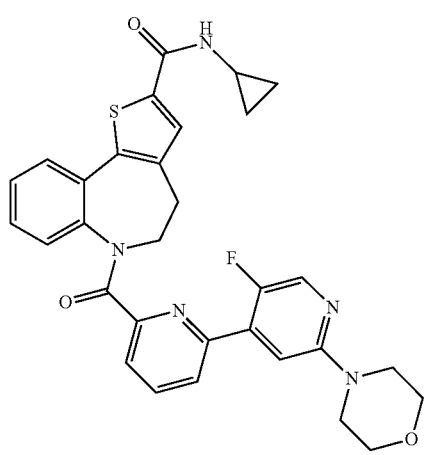 [SMILES: O=C(NC1CC1)c1cc2c(s1)-c1ccccc1N(C(=O)c1cccc(-c3cc(N4CCOCC4)ncc3F)n1)CC2]

Example 91 was prepared using a procedure similar to that used to prepare Example 84. ESI MS m z=570.19 [M+H]+.

Example 92

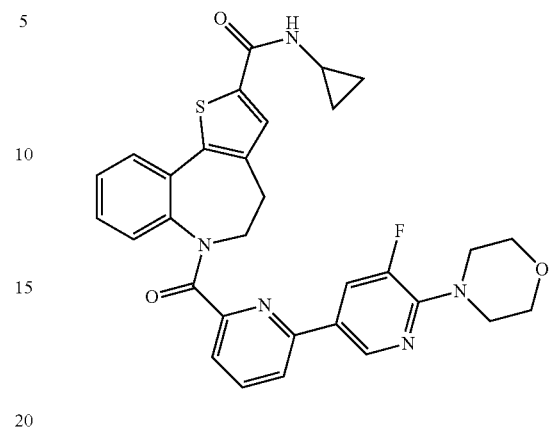

Example 92 was prepared using a procedure similar to that used to prepare Example 84. ESI MS m z=570.19 [M+H]+.

Example 93

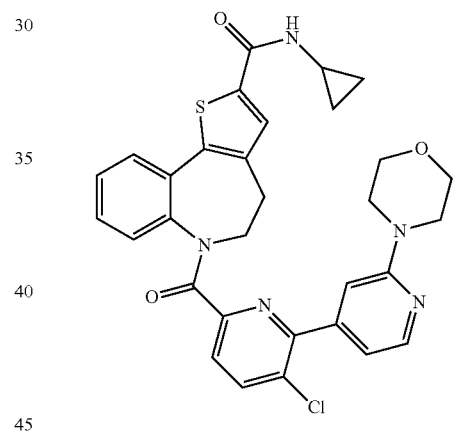

Example 93 was prepared using a procedure similar to that used to prepare Example 84. ESI MS m/z=586.16 [M+H]+.

Scheme 7

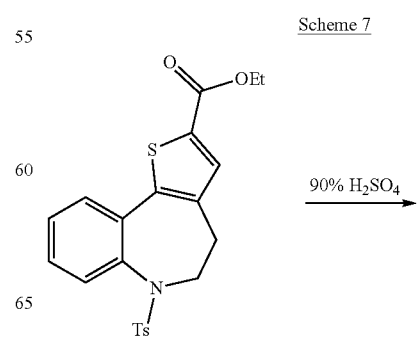

90% $H_2SO_4$

-continued

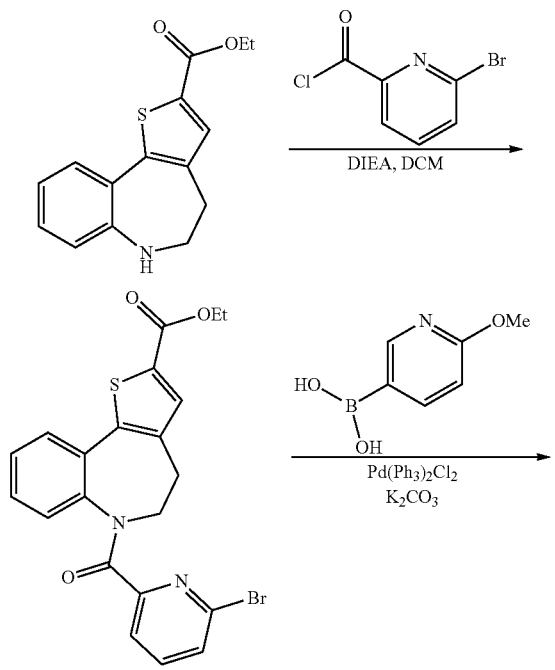

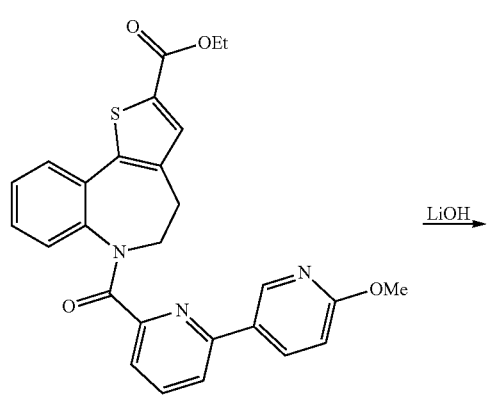

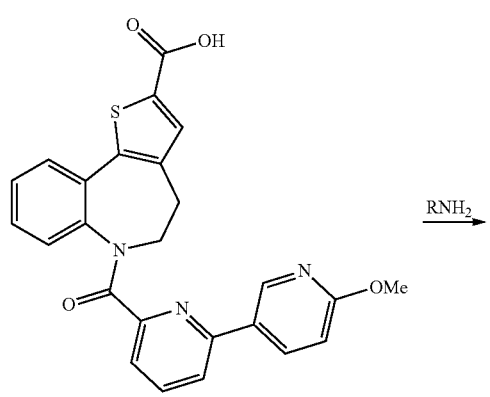

-continued

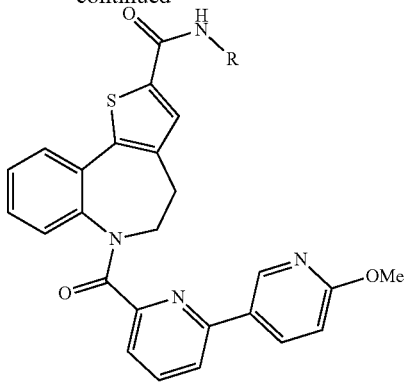

Example 94

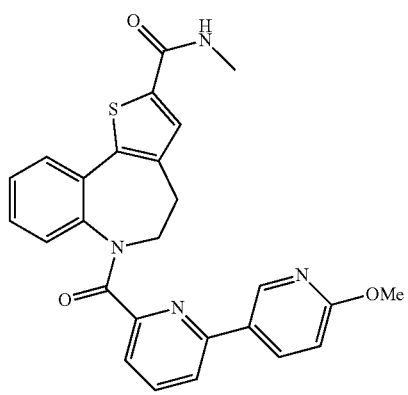 [SMILES: CNC(=O)c1cc2c(s1)-c1ccccc1N(C(=O)c1cccc(-c3ccc(OC)nc3)n1)CC2]

Example 94 Step a

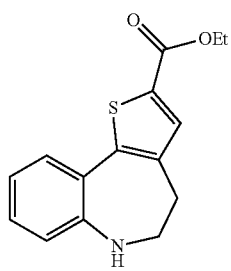 [SMILES: CCOC(=O)c1cc2c(s1)-c1ccccc1NCC2]

Compound from Example 1 step c (10 g, 23.4 mmol) was added to 90% $H_2SO_4$ (100 mL) at 0° C. The mixture was stirred for 10 min at 0° C. and then warmed to room temperature overnight. Ice water was added to the mixture and the precipitated solid was filtered. The filter cake was washed with water and dried under reduced pressure to give the desired product as a yellow solid (5.0 g, 78%). ESI MS m/z=274.05 [M+H]$^+$.

Example 94 Step b

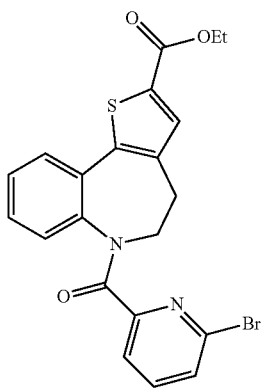 [SMILES: CCOC(=O)c1cc2c(s1)-c1ccccc1N(C(=O)c1cccc(Br)n1)CC2]

To a stirring solution of compound from Example 94 step a (3.0 g, 10.97 mmol) in DCM (50 mL) was added DIEA (9.0 mL, 54.85 mmol). The mixture was cooled with ice bath and 6-bromopicolinoyl chloride (3.13 g, 14.27 mmol) was added. The mixture was then warmed to room temperature and stirred for 2 hrs. Water (50 mL) was added and the mixture was extracted with DCM. The organic layer was dried, filtered and evaporated in vacuo. The resulted residue was purified by silica gel column chromatography to give the desired product as a yellow solid (3.9 g, 76%). ESI MS m/z=274.05 [M+H]$^+$.

Example 94 Step c

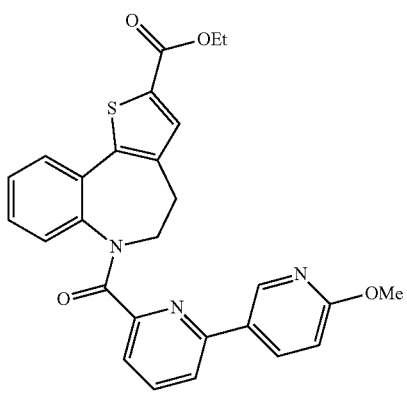 [SMILES: CCOC(=O)c1cc2c(s1)-c1ccccc1N(C(=O)c1cccc(-c3ccc(OC)nc3)n1)CC2]

To a stirring solution of compound from Example 94 step b (1.5 g, 3.28 mmol) in DME/H$_2$O/EtOH (2/1/2, 50 mL) were added 6-methoxypyridin-3-ylboronic acid (606 mg, 3.96 mmol) and K$_2$CO$_3$ (684 mg, 4.95 mmol). The mixture was refluxed for 4 hrs and then it was concentrated under reduced pressure. The residue was purified by silica gel column chromatography to give desired product (1.5 g, 94%) as a yellow solid. ESI MS m/z=486.15 [M+H]$^+$.

Example 94 Step d

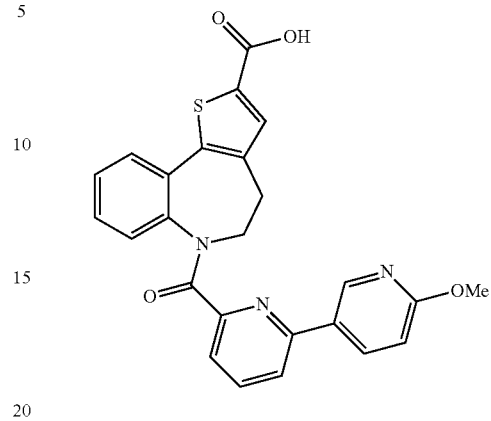

To a stirring solution of compound from Example 94 step c (1.2 g, 2.47 mmol) in THF/MeOH/H$_2$O (3/1/1, 15 mL) was added LiOH (119 mg, 2.94 mmol). The mixture was stirred at room temperature for 2 hrs. After adjusting the pH to 5 by adding aq. 2 N HCl, the mixture was concentrated under reduced pressure and the residue was purified by silica gel column chromatography to give the desired product (905 mg, 80%) as a white solid. ESI MS m/z=458.10 [M+H]$^+$. $^1$H NMR (300 MHz, DMSO-d$_6$) δ 3.04-3.29 (m, 3H), 3.87 (s, 3H), 4.81-4.94 (m, 1H), 6.73 (dd, J=21.3, 8.4 Hz, 2H), 6.95 (t, J=7.7 Hz, 1H), 7.17 (t, J=7.3 Hz, 1H), 7.42 (s, 1H), 7.53-7.64 (m, 2H), 7.74-7.95 (m, 3H), 8.19-8.21 (m, 1H), 8.44 (d, J=2.4 Hz, 1H).

Example 94 Step e

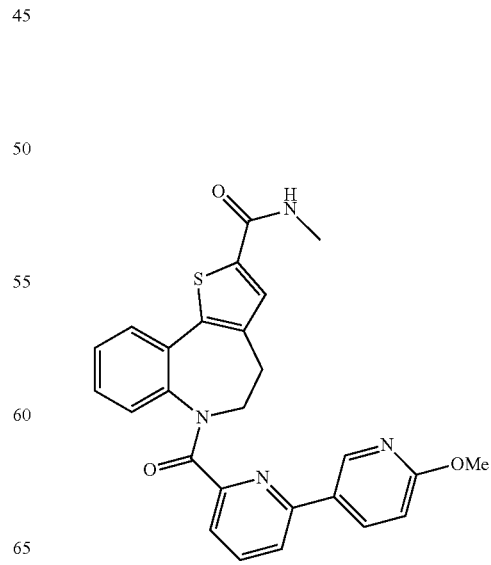

To a stirring solution of compound from Example 94 step d (80 mg, 0.18 mmol) in DMF (2 mL) was added DIEA (0.43 mL, 2.6 mmol) and BOP (387 mg, 0.88 mmol). Then a solution of 2M MeNH$_2$ in THF (1 mL, 2.0 mmol) was added and the mixture was stirred at room temperature for 2 hrs. Solvent was removed and the residue was purified by prep-HPLC to give the title product as a white solid (51.2 mg, 62%). ESI MS m/z=471.15 [M+H]$^+$. $^1$H NMR (300 MHz, DMSO-d$_6$) δ 2.76 (d, J=4.4 Hz, 3H), 3.07-3.42 (m, 3H), 3.87 (s, 3H), 4.83-4.96 (m, 1H), 6.70 (d, J=8.7 Hz, 1H), 6.79 (dd, J=7.8 Hz, 1.3 Hz, 1H), 6.97 (td, J=7.6, 1.4 Hz, 1H), 7.18 (td, J=7.6, 1.3 Hz, 1H), 7.50-7.67 (m, 2H), 7.76-7.96 (m, 3H), 8.42 (d, J=2.4 Hz, 1H), 8.50 (d, J=4.7 Hz, 1H).

Example 95

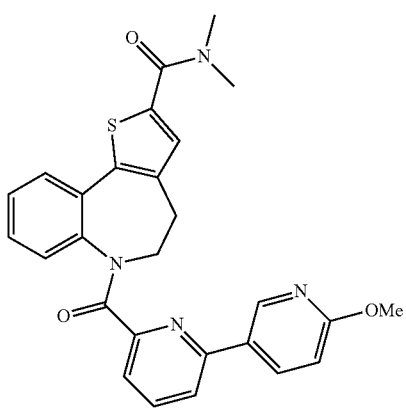 [SMILES: COc1ccc(-c2cccc(C(=O)N3CCc4cc(C(=O)N(C)C)sc4-c4ccccc43)n2)cn1]

To a stirring solution of compound from Example 94 step d (80 mg, 0.18 mmol) in DMF (2 mL) was added DIEA (0.43 mL, 2.6 mmol) and HATU (333 mg, 0.88 mmol). Then dimethylamine hydrochloride (143 mg, 1.75 mmol) was added and the mixture was stirred at room temperature for 2 hrs. Water was added and the mixture was extracted with ethyl acetate. The combined organic phases were concentrated and purified by prep-HPLC to give the title product as a white solid (30.4 mg, 36%). ESI MS m/z=485.15 [M+H]$^+$. $^1$H NMR (300 MHz, DMSO-d$_6$) δ 3.04-3.33 (m, 9H), 3.86 (s, 3H), 4.90 (dd, J=13.1, 5.3 Hz, 1H), 6.75 (dd, J=24.8, 8.3 Hz, 2H), 6.97 (t, J=7.6 Hz, 1H), 7.17 (t, J=7.6 Hz, 1H), 7.45 (s, 1H), 7.60 (dd, J=17.4, 8.0 Hz, 2H), 7.75-7.94 (m, 3H), 8.43 (s, 1H).

Example 96

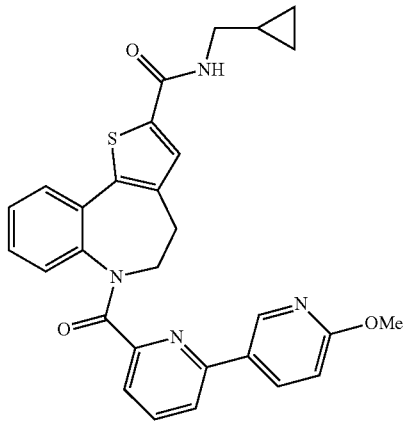 [SMILES: COc1ccc(-c2cccc(C(=O)N3CCc4cc(C(=O)NCC5CC5)sc4-c4ccccc43)n2)cn1]

Example 96 was prepared using a procedure similar to that used to prepare Example 95 where cyclopropylmethanarine was used in place of dimethylamine. ESI MS m/z=511.20 [M+H]$^+$. $^1$H NMR (300 MHz, DMSO-d$_6$) δ 0.16-0.27 (m, 2H), 0.36-0.49 (m, 2H), 1.00 (tdd, J=7.6, 5.3, 4.0 Hz, 1H), 3.09-3.16 (m, 2H), 3.25-3.35 (m, 2H), 3.31-3.39 (m, 1H), 3.87 (s, 3H), 4.84-4.97 (m, 1H), 6.70 (d, J=8.7 Hz, 1H), 6.79 (dd, J=8.7 Hz, 1.3 Hz, 1H), 6.98 (td, J=7.6, 1.4 Hz, 1H), 7.18 (td, J=7.6, 1.3 Hz, 1H), 7.51-7.67 (m, 2H), 7.70 (s, 1H), 7.76-7.96 (m, 3H), 8.43 (d, J=2.4 Hz, 1H), 8.63 (t, J=5.7 Hz, 1H).

Example 97

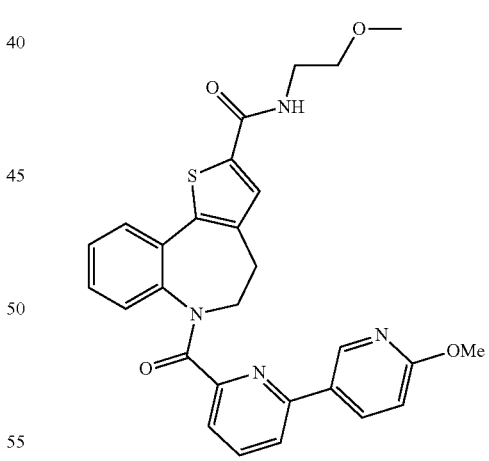

Example 97 was prepared using a procedure similar to that used to prepare Example 95 where 2-methoxyethan-1-amine was used in place of dimethylamine. ESI MS m/z=515.20 [M+H]$^+$. $^1$H NMR (300 MHz, DMSO-d$_6$) δ 3.11-3.17 (m, 1H), 3.25 (s, 3H), 3.29-3.33 (m, 2H), 3.39-3.46 (m, 4H), 3.87 (s, 3H), 4.85-4.96 (m, 1H), 6.70 (d, J=8.7 Hz, 1H), 6.79 (dd, J=7.8 Hz, 1.4 Hz), 6.98 (td, J=7.6 Hz, 1.4 Hz, 1H), 7.18 (td, J=7.6 Hz, 1.3 Hz, 1H), 7.53-7.65 (m, 2H), 7.70 (s, 2H), 7.76-7.93 (m, 3H), 8.43 (d, J=2.4 Hz, 1H), 8.61 (t, J=5.3 Hz, 1H).

Scheme 8
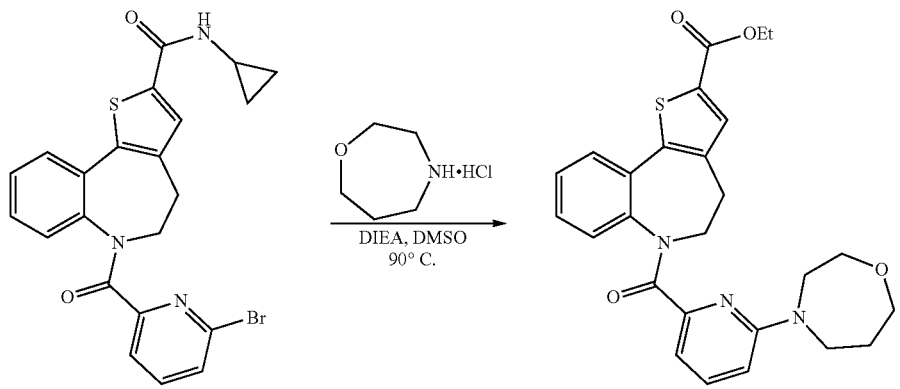
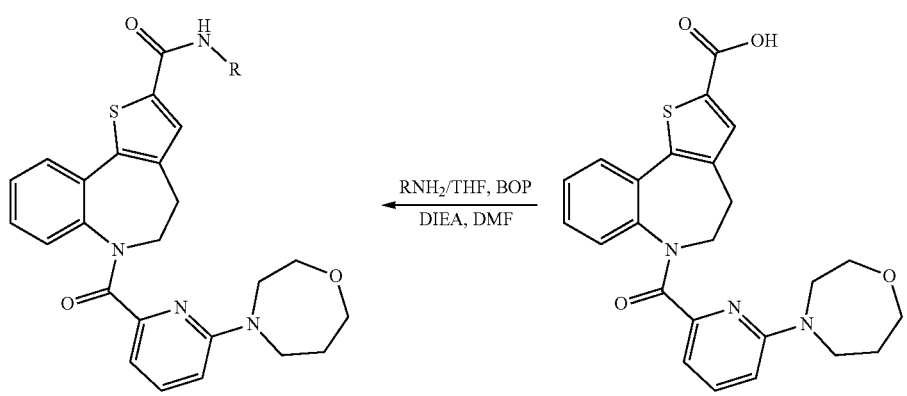
Example 98                              Example 98 Step a
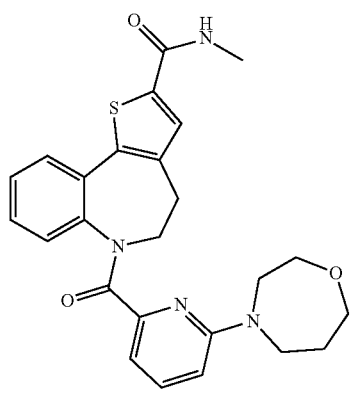 [SMILES: CNC(=O)c1cc2c(s1)-c1ccccc1N(C(=O)c1cccc(N3CCCOCC3)n1)CC2]
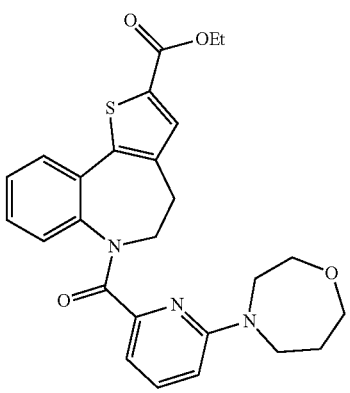 [SMILES: CCOC(=O)c1cc2c(s1)-c1ccccc1N(C(=O)c1cccc(N3CCCOCC3)n1)CC2]

To a stirring solution of compound from Example 94 step b (1.5 g, 3.28 mmol) in DMSO (15 mL) was added DIEA (5.4 mL, 32.8 mmol) and 1,4-oxazepane hydrochloride (2.26 g, 16.4 mmol). The mixture was heated to 90° C. for 24 hrs and then cooled to room temperature. The mixture was diluted with water and extracted with EtOAc. The residue was purified by silica gel column chromatography to give the desired product as a yellow solid (1.2 g, 77%). ESI MS m/z=478.20 [M+H]$^+$.

Example 98 Step b

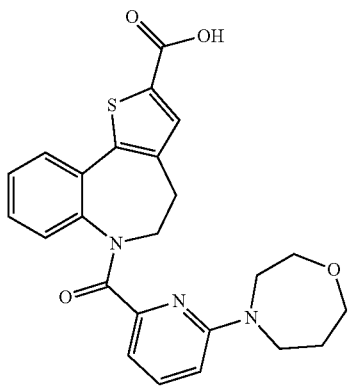 [SMILES: O=C(O)c1cc2c(s1)-c1ccccc1N(C(=O)c1cccc(N3CCCOCC3)n1)CC2]

To a stirring solution of the compound from Example 98 step a (1.2 g, 2.51 mmol) in THF/MeOH/H$_2$O (3/1/1, 15 mL) was added LiOH (121 mg, 5.0 mmol). The mixture was stirred at room temperature for 2 hrs. After adjusting the pH to 5 by adding aq. 2 N HCl, the mixture was concentrated under reduced pressure and the residue was purified by silica gel column chromatography to give the desired product as a yellow solid (790 mg, 70%). ESI MS m/z=450.10 [M+H]$^+$.

Example 98 Step c

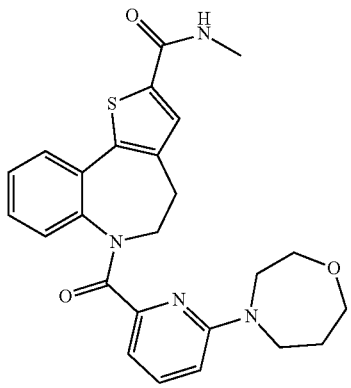 [SMILES: CNC(=O)c1cc2c(s1)-c1ccccc1N(C(=O)c1cccc(N3CCCOCC3)n1)CC2]

To a stirring solution of the compound from Example 98 step b (80 mg, 0.178 mmol) in DMF (2 mL) was added DIEA (0.44 mL, 2.67 mmol) and BOP (394 mg, 0.89 mmol). Then a solution of 2M MeNH$_2$ in THF (1 mL, 2 mmol) was added and the mixture was stirred at room temperature for 2 h. Water (5 mL) was added and the mixture was extracted with EtOAc. The combined organic phase was concentrated under reduced pressure. The residue was purified by prep-HPLC to give the desired product as white solid (19.6 mg, 24%). ESI MS m/z=463.15 [M+H]$^+$. $^1$H NMR (300 MHz, DMSO-d$_6$) δ 1.50-1.59 (m, 2H), 2.76 (d, J=4.4 Hz, 3H), 3.06-3.15 (m, 4H), 3.19-3.31 (m, 6H), 3.35-3.41 (m, 1H), 4.79-4.92 (m, 1H), 6.53 (d, J=8.6 Hz, 1H), 6.74 (dd, J=7.8, 1.3 Hz, 1H), 6.91 (d, J=7.2 Hz, 1H), 7.04 (td, J=7.6 Hz, 1.5 Hz, 1H), 7.21 (td, J=7.6 Hz, 1.4 Hz, 1H), 7.50 (J=8.6 Hz, 7.2 Hz), 7.59 (S, 1H), 7.72 (dd, J=7.9, 1.4 Hz, 1H), 8.49 (d, J=4.7 Hz, 1H).

Example 99

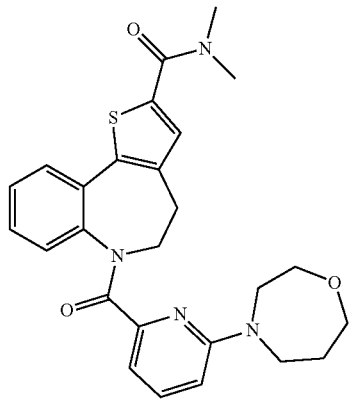 [SMILES: CN(C)C(=O)c1cc2c(s1)-c1ccccc1N(C(=O)c1cccc(N3CCCOCC3)n1)CC2]

To a stirring solution of compound from Example 98 step b (80 mg, 0.18 mmol) in DMF (2 mL) was added DIEA (0.44 mL, 2.67 mmol) and HATU (338 mg, 0.89 mmol). Then dimethylamine hydrochloride was added and the mixture was stirred at room temperature for 2 hrs. Water (5 mL) was added and the mixture was extracted with ethyl acetate. The combined organic phase was concentrated under reduced pressure. The residue was purified by prep-HPLC to give the desired product as a white solid (19.4 mg, 23%). ESI MS m/z=477.15 [M+H]$^+$. $^1$H NMR (300 MHz, DMSO-d$_6$) δ 1.49-1.60 (m, 2H), 3.03-3.32 (m, 15H), 3.34-3.41 (m, 2H), 4.80-4.92 (m, 1H), 6.53 (d, J=8.6 Hz, 1H), 6.75 (dd, J=7.9, 1.3 Hz, 1H), 6.91 (d, J=7.2 Hz, 1H), 7.04 (td, J=7.6, 1.5 Hz, 1H), 7.20 (td, J=7.6, 1.3 Hz, 1H), 7.42 (s, 1H), 7.50 (dd, J=8.6, 7.2 Hz, 1H), 7.71 (dd, J=7.8, 1.4 Hz, 1H).

Example 100

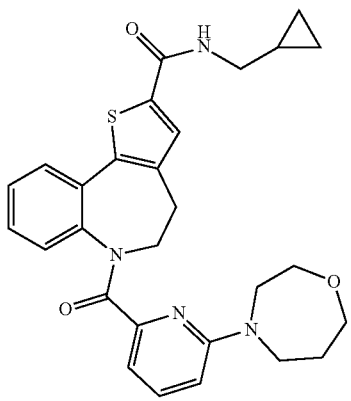 [SMILES: O=C(NCC1CC1)c1cc2c(s1)-c1ccccc1N(C(=O)c1cccc(N3CCCOCC3)n1)CC2]

Example 101

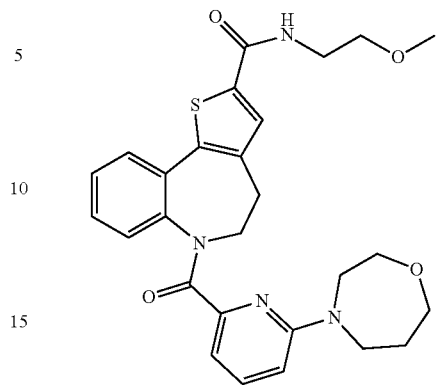

Example 100 was prepared using a procedure similar to that used to prepare Example 99 where cyclopropylmethanmine was used in place of dimethylamine. ESI MS m/z=503.20 [M+H]$^+$. $^1$H NMR (300 MHz, DMSO-d$_6$) δ 0.16-0.28 (m, 2H), 0.37-0.50 (m, 2H), 0.94-1.06 (m, 1H), 1.45-1.64 (m, 2H), 3.07-3.30 (m, 11H), 3.34-3.40 (m, 2H), 4.80-4.93 (m, 1H), 6.53 (d, J=8.6 Hz, 1H), 6.74 (dd, J=7.8, 1.3 Hz, 1H), 6.91 (d, J=7.2 Hz, 1H), 7.05 (td, J=7.6, 1.4 Hz, 1H), 7.21 (td, J=7.6, 1.3 Hz, 1H), 7.50 (dd, J=8.6, 7.2 Hz, 1H), 7.68 (s, 1H), 7.73 (dd, J=7.9, 1.4 Hz, 1H), 8.62 (t, J=5.7 Hz, 1H).

Example 101 was prepared using a procedure similar to that used to prepare Example 99 where 2-methoxyethan-1-amine was used in place of dimethylamine. ESI MS m/z=507.20 [M+H]$^+$. $^1$H NMR (300 MHz, DMSO-d$_6$) δ 1.54-1.59 (m, 2H), 3.06-3.29 (m, 12H), 3.33-3.50 (m, 6H), 4.79-4.92 (m, 1H), 6.53 (d, J=8.6 Hz, 1H), 6.74 (dd, J=7.8, 1.3 Hz, 1H), 6.91 (d, J=7.2 Hz, 1H), 7.05 (td, J=7.6, 1.4 Hz, 1H), 7.21 (td, J=7.6, 1.4 Hz, 1H), 7.50 (dd, J=8.6, 7.2 Hz, 1H), 7.68 (s, 1H), 7.73 (dd, J=7.9, 1.4 Hz, 1H), 8.59 (t, J=5.5 Hz, 1H).

Scheme 9

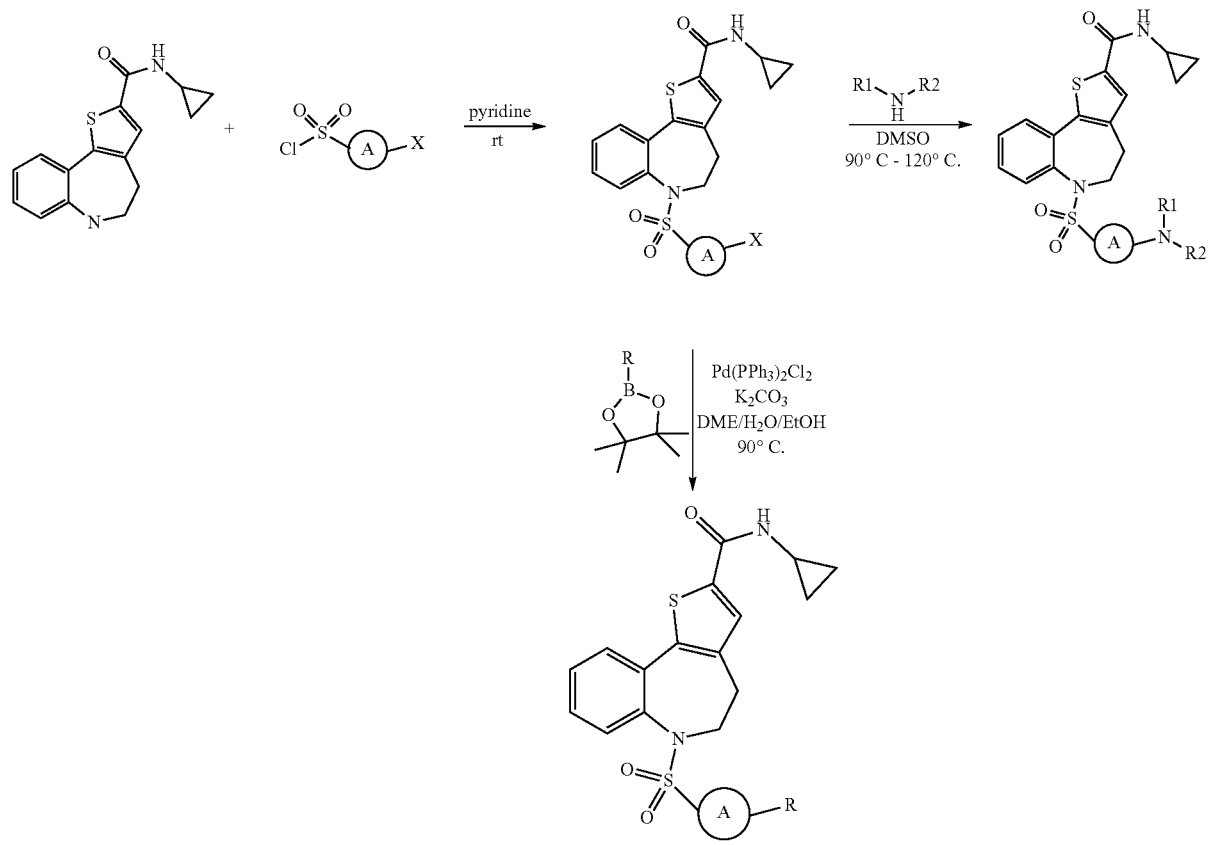

Example 102

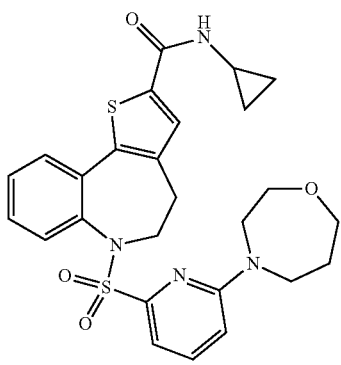 [SMILES: O=C(NC1CC1)c1cc2c(s1)-c1ccccc1N(S(=O)(=O)c1cccc(N3CCCOCC3)n1)CC2]

Example 102 Step a

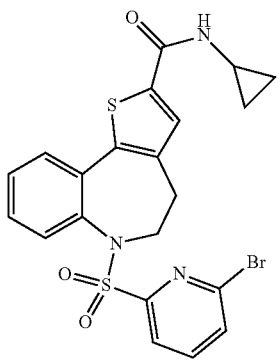 [SMILES: O=C(NC1CC1)c1cc2c(s1)-c1ccccc1N(S(=O)(=O)c1cccc(Br)n1)CC2]

To a solution of compound from Example 1 step e (142 mg, 0.5 mmol) in pyridine (2 mL) was added 6-bromopyridine-2-sulfonyl chloride (128 mg, 0.5 mmol). The mixture was stirred at rt overnight. After evaporated most of the pyridine, the residue was purified by silica gel column chromatography to obtain the desired product (120 mg, 48%) as a pale-yellow foam which will be used directly for the next step.

Example 102 Step b

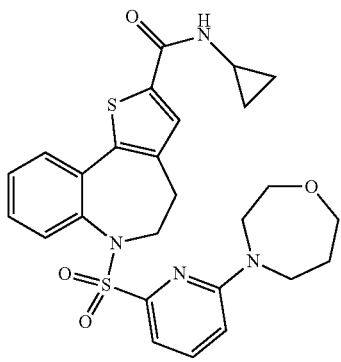 [SMILES: O=C(NC1CC1)c1cc2c(s1)-c1ccccc1N(S(=O)(=O)c1cccc(N3CCCOCC3)n1)CC2]

To a solution of compound from Example 102 step a (50 mg, 0.1 mmol) in DMSO (2 mL) was added 1,4-oxazepane (0.1 mL), the resulting mixture was heated at 90° C. for 12 hrs. After diluted with EtOAc (50 m), the solution was washed with water (20 mL×2) and brine (20 mL). The organic layer was dried over $Na_2SO_4$, filtered and evaporated. The residue was purified by silica gel column chromatography to give the title compound (25 mg, 48%) as a white foam. ESI MS m/z=525.16 [M+H]$^+$.

Example 103

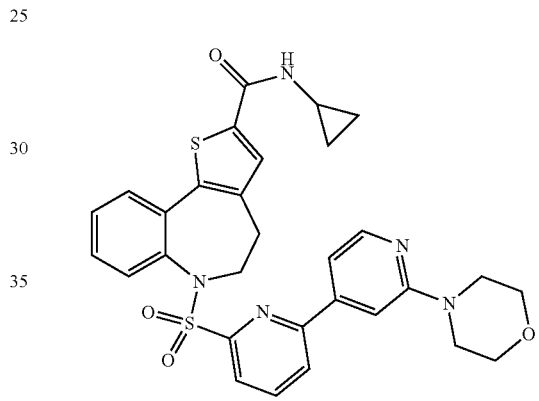

To a round-bottomed flask bottomed flask was charged with compound from Example 102 step a (50 mg, 0.1 mmol), pinacol ester (37 mg, 0.12 mmol, 1.2 eq), Pd(PPh$_3$)$_2$Cl$_2$ (7 mg, 0.01 mmol), potassium carbonate (20 mg, 0.15 mmol, 1.5 eq), and a mixture of DME/EtOH/H$_2$O (2/1/2, 7.5 mL). The reaction mixture was degassed and heated at 90° C. with vigorous stirring. After 12 hrs, the reaction mixture was cooled to room temperature and diluted with ethyl acetate (50 mL). The organic layer was washed with brine, dried over $Na_2SO_4$, filtered and concentrated. The residue was purified by silica gel column chromatography to give the title compound (28 mg, 48%) as a white foam. ESI MS m/z=588.17 [M+H]$^+$.

309 310
Scheme 10
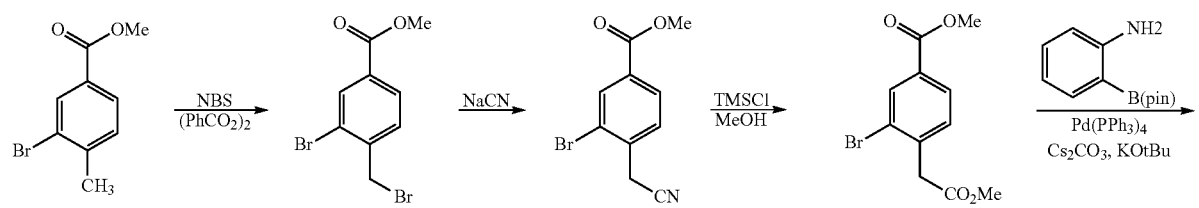
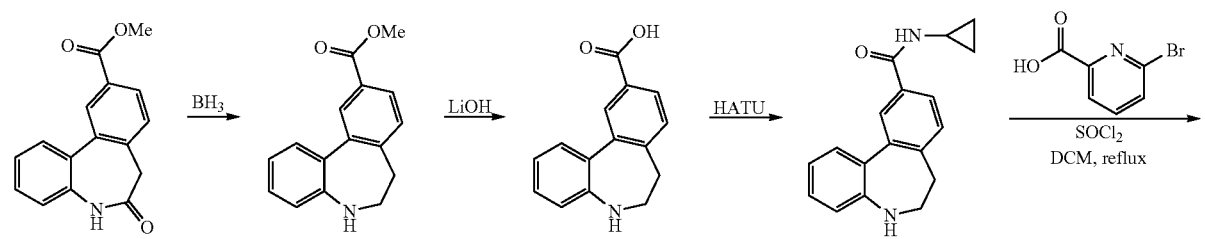
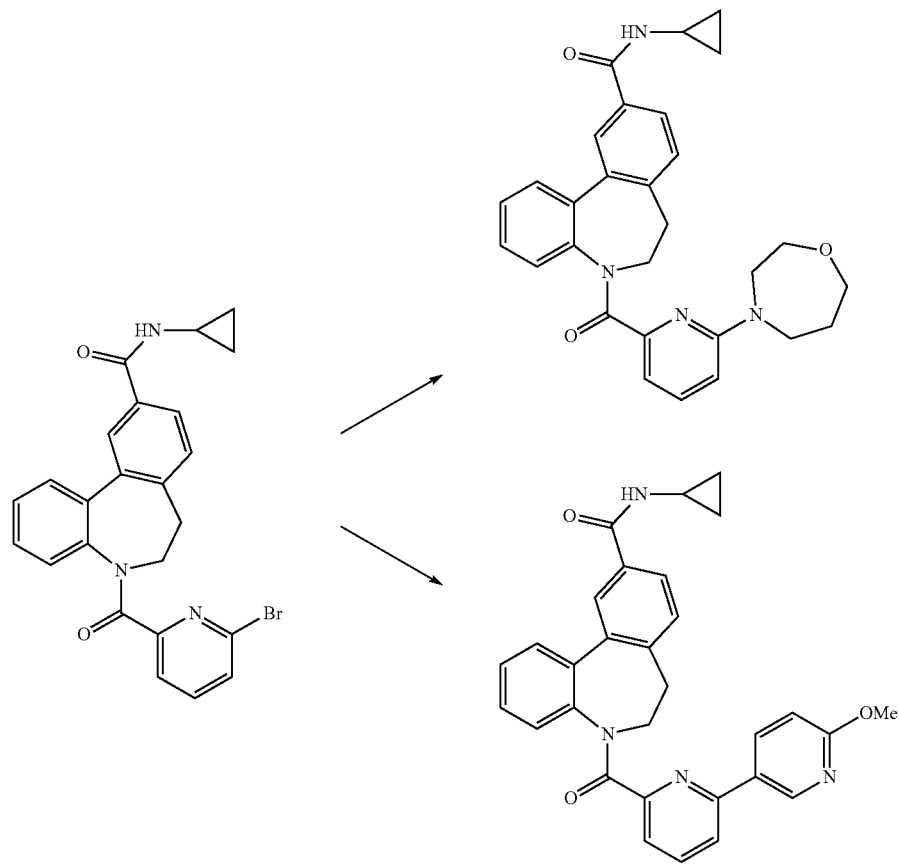

Example 104

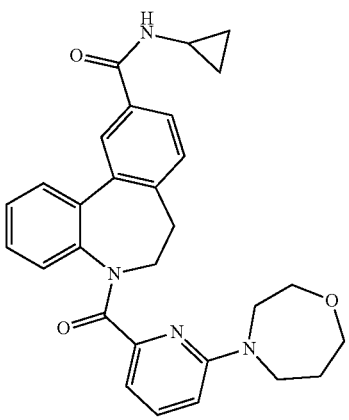 [SMILES: O=C(NC1CC1)c1ccc2c(c1)-c1ccccc1N(C(=O)c1cccc(N3CCCOCC3)n1)CC2]

Example 104 Step a

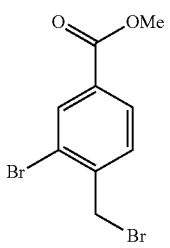

To a 50 mL flask equipped with a magnetic stir bar and reflux condenser was added N-bromosuccinimide (3.7 g, 21.0 mmol, 1.05 eq), benzoyl peroxide (0.97 g, 4.0 mmol, 1.0 eq) and carbon tetrachloride (6 mL). To the resulting solution was added methyl 3-bromo-4-methylbenzoate (4.6 g, 20 mmol, 1.0 eq) in carbon tetrachloride (4 mL). The reaction mixture was heated to 80° C. in an oil bath overnight. The resulting mixture was cooled and diluted with dichloromethane (50 mL). The reaction mixture was washed with saturated sodium bicarbonate and water. The organic layer was dried with anhydrous sodium sulfate, filtered and concentrated in vacuo. The crude residue was purified using silica gel column chromatography to give the desired product (4.6 g, 74%) as a viscous oil.

Example 104 Step b

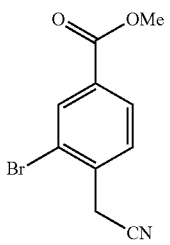

To a 100 mL flask equipped with a magnetic stir bar and reflux condenser were added compound from Example 104 step a (4.6 g, 14.9 mmol, 1.0 eq) and methanol (10 mL). The reaction mixture was heated to reflux. To the flask was added sodium cyanide (1.5 g, 29.7 mmol, 2.0 eq) in water (4 mL) portionwise. The reaction mixture was heated at reflux for 1 hr. The resulting mixture was cooled and poured into ice water (50 mL). The aqueous layer was extracted with dichloromethane (100 mL×3). The organic layer was dried with anhydrous sodium sulfate, filtered and concentrated in vacuo. The brown oil was taken forward without purification.

Example 104 Step c

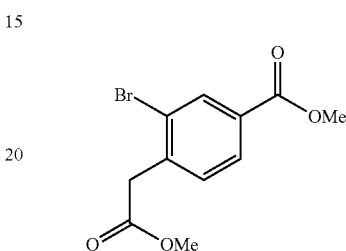

To a 100 mL flask equipped with a magnetic stir bar and reflux condenser was added methanol (6 mL) followed by chlorotrimethylsilane (3 mL). To the flask was added crude compound from Example 104 step b in methanol (4 mL). The reaction mixture was heated to 60° C. for 8 hrs. The resulting mixture was cooled to room temperature and concentrated in vacuo. The crude residue was purified using silica gel column chromatography to give the desired product (2.1 g, 48%) as a viscous oil.

Example 104 Step d

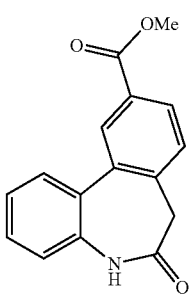 [SMILES: COC(=O)c1ccc2c(c1)-c1ccccc1NC(=O)C2]

To a 2-5 mL microwave vial equipped with a magnetic stir bar was added compound from Example 104 step c (0.12 g, 0.43 mmol, 1.0 eq), 2-(4,4,5,5-tetramethyl-1,3,2-dioxaborolan-2-yl)aniline (0.12 g, 0.52 mmol, 1.22 eq), cesium carbonate (280 mg, 0.86 mmol, 2.0 eq), and Pd(PPh$_3$)$_4$ (25 mg, 22.0 µmol, 0.05 eq). The vial was sealed and evacuated and refilled (30 mL×3) with nitrogen. To the flask was added 1,2-dimethoxyethane (4 mL). The reaction mixture was irradiated at 125° C. for 30 min. The resulting solution was cooled to 0° C. and potassium tert-butoxide in THF (0.65 mL, 1M, 1.51 eq) was added dropwise. The reaction mixture was allowed to warm to room temperature overnight. The reaction mixture was quenched with saturated ammonium chloride (2 mL) and diluted with ethyl acetate (4 mL) and water (2 mL). The organic layer was dried with anhydrous sodium sulfate, filtered and concentrated in vacuo. The crude residue was purified using silica gel column chromatography to give the desired product (72 mg, 63%) as a viscous oil. $^1$H NMR (300 MHz, CDCl$_3$) δ 8.27 (s, 1H), 8.08 (d, J=8.0 Hz, 1H), 7.72 (d, J=7.9 Hz, 1H), 7.45 (t, J=8.9 Hz, 2H), 7.35 (t, J=8.9 Hz, 2H), 7.10 (d, J=7.9 Hz, 1H), 3.96 (s, 3H), 3.65 (m, 1H), 3.54 (m, 1H).

Example 104 Step e

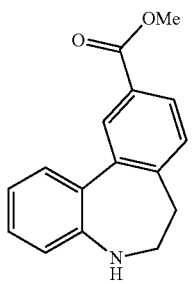 [SMILES: COC(=O)c1ccc2c(c1)-c1ccccc1NCC2]

To an oven-dried vial equipped with a magnetic stir bar was added compound from Example 104 step d (50 mg, 0.19 mmol, 1.0 eq) and tetrahydrofuran (1.1 mL) under nitrogen. The vial was cooled to 0° C. and BH$_3$.THF in tetrahydrofuran (0.37 mL, 1M, 1.97 eq). The reaction mixture was allowed to warm to room temperature overnight. The resulting mixture was quenched with methanol (0.25 mL) and water (2 mL). The aqueous layer was extracted with ethyl acetate (20 mL×3). The organic layer was dried with anhydrous sodium sulfate, filtered and concentrated in vacuo. The crude residue was purified using silica gel chromatography to give the desired product (35 mg, 74%) as an off-white solid. ESI-MS m/z: 254.12 [M+H]$^+$.

Example 104 Step f

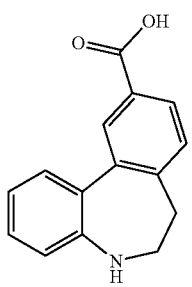 [SMILES: O=C(O)c1ccc2c(c1)-c1ccccc1NCC2]

To a 25 mL flask equipped with a magnetic stir bar and reflux condenser was added compound from Example 104 step e (72 mg, 0.28 mmol, 1.0 eq), tetrahydrofuran (0.6 mL), methanol (0.6 mL), water (0.6 mL) and lithium hydroxide monohydrate (22 mg, 0.51 mmol, 1.80 eq). The reaction mixture was heated reflux for 3 hours. The resulting mixture was cooled to 0° C. and neutralized with 1N HCl (aq.). The reaction mixture was then diluted with water and warmed to room temperature. The aqueous layer was extracted with ethyl acetate (20 mL×3). The organic layer was dried with anhydrous sodium sulfate, filtered and concentrated in vacuo to give the desired product (67 mg, 100%) as a white solid that was used without further purification. ESI-MS m/z: 240.10 [M+H]$^+$.

Example 104 Step g

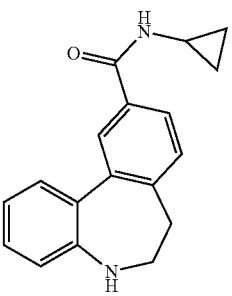 [SMILES: O=C(NC1CC1)c1ccc2c(c1)-c1ccccc1NCC2]

Compound was prepared using a procedure similar to that used to prepare Example 1 step e. ESI-MS m/z: 279.15 [M+H]$^+$.

Example 104 Step h

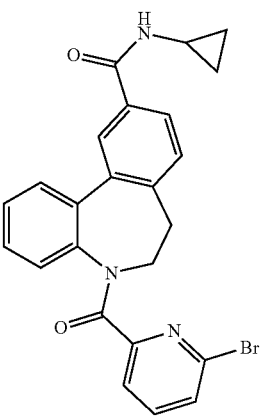 [SMILES: O=C(NC1CC1)c1ccc2c(c1)-c1ccccc1N(C(=O)c1cccc(Br)n1)CC2]

Compound was prepared using a procedure similar to that used to prepare Example 16 step a. ESI-MS m/z: 464.08 [M+H]$^+$.

Example 104 Step i

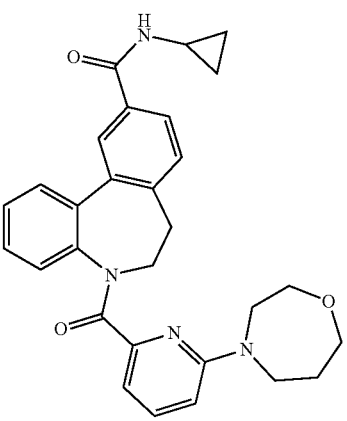 [SMILES: O=C(NC1CC1)c1ccc2c(c1)-c1ccccc1N(C(=O)c1cccc(N3CCCOCC3)n1)CC2]

Example 104 was prepared using a procedure similar to that used to prepare Example 16 step b. ESI-MS m/z: 483.24 [M+H]+.
Example 105
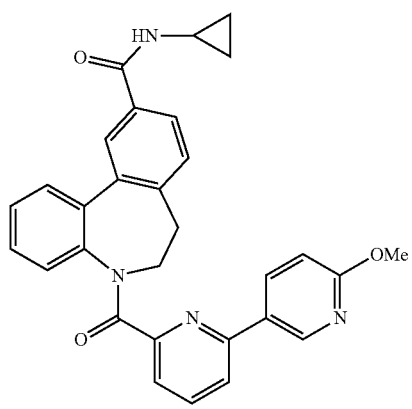 [SMILES: COc1ccc(-c2cccc(C(=O)N3CCc4ccc(C(=O)NC5CC5)cc4-c4ccccc43)n2)cn1]
Example 105 was prepared using a procedure similar to that used to prepare Example 54. ESI-MS m/z: 491.20 [M+H]+.
Scheme 11
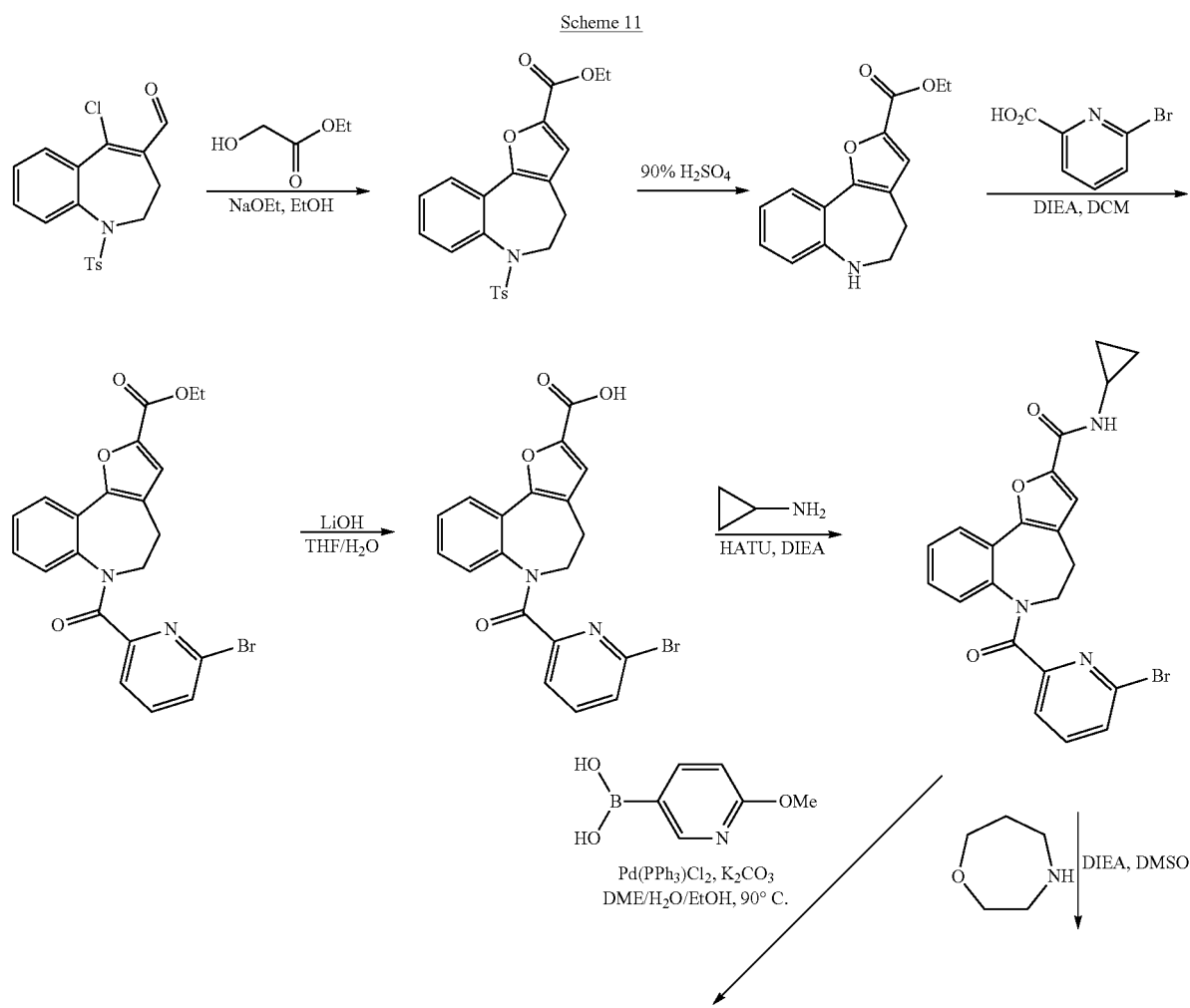

-continued

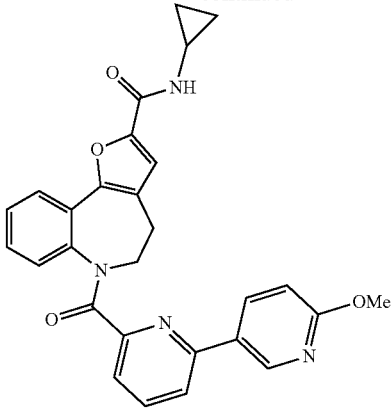

Example 106

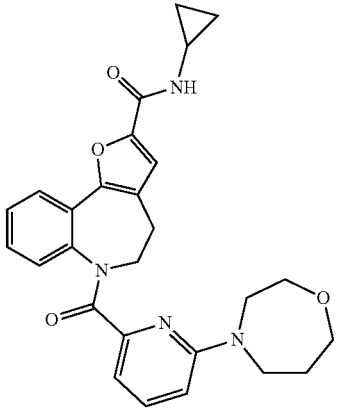

Example 106 Step b

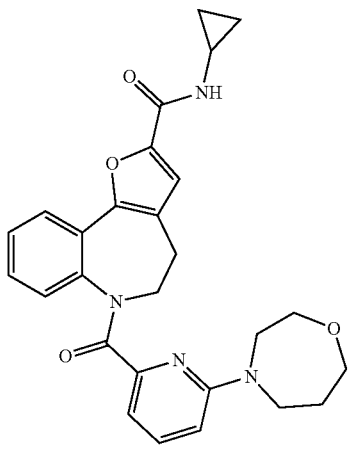 [SMILES: O=C(NC1CC1)c1cc2c(o1)-c1ccccc1N(C(=O)c1cccc(N3CCCOCC3)n1)CC2]

Example 106 Step a

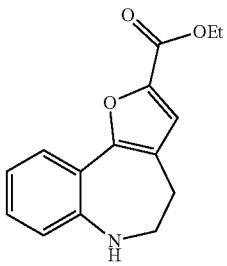 [SMILES: CCOC(=O)c1cc2c(o1)-c1ccccc1NCC2]

The compound from Example 106 step a (720 mg, 1.752 mmol) was dissolved in 90% $H_2SO_4$ (10 mL) at 0° C., and then it was stirred at 40° C. for 3 hrs. The reaction mixture was adjusted to PH=10 with $Na_2CO_3$ at 0° C. and extracted with ethyl acetate. The organic phase was washed with brine, dried, and concentrated. The residue was purified by silica gel column chromatography to give the desired compound as a yellow solid (370 mg, 82%). ESI MS m/z=258.25 [M+1].

Example 106 Step c

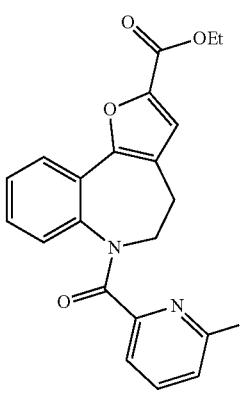

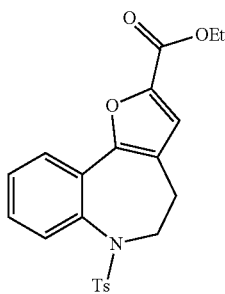

Ethyl 2-hydroxyacetate (1.15 g, 11.1 mmol) and NaOEt (4.2 ml, 11.1 mmol) were dissolved in EtOH (30 mL). The mixture was stirred at 0° C. for 30 min. Compound from Example 1 step 2 (2.00 g, 5.54 mmol) was added at 0° C. The mixture was stirred at 80° C. for 1 hr and concentrated. The residue was purified by silica gel column chromatography to give the desired compound as a yellow solid (720 mg, 31%). ESI MS m/z 411.90 [M+1].

6-Bromopyridine-2-carbonyl chloride (380 mg, 1.727 mmol) was added to a solution of the compound from Example 106 step b (370 mg, 1.44 mmol) and DIEA (929 mg, 7.20 mmol) in DCM (10 mL) at 0° C. The mixture was stirred at 20° C. for 3 hrs and then quenched with water and extracted with DCM. The organic phase was washed with brine, dried and concentrated. The residue was purified by silica gel column chromatography to give the desired compound as a yellow solid (500 mg, 79%). ESI MS m/z=441.05 [M+1].

Example 106 Step d

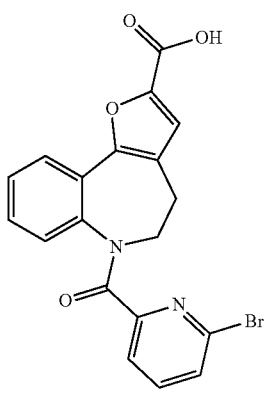 [SMILES: O=C(O)c1cc2c(o1)-c1ccccc1N(C(=O)c1cccc(Br)n1)CC2]

To a solution compound from Example 106 step c (420 mg, 1.022 mmol) in THF/H$_2$O (9:3, 12 mL) was added LiOH (12 mg, 0.500 mmol) at r.t., then it was stirred at rt for 5 hrs. It was adjusted to PH=3 with 2N HCl at 0° C. and it was extracted with ethyl acetate, washed with brine, dried by Na$_2$SO$_4$. The mixture was concentrated to give the desired crude compound (450 mg) as a yellow solid. ESI MS m/z=412.95 [M+1].

Example 106 Step e

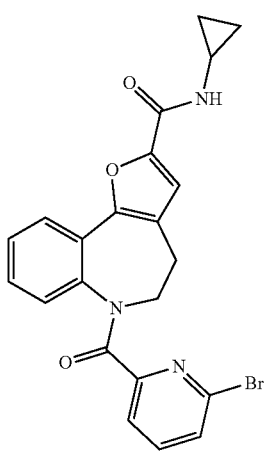 [SMILES: O=C(NC1CC1)c1cc2c(o1)-c1ccccc1N(C(=O)c1cccc(Br)n1)CC2]

Cyclopropanamine (124 mg, 2.180 mmol) was added to the compound from Example 106 step d (450 mg, 1.090 mmol), HATU (497 mg, 1.308 mmol) and DIEA (422 mg, 3.269 mmol) in DMF (10 mL) at rt. The mixture was stirred at rt for 2 hrs and then quenched by water and extracted with DCM. The organic phase was dried, concentrated and purified by silica gel column chromatography to give the desired compound (520 mg, 98%) as a yellow solid. ESI MS m/z=454.20 [M+1].

Example 106 Step f

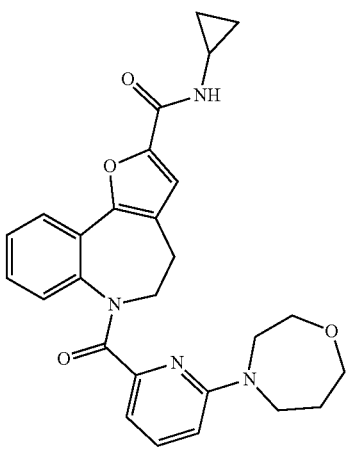 [SMILES: O=C(NC1CC1)c1cc2c(o1)-c1ccccc1N(C(=O)c1cccc(N3CCCOCC3)n1)CC2]

A solution of the compound from Example 106 step e (80 mg, 0.176 mmol), 1,4-oxazepane hydrochloride (122 mg, 0.884 mmol) and DIEA (136 mg, 1.054 mmol) in DMSO (2 mL) was stirred for 7 days at 100° C. The mixture was purified by prep-HPLC to give the title compound (62 mg, 84%) as a white solid. ESI MS m/z=473.35 [M+1]. $^1$H NMR (300 MHz, DMSO-d$_6$) δ 0.54-0.79 (m, 4H), 1.55 (m, 2H), 2.74-3.42 (m, 9H), 4.81-4.94 (m, 1H), 6.50 (d, J=8.6 Hz, 1H), 6.78 (m, 2H), 6.97-7.18 (m, 2H), 7.18-7.51 (m, 2H), 8.14 (m, 1H), 8.48 (d, J=4.1 Hz, 1H).

Example 107

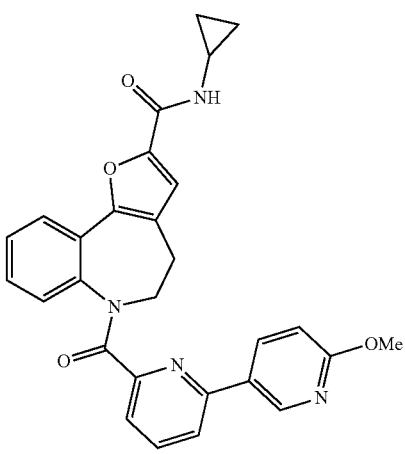 [SMILES: COc1ccc(-c2cccc(C(=O)N3CCc4cc(C(=O)NC5CC5)oc4-c4ccccc43)n2)cn1]

A solution of the compound from Example 106 step e (80 mg, 0.18 mmol), (6-methoxypyridin-3-yl)boronic acid (32 mg, 0.21 mmol), Pd(PPh$_3$)Cl$_2$ (12 mg, 0.017 mmol) and K$_2$CO$_3$ (36 mg, 0.26 mmol) in DME/H$_2$O/EtOH (2/1/2, 5 mL) was stirred for 2 hrs at 90° C. under N$_2$. The mixture was purified by prep-HPLC to give the title compound (42 mg, 55%) as a white solid. ESI MS m/z=481.40 [M+1]. $^1$H NMR (300 MHz, DMSO-d$_6$) δ 0.71 (m, 4H), 2.79-3.23 (m, 4H), 3.89 (s, 3H), 4.87-5.02 (m, 1H), 6.69-6.86 (m, 2H), 6.91-7.06 (m, 1H), 7.15-7.29 (m, 2H), 7.48-7.66 (m, 2H), 7.78-7.93 (m, 2H), 8.23 (m, 1H), 8.42 (d, J=2.4 Hz, 1H), 8.60 (d, J=4.0 Hz, 1H).

321 322
Scheme 12
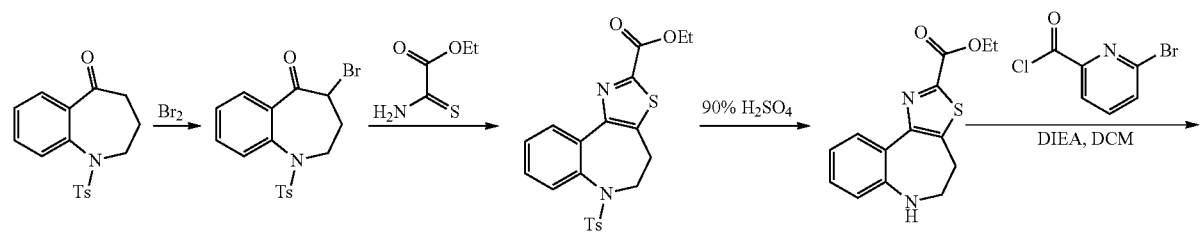
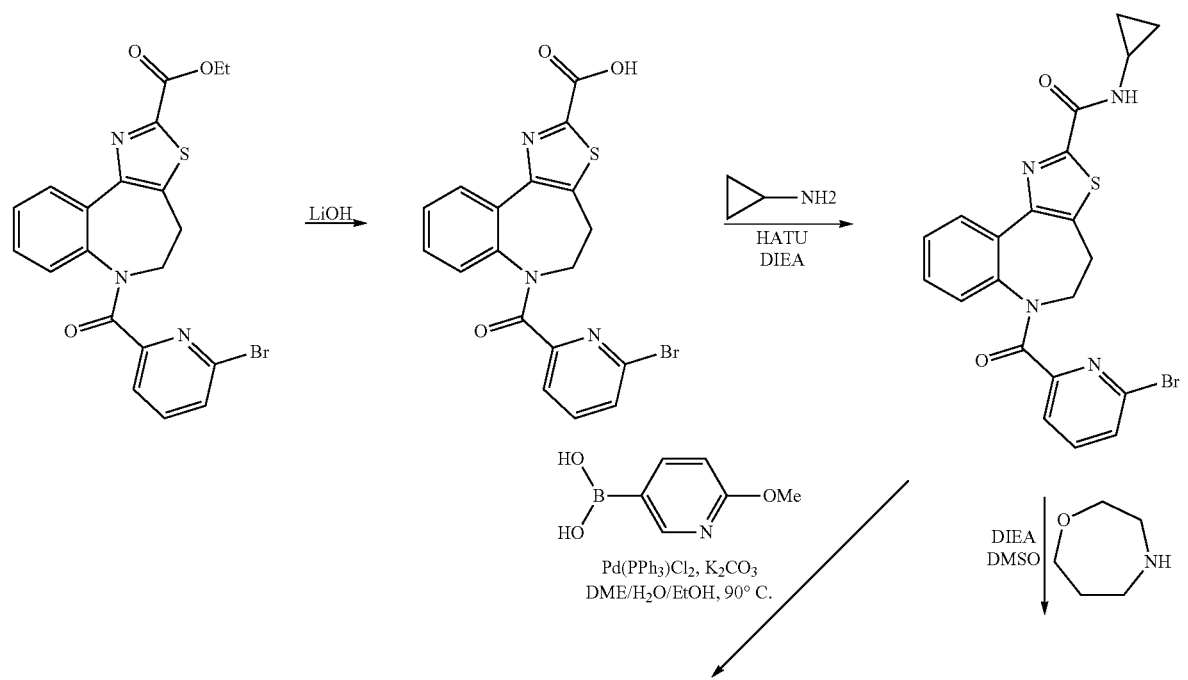
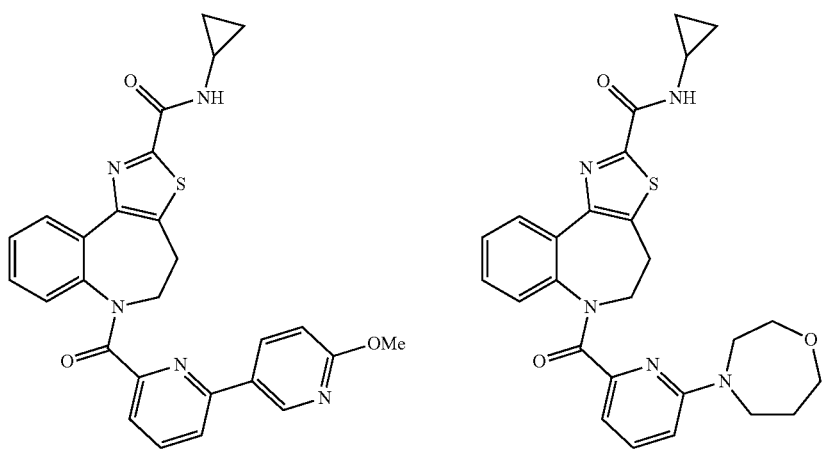

Example 108

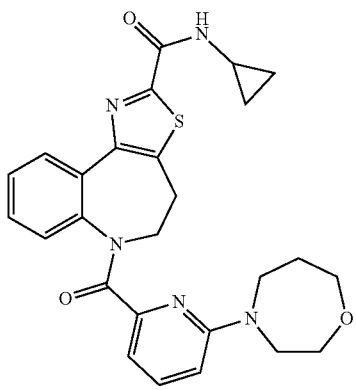 [SMILES: O=C(NC1CC1)c1nc2c(s1)CCN(C(=O)c1cccc(N3CCCOCC3)n1)c1ccccc1-2]

Example 108 Step a

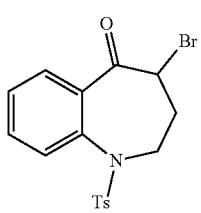 [SMILES: Cc1ccc(S(=O)(=O)N2CCC(Br)C(=O)c3ccccc32)cc1]

A solution of Br$_2$ (558 mg, 3.48 mmol) in DCM (10 mL) was added dropwise to compound from Example 1 step 1 (1.00 g, 3.17 mmol), NBS (57 mg, 0.32 mmol), Et$_3$N (352 mg, 3.48 mmol) in DCM (50 mL) at rt. The mixture was stirred at 50° C. for 5 hrs and then quenched with water, extracted with DCM. The organic layer was washed with NaHCO$_3$ (aq), concentrated and purified by silica gel column chromatography to give the desired compound (1.2 g, 96%) as brown solid. ESI MS m/z=394.15 [M+1].

Example 108 Step b

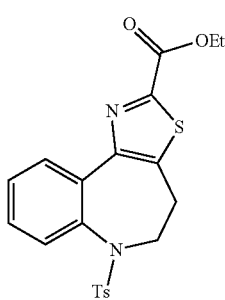 [SMILES: CCOC(=O)c1nc2c(s1)CCN(S(=O)(=O)c1ccc(C)cc1)c1ccccc1-2]

A solution of compound from Example 108 step a (900 mg, 2.86 mmol), ethyl 2-amino-2-thioxoacetate (1.14 g, 8.57 mmol) in EtOH (50 mL) was stirred at 90° C. overnight. Then it was concentrated, purified by silica gel column chromatography to give the desired compound (600 mg, 61%) as a yellow solid. ESI MS m/z=429.30 [M+1].

Example 108 Step c

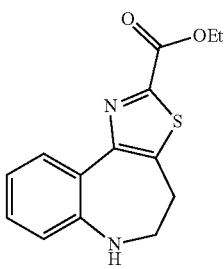 [SMILES: CCOC(=O)c1nc2c(s1)CCNc1ccccc1-2]

A solution of the compound from Example 108 step b (600 mg, 1.40 mmol) in H$_2$SO$_4$ (90%, 10 mL) was stirred at 50° C. for 2 hrs. After that, the mixture was poured into ice water and adjusted to PH=7 by adding NaOH (aq). The precipitate was collected by filtration and washed with water, dried to give the desired compound (370 mg, 96%) as a yellow solid. ESI MS m/z=275.10 [M+1].

Example 108 Step d

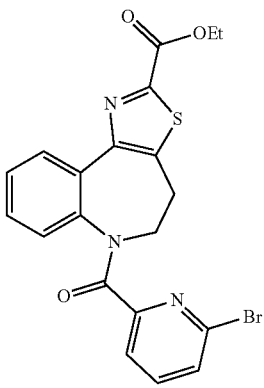 [SMILES: CCOC(=O)c1nc2c(s1)CCN(C(=O)c1cccc(Br)n1)c1ccccc1-2]

6-Bromopicolinoyl chloride (575 mg, 2.63 mmol) was added to a solution of the compound from Example 108 step c (360 mg, 1.31 mmol) and DIEA (508 mg, 3.94 mmol) in DCM (30 mL) at 0° C. The mixture was stirred at rt overnight and then quenched by water and extracted with DCM. The organic phase was dried, concentrated and purified by silica gel column chromatography to give the desired compound (300 mg, 50%) as a yellow solid. ESI MS m/z=458.20 [M+1].

Example 108 Step e

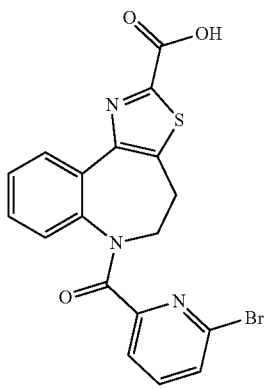 [SMILES: O=C(O)c1nc2c(s1)CCN(C(=O)c1cccc(Br)n1)c1ccccc1-2]

Lithium hydroxide (40 mg, 1.75 mmol) was added to the compound from Example 108 step d (400 mg, 0.87 mmol) in THF/H₂O=12/4 ml at rt for 1 h. Then the mixture was adjusted to PH=4 with 2N HCl at 0° C. and extracted with EtOAc. The organic layer was dried and concentrated to give the crude desired compound (425 mg) as a yellow solid. ESI MS m/z=432.10 [M+1].

Example 108 Step f

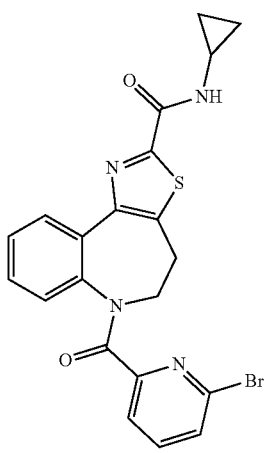 [SMILES: O=C(NC1CC1)c1nc2c(s1)CCN(C(=O)c1cccc(Br)n1)c1ccccc1-2]

Cyclopropanamine (113 mg, 1.98 mmol) was added dropwise to the compound from Example 108 step e (425 mg, 0.99 mmol), HATU (451 mg, 1.19 mmol) and DIEA (383 mg, 2.97 mmol) in DMF (10 mL) at rt. The mixture was stirred at rt for 2 hrs and then it was poured into water and extracted with DCM. The organic phase was dried, concentrated and purified by silica gel column chromatography to give the desired compound (298 mg, 91%) as a yellow solid. ESI MS m/z=469.00 [M+1].

Example 108 Step g

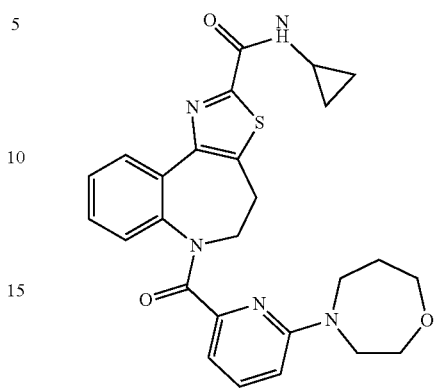

A solution of the compound from Example 108 step f (80 mg, 0.17 mmol), 1,4-oxazepane hydrochloride (118 mg, 0.86 mmol) and DIEA (132 mg, 1.02 mmol) in DMSO (2 mL) was heated at 100° C. for 7 days. The mixture was purified by prep-HPLC to give the title compound (34 mg, 83%) as a light white solid. ESI MS m/z=490.20 [M+1]. ¹H NMR (300 MHz, DMSO-d₆) δ 0.65-0.82 (m, 4H), 1.52 (m, 2H), 2.82-2.96 (m, 1H), 2.96-3.49 (m, 14H), 4.95 (m, 1H), 6.50 (d, J=8.6 Hz, 1H), 6.79 (m, 2H), 7.07 (m, 1H), 7.24 (m, 1H), 7.45 (m, 1H), 8.51 (m, 1H), 8.75 (s, 1H).

Example 109

A solution of the compound from Example 108 step f (80 mg, 0.17 mmol), (6-methoxypyridin-3-yl)boronic acid (32 mg, 0.21 mmol), Pd(PPh₃)Cl₂ (12 mg, 0.017 mmol) and K₂CO₃ (36 mg, 0.26 mmol) in DME/H₂O/EtOH (2/1/2, 5 mL) was stirred for 3 hrs at 90° C. The mixture was purified by prep-HPLC to give the title compound (38.4 mg, 85%) as a yellow solid. ESI MS m/z=498.15 [M+1]. ¹H NMR (400 MHz, DMSO-d₆) δ 0.70-0.84 (m, 4H), 2.93 (m, 1H), 3.25 (m, 1H), 3.43 (m, 1H), 3.55 (m, 1H), 3.88 (s, 3H), 5.01 (m, 1H), 6.73 (d, J=8.7 Hz, 1H), 6.83 (m, 1H), 7.01 (m, 1H), 7.21 (m, 1H), 7.49-7.63 (m, 2H), 7.78-7.91 (m, 2H), 8.44 (d, J=2.5 Hz, 1H), 8.58 (m, 1H), 8.95 (d, J=4.3 Hz, 1H).

Scheme 13
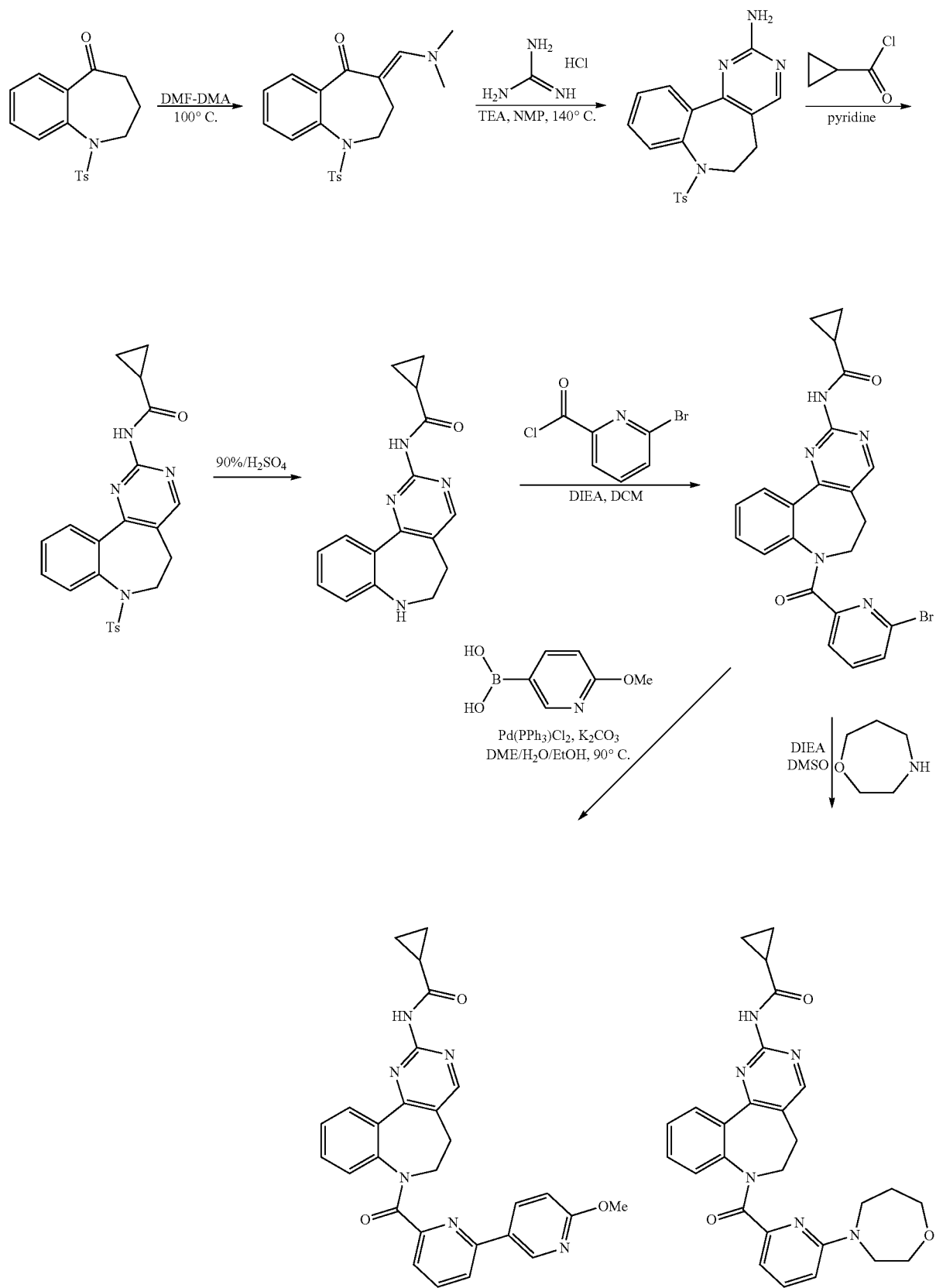

Example 110

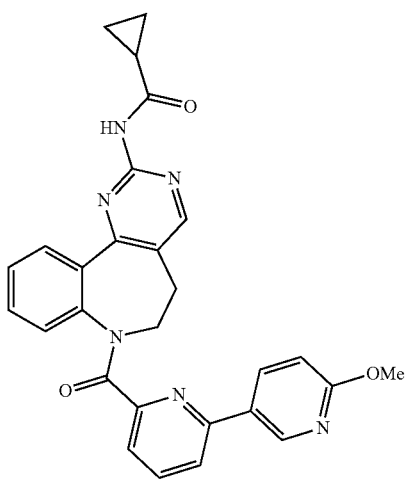 [SMILES: COc1ccc(-c2cccc(C(=O)N3CCc4cnc(NC(=O)C5CC5)nc4-c4ccccc43)n2)cn1]

Example 110 Step a

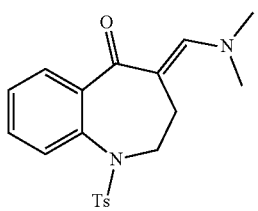 [SMILES: Cc1ccc(S(=O)(=O)N2CC/C(=C\N(C)C)C(=O)c3ccccc32)cc1]

A solution of compound from Example 1 step a (1.00 g, 0.003 mol) in DMF-DMA (10 mL) was stirred at 100° C. for 12 hrs under N₂. After cooling to room temperature, the precipitate was collected by filtration and washed by hexane to give the desired compound (900 mg, 77%) as a yellow solid. ESI MS m/z=371.25 [M+1].

Example 110 for Step b

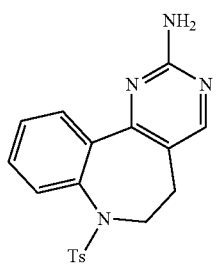 [SMILES: Cc1ccc(S(=O)(=O)N2CCc3cnc(N)nc3-c3ccccc32)cc1]

A solution of the compound from Example 110 step a (800 mg, 1.081 mmol), guanidine hydrochloride (1.2 g, 3.24 mmol), and TEA (1.3 g, 3.24 mmol) in NMP (10 mL) was stirred at 140° C. for 12 hrs. The precipitate was collected by filtration to give the desired compound (600 mg, 76%) as a yellow solid. ESI MS m/z=367.00 [M+1].

Example 110 for Step c

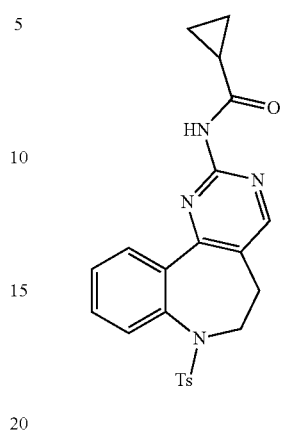

Cyclopropanecarbonyl chloride (131 mg, 1.25 mmol) was added into a solution of compound from Example 110 step b (435 mg, 1.19 mmol) in pyridine (10 mL) at 20° C. The reaction mixture was stirred at 20° C. for 5 hrs, and then quenched with MeOH. Solvent was removed and the residue was purified by silica gel column chromatography to give the desired compound (440 mg, 85%) as a yellow solid. ESI MS m/z=435.10 [M+1].

Example 110 for Step d

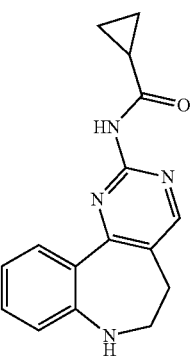 [SMILES: O=C(Nc1ncc2c(n1)-c1ccccc1NCC2)C1CC1]

Compound from Example 110 step c (500 mg, 1.149 mmol) was added to 90% H₂SO₄ (0.5 ml) at ice salt bath and the resulting mixture was stirred at 0° C. for 3 hrs. The solution was adjusted to PH=10 with Na₂CO₃ at 0° C. and extracted with ethyl acetate (50 mL×2). The organic layer was dried, concentrated and purified by silica gel column chromatography to give desired compound (300 mg, 94%) as a yellow solid. ESI MS m/z=281.05 [M+1].

Example 110 for Step e

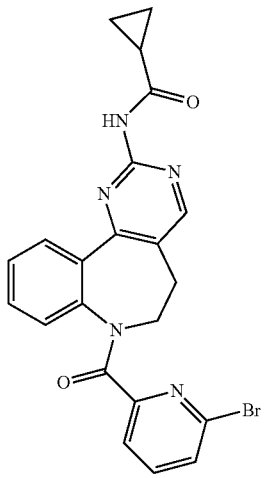 [SMILES: O=C(Nc1ncc2c(n1)-c1ccccc1N(C(=O)c1cccc(Br)n1)CC2)C1CC1]

6-Bromopyridine-2-carbonyl chloride (283 mg, 1.29 mmol) was added to a solution of compound from Example 110 step d (300 mg, 1.07 mmol) and DIEA (691 mg, 5.36 mmol) in DCM (10 mL) at 0° C. The mixture was stirred at 20° C. for 12 hrs and then quenched with water and extracted with DCM. The organic layer was dried, concentrated and purified by silica gel column chromatography to give the desired compound (300 mg, 60%) as a yellow solid. ESI MS m/z=464.10 [M+1].

Example 110 Step f

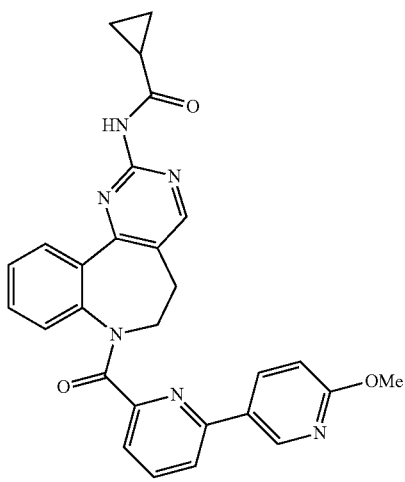 [SMILES: COc1ccc(-c2cccc(C(=O)N3CCc4cnc(NC(=O)C5CC5)nc4-c4ccccc43)n2)cn1]

A solution of compound from Example 110 step e (80 mg, 0.17 mmol), (6-methoxypyridin-3-yl)boronic acid (32 mg, 0.21 mmol), Pd(PPh$_3$)Cl$_2$ (12 mg, 0.017 mmol) and K$_2$CO$_3$ (36 mg, 0.26 mmol) in DME/H$_2$O/EtOH (2/1/2, 5 mL) was heated at 90° C. for 3 hrs under N$_2$. The mixture was purified by prep-HPLC to give the title compound (45.8 mg, 54%) as a yellow solid. ESI MS m/z=493.20 [M+1]. $^1$H NMR (400 MHz, DMSO-d$_6$) δ 0.77-0.99 (m, 4H), 2.23 (m, 1H), 2.67 (m 1H), 3.05 (m, 1H), 3.90 (s, 4H), 4.69 (m, 1H), 6.99 (m, 2H), 7.16 (m, 1H), 7.28 (m, 1H), 7.47 (m, 1H), 7.76 (d, J=7.7 Hz, 1H), 7.79-7.89 (m, 2H), 8.02 (m, 1H), 8.61 (d, J=2.5 Hz, 1H), 8.69 (s, 1H), 10.95 (s, 1H).

Example 111

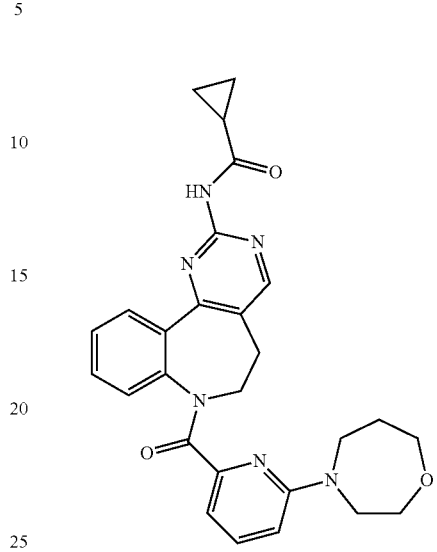

A solution of the compound from Example 110 step e (80 mg, 0.172 mmol), 1,4-oxazepane hydrochloride (119 mg, 0.86 mmol) and DIEA (134 mg, 1.04 mmol) in DMSO (3 mL) was heated at 100° C. for 7 days. The mixture was purified by prep-HPLC to give the title compound (50.3 mg, 60%) as a light brown solid. ESI MS m/z=485.40 [M+1]. $^1$H NMR (300 MHz, DMSO-d$_6$) δ 0.78-0.88 (m, 4H), 1.65 (m, 2H), 2.21 (m, 1H), 2.59 (m, 1H), 2.99 (m, 1H), 3.32 (m, 2H), 3.33-3.52 (m, 6H), 3.73-3.85 (m, 1H), 4.59 (m, 1H), 6.43 (d, J=8.6 Hz, 1H), 6.68 (d, J=7.2 Hz, 1H), 6.88 (d, J=7.8 Hz, 1H), 7.23 (m, 1H), 7.31-7.45 (m, 2H), 7.71 (m, 1H), 8.62 (s, 1H).

Example 112

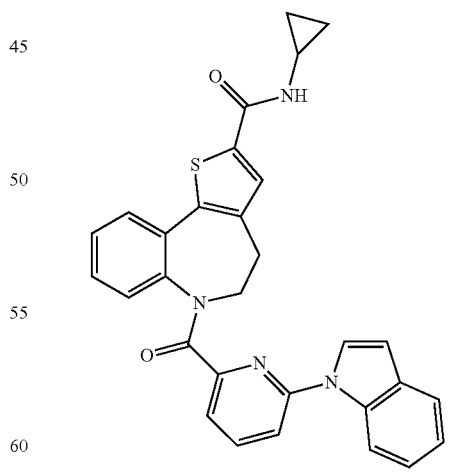

In a vial, compounds from Example 16 step a (110 mg, 0.235 mmol) was dissolved in THF (2349 µl). Indole (33.0 mg, 0.282 mmol), Cs$_2$CO$_3$ (153 mg, 0.470 mmol), (2-dicyclohexylphosphino-2',6'-diisopropoxy-1,1'-biphenyl)[2-(2'-amino-1,1'-biphenyl)]palladium-(II) methanesulfonate (13.68 mg, 0.018 mmol), and 2-dicyclohexylphosphino-2', 6'-diisopropoxybiphenyl (16.44 mg, 0.035 mmol) were added and the vial was sealed. The reaction was heated to 80° C. for 3 h. After cooling to room temperature, the mixture was diluted with EtOAc and washed with water and brine. The organic layer was concentrated and purified by silica gel chromatography to give the desired product (80 mg, 68% yield) as a white solid. ESI-MS m/z=505.2 [M+H]+.

Example 113

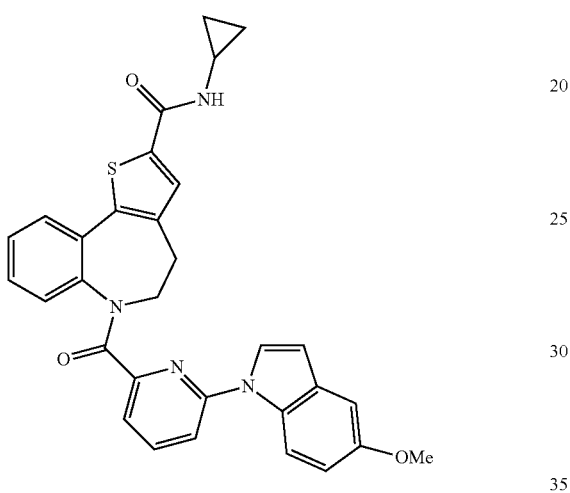

Example 113 was prepared using a procedure similar to that used to prepare Example 112 where indole was replaced with 5-methoxy-1H-indole. ESI-MS m/z=535.2 [M+H]+.

Example 114

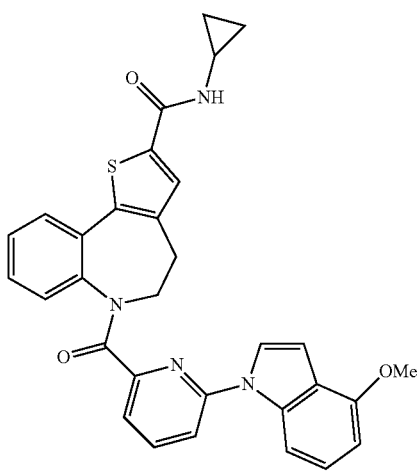 [SMILES: COc1cccc2c1ccn2-c1cccc(C(=O)N2CCc3cc(C(=O)NC4CC4)sc3-c3ccccc32)n1]

Example 114 was prepared using a procedure similar to that used to prepare Example 112 where indole was replaced with 4-methoxy-1H-indole. ESI-MS m/z=535.2 [M+H]+.

Example 115

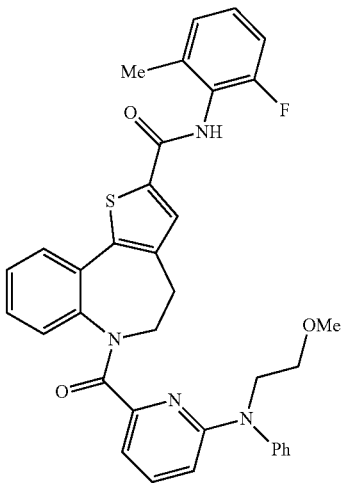 [SMILES: COCCN(c1ccccc1)c1cccc(C(=O)N2CCc3cc(C(=O)Nc4c(C)cccc4F)sc3-c3ccccc32)n1]

Example 115 Step a

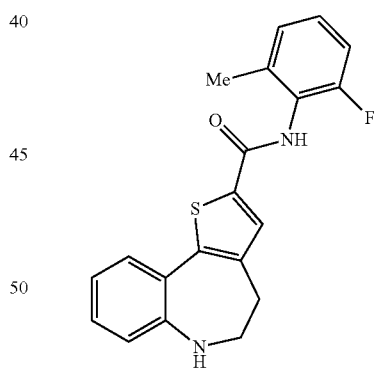

To a solution of acid from Example 1 step d (245 mg, 1.0 mmol) in DCM (5 mL), 1-chloro-N,N,2-trimethylprop-1-en-1-amine (266 mg, 2.0 mmol) was added. The resulting mixture was stirred at rt for 30 min and then concentrated in vacuo. The residue was taken into DCM (5 mL) and a solution of 2-fluoro-6-methylaniline (600 mg, 4.0 mmol) in pyridine (2 mL) was added. After stirred at rt for 2 hrs, the mixture was partitioned between DCM (50 mL) and water (20 mL). The organic layer was separated, dried, evaporated, and purified by combiflash eluting with 0-40% EtOAc/hexanes to obtain the desired product (278 mg, 79% yield) as a pale yellow solid. ESI-MS m/z=353.1 [M+H]+.

Example 115 Step b

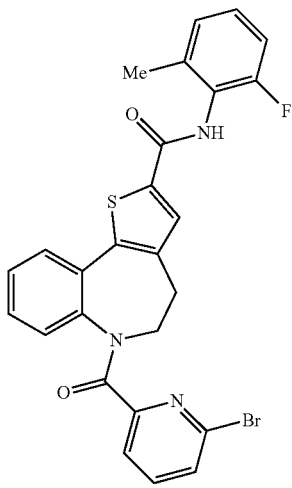 [SMILES: Cc1cccc(F)c1NC(=O)c1cc2c(s1)-c1ccccc1N(C(=O)c1cccc(Br)n1)CC2]

Compound was prepared using a procedure similar to that used to prepare Example 16 step a. ESI-MS m/z=536.0 [M+H]+.

Example 115 Step c

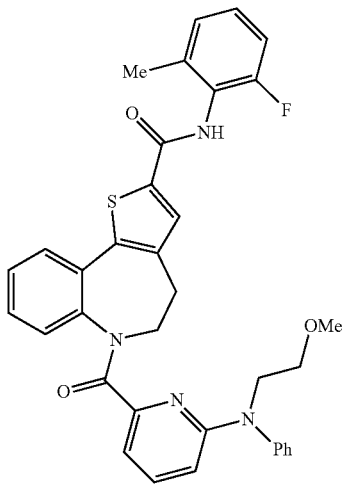 [SMILES: COCCN(c1ccccc1)c1cccc(C(=O)N2CCc3cc(C(=O)Nc4c(C)cccc4F)sc3-c3ccccc32)n1]

Example 115 was prepared using a procedure similar to that used to prepare Example 112 where indole was replaced with N-(2-methoxyethyl)aniline and 6-(6-bromopicolinoyl)-N-cyclopropyl-5,6-dihydro-4H-benzo[b]thieno[2,3-d]azepine-2-carboxamide was replaced with 6-(6-bromopicolinoyl)-N-(2-fluoro-6-methylphenyl)-5,6-dihydro-4H-benzo[b]thieno[2,3-d]-azepine-2-carboxamide. ESI-MS m/z=607.0 [M+H]+.

Example 116

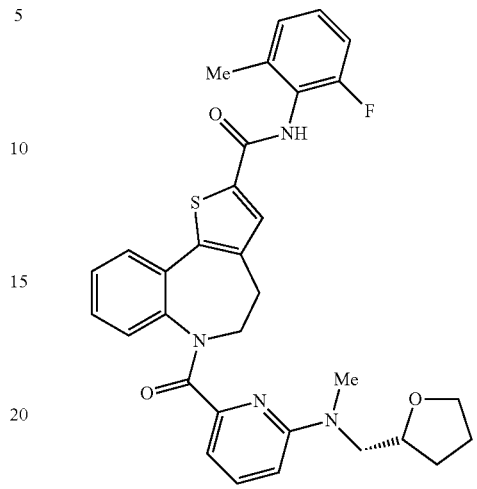

Example 116 was prepared using a prodcedure similar to that used to prepare Example 112 where indole was replaced with (R)—N-methyl-1-(tetrahydrofuran-2-yl)methanamine and 6-(6-bromopicolinoyl)-N-cyclopropyl-5,6-dihydro-4H-benzo[b]thieno[2,3-d]azepine-2-carboxamide was replaced with 6-(6-bromopicolinoyl)-N-(2-fluoro-6-methylphenyl)-5,6-dihydro-4H-benzo[b]thieno[2,3-d]azepine-2-carboxamide. ESI-MS m/z=571.0 [M+H]+.

Example 117

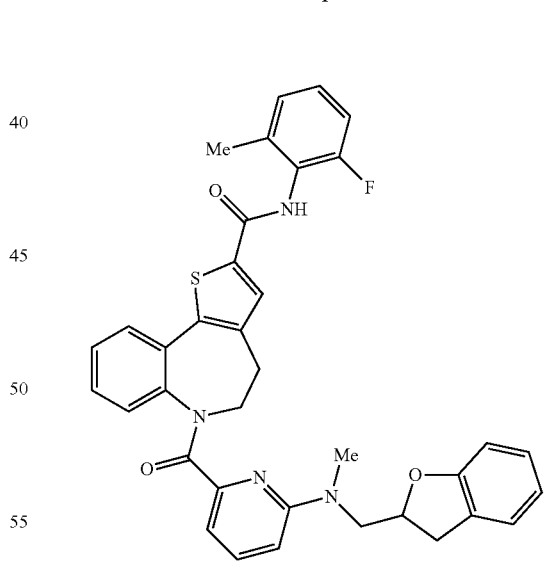

Example 117 was prepared using a prodcedure similar to that used to prepare Example 112 where indole was replaced with 1-(2,3-dihydrobenzofuran-2-yl)-N-methylmethanamine and 6-(6-bromopicolinoyl)-N-cyclopropyl-5,6-dihydro-4H-benzo[b]thieno[2,3-d]azepine-2-carboxamide was replaced with 6-(6-bromopicolinoyl)-N-(2-fluoro-6-methylphenyl)-5,6-dihydro-4H-benzo[b]thieno[2,3-d]azepine-2-carboxamide. ESI-MS m/z=619.0 [M+H]+.

Example 118

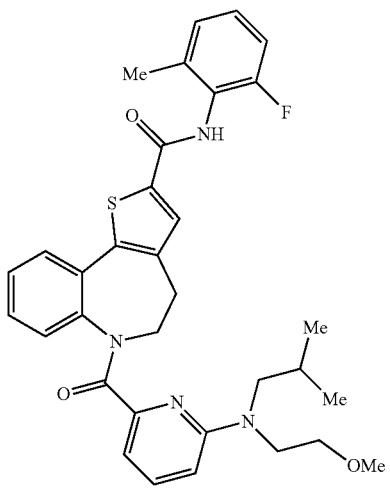 [SMILES: COCCN(CC(C)C)c1cccc(C(=O)N2CCc3cc(C(=O)Nc4c(C)cccc4F)sc3-c3ccccc32)n1]

Example 118 was prepared using a prodcedure similar to that used to prepare Example 112 where indole was replaced with N-(2-methoxyethyl)-2-methylpropan-1-amine and 6-(6-bromopicolinoyl)-N-cyclopropyl-5,6-dihydro-4H-benzo[b]thieno[2,3-d]azepine-2-carboxamide was replaced with 6-(6-bromopicolinoyl)-N-(2-fluoro-6-methylphenyl)-5,6-dihydro-4H-benzo[b]thieno[2,3-d]azepine-2-carboxamide. ESI-MS m/z=587.1 [M+H]+.

Example 119

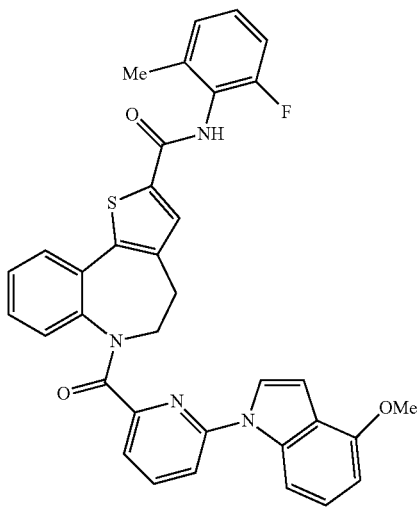 [SMILES: COc1cccc2c1ccn2-c1cccc(C(=O)N2CCc3cc(C(=O)Nc4c(C)cccc4F)sc3-c3ccccc32)n1]

Example 119 was prepared using a prodcedure similar to that used to prepare Example 112 where indole was replaced with 4-methoxy-1H-indole and 6-(6-bromopicolinoyl)-N-cyclopropyl-5,6-dihydro-4H-benzo[b]thieno[2,3-d]azepine-2-carboxamide was replaced with 6-(6-bromopicolinoyl)-N-(2-fluoro-6-methylphenyl)-5,6-dihydro-4H-benzo[b]thieno[2,3-d]azepine-2-carboxamide. ESI-MS m/z=603.0 [M+H]$^+$.

Example 120

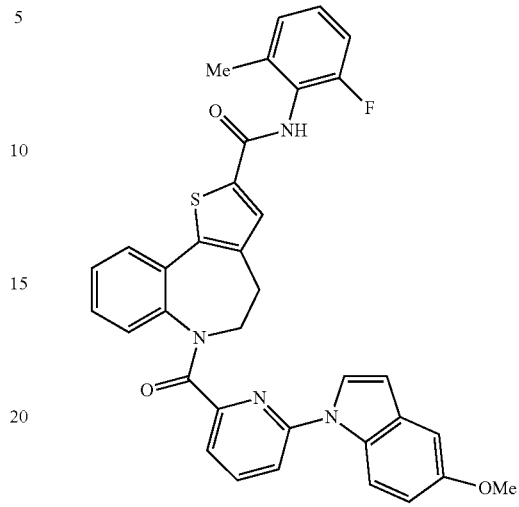

Example 120 was prepared using a prodcedure similar to that used to prepare Example 112 where indole was replaced with 5-methoxy-1H-indole and 6-(6-bromopicolinoyl)-N-cyclopropyl-5,6-dihydro-4H-benzo[b]thieno[2,3-d]azepine-2-carboxamide was replaced with 6-(6-bromopicolinoyl)-N-(2-fluoro-6-methylphenyl)-5,6-dihydro-4H-benzo[b]thieno[2,3-d]azepine-2-carboxamide. ESI-MS m/z=603.0 [M+H]$^+$.

Example 121

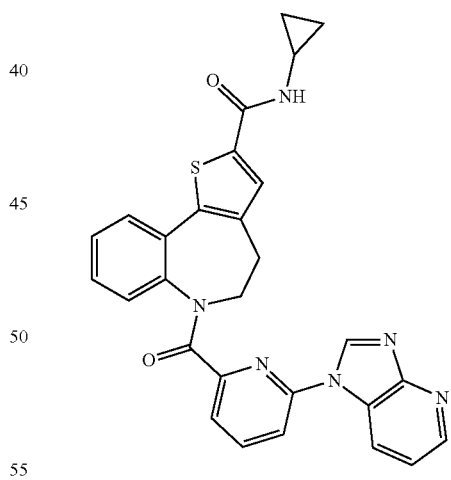

In a vial, 6-(6-bromopicolinoyl)-N-cyclopropyl-5,6-dihydro-4H-benzo[b]thieno[2,3-d]azepine-2-carboxamide (100 mg, 0.214 mmol), 1H-imidazo[4,5-b]pyridine (38.2 mg, 0.320 mmol), copper(I) iodide (8.13 mg, 0.043 mmol), (1S,2S)—N1,N2-dimethylcyclohexane-1,2-diamine (6.73 µl, 0.043 mmol), and cesium carbonate (139 mg, 0.427 mmol) were dissolved in DMF (712 µl). The reaction was heated to 130° C. for 2 h. The reaction was quenched upon addition of water and extracted with EtOAc. The organic layer was washed with water and brine before drying over MgSO$_4$. The mixture was purified by silica gel chromatography to afford the desired product (55 mg, 51% yield) as a white solid. ESI-MS m/z=507.2 [M+H]+.

Example 122

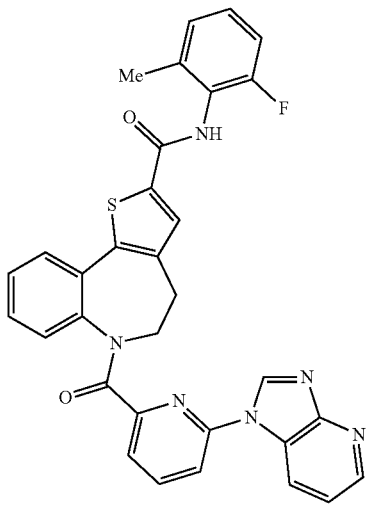 [SMILES: Cc1cccc(F)c1NC(=O)c1cc2c(s1)-c1ccccc1N(C(=O)c1cccc(-n3cnc4ncccc43)n1)CC2]

Example 122 was prepared using a prodcedure similar to that used to prepare Example 121 where 6-(6-bromopicolinoyl)-N-cyclopropyl-5,6-dihydro-4H-benzo[b]thieno[2,3-d]azepine-2-carboxamide was replaced with 6-(6-bromopicolinoyl)-N-(2-fluoro-6-methylphenyl)-5,6-dihydro-4H-benzo[b]thieno[2,3-d]azepine-2-carboxamide. ESI-MS m/z=574.8 [M+H]+.

Example 123

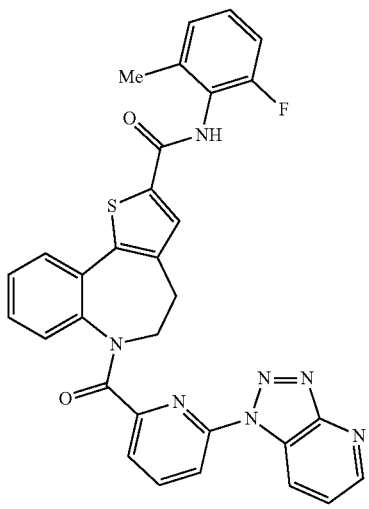 [SMILES: Cc1cccc(F)c1NC(=O)c1cc2c(s1)-c1ccccc1N(C(=O)c1cccc(-n3nnc4ncccc43)n1)CC2]

Example 123 was prepared using a prodcedure similar to that used to prepare Example 121 where 1H-imidazo[4,5-b]pyridine was replaced with 1H-[1,2,3]triazolo[4,5-b]pyridine and 6-(6-bromopicolinoyl)-N-cyclopropyl-5,6-dihydro-4H-benzo[b]thieno[2,3-d]azepine-2-carboxamide was replaced with 6-(6-bromopicolinoyl)-N-(2-fluoro-6-methylphenyl)-5,6-dihydro-4H-benzo[b]thieno[2,3-d]azepine-2-carboxamide. ESI-MS m/z=575.9 [M+H]+.

Example 124

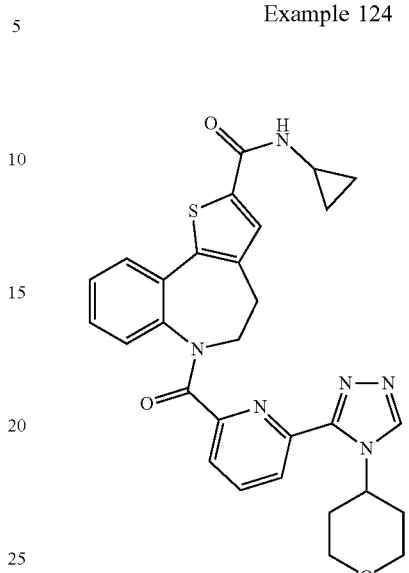

Example 124 Step a

[structure]

To a solution of 6-(methoxycarbonyl)picolinic acid (0.71 g, 3.91 mmol) in DCM (50 mL) was added 1-chloro-N,N,2-trimethylprop-1-en-1-amine (1.04 g, 2.0 mmol). The reaction mixture was stirred at rt for 2 hrs and was then concentrated in vacuo. The resulting residue was taken into DCM (50 mL) and a solution of N-cyclopropyl-5,6-dihydro-4H-benzo[b]thieno[2,3-d]azepine-2-carboxamide (1.0 g, 3.52 mmol) in pyridine (2 mL) was added. After stirred at rt for 2 hrs, the mixture was partitioned between DCM (200 mL) and 1N HCl (20 mL). The organic layer was washed with brine (50 mL), dried, evaporated, and purified by combiflash eluting with 0-8% MeOH/DCM to obtain the desired product (1.20 g, 68.6% yield) as a yellowish solid. ESI MS m/z=448.1 [M+H]+.

Example 124 Step b

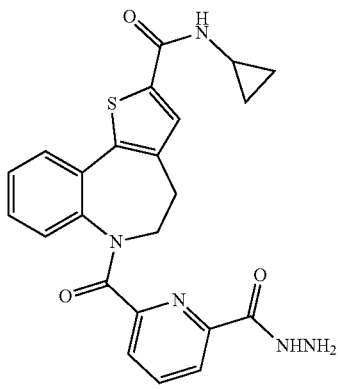 [SMILES: NNC(=O)c1cccc(C(=O)N2CCc3cc(C(=O)NC4CC4)sc3-c3ccccc32)n1]

To a round-bottomed flask were charged methyl 6-(2-(cyclopropylcarbamoyl)-5,6-dihydro-4H-benzo[b]thieno[2,3-d]azepine-6-carbonyl)picolinate (1.20 g, 2.68 mmol) and hydrazine hydrate (0.134 g, 2.68 mmol) in EtOH. The reaction mixture was stirred at rt for 10 hrs and continued at 60° C. for 4 hrs. After removed most of solvent and diluted with DCM (200 mL), the organic layer was washed with brine (50 mL), dried, and evaporated to obtain a pale yellow solid. After added EtOAc/hexanes 50 mL (1:1), the suspension was sonicated and then filtered to obtain the desired product (1.0 g, 83% yield) as a white solid which was used directly for the next step.

Example 124 Step c

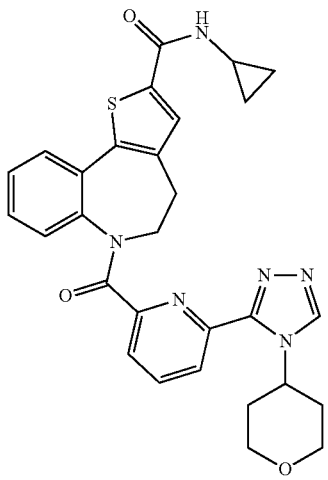 [SMILES: O=C(NC1CC1)c1cc2c(s1)-c1ccccc1N(C(=O)c1cccc(-c3nncn3C3CCOCC3)n1)CC2]

In a microwave reactor was charged with acyl hydrazide (150 mg, 0.335 mmol), 4-amino-tetrahydro-pyran (244 mg, 2.413 mmol) and DMF-DPA (159 mg, 0.905 mmol) in toluene (4 mL). To this resulting slurry was charged AcOH (4 drops). The mixture was heated at 95° C. for 20 hrs. The mixture was purified by combiflash eluting with 0-10% MeOH/DCM (0-10%) to obtain the desired product (100 mg, 55.2% yield) as a white solid. ESI MS m/z=541.2 [M+H]+.

Example 125

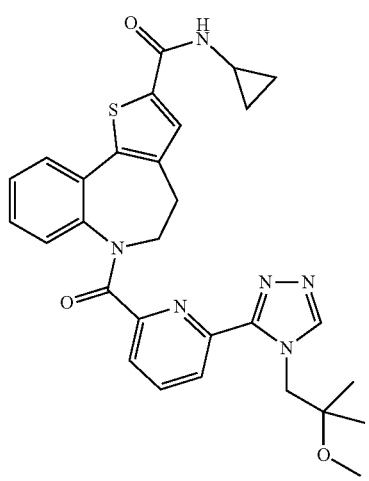 [SMILES: COC(C)(C)Cn1cnnc1-c1cccc(C(=O)N2CCc3cc(C(=O)NC4CC4)sc3-c3ccccc32)n1]

Example 125 was prepared using a procedure similar to that used to prepare Example 124 where 2-methoxy-2-methylpropan-1-amine was used in place of 4-amino-tetrahydro-pyran in step c. ESI MS m/z=543.2 [M+H]+.

Example 126

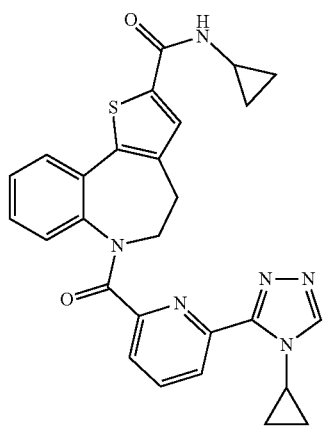 [SMILES: O=C(NC1CC1)c1cc2c(s1)-c1ccccc1N(C(=O)c1cccc(-c3nncn3C3CC3)n1)CC2]

Example 126 was prepared using a procedure similar to that used to prepare Example 124 where cyclopropylamine was used in place of 4-amino-tetrahydro-pyran in step c. ESI MS m/z=497.2 [M+H]+.

Example 127

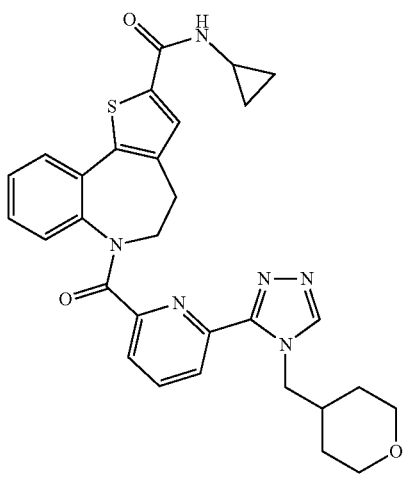 [SMILES: O=C(NC1CC1)c1cc2c(s1)-c1ccccc1N(C(=O)c1cccc(-c3nncn3CC3CCOCC3)n1)CC2]

Example 127 was prepared using a procedure similar to that used to prepare Example 124 where (tetrahydro-2H-pyran-4-yl)methanamine was used in place of 4-amino-tetrahydro-pyran in step c. ESI MS m/z=555.2 [M+H]+.

Example 128

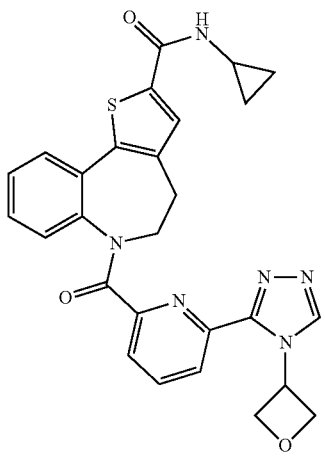 [SMILES: O=C(NC1CC1)c1cc2c(s1)-c1ccccc1N(C(=O)c1cccc(-c3nncn3C3COC3)n1)CC2]

Example 128 was prepared using a procedure similar to that used to prepare Example 124 where oxetan-3-amine was used in place of 4-amino-tetrahydro-pyran in step c. ESI MS m/z=513.2 [M+H]+.

Example 129

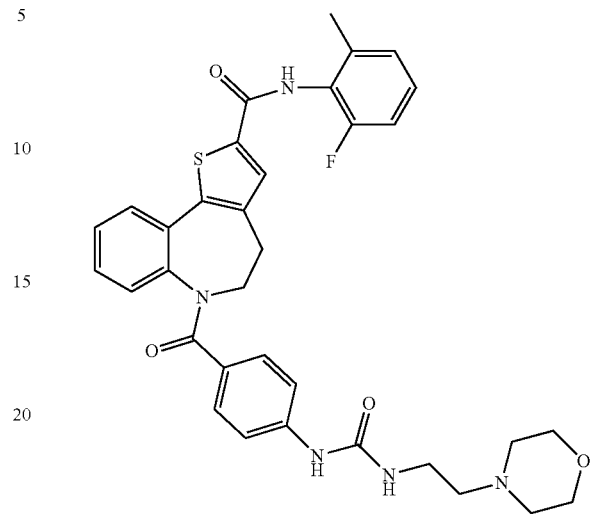

Example 129 Step a

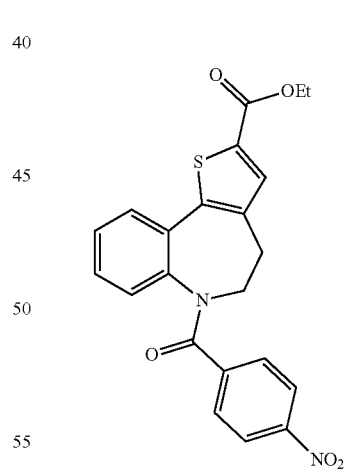

Ethyl 5,6-dihydro-4H-benzo[b]thieno[2,3-d]azepine-2-carboxylate and 4-nitrobenzoyl chloride were dissolved in DCM (50 mL), then DIEA was added slowly at rt. The reaction mixture was stirred at rt for 14 hrs. After diluted with DCM (300 mL), the mixture was washed with brine, dried, evaporated and purified combiflash eluting with 0-30% EtOAc/hexane to obtain the desired product (2.67 g, 75% yield) as a pale yellow solid which was used directly for the next step.

Example 129 Step b

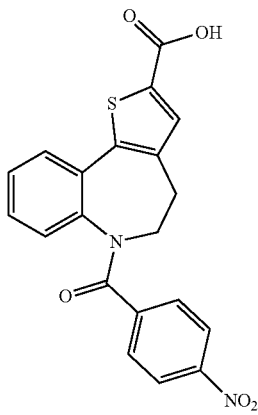 [SMILES: O=C(O)c1cc2c(s1)-c1ccccc1N(C(=O)c1ccc([N+](=O)[O-])cc1)CC2]

Ethyl ester (2.67 g, 6.32 mmol) was dissolved in THF (60 mL) and MeOH (60 mL), then 2N aq. NaOH (10 mL) was added. After the reaction mixture was stirred at rt for 3 hrs, reaction was completed. Evaporated most of the solvents and then diluted with water (20 mL). The mixture was neutralized with 2M HCl to pH ~2. The solid formed was filtered, washed with water and dried in oven overnight to obtain the desired product (2.40 g, 96% yield) as a pale yellow solid. ESI MS m/z=395.1 [M+H]$^+$.

Example 129 Step c

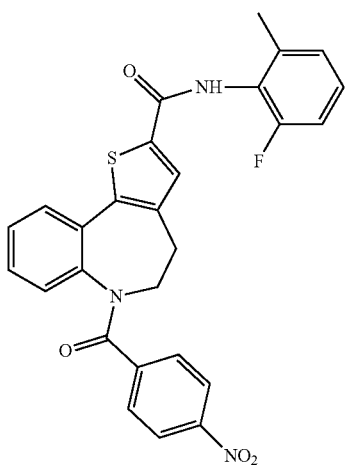 [SMILES: Cc1cccc(F)c1NC(=O)c1cc2c(s1)-c1ccccc1N(C(=O)c1ccc([N+](=O)[O-])cc1)CC2]

To a solution of acid (120 mg, 0.304 mmol) in DCM (10 mL), 1-chloro-N,N,2-trimethylprop-1-en-1-amine (81 mg, 0.609 mmol) was added. The resulting mixture was stirred at rt for 30 min and then concentrated in vacuo. The residue was taken into DCM (6 mL) and a solution of 2-fluoro-6-methylaniline (152 mg, 1.217 mmol) in pyridine (1.2 mL) was added. After stirred at rt for 2 hrs, the mixture was partitioned between DCM (100 mL) and water (30 mL). The organic layer was separated, dried, evaporated, and purified by combiflash eluting with 0-40% EtOAc/hexanes to obtain the desired product (120 mg, 79% yield) as a pale yellow foam which was directly for the next step.

Example 129 Step d

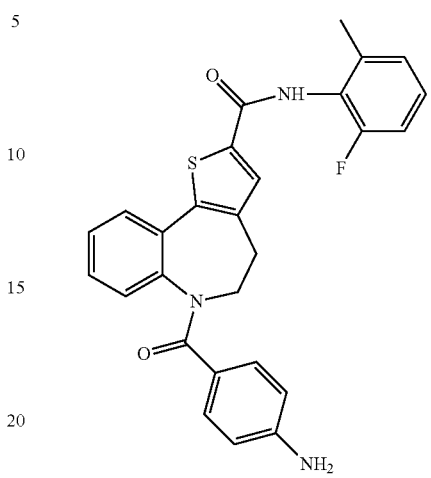

The nitro compound (1.50 g, 2.99 mmol) was dissolved in MeOH (30 mL) and DCM (60 mL). After degass, the reaction flask was filled with hydrogen gas by using a balloon. After stirred at rt for 16 hrs, reaction was completed. After filtered through celite and washed with MeOH/DCM (9:1) (50 mL), the solvents were evaporated and dried to obtain the desired product (1.41 g, 100% yield) as a light brown foam. ESI MS m/z=472.2 [M+H]$^+$.

Example 129 Step e

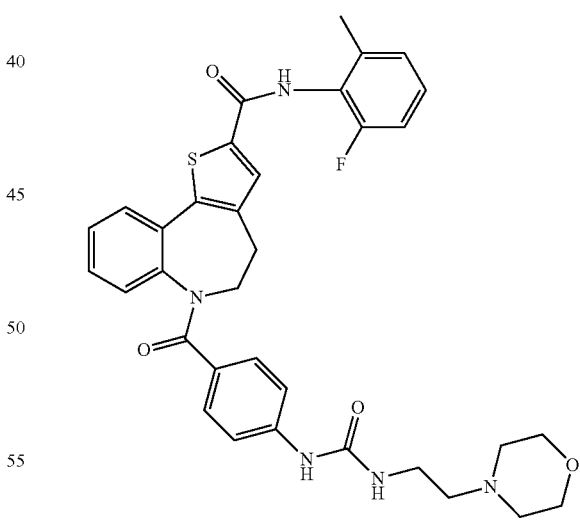

Aniline (100 mg, 0.212 mmol) was suspended in DCM, and then 4-nitrophenyl carbonochloridate (47 mg, 0.233 mmol), pyridine (5 drops) and DIEA (0.2 mL) were added. The reaction mixture was stirred at rt overnight. After loading the solution directly to cartridge and purified by combiflash eluting with 0-8% MeOH/DCM, the desired product (91 mg, 68.4% yield) was obtained as a white foam. ESI MS m/z=628.3 [M+H]$^+$.

Example 130

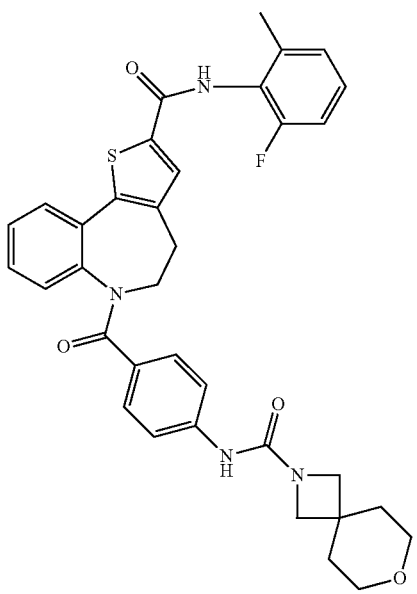 [SMILES: Cc1cccc(F)c1NC(=O)c1cc2c(s1)-c1ccccc1N(C(=O)c1ccc(NC(=O)N3CC4(CCOCC4)C3)cc1)CC2]

Example 130 was prepared using a procedure similar to that used to prepare Example 129 where 7-oxa-2-azaspiro[3.5]nonane was used in place of 2-morpholinoethan-1-amine in step e. ESI MS m/z=625.2 [M+H]+.

Example 131

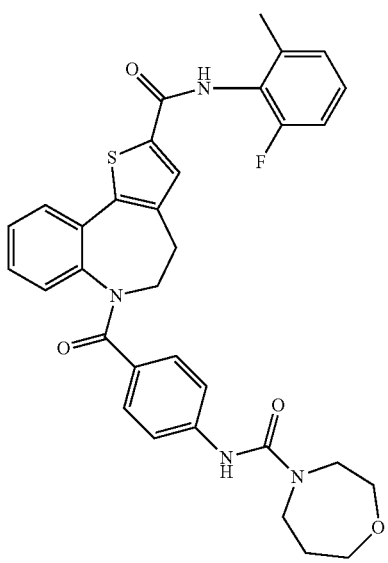 [SMILES: Cc1cccc(F)c1NC(=O)c1cc2c(s1)-c1ccccc1N(C(=O)c1ccc(NC(=O)N3CCCOCC3)cc1)CC2]

Example 131 was prepared using a procedure similar to that used to prepare Example 129 where 1,4-oxazepane was used in place of 2-morpholinoethan-1-amine in step e. ESI MS m/z=599.2 [M+H]+.

Example 132

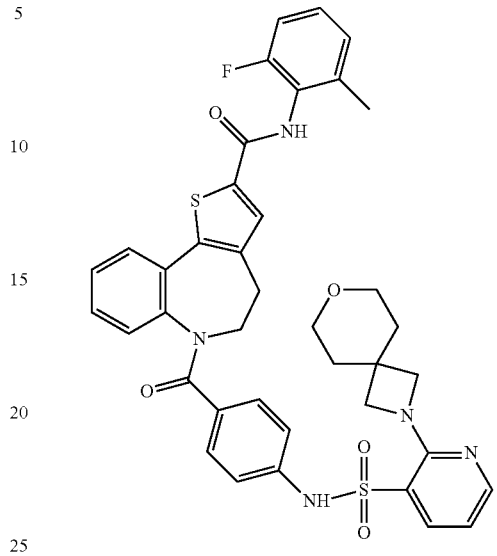

Example 132 Step a

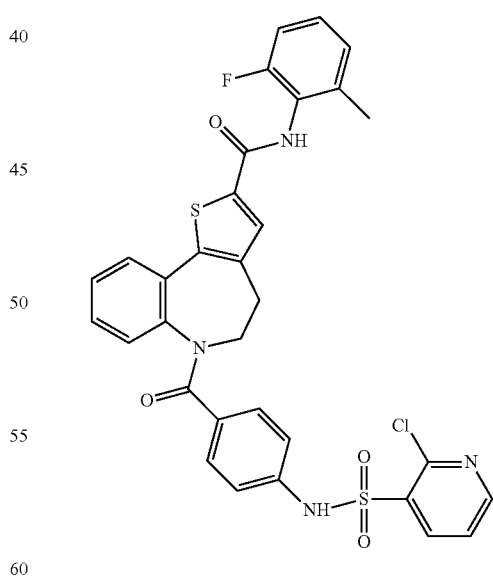

An oven-dried vial was charged with Example 129 step d (215 mg, 0.456 mmol), 2-chloropyridine-3-sulfonyl chloride (97 mg, 0.456 mmol), DIPEA (0.239 mL, 0.239 mmol), and DMF (5 mL). The reaction mixture was stirred for 1 h at 60° C., then purified by RPHPLC to provide the titled product (15 mg, 5%). ESI MS m/z=648.3 [M+H].

Example 132 Step b

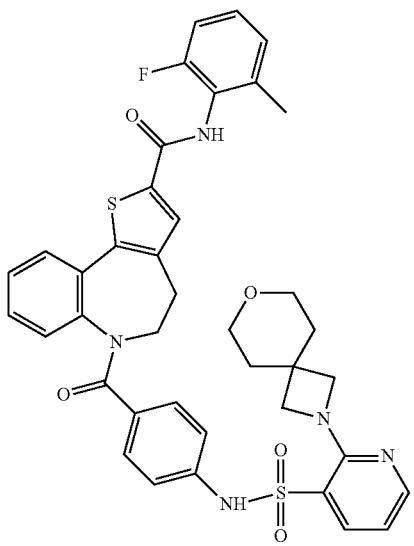 [SMILES: Cc1cccc(F)c1NC(=O)c1cc2c(s1)-c1ccccc1N(C(=O)c1ccc(NS(=O)(=O)c3cccnc3N3CC4(CCOCC4)C3)cc1)CC2]

An oven-dried vial was charged with compound from Example 132 step a (12 mg, 0.019 mmol), 7-oxa-2-azaspiro[3.5]nonane (4 mg, 0.019 mmol), DIPEA (0.010 mL, 0.056 mmol), and DMSO (1 mL). The reaction mixture was stirred for 2 h at 90° C., then purified by RPHPLC to provide the titled product (3 mg, 22%). ESI MS m/z=738.5 [M+H].

Example 133

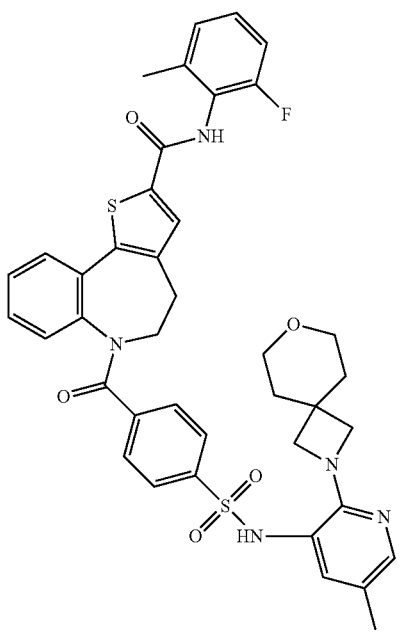 [SMILES: Cc1cnc(N2CC3(CCOCC3)C2)c(NS(=O)(=O)c2ccc(C(=O)N3CCc4cc(C(=O)Nc5c(C)cccc5F)sc4-c4ccccc43)cc2)c1]

Example 133 Step a

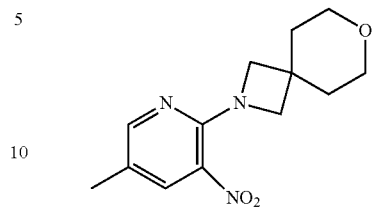

An oven-dried vial was charged with 2-chloro-5-methyl-3-nitropyridine (254 mg, 1.472 mmol), 7-oxa-2-azaspiro[3.5]nonane (319 mg, 1.472 mmol), DMSO (10 mL), and DIPEA (0.771 mL, 4.42 mmol). The reaction mixture was stirred for 1 h at 50° C., then purified by RPHPLC to provide the titled product (350 mg, 90%). ESI MS m/z=264.2 [M+H].

Example 133 Step b

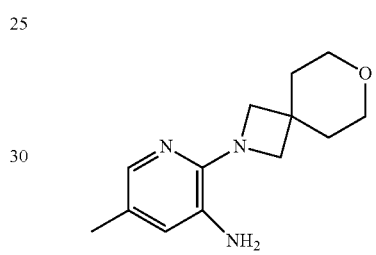

An oven-dried vial was charged with compound from Example 133 step a (388 mg, 1.474 mmol), 10% Pd/C (500 mg) and EtOAc (20 mL). The reaction mixture was placed under an atmosphere of hydrogen gas. The reaction mixture was stirred for 5 h at 50° C. then filtered over a celite pad. The filter cake was washed with EtOAc (50 mL) and the filtrate was dried to afford the titled product (344 mg, 100%). ESI MS m/z=234.1 [M+H].

Example 133 Step c

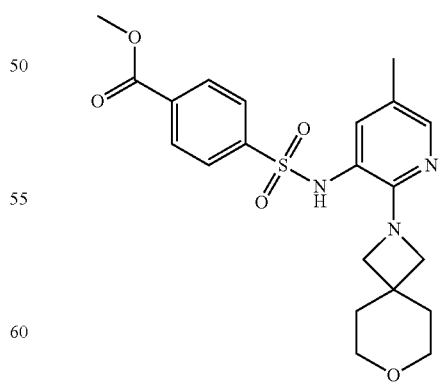

An oven-dried vial was charged with compound from Example 133 step b (200 mg, 0.857 mmol), methyl 4-(chlorosulfonyl)benzoate (201 mg, 0.857 mmol), and DCM (15 mL). The reaction mixture was stirred overnight, then evaporated to dryness. The residue was purified by RPHPLC to provide the tilted product (51 mg, 14%). ESI MS m/z=432.3 [M+H].

Example 133 Step d

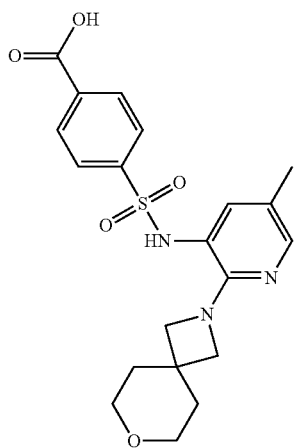 [SMILES: Cc1cnc(N2CC3(CCOCC3)C2)c(NS(=O)(=O)c2ccc(C(=O)O)cc2)c1]

Compound was prepared using a procedure similar hydrolysis condition to that used to prepare Example 94 step d. ESI MS m/z=418.1 [M+H].

Example 133 Step e

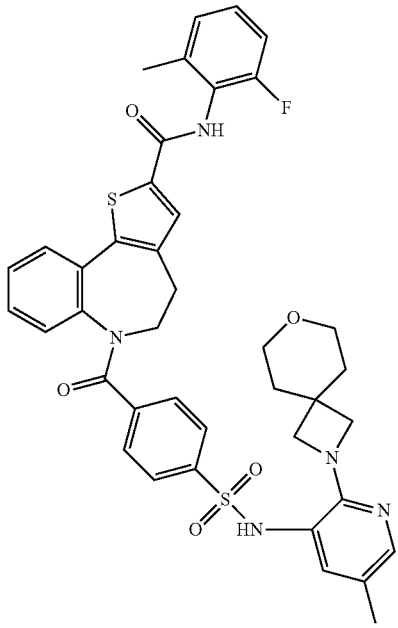 [SMILES: Cc1cnc(N2CC3(CCOCC3)C2)c(NS(=O)(=O)c2ccc(C(=O)N3CCc4cc(C(=O)Nc5c(C)cccc5F)sc4-c4ccccc43)cc2)c1]

Compound was prepared using a procedure similar to that used to prepare Example 16 step a by coupling compound from Example 133 step d with compound from Example 115 step b. ESI-MS m/z 752.9 [M+H]+.

Example 134

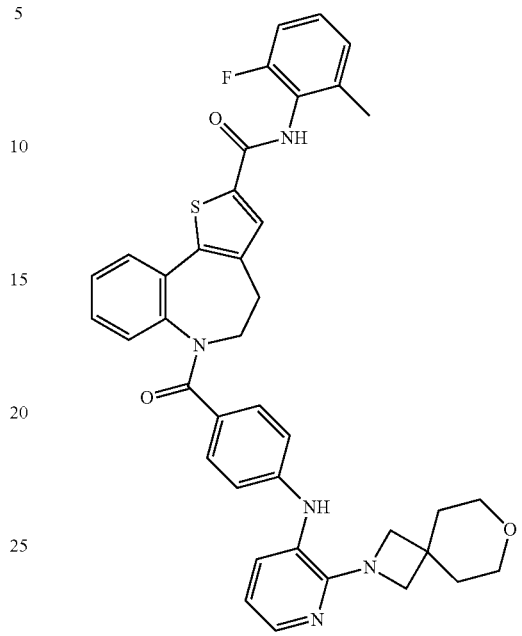

Example 134 Step a

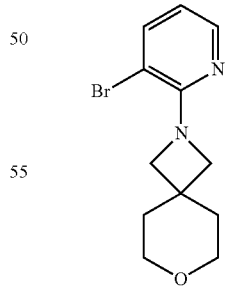

An oven-dried vial was charged with 7-oxa-2-azaspiro[3.5]nonane (90 mg, 0.551 mmol), 3-bromo-2-fluoropyridine (97 mg, 0.551 mmol), DIPEA (0.289 mL, 1.654 mmol), and DMSO (5 mL). The reaction mixture was stirred for 2 h at 50° C., then purified by RPHPLC to provide the titled product (50 mg, 32%). ESI MS m/z=284.2 [M+H].

Example 134 Step b

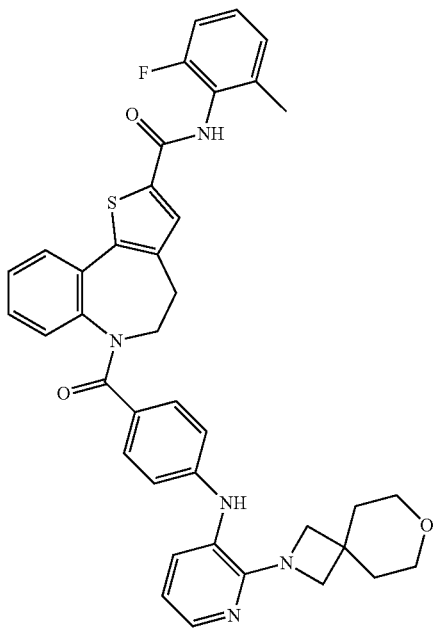 [SMILES: Cc1cccc(F)c1NC(=O)c1cc2c(s1)-c1ccccc1N(C(=O)c1ccc(Nc3cccnc3N3CC4(CCOCC4)C3)cc1)CC2]

An oven-dried vial was charged with compound from Example 134 step a (83 mg, 0.177 mmol), Example 129 step d (50 mg, 0.177 mmol), tBuOK (59 mg, 0.530 mmol), tBuXPhos (8 mg, 0.018 mmol), PdtBuXPhos G3 (7 mg, 0.009 mmol), and tBuOH (5 mL). The reaction mixture was stirred for 2 h at 50° C., then filtered. The filtrate was purified by RPHPLC to provide the titled product (29 mg, 24%). ESI MS m/z=674.7 [M+H].

Example 135

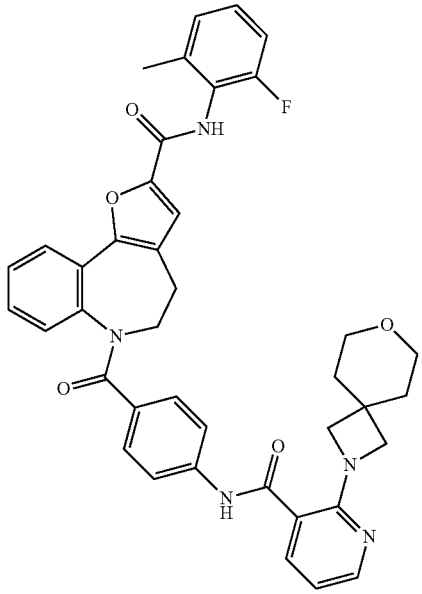

Example 135 Step a

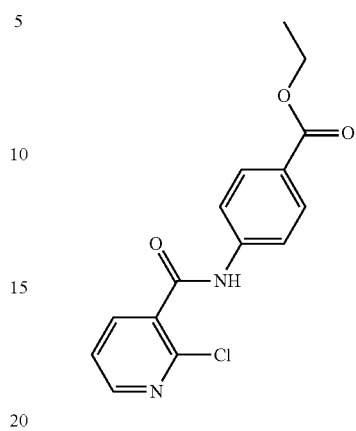

An oven-dried vial was charged with 2-chloronicotinoyl chloride (200 mg, 1.136 mmol), ethyl 4-aminobenzoate (188 mg, 1.136 mmol), DIPEA (0.397 mL, 2.273 mmol), and DCM (15 mL). The reaction mixture was stirred for 30 min at 0° C., then room temperature for 2 h. The reaction mixture was concentrated and the residue was purified on silica gel (1:1 EtOAc:hexanes) to provide the titled product (200 mg, 58%). ESI MS m/z=305.2 [M+H].

Example 135 Step b

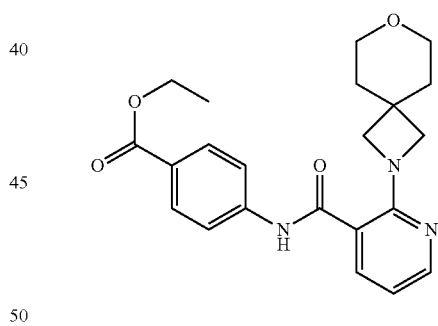

An oven-dried vial was charged with compound from Example 135 step a (1.524 g, 5.000 mmol), 7-oxa-2-azaspiro[3.5]nonane (1.085 g, 5.000 mmol), DIPEA (2.62 mL, 15.000 mmol), and NMP (20 mL). The reaction mixture was stirred for 24 h at 100° C. The reaction mixture was partitioned between water (50 mL) and EtOAc (50 mL). The product was extracted with EtOAc (3×50 mL). The combined organic layers were washed with brine and concentrated. The residue was purified on silica gel with 1:1 EtOAc:hexanes to provide the titled product (1.58 g, 80%). ESI MS m/z=396.3 [M+H].

Example 135 Step c

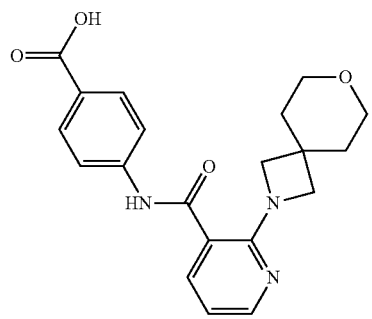 [SMILES: O=C(O)c1ccc(NC(=O)c2cccnc2N2CC3(CCOCC3)C2)cc1]

Compound was prepared using a procedure similar hydrolysis condition to that used to prepare Example 94 step d. ESI MS m/z=368.4 [M+H].

Example 135 Step d

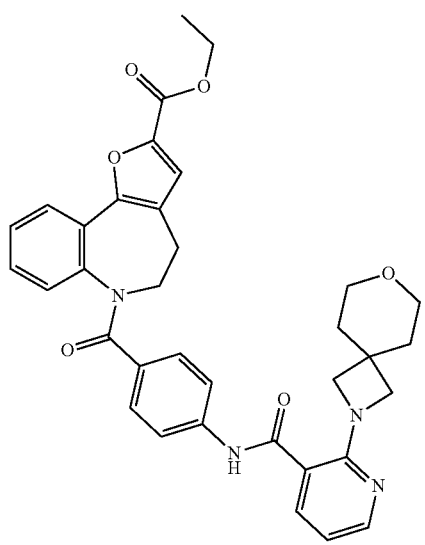 [SMILES: CCOC(=O)c1cc2c(o1)-c1ccccc1N(C(=O)c1ccc(NC(=O)c3cccnc3N3CC4(CCOCC4)C3)cc1)CC2]

Compound was prepared using a procedure similar Example 16 step a by coupling the above intermediate with compound from Example 106 step b. ESI MS m/z=607.2 [M+H].

Example 135 Step e

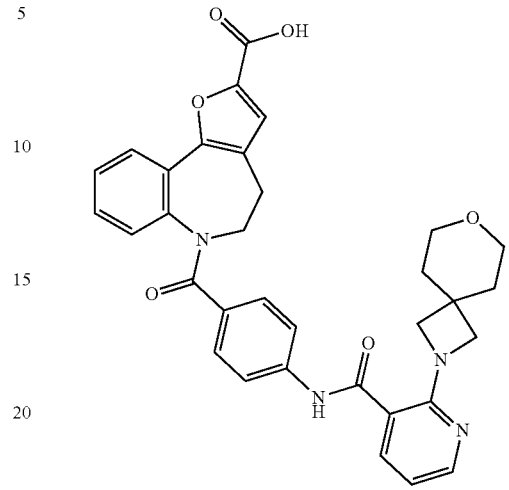

Compound was prepared using a procedure similar hydrolysis condition to that used to prepare Example 94 step d. ESI MS m/z=579.4 [M+H].

Example 135 Step f

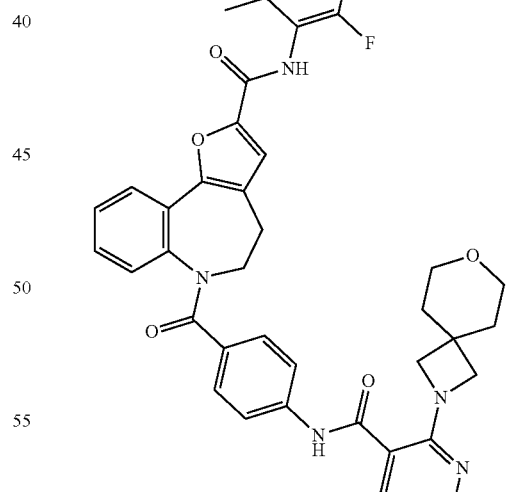

Compound was prepared using a procedure similar to that used to prepare Example 129 step c. ESI MS m/z=686.1 [M+H].

Example 136

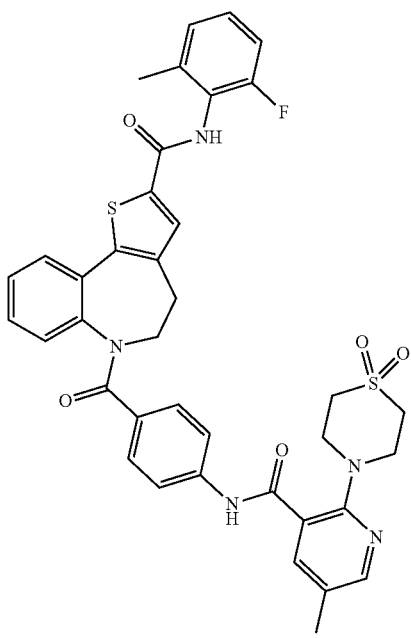 [SMILES: Cc1cnc(N2CCS(=O)(=O)CC2)c(C(=O)Nc2ccc(C(=O)N3CCc4cc(C(=O)Nc5c(C)cccc5F)sc4-c4ccccc43)cc2)c1]

Example 136 Step a

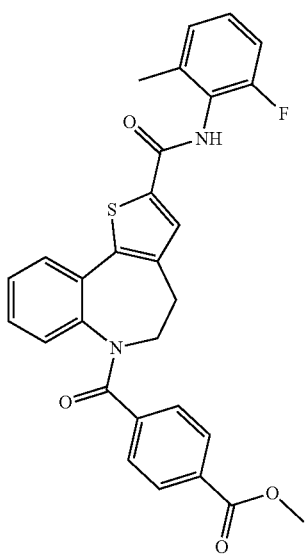 [SMILES: COC(=O)c1ccc(C(=O)N2CCc3cc(C(=O)Nc4c(C)cccc4F)sc3-c3ccccc32)cc1]

To a stirring solution of compound from (1.5 g, 4.61 mmol) in DCM (20 mL) was added DIPEA (3 mL) and methyl 4-(chlorocarbonyl)benzoate (1.7 g, 9.22 mmol). The mixture was stirred at room temperature for 3 hrs. Water was added and the mixture was extracted with DCM. Solvent was removed and the resulted residue was purified by flash chromatography column eluting with 0-50% EoOAc/hexanes to give the desired product as yellow solid (1.7 g, 71%). ESI MS m/z=537.1 [M+H]$^+$.

Example 136 Step b

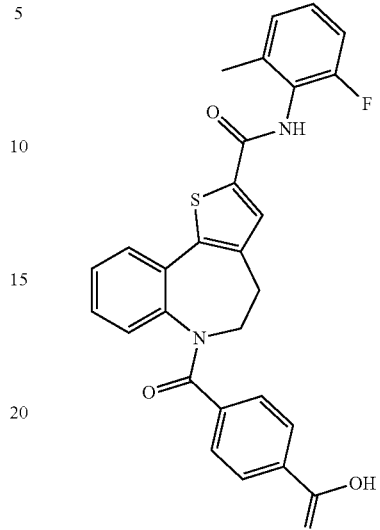

To a stirring solution of compound from Example 136 step a (1.7 g, 3.3 mmol) in THF/MeOH/H$_2$O (27 mL/3 mL/3 mL) was added LiOH (792 mg, 33 mmol). The mixture was stirred at rt overnight, and then adjusted to pH ~3 by adding 2N HCl aqueous solution. After concentrated under reduced pressure, the residue was purified by flash chromatography column (MeCN/H$_2$O) to give the desired product (1.0 g, 60%) as a white solid. ESI MS m/z=501.1 [M+H]$^+$.

Example 136 Step c

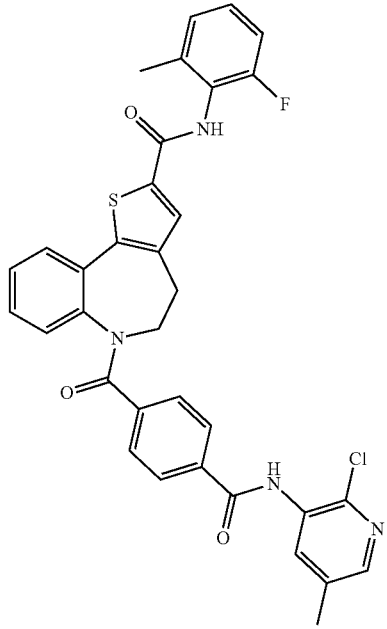 [SMILES: Cc1cnc(Cl)c(NC(=O)c2ccc(C(=O)N3CCc4cc(C(=O)Nc5c(C)cccc5F)sc4-c4ccccc43)cc2)c1]

To a stirring solution of compound from Example 136 step b (1.0 g, 2 mmol) in DCM (30 mL) was added 1-chloro-N,N,2-trimethylprop-1-en-1-amine (481 mg, 4 mmol), the mixture was stirred at rt for 30 min and then concentrated in vacuum. The residue was taken to DCM (6 mL) and a solution of 2-chloro-5-methylpyridin-3-amine (1.03 mg, 8 mmol) in pyridine (4 mL) was added. The resulting solution was stirred at rt overnight. The resulting mixture was concentrated under vacuum. The residue was applied onto a silica gel column eluting with 0-5% MeOH/DCM to give the desired product (950 mg, 76%) as a white solid. ESI MS m/z=625.1 [M+H]⁺.

Example 136 Step d

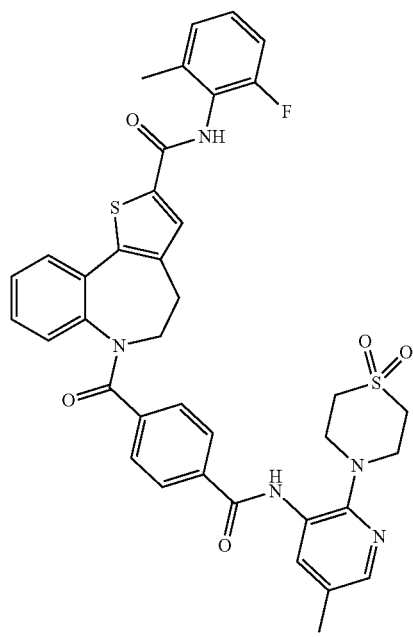 [SMILES: Cc1cnc(N2CCS(=O)(=O)CC2)c(NC(=O)c2ccc(C(=O)N3CCc4cc(C(=O)Nc5c(C)cccc5F)sc4-c4ccccc43)cc2)c1]

To a stirring solution of compound from Example 136 step c (150 mg, 0.24 mmol) in DMSO (1 mL) was added DIPEA (1 mL) and thiomorpholine 1,1-dioxide (970 mg, 7.2 mmol). The mixture was degassed with nitrogen and then heated 180° C. for 3 days. Water was added and the mixture was extracted with EtOAc. The residue was purified by prep-HPLC to give the title product (26.0 mg, 15%) as white solid. ESI MS m/z=724.3 [M+H]⁺.

Examples 137-142 shown in Table 2 were prepared using the procedure similar to that of Example 136.

TABLE 2

| Example | Structure |
|---------|-----------|
| 137 | 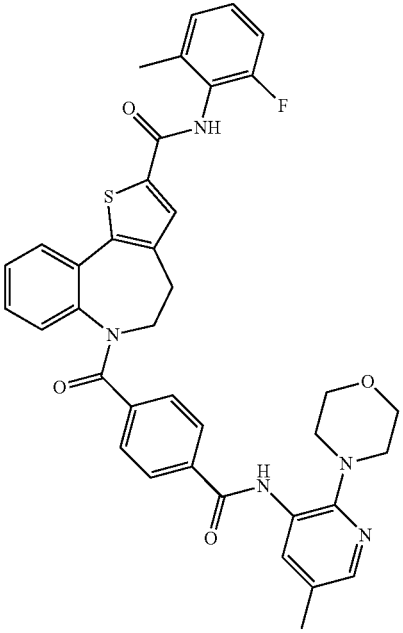 [SMILES: Cc1cnc(N2CCOCC2)c(NC(=O)c2ccc(C(=O)N3CCc4cc(C(=O)Nc5c(C)cccc5F)sc4-c4ccccc43)cc2)c1] |
| 138 | 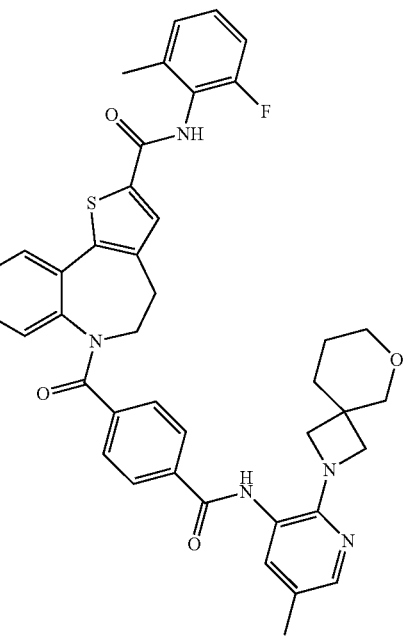 |

TABLE 2-continued
| Example | Structure |
|---|---|
| 139 | 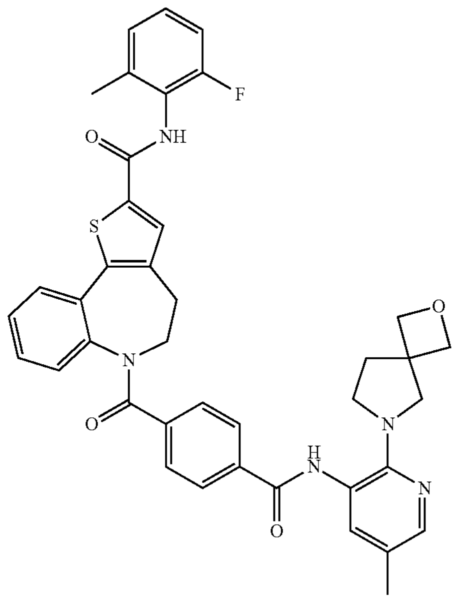 [SMILES: Cc1cnc(N2CCC3(COC3)C2)c(NC(=O)c2ccc(C(=O)N3CCc4cc(C(=O)Nc5c(C)cccc5F)sc4-c4ccccc43)cc2)c1] |
| 140 | 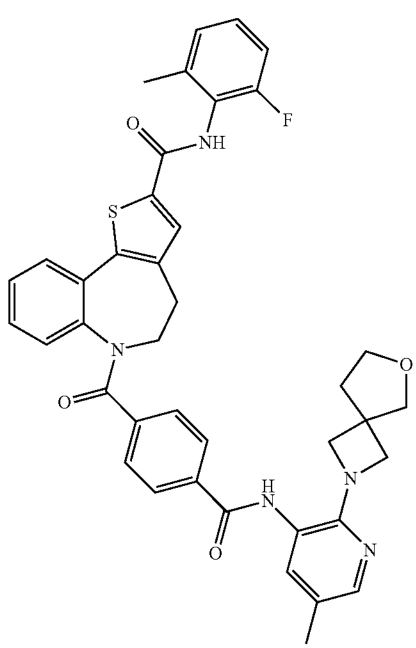 [SMILES: Cc1cnc(N2CC3(CCOC3)C2)c(NC(=O)c2ccc(C(=O)N3CCc4cc(C(=O)Nc5c(C)cccc5F)sc4-c4ccccc43)cc2)c1] |
| 141 | |
| 142 | |
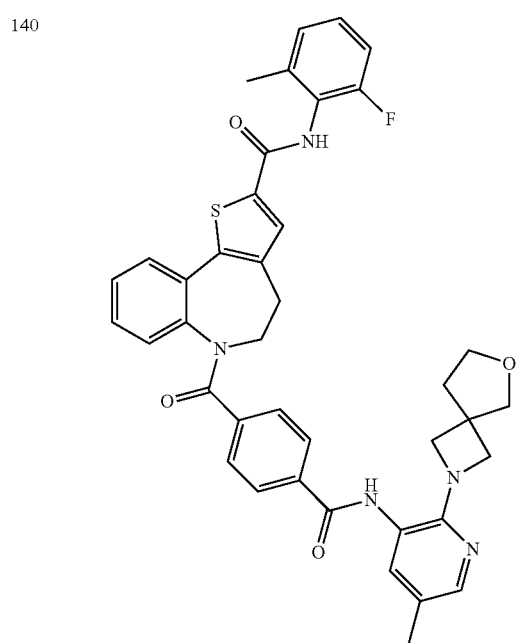
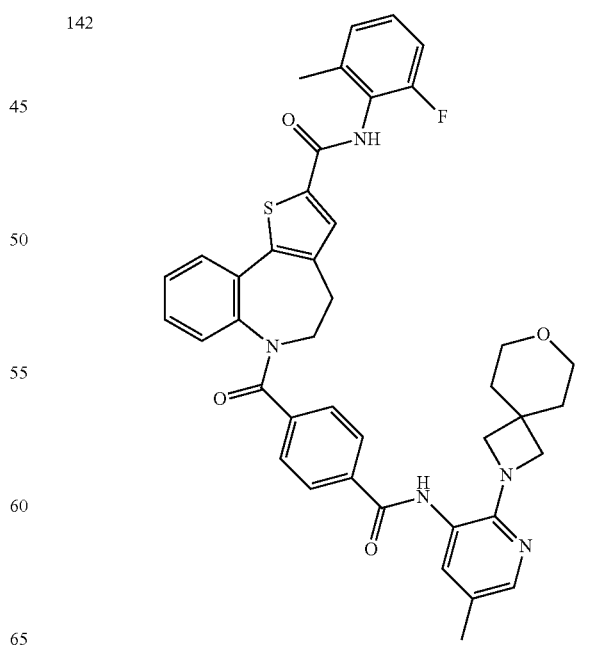

Example 143

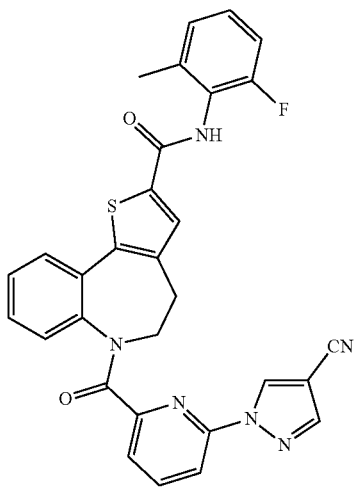 [SMILES: Cc1cccc(F)c1NC(=O)c1cc2c(s1)-c1ccccc1N(C(=O)c1cccc(-n3cc(C#N)cn3)n1)CC2]

A solution of compound from Example 115 step b (100 mg, 0.19 mmol), 1H-pyrazole-4-carbonitrile (43 mg, 0.46 mmol), CuI (53 mg, 0.28 mmol), K$_2$CO$_3$ (102 mg, 0.74 mmol), (1S,2S)-1-N,2-N-dimethylcyclohexane-1,2-diamine (52.8 mg, 0.37 mmol) in DMF (3 mL) was stirred for 2 hrs at 100° C. under N$_2$. The crude product was purified by HPLC to give the desired compound (66 mg, 65%) as a white solid. ESI MS m/z=549.2 [M+H]$^+$.

Examples 144-149 shown in Table 3 were prepared using the procedure similar to that of Example 143.

TABLE 3-continued
| Example | Structure |
|---------|-----------|
| 148 | 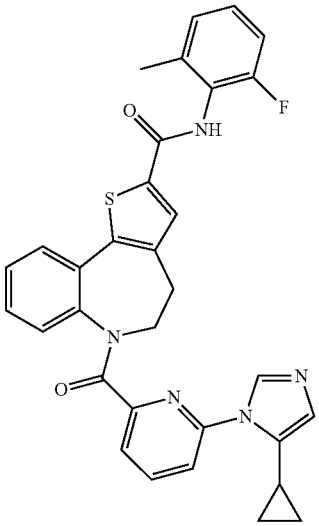 [SMILES: Cc1cccc(F)c1NC(=O)c1cc2c(s1)-c1ccccc1N(C(=O)c1cccc(-n3cncc3C3CC3)n1)CC2] |
| 149 | 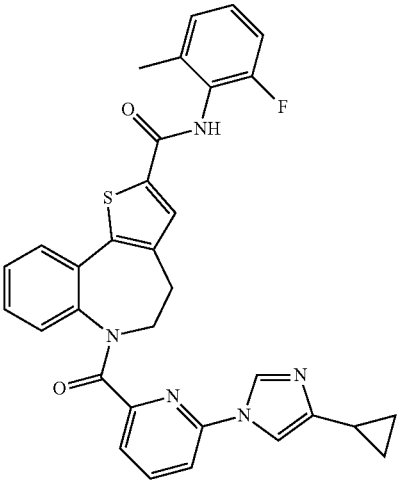 [SMILES: Cc1cccc(F)c1NC(=O)c1cc2c(s1)-c1ccccc1N(C(=O)c1cccc(-n3cnc(C4CC4)c3)n1)CC2] |
TABLE 4
| Example | Structure |
|---------|-----------|
| 150 | 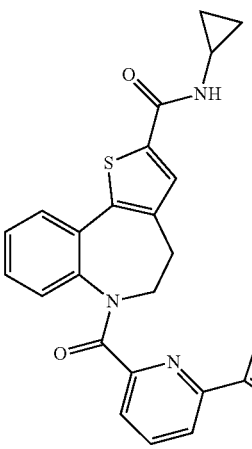 |
| 151 | 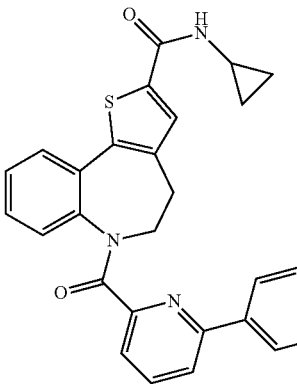 |
| 152 | 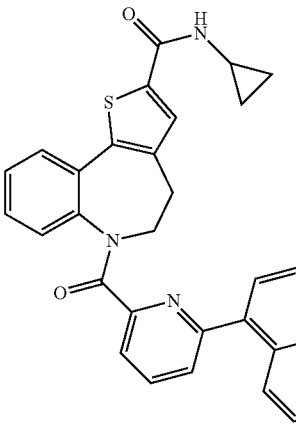 |
Examples 150-275 shown in Table 4 were prepared using the procedure similar to that of Example 54.

TABLE 4-continued
| Example | Structure |
|---|---|
| 153 | 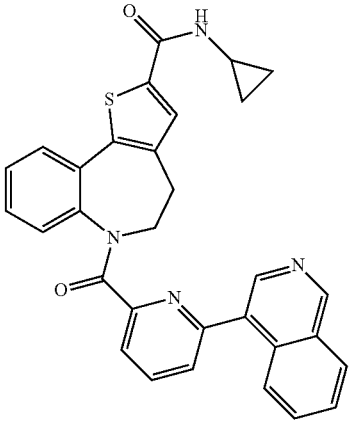 [SMILES: O=C(NC1CC1)c1cc2c(s1)-c1ccccc1N(C(=O)c1cccc(-c3cncc4ccccc34)n1)CC2] |
| 154 | 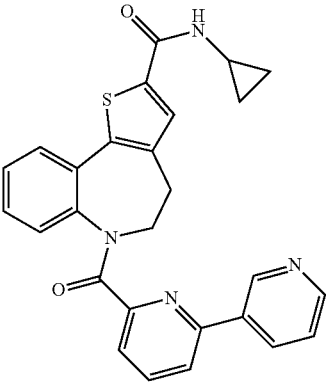 [SMILES: O=C(NC1CC1)c1cc2c(s1)-c1ccccc1N(C(=O)c1cccc(-c3cccnc3)n1)CC2] |
| 155 | 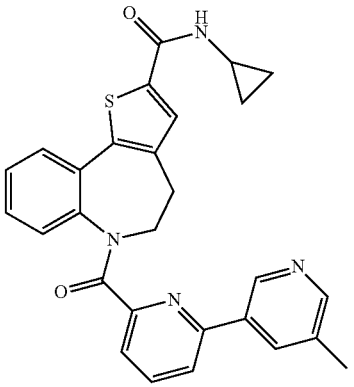 [SMILES: Cc1cncc(-c2cccc(C(=O)N3CCc4cc(C(=O)NC5CC5)sc4-c4ccccc43)n2)c1] |
| 156 | 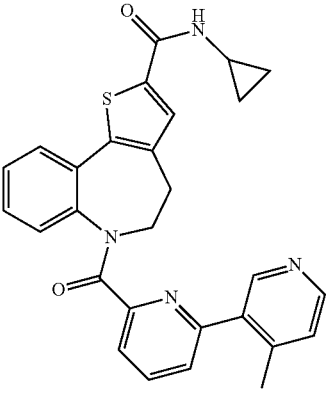 [SMILES: Cc1ccncc1-c1cccc(C(=O)N2CCc3cc(C(=O)NC4CC4)sc3-c3ccccc32)n1] |
| 157 | 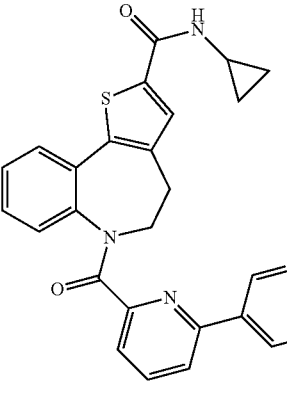 |
| 158 | 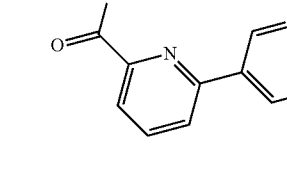 |
| 159 | 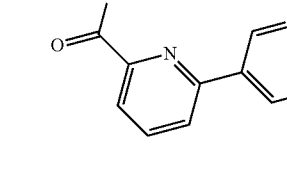 |

TABLE 4-continued
| Example | Structure |
|---|---|
| 160 | 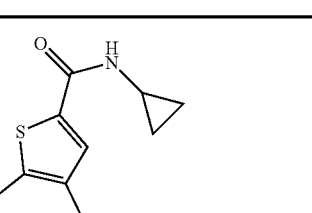 |
| 161 | 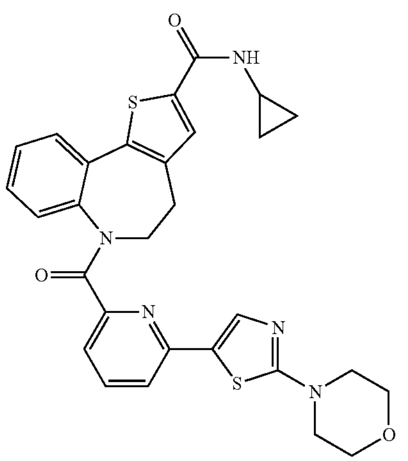 [SMILES: O=C(NC1CC1)c1cc2c(s1)-c1ccccc1N(C(=O)c1cccc(-c3cnc(N4CCOCC4)s3)n1)CC2] |
| 162 | 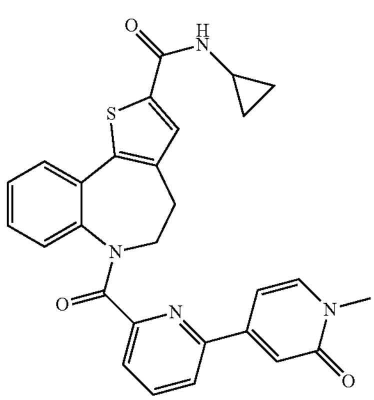 [SMILES: Cn1ccc(-c2cccc(C(=O)N3CCc4cc(C(=O)NC5CC5)sc4-c4ccccc43)n2)cc1=O] |
| 163 | |
| 164 | |
| 165 | |

TABLE 4-continued
| Example | Structure |
|---|---|
| 166 | 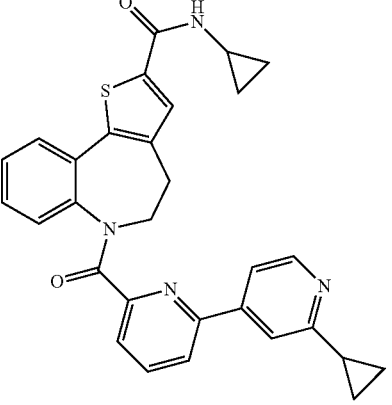 [SMILES: O=C(NC1CC1)c1cc2c(s1)-c1ccccc1N(C(=O)c1cccc(-c3ccnc(C4CC4)c3)n1)CC2] |
| 167 | 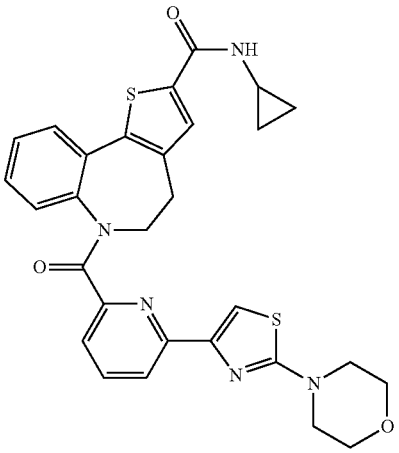 [SMILES: O=C(NC1CC1)c1cc2c(s1)-c1ccccc1N(C(=O)c1cccc(-c3csc(N4CCOCC4)n3)n1)CC2] |
| 168 | 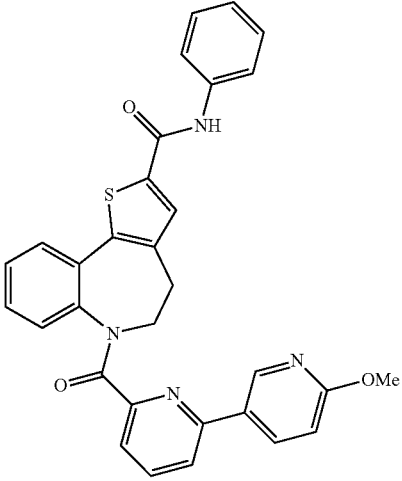 [SMILES: COc1ccc(-c2cccc(C(=O)N3CCc4cc(C(=O)Nc5ccccc5)sc4-c4ccccc43)n2)cn1] |
| 169 | 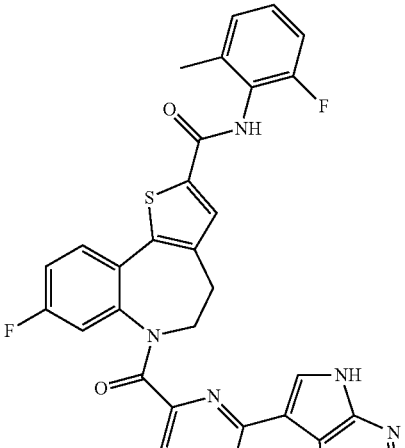 |
| 170 | 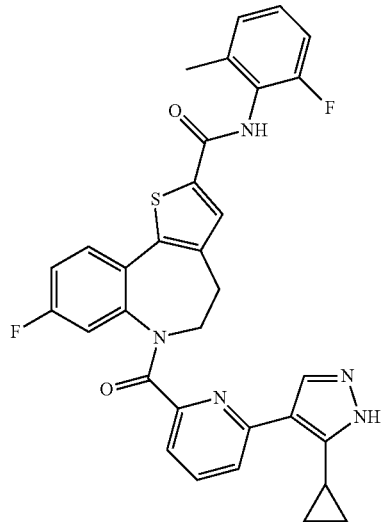 [SMILES: Cc1cccc(F)c1NC(=O)c1cc2c(s1)-c1ccc(F)cc1N(C(=O)c1cccc(-c3cn[nH]c3C3CC3)n1)CC2] |
| 171 | 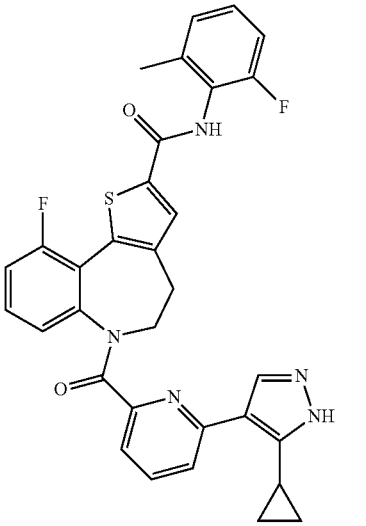 [SMILES: Cc1cccc(F)c1NC(=O)c1cc2c(s1)-c1c(F)cccc1N(C(=O)c1cccc(-c3cn[nH]c3C3CC3)n1)CC2] |

TABLE 4-continued

| Example | Structure |
|---|---|
| 172 | *(structure)* |
| 173 | *(structure)* |
| 174 | *(structure)* |
| 175 | *(structure)* |
| 176 | *(structure)* |
| 177 | *(structure)* |

TABLE 4-continued

| Example | Structure |
|---|---|
| 178 | 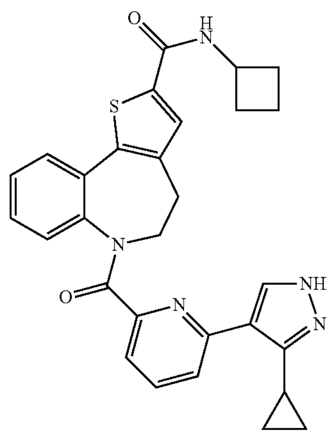 [SMILES: O=C(NC1CCC1)c1cc2c(s1)-c1ccccc1N(C(=O)c1cccc(-c3c[nH]nc3C3CC3)n1)CC2] |
| 179 | 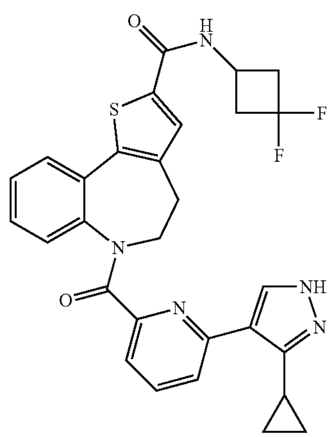 [SMILES: O=C(NC1CC(F)(F)C1)c1cc2c(s1)-c1ccccc1N(C(=O)c1cccc(-c3c[nH]nc3C3CC3)n1)CC2] |
| 180 | 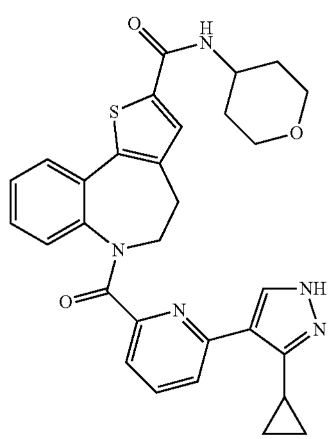 [SMILES: O=C(NC1CCOCC1)c1cc2c(s1)-c1ccccc1N(C(=O)c1cccc(-c3c[nH]nc3C3CC3)n1)CC2] |
| 181 | |
| 182 | |
| 183 | |

TABLE 4-continued
| Example | Structure |
|---|---|
| 184 | 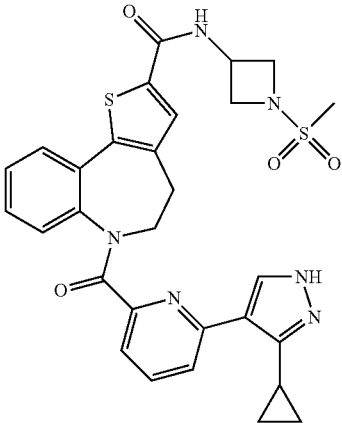 [SMILES: CS(=O)(=O)N1CC(NC(=O)c2cc3c(s2)-c2ccccc2N(C(=O)c2cccc(-c4c[nH]nc4C4CC4)n2)CC3)C1] |
| 185 | 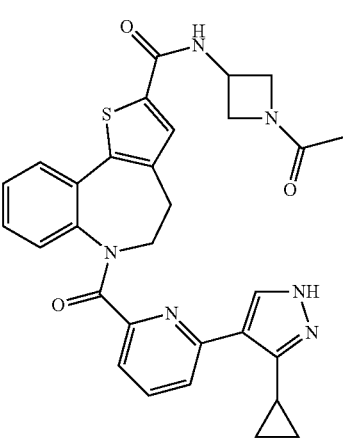 [SMILES: CC(=O)N1CC(NC(=O)c2cc3c(s2)-c2ccccc2N(C(=O)c2cccc(-c4c[nH]nc4C4CC4)n2)CC3)C1] |
| 186 | 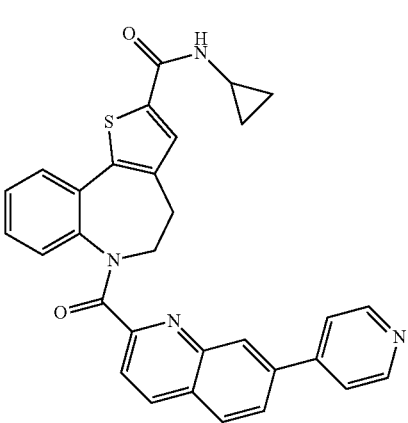 [SMILES: O=C(NC1CC1)c1cc2c(s1)-c1ccccc1N(C(=O)c1ccc3ccc(-c4ccncc4)cc3n1)CC2] |
| 187 | 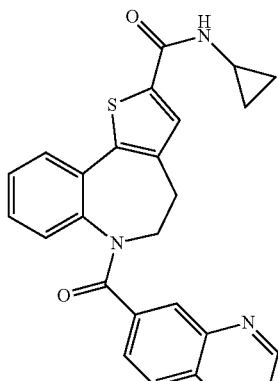 |
| 188 | 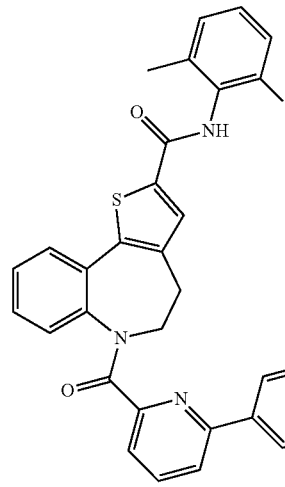 |
| 189 | 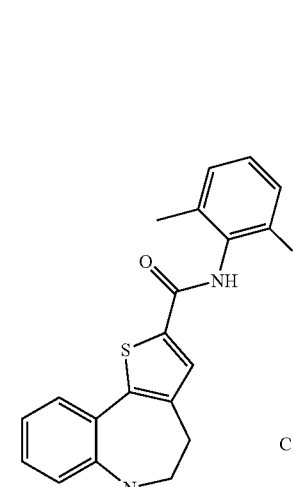 |

TABLE 4-continued
| Example | Structure |
|---|---|
| 190 | 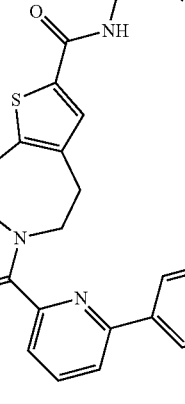 |
| 191 | 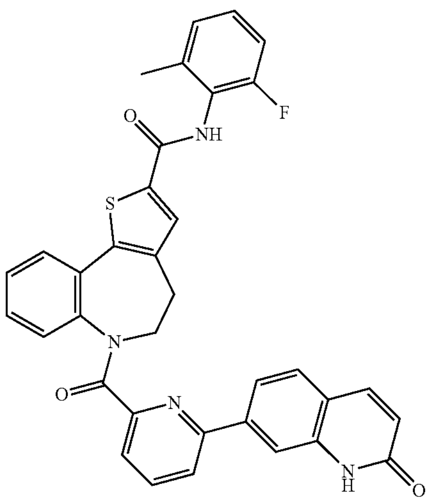 [SMILES: Cc1cccc(F)c1NC(=O)c1cc2c(s1)-c1ccccc1N(C(=O)c1cccc(-c3ccc4ccc(=O)[nH]c4c3)n1)CC2] |
| 192 | 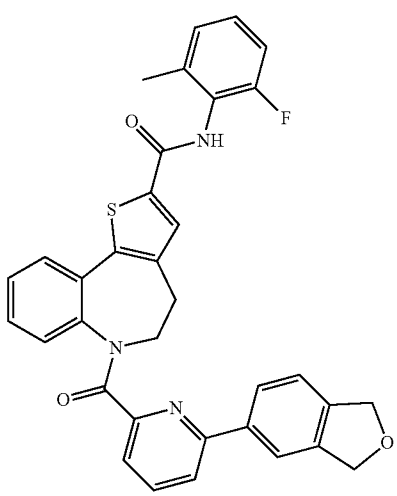 [SMILES: Cc1cccc(F)c1NC(=O)c1cc2c(s1)-c1ccccc1N(C(=O)c1cccc(-c3ccc4c(c3)COC4)n1)CC2] |
| 193 | 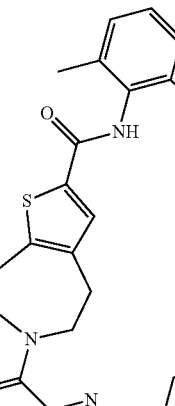 |
| 194 | |
| 195 | 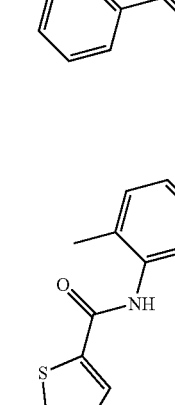 |

TABLE 4-continued
| Example | Structure |
|---|---|
| 196 | 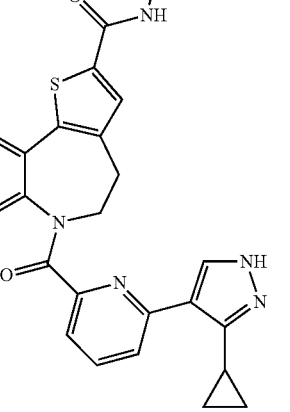 |
| 197 | 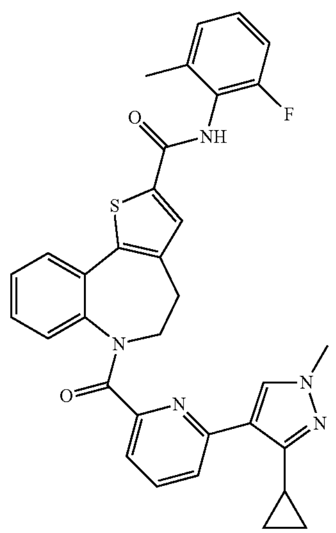 [SMILES: Cc1cccc(F)c1NC(=O)c1cc2c(s1)-c1ccccc1N(C(=O)c1cccc(-c3cn(C)nc3C3CC3)n1)CC2] |
| 198 | 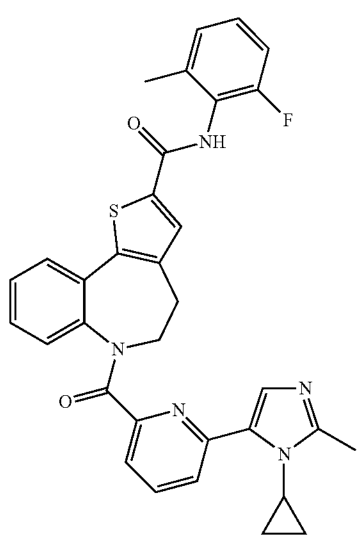 [SMILES: Cc1cccc(F)c1NC(=O)c1cc2c(s1)-c1ccccc1N(C(=O)c1cccc(-c3cnc(C)n3C3CC3)n1)CC2] |
| 199 | 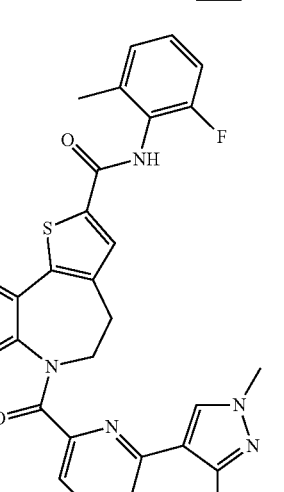 |
| 200 | |
| 201 | 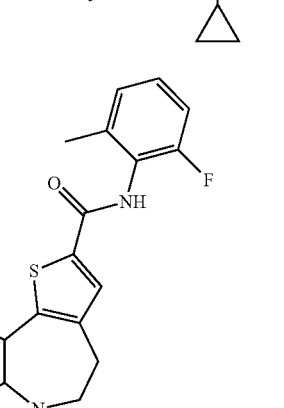 |

TABLE 4-continued
| Example | Structure |
|---|---|
| 202 | 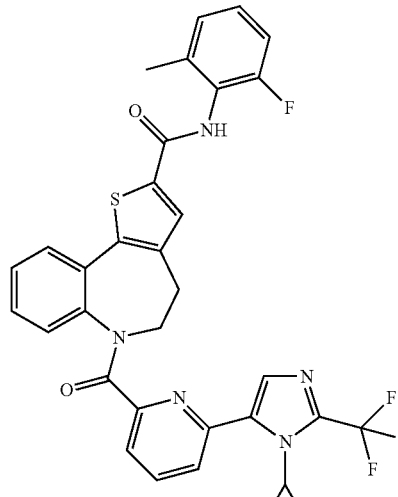 |
| 203 | 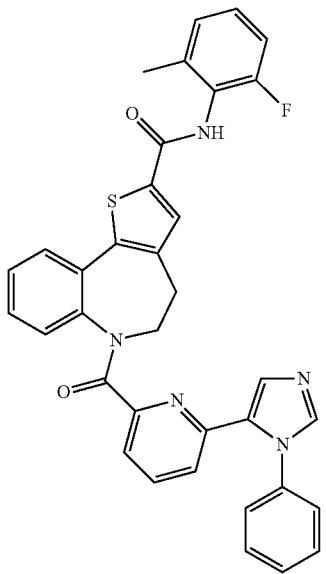 [SMILES: Cc1cccc(F)c1NC(=O)c1cc2c(s1)-c1ccccc1N(C(=O)c1cccc(-c3cncn3-c3ccccc3)n1)CC2] |
| 204 | 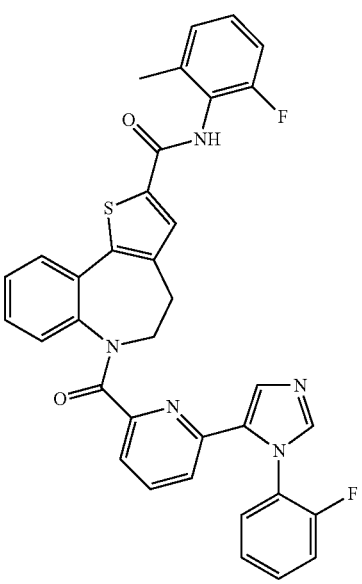 [SMILES: Cc1cccc(F)c1NC(=O)c1cc2c(s1)-c1ccccc1N(C(=O)c1cccc(-c3cncn3-c3ccccc3F)n1)CC2] |
| 205 | 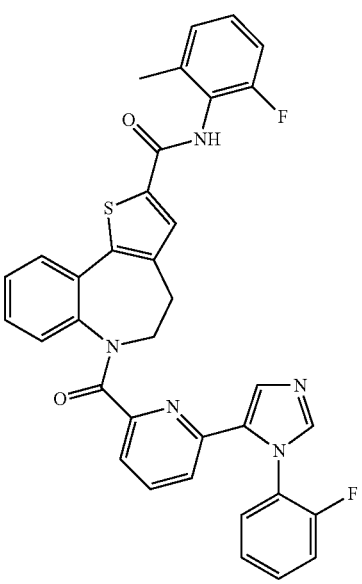 [SMILES: Cc1cccc(F)c1NC(=O)c1cc2c(s1)-c1ccccc1N(C(=O)c1cccc(-c3cncn3-c3ccccc3F)n1)CC2] |

TABLE 4-continued

| Example | Structure |
|---|---|
| 206 | 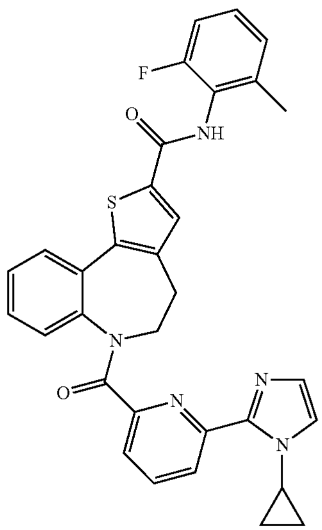 |
| 207 | 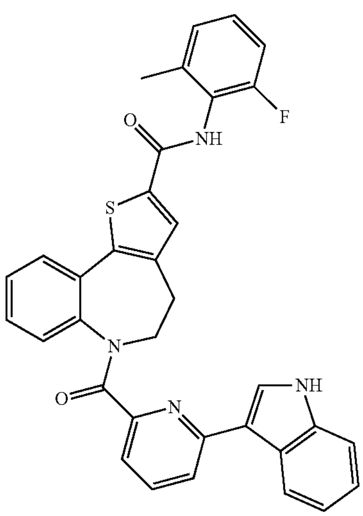 [SMILES: Cc1cccc(F)c1NC(=O)c1cc2c(s1)-c1ccccc1N(C(=O)c1cccc(-c3c[nH]c4ccccc34)n1)CC2] |
| 208 | 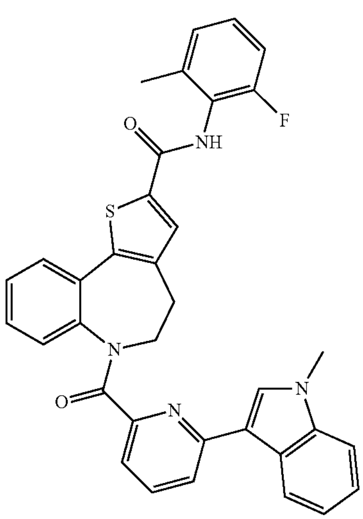 [SMILES: Cc1cccc(F)c1NC(=O)c1cc2c(s1)-c1ccccc1N(C(=O)c1cccc(-c3cn(C)c4ccccc34)n1)CC2] |
| 209 | |
| 210 | |
| 211 | |

TABLE 4-continued

| Example | Structure |
|---|---|
| 212 | 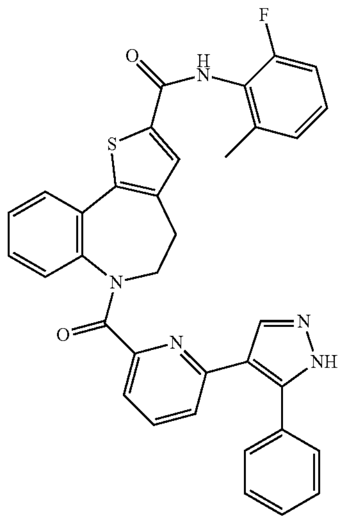 [SMILES: Cc1cccc(F)c1NC(=O)c1cc2c(s1)-c1ccccc1N(C(=O)c1cccc(-c3cn[nH]c3-c3ccccc3)n1)CC2] |
| 213 | 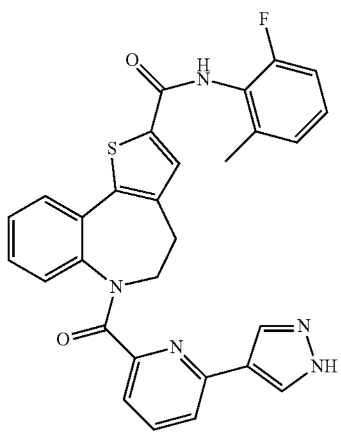 [SMILES: Cc1cccc(F)c1NC(=O)c1cc2c(s1)-c1ccccc1N(C(=O)c1cccc(-c3cn[nH]c3)n1)CC2] |
| 214 | 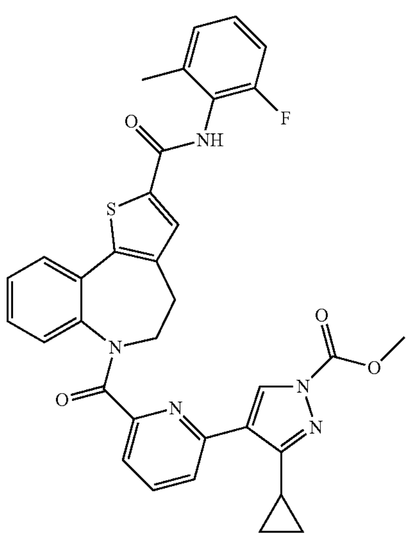 [SMILES: COC(=O)n1cc(-c2cccc(C(=O)N3CCc4cc(C(=O)Nc5c(C)cccc5F)sc4-c4ccccc43)n2)c(C2CC2)n1] |
| 215 | 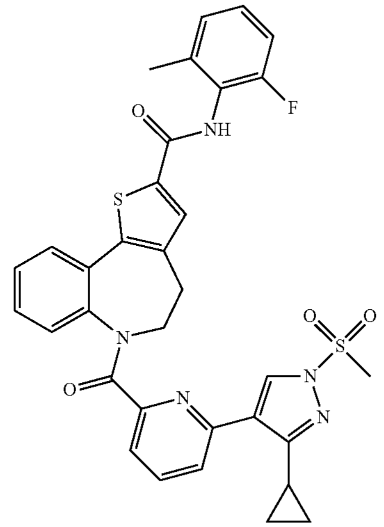 [SMILES: Cc1cccc(F)c1NC(=O)c1cc2c(s1)-c1ccccc1N(C(=O)c1cccc(-c3cn(S(C)(=O)=O)nc3C3CC3)n1)CC2] |
| 216 | 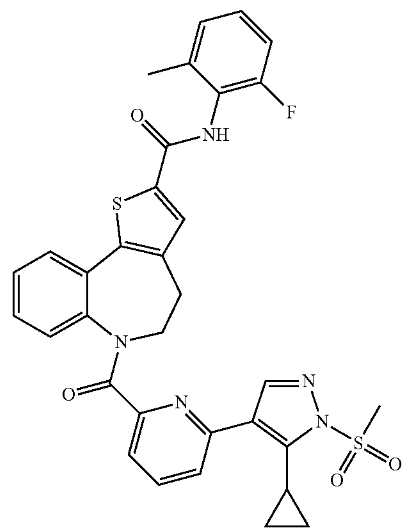 [SMILES: Cc1cccc(F)c1NC(=O)c1cc2c(s1)-c1ccccc1N(C(=O)c1cccc(-c3cnn(S(C)(=O)=O)c3C3CC3)n1)CC2] |
| 217 | 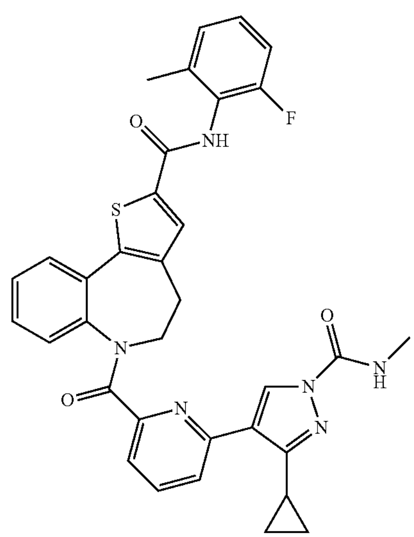 [SMILES: CNC(=O)n1cc(-c2cccc(C(=O)N3CCc4cc(C(=O)Nc5c(C)cccc5F)sc4-c4ccccc43)n2)c(C2CC2)n1] |

TABLE 4-continued
| Example | Structure |
|---------|-----------|
| 218 | 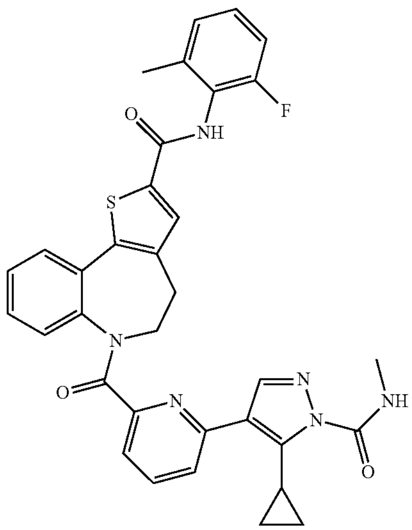 [SMILES: CNC(=O)n1ncc(-c2cccc(C(=O)N3CCc4cc(C(=O)Nc5c(C)cccc5F)sc4-c4ccccc43)n2)c1C1CC1] |
| 219 | 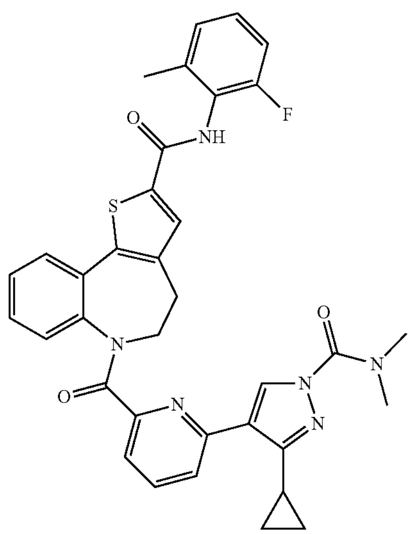 [SMILES: Cc1cccc(F)c1NC(=O)c1cc2c(s1)-c1ccccc1N(C(=O)c1cccc(-c3cn(C(=O)N(C)C)nc3C3CC3)n1)CC2] |
| 220 | 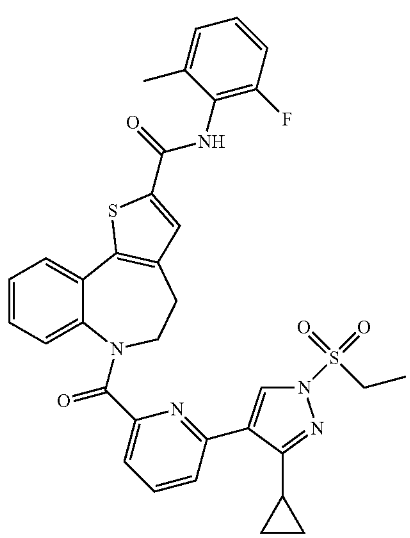 [SMILES: CCS(=O)(=O)n1cc(-c2cccc(C(=O)N3CCc4cc(C(=O)Nc5c(C)cccc5F)sc4-c4ccccc43)n2)c(C2CC2)n1] |
| 221 |  |
| 222 |  |
| 223 |  |

TABLE 4-continued
| Example | Structure |
|---|---|
| 224 | 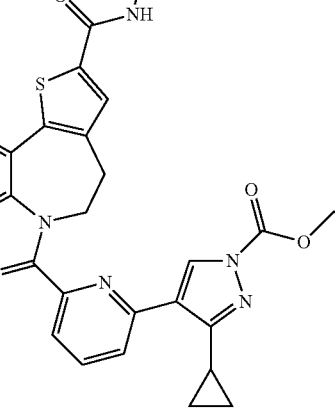 |
| 225 | 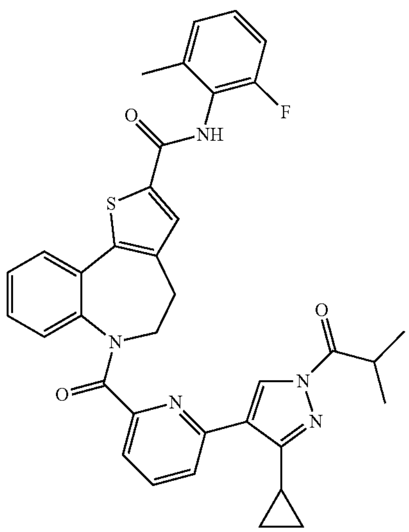 [SMILES: Cc1cccc(F)c1NC(=O)c1cc2c(s1)-c1ccccc1N(C(=O)c1cccc(-c3cn(C(=O)C(C)C)nc3C3CC3)n1)CC2] |
| 226 | 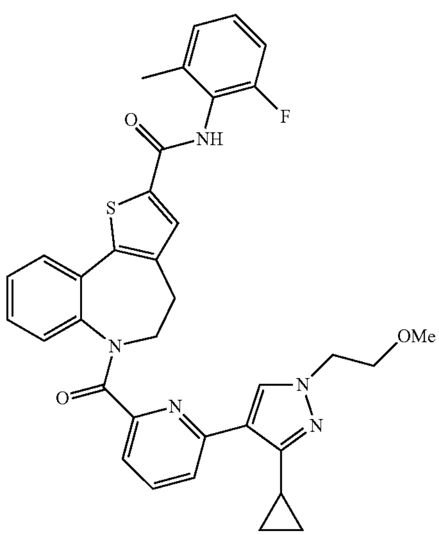 [SMILES: COCCn1cc(-c2cccc(C(=O)N3CCc4cc(C(=O)Nc5c(C)cccc5F)sc4-c4ccccc43)n2)c(C2CC2)n1] |
| 227 | 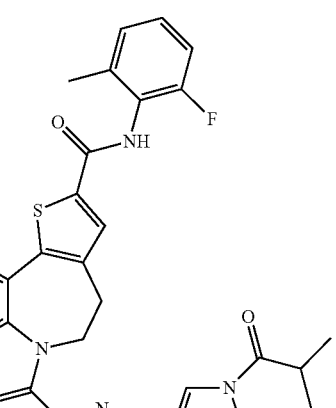 |
| 228 | |
| 229 | 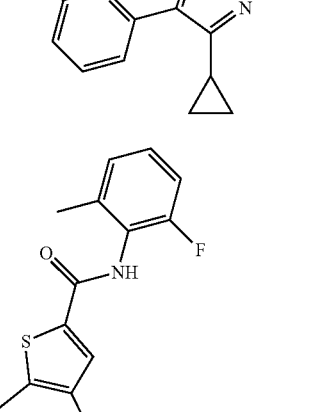 |

TABLE 4-continued

| Example | Structure |
|---|---|
| 230 | (structure) |
| 231 | (structure) |
| 232 | (structure) |
| 233 | (structure) |
| 234 | (structure) |
| 235 | (structure) |

TABLE 4-continued
| Example | Structure |
|---|---|
| 236 | 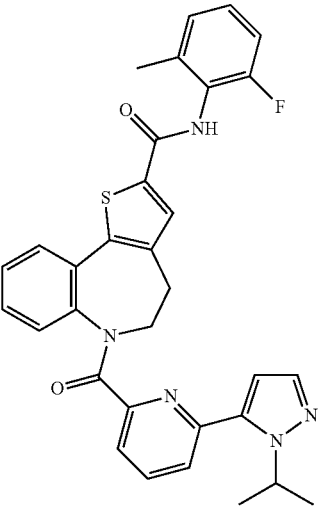 |
| 237 | 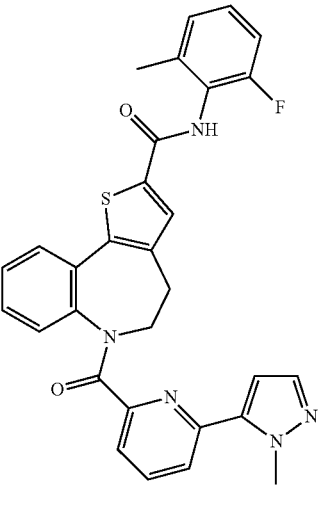 [SMILES: Cc1cccc(F)c1NC(=O)c1cc2c(s1)-c1ccccc1N(C(=O)c1cccc(-c3ccnn3C)n1)CC2] |
| 238 | 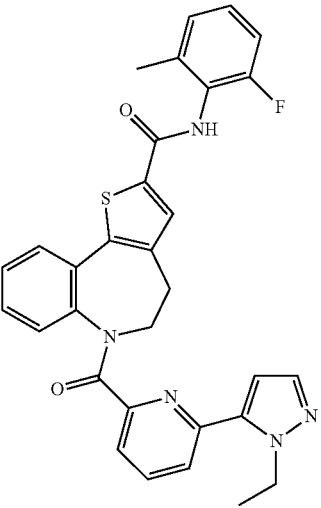 [SMILES: CCn1nccc1-c1cccc(C(=O)N2CCc3cc(C(=O)Nc4c(C)cccc4F)sc3-c3ccccc32)n1] |
| 239 | 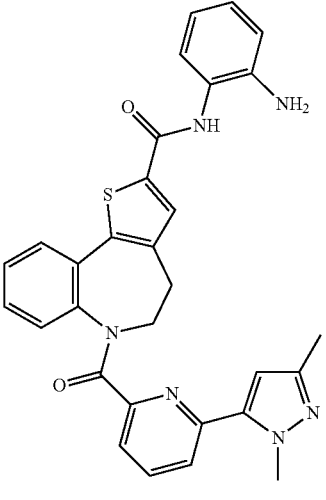 [SMILES: Cc1cc(-c2cccc(C(=O)N3CCc4cc(C(=O)Nc5ccccc5N)sc4-c4ccccc43)n2)n(C)n1] |
| 240 | 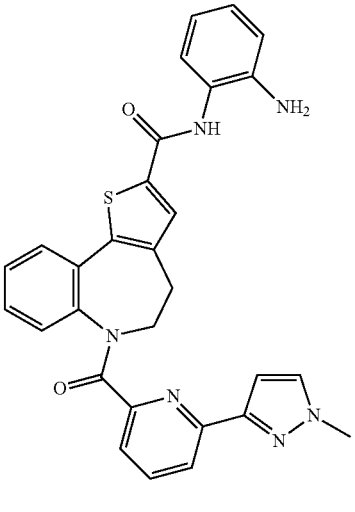 [SMILES: Cn1ccc(-c2cccc(C(=O)N3CCc4cc(C(=O)Nc5ccccc5N)sc4-c4ccccc43)n2)n1] |
| 241 | 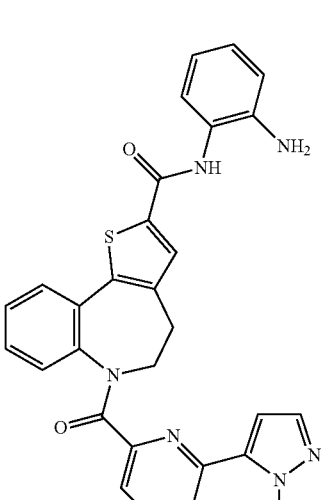 |

TABLE 4-continued

| Example | Structure |
|---|---|
| 242 | 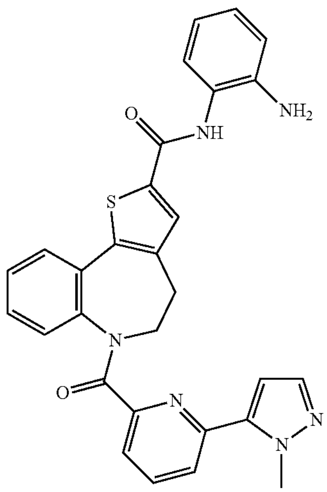 [SMILES: Cn1nccc1-c1cccc(C(=O)N2CCc3cc(C(=O)Nc4ccccc4N)sc3-c3ccccc32)n1] |
| 243 | 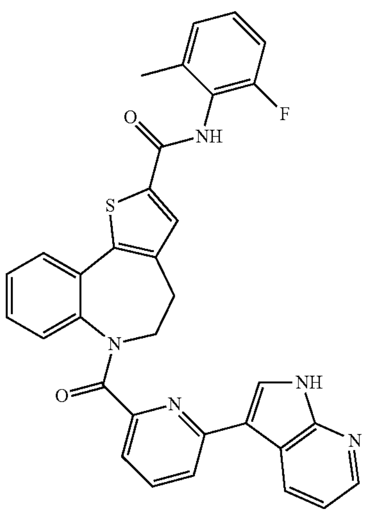 [SMILES: Cc1cccc(F)c1NC(=O)c1cc2c(s1)-c1ccccc1N(C(=O)c1cccc(-c3c[nH]c4ncccc34)n1)CC2] |
| 244 | 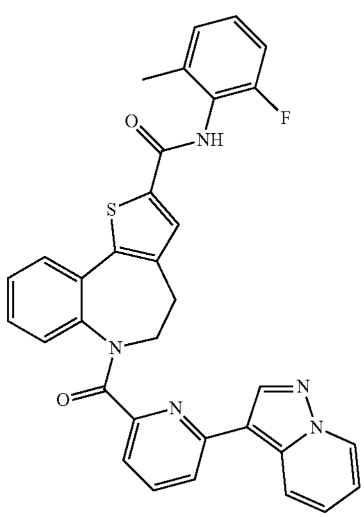 [SMILES: Cc1cccc(F)c1NC(=O)c1cc2c(s1)-c1ccccc1N(C(=O)c1cccc(-c3cnn4ccccc34)n1)CC2] |
| 245 | |
| 246 | |
| 247 | |

TABLE 4-continued
| Example | Structure |
|---|---|
| 248 | 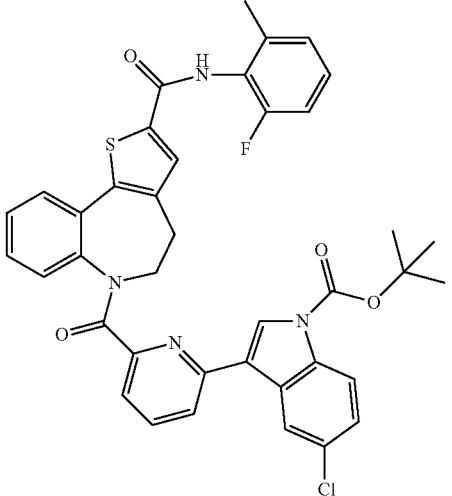 [SMILES: Cc1cccc(F)c1NC(=O)c1cc2c(s1)-c1ccccc1N(C(=O)c1cccc(-c3cn(C(=O)OC(C)(C)C)c4ccc(Cl)cc34)n1)CC2] |
| 249 | 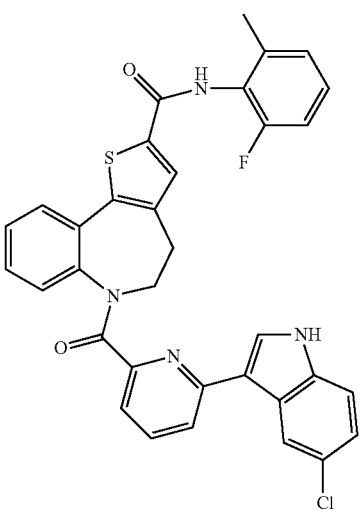 [SMILES: Cc1cccc(F)c1NC(=O)c1cc2c(s1)-c1ccccc1N(C(=O)c1cccc(-c3c[nH]c4ccc(Cl)cc34)n1)CC2] |
| 250 | 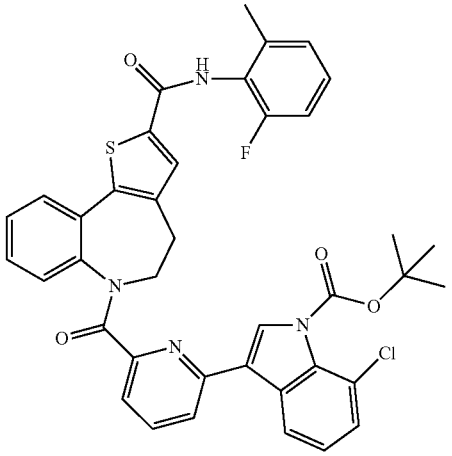 [SMILES: Cc1cccc(F)c1NC(=O)c1cc2c(s1)-c1ccccc1N(C(=O)c1cccc(-c3cn(C(=O)OC(C)(C)C)c4c(Cl)cccc34)n1)CC2] |
| 251 | 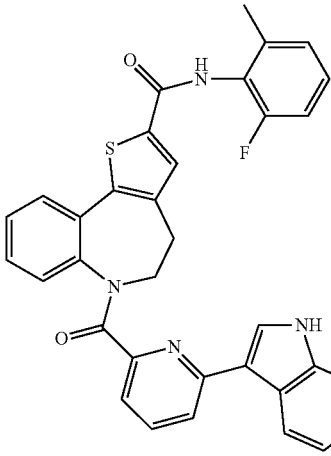 |
| 252 | 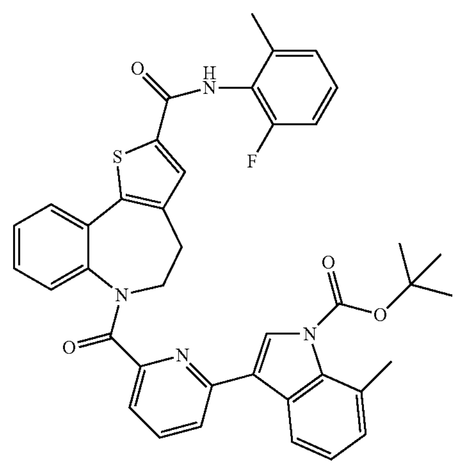 [SMILES: Cc1cccc(F)c1NC(=O)c1cc2c(s1)-c1ccccc1N(C(=O)c1cccc(-c3cn(C(=O)OC(C)(C)C)c4c(C)cccc34)n1)CC2] |
| 253 | 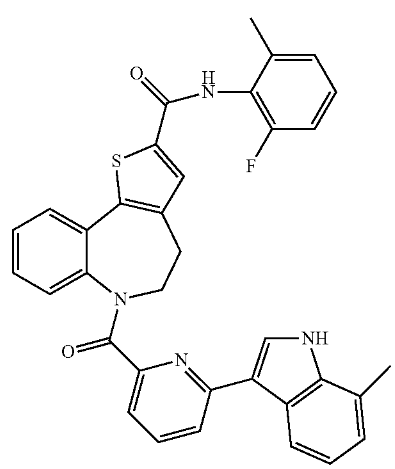 [SMILES: Cc1cccc(F)c1NC(=O)c1cc2c(s1)-c1ccccc1N(C(=O)c1cccc(-c3c[nH]c4c(C)cccc34)n1)CC2] |

TABLE 4-continued

| Example | Structure |
|---|---|
| 254 | 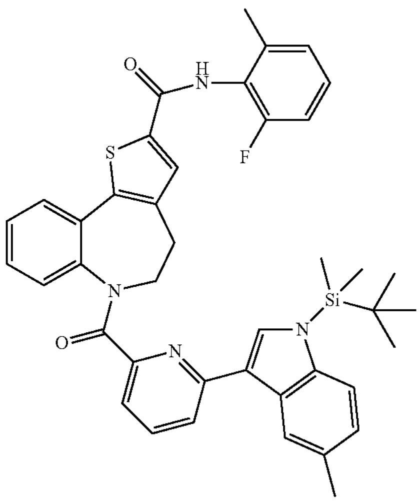 [SMILES: Cc1ccc2c(c1)c(-c1cccc(C(=O)N3CCc4cc(C(=O)Nc5c(C)cccc5F)sc4-c4ccccc43)n1)cn2[Si](C)(C)C(C)(C)C] |
| 255 | 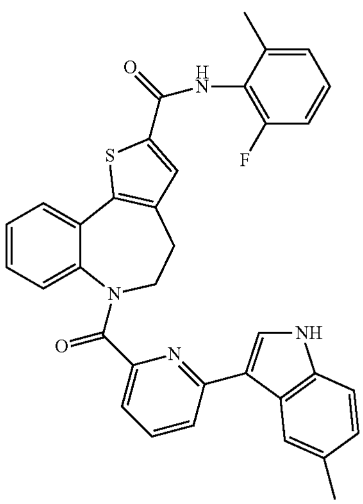 [SMILES: Cc1ccc2[nH]cc(-c3cccc(C(=O)N4CCc5cc(C(=O)Nc6c(C)cccc6F)sc5-c5ccccc54)n3)c2c1] |
| 256 | 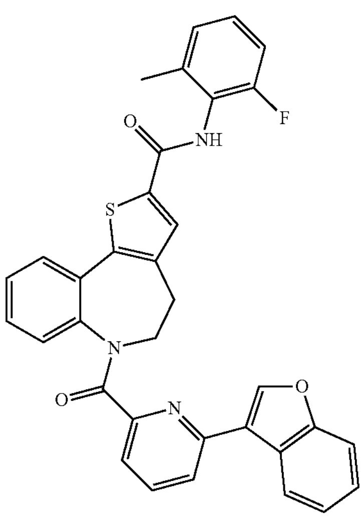 [SMILES: Cc1cccc(F)c1NC(=O)c1cc2c(s1)-c1ccccc1N(C(=O)c1cccc(-c3coc4ccccc34)n1)CC2] |
| 257 | 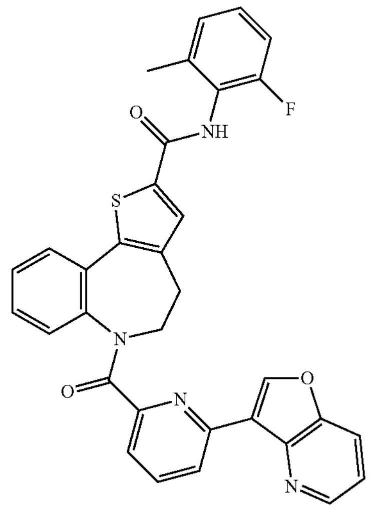 [SMILES: Cc1cccc(F)c1NC(=O)c1cc2c(s1)-c1ccccc1N(C(=O)c1cccc(-c3coc4cccnc34)n1)CC2] |
| 258 | 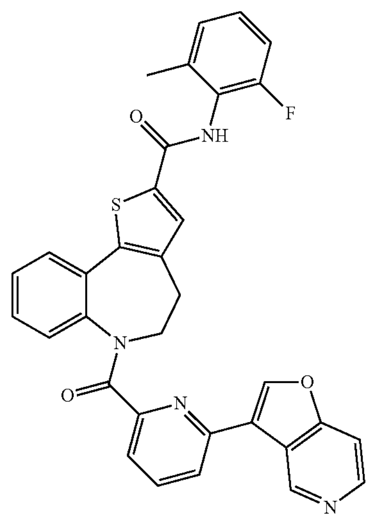 [SMILES: Cc1cccc(F)c1NC(=O)c1cc2c(s1)-c1ccccc1N(C(=O)c1cccc(-c3coc4ccncc34)n1)CC2] |
| 259 | 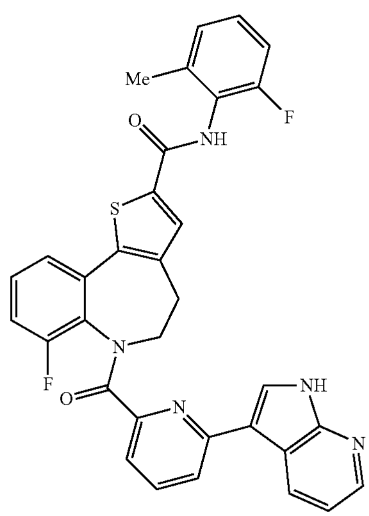 [SMILES: Cc1cccc(F)c1NC(=O)c1cc2c(s1)-c1cccc(F)c1N(C(=O)c1cccc(-c3c[nH]c4ncccc34)n1)CC2] |

TABLE 4-continued
| Example | Structure |
|---------|-----------|
| 260 | 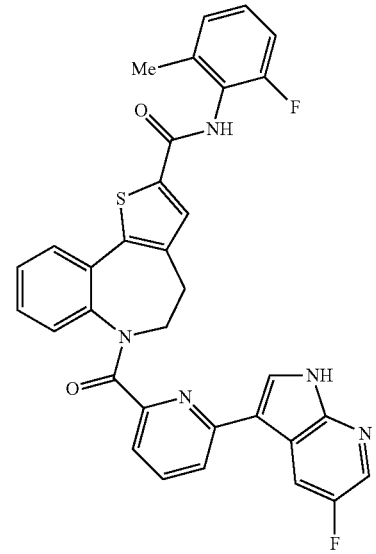 [SMILES: Cc1cccc(F)c1NC(=O)c1cc2c(s1)-c1ccccc1N(C(=O)c1cccc(-c3c[nH]c4ncc(F)cc34)n1)CC2] |
| 261 | 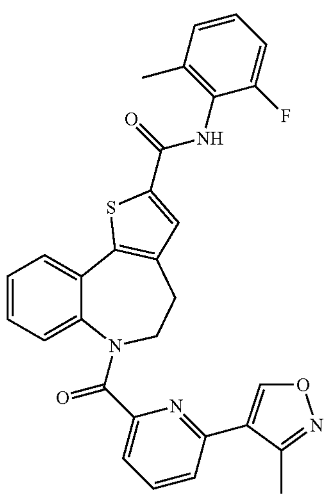 [SMILES: Cc1cccc(F)c1NC(=O)c1cc2c(s1)-c1ccccc1N(C(=O)c1cccc(-c3conc3C)n1)CC2] |
| 262 | 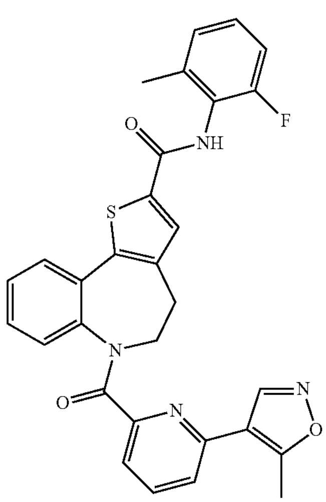 [SMILES: Cc1cccc(F)c1NC(=O)c1cc2c(s1)-c1ccccc1N(C(=O)c1cccc(-c3cnoc3C)n1)CC2] |
| 263 | 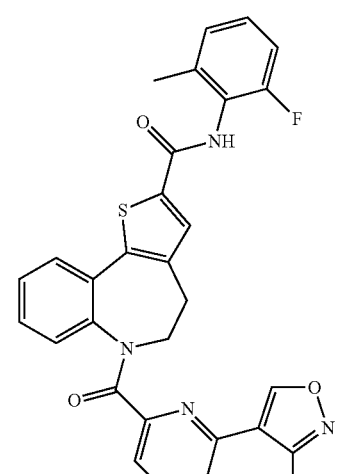 |
| 264 | 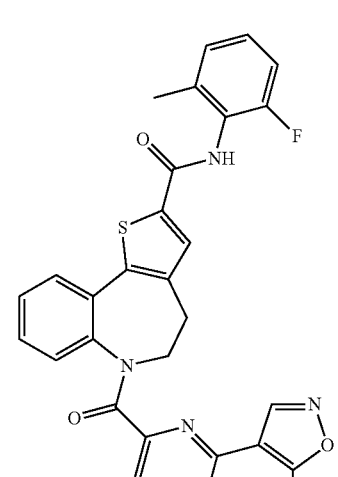 |

TABLE 4-continued
| Example | Structure |
|---|---|
| 265 | 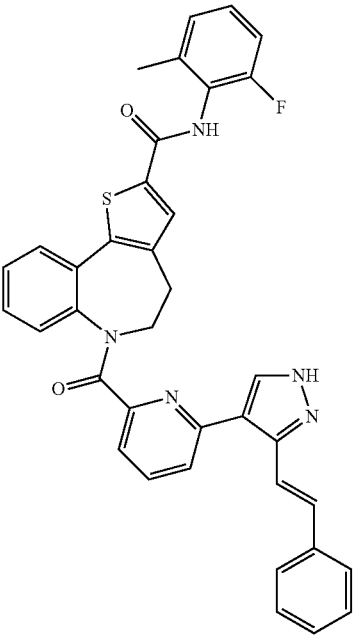 [SMILES: Cc1cccc(F)c1NC(=O)c1cc2c(s1)-c1ccccc1N(C(=O)c1cccc(-c3c[nH]nc3/C=C/c3ccccc3)n1)CC2] |
| 266 | 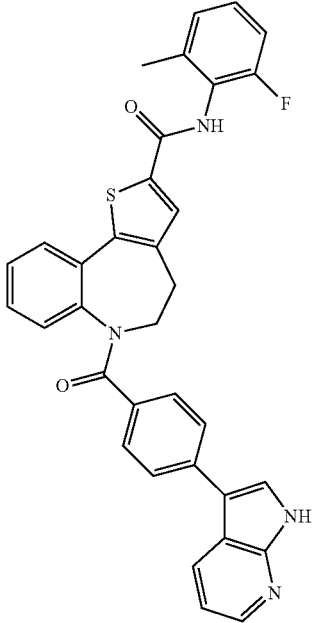 [SMILES: Cc1cccc(F)c1NC(=O)c1cc2c(s1)-c1ccccc1N(C(=O)c1ccc(-c3c[nH]c4ncccc34)cc1)CC2] |
| 267 | 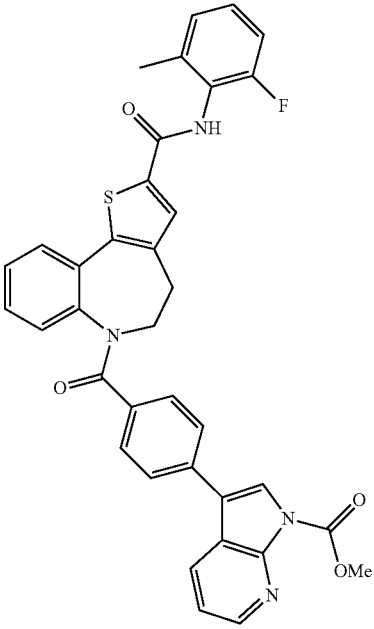 [SMILES: COC(=O)n1cc(-c2ccc(C(=O)N3CCc4cc(C(=O)Nc5c(C)cccc5F)sc4-c4ccccc43)cc2)c2cccnc21] |
| 268 | 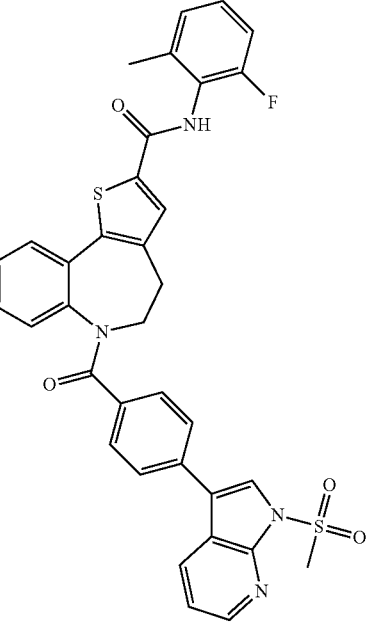 |

TABLE 4-continued
| Example | Structure |
|---|---|
| 269 | 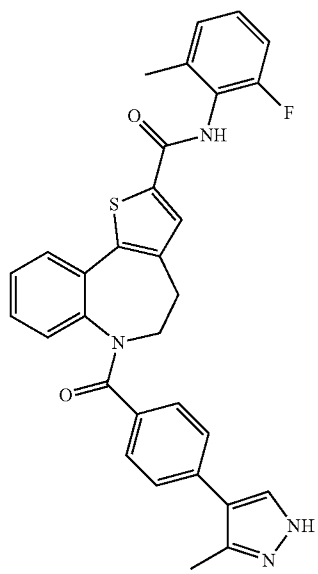 [SMILES: Cc1cccc(F)c1NC(=O)c1cc2c(s1)-c1ccccc1N(C(=O)c1ccc(-c3c[nH]nc3C)cc1)CC2] |
| 270 | 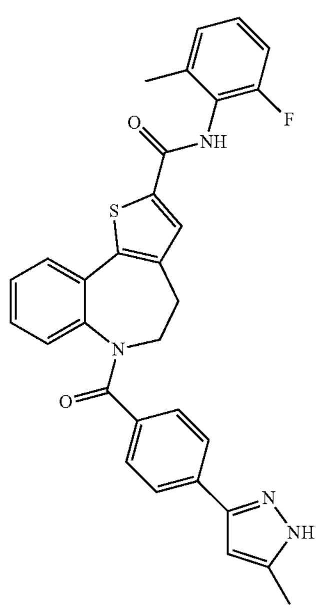 [SMILES: Cc1cc(-c2ccc(C(=O)N3CCc4cc(C(=O)Nc5c(C)cccc5F)sc4-c4ccccc43)cc2)n[nH]1] |
| 271 | 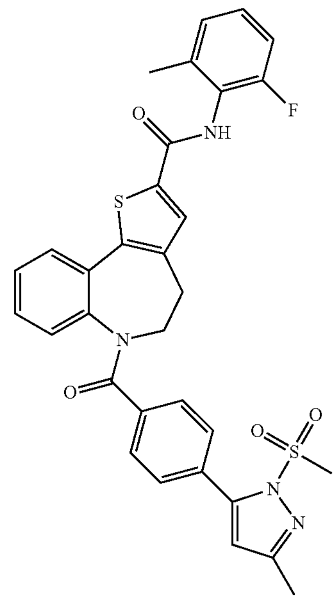 [SMILES: Cc1cc(-c2ccc(C(=O)N3CCc4cc(C(=O)Nc5c(C)cccc5F)sc4-c4ccccc43)cc2)n(S(C)(=O)=O)n1] |
| 272 | 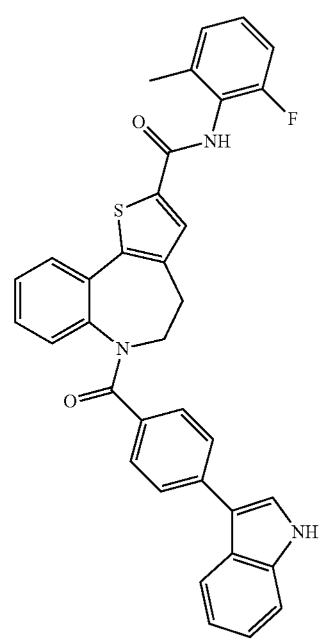 [SMILES: Cc1cccc(F)c1NC(=O)c1cc2c(s1)-c1ccccc1N(C(=O)c1ccc(-c3c[nH]c4ccccc34)cc1)CC2] |
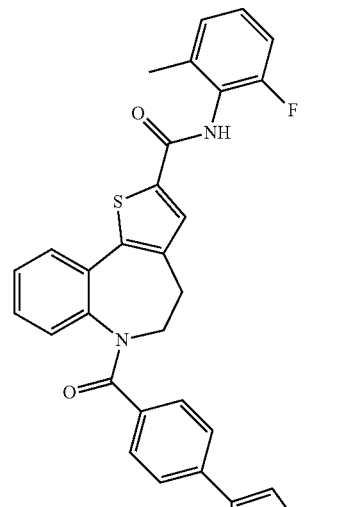

US 10,759,816 B2
409
TABLE 4-continued
| Example | Structure |
|---|---|
| 273 | 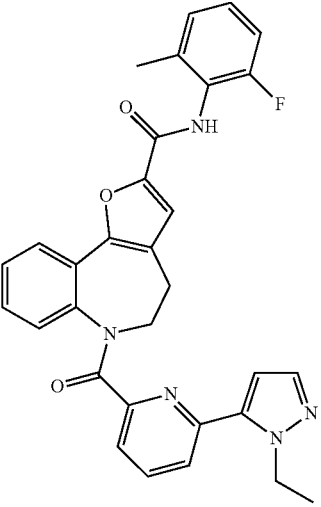 [SMILES: CCn1nccc1-c1cccc(C(=O)N2CCc3cc(C(=O)Nc4c(C)cccc4F)oc3-c3ccccc32)n1] |
| 274 | 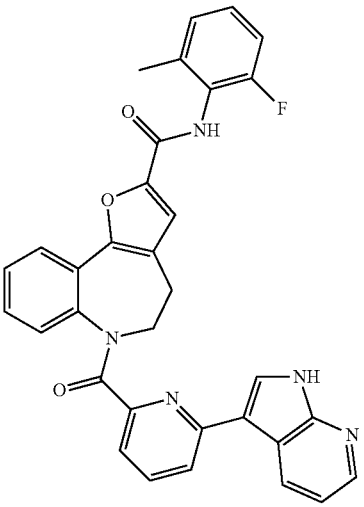 [SMILES: Cc1cccc(F)c1NC(=O)c1cc2c(o1)-c1ccccc1N(C(=O)c1cccc(-c3c[nH]c4ncccc34)n1)CC2] |
| 275 | 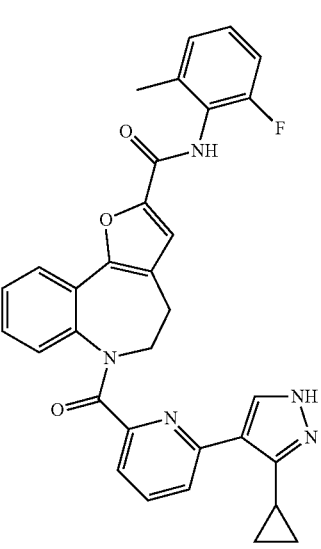 [SMILES: Cc1cccc(F)c1NC(=O)c1cc2c(o1)-c1ccccc1N(C(=O)c1cccc(-c3c[nH]nc3C3CC3)n1)CC2] |
410
TABLE 5
| Example | Structure |
|---|---|
| 276 | 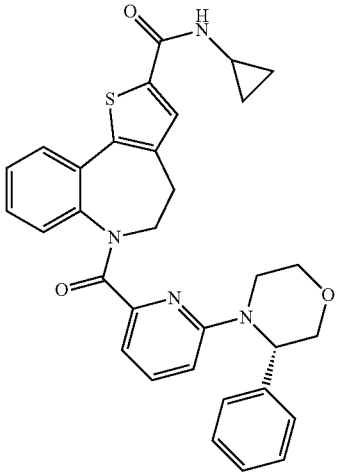 [SMILES: O=C(NC1CC1)c1cc2c(s1)-c1ccccc1N(C(=O)c1cccc(N3CCOC[C@@H]3c3ccccc3)n1)CC2] |
| 277 | 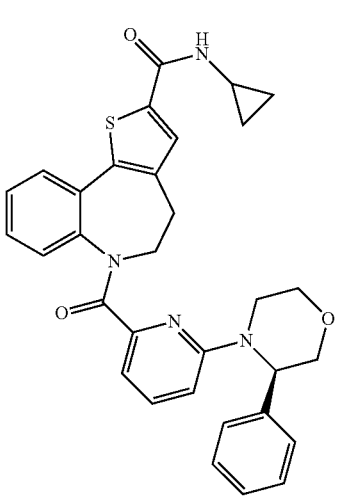 [SMILES: O=C(NC1CC1)c1cc2c(s1)-c1ccccc1N(C(=O)c1cccc(N3CCOC[C@H]3c3ccccc3)n1)CC2] |
| 278 | 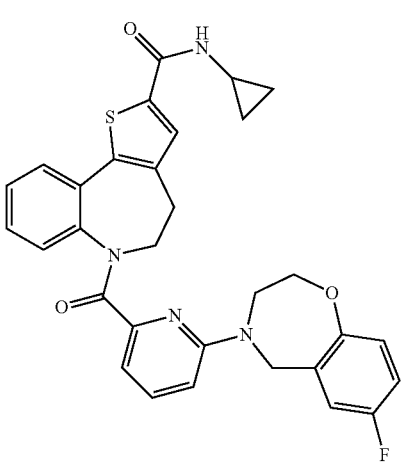 [SMILES: O=C(NC1CC1)c1cc2c(s1)-c1ccccc1N(C(=O)c1cccc(N3CCOc4ccc(F)cc4C3)n1)CC2] |
Examples 276-399 showed in Table 5 were prepared using the procedure similar to that of Example 16.

TABLE 5-continued
| Example | Structure |
|---|---|
| 279 | 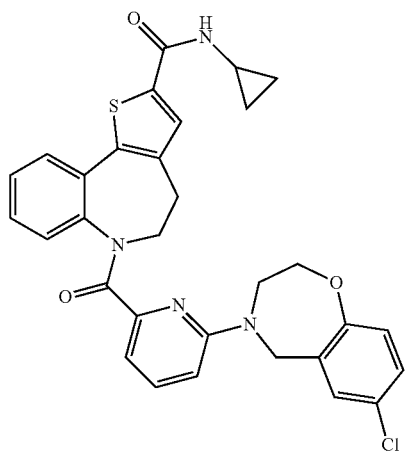 [SMILES: O=C(NC1CC1)c1cc2c(s1)-c1ccccc1N(C(=O)c1cccc(N3CCOc4ccc(Cl)cc4C3)n1)CC2] |
| 280 | 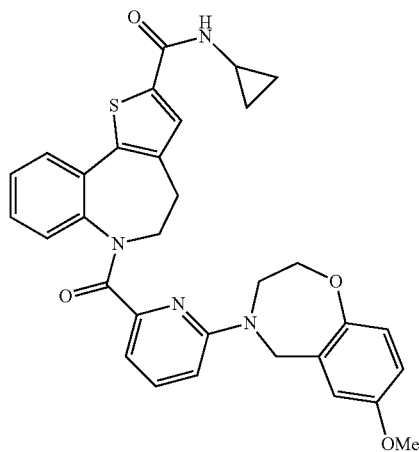 [SMILES: COc1ccc2c(c1)CN(c1cccc(C(=O)N3CCc4cc(C(=O)NC5CC5)sc4-c4ccccc43)n1)CCO2] |
| 281 | 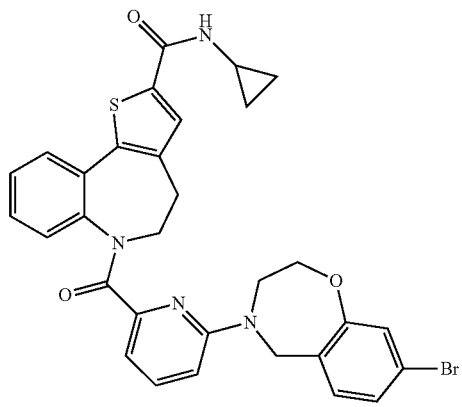 [SMILES: O=C(NC1CC1)c1cc2c(s1)-c1ccccc1N(C(=O)c1cccc(N3CCOc4cc(Br)ccc4C3)n1)CC2] |
| 282 | 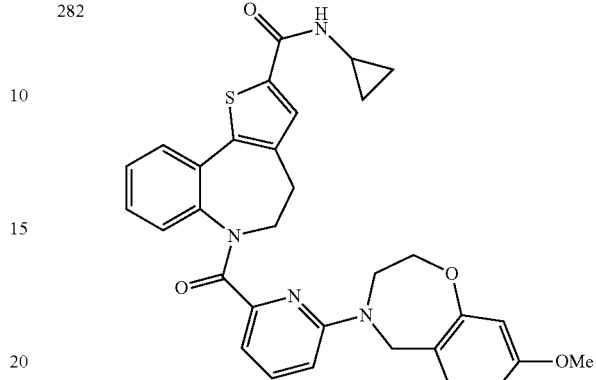 |
| 283 | 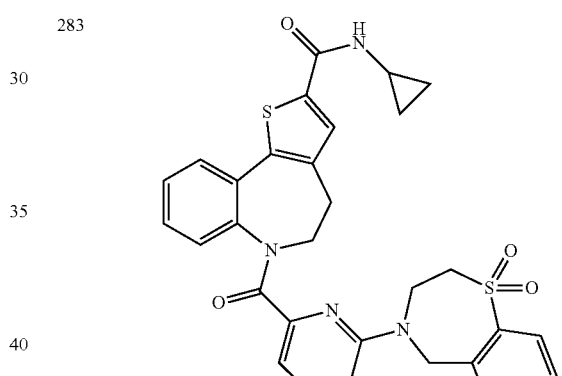 |
| 284 | 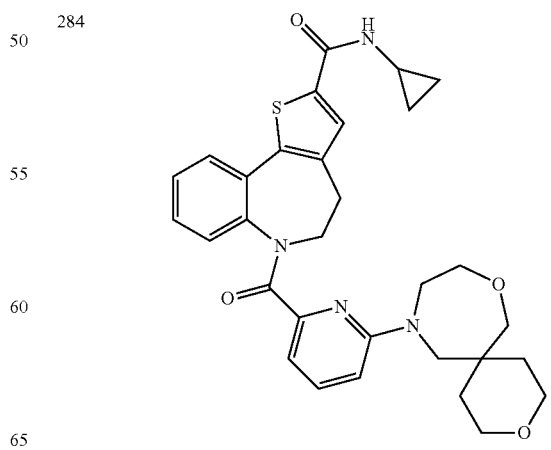 |

TABLE 5-continued
| Example | Structure |
|---|---|
| 285 | 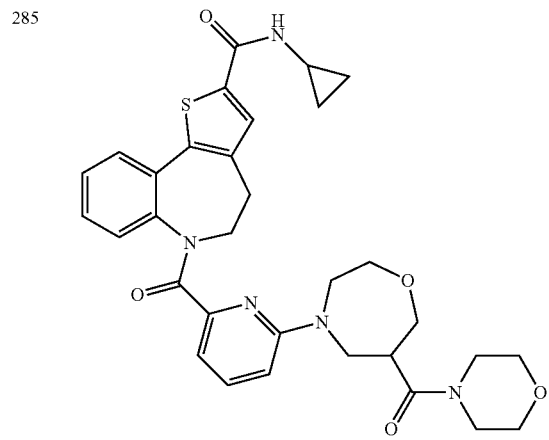 |
| 286 | 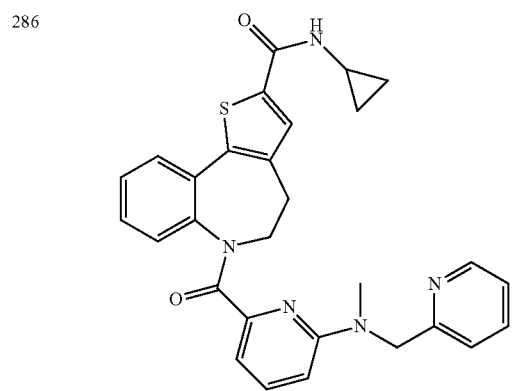 |
| 287 | 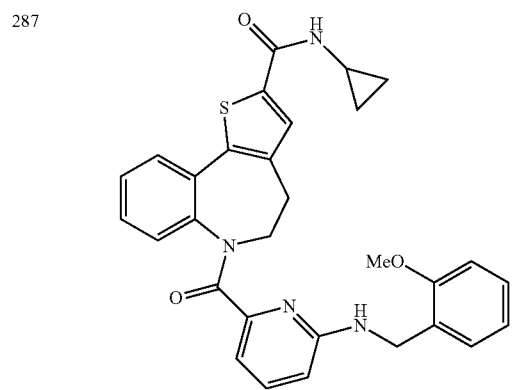 |
| 288 | 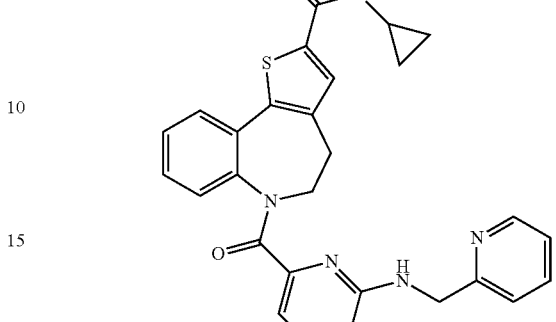 |
| 289 | 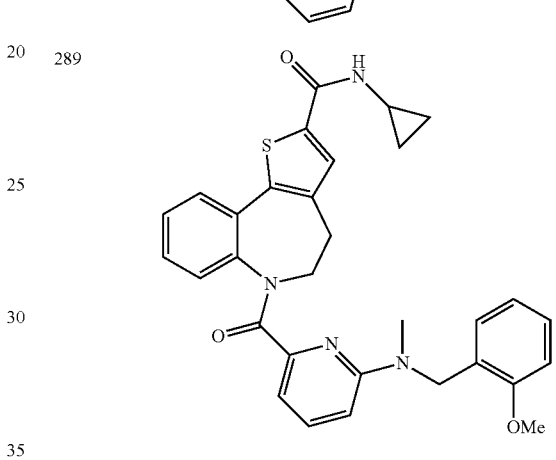 |
| 290 | 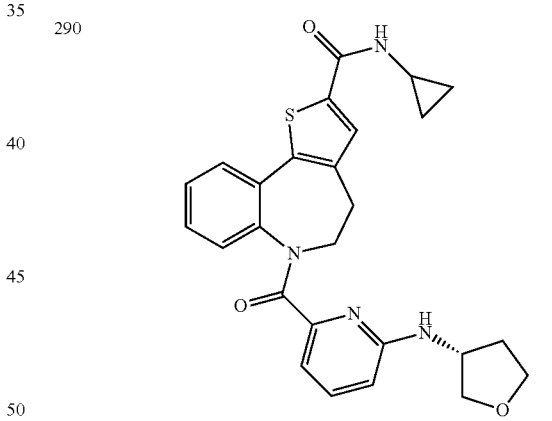 |
| 291 | 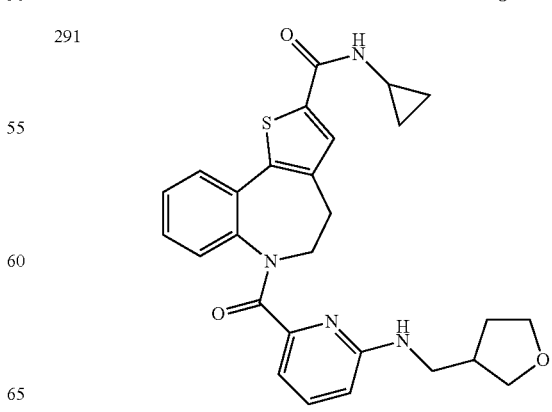 |

TABLE 5-continued
| Example | Structure |
|---|---|
| 292 | 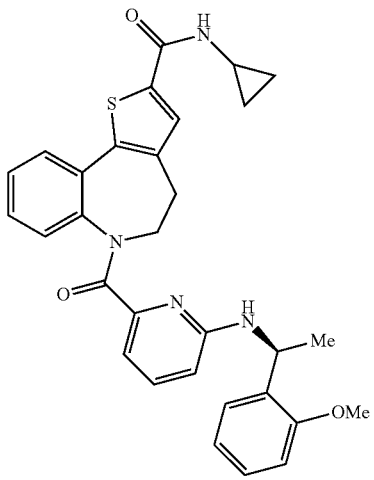 [SMILES: COc1ccccc1[C@H](C)Nc1cccc(C(=O)N2CCc3cc(C(=O)NC4CC4)sc3-c3ccccc32)n1] |
| 293 | 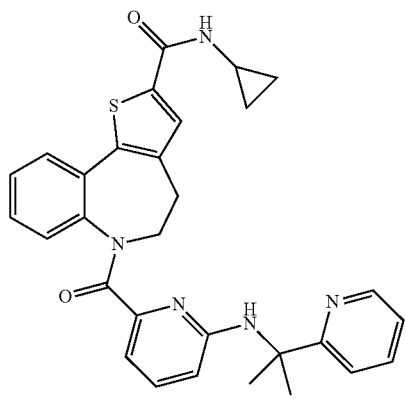 [SMILES: CC(C)(Nc1cccc(C(=O)N2CCc3cc(C(=O)NC4CC4)sc3-c3ccccc32)n1)c1ccccn1] |
| 294 | 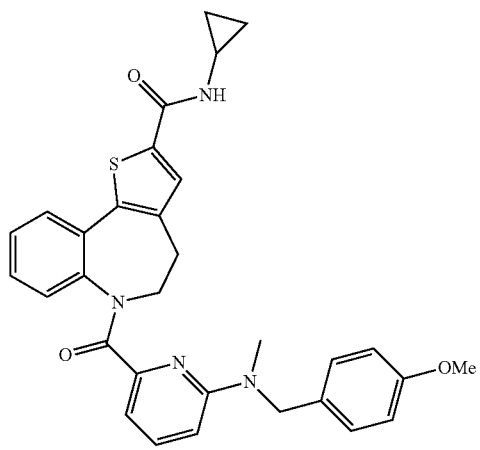 [SMILES: COc1ccc(CN(C)c2cccc(C(=O)N3CCc4cc(C(=O)NC5CC5)sc4-c4ccccc43)n2)cc1] |
| 295 | 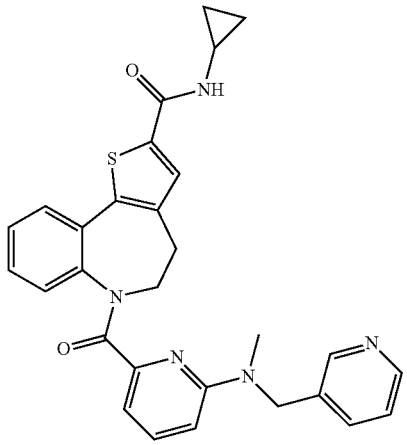 [SMILES: CN(Cc1cccnc1)c1cccc(C(=O)N2CCc3cc(C(=O)NC4CC4)sc3-c3ccccc32)n1] |
| 296 | 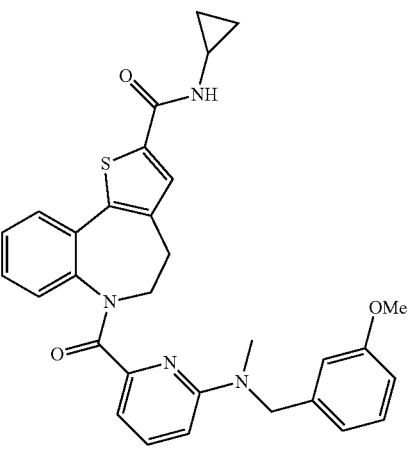 [SMILES: COc1cccc(CN(C)c2cccc(C(=O)N3CCc4cc(C(=O)NC5CC5)sc4-c4ccccc43)n2)c1] |
| 297 | 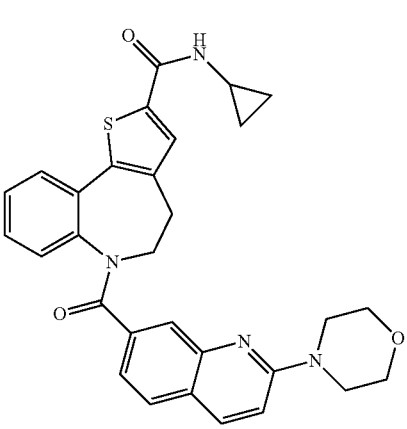 [SMILES: O=C(NC1CC1)c1cc2c(s1)-c1ccccc1N(C(=O)c1ccc3ccc(N4CCOCC4)nc3c1)CC2] |

TABLE 5-continued

| Example | Structure |
|---|---|
| 298 | (structure) |
| 299 | (structure) |
| 300 | (structure) |
| 301 | (structure) |
| 302 | (structure) |
| 303 | (structure) |

TABLE 5-continued
| Example | Structure |
|---|---|
| 304 | 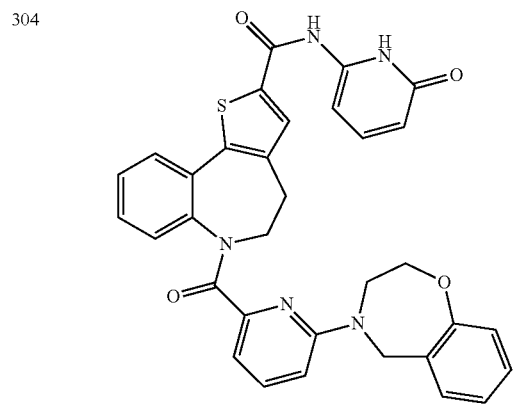 |
| 305 | 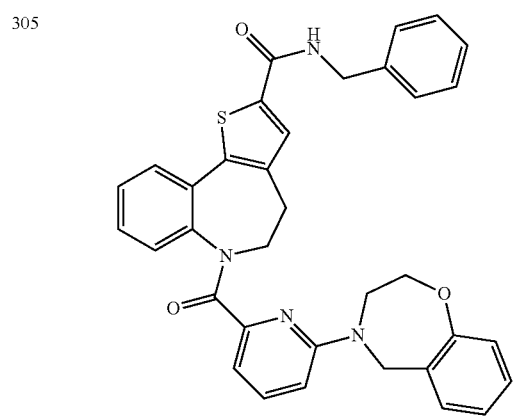 |
| 306 | 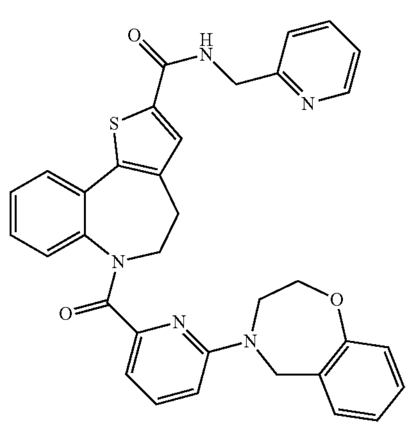 |
| 307 | 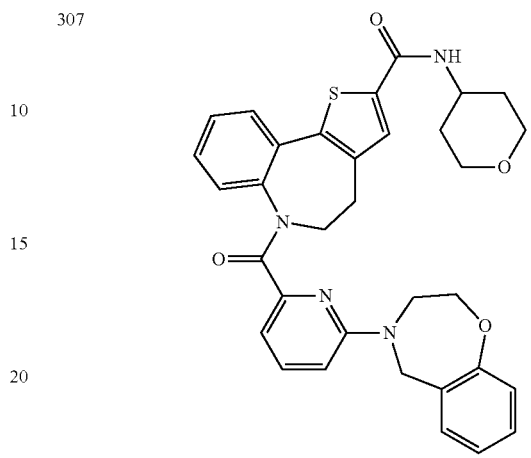 |
| 308 | 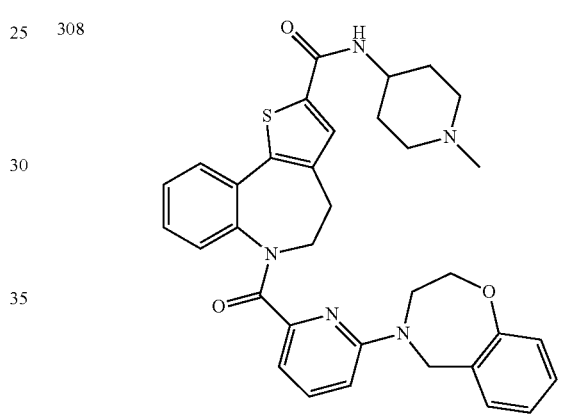 |
| 309 | 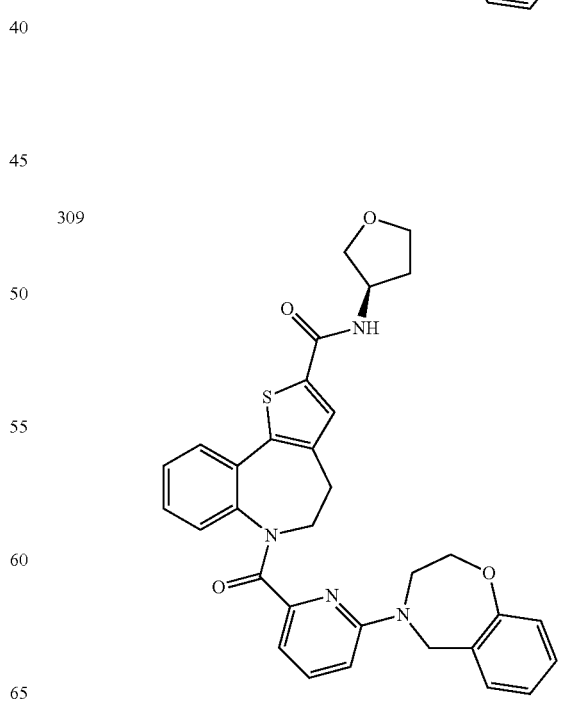 |

TABLE 5-continued
| Example | Structure |
|---|---|
| 310 | 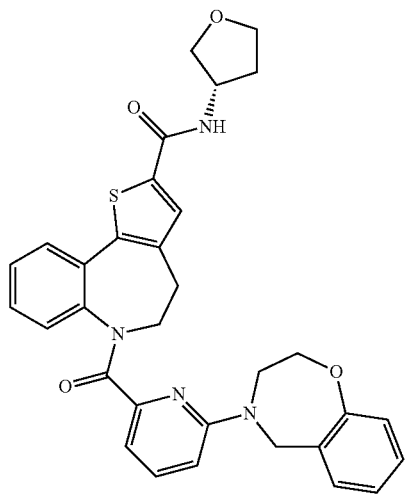 [SMILES: O=C(N[C@H]1CCOC1)c1cc2c(s1)-c1ccccc1N(C(=O)c1cccc(N3CCOc4ccccc4C3)n1)CC2] |
| 311 | 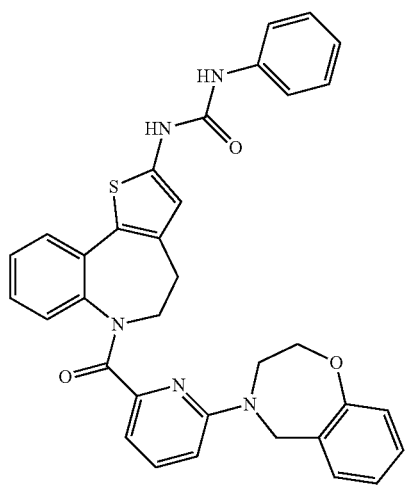 [SMILES: O=C(Nc1ccccc1)Nc1cc2c(s1)-c1ccccc1N(C(=O)c1cccc(N3CCOc4ccccc4C3)n1)CC2] |
| 312 | 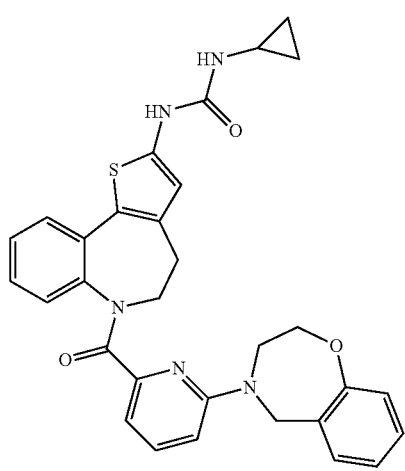 [SMILES: O=C(Nc1cc2c(s1)-c1ccccc1N(C(=O)c1cccc(N3CCOc4ccccc4C3)n1)CC2)NC1CC1] |
| 313 | 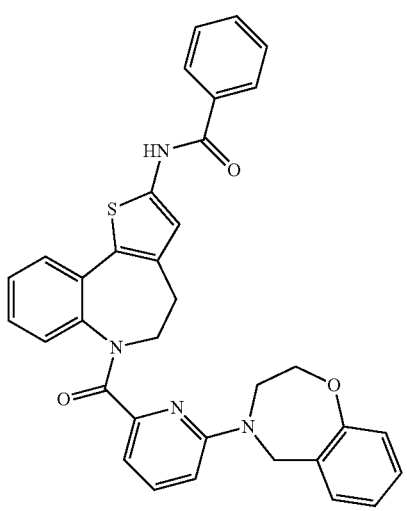 [SMILES: O=C(Nc1cc2c(s1)-c1ccccc1N(C(=O)c1cccc(N3CCOc4ccccc4C3)n1)CC2)c1ccccc1] |
| 314 | 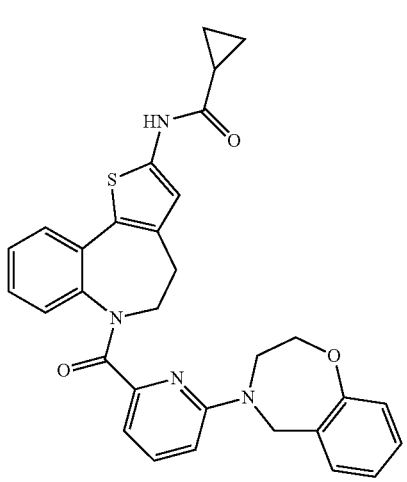 [SMILES: O=C(Nc1cc2c(s1)-c1ccccc1N(C(=O)c1cccc(N3CCOc4ccccc4C3)n1)CC2)C1CC1] |
| 315 | 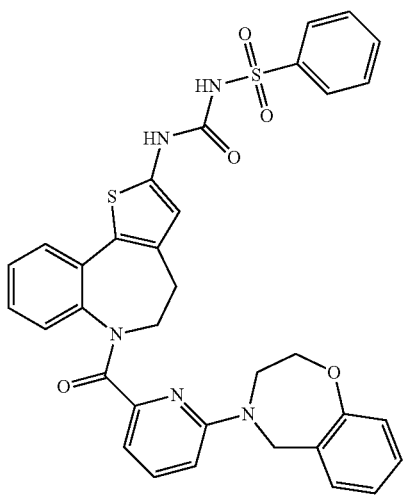 [SMILES: O=C(Nc1cc2c(s1)-c1ccccc1N(C(=O)c1cccc(N3CCOc4ccccc4C3)n1)CC2)NS(=O)(=O)c1ccccc1] |

TABLE 5-continued
| Example | Structure |
|---|---|
| 316 | 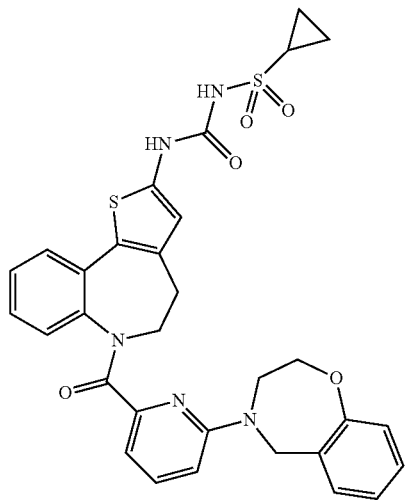 [SMILES: O=C(Nc1cc2c(s1)-c1ccccc1N(C(=O)c1cccc(N3CCOc4ccccc4C3)n1)CC2)NS(=O)(=O)C1CC1] |
| 317 | 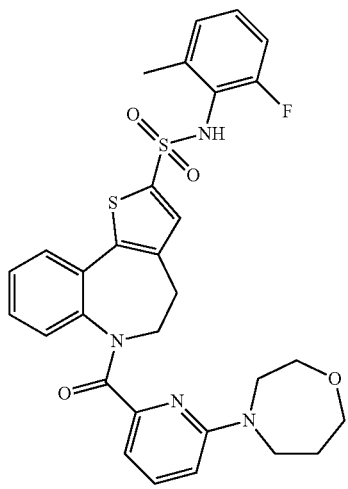 [SMILES: Cc1cccc(F)c1NS(=O)(=O)c1cc2c(s1)-c1ccccc1N(C(=O)c1cccc(N3CCCOCC3)n1)CC2] |
| 318 | 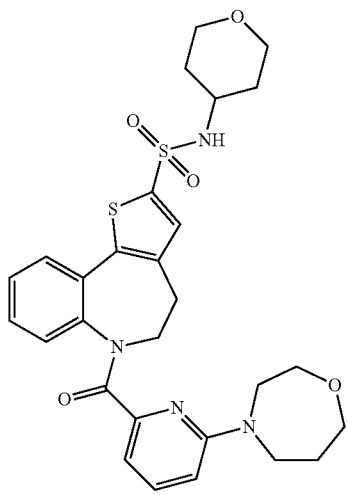 [SMILES: O=C(c1cccc(N2CCCOCC2)n1)N1CCc2cc(S(=O)(=O)NC3CCOCC3)sc2-c2ccccc21] |
TABLE 5-continued
| Example | Structure |
|---|---|
| 319 | 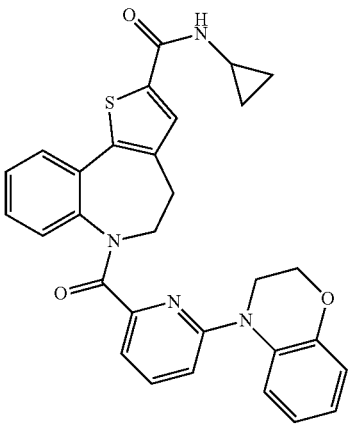 [SMILES: O=C(NC1CC1)c1cc2c(s1)-c1ccccc1N(C(=O)c1cccc(N3CCOc4ccccc43)n1)CC2] |
| 320 | |
| 321 | 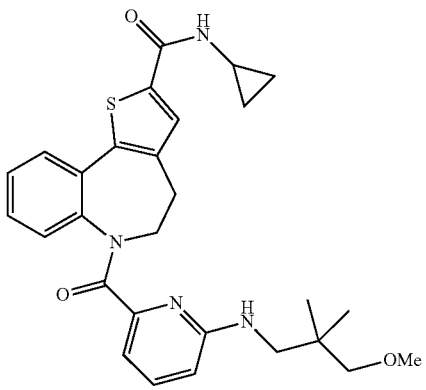 [SMILES: COCC(C)(C)CNc1cccc(C(=O)N2CCc3cc(C(=O)NC4CC4)sc3-c3ccccc32)n1] |

TABLE 5-continued
| Example | Structure |
|---|---|
| 322 | 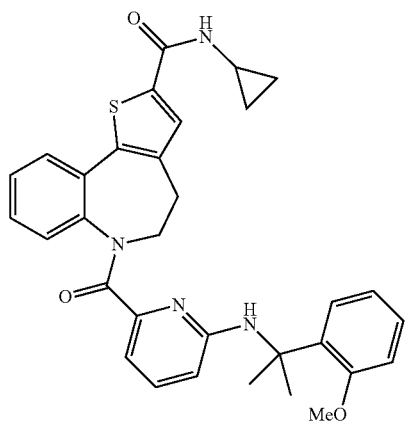 [SMILES: COc1ccccc1C(C)(C)Nc1cccc(C(=O)N2CCc3cc(C(=O)NC4CC4)sc3-c3ccccc32)n1] |
| 323 | 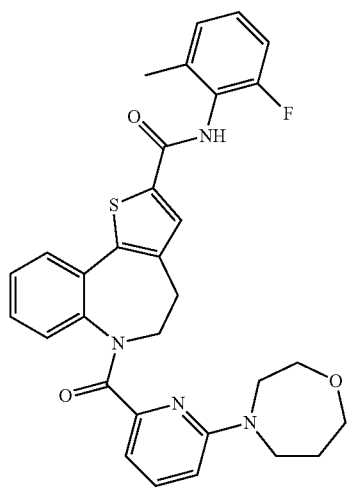 [SMILES: Cc1cccc(F)c1NC(=O)c1cc2c(s1)-c1ccccc1N(C(=O)c1cccc(N3CCCOCC3)n1)CC2] |
| 324 | 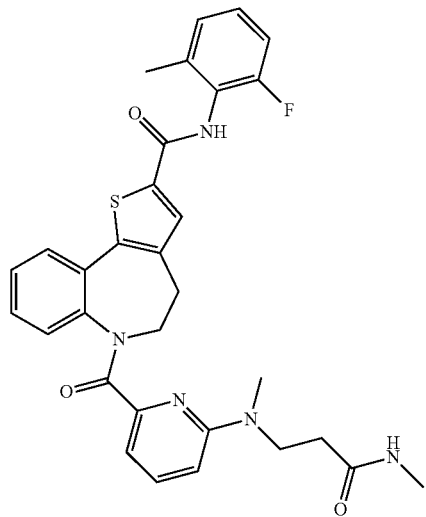 [SMILES: CNC(=O)CCN(C)c1cccc(C(=O)N2CCc3cc(C(=O)Nc4c(C)cccc4F)sc3-c3ccccc32)n1] |
TABLE 5-continued
| Example | Structure |
|---|---|
| 325 | 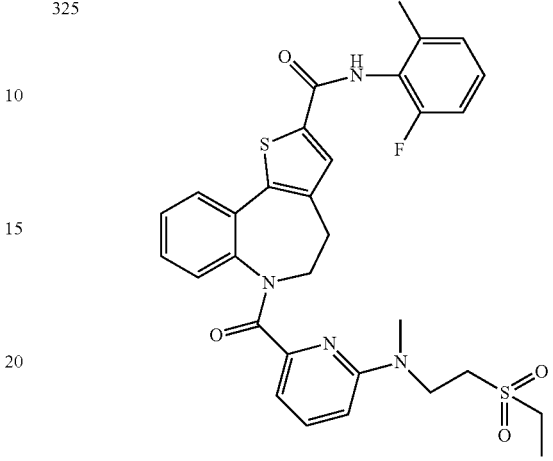 |
| 326 | 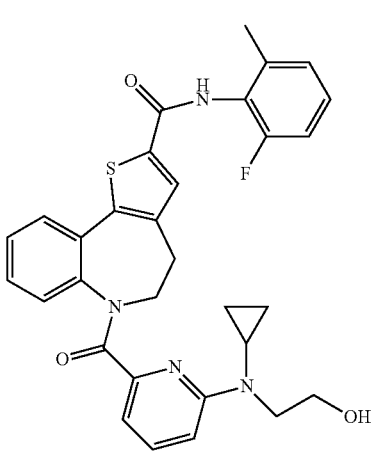 [SMILES: Cc1cccc(F)c1NC(=O)c1cc2c(s1)-c1ccccc1N(C(=O)c1cccc(N(CCO)C3CC3)n1)CC2] |
| 327 | 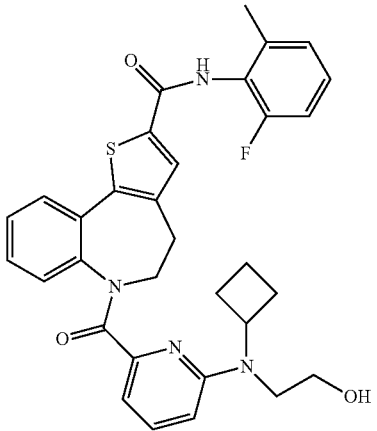 [SMILES: Cc1cccc(F)c1NC(=O)c1cc2c(s1)-c1ccccc1N(C(=O)c1cccc(N(CCO)C3CCC3)n1)CC2] |

TABLE 5-continued
| Example | Structure |
|---|---|
| 328 | 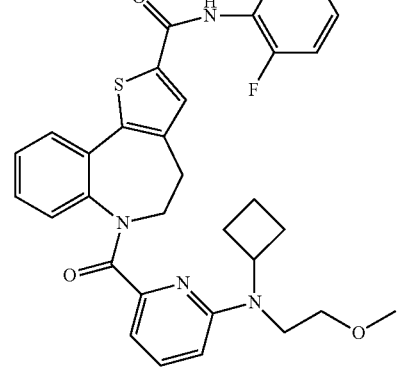 |
| 329 | 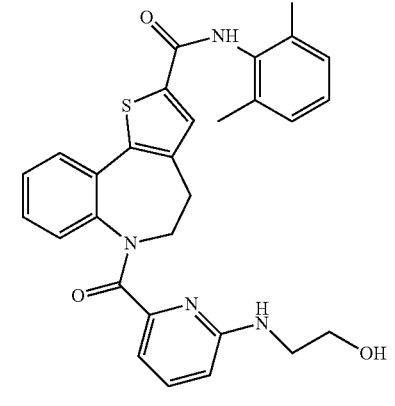 |
| 330 | 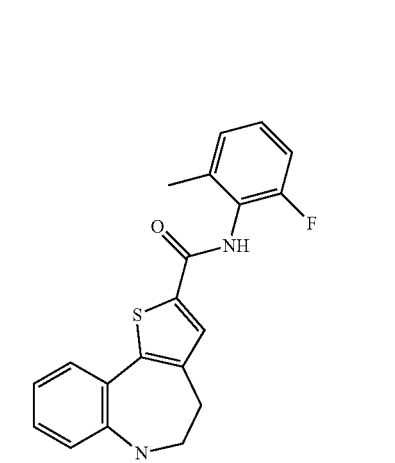 |
| 331 | 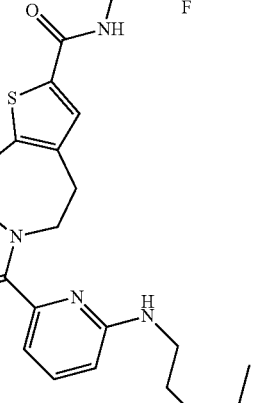 |
| 332 | 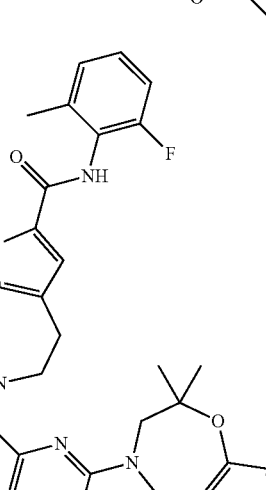 |
| 333 | 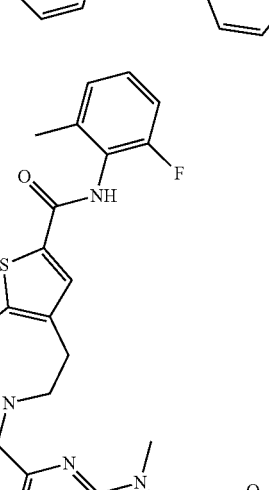 |

TABLE 5-continued
| Example | Structure |
|---|---|
| 334 | 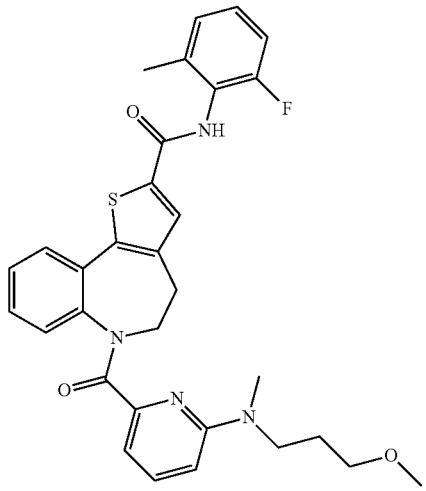 [SMILES: COCCCN(C)c1cccc(C(=O)N2CCc3cc(C(=O)Nc4c(C)cccc4F)sc3-c3ccccc32)n1] |
| 335 | 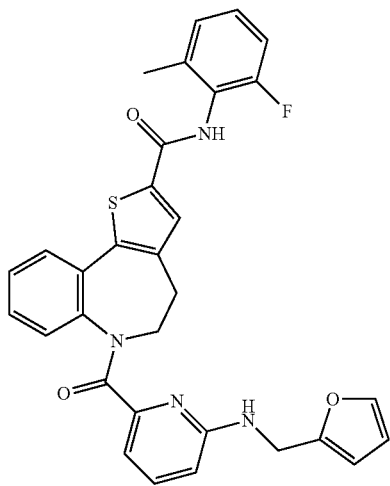 [SMILES: Cc1cccc(F)c1NC(=O)c1cc2c(s1)-c1ccccc1N(C(=O)c1cccc(NCc3ccco3)n1)CC2] |
| 336 | 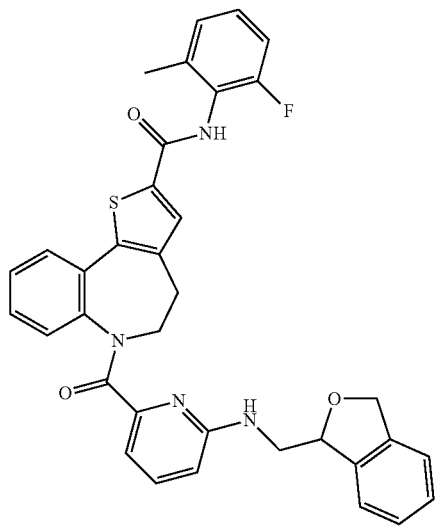 [SMILES: Cc1cccc(F)c1NC(=O)c1cc2c(s1)-c1ccccc1N(C(=O)c1cccc(NCC3OCc4ccccc43)n1)CC2] |
| 337 | 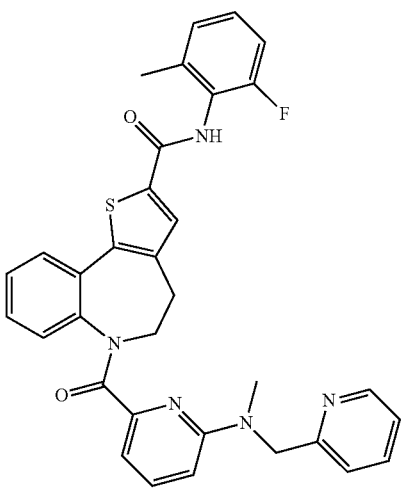 [SMILES: Cc1cccc(F)c1NC(=O)c1cc2c(s1)-c1ccccc1N(C(=O)c1cccc(N(C)Cc3ccccn3)n1)CC2] |
| 338 | 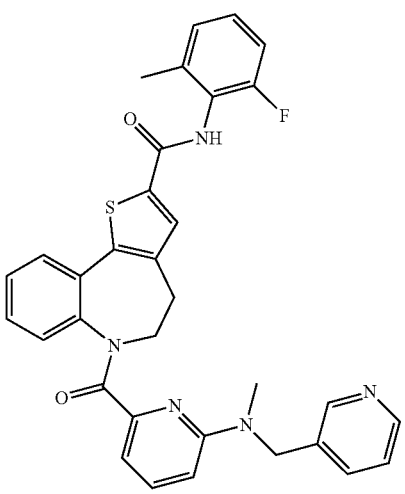 [SMILES: Cc1cccc(F)c1NC(=O)c1cc2c(s1)-c1ccccc1N(C(=O)c1cccc(N(C)Cc3cccnc3)n1)CC2] |
| 339 | 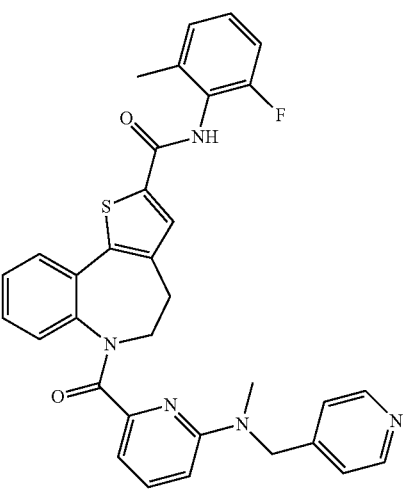 [SMILES: Cc1cccc(F)c1NC(=O)c1cc2c(s1)-c1ccccc1N(C(=O)c1cccc(N(C)Cc3ccncc3)n1)CC2] |

TABLE 5-continued
| Example | Structure |
|---|---|
| 340 | 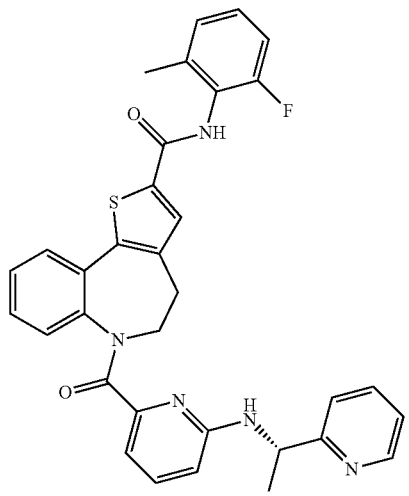 [SMILES: Cc1cccc(F)c1NC(=O)c1cc2c(s1)-c1ccccc1N(C(=O)c1cccc(N[C@@H](C)c3ccccn3)n1)CC2] |
| 341 | 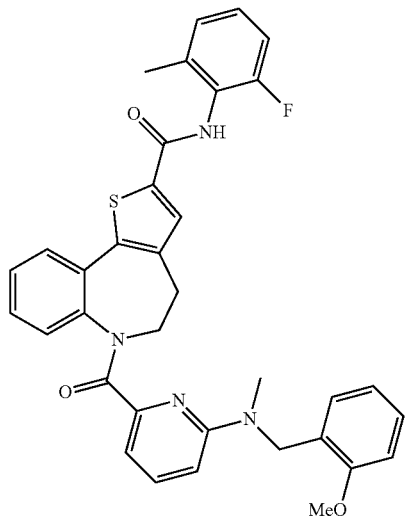 [SMILES: COc1ccccc1CN(C)c1cccc(C(=O)N2CCc3cc(C(=O)Nc4c(C)cccc4F)sc3-c3ccccc32)n1] |
| 342 | 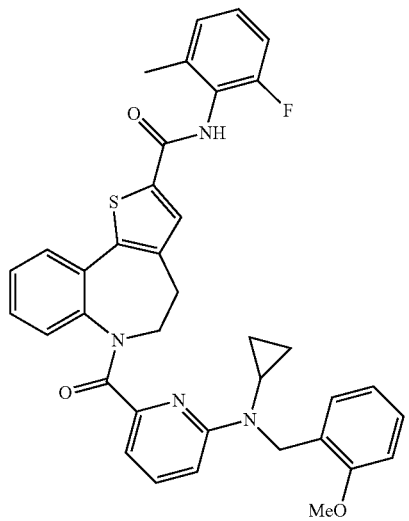 [SMILES: COc1ccccc1CN(c1cccc(C(=O)N2CCc3cc(C(=O)Nc4c(C)cccc4F)sc3-c3ccccc32)n1)C1CC1] |
| 343 | 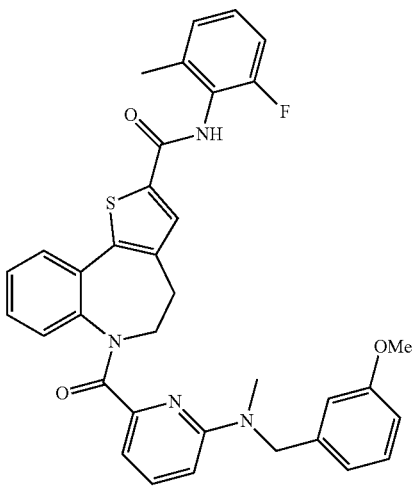 [SMILES: COc1cccc(CN(C)c2cccc(C(=O)N3CCc4cc(C(=O)Nc5c(C)cccc5F)sc4-c4ccccc43)n2)c1] |
| 344 | 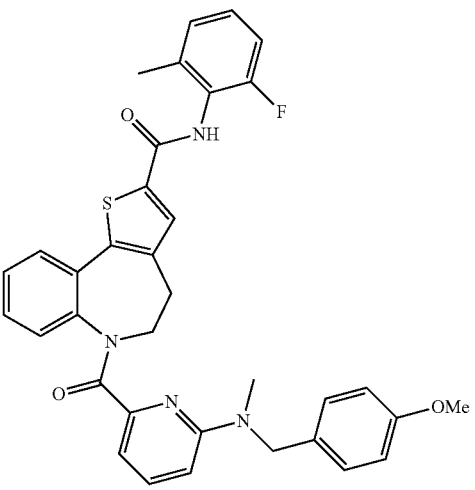 [SMILES: COc1ccc(CN(C)c2cccc(C(=O)N3CCc4cc(C(=O)Nc5c(C)cccc5F)sc4-c4ccccc43)n2)cc1] |
| 345 | 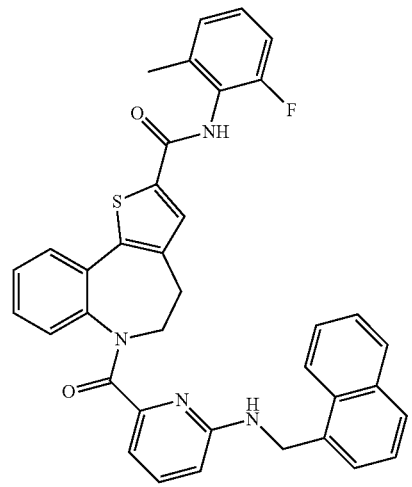 [SMILES: Cc1cccc(F)c1NC(=O)c1cc2c(s1)-c1ccccc1N(C(=O)c1cccc(NCc3cccc4ccccc34)n1)CC2] |

TABLE 5-continued
| Example | Structure |
|---|---|
| 346 | 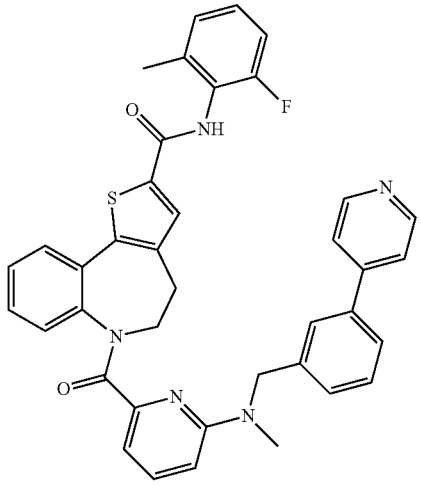 [SMILES: Cc1cccc(F)c1NC(=O)c1cc2c(s1)-c1ccccc1N(C(=O)c1cccc(N(C)Cc3cccc(-c4ccncc4)c3)n1)CC2] |
| 347 | 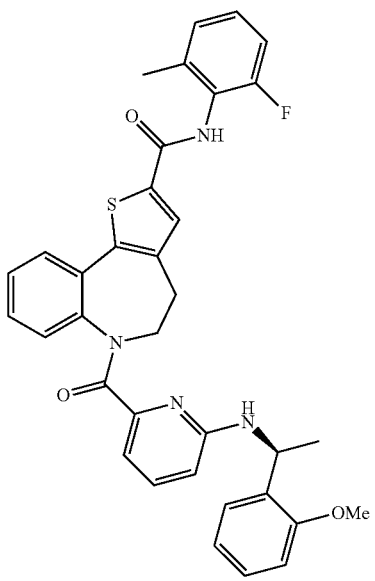 [SMILES: COc1ccccc1[C@H](C)Nc1cccc(C(=O)N2CCc3cc(C(=O)Nc4c(C)cccc4F)sc3-c3ccccc32)n1] |
| 348 | 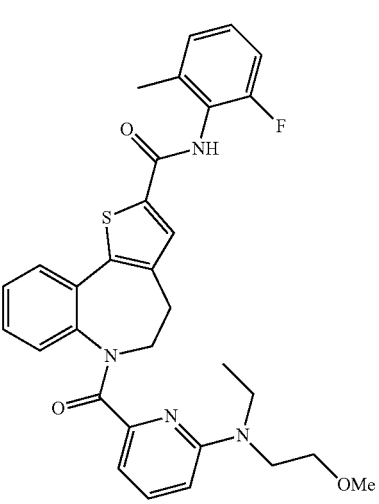 [SMILES: CCN(CCOC)c1cccc(C(=O)N2CCc3cc(C(=O)Nc4c(C)cccc4F)sc3-c3ccccc32)n1] |
| 349 | 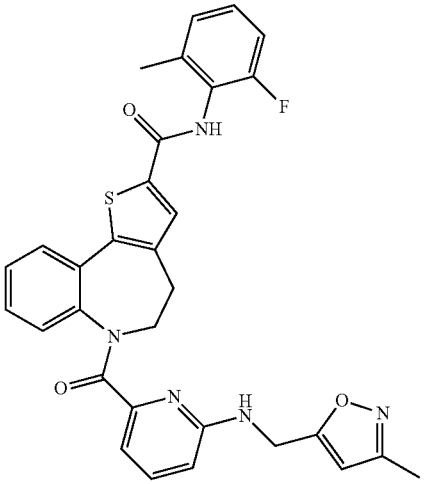 [SMILES: Cc1cc(CNc2cccc(C(=O)N3CCc4cc(C(=O)Nc5c(C)cccc5F)sc4-c4ccccc43)n2)on1] |
| 350 | 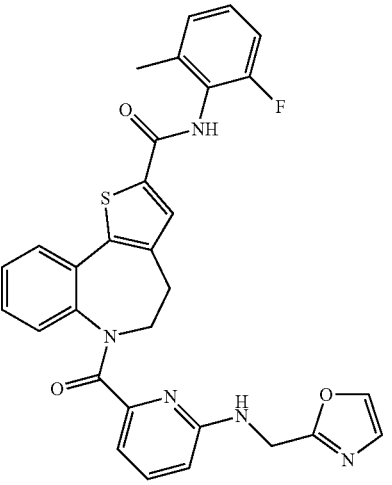 [SMILES: Cc1cccc(F)c1NC(=O)c1cc2c(s1)-c1ccccc1N(C(=O)c1cccc(NCc3ncco3)n1)CC2] |
| 351 | 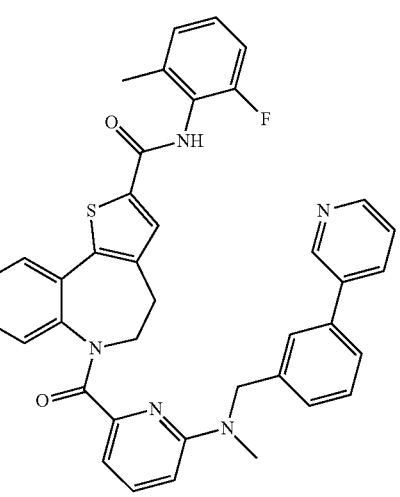 |

TABLE 5-continued
| Example | Structure |
|---|---|
| 352 | 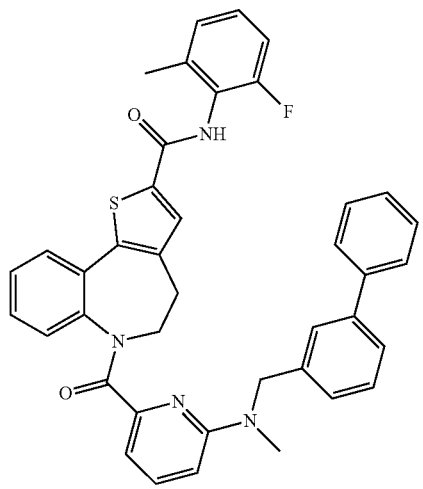 [SMILES: Cc1cccc(F)c1NC(=O)c1cc2c(s1)-c1ccccc1N(C(=O)c1cccc(N(C)Cc3cccc(-c4ccccc4)c3)n1)CC2] |
| 353 | 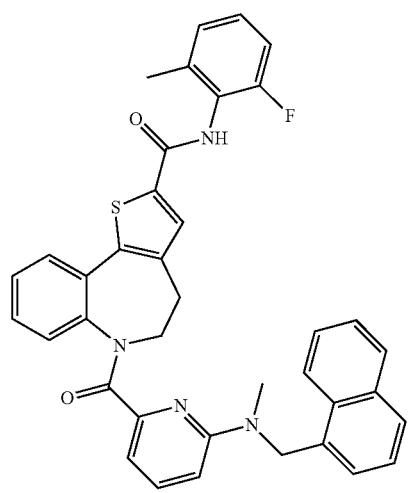 [SMILES: Cc1cccc(F)c1NC(=O)c1cc2c(s1)-c1ccccc1N(C(=O)c1cccc(N(C)Cc3cccc4ccccc34)n1)CC2] |
| 354 | 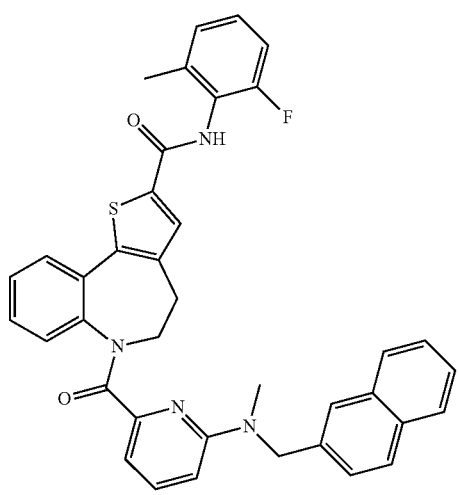 [SMILES: Cc1cccc(F)c1NC(=O)c1cc2c(s1)-c1ccccc1N(C(=O)c1cccc(N(C)Cc3ccc4ccccc4c3)n1)CC2] |
| 355 | 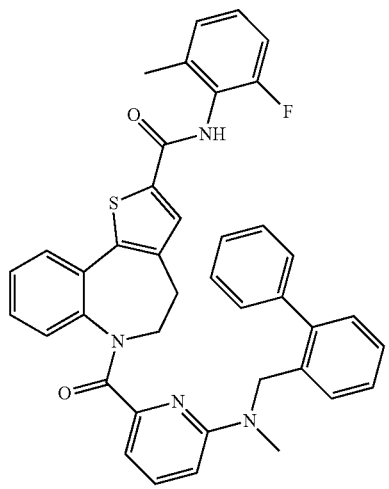 [SMILES: Cc1cccc(F)c1NC(=O)c1cc2c(s1)-c1ccccc1N(C(=O)c1cccc(N(C)Cc3ccccc3-c3ccccc3)n1)CC2] |
| 356 | 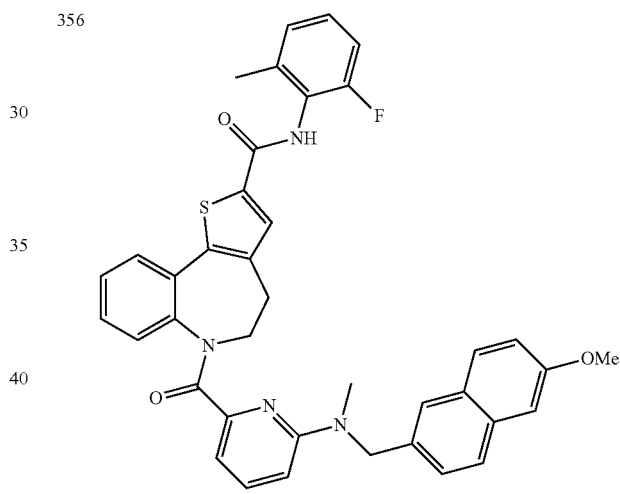 |
| 357 | 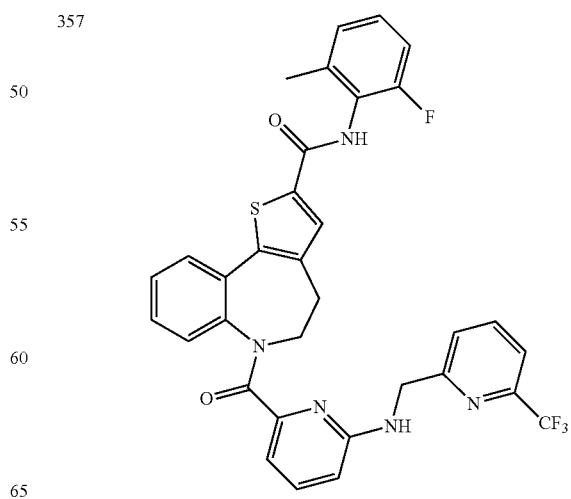 |

TABLE 5-continued
| Example | Structure |
|---|---|
| 358 | 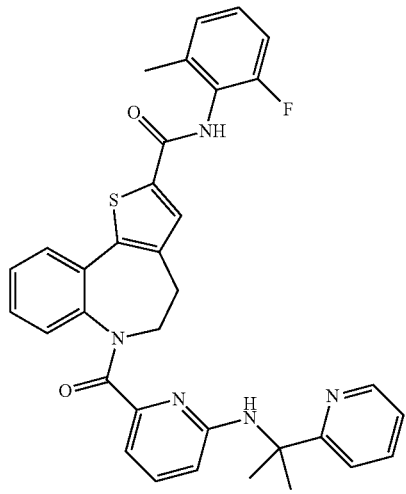 [SMILES: Cc1cccc(F)c1NC(=O)c1cc2c(s1)-c1ccccc1N(C(=O)c1cccc(NC(C)(C)c3ccccn3)n1)CC2] |
| 359 | 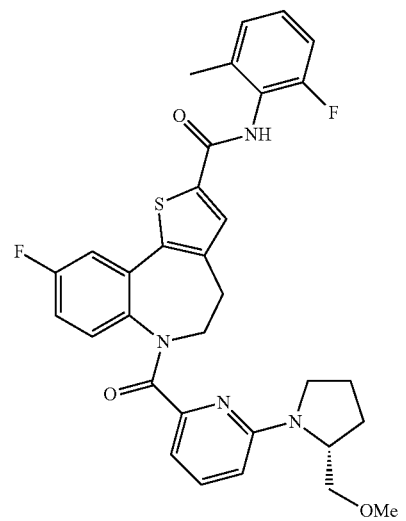 [SMILES: COC[C@H]1CCCN1c1cccc(C(=O)N2CCc3cc(C(=O)Nc4c(C)cccc4F)sc3-c3cc(F)ccc32)n1] |
| 360 | 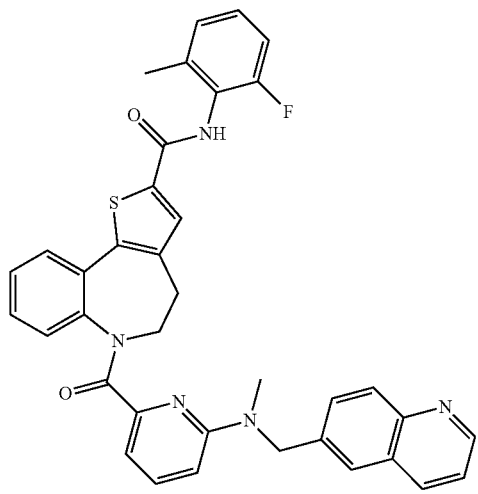 [SMILES: Cc1cccc(F)c1NC(=O)c1cc2c(s1)-c1ccccc1N(C(=O)c1cccc(N(C)Cc3ccc4ncccc4c3)n1)CC2] |
| 361 | 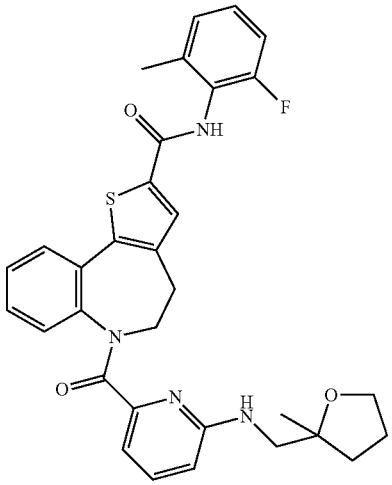 [SMILES: Cc1cccc(F)c1NC(=O)c1cc2c(s1)-c1ccccc1N(C(=O)c1cccc(NCC3(C)CCCO3)n1)CC2] |
| 362 | 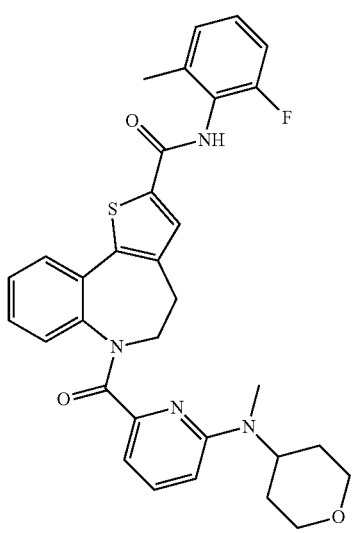 [SMILES: Cc1cccc(F)c1NC(=O)c1cc2c(s1)-c1ccccc1N(C(=O)c1cccc(N(C)C3CCOCC3)n1)CC2] |
| 363 | 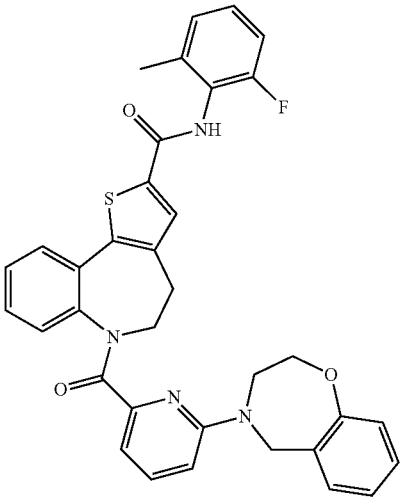 [SMILES: Cc1cccc(F)c1NC(=O)c1cc2c(s1)-c1ccccc1N(C(=O)c1cccc(N3CCOc4ccccc4C3)n1)CC2] |

TABLE 5-continued
| Example | Structure |
|---|---|
| 364 | 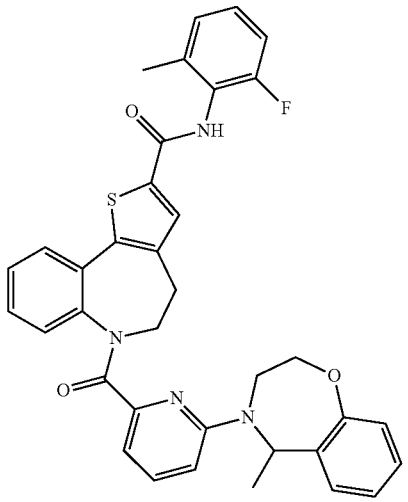 [SMILES: Cc1cccc(F)c1NC(=O)c1cc2c(s1)-c1ccccc1N(C(=O)c1cccc(N3CCOc4ccccc4C3C)n1)CC2] |
| 365 | 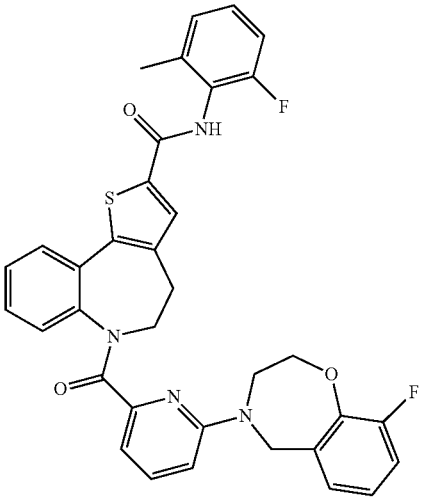 [SMILES: Cc1cccc(F)c1NC(=O)c1cc2c(s1)-c1ccccc1N(C(=O)c1cccc(N3CCOc4c(F)cccc4C3)n1)CC2] |
| 366 | 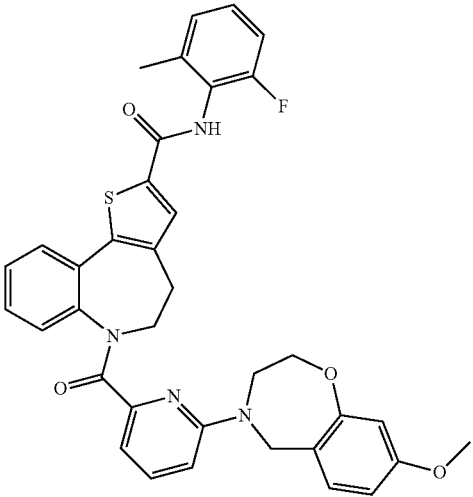 [SMILES: COc1ccc2c(c1)OCCN(c1cccc(C(=O)N3CCc4cc(C(=O)Nc5c(C)cccc5F)sc4-c4ccccc43)n1)C2] |
| 367 | 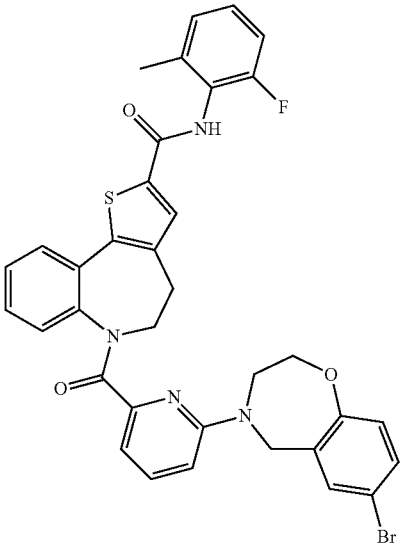 |
| 368 | 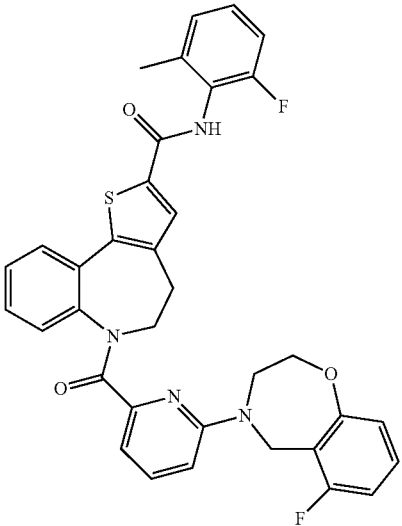 [SMILES: Cc1cccc(F)c1NC(=O)c1cc2c(s1)-c1ccccc1N(C(=O)c1cccc(N3CCOc4cccc(F)c4C3)n1)CC2] |

TABLE 5-continued

| Example | Structure |
|---|---|
| 369 | 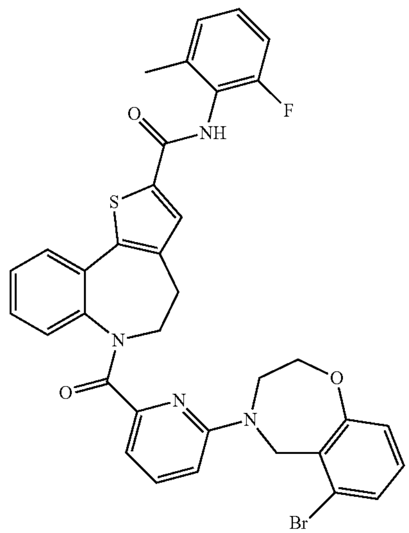 [SMILES: Cc1cccc(F)c1NC(=O)c1cc2c(s1)-c1ccccc1N(C(=O)c1cccc(N3CCOc4cccc(Br)c4C3)n1)CC2] |
| 370 | 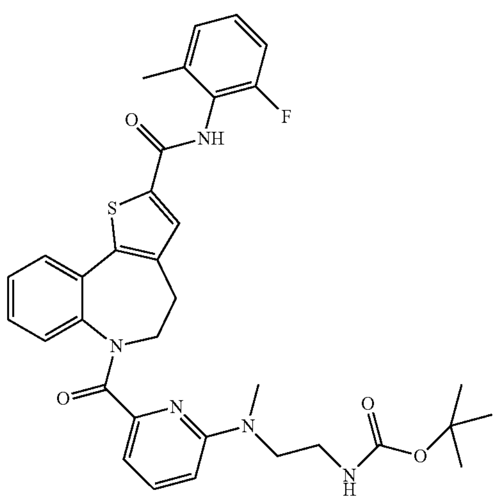 [SMILES: Cc1cccc(F)c1NC(=O)c1cc2c(s1)-c1ccccc1N(C(=O)c1cccc(N(C)CCNC(=O)OC(C)(C)C)n1)CC2] |
| 371 | 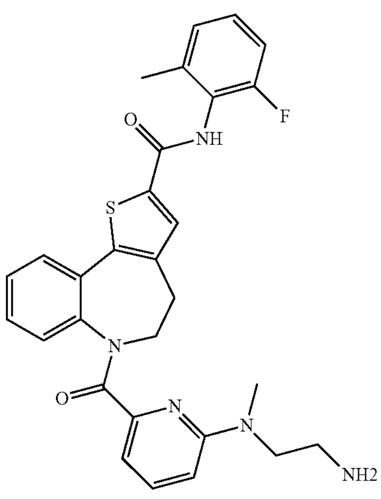 [SMILES: Cc1cccc(F)c1NC(=O)c1cc2c(s1)-c1ccccc1N(C(=O)c1cccc(N(C)CCN)n1)CC2] |
| 372 | |
| 373 | |
| 374 | |

TABLE 5-continued

| Example | Structure |
|---|---|
| 375 | (structure) |
| 376 | (structure) |
| 377 | (structure) |
| 378 | (structure) |
| 379 | (structure) |
| 380 | (structure) |

TABLE 5-continued
| Example | Structure |
|---|---|
| 381 | 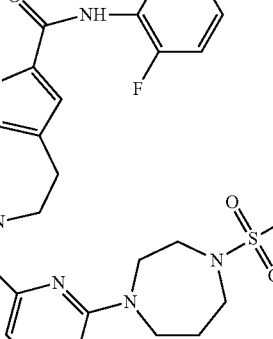 |
| 382 | 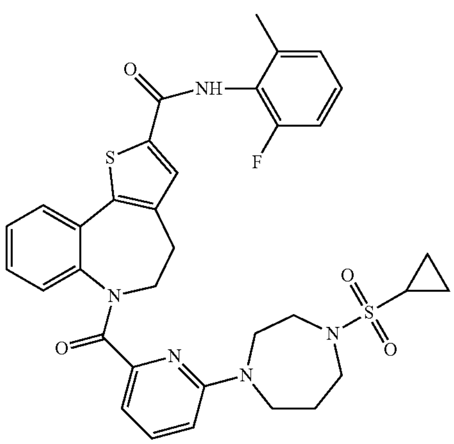 [SMILES: Cc1cccc(F)c1NC(=O)c1cc2c(s1)-c1ccccc1N(C(=O)c1cccc(N3CCCN(S(=O)(=O)C4CC4)CC3)n1)CC2] |
| 383 | 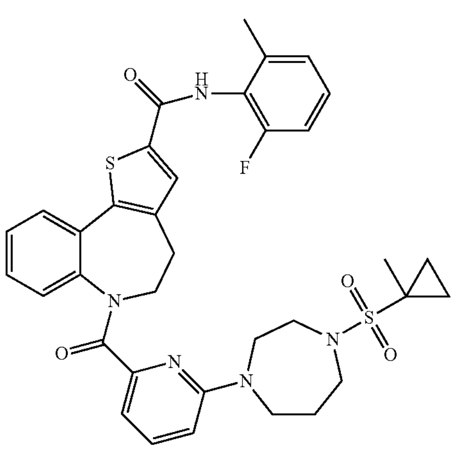 [SMILES: Cc1cccc(F)c1NC(=O)c1cc2c(s1)-c1ccccc1N(C(=O)c1cccc(N3CCCN(S(=O)(=O)C4(C)CC4)CC3)n1)CC2] |
| 384 | 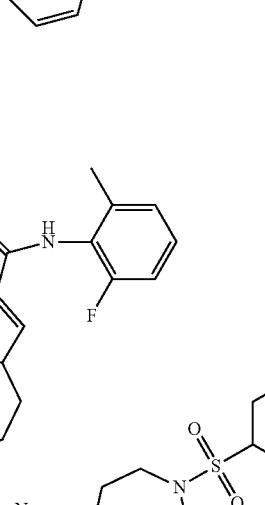 |
| 385 | 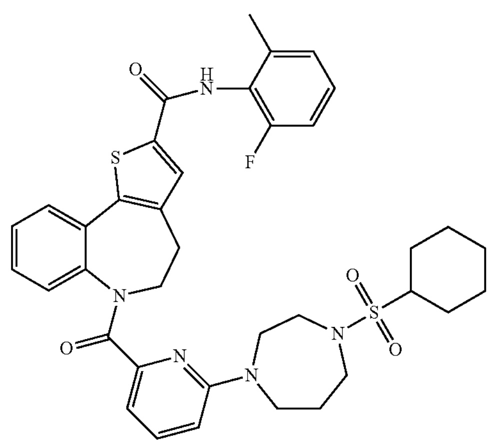 [SMILES: Cc1cccc(F)c1NC(=O)c1cc2c(s1)-c1ccccc1N(C(=O)c1cccc(N3CCCN(S(=O)(=O)C4CCCCC4)CC3)n1)CC2] |
| 386 | 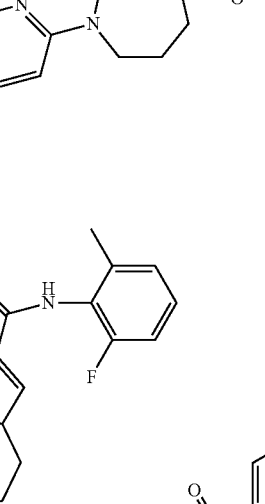 |

TABLE 5-continued
| Example | Structure |
|---|---|
| 387 | 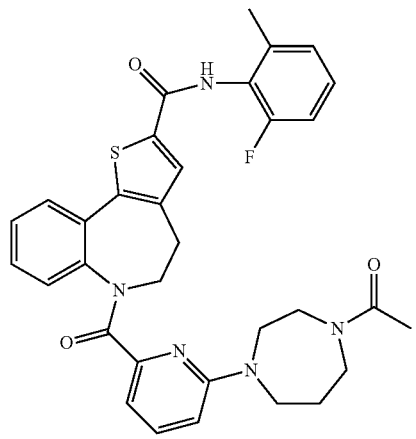 [SMILES: CC(=O)N1CCCN(c2cccc(C(=O)N3CCc4cc(C(=O)Nc5c(C)cccc5F)sc4-c4ccccc43)n2)CC1] |
| 388 | 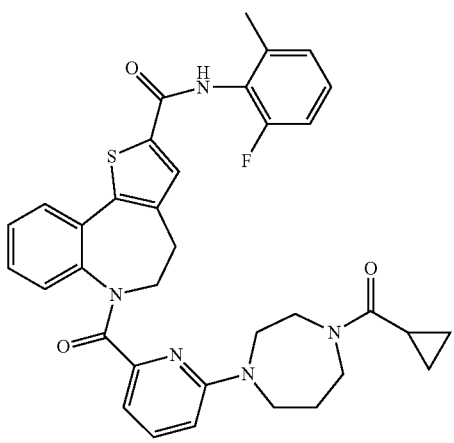 [SMILES: Cc1cccc(F)c1NC(=O)c1cc2c(s1)-c1ccccc1N(C(=O)c1cccc(N3CCCN(C(=O)C4CC4)CC3)n1)CC2] |
| 389 | 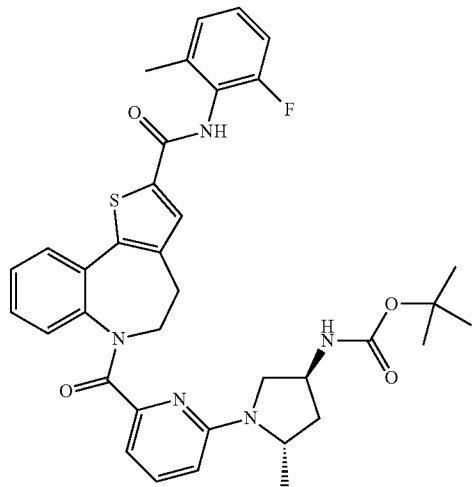 [SMILES: Cc1cccc(F)c1NC(=O)c1cc2c(s1)-c1ccccc1N(C(=O)c1cccc(N3C[C@@H](NC(=O)OC(C)(C)C)C[C@@H]3C)n1)CC2] |
| 390 | 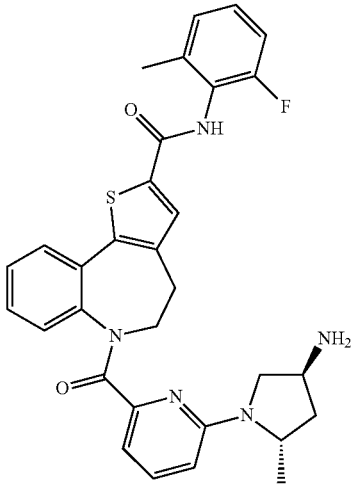 [SMILES: Cc1cccc(F)c1NC(=O)c1cc2c(s1)-c1ccccc1N(C(=O)c1cccc(N3C[C@@H](N)C[C@@H]3C)n1)CC2] |
| 391 | 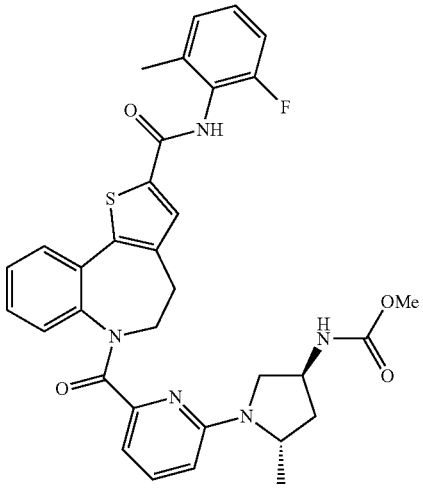 [SMILES: COC(=O)N[C@H]1C[C@H](C)N(c2cccc(C(=O)N3CCc4cc(C(=O)Nc5c(C)cccc5F)sc4-c4ccccc43)n2)C1] |
| 392 | 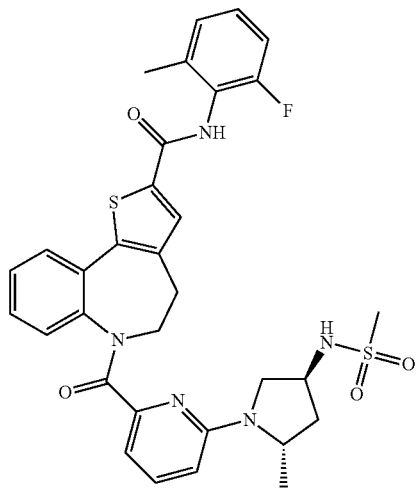 [SMILES: Cc1cccc(F)c1NC(=O)c1cc2c(s1)-c1ccccc1N(C(=O)c1cccc(N3C[C@@H](NS(C)(=O)=O)C[C@@H]3C)n1)CC2] |

TABLE 5-continued
| Example | Structure |
|---|---|
| 393 | 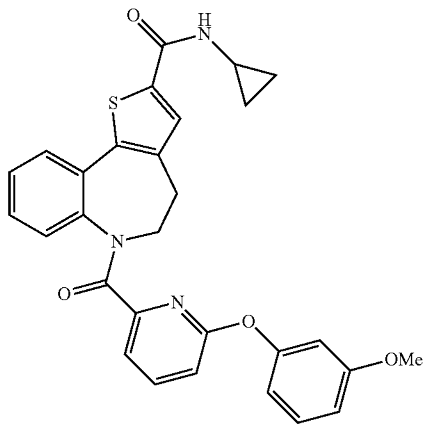 [SMILES: COc1cccc(Oc2cccc(C(=O)N3CCc4cc(C(=O)NC5CC5)sc4-c4ccccc43)n2)c1] |
| 394 | 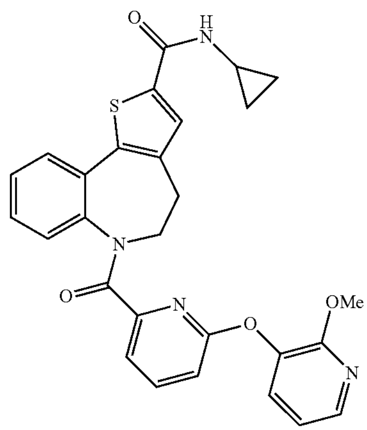 [SMILES: COc1ncccc1Oc1cccc(C(=O)N2CCc3cc(C(=O)NC4CC4)sc3-c3ccccc32)n1] |
| 395 | 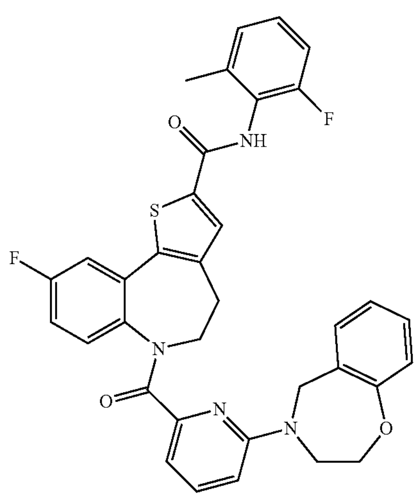 [SMILES: Cc1cccc(F)c1NC(=O)c1cc2c(s1)-c1cc(F)ccc1N(C(=O)c1cccc(N3CCOc4ccccc4C3)n1)CC2] |
| 396 |  |
| 397 | |
| 398 | 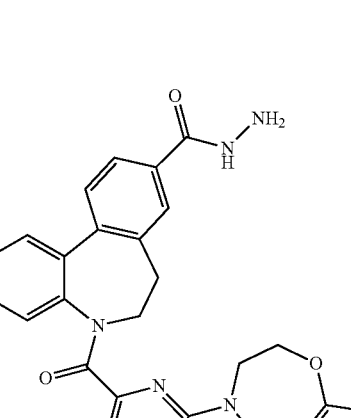 |

TABLE 5-continued

| Example | Structure |
|---|---|
| 399 | 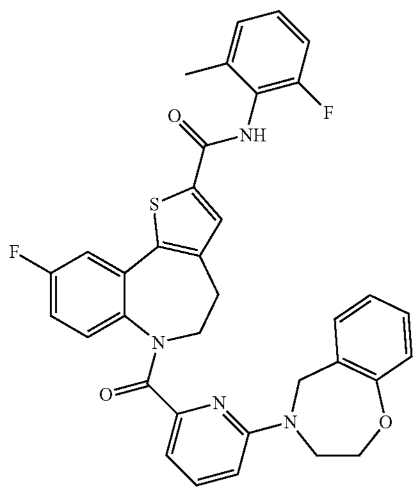 [SMILES: Cc1cccc(F)c1NC(=O)c1cc2c(s1)-c1cc(F)ccc1N(C(=O)c1cccc(N3CCOc4ccccc4C3)n1)CC2] |

Example 400

A solution of 6,6-difluoro-1,4-oxazepane (26 mg, 0.19 mmol), the compound from Example 115 step b (100 mg, 0.19 mmol), Ruphos (18 mg, 0.038 mmol), 2nd Ruphos Precat (15 mg, 0.019 mmol) and Cs$_2$CO$_3$ (120 mg, 0.38 mmol) in 1,4-dioxane (3 mL) was stirred for 1 hour at 100° C. The mixture was diluted with water, extracted with EtOAc (50 mL×3), the organic layer was dried, evaporated. The crude product (5 mL) was purified by Prep-TLC (EtOAc), then Prep-HPLC (MeCN/H$_2$O) to give the desired compound (16.0 mg, 14.2%) as a white solid. ESI MS m/z=593.6 [M+H]$^+$.

Examples 401-507 shown in table 6 were prepared using a procedure similar to that of Example 400. Examples 508-527 can also be prepared using similar methods.

TABLE 6

| Example | Structure |
|---|---|
| 401 | 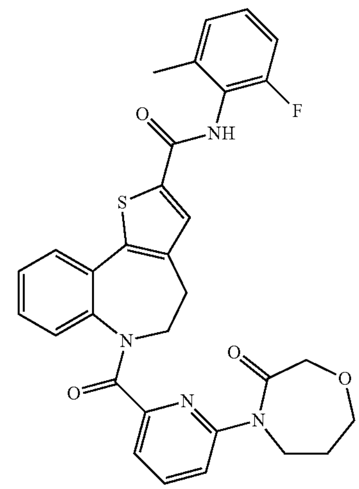 [SMILES: Cc1cccc(F)c1NC(=O)c1cc2c(s1)-c1ccccc1N(C(=O)c1cccc(N3CCCOCC3=O)n1)CC2] |
| 402 | 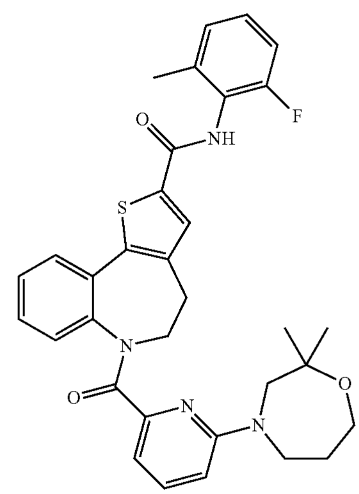 [SMILES: Cc1cccc(F)c1NC(=O)c1cc2c(s1)-c1ccccc1N(C(=O)c1cccc(N3CCCOC(C)(C)C3)n1)CC2] |
| 403 | 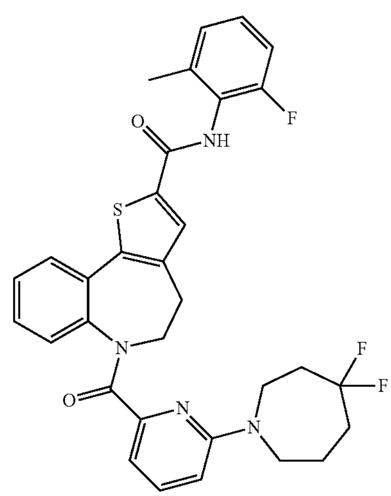 [SMILES: Cc1cccc(F)c1NC(=O)c1cc2c(s1)-c1ccccc1N(C(=O)c1cccc(N3CCCC(F)(F)CC3)n1)CC2] |

TABLE 6-continued
| Example | Structure |
|---------|-----------|
| 404 | 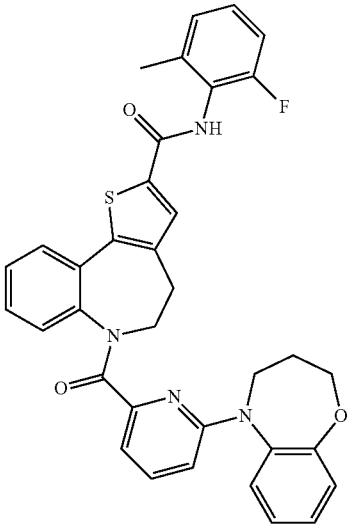 [SMILES: Cc1cccc(F)c1NC(=O)c1cc2c(s1)-c1ccccc1N(C(=O)c1cccc(N3CCCOc4ccccc43)n1)CC2] |
| 405 | 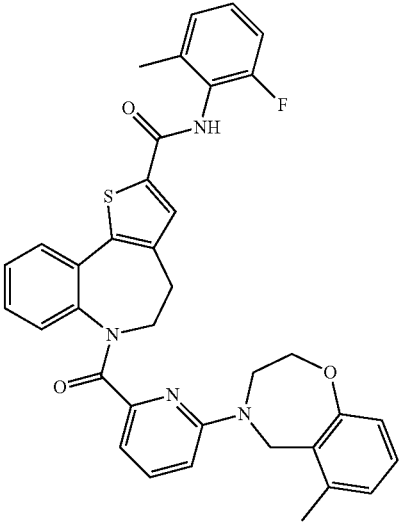 [SMILES: Cc1cccc2c1CN(c1cccc(C(=O)N3CCc4cc(C(=O)Nc5c(C)cccc5F)sc4-c4ccccc43)n1)CCO2] |
| 406 | 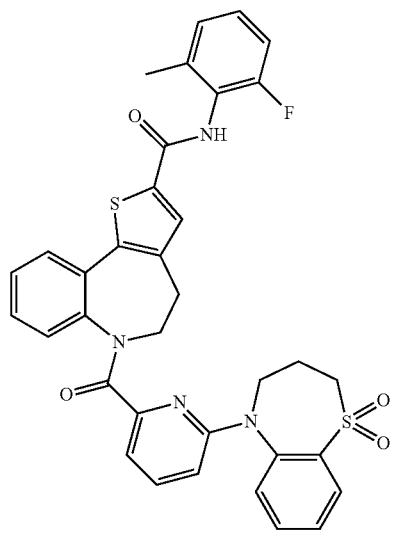 [SMILES: Cc1cccc(F)c1NC(=O)c1cc2c(s1)-c1ccccc1N(C(=O)c1cccc(N3CCCS(=O)(=O)c4ccccc43)n1)CC2] |
| 407 | 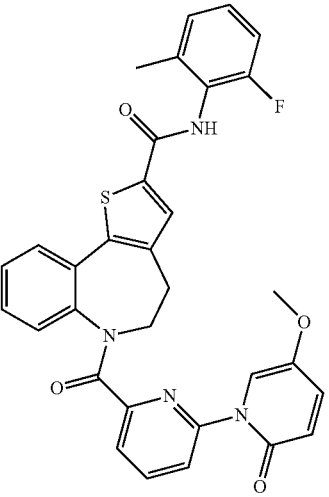 [SMILES: COc1ccc(=O)n(-c2cccc(C(=O)N3CCc4cc(C(=O)Nc5c(C)cccc5F)sc4-c4ccccc43)n2)c1] |
| 408 | 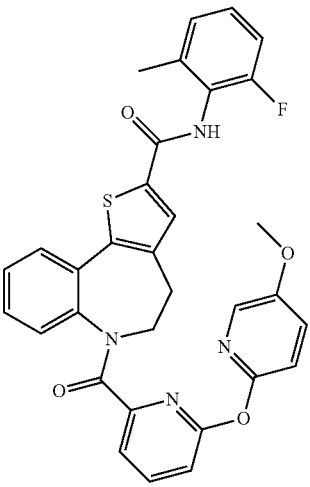 [SMILES: COc1ccc(Oc2cccc(C(=O)N3CCc4cc(C(=O)Nc5c(C)cccc5F)sc4-c4ccccc43)n2)nc1] |
| 409 | 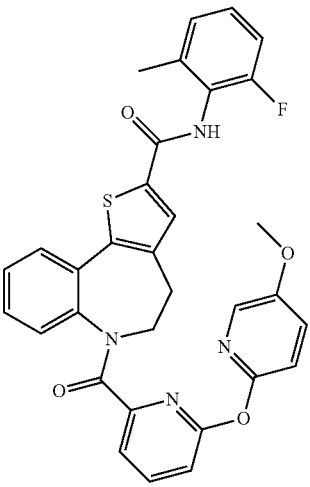 [SMILES: COc1ccc(Oc2cccc(C(=O)N3CCc4cc(C(=O)Nc5c(C)cccc5F)sc4-c4ccccc43)n2)nc1] |

TABLE 6-continued
| Example | Structure |
|---|---|
| 410 | 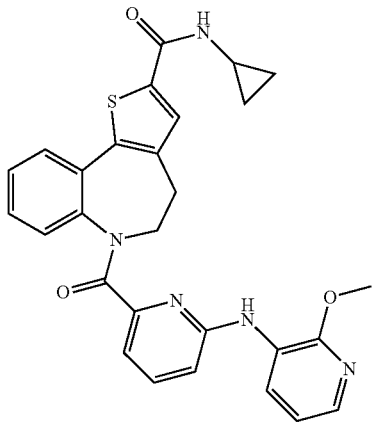 [SMILES: COc1ncccc1Nc1cccc(C(=O)N2CCc3cc(C(=O)NC4CC4)sc3-c3ccccc32)n1] |
| 411 | 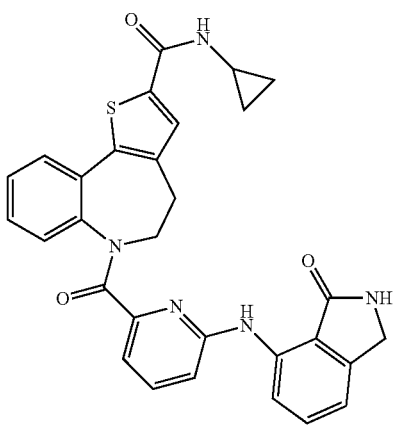 [SMILES: O=C(NC1CC1)c1cc2c(s1)-c1ccccc1N(C(=O)c1cccc(Nc3cccc4c3C(=O)NC4)n1)CC2] |
| 412 | 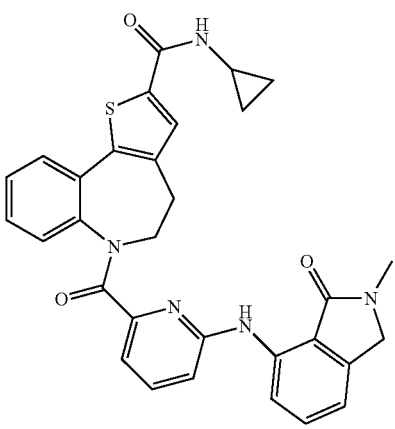 [SMILES: CN1Cc2cccc(Nc3cccc(C(=O)N4CCc5cc(C(=O)NC6CC6)sc5-c5ccccc54)n3)c2C1=O] |
| 413 | 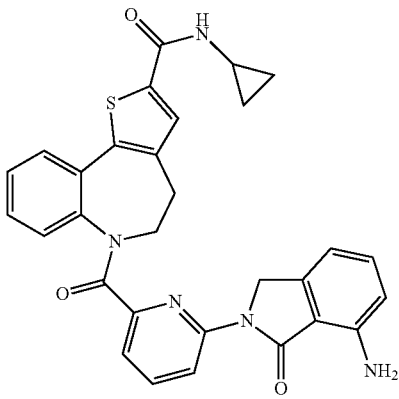 [SMILES: Nc1cccc2c1C(=O)N(c1cccc(C(=O)N3CCc4cc(C(=O)NC5CC5)sc4-c4ccccc43)n1)C2] |
| 414 | 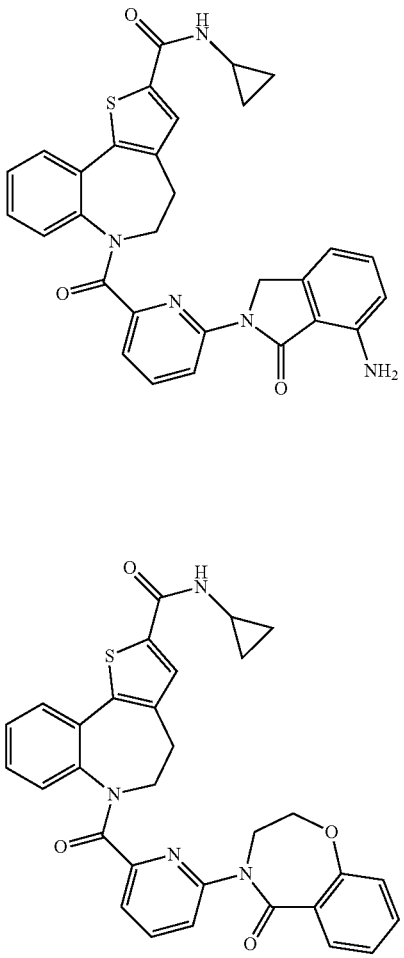 |
| 415 | 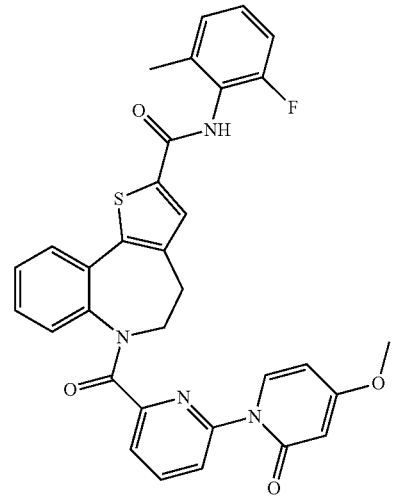 [SMILES: COc1ccn(-c2cccc(C(=O)N3CCc4cc(C(=O)Nc5c(C)cccc5F)sc4-c4ccccc43)n2)c(=O)c1] |

TABLE 6-continued

| Example | Structure |
|---|---|
| 416 | 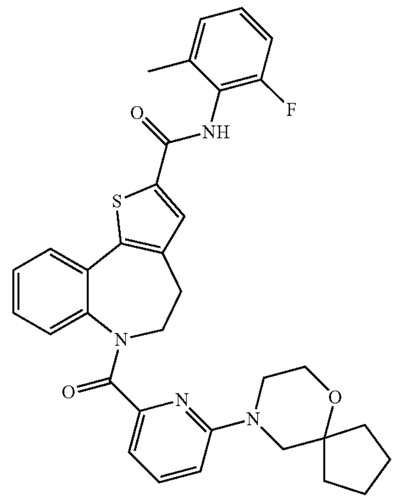 [SMILES: Cc1cccc(F)c1NC(=O)c1cc2c(s1)-c1ccccc1N(C(=O)c1cccc(N3CCOC4(CCCC4)C3)n1)CC2] |
| 417 | 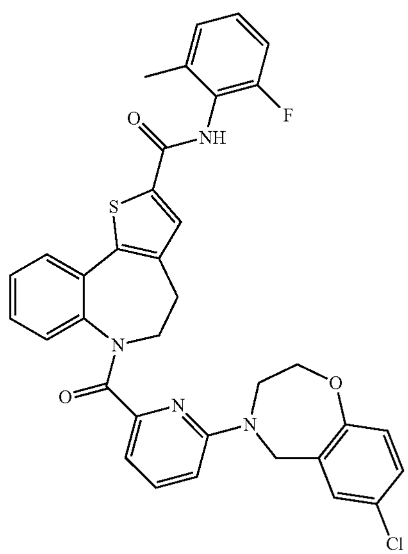 [SMILES: Cc1cccc(F)c1NC(=O)c1cc2c(s1)-c1ccccc1N(C(=O)c1cccc(N3CCOc4ccc(Cl)cc4C3)n1)CC2] |
| 418 | 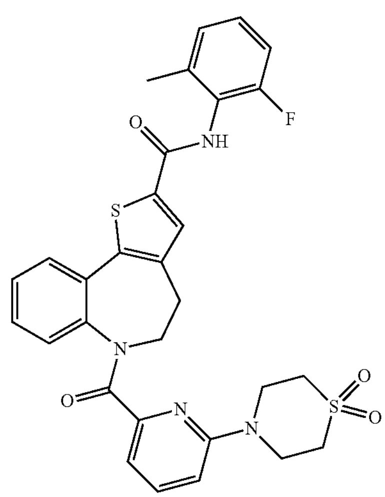 [SMILES: Cc1cccc(F)c1NC(=O)c1cc2c(s1)-c1ccccc1N(C(=O)c1cccc(N3CCS(=O)(=O)CC3)n1)CC2] |
| 419 | 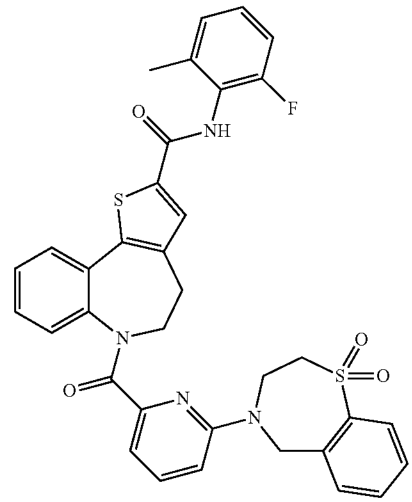 [SMILES: Cc1cccc(F)c1NC(=O)c1cc2c(s1)-c1ccccc1N(C(=O)c1cccc(N3CCS(=O)(=O)c4ccccc4C3)n1)CC2] |
| 420 | 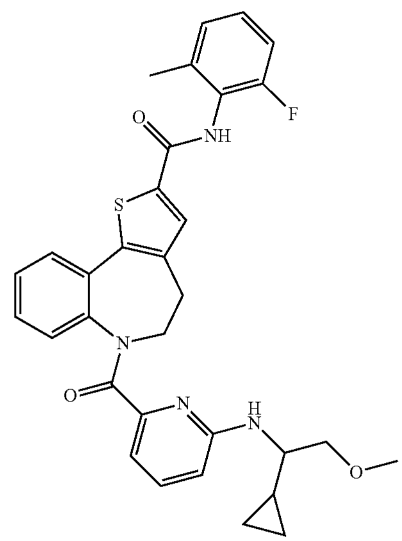 [SMILES: COCC(Nc1cccc(C(=O)N2CCc3cc(C(=O)Nc4c(C)cccc4F)sc3-c3ccccc32)n1)C1CC1] |
| 421 | 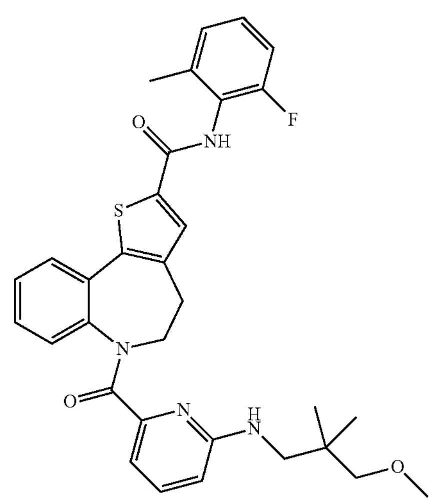 [SMILES: COCC(C)(C)CNc1cccc(C(=O)N2CCc3cc(C(=O)Nc4c(C)cccc4F)sc3-c3ccccc32)n1] |

TABLE 6-continued
| Example | Structure |
|---|---|
| 422 | 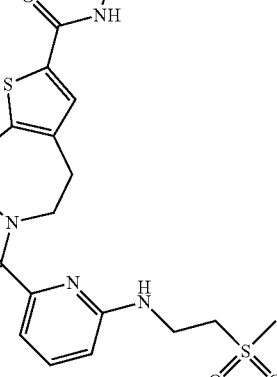 |
| 423 | 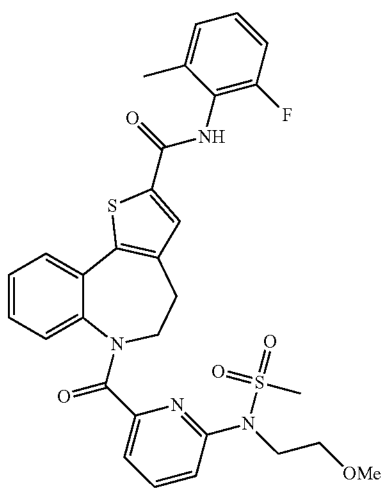 [SMILES: COCCN(c1cccc(C(=O)N2CCc3cc(C(=O)Nc4c(C)cccc4F)sc3-c3ccccc32)n1)S(C)(=O)=O] |
| 424 | 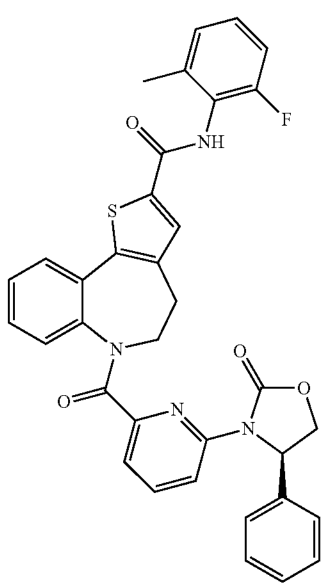 [SMILES: Cc1cccc(F)c1NC(=O)c1cc2c(s1)-c1ccccc1N(C(=O)c1cccc(N3C(=O)OC[C@H]3c3ccccc3)n1)CC2] |
| 425 | 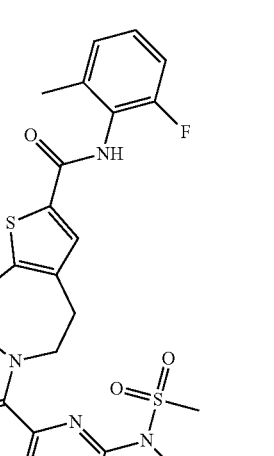 |
| 426 | |
| 427 | 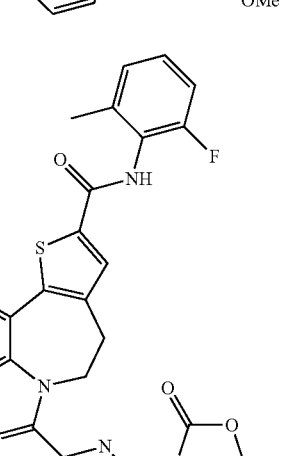 |

TABLE 6-continued
| Example | Structure |
|---|---|
| 428 | 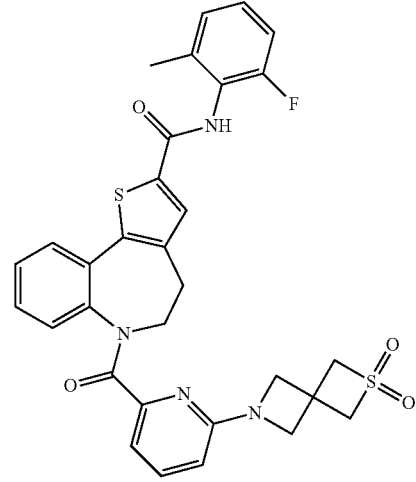 [SMILES: Cc1cccc(F)c1NC(=O)c1cc2c(s1)-c1ccccc1N(C(=O)c1cccc(N3CC4(C3)CS(=O)(=O)C4)n1)CC2] |
| 429 | 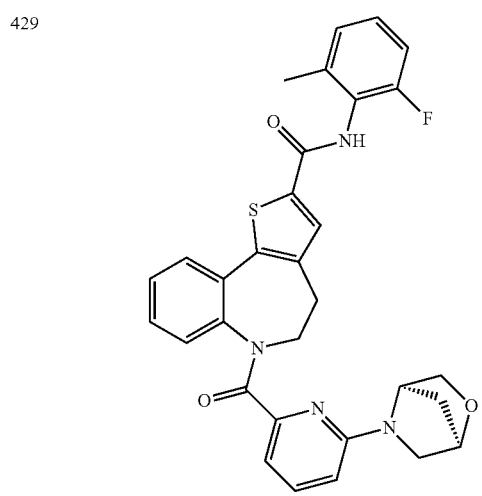 |
| 430 | 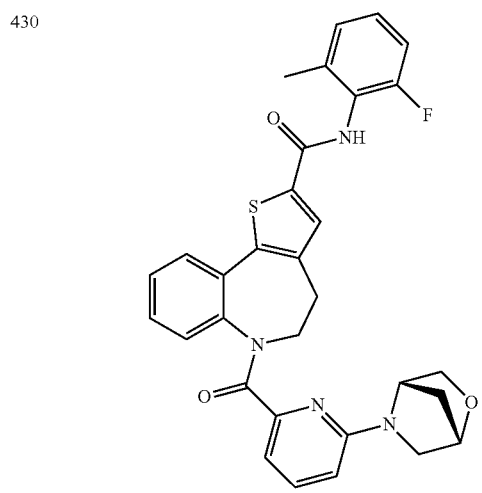 |
| 431 | 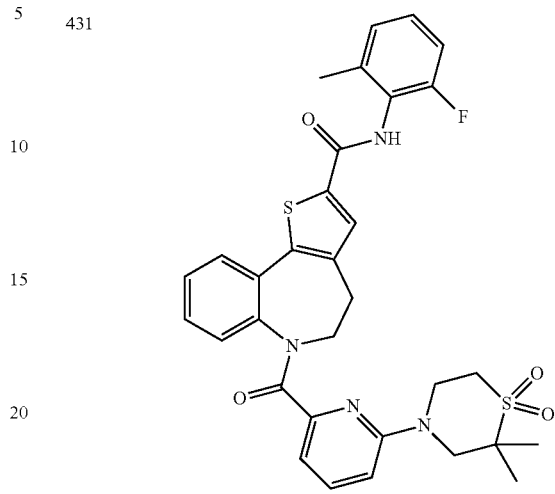 |
| 432 | 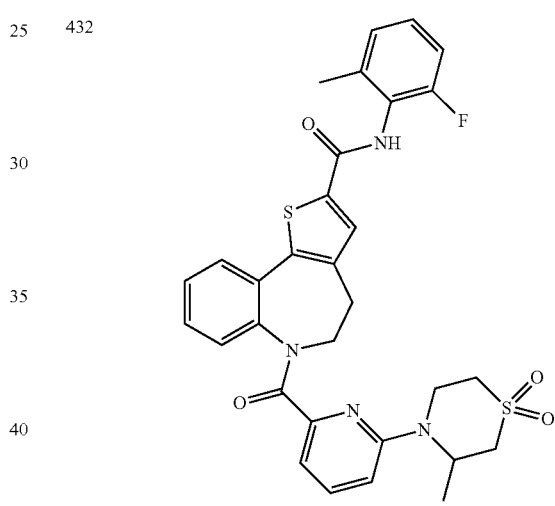 |
| 433 | 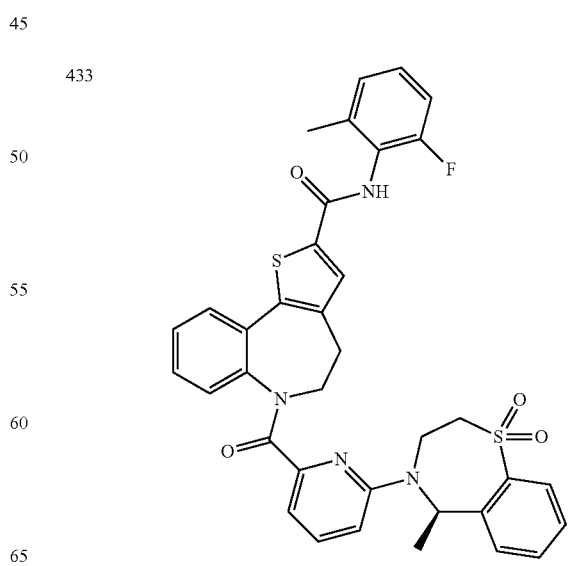 |

TABLE 6-continued

| Example | Structure |
|---|---|
| 434 | (structure) |
| 435 | (structure) |
| 436 | (structure) |
| 437 | (structure) |
| 438 | (structure) |
| 439 | (structure) |

TABLE 6-continued
| Example | Structure |
|---|---|
| 440 | 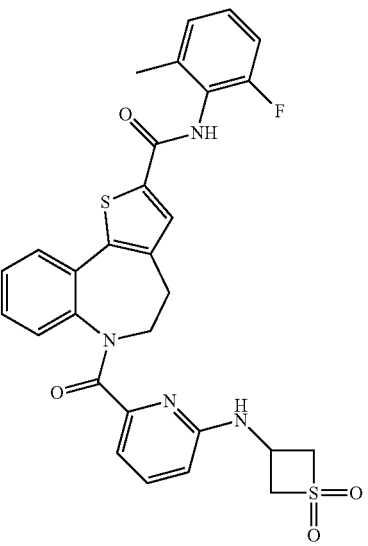 [SMILES: Cc1cccc(F)c1NC(=O)c1cc2c(s1)-c1ccccc1N(C(=O)c1cccc(NC3CS(=O)(=O)C3)n1)CC2] |
| 441 | 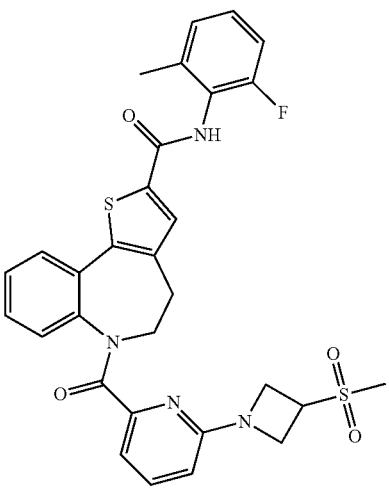 [SMILES: Cc1cccc(F)c1NC(=O)c1cc2c(s1)-c1ccccc1N(C(=O)c1cccc(N3CC(S(C)(=O)=O)C3)n1)CC2] |
| 442 | 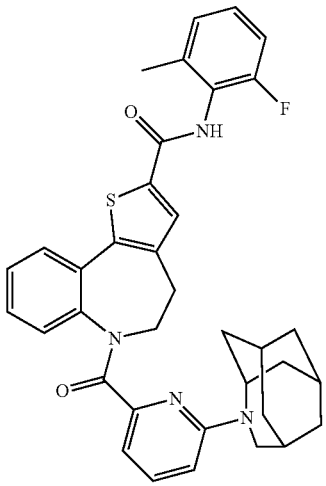 [SMILES: Cc1cccc(F)c1NC(=O)c1cc2c(s1)-c1ccccc1N(C(=O)c1cccc(N3CC4CC5CC(C4)CC3C5)n1)CC2] |
| 443 | 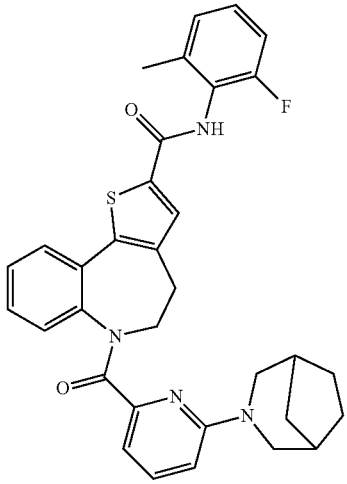 [SMILES: Cc1cccc(F)c1NC(=O)c1cc2c(s1)-c1ccccc1N(C(=O)c1cccc(N3CC4CCC(C4)C3)n1)CC2] |
| 444 | 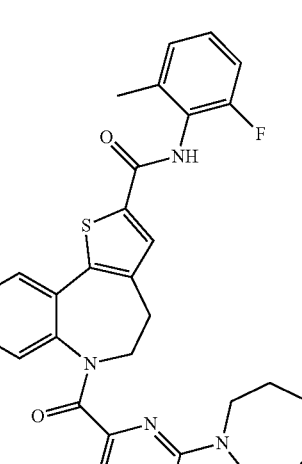 |
| 445 | 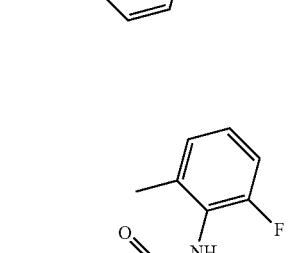 |

TABLE 6-continued
| Example | Structure |
|---------|-----------|
| 446 | 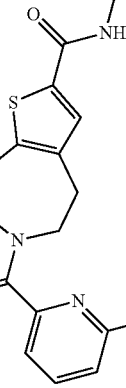 |
| 447 | 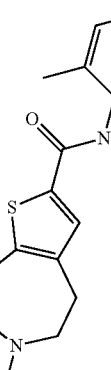 |
| 448 | 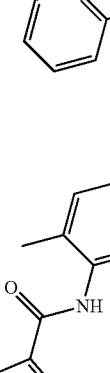 |
| 449 | 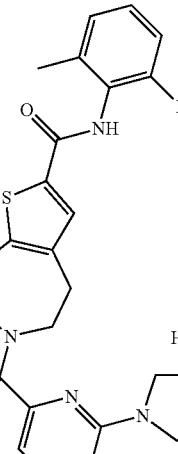 |
| 450 | 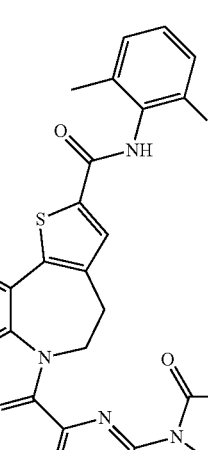 |
| 451 | 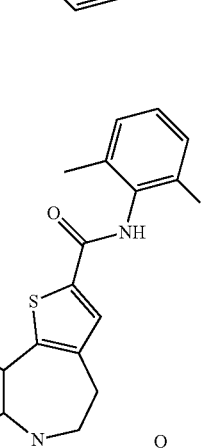 |

TABLE 6-continued

| Example | Structure |
|---------|-----------|
| 452 | 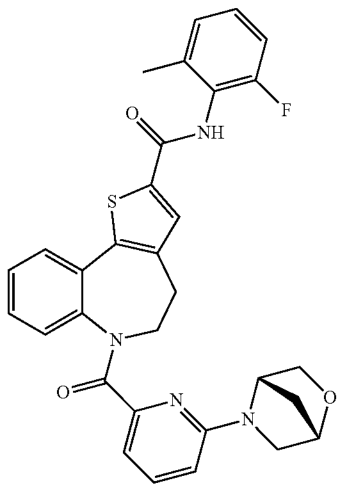 [SMILES: Cc1cccc(F)c1NC(=O)c1cc2c(s1)-c1ccccc1N(C(=O)c1cccc(N3C[C@@H]4C[C@H]3CO4)n1)CC2] |
| 453 | 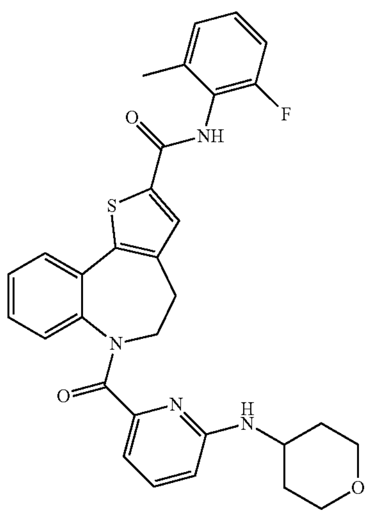 [SMILES: Cc1cccc(F)c1NC(=O)c1cc2c(s1)-c1ccccc1N(C(=O)c1cccc(NC3CCOCC3)n1)CC2] |
| 454 | 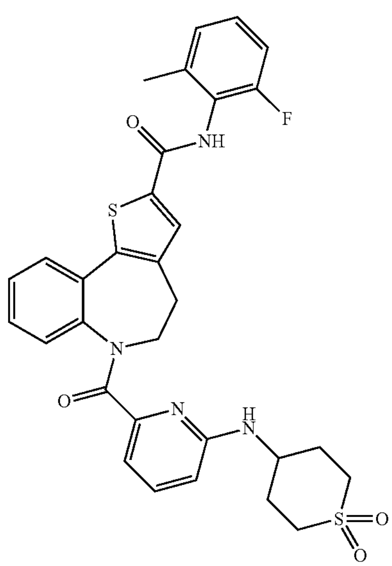 [SMILES: Cc1cccc(F)c1NC(=O)c1cc2c(s1)-c1ccccc1N(C(=O)c1cccc(NC3CCS(=O)(=O)CC3)n1)CC2] |
| 455 | |
| 456 | |
| 457 | |

TABLE 6-continued
| Example | Structure |
|---|---|
| 458 | 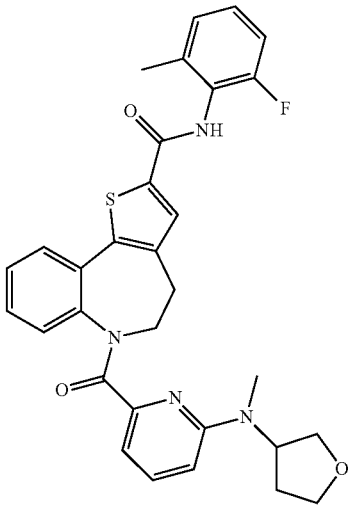 [SMILES: Cc1cccc(F)c1NC(=O)c1cc2c(s1)-c1ccccc1N(C(=O)c1cccc(N(C)C3CCOC3)n1)CC2] |
| 459 | 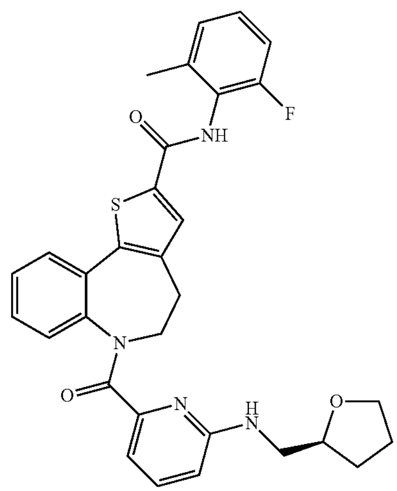 [SMILES: Cc1cccc(F)c1NC(=O)c1cc2c(s1)-c1ccccc1N(C(=O)c1cccc(NC[C@@H]3CCCO3)n1)CC2] |
| 460 | 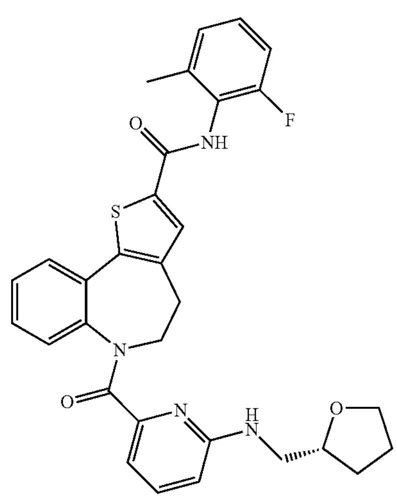 [SMILES: Cc1cccc(F)c1NC(=O)c1cc2c(s1)-c1ccccc1N(C(=O)c1cccc(NC[C@H]3CCCO3)n1)CC2] |
| 461 | 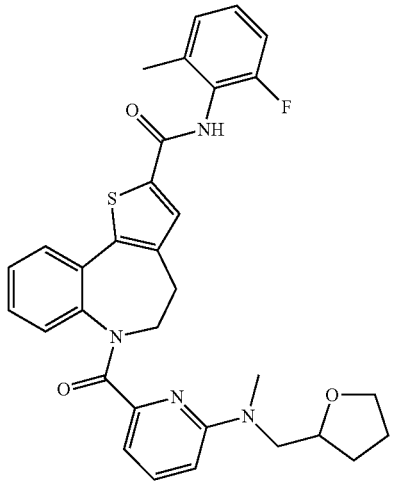 [SMILES: Cc1cccc(F)c1NC(=O)c1cc2c(s1)-c1ccccc1N(C(=O)c1cccc(N(C)CC3CCCO3)n1)CC2] |
| 462 | 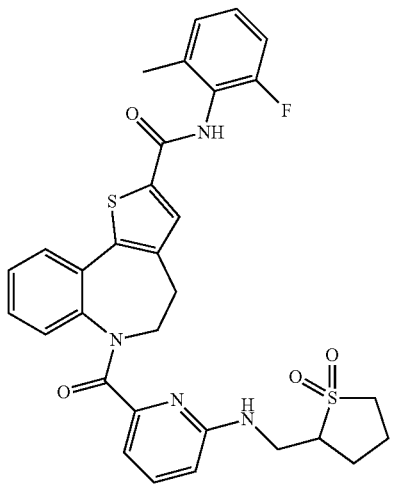 [SMILES: Cc1cccc(F)c1NC(=O)c1cc2c(s1)-c1ccccc1N(C(=O)c1cccc(NCC3CCCS3(=O)=O)n1)CC2] |
| 463 | 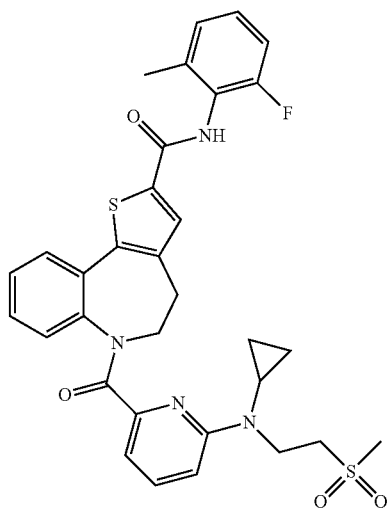 [SMILES: Cc1cccc(F)c1NC(=O)c1cc2c(s1)-c1ccccc1N(C(=O)c1cccc(N(CCS(C)(=O)=O)C3CC3)n1)CC2] |

TABLE 6-continued

| Example | Structure |
|---|---|
| 464 | 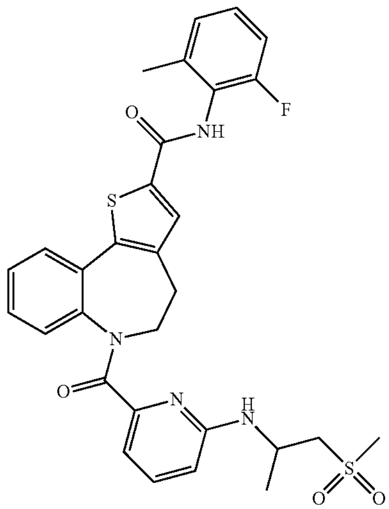 [SMILES: Cc1cccc(F)c1NC(=O)c1cc2c(s1)-c1ccccc1N(C(=O)c1cccc(NC(C)CS(C)(=O)=O)n1)CC2] |
| 465 | 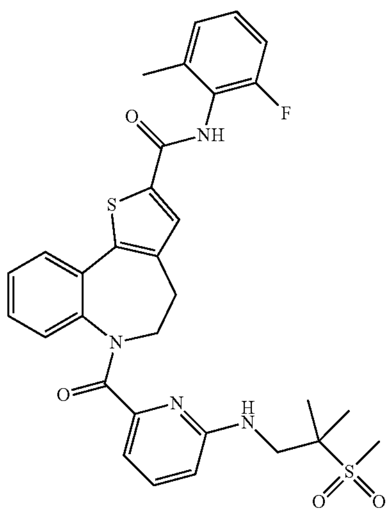 [SMILES: Cc1cccc(F)c1NC(=O)c1cc2c(s1)-c1ccccc1N(C(=O)c1cccc(NCC(C)(C)S(C)(=O)=O)n1)CC2] |
| 466 | 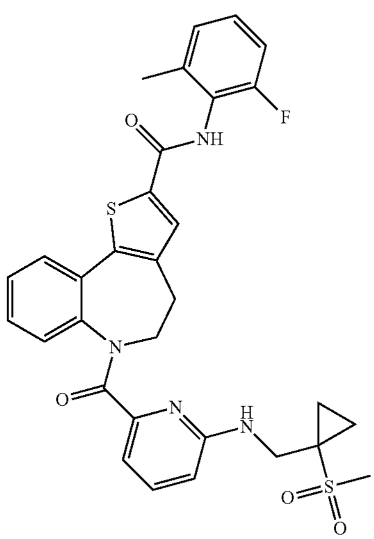 [SMILES: Cc1cccc(F)c1NC(=O)c1cc2c(s1)-c1ccccc1N(C(=O)c1cccc(NCC3(S(C)(=O)=O)CC3)n1)CC2] |
| 467 | |
| 468 | |
| 469 | |

TABLE 6-continued
| Example | Structure |
|---|---|
| 470 | 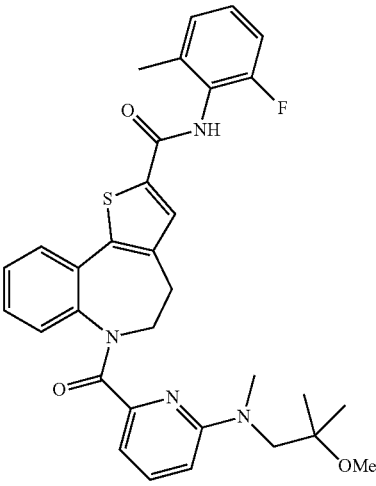 [SMILES: COC(C)(C)CN(C)c1cccc(C(=O)N2CCc3cc(C(=O)Nc4c(C)cccc4F)sc3-c3ccccc32)n1] |
| 471 | 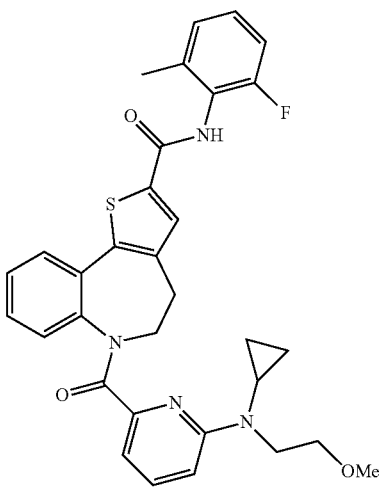 [SMILES: COCCN(c1cccc(C(=O)N2CCc3cc(C(=O)Nc4c(C)cccc4F)sc3-c3ccccc32)n1)C1CC1] |
| 472 | 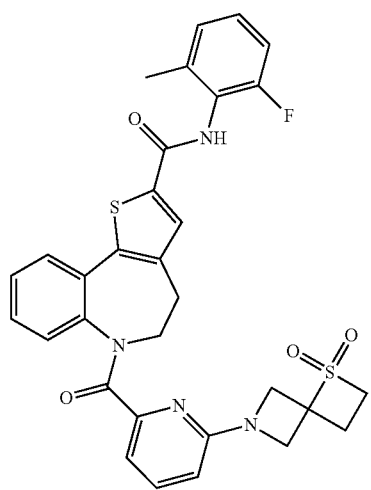 [SMILES: Cc1cccc(F)c1NC(=O)c1cc2c(s1)-c1ccccc1N(C(=O)c1cccc(N3CC4(CCS4(=O)=O)C3)n1)CC2] |
TABLE 6-continued
| Example | Structure |
|---|---|
| 473 | 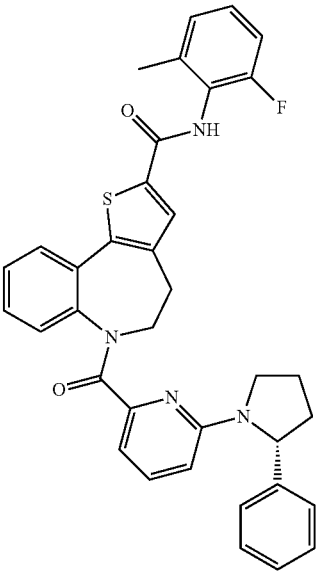 [SMILES: Cc1cccc(F)c1NC(=O)c1cc2c(s1)-c1ccccc1N(C(=O)c1cccc(N3CCC[C@@H]3c3ccccc3)n1)CC2] |
| 474 | 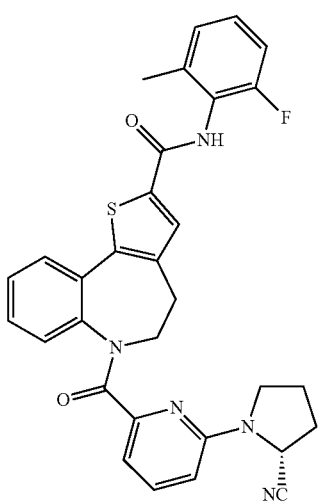 [SMILES: Cc1cccc(F)c1NC(=O)c1cc2c(s1)-c1ccccc1N(C(=O)c1cccc(N3CCC[C@@H]3C#N)n1)CC2] |
| 475 | 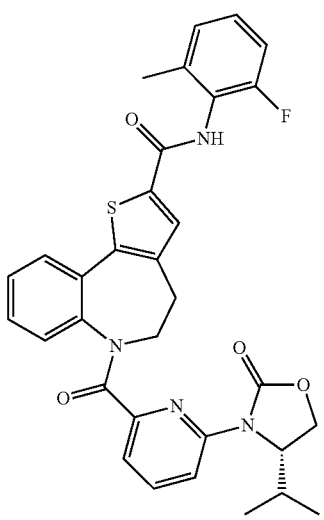 [SMILES: Cc1cccc(F)c1NC(=O)c1cc2c(s1)-c1ccccc1N(C(=O)c1cccc(N3C(=O)OC[C@@H]3C(C)C)n1)CC2] |

TABLE 6-continued
| Example | Structure |
|---|---|
| 476 | 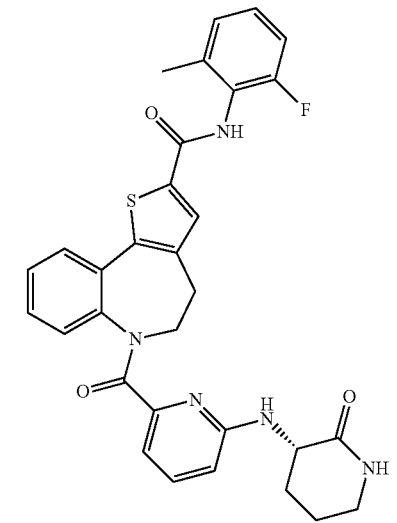 |
| 477 | 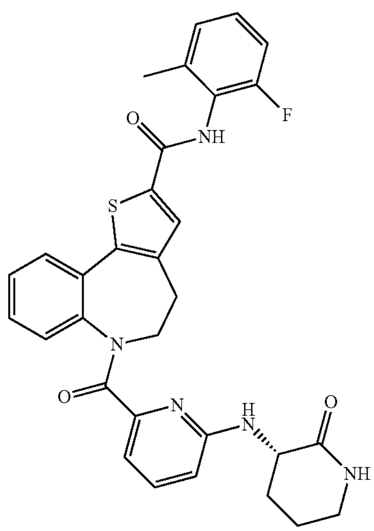 [SMILES: Cc1cccc(F)c1NC(=O)c1cc2c(s1)-c1ccccc1N(C(=O)c1cccc(N[C@H]3CCCNC3=O)n1)CC2] |
| 478 | 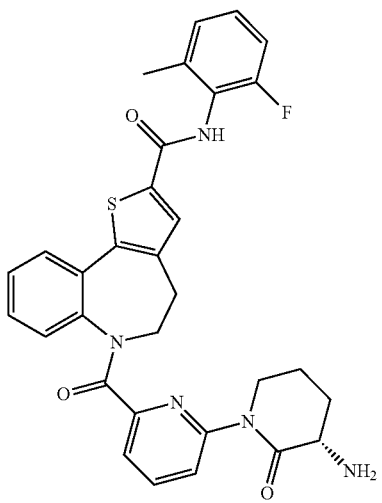 [SMILES: Cc1cccc(F)c1NC(=O)c1cc2c(s1)-c1ccccc1N(C(=O)c1cccc(N3CCC[C@H](N)C3=O)n1)CC2] |
TABLE 6-continued
| Example | Structure |
|---|---|
| 479 | 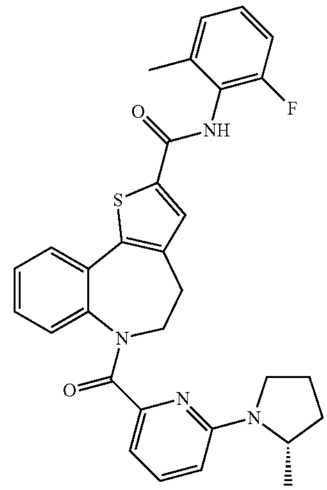 [SMILES: Cc1cccc(F)c1NC(=O)c1cc2c(s1)-c1ccccc1N(C(=O)c1cccc(N3CCC[C@@H]3C)n1)CC2] |
| 480 | 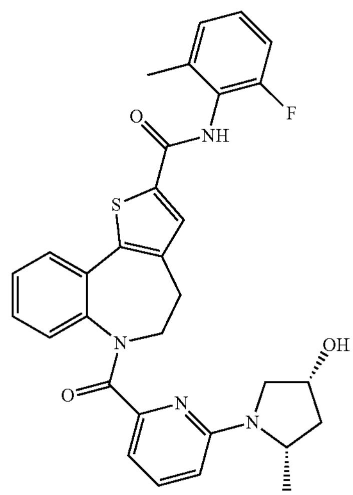 [SMILES: Cc1cccc(F)c1NC(=O)c1cc2c(s1)-c1ccccc1N(C(=O)c1cccc(N3C[C@H](O)C[C@@H]3C)n1)CC2] |
| 481 | 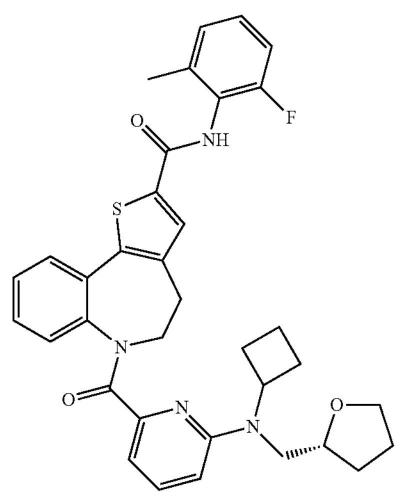 [SMILES: Cc1cccc(F)c1NC(=O)c1cc2c(s1)-c1ccccc1N(C(=O)c1cccc(N(C[C@H]3CCCO3)C3CCC3)n1)CC2] |

TABLE 6-continued

| Example | Structure |
|---------|-----------|
| 482 | 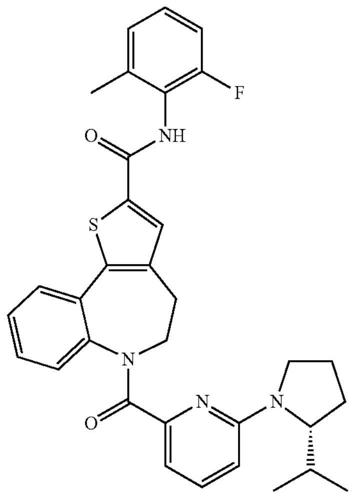 [SMILES: Cc1cccc(F)c1NC(=O)c1cc2c(s1)-c1ccccc1N(C(=O)c1cccc(N3CCC[C@@H]3C(C)C)n1)CC2] |
| 483 | 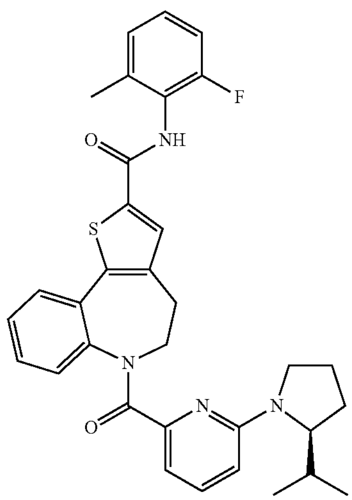 [SMILES: Cc1cccc(F)c1NC(=O)c1cc2c(s1)-c1ccccc1N(C(=O)c1cccc(N3CCC[C@H]3C(C)C)n1)CC2] |
| 484 | 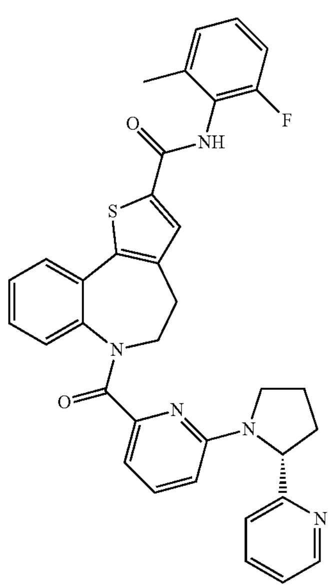 [SMILES: Cc1cccc(F)c1NC(=O)c1cc2c(s1)-c1ccccc1N(C(=O)c1cccc(N3CCC[C@@H]3c3ccccn3)n1)CC2] |
| 485 | 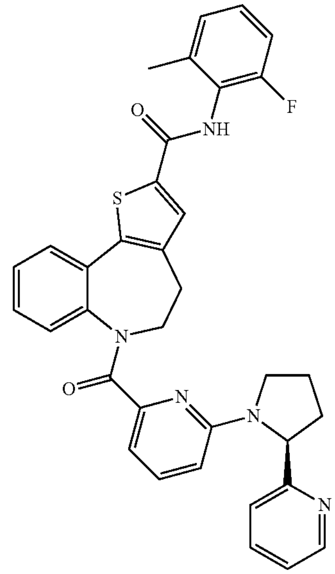 [SMILES: Cc1cccc(F)c1NC(=O)c1cc2c(s1)-c1ccccc1N(C(=O)c1cccc(N3CCC[C@H]3c3ccccn3)n1)CC2] |
| 486 | 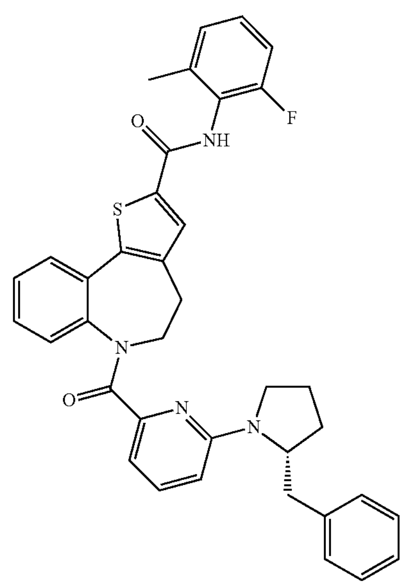 [SMILES: Cc1cccc(F)c1NC(=O)c1cc2c(s1)-c1ccccc1N(C(=O)c1cccc(N3CCC[C@@H]3Cc3ccccc3)n1)CC2] |

TABLE 6-continued

| Example | Structure |
|---|---|
| 487 | (structure) |
| 488 | (structure) |
| 489 | (structure) |
| 490 | (structure) |
| 491 | (structure) |
| 492 | (structure) |

TABLE 6-continued

| Example | Structure |
|---|---|
| 493 | (structure) |
| 494 | (structure) |
| 495 | (structure) |
| 496 | (structure) |
| 497 | (structure) |

TABLE 6-continued

| Example | Structure |
|---------|-----------|
| 498 | 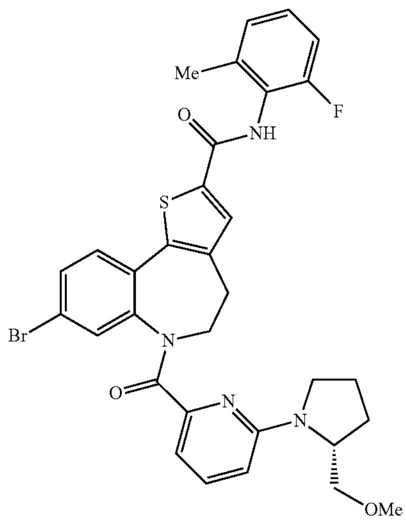 |
| 499 | 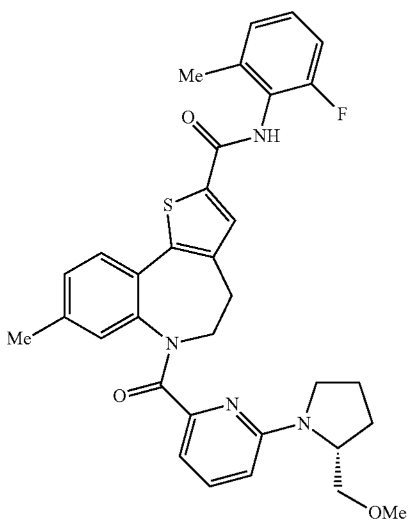 |
| 500 | 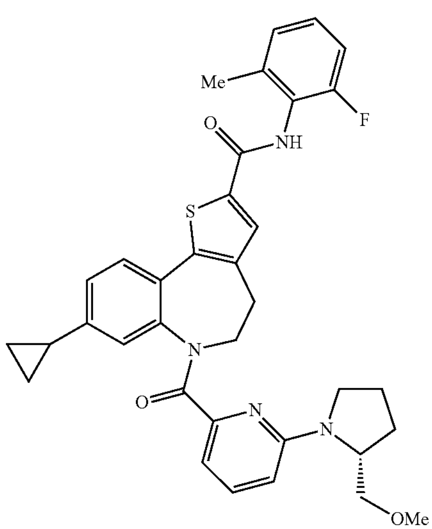 [SMILES: COC[C@H]1CCCN1c1cccc(C(=O)N2CCc3cc(C(=O)Nc4c(C)cccc4F)sc3-c3ccc(C4CC4)cc32)n1] |
| 501 | 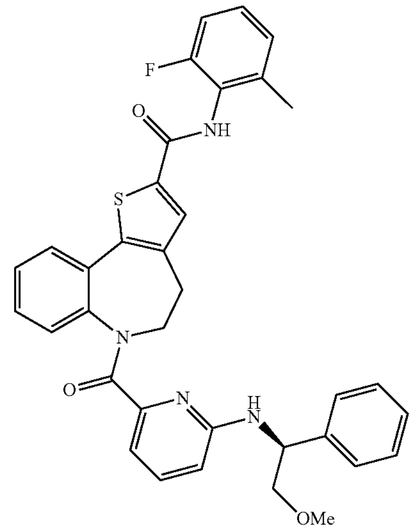 [SMILES: COC[C@@H](Nc1cccc(C(=O)N2CCc3cc(C(=O)Nc4c(C)cccc4F)sc3-c3ccccc32)n1)c1ccccc1] |
| 502 | 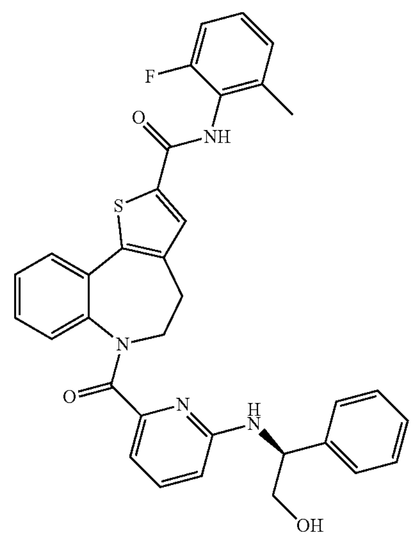 [SMILES: Cc1cccc(F)c1NC(=O)c1cc2c(s1)-c1ccccc1N(C(=O)c1cccc(N[C@H](CO)c3ccccc3)n1)CC2] |
| 503 | 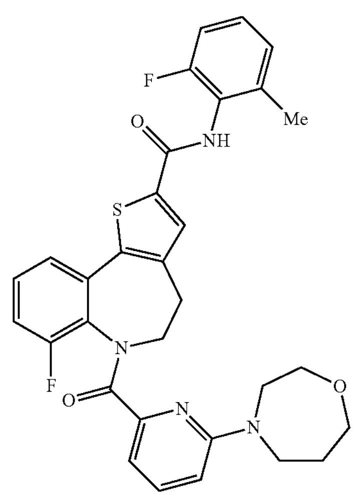 [SMILES: Cc1cccc(F)c1NC(=O)c1cc2c(s1)-c1cccc(F)c1N(C(=O)c1cccc(N3CCCOCC3)n1)CC2] |

TABLE 6-continued

| Example | Structure |
|---------|-----------|
| 504 | 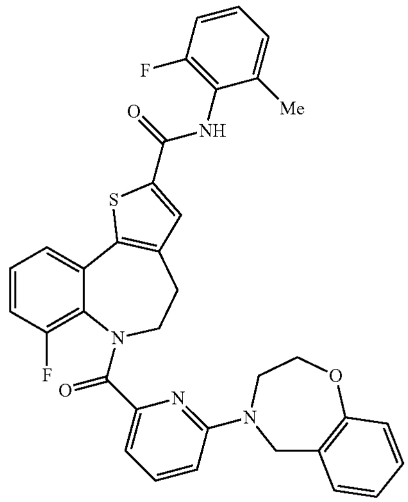 [SMILES: Cc1cccc(F)c1NC(=O)c1cc2c(s1)-c1cccc(F)c1N(C(=O)c1cccc(N3CCOc4ccccc4C3)n1)CC2] |
| 505 | 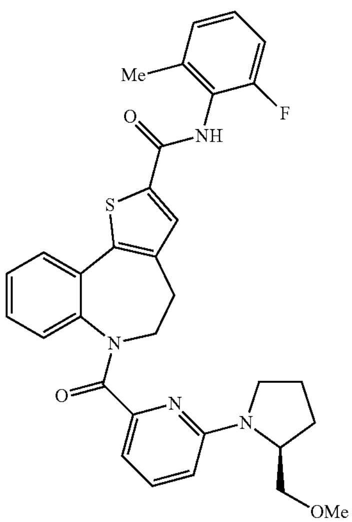 [SMILES: COC[C@@H]1CCCN1c1cccc(C(=O)N2CCc3cc(C(=O)Nc4c(C)cccc4F)sc3-c3ccccc32)n1] |
| 506 | 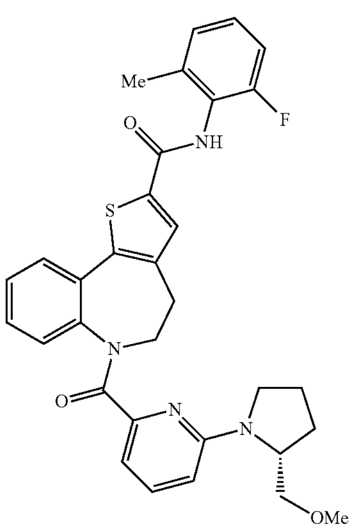 [SMILES: COC[C@H]1CCCN1c1cccc(C(=O)N2CCc3cc(C(=O)Nc4c(C)cccc4F)sc3-c3ccccc32)n1] |
| 507 | 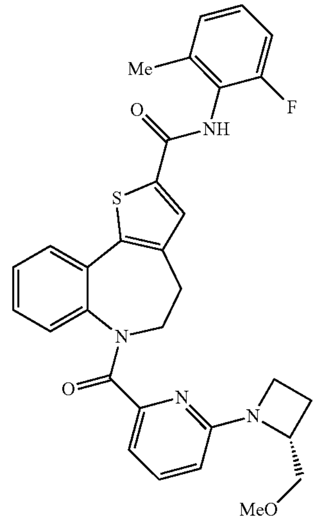 [SMILES: COC[C@H]1CCN1c1cccc(C(=O)N2CCc3cc(C(=O)Nc4c(C)cccc4F)sc3-c3ccccc32)n1] |
| 508 | 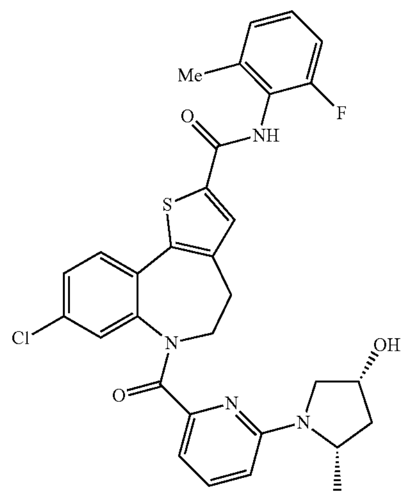 [SMILES: Cc1cccc(F)c1NC(=O)c1cc2c(s1)-c1ccc(Cl)cc1N(C(=O)c1cccc(N3C[C@H](O)C[C@@H]3C)n1)CC2] |
| 509 | 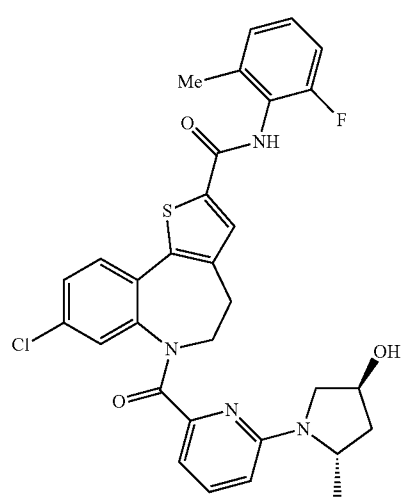 [SMILES: Cc1cccc(F)c1NC(=O)c1cc2c(s1)-c1ccc(Cl)cc1N(C(=O)c1cccc(N3C[C@@H](O)C[C@@H]3C)n1)CC2] |

TABLE 6-continued

| Example | Structure |
|---|---|
| 510 | 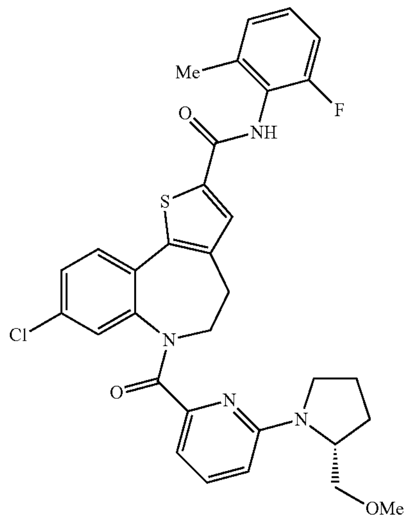 [SMILES: COC[C@H]1CCCN1c1cccc(C(=O)N2CCc3cc(C(=O)Nc4c(C)cccc4F)sc3-c3ccc(Cl)cc32)n1] |
| 511 | 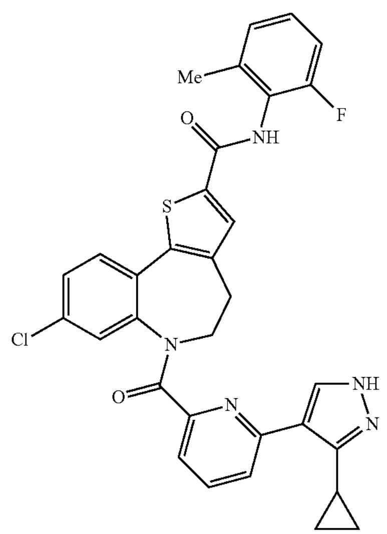 [SMILES: Cc1cccc(F)c1NC(=O)c1cc2c(s1)-c1ccc(Cl)cc1N(C(=O)c1cccc(-c3c[nH]nc3C3CC3)n1)CC2] |
| 512 | 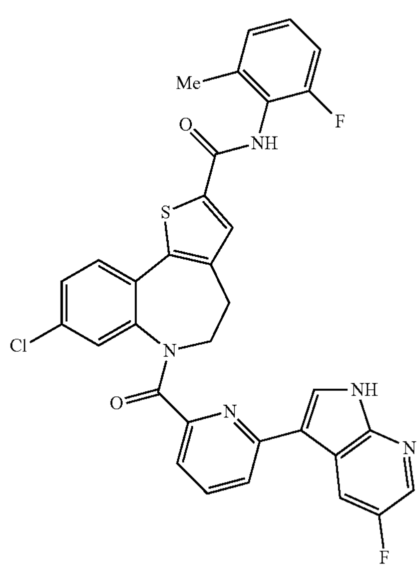 [SMILES: Cc1cccc(F)c1NC(=O)c1cc2c(s1)-c1ccc(Cl)cc1N(C(=O)c1cccc(-c3c[nH]c4ncc(F)cc34)n1)CC2] |
| 513 | |
| 514 | |
| 515 | |

TABLE 6-continued

| Example | Structure |
|---------|-----------|
| 516 | 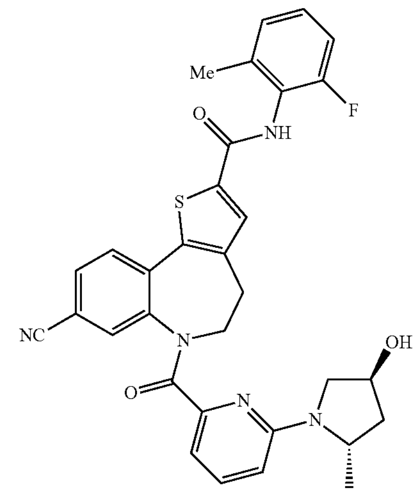 [SMILES: Cc1cccc(F)c1NC(=O)c1cc2c(s1)-c1ccc(C#N)cc1N(C(=O)c1cccc(N3C[C@@H](O)C[C@@H]3C)n1)CC2] |
| 517 | 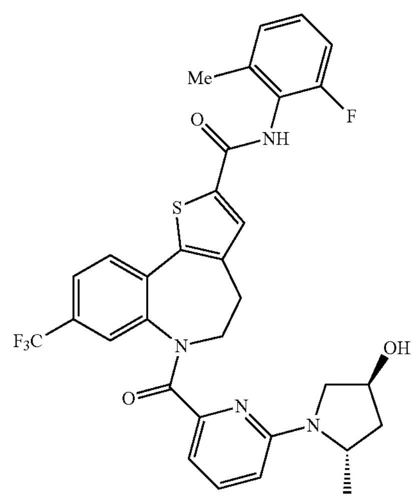 |
| 518 | 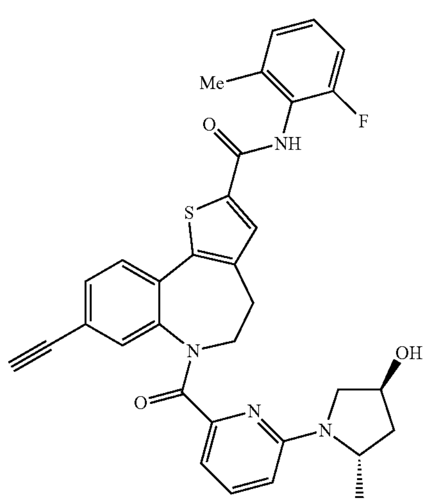 [SMILES: C#Cc1ccc2c(c1)N(C(=O)c1cccc(N3C[C@@H](O)C[C@@H]3C)n1)CCc1cc(C(=O)Nc3c(C)cccc3F)sc1-2] |
| 519 | 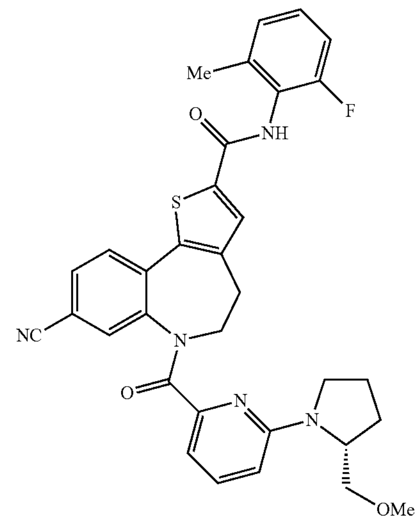 [SMILES: COC[C@H]1CCCN1c1cccc(C(=O)N2CCc3cc(C(=O)Nc4c(C)cccc4F)sc3-c3ccc(C#N)cc32)n1] |
| 520 | 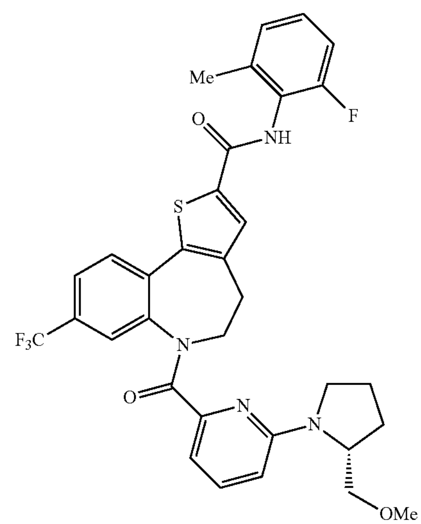 |
| 521 | 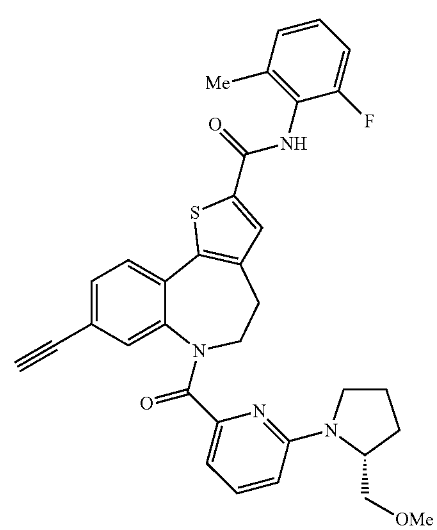 [SMILES: C#Cc1ccc2c(c1)N(C(=O)c1cccc(N3CCC[C@@H]3COC)n1)CCc1cc(C(=O)Nc3c(C)cccc3F)sc1-2] |

TABLE 6-continued

| Example | Structure |
| --- | --- |
| 522 | 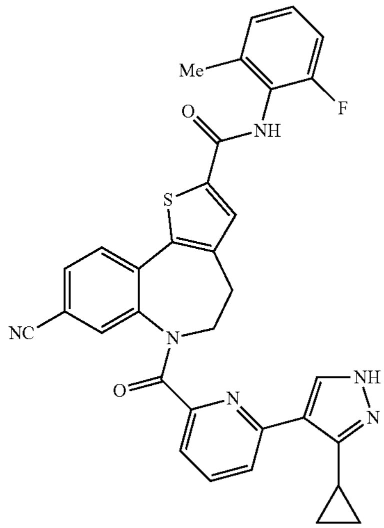 [SMILES: Cc1cccc(F)c1NC(=O)c1cc2c(s1)-c1ccc(C#N)cc1N(C(=O)c1cccc(-c3c[nH]nc3C3CC3)n1)CC2] |
| 523 | 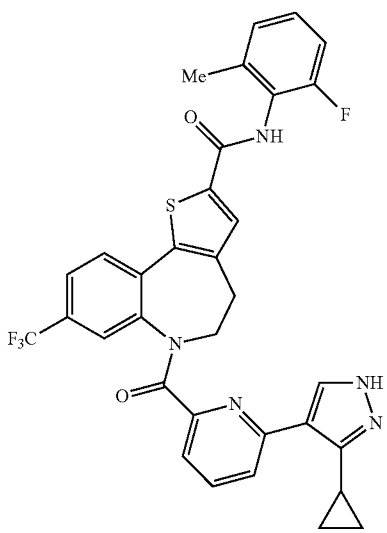 [SMILES: Cc1cccc(F)c1NC(=O)c1cc2c(s1)-c1ccc(C(F)(F)F)cc1N(C(=O)c1cccc(-c3c[nH]nc3C3CC3)n1)CC2] |
| 524 | 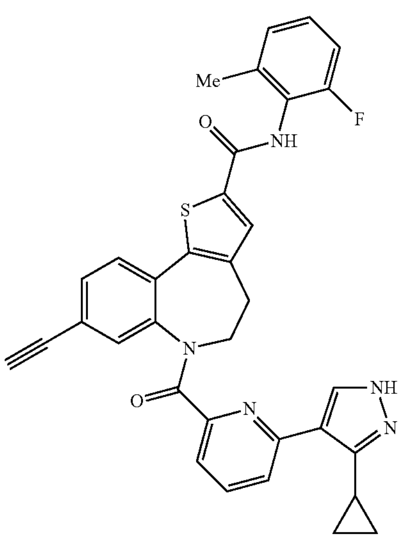 [SMILES: C#Cc1ccc2c(c1)N(C(=O)c1cccc(-c3c[nH]nc3C3CC3)n1)CCc1cc(C(=O)Nc3c(C)cccc3F)sc1-2] |
| 525 | |
| 526 | |

TABLE 6-continued

| Example | Structure |
|---|---|
| 527 | (structure: methyl, fluoro-substituted phenyl carboxamide linked via NH to a thiophene-fused benzazepine bearing an ethynyl group, with N-acyl pyridine-pyrrolopyridine substituent containing F) |

Assays

Introduction

RSV is a single stranded negative sense RNA virus that causes respiratory tract infections which can be dangerous to infants, the elderly, and immunosuppressed individuals. Currently there is no vaccine, and therapeutic options are both costly and of limited effectiveness. These approved treatments are Ribavirin, and Palivizumab/Synagis (a monoclonal antibody). RSV has two genotypes, A and B, which differ primarily in the structure of the virus' surface "G" attachment protein. Our current primary screen focuses on RSV-A and uses an in vitro cytoprotection assay where compounds are added in 2-fold dilutions to cells which are then subjected to fully replicative viral particles. Cell viability is measured several days later along with separate measurements of compound cytotoxicity. This report focuses on the results of our most recent screening of compounds.

Methods

HEp-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days.

The control compound currently used in the RSV assay is RSV-604, a ~2.4 µM $EC_{50}$ nucleocapsid inhibitor previously developed by Novartis. Following extensive parameter testing, the final assay is run as follows: HEp-2 cells are seeded into the inner 60 wells of a 96-well plate at 8,000 cells per well in a volume of 50 µL using Growth Media (DMEM without phenol red, 1% L-Glut, 1% Penn/Strep, 1% nonessential amino acids, 10% FBS). 2-Fold serial dilutions of control and test compounds are added to the wells in duplicate in a total volume of 25 µL. Viral stock is then added to the wells in a volume of 25 µL, bringing the total volume of each well to 100 µL. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 25 uL of growth media containing an equal quantity of sucrose as those wells receiving the viral stock in order to keep consistent in media and volume conditions. The outer wells of the plate are filled with 125 µL of growth media to act as a thermal and evaporative moat around the test wells. Following a 4-day incubation period, the plates are read using ATPlite (50 uL added per well), which quantifies the amount of ATP (a measure of cell health) present in each well. Assay plates are read using the Envision luminometer. In parallel, cytotoxicity is examined on an additional 96-well plate treated in an identical manner, but substituting the 25 µL of viral stock for 25 µL of growth media. These data are used to calculate the $EC_{50}$ of each compound. $EC_{50}$ ranges are as follows: A <0.4 µM; B 0.4-0.8 µM; C >0.8 µM.

TABLE 7

Summary of Activities

| Example | Human RSV-A ("Long" strain) $EC_{50}$ | Example | Human RSV-A ("Long" strain) $EC_{50}$ |
|---|---|---|---|
| 1 | C | 2 | C |
| 3 | C | 4 | C |
| 5 | B | 6 | C |
| 7 | B | 8 | C |
| 9 | C | 10 | C |
| 11 | C | 12 | B |
| 13 | C | 14 | C |
| 15 | C | 16 | B |
| 17 | A | 18 | B |
| 19 | C | 20 | B |
| 21 | B | 22 | B |
| 23 | A | 24 | B |
| 25 | B | 26 | B |
| 27 | B | 28 | A |
| 29 | B | 30 | C |
| 31 | C | 32 | A |
| 33 | B | 34 | B |
| 35 | B | 36 | B |
| 37 | C | 38 | C |
| 39 | C | 40 | B |
| 41 | C | 42 | B |
| 43 | B | 44 | B |
| 45 | A | 46 | C |
| 47 | C | 48 | C |
| 49 | C | 50 | C |
| 51 | B | 52 | B |
| 53 | B | 54 | C |
| 55 | C | 56 | C |
| 57 | B | 58 | B |
| 59 | B | 60 | B |
| 61 | C | 62 | B |
| 63 | B | 64 | B |
| 65 | A | 66 | B |
| 67 | C | 68 | B |
| 69 | B | 70 | C |
| 71 | B | 72 | B |
| 73 | B | 74 | B |
| 75 | B | 76 | B |
| 77 | B | 78 | B |
| 79 | B | 80 | C |
| 81 | B | 82 | C |
| 83 | B | 84 | B |
| 85 | A | 86 | A |
| 87 | B | 88 | B |

TABLE 7-continued

Summary of Activities

| Example | Human RSV-A ("Long" strain) EC$_{50}$ | Example | Human RSV-A ("Long" strain) EC$_{50}$ |
|---|---|---|---|
| 89 | B | 90 | B |
| 91 | B | 92 | B |
| 93 | C | 94 | C |
| 95 | B | 96 | B |
| 97 | B | 98 | A |
| 99 | C | 100 | A |
| 101 | A | 102 | C |
| 103 | C | 104 | C |
| 105 | C | 106 | B |
| 107 | B | 108 | B |
| 109 | C | 110 | C |
| 111 | C | 112 | C |
| 113 | C | 114 | C |
| 115 | A | 116 | A |
| 117 | A | 118 | A |
| 119 | B | 120 | A |
| 121 | C | 122 | C |
| 123 | C | 124 | C |
| 125 | C | 126 | C |
| 127 | C | 128 | C |
| 129 | C | 130 | C |
| 131 | C | 132 | C |
| 133 | C | 134 | C |
| 135 | A | 136 | C |
| 137 | C | 138 | C |
| 139 | C | 140 | C |
| 141 | C | 142 | A |
| 143 | C | 144 | C |
| 145 | C | 146 | A |
| 147 | A | 148 | C |
| 149 | A | 150 | C |
| 151 | C | 152 | C |
| 153 | C | 154 | C |
| 155 | C | 156 | C |
| 157 | B | 158 | C |
| 159 | C | 160 | C |
| 161 | B | 162 | C |
| 163 | A | 164 | A |
| 165 | A | 166 | C |
| 167 | C | 168 | C |
| 169 | A | 170 | A |
| 171 | A | 172 | A |
| 173 | A | 174 | A |
| 175 | A | 176 | A |
| 177 | A | 178 | A |
| 179 | A | 180 | A |
| 181 | C | 182 | C |
| 183 | C | 184 | C |
| 185 | C | 186 | C |
| 187 | C | 188 | A |
| 189 | C | 190 | A |
| 191 | C | 192 | B |
| 193 | C | 194 | B |
| 195 | A | 196 | A |
| 197 | A | 198 | A |
| 199 | A | 200 | A |
| 201 | C | 202 | A |
| 203 | C | 204 | C |
| 205 | C | 206 | A |
| 207 | A | 208 | C |
| 209 | A | 210 | A |
| 211 | C | 212 | A |
| 213 | A | 214 | A |
| 215 | A | 216 | A |
| 217 | A | 218 | A |
| 219 | B | 220 | B |
| 221 | A | 222 | B |
| 223 | A | 224 | A |
| 225 | A | 226 | C |
| 227 | C | 228 | C |
| 229 | C | 230 | C |
| 231 | C | 232 | C |
| 233 | A | 234 | A |
| 235 | C | 236 | A |
| 237 | A | 238 | A |
| 239 | C | 240 | C |
| 241 | A | 242 | A |
| 243 | A | 244 | A |
| 245 | A | 246 | C |
| 247 | A | 248 | C |
| 249 | A | 250 | B |
| 251 | A | 252 | C |
| 253 | A | 254 | C |
| 255 | B | 256 | A |
| 257 | C | 258 | C |
| 259 | A | 260 | C |
| 261 | A | 262 | C |
| 263 | A | 264 | C |
| 265 | C | 266 | C |
| 267 | C | 268 | C |
| 269 | C | 270 | C |
| 271 | C | 272 | C |
| 273 | C | 274 | A |
| 275 | A | 276 | C |
| 277 | C | 278 | A |
| 279 | A | 280 | A |
| 281 | A | 282 | A |
| 283 | A | 284 | A |
| 285 | C | 286 | C |
| 287 | C | 288 | C |
| 289 | C | 290 | C |
| 291 | C | 292 | C |
| 293 | C | 294 | C |
| 295 | C | 296 | C |
| 297 | C | 298 | C |
| 299 | B | 300 | C |
| 301 | A | 302 | C |
| 303 | C | 304 | C |
| 305 | B | 306 | A |
| 307 | A | 308 | A |
| 309 | A | 310 | A |
| 311 | C | 312 | C |
| 313 | B | 314 | C |
| 315 | C | 316 | C |
| 317 | C | 318 | C |
| 319 | C | 320 | C |
| 321 | C | 322 | C |
| 323 | A | 324 | B |
| 325 | A | 326 | B |
| 327 | A | 328 | A |
| 329 | C | 330 | A |
| 331 | A | 332 | A |
| 333 | A | 334 | C |
| 335 | A | 336 | A |
| 337 | A | 338 | A |
| 339 | A | 340 | C |
| 341 | A | 342 | B |
| 343 | A | 344 | A |
| 345 | C | 346 | B |
| 347 | C | 348 | A |
| 349 | A | 350 | A |
| 351 | C | 352 | B |
| 353 | C | 354 | C |
| 355 | C | 356 | C |
| 357 | C | 358 | A |
| 359 | A | 360 | A |
| 361 | C | 362 | A |
| 363 | A | 364 | C |
| 365 | A | 366 | A |
| 367 | A | 368 | A |
| 369 | B | 370 | B |
| 371 | B | 372 | B |
| 373 | A | 374 | B |
| 375 | B | 376 | C |
| 377 | C | 378 | A |
| 379 | C | 380 | A |
| 381 | C | 382 | A |
| 383 | A | 384 | A |

TABLE 7-continued

Summary of Activities

| Example | Human RSV-A ("Long" strain) EC$_{50}$ | Example | Human RSV-A ("Long" strain) EC$_{50}$ |
|---|---|---|---|
| 385 | A | 386 | A |
| 387 | A | 388 | A |
| 389 | A | 390 | C |
| 391 | A | 392 | B |
| 393 | C | 394 | C |
| 395 | A | 396 | C |
| 397 | C | 398 | C |
| 399 | A | 400 | A |
| 401 | C | 402 | A |
| 403 | A | 404 | A |
| 405 | A | 406 | B |
| 407 | C | 408 | C |
| 409 | C | 410 | C |
| 411 | C | 412 | C |
| 413 | C | 414 | C |
| 415 | C | 416 | A |
| 417 | A | 418 | A |
| 419 | A | 420 | B |
| 421 | A | 422 | C |
| 423 | C | 424 | C |
| 425 | A | 426 | C |
| 427 | C | 428 | C |
| 429 | A | 430 | A |
| 431 | A | 432 | A |
| 433 | C | 434 | C |
| 435 | A | 436 | A |
| 437 | A | 438 | A |
| 439 | C | 440 | A |
| 441 | C | 442 | C |
| 443 | C | 444 | A |
| 445 | A | 446 | A |
| 447 | A | 448 | A |
| 449 | C | 450 | A |
| 451 | C | 452 | A |
| 453 | A | 454 | C |
| 455 | C | 456 | A |
| 457 | A | 458 | — |
| 459 | A | 460 | A |
| 461 | A | 462 | A |
| 463 | B | 464 | C |
| 465 | B | 466 | A |
| 467 | B | 468 | A |
| 469 | B | 470 | A |
| 471 | A | 472 | C |
| 473 | A | 474 | A |
| 475 | A | 476 | A |
| 477 | C | 478 | C |
| 479 | A | 480 | A |
| 481 | A | 482 | C |
| 483 | A | 484 | A |
| 485 | C | 486 | C |
| 487 | B | 488 | A |
| 489 | A | 490 | A |
| 491 | A | 492 | C |
| 493 | A | 494 | A |
| 495 | A | 496 | C |
| 497 | C | 498 | A |
| 499 | A | 500 | C |
| 501 | C | 502 | A |
| 503 | A | 504 | C |
| 505 | A | 506 | A |
| 507 | A | | |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula (I):

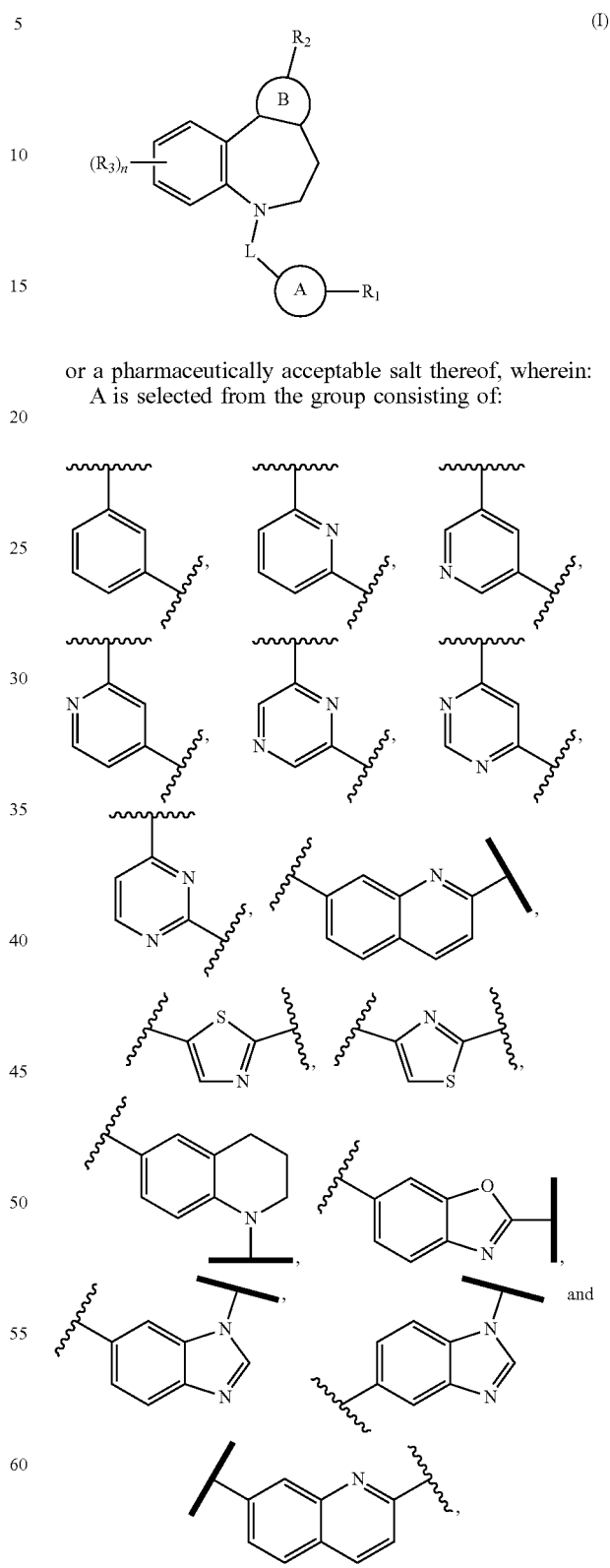

or a pharmaceutically acceptable salt thereof, wherein:

A is selected from the group consisting of:

each of which is optionally substituted with 1 or 2 substituents independently selected from halogen, —CN, —OH, —NH₂, —NO₂, —CH₃, —CF₃, —OCH₃, —OCF₃, —SO₂CH₃, —CH₂N(CH₃)₂, and —C(O)CH₃, and wherein in the bicyclic groups, denotes the bond to L and denotes the bond to R₁;

L is —CH₂—, —CO—, or —SO₂—;

B is aryl or heteroaryl, each of which is optionally substituted with one or two substituents selected from halogen, cyano and nitro;

R₁ is selected from the group consisting of:
1) Optionally substituted —C₃-C₁₂ cycloalkyl;
2) Optionally substituted —C₃-C₁₂ cycloalkenyl;
3) Optionally substituted 3- to 12-membered heterocycloalkyl;
4) Optionally substituted aryl;
5) Optionally substituted heteroaryl;
6) —C(O)R₁₂;
7) —C(O)NR₁₁S(O)₂R₁₂;
8) —S(O)₂NR₁₃R₁₄;
9) —NR₁₃R₁₄;
10) —NR₁₁S(O)₂R₁₂;
11) —NR₁₁C(O)NR₁₃R₁₄; and
12) —NR₁₁C(O)NHS(O)₂R₁₂;

R₂ is selected from the group consisting of:
1) Optionally substituted —C₁-C₈ alkoxy;
2) Optionally substituted —C₁-C₈ alkyl;
3) Optionally substituted —C₂-C₈ alkenyl;
4) Optionally substituted —C₂-C₈ alkynyl;
5) Optionally substituted —C₃-C₁₂ cycloalkyl;
6) Optionally substituted —C₃-C₁₂ cycloalkenyl;
7) Optionally substituted 3- to 12-membered heterocycloalkyl;
8) —C(O)R₁₂;
9) —C(O)NR₁₃R₁₄;
10) —C(O)NR₁₁S(O)₂R₁₂;
11) —S(O)₂NR₁₃R₁₄;
12) —NR₁₃R₁₄;
13) —NR₁₁S(O)₂R₁₂;
14) —NR₁₁C(O)R₁₂;
15) —NR₁₁C(O)NR₁₃R₁₄; and
16) —NR₁₁C(O)NHS(O)₂R₁₂;

Each R₃ is independently selected from halogen, hydroxyl, protected hydroxyl, cyano, amino, protected amino, nitro, optionally substituted —C₁-C₈ alkyl, optionally substituted —C₁-C₈ alkoxy, and optionally substituted —C₁-C₈ alkyl-O—C₁-C₈ alkoxy;

R₁₂ at each occurrence is independently selected from the group consisting of:
1) Optionally substituted —C₁-C₈ alkoxy;
2) Optionally substituted —C₁-C₈ alkyl;
3) Optionally substituted —C₂-C₈ alkenyl;
4) Optionally substituted —C₂-C₈ alkynyl;
5) Optionally substituted —C₃-C₈ cycloalkyl;
6) Optionally substituted —C₃-C₈ cycloalkenyl;
7) Optionally substituted 3- to 8-membered heterocycloalkyl;

8) Optionally substituted aryl;
9) Optionally substituted arylalkyl;
10) Optionally substituted heteroaryl; and
11) Optionally substituted heteroarylalkyl;

R₁₁, R₁₃ and R₁₄ are each independently selected from hydrogen, optionally substituted —C₁-C₅-alkyl, optionally substituted —C₂-C₈-alkenyl, optionally substituted —C₂-C₈-alkynyl; optionally substituted —C₃-C₈-cycloalkyl, optionally substituted 3- to 8-membered heterocyclic, optionally substituted aryl, optionally substituted arylalkyl, optionally substituted heteroaryl, and optionally substituted heteroarylalkyl; alternatively, R₁₃ and R₁₄ are taken together with the nitrogen atom to which they are attached to form a 3- to 12-membered heterocyclic ring; and n is 0, 1, 2, 3 or 4.

2. The compound of claim 1, wherein L is —CO—.

3. The compound of claim 1, wherein R₂ is —C(O)NR₁₃R₁₄, and R₁₃ and R₁₄ are as defined in claim 1.

4. The compound of claim 1, wherein R₁ is selected from one of the following groups by removal of one hydrogen atom, wherein each of the groups is optionally substituted:

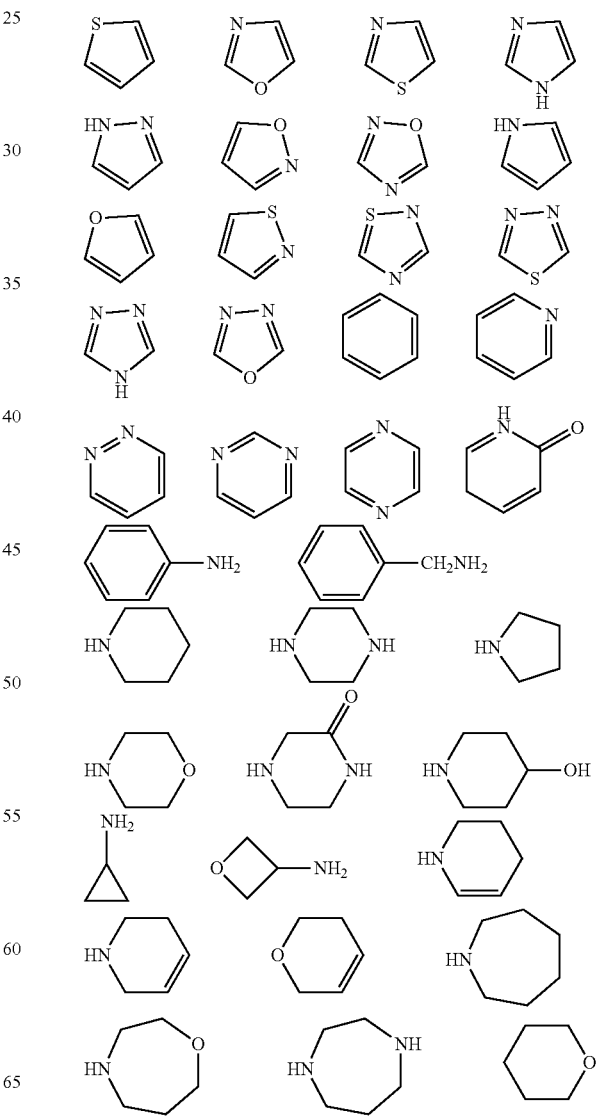

503
-continued
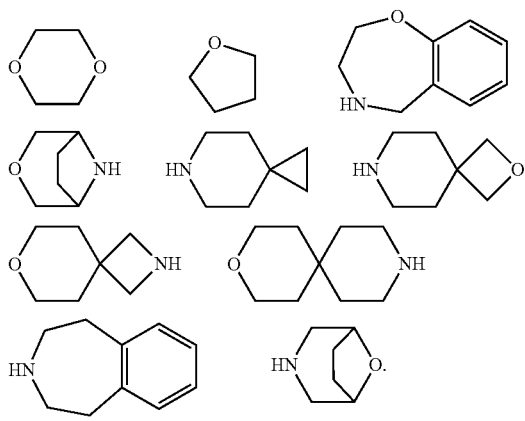
5. The compound of claim 1, represented by one of Formulas (IIIa)-(IIIh), or a pharmaceutically acceptable salt thereof:
(IIIa)
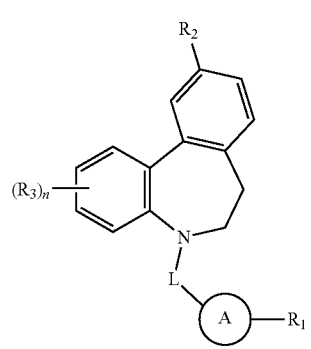
(IIIb)
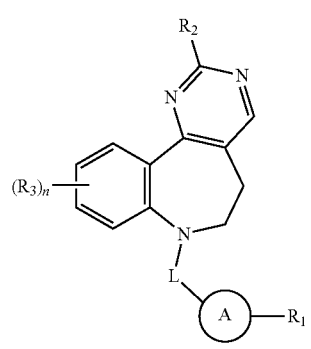
(IIIc)
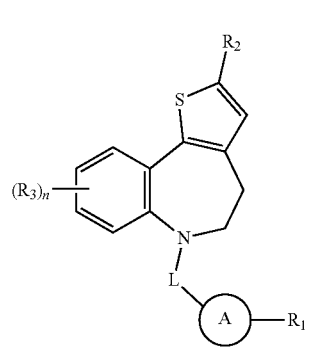
504
-continued
(IIId)
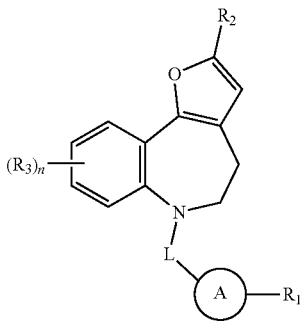
(IIIe)
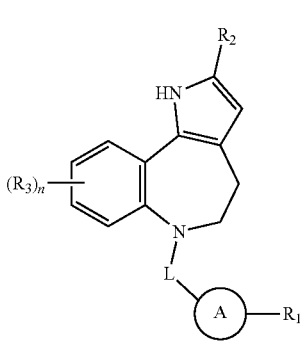
(IIIf)
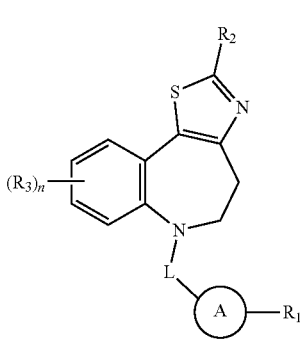
(IIIg)
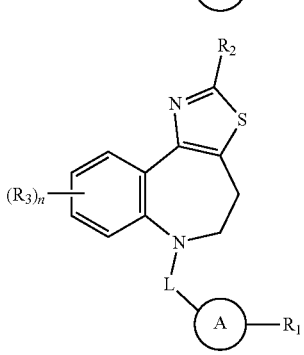
(IIIh)
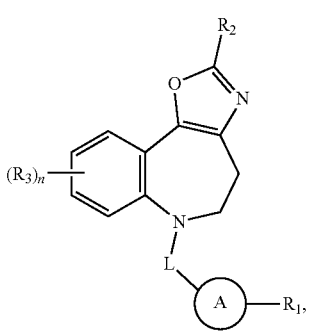

wherein A, L, R$_1$, R$_2$, R$_3$, and n are as defined in claim 1.

6. A compound of claim 1, represented by one of Formulas (IVa)-(IVc), or a pharmaceutically acceptable salt thereof:

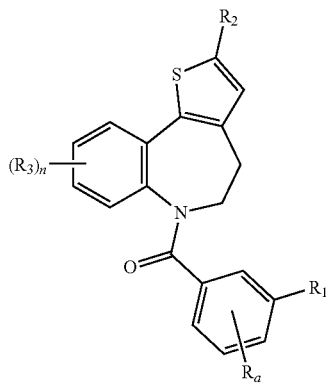

(IVa)

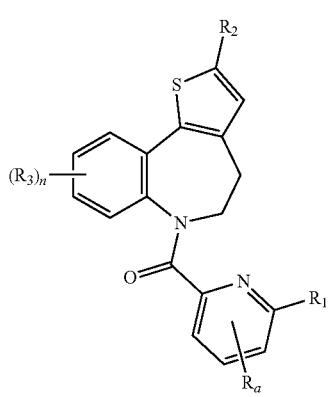

(IVb)

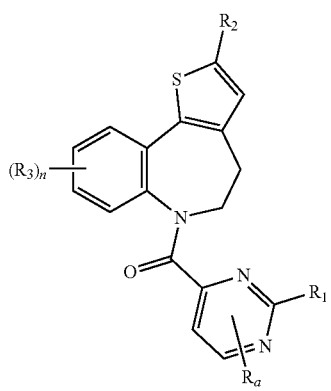

(IVc)

wherein R$_1$, R$_2$, R$_3$, and n are as defined in claim 1, and R$_a$ is hydrogen, halogen, optionally substituted alkyl, optionally substituted alkoxy, or —CN.

7. The compound of claim 1, represented by one of Formulas (Va)-(Vc), or a pharmaceutically acceptable salt thereof, wherein:

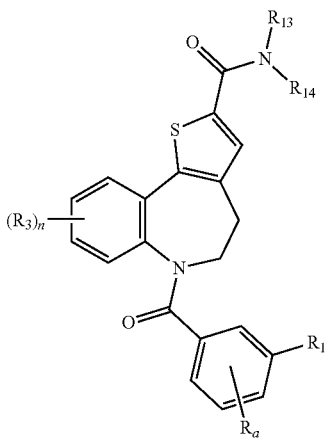

(Va)

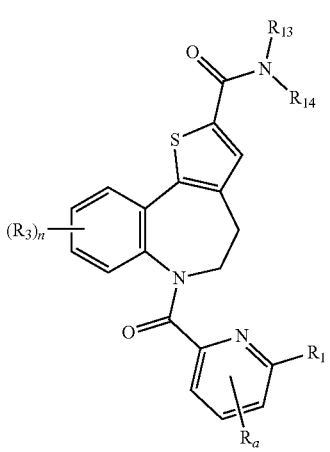

(Vb)

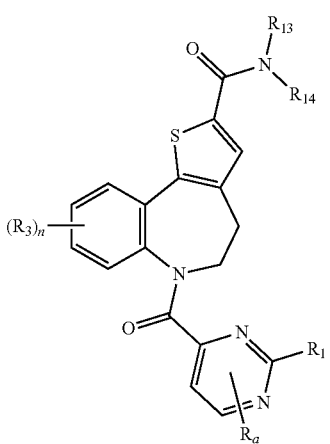

(Vc)

-continued
(Vd)
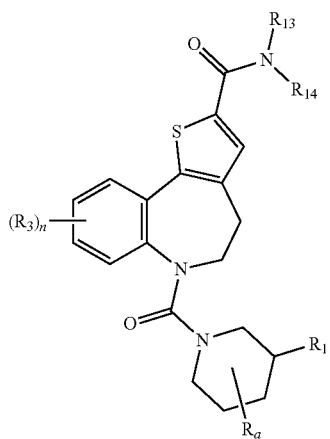
wherein $R_1$, $R_3$, $R_{13}$, $R_{14}$, and n are as defined in claim 1, and $R_a$ is hydrogen, halogen, optionally substituted alkyl, optionally substituted alkoxy, or —CN.
8. A compound of claim 1, represented by one of Formulas (VIa)-(VIc) and (VIe)-(VIg), or a pharmaceutically acceptable salt thereof:
(VIa)
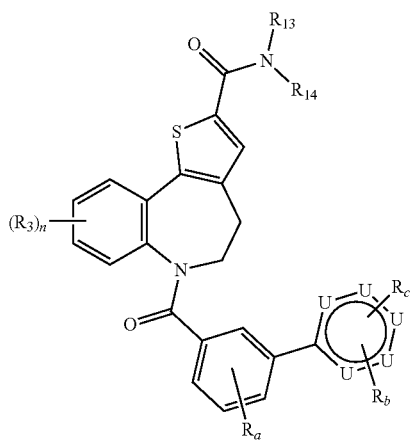
(VIb)
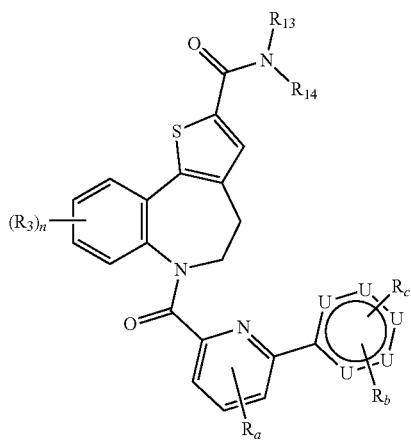
(VIc)
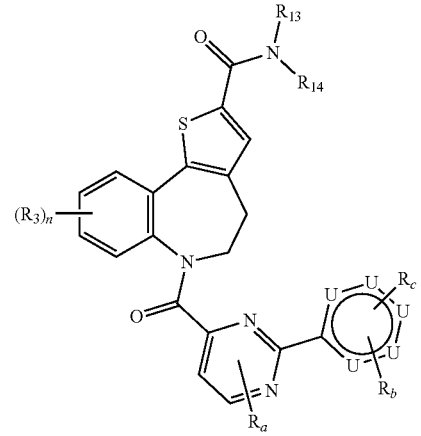
(VIe)
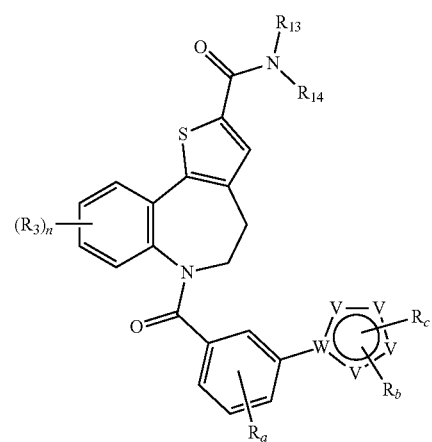
(VIf)
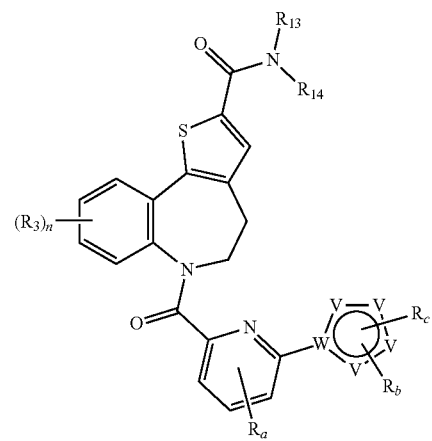

509
-continued

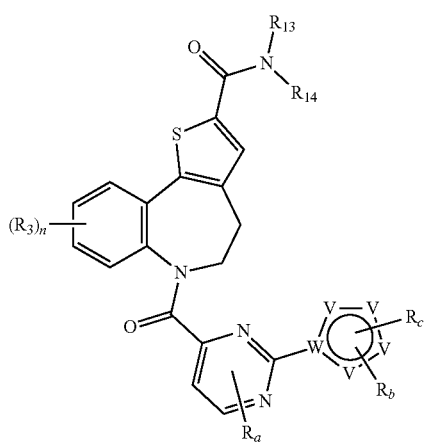

(VIg)

wherein $R_3$, $R_{13}$, $R_{14}$, and n are as defined in claim 1; $R_a$ is hydrogen, halogen, optionally substituted alkyl, optionally substituted alkoxy, or —CN; each U is independently selected from N, C and CH; W is C or N; each V is independently selected from N, NH, O, S, C and CH; $R_a$ and $R_b$ are each independently selected from hydrogen, halogen, optionally substituted alkyl, optionally substituted alkoxy, and —CN; and $R_c$ is hydrogen, optionally substituted alkyl or selected from one of the following groups by removal of one hydrogen atom, and each group is optionally substituted:

510
-continued

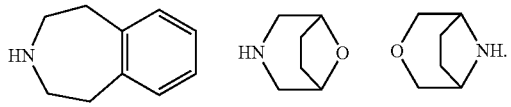

9. A compound selected from the compounds set forth in the table below or a pharmaceutically acceptable salt thereof:

| Entry | Compound |
|---|---|
| 2 | |
| 4 | |
| 5 | |

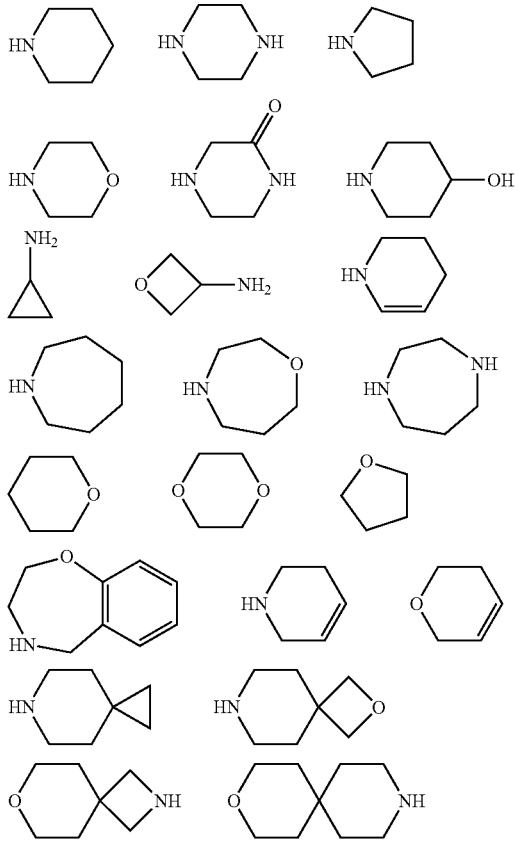

| Entry | Compound |
|---|---|
| 6 | 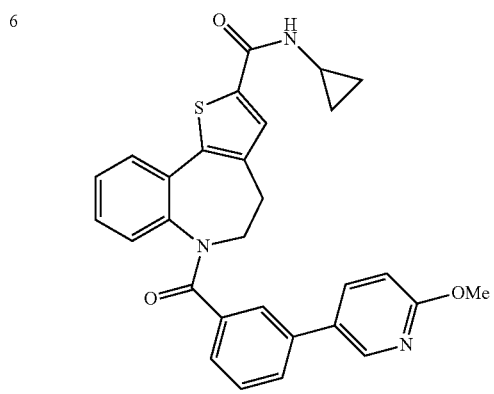 |
| 7 | 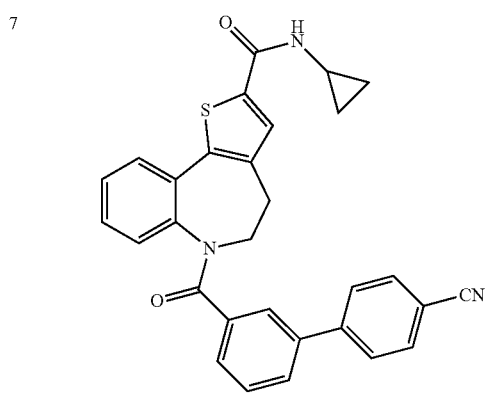 |
| 9 | 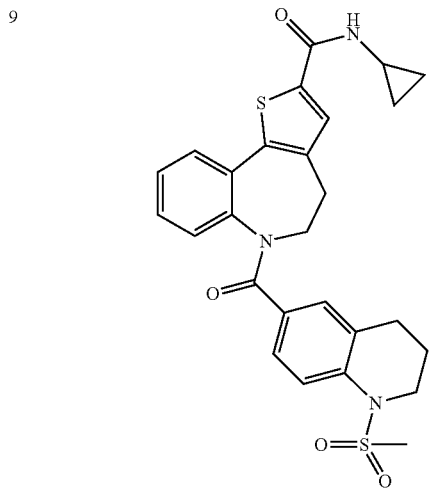 |
| Entry | Compound |
|---|---|
| 10 | 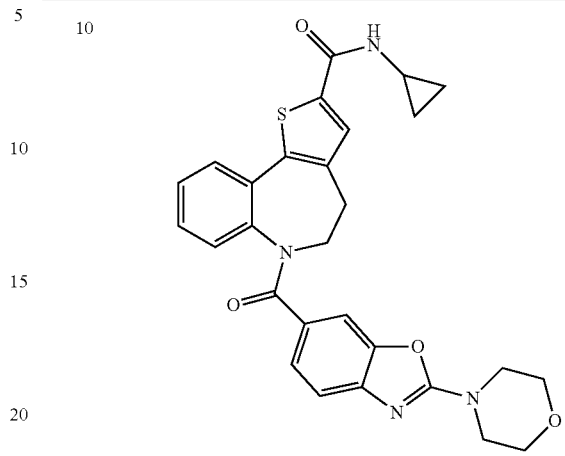 |
| 11 | 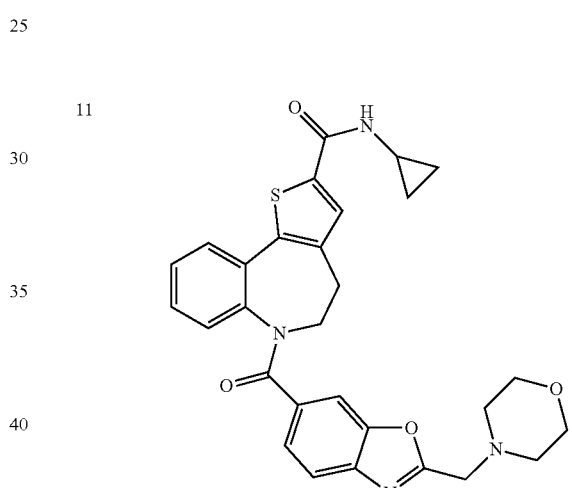 |
| 12 | 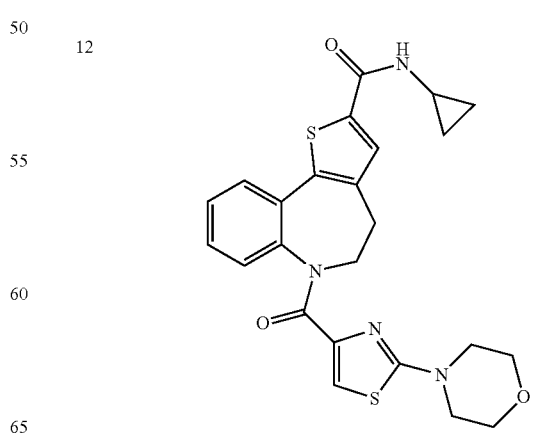 |

-continued

| Entry | Compound |
|---|---|
| 13 | |
| 14 | |
| 16 | |

-continued

| Entry | Compound |
|---|---|
| 17 | |
| 18 | |
| 19 | |
| 20 | |

515
-continued
| Entry | Compound |
|---|---|
| 21 | 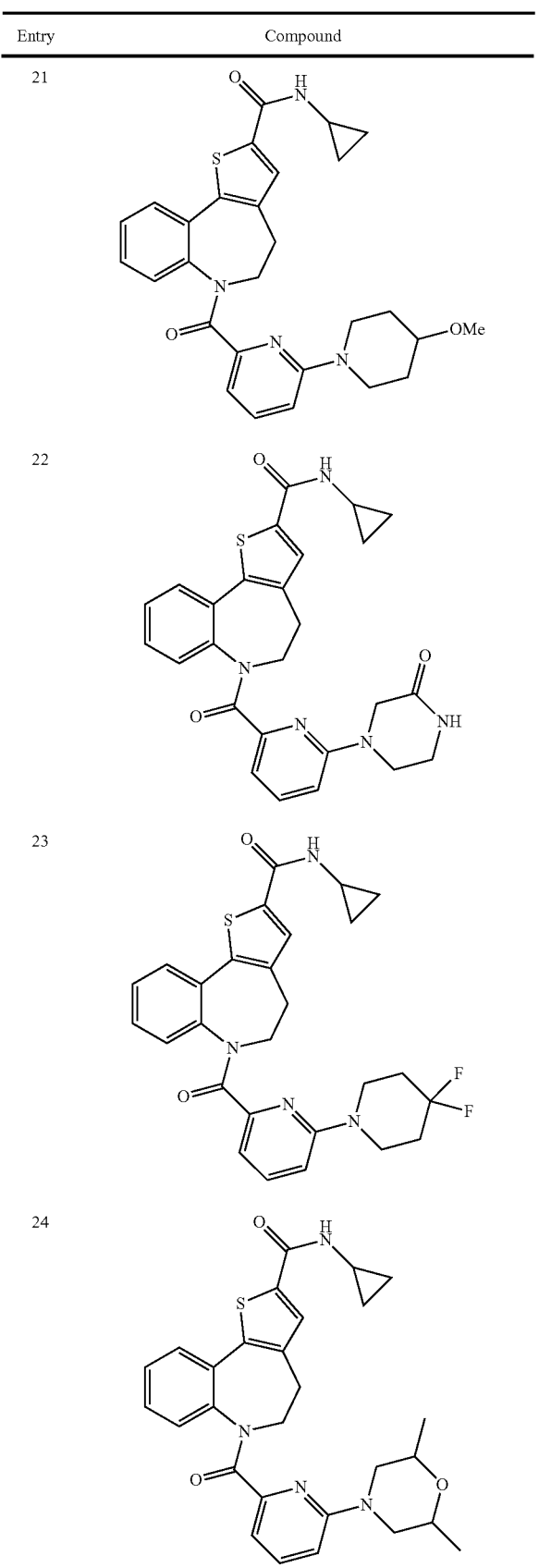 |
| 22 | |
| 23 | |
| 24 | |
516
-continued
| Entry | Compound |
|---|---|
| 25 | 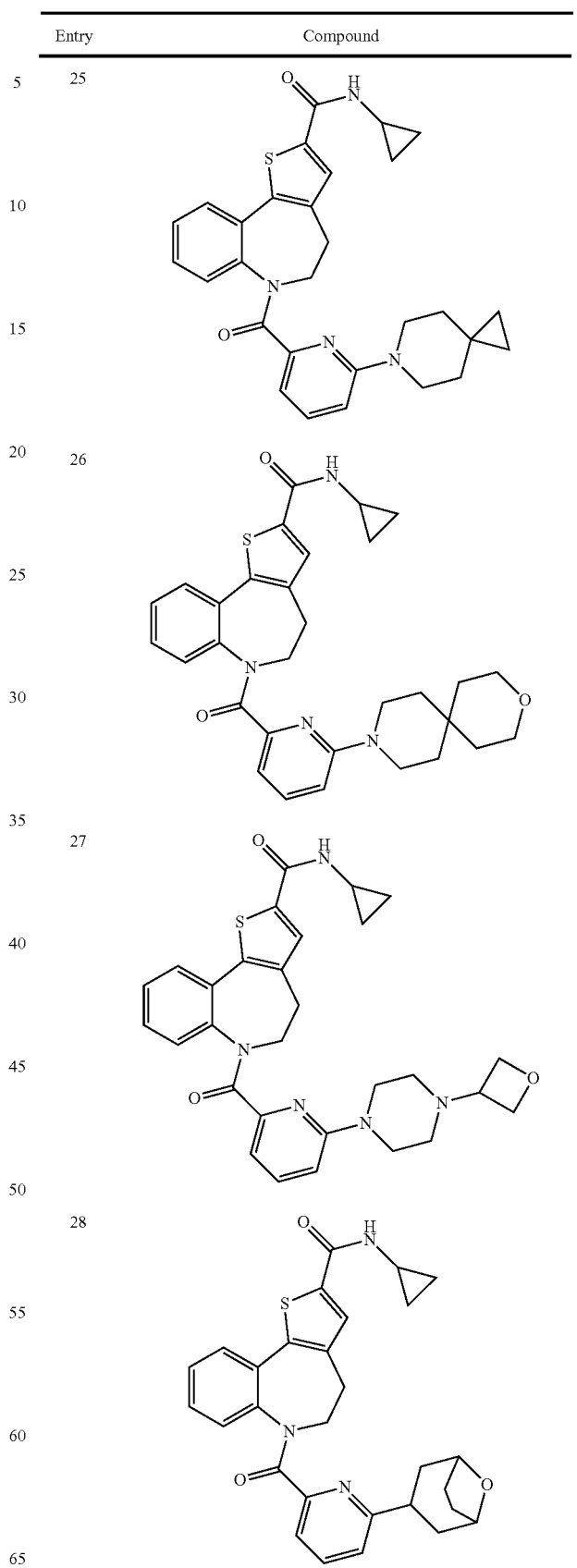 |
| 26 | |
| 27 | |
| 28 | |

517
-continued
| Entry | Compound |
|---|---|
| 29 | 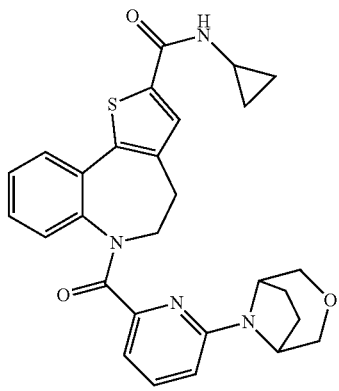 [SMILES: O=C(NC1CC1)c1cc2c(s1)-c1ccccc1N(C(=O)c1cccc(N3C4CCC3COC4)n1)CC2] |
| 30 | 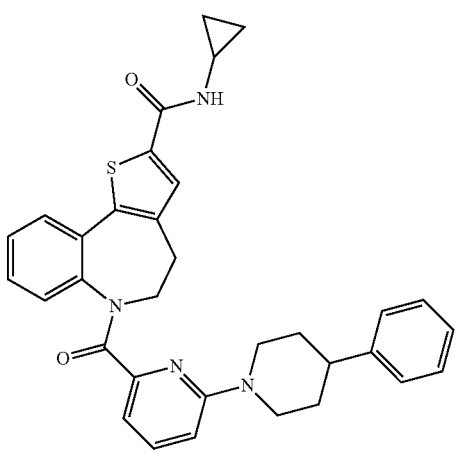 [SMILES: O=C(NC1CC1)c1cc2c(s1)-c1ccccc1N(C(=O)c1cccc(N3CCC(c4ccccc4)CC3)n1)CC2] |
| 31 | 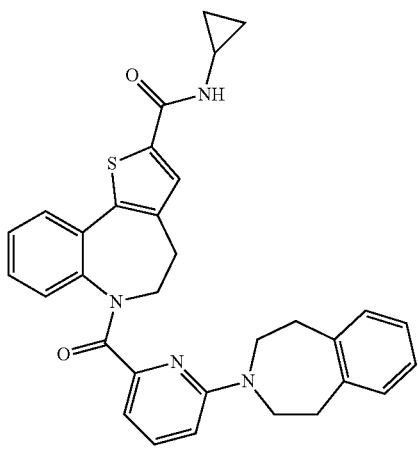 [SMILES: O=C(NC1CC1)c1cc2c(s1)-c1ccccc1N(C(=O)c1cccc(N3CCc4ccccc4CC3)n1)CC2] |
518
-continued
| Entry | Compound |
|---|---|
| 32 | 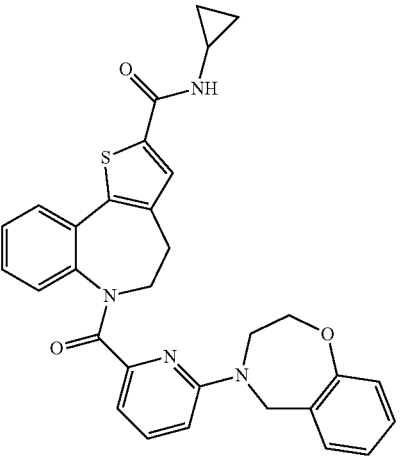 [SMILES: O=C(NC1CC1)c1cc2c(s1)-c1ccccc1N(C(=O)c1cccc(N3CCOc4ccccc4C3)n1)CC2] |
| 33 | 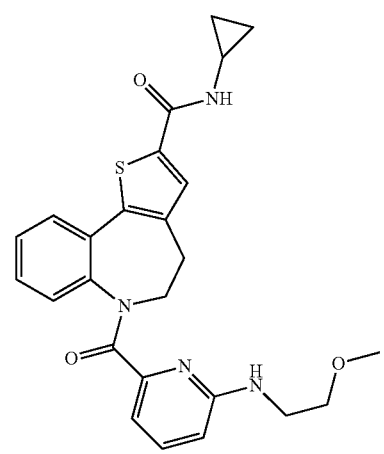 [SMILES: COCCNc1cccc(C(=O)N2CCc3cc(C(=O)NC4CC4)sc3-c3ccccc32)n1] |
| 34 | 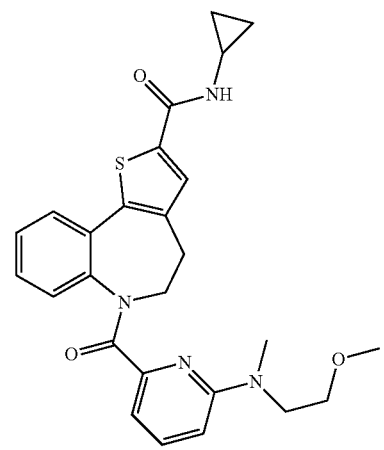 [SMILES: COCCN(C)c1cccc(C(=O)N2CCc3cc(C(=O)NC4CC4)sc3-c3ccccc32)n1] |

| 519 -continued | 520 -continued |
|---|---|
| Entry Compound | Entry Compound |
| 35 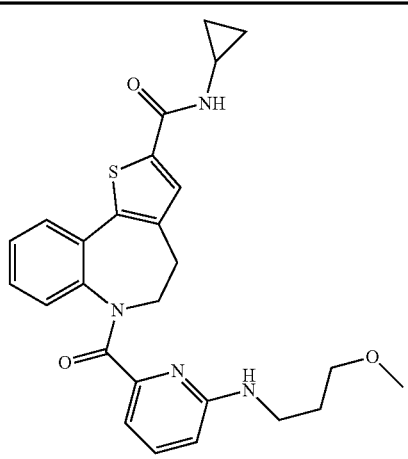 | 38 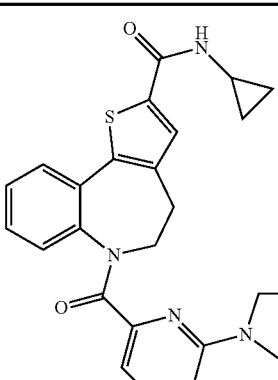 |
| 36 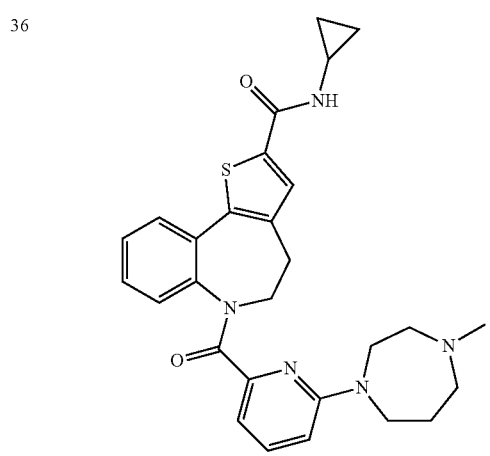 | 39 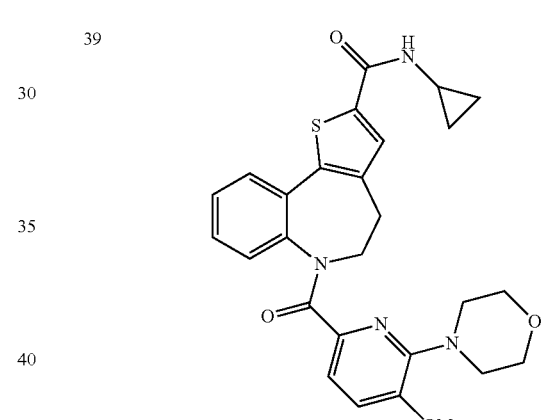 |
| 37 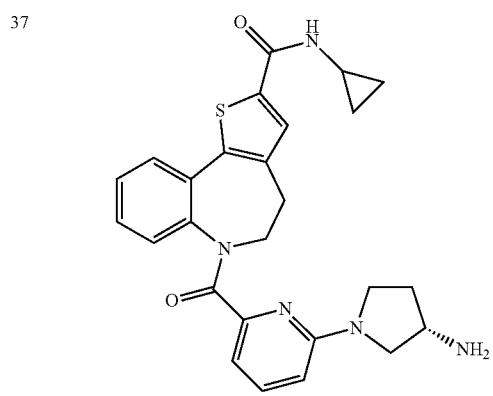 | 40 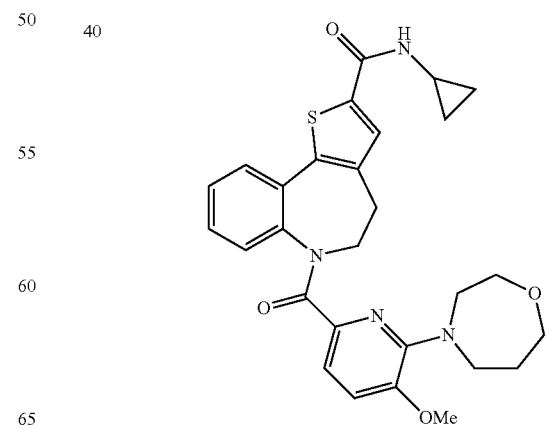 |

| Entry | Compound |
|---|---|
| 41 | 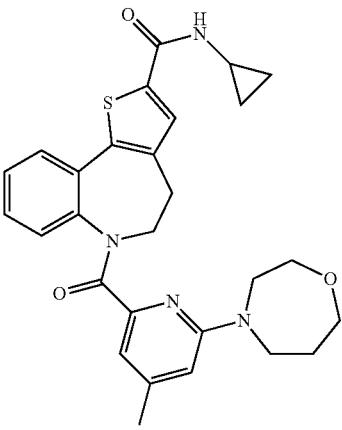 [SMILES: Cc1cc(C(=O)N2CCc3cc(C(=O)NC4CC4)sc3-c3ccccc32)nc(N2CCCOCC2)c1] |
| 42 | 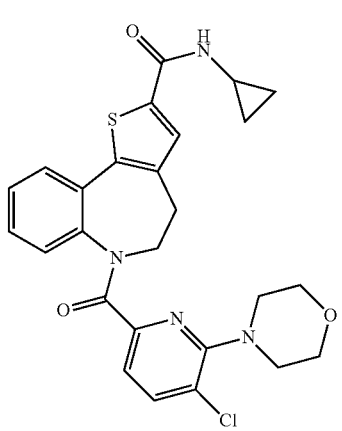 |
| 43 | 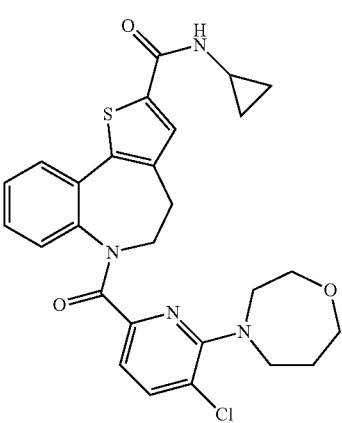 [SMILES: O=C(NC1CC1)c1cc2c(s1)-c1ccccc1N(C(=O)c1ccc(Cl)c(N3CCCOCC3)n1)CC2] |
| Entry | Compound |
|---|---|
| 44 | 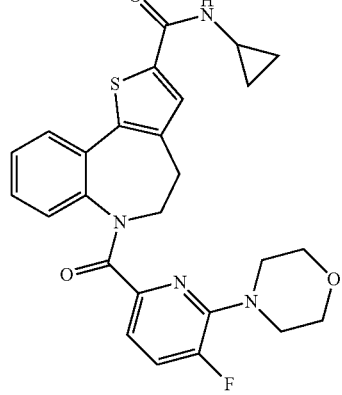 |
| 45 | 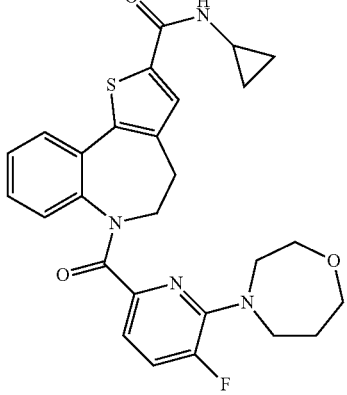 |
| 46 | 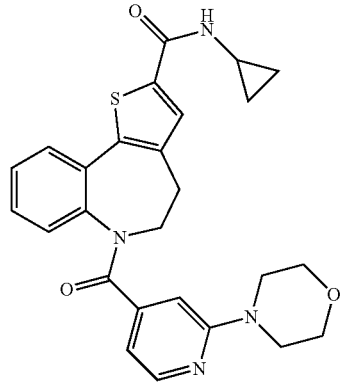 |
| 47 | 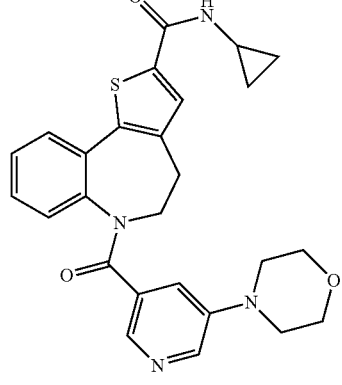 |

| Entry | Compound |
|---|---|
| 48 | 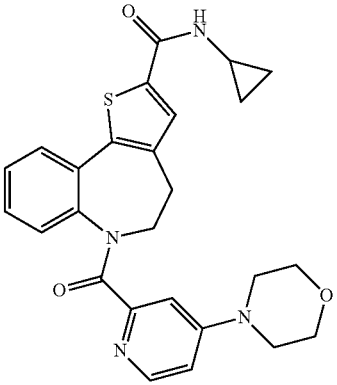 |
| 49 | 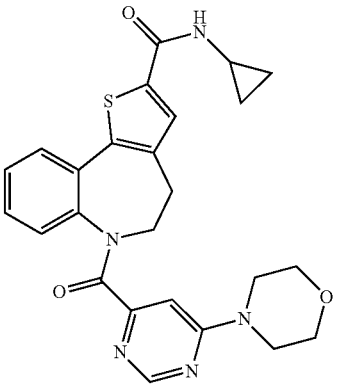 |
| 50 | 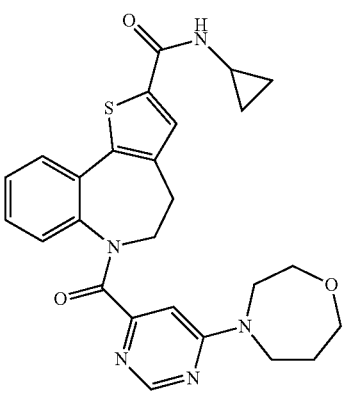 [SMILES: O=C(NC1CC1)c1cc2c(s1)-c1ccccc1N(C(=O)c1cc(N3CCCOCC3)ncn1)CC2] |
| 51 | 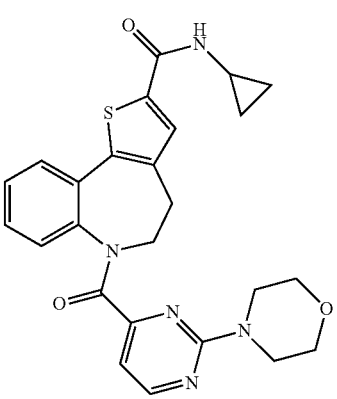 |
| Entry | Compound |
|---|---|
| 52 | 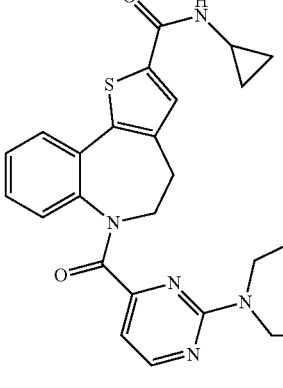 |
| 53 | 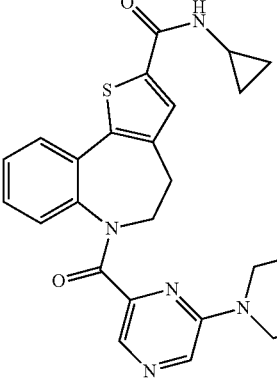 |
| 54 | 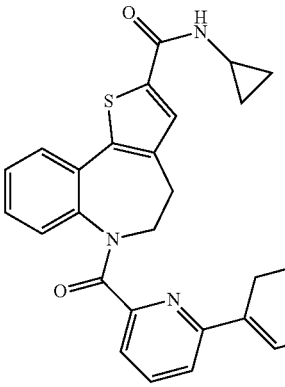 |
| 55 | 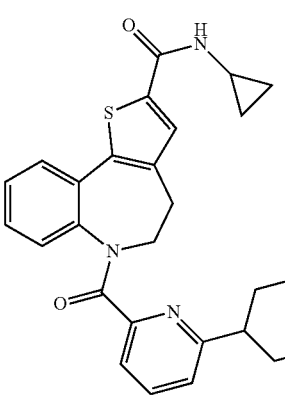 |

| Entry | Compound |
|---|---|
| 56 | 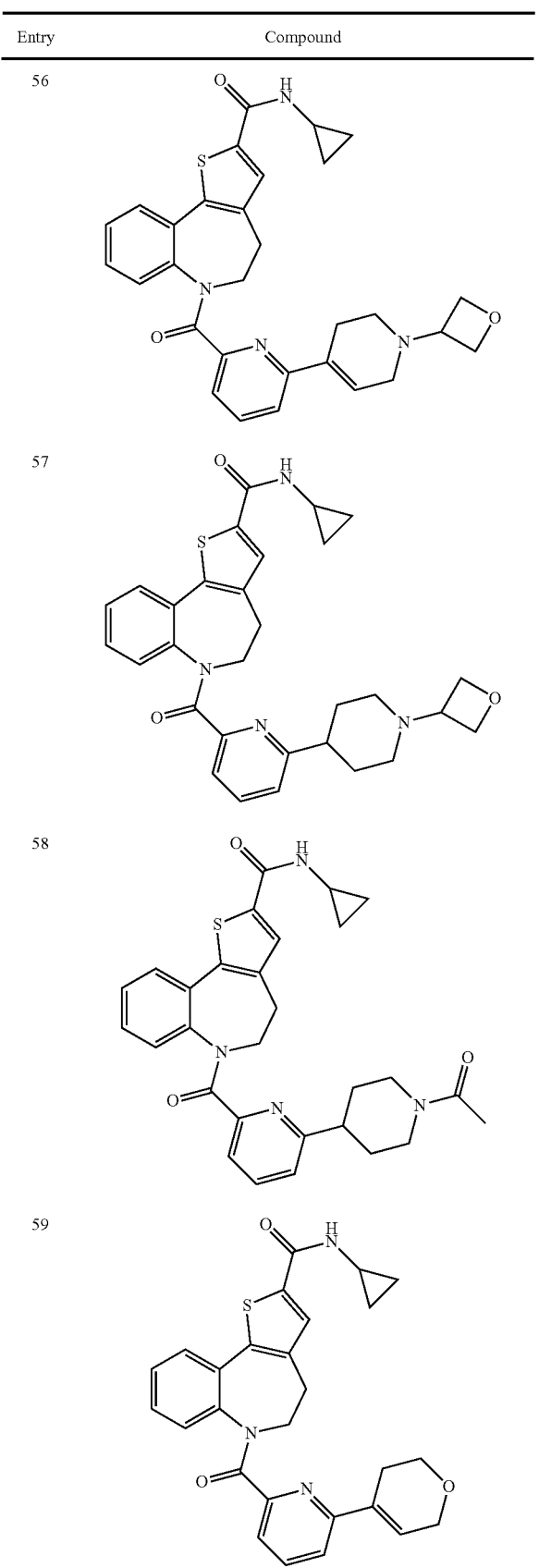 |
| 57 | |
| 58 | |
| 59 | |
| Entry | Compound |
|---|---|
| 60 | 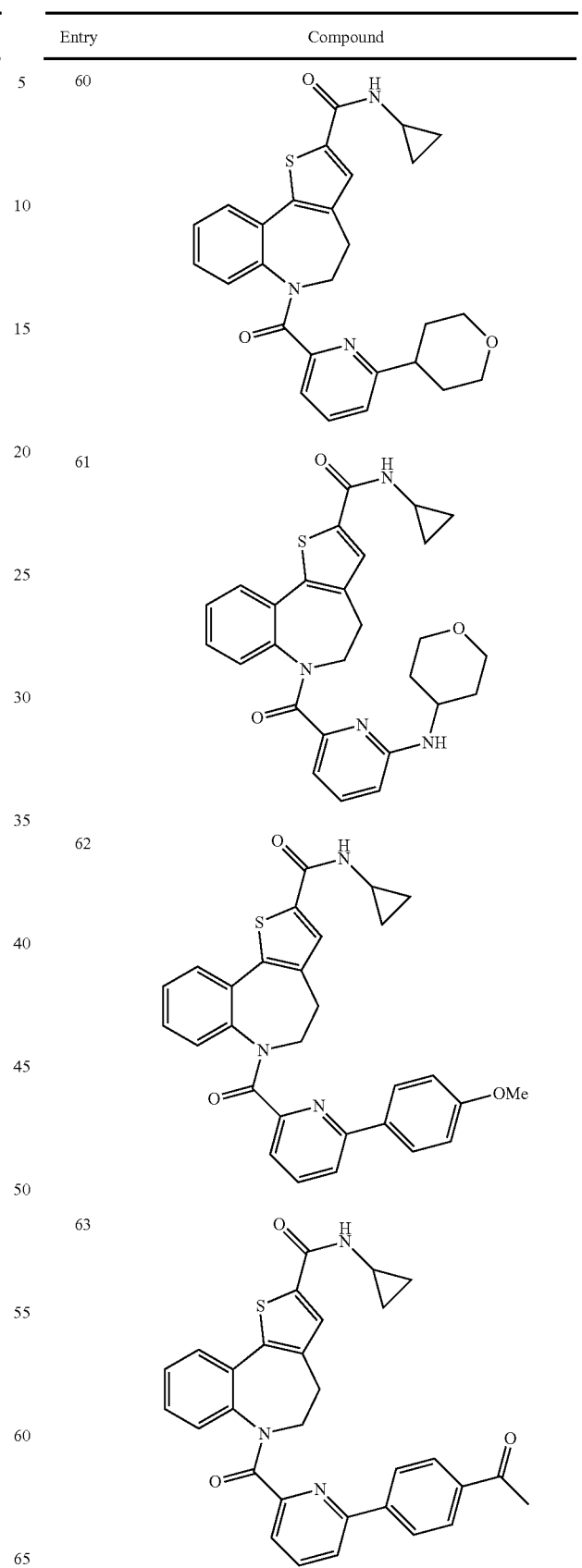 |
| 61 | |
| 62 | |
| 63 | |

527
-continued

| Entry | Compound |
|---|---|
| 64 | (structure) |
| 65 | (structure) |
| 66 | (structure) |
| 67 | (structure) |

528
-continued

| Entry | Compound |
|---|---|
| 68 | (structure) |
| 69 | (structure) |
| 70 | (structure) |
| 71 | (structure) |

| Entry | Compound |
|---|---|
| 72 | 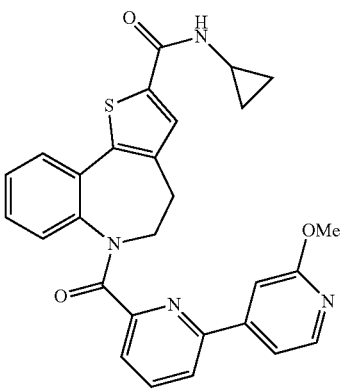 [SMILES: COc1cc(-c2cccc(C(=O)N3CCc4cc(C(=O)NC5CC5)sc4-c4ccccc43)n2)ccn1] |
| 73 | 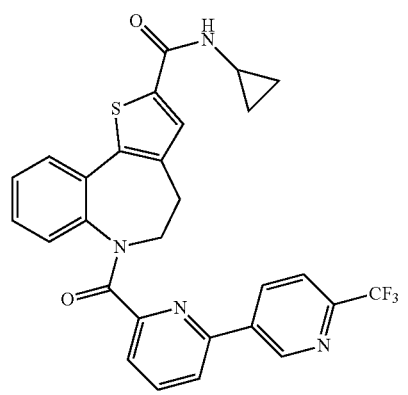 [SMILES: O=C(NC1CC1)c1cc2c(s1)-c1ccccc1N(C(=O)c1cccc(-c3ccc(C(F)(F)F)nc3)n1)CC2] |
| 74 | 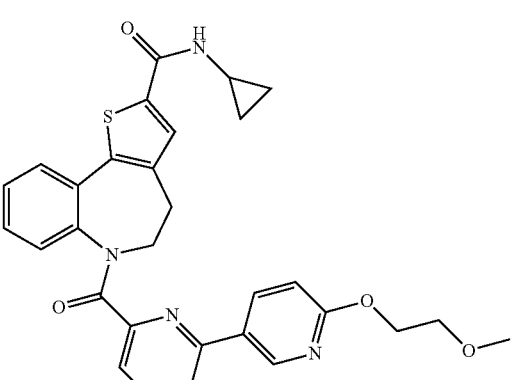 |
| 75 | 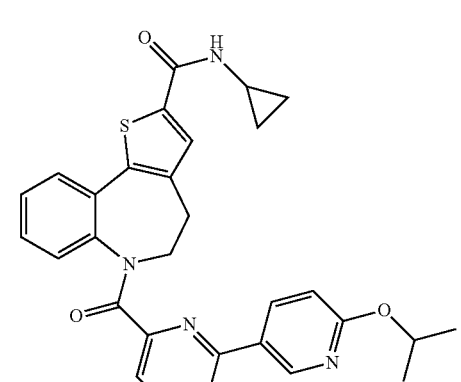 |
| 76 | 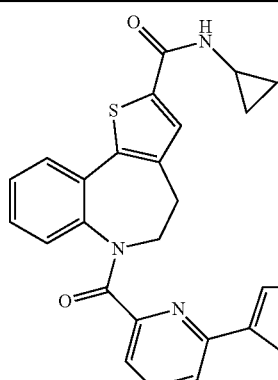 |
| 77 | 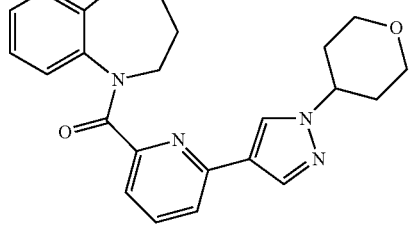 |
| 78 | 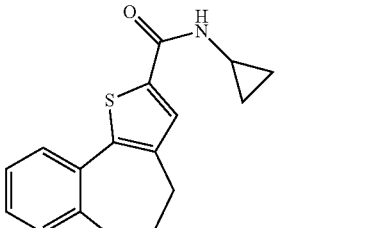 |
| 79 | 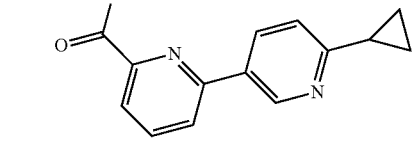 |

| Entry | Compound |
|---|---|
| 80 | 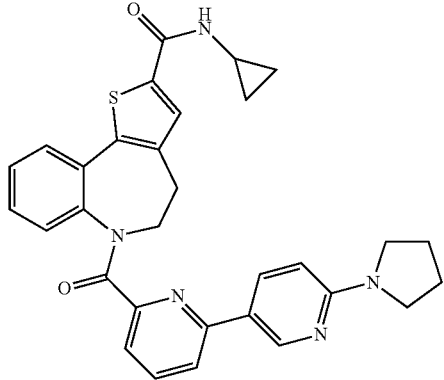 [SMILES: O=C(NC1CC1)c1cc2c(s1)-c1ccccc1N(C(=O)c1cccc(-c3ccc(N4CCCC4)nc3)n1)CC2] |
| 81 | 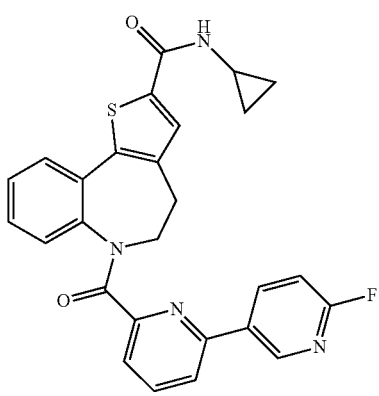 [SMILES: O=C(NC1CC1)c1cc2c(s1)-c1ccccc1N(C(=O)c1cccc(-c3ccc(F)nc3)n1)CC2] |
| 82 | 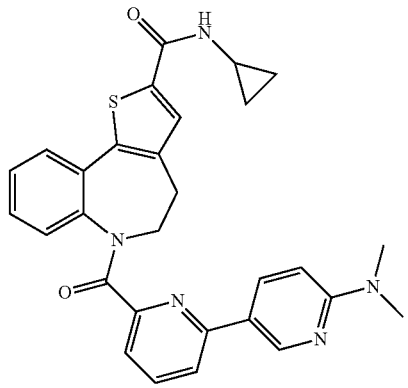 [SMILES: CN(C)c1ccc(-c2cccc(C(=O)N3CCc4cc(C(=O)NC5CC5)sc4-c4ccccc43)n2)cn1] |
| 83 | 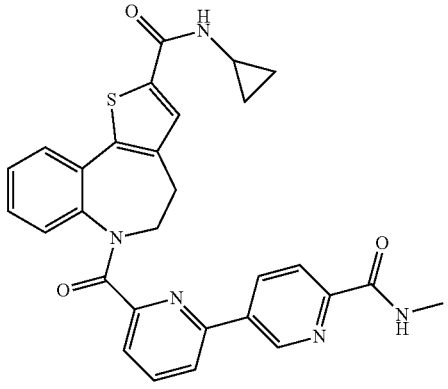 [SMILES: CNC(=O)c1ccc(-c2cccc(C(=O)N3CCc4cc(C(=O)NC5CC5)sc4-c4ccccc43)n2)cn1] |
| Entry | Compound |
|---|---|
| 84 | 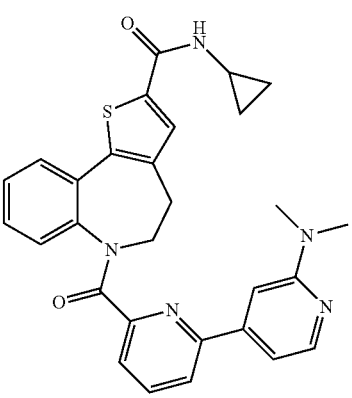 [SMILES: CN(C)c1cc(-c2cccc(C(=O)N3CCc4cc(C(=O)NC5CC5)sc4-c4ccccc43)n2)ccn1] |
| 85 | 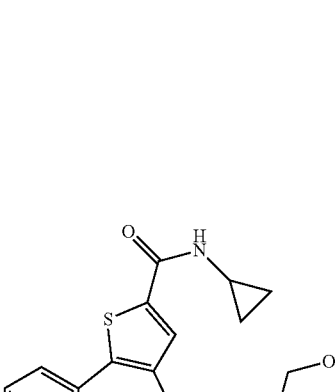 |
| 86 | 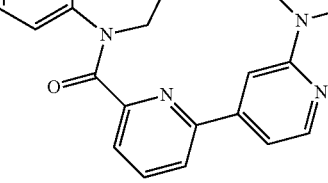 |

| Entry | Compound |
|---|---|
| 87 | 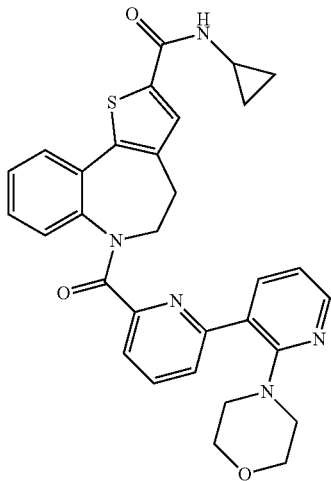 [SMILES: O=C(NC1CC1)c1cc2c(s1)-c1ccccc1N(C(=O)c1cccc(-c3cccnc3N3CCOCC3)n1)CC2] |
| 88 | 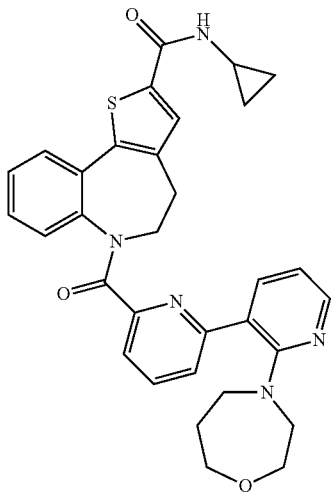 [SMILES: O=C(NC1CC1)c1cc2c(s1)-c1ccccc1N(C(=O)c1cccc(-c3cccnc3N3CCCOCC3)n1)CC2] |
| 89 | 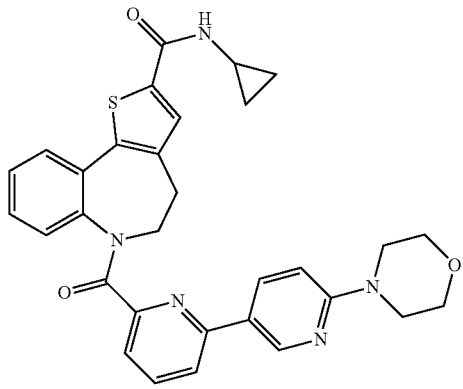 |
| Entry | Compound |
|---|---|
| 90 | 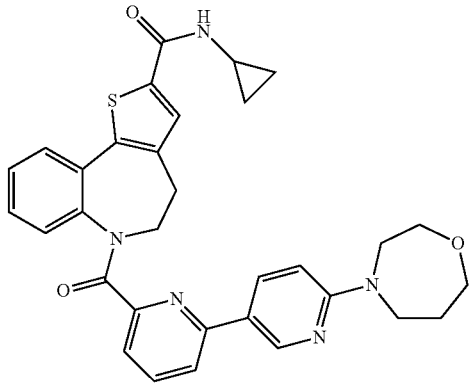 [SMILES: O=C(NC1CC1)c1cc2c(s1)-c1ccccc1N(C(=O)c1cccc(-c3ccc(N4CCCOCC4)nc3)n1)CC2] |
| 91 | 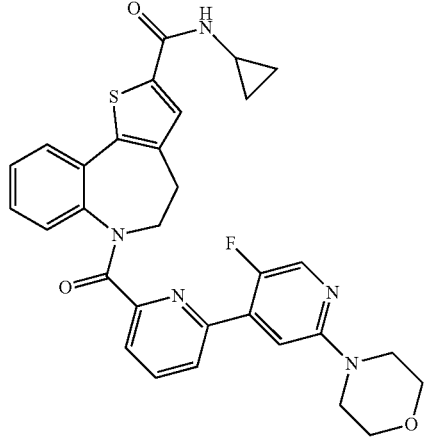 [SMILES: O=C(NC1CC1)c1cc2c(s1)-c1ccccc1N(C(=O)c1cccc(-c3cc(N4CCOCC4)ncc3F)n1)CC2] |
| 92 | 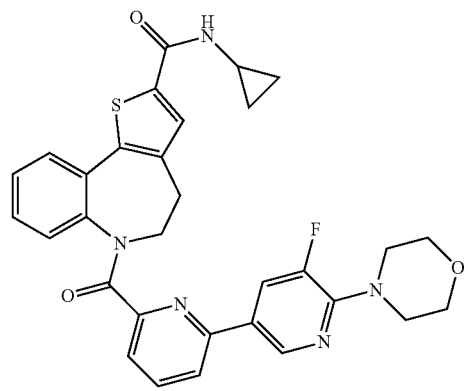 [SMILES: O=C(NC1CC1)c1cc2c(s1)-c1ccccc1N(C(=O)c1cccc(-c3cnc(N4CCOCC4)c(F)c3)n1)CC2] |

535
-continued
| Entry | Compound |
|---|---|
| 93 | 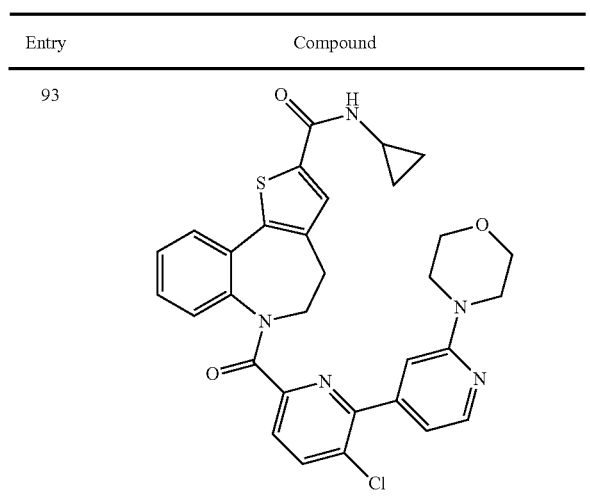 |
| 94 | 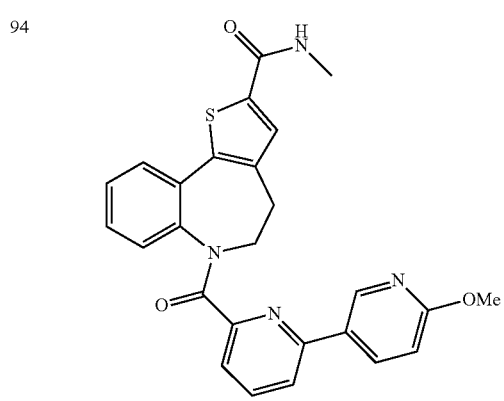 |
| 95 | 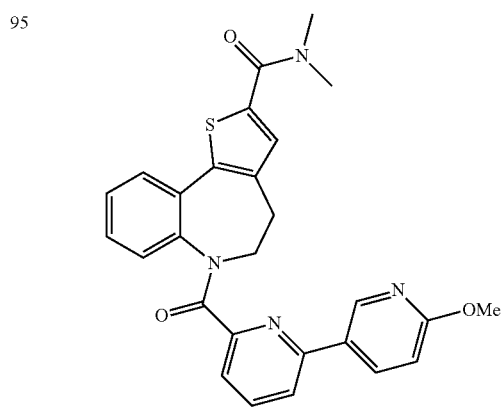 |
536
-continued
| Entry | Compound |
|---|---|
| 96 | 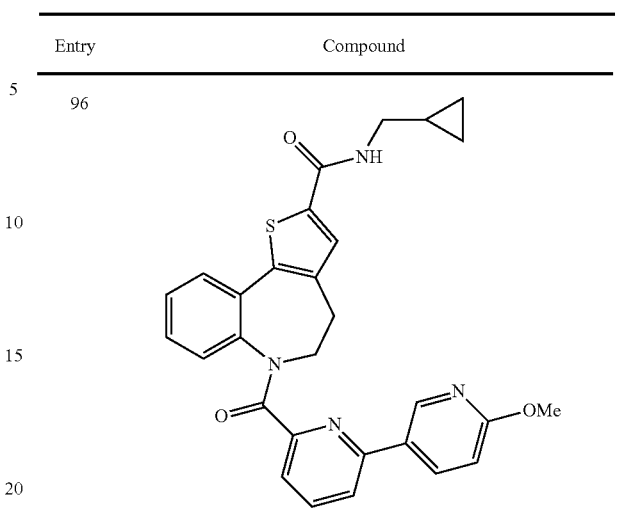 |
| 97 | 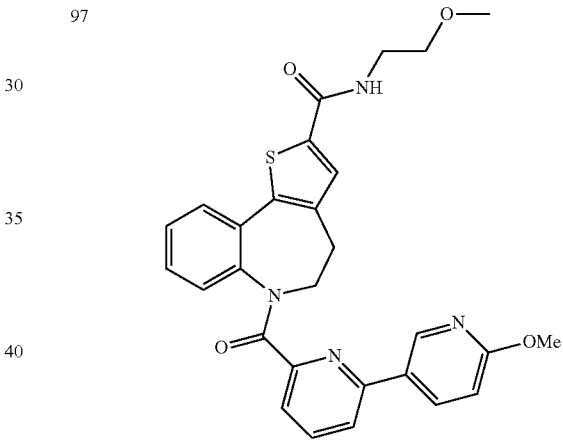 |
| 98 | 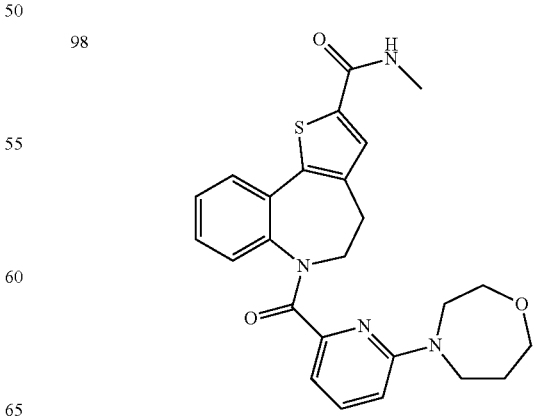 |

| Entry | Compound |
|---|---|
| 99 | |
| 100 | |
| 101 | |
| 102 | |

| Entry | Compound |
|---|---|
| 103 | |
| 104 | |
| 105 | |

| Entry | Compound |
|---|---|
| 106 | 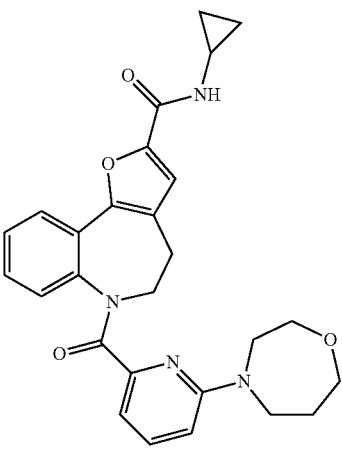 [SMILES: O=C(NC1CC1)c1cc2c(o1)-c1ccccc1N(C(=O)c1cccc(N3CCCOCC3)n1)CC2] |
| 107 | 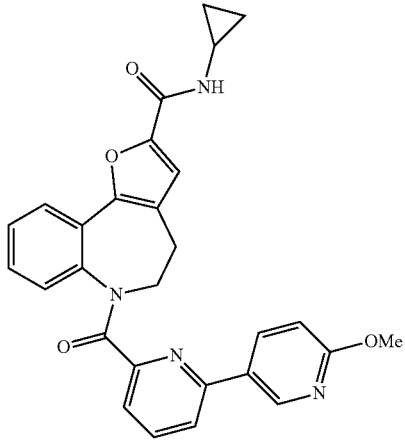 [SMILES: COc1ccc(-c2cccc(C(=O)N3CCc4cc(C(=O)NC5CC5)oc4-c4ccccc43)n2)cn1] |
| 108 | 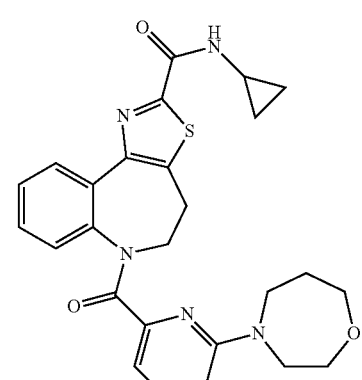 |
| Entry | Compound |
|---|---|
| 109 | 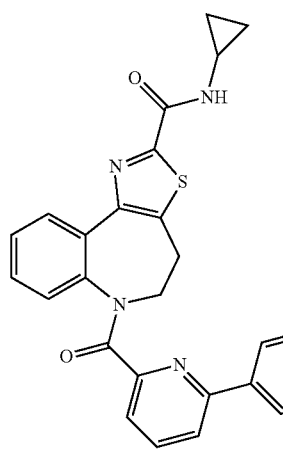 |
| 110 | 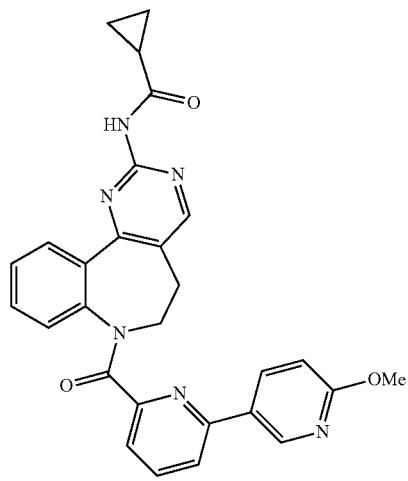 [SMILES: COc1ccc(-c2cccc(C(=O)N3CCc4cnc(NC(=O)C5CC5)nc4-c4ccccc43)n2)cn1] |
| 111 | 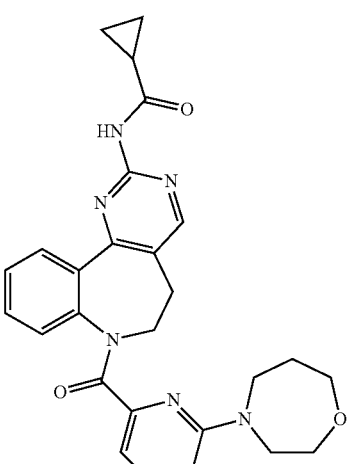 |

| Entry | Compound |
|---|---|
| 112 | 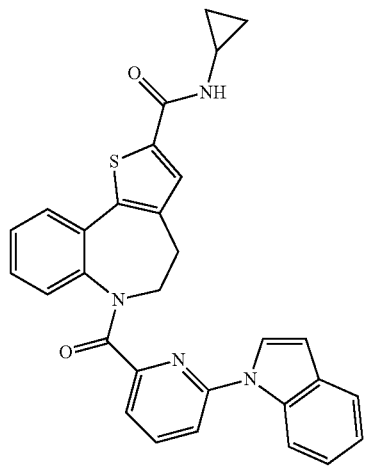 [SMILES: O=C(NC1CC1)c1cc2c(s1)-c1ccccc1N(C(=O)c1cccc(-n3ccc4ccccc43)n1)CC2] |
| 113 | 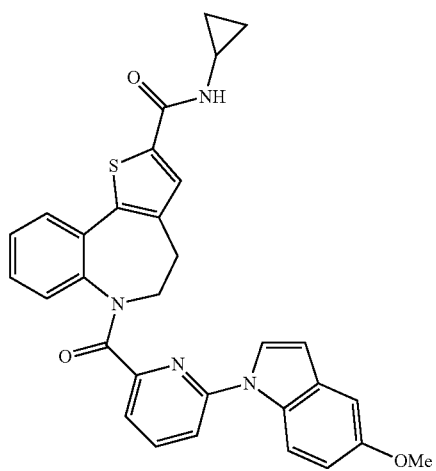 [SMILES: COc1ccc2c(ccn2-c2cccc(C(=O)N3CCc4cc(C(=O)NC5CC5)sc4-c4ccccc43)n2)c1] |
| 114 | 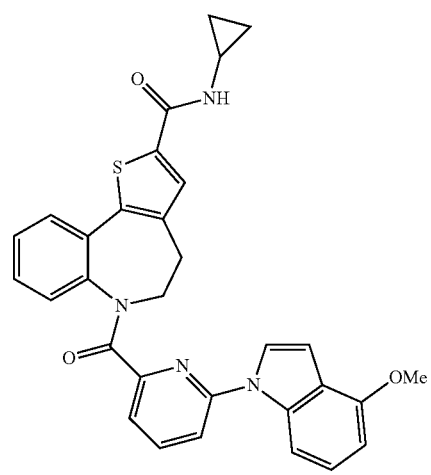 [SMILES: COc1cccc2c1ccn2-c1cccc(C(=O)N2CCc3cc(C(=O)NC4CC4)sc3-c3ccccc32)n1] |
| Entry | Compound |
|---|---|
| 115 | 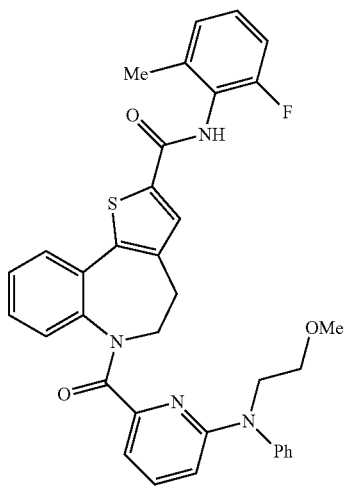 [SMILES: COCCN(c1ccccc1)c1cccc(C(=O)N2CCc3cc(C(=O)Nc4c(C)cccc4F)sc3-c3ccccc32)n1] |
| 116 | 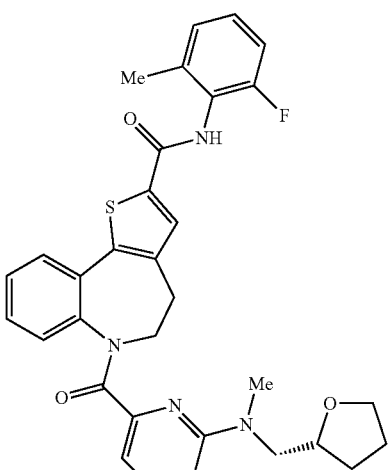 |
| 117 | 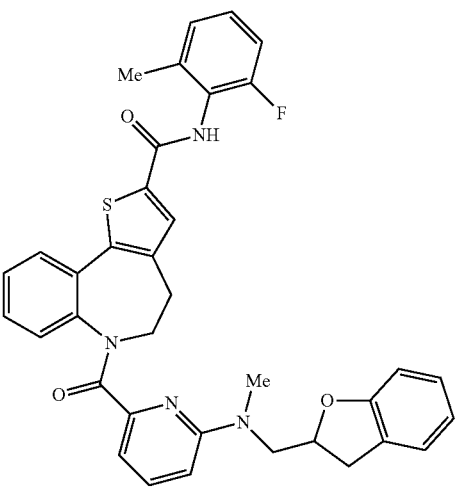 [SMILES: Cc1cccc(F)c1NC(=O)c1cc2c(s1)-c1ccccc1N(C(=O)c1cccc(N(C)CC3Cc4ccccc4O3)n1)CC2] |

| Entry | Compound |
|---|---|
| 118 | |
| 119 | |
| 120 | |
| 121 | |
| 122 | |
| 123 | |

| Entry | Compound |
|---|---|
| 124 | 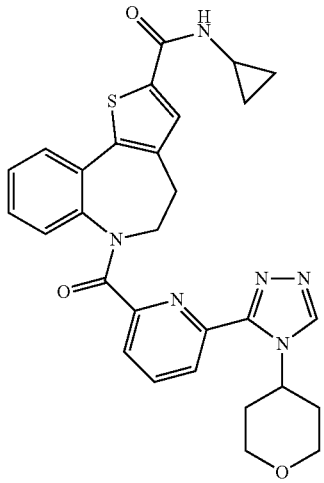 [SMILES: O=C(NC1CC1)c1cc2c(s1)-c1ccccc1N(C(=O)c1cccc(-c3nncn3C3CCOCC3)n1)CC2] |
| 125 | 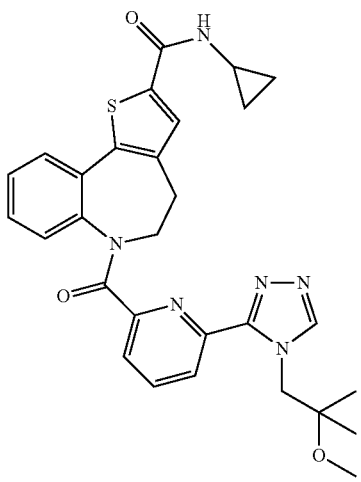 [SMILES: COC(C)(C)Cn1cnnc1-c1cccc(C(=O)N2CCc3cc(C(=O)NC4CC4)sc3-c3ccccc32)n1] |
| 126 | 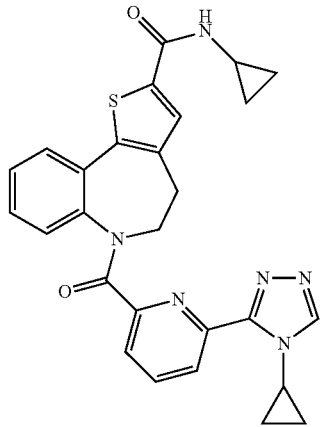 [SMILES: O=C(NC1CC1)c1cc2c(s1)-c1ccccc1N(C(=O)c1cccc(-c3nncn3C3CC3)n1)CC2] |
| Entry | Compound |
|---|---|
| 127 | 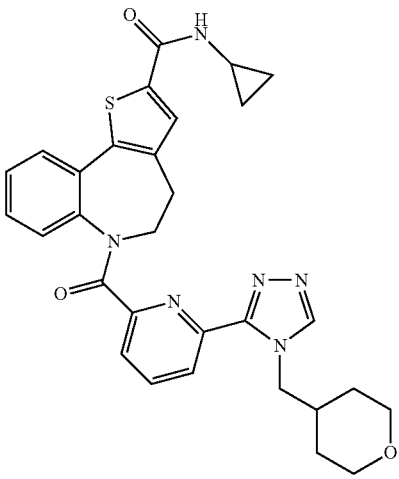 [SMILES: O=C(NC1CC1)c1cc2c(s1)-c1ccccc1N(C(=O)c1cccc(-c3nncn3CC3CCOCC3)n1)CC2] |
| 128 | |
| 143 | 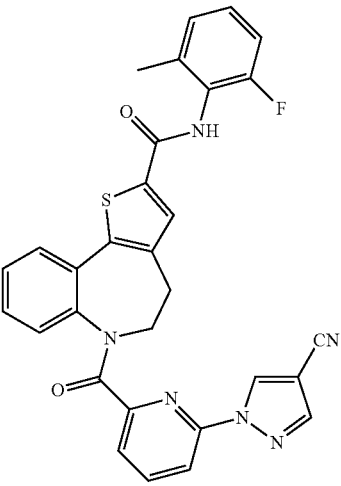 [SMILES: Cc1cccc(F)c1NC(=O)c1cc2c(s1)-c1ccccc1N(C(=O)c1cccc(-n3cc(C#N)cn3)n1)CC2] |

547
-continued
| Entry | Compound |
|---|---|
| 144 | 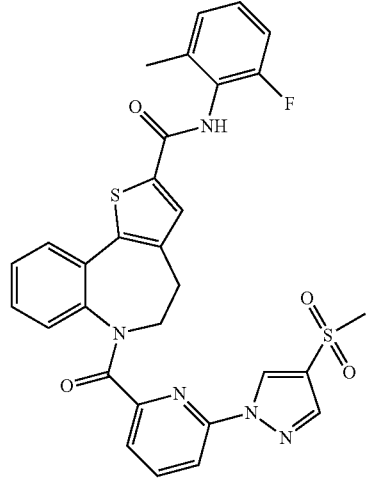 [SMILES: Cc1cccc(F)c1NC(=O)c1cc2c(s1)-c1ccccc1N(C(=O)c1cccc(-n3cc(S(C)(=O)=O)cn3)n1)CC2] |
| 145 | 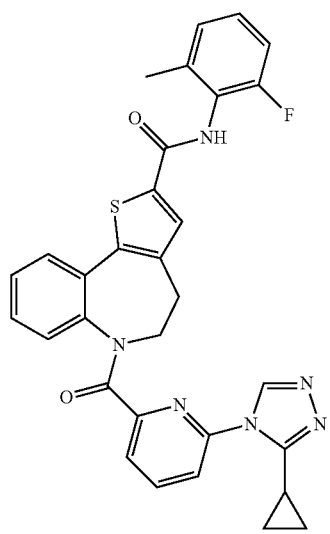 [SMILES: Cc1cccc(F)c1NC(=O)c1cc2c(s1)-c1ccccc1N(C(=O)c1cccc(-n3cnnc3C3CC3)n1)CC2] |
| 146 | 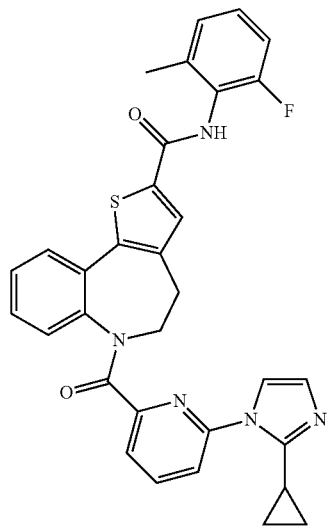 [SMILES: Cc1cccc(F)c1NC(=O)c1cc2c(s1)-c1ccccc1N(C(=O)c1cccc(-n3ccnc3C3CC3)n1)CC2] |
548
-continued
| Entry | Compound |
|---|---|
| 147 | 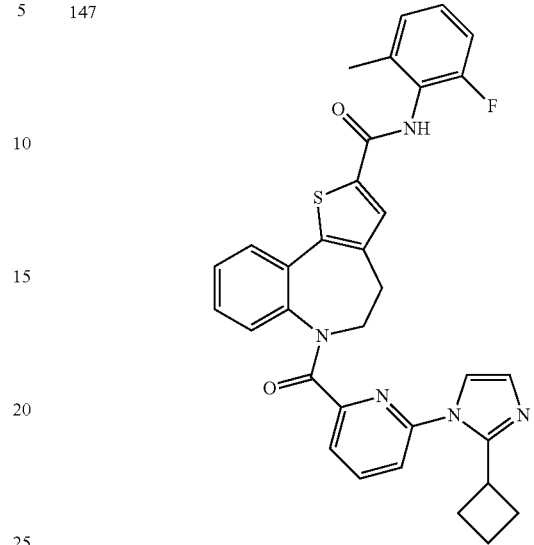 |
| 148 | 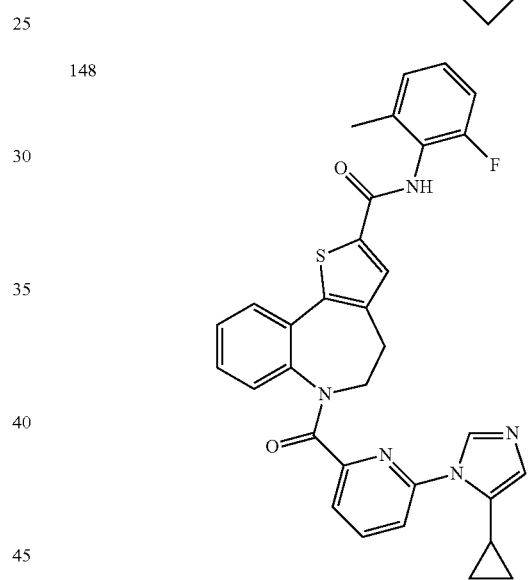 |
| 149 | 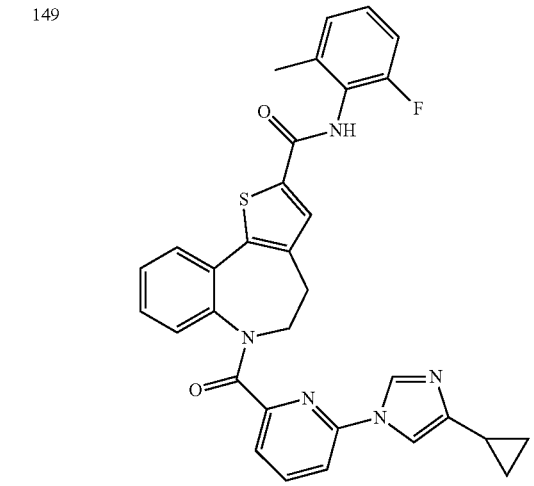 |

| Entry | Compound |
|---|---|
| 150 | (structure) |
| 151 | (structure) |
| 152 | (structure) |

| Entry | Compound |
|---|---|
| 153 | (structure) |
| 154 | (structure) |
| 155 | (structure) |
| 156 | (structure) |

| Entry | Compound |
|---|---|
| 157 | 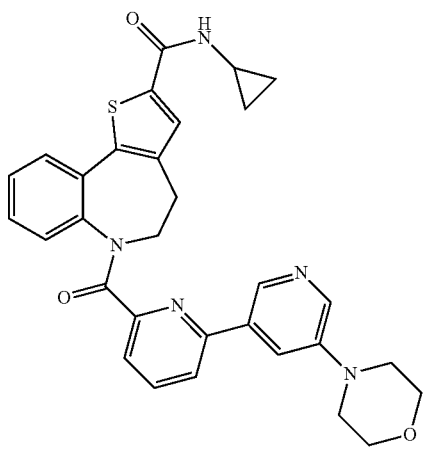 [SMILES: O=C(NC1CC1)c1cc2c(s1)-c1ccccc1N(C(=O)c1cccc(-c3cncc(N4CCOCC4)c3)n1)CC2] |
| 158 | 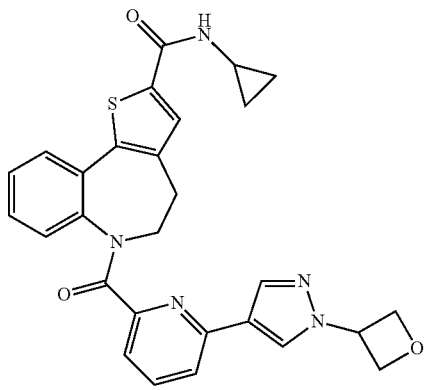 [SMILES: O=C(NC1CC1)c1cc2c(s1)-c1ccccc1N(C(=O)c1cccc(-c3cnn(C4COC4)c3)n1)CC2] |
| 159 | 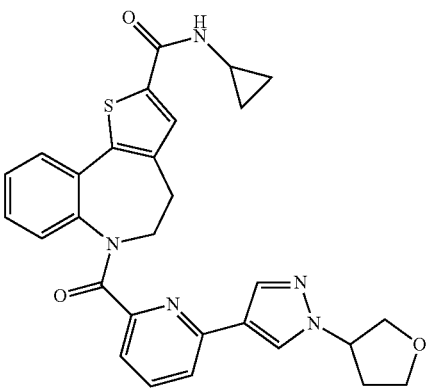 [SMILES: O=C(NC1CC1)c1cc2c(s1)-c1ccccc1N(C(=O)c1cccc(-c3cnn(C4CCOC4)c3)n1)CC2] |
| Entry | Compound |
|---|---|
| 160 | 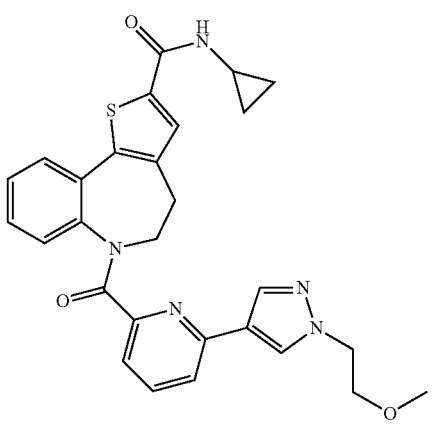 [SMILES: COCCn1cc(-c2cccc(C(=O)N3CCc4cc(C(=O)NC5CC5)sc4-c4ccccc43)n2)cn1] |
| 161 | 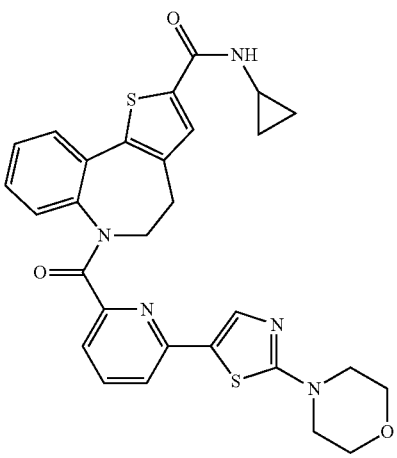 [SMILES: O=C(NC1CC1)c1cc2c(s1)-c1ccccc1N(C(=O)c1cccc(-c3cnc(N4CCOCC4)s3)n1)CC2] |
| 162 | 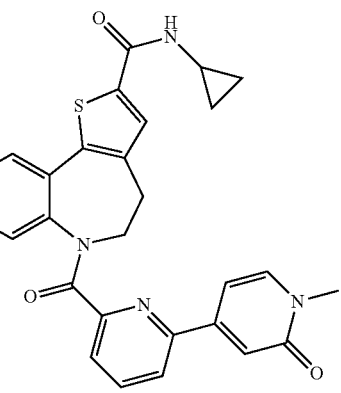 |

| Entry | Compound |
|---|---|
| 163 | 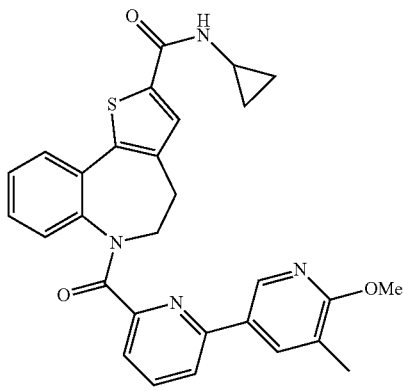 [SMILES: COc1ncc(-c2cccc(C(=O)N3CCc4cc(C(=O)NC5CC5)sc4-c4ccccc43)n2)cc1C] |
| 164 | 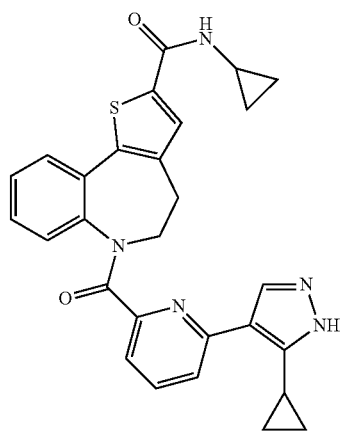 [SMILES: O=C(NC1CC1)c1cc2c(s1)-c1ccccc1N(C(=O)c1cccc(-c3cn[nH]c3C3CC3)n1)CC2] |
| 165 | 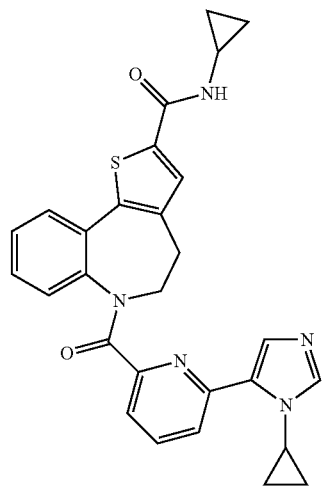 [SMILES: O=C(NC1CC1)c1cc2c(s1)-c1ccccc1N(C(=O)c1cccc(-c3cncn3C3CC3)n1)CC2] |
| Entry | Compound |
|---|---|
| 166 | 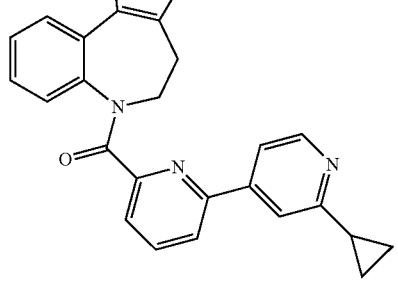 |
| 167 | 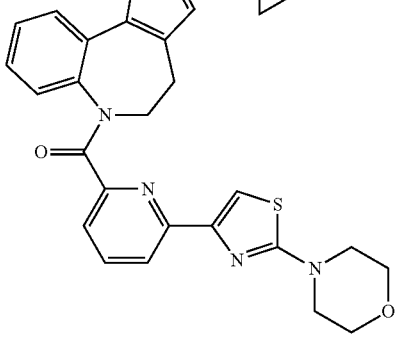 |
| 168 | 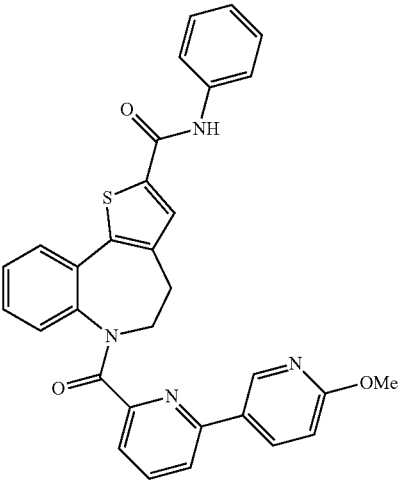 [SMILES: COc1ccc(-c2cccc(C(=O)N3CCc4cc(C(=O)Nc5ccccc5)sc4-c4ccccc43)n2)cn1] |

| Entry | Compound |
|---|---|
| 169 | 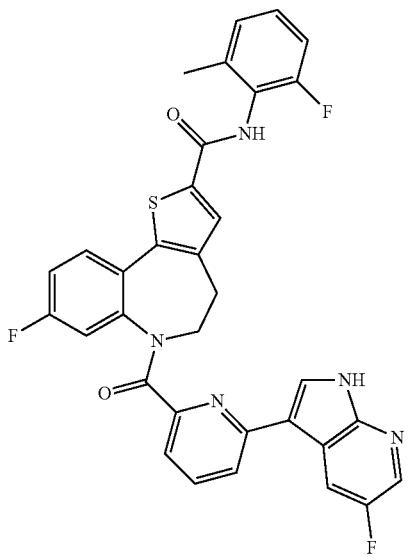 [SMILES: Cc1cccc(F)c1NC(=O)c1cc2c(s1)-c1ccc(F)cc1N(C(=O)c1cccc(-c3c[nH]c4ncc(F)cc34)n1)CC2] |
| 170 | 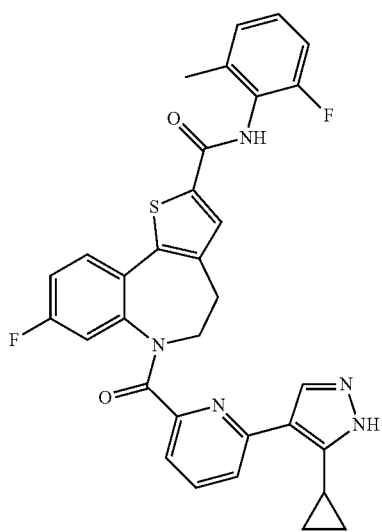 |
| 171 | 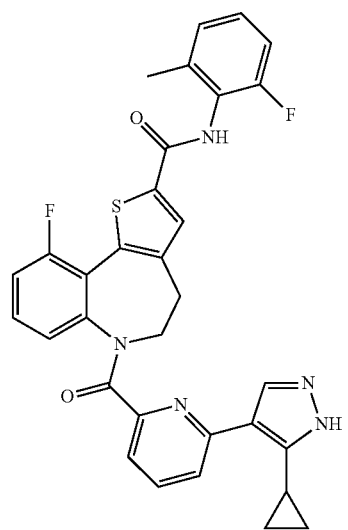 [SMILES: Cc1cccc(F)c1NC(=O)c1cc2c(s1)-c1c(F)cccc1N(C(=O)c1cccc(-c3cn[nH]c3C3CC3)n1)CC2] |
| Entry | Compound |
|---|---|
| 172 | 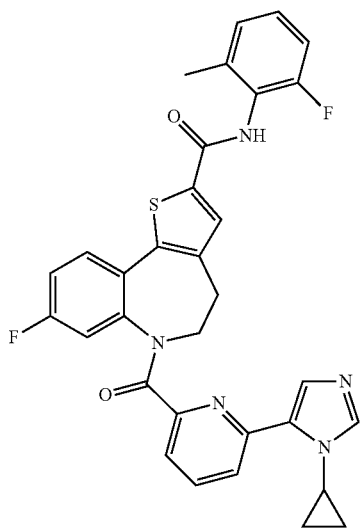 [SMILES: Cc1cccc(F)c1NC(=O)c1cc2c(s1)-c1ccc(F)cc1N(C(=O)c1cccc(-c3cncn3C3CC3)n1)CC2] |
| 173 | 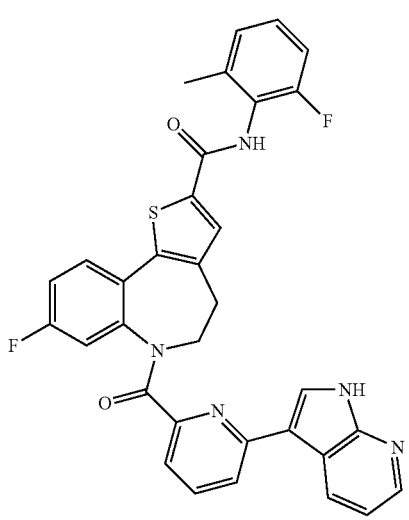 [SMILES: Cc1cccc(F)c1NC(=O)c1cc2c(s1)-c1ccc(F)cc1N(C(=O)c1cccc(-c3c[nH]c4ncccc34)n1)CC2] |
| 174 | 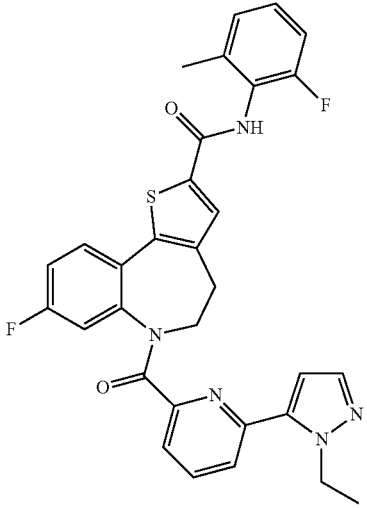 [SMILES: CCn1nccc1-c1cccc(C(=O)N2CCc3cc(C(=O)Nc4c(C)cccc4F)sc3-c3ccc(F)cc32)n1] |

| Entry | Compound |
|---|---|
| 175 | 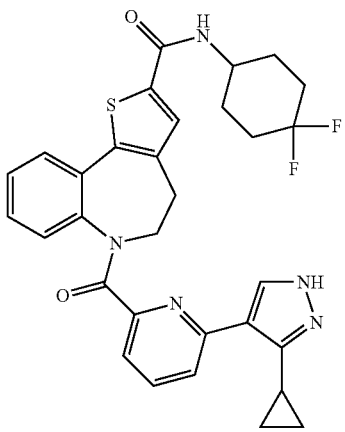 [SMILES: O=C(NC1CCC(F)(F)CC1)c1cc2c(s1)-c1ccccc1N(C(=O)c1cccc(-c3c[nH]nc3C3CC3)n1)CC2] |
| 176 | 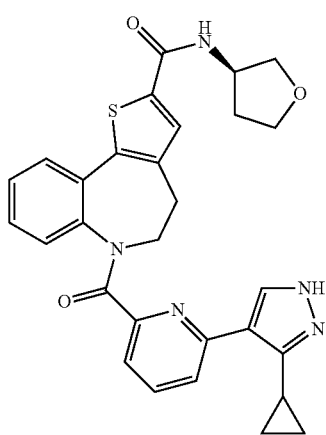 [SMILES: O=C(N[C@@H]1CCOC1)c1cc2c(s1)-c1ccccc1N(C(=O)c1cccc(-c3c[nH]nc3C3CC3)n1)CC2] |
| 177 | 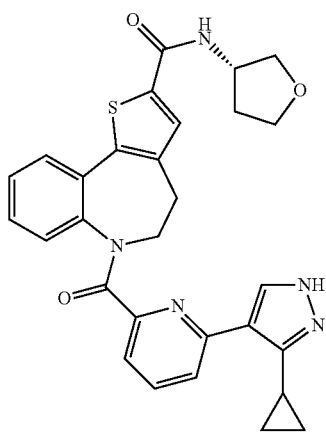 [SMILES: O=C(N[C@H]1CCOC1)c1cc2c(s1)-c1ccccc1N(C(=O)c1cccc(-c3c[nH]nc3C3CC3)n1)CC2] |
| Entry | Compound |
|---|---|
| 178 | 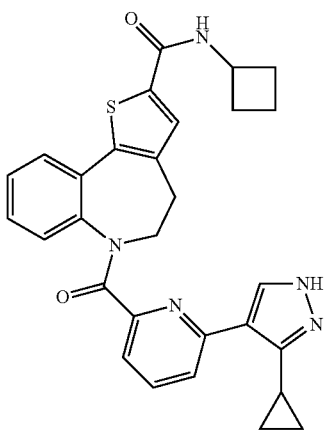 [SMILES: O=C(NC1CCC1)c1cc2c(s1)-c1ccccc1N(C(=O)c1cccc(-c3c[nH]nc3C3CC3)n1)CC2] |
| 179 | 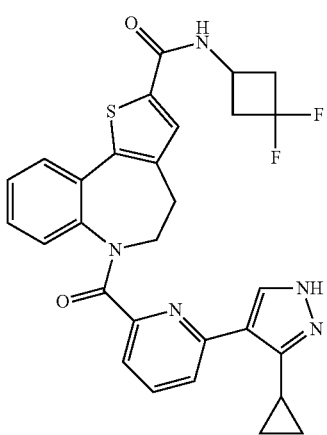 [SMILES: O=C(NC1CC(F)(F)C1)c1cc2c(s1)-c1ccccc1N(C(=O)c1cccc(-c3c[nH]nc3C3CC3)n1)CC2] |
| 180 | 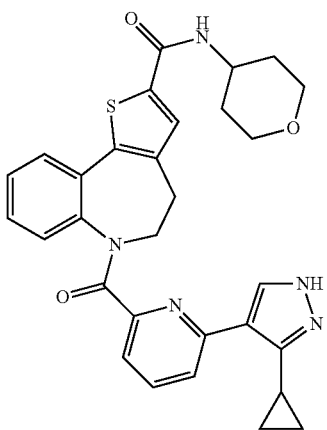 [SMILES: O=C(NC1CCOCC1)c1cc2c(s1)-c1ccccc1N(C(=O)c1cccc(-c3c[nH]nc3C3CC3)n1)CC2] |

| Entry | Compound |
|---|---|
| 181 | 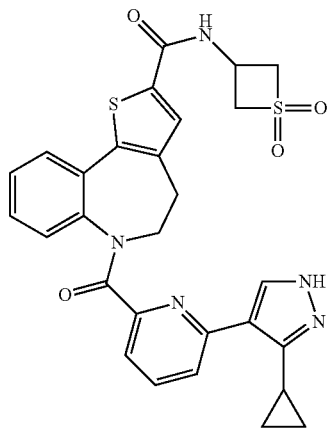 [SMILES: O=C(NC1CS(=O)(=O)C1)c1cc2c(s1)-c1ccccc1N(C(=O)c1cccc(-c3c[nH]nc3C3CC3)n1)CC2] |
| 182 | 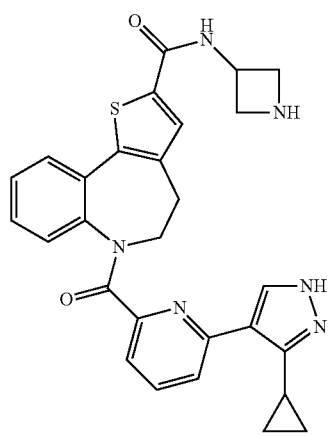 |
| 183 | 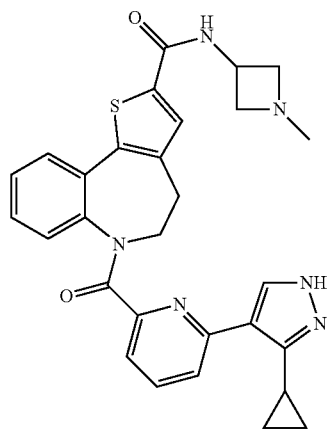 [SMILES: CN1CC(NC(=O)c2cc3c(s2)-c2ccccc2N(C(=O)c2cccc(-c4c[nH]nc4C4CC4)n2)CC3)C1] |
| Entry | Compound |
|---|---|
| 184 | 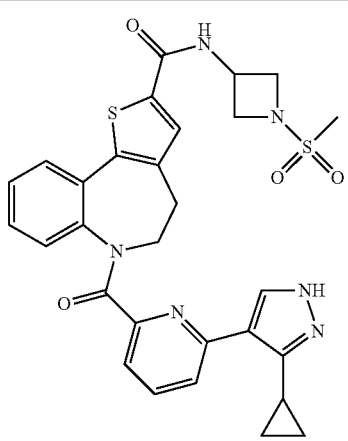 [SMILES: CS(=O)(=O)N1CC(NC(=O)c2cc3c(s2)-c2ccccc2N(C(=O)c2cccc(-c4c[nH]nc4C4CC4)n2)CC3)C1] |
| 185 | 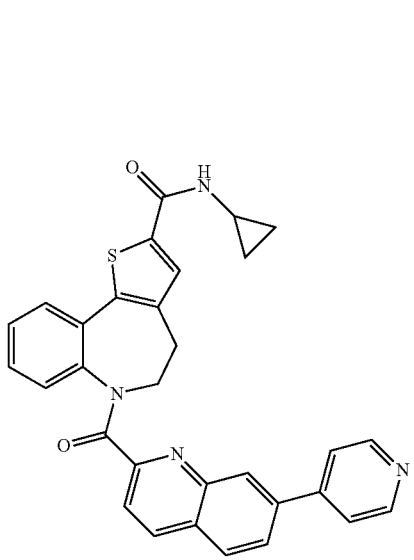 [SMILES: O=C(NC1CC1)c1cc2c(s1)-c1ccccc1N(C(=O)c1ccc3ccc(-c4ccncc4)cc3n1)CC2] |
| 186 | |

| Entry | Compound |
|---|---|
| 187 | 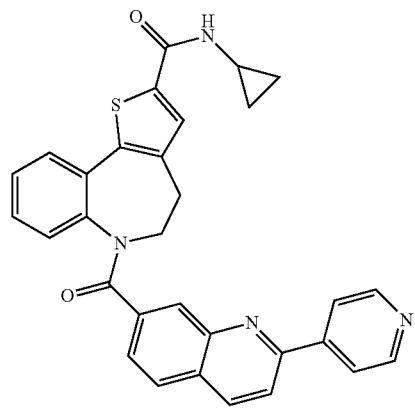 [SMILES: O=C(NC1CC1)c1cc2c(s1)-c1ccccc1N(C(=O)c1ccc3ccc(-c4ccncc4)nc3c1)CC2] |
| 188 | 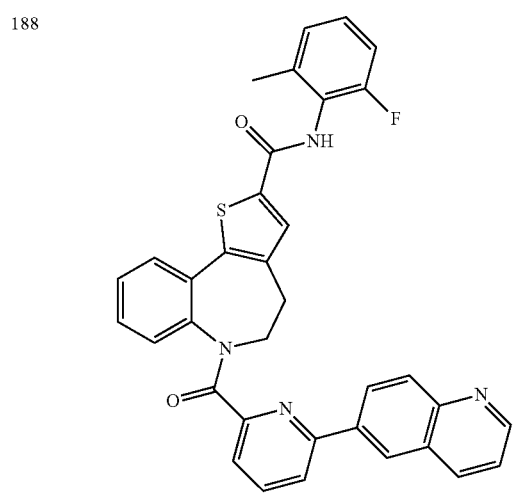 |
| 189 | 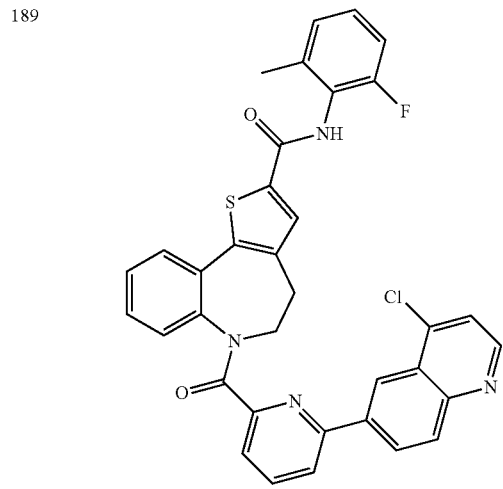 |
| Entry | Compound |
|---|---|
| 190 | 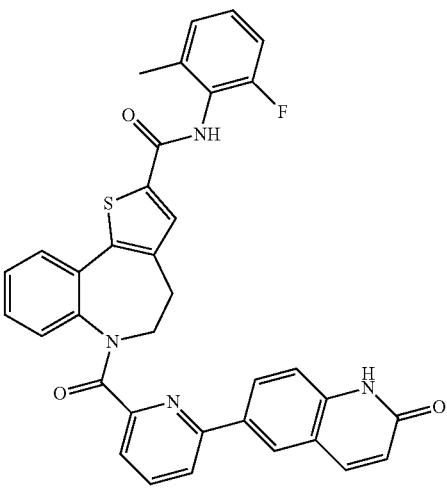 [SMILES: Cc1cccc(F)c1NC(=O)c1cc2c(s1)-c1ccccc1N(C(=O)c1cccc(-c3ccc4[nH]c(=O)ccc4c3)n1)CC2] |
| 191 | 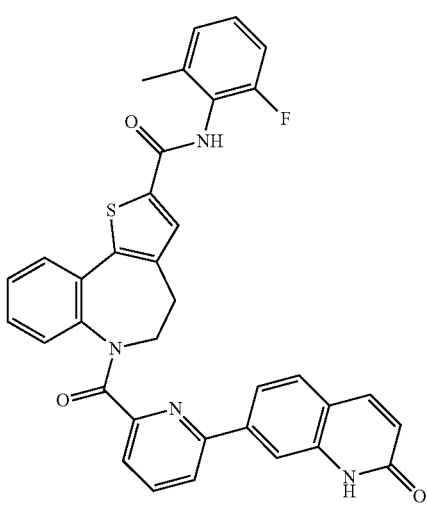 [SMILES: Cc1cccc(F)c1NC(=O)c1cc2c(s1)-c1ccccc1N(C(=O)c1cccc(-c3ccc4ccc(=O)[nH]c4c3)n1)CC2] |
| 192 | 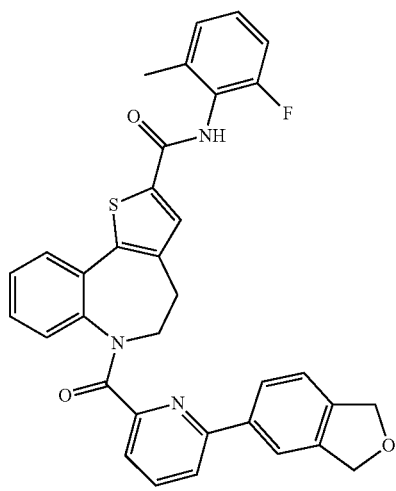 [SMILES: Cc1cccc(F)c1NC(=O)c1cc2c(s1)-c1ccccc1N(C(=O)c1cccc(-c3ccc4c(c3)COC4)n1)CC2] |

| Entry | Compound |
|---|---|
| 193 | (structure) |
| 194 | (structure) |
| 195 | (structure) |
| 196 | (structure) |
| 197 | (structure) |
| 198 | (structure) |

| Entry | Compound |
|---|---|
| 199 | (structure) |
| 200 | (structure) |
| 201 | (structure) |

| Entry | Compound |
|---|---|
| 202 | (structure) |
| 203 | (structure) |

| Entry | Compound |
|---|---|
| 204 | 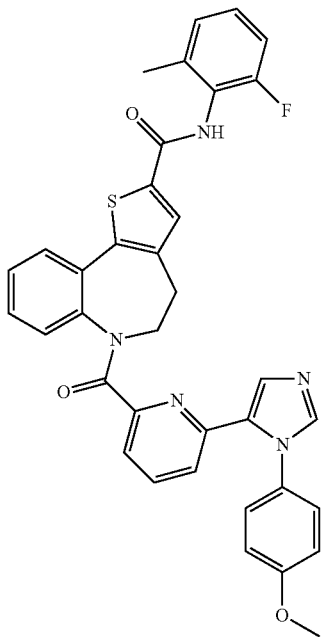 [SMILES: COc1ccc(-n2cncc2-c2cccc(C(=O)N3CCc4cc(C(=O)Nc5c(C)cccc5F)sc4-c4ccccc43)n2)cc1] |
| 205 | 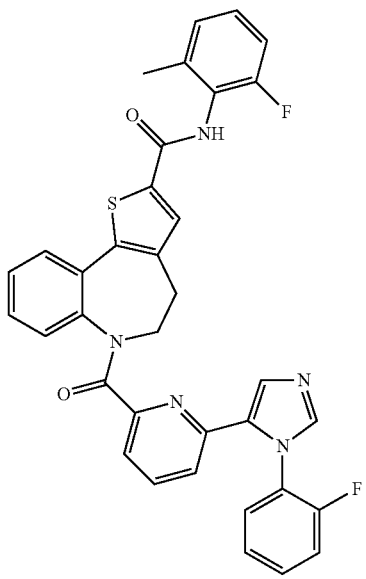 [SMILES: Cc1cccc(F)c1NC(=O)c1cc2c(s1)-c1ccccc1N(C(=O)c1cccc(-c3cncn3-c3ccccc3F)n1)CC2] |
| Entry | Compound |
|---|---|
| 206 | 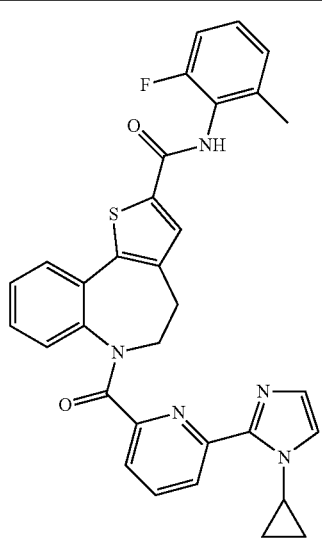 |
| 207 | 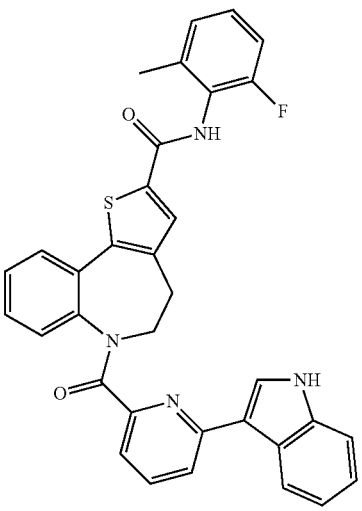 [SMILES: Cc1cccc(F)c1NC(=O)c1cc2c(s1)-c1ccccc1N(C(=O)c1cccc(-c3c[nH]c4ccccc34)n1)CC2] |
| 208 | 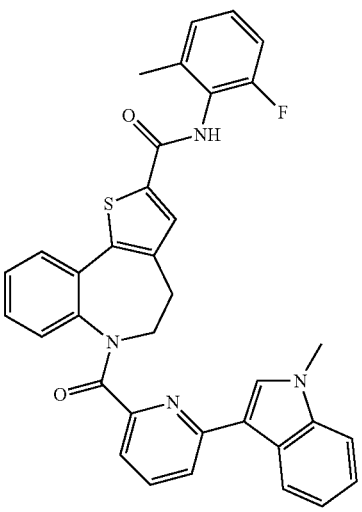 [SMILES: Cc1cccc(F)c1NC(=O)c1cc2c(s1)-c1ccccc1N(C(=O)c1cccc(-c3cn(C)c4ccccc34)n1)CC2] |

US 10,759,816 B2
| | 569 -continued | | 570 -continued |
|---|---|---|---|
| Entry | Compound | Entry | Compound |
| 209 | 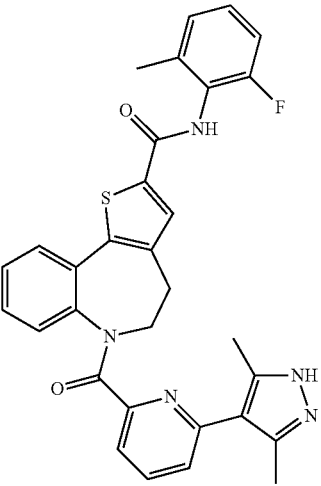 [SMILES: Cc1cccc(F)c1NC(=O)c1cc2c(s1)-c1ccccc1N(C(=O)c1cccc(-c3c(C)n[nH]c3C)n1)CC2] | 212 | 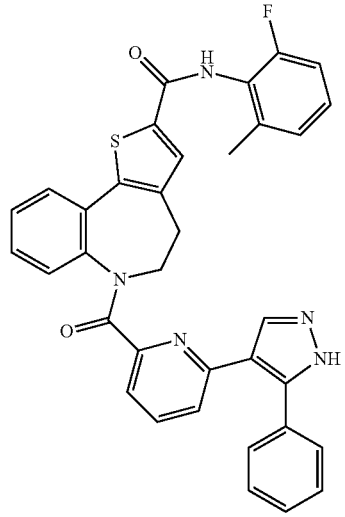 |
| 210 | 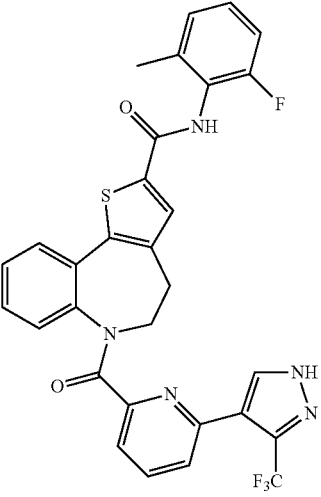 [SMILES: Cc1cccc(F)c1NC(=O)c1cc2c(s1)-c1ccccc1N(C(=O)c1cccc(-c3c[nH]nc3C(F)(F)F)n1)CC2] | 213 | 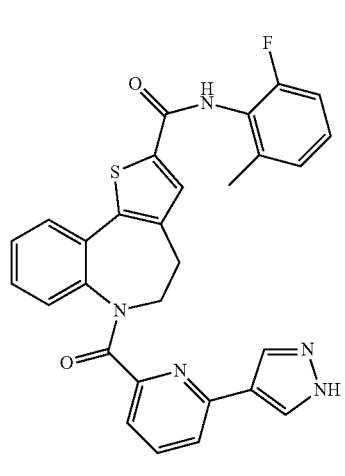 |
| 211 | 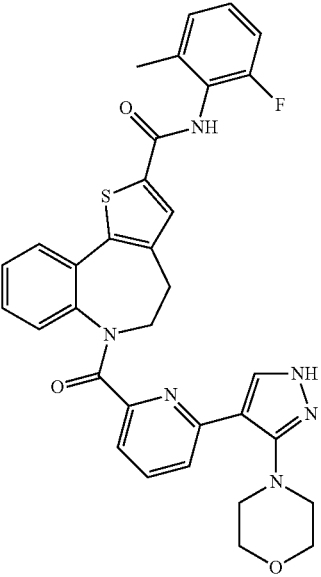 [SMILES: Cc1cccc(F)c1NC(=O)c1cc2c(s1)-c1ccccc1N(C(=O)c1cccc(-c3c[nH]nc3N3CCOCC3)n1)CC2] | 214 | 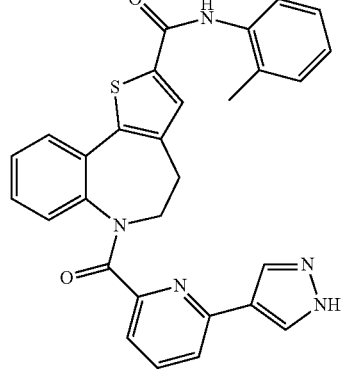 |

571
-continued

| Entry | Compound |
|---|---|
| 215 | (structure) |
| 216 | (structure) |
| 217 | (structure) |

572
-continued

| Entry | Compound |
|---|---|
| 218 | (structure) |
| 219 | (structure) |
| 220 | (structure) |

573
-continued
| Entry | Compound |
|---|---|
| 221 | 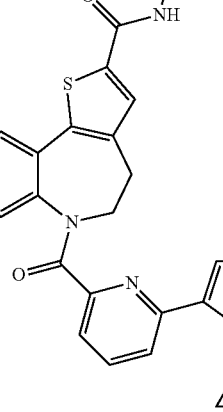 |
| 222 | 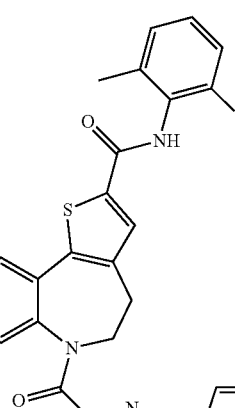 |
| 223 | 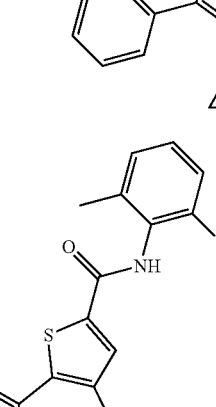 |
574
-continued
| Entry | Compound |
|---|---|
| 224 | 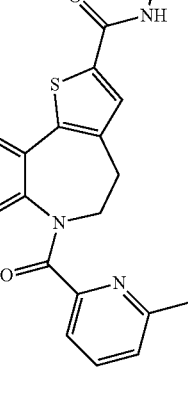 |
| 225 | 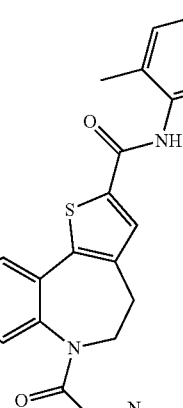 |
| 226 | 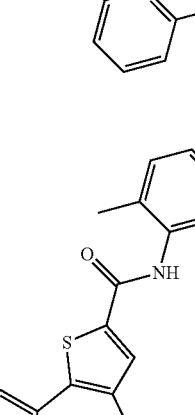 |

575
-continued
| Entry | Compound |
|---|---|
| 227 | 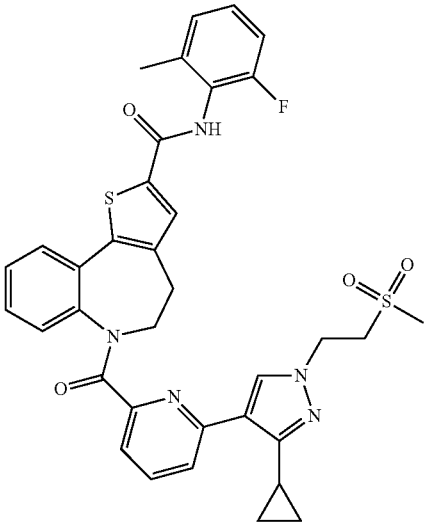 [SMILES: Cc1cccc(F)c1NC(=O)c1cc2c(s1)-c1ccccc1N(C(=O)c1cccc(-c3cn(CCS(C)(=O)=O)nc3C3CC3)n1)CC2] |
| 228 | 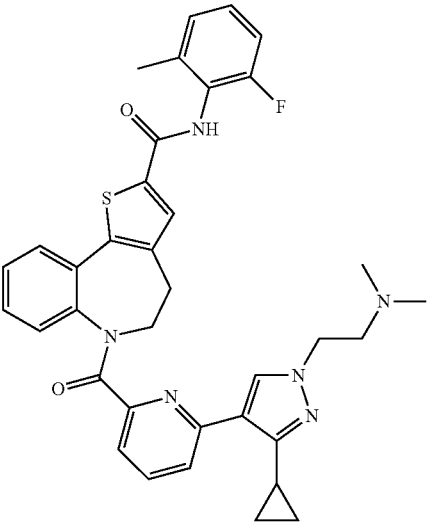 [SMILES: Cc1cccc(F)c1NC(=O)c1cc2c(s1)-c1ccccc1N(C(=O)c1cccc(-c3cn(CCN(C)C)nc3C3CC3)n1)CC2] |
| 229 | 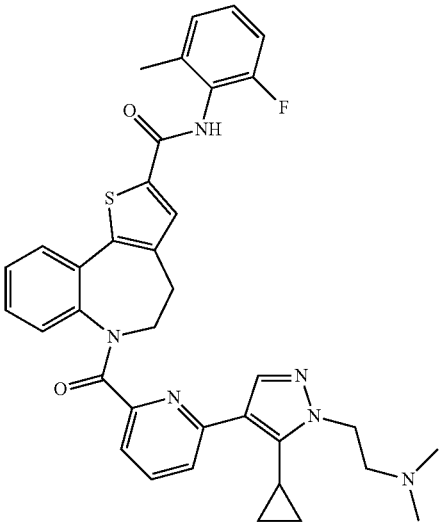 [SMILES: Cc1cccc(F)c1NC(=O)c1cc2c(s1)-c1ccccc1N(C(=O)c1cccc(-c3cnn(CCN(C)C)c3C3CC3)n1)CC2] |
576
-continued
| Entry | Compound |
|---|---|
| 230 | 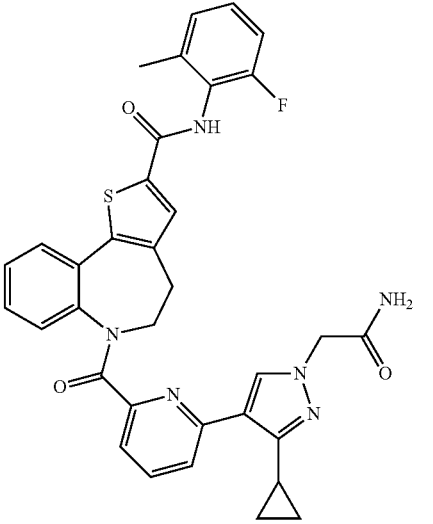 [SMILES: Cc1cccc(F)c1NC(=O)c1cc2c(s1)-c1ccccc1N(C(=O)c1cccc(-c3cn(CC(N)=O)nc3C3CC3)n1)CC2] |
| 231 | 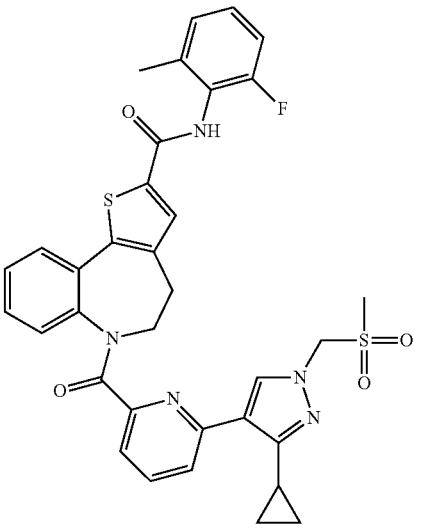 [SMILES: Cc1cccc(F)c1NC(=O)c1cc2c(s1)-c1ccccc1N(C(=O)c1cccc(-c3cn(CS(C)(=O)=O)nc3C3CC3)n1)CC2] |
| 232 | 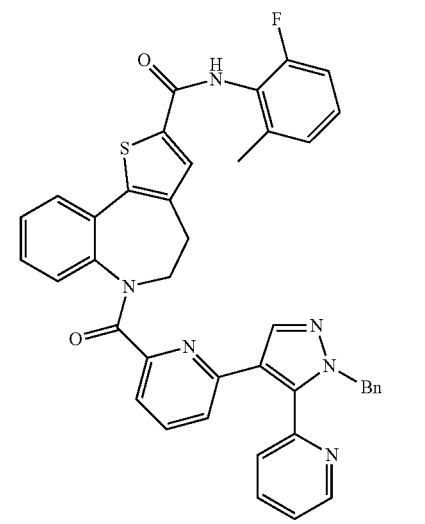 [SMILES: Cc1cccc(F)c1NC(=O)c1cc2c(s1)-c1ccccc1N(C(=O)c1cccc(-c3cnn(Cc4ccccc4)c3-c3ccccn3)n1)CC2] |

| Entry | Compound |
|---|---|
| 233 | (structure) |
| 234 | (structure) |
| 235 | (structure) |
| 236 | (structure) |
| 237 | (structure) |
| 238 | (structure) |

579
-continued

| Entry | Compound |
|---|---|
| 239 | |
| 240 | |
| 241 | |

580
-continued

| Entry | Compound |
|---|---|
| 242 | |
| 243 | |
| 244 | |

| Entry | Compound |
|---|---|
| 245 | 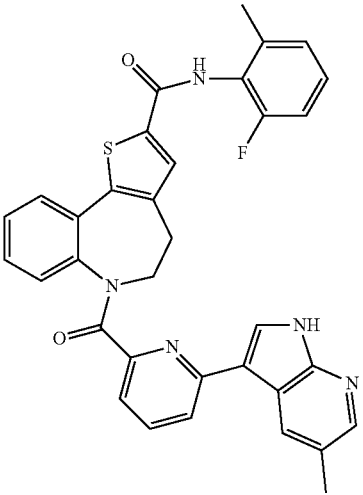 [SMILES: Cc1cnc2[nH]cc(-c3cccc(C(=O)N4CCc5cc(C(=O)Nc6c(C)cccc6F)sc5-c5ccccc54)n3)c2c1] |
| 246 | 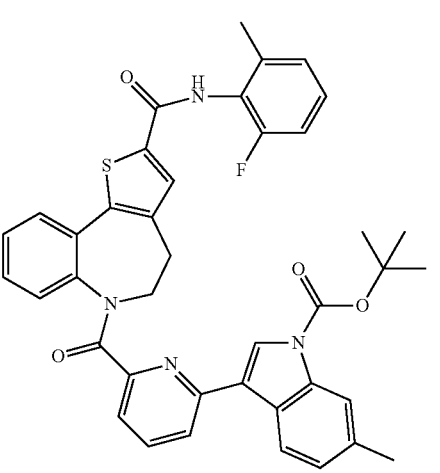 [SMILES: Cc1ccc2c(-c3cccc(C(=O)N4CCc5cc(C(=O)Nc6c(C)cccc6F)sc5-c5ccccc54)n3)cn(C(=O)OC(C)(C)C)c2c1] |
| 247 | 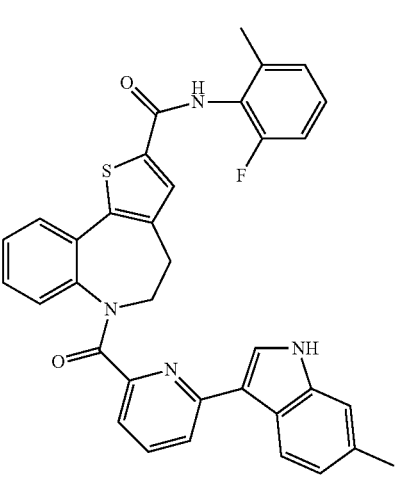 [SMILES: Cc1ccc2c(-c3cccc(C(=O)N4CCc5cc(C(=O)Nc6c(C)cccc6F)sc5-c5ccccc54)n3)c[nH]c2c1] |
| Entry | Compound |
|---|---|
| 248 | 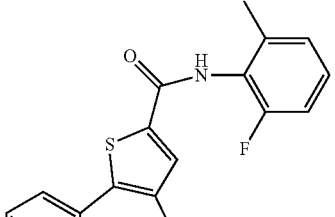 |
| 249 | 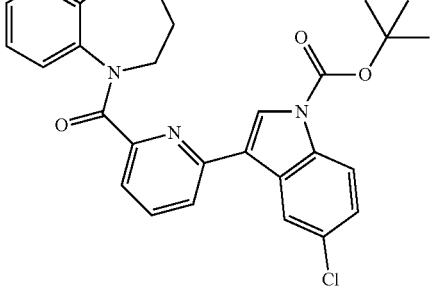 |
| 250 |  |

| Entry | Compound |
|---|---|
| 251 | 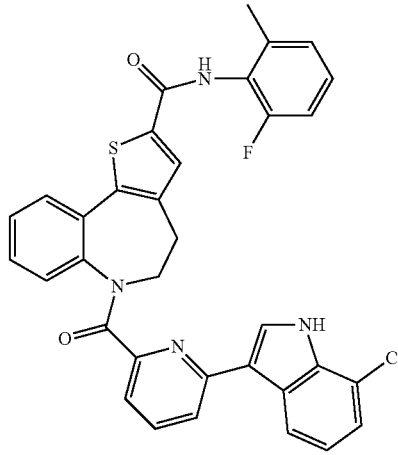 |
| 252 | 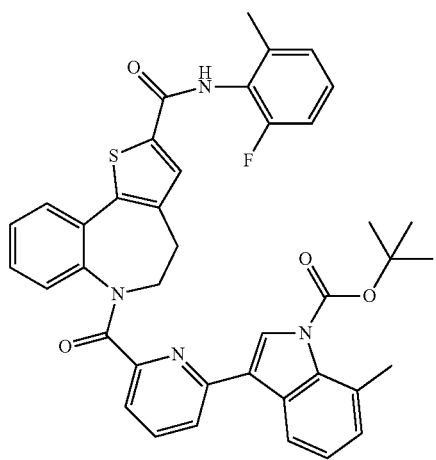 [SMILES: Cc1cccc(F)c1NC(=O)c1cc2c(s1)-c1ccccc1N(C(=O)c1cccc(-c3cn(C(=O)OC(C)(C)C)c4c(C)cccc34)n1)CC2] |
| 253 | 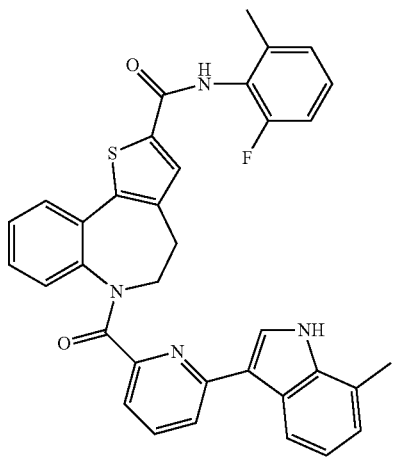 [SMILES: Cc1cccc(F)c1NC(=O)c1cc2c(s1)-c1ccccc1N(C(=O)c1cccc(-c3c[nH]c4c(C)cccc34)n1)CC2] |
| Entry | Compound |
|---|---|
| 254 | 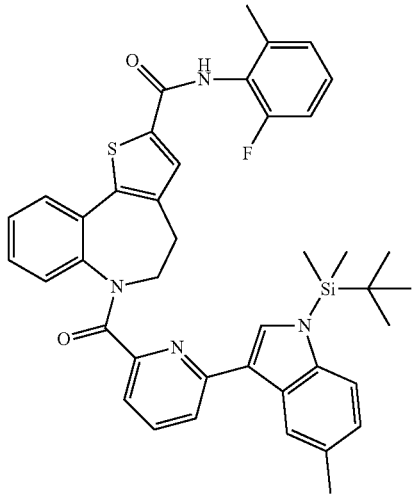 [SMILES: Cc1ccc2c(c1)c(-c1cccc(C(=O)N3CCc4cc(C(=O)Nc5c(C)cccc5F)sc4-c4ccccc43)n1)cn2[Si](C)(C)C(C)(C)C] |
| 255 | 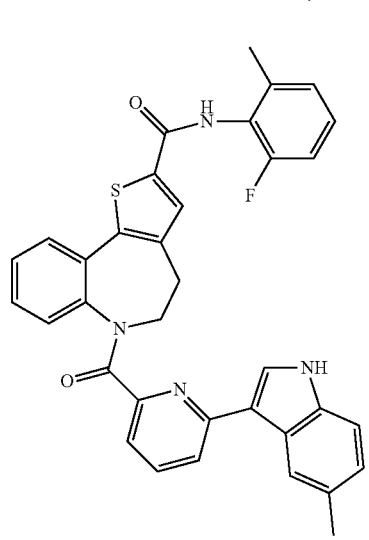 |
| 256 | 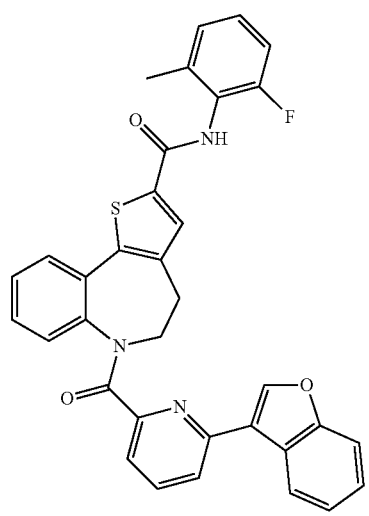 [SMILES: Cc1cccc(F)c1NC(=O)c1cc2c(s1)-c1ccccc1N(C(=O)c1cccc(-c3coc4ccccc34)n1)CC2] |

| Entry | Compound |
|---|---|
| 257 | |
| 258 | |
| 259 | |
| 260 | |
| 261 | |
| 262 | |

| Entry | Compound |
|---|---|
| 263 | 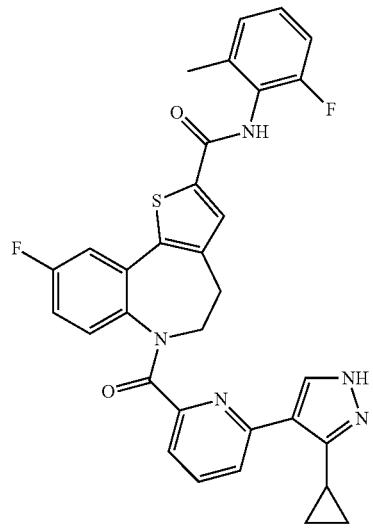 [SMILES: Cc1cccc(F)c1NC(=O)c1cc2c(s1)-c1cc(F)ccc1N(C(=O)c1cccc(-c3c[nH]nc3C3CC3)n1)CC2] |
| 264 | 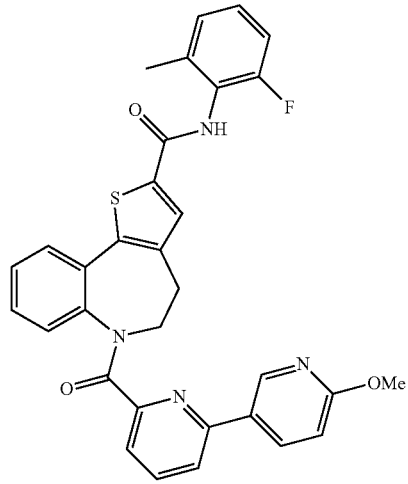 [SMILES: COc1ccc(-c2cccc(C(=O)N3CCc4cc(C(=O)Nc5c(C)cccc5F)sc4-c4ccccc43)n2)cn1] |
| Entry | Compound |
|---|---|
| 265 | 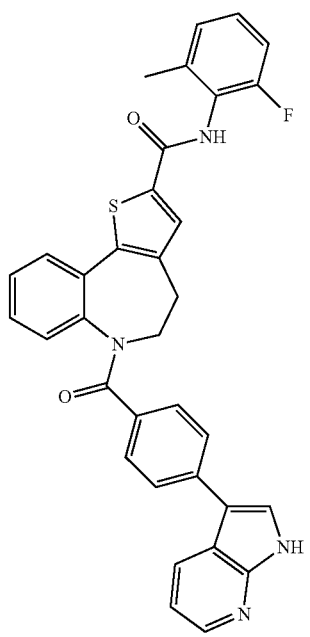 [SMILES: Cc1cccc(F)c1NC(=O)c1cc2c(s1)-c1ccccc1N(C(=O)c1ccc(-c3c[nH]c4ncccc34)cc1)CC2] |
| 266 | |

| 589 -continued | | 590 -continued | |
|---|---|---|---|
| Entry | Compound | Entry | Compound |
| 273 | 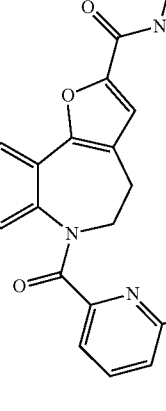 | 276 | 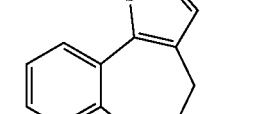 |
| 274 | 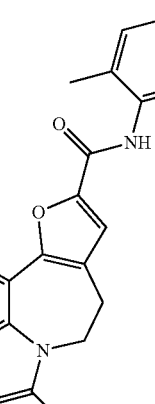 | 277 | 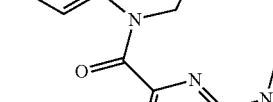 |
| 275 | 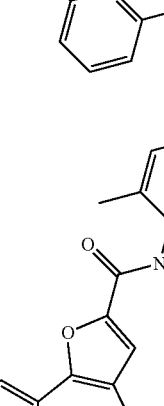 | 278 | 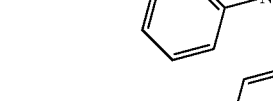 |

591
-continued
| Entry | Compound |
|---|---|
| 279 | 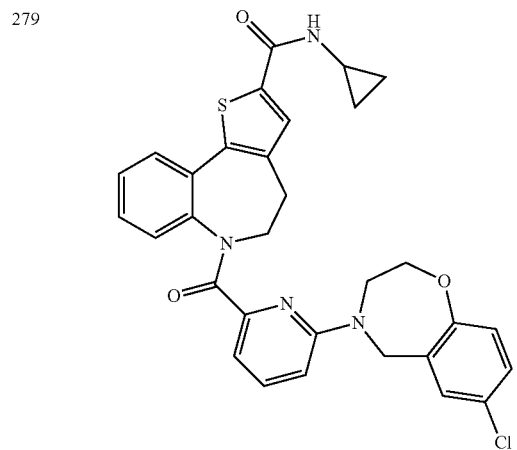 |
| 280 | 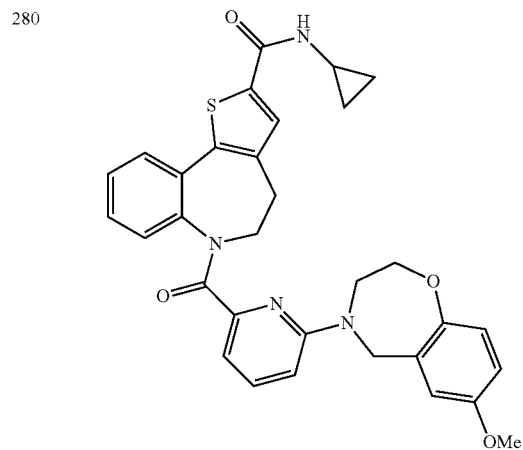 |
| 281 | 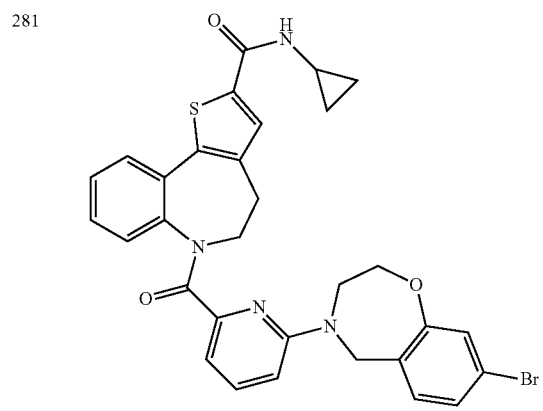 |
592
-continued
| Entry | Compound |
|---|---|
| 282 | 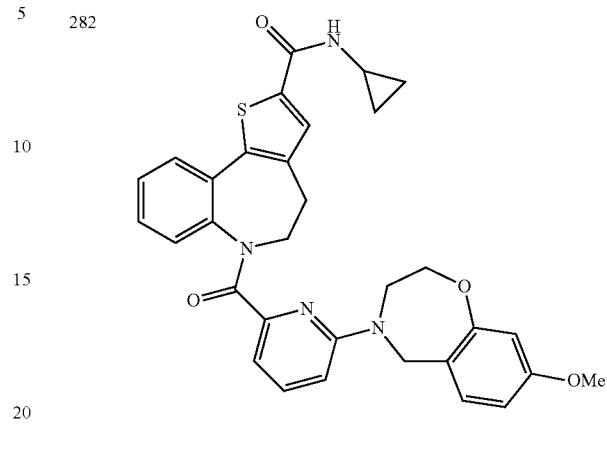 |
| 283 | 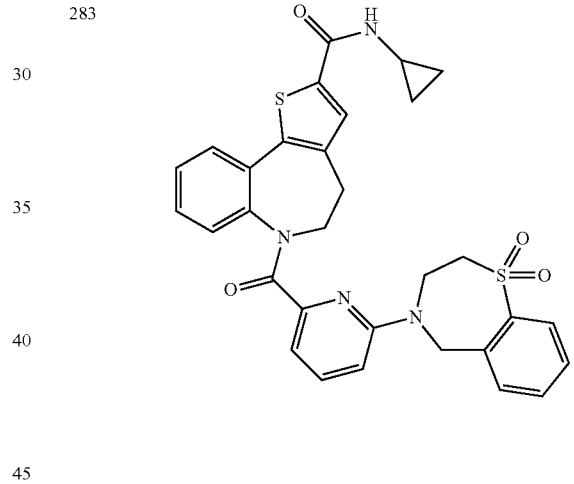 |
| 284 | 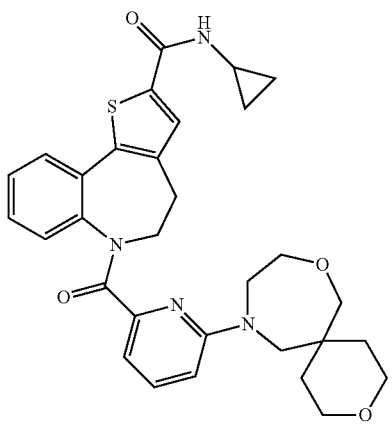 [SMILES: O=C(NC1CC1)c1cc2c(s1)-c1ccccc1N(C(=O)c1cccc(N3CCOCC4(CCOCC4)C3)n1)CC2] |

593
-continued

| Entry | Compound |
|---|---|
| 285 | |
| 286 | |
| 287 | |
| 288 | |

594
-continued

| Entry | Compound |
|---|---|
| 289 | |
| 290 | |
| 291 | |

| Entry | Compound |
|---|---|
| 292 | 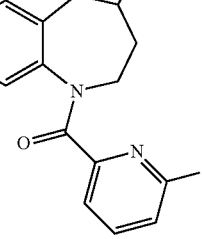 |
| 293 | 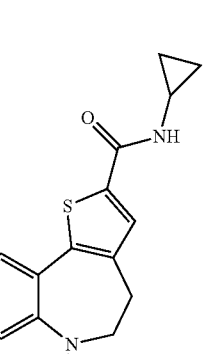 |
| 294 | 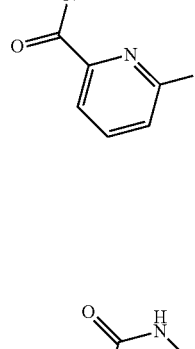 |
| Entry | Compound |
|---|---|
| 295 | 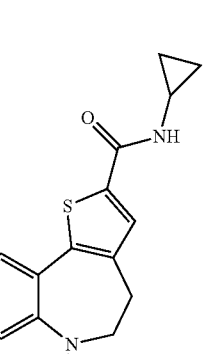 |
| 296 | 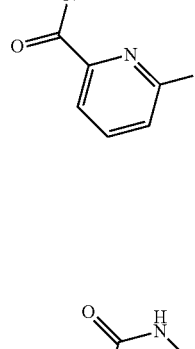 |
| 297 | 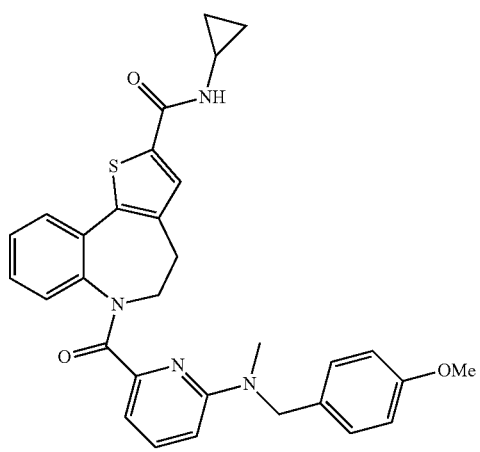 [SMILES: COc1ccc(CN(C)c2cccc(C(=O)N3CCc4cc(C(=O)NC5CC5)sc4-c4ccccc43)n2)cc1] |

597

-continued

| Entry | Compound |
|---|---|
| 298 | |
| 299 | |
| 300 | |

598

-continued

| Entry | Compound |
|---|---|
| 301 | |
| 302 | |
| 303 | |

-continued

| Entry | Compound |
|---|---|
| 304 | |
| 305 | |
| 306 | |

-continued

| Entry | Compound |
|---|---|
| 307 | |
| 308 | |
| 309 | |

| Entry | Compound |
|---|---|
| 310 | 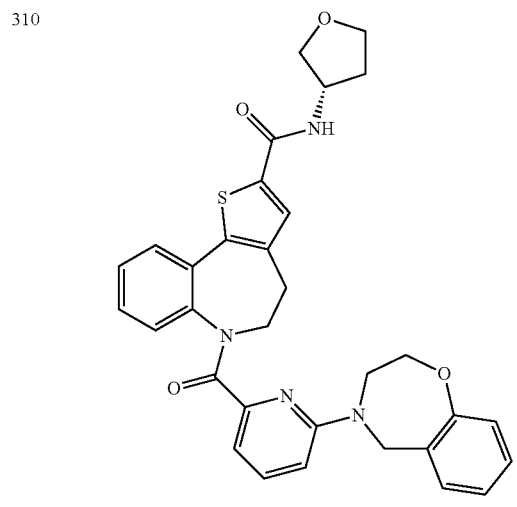 |
| 311 | 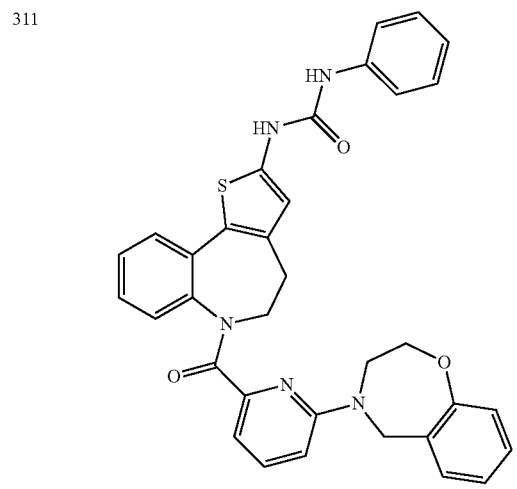 |
| 312 | 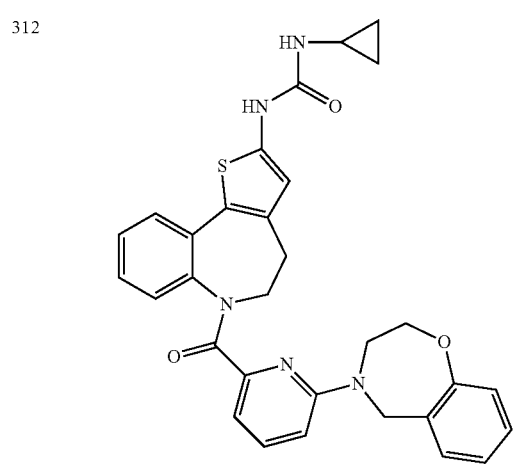 |
| Entry | Compound |
|---|---|
| 313 | 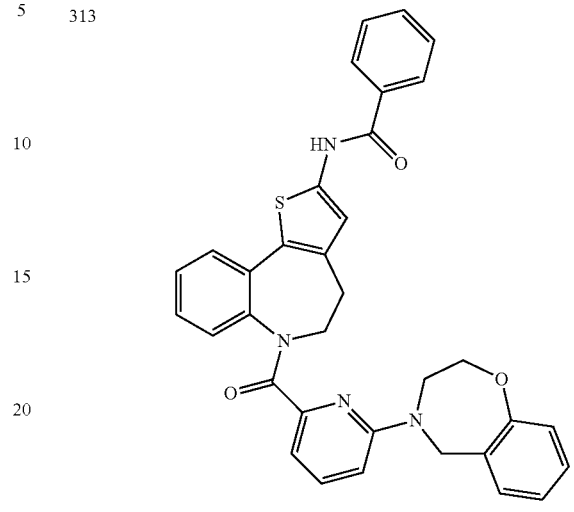 |
| 314 | 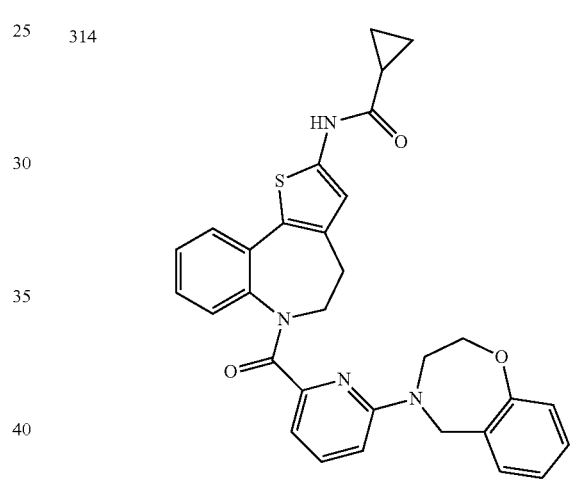 |
| 315 | 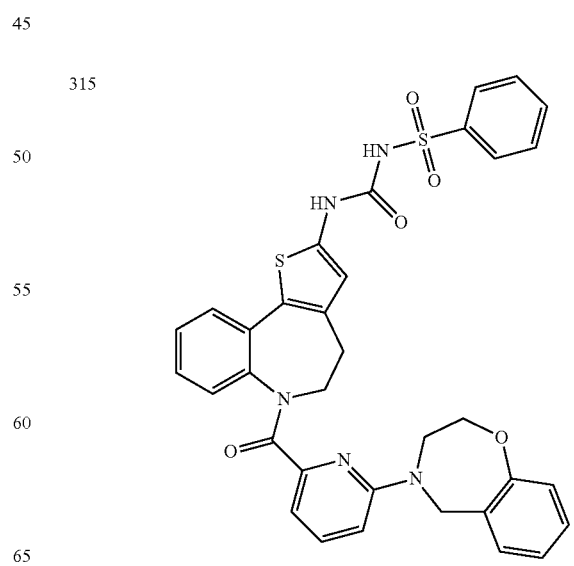 |

| Entry | Compound |
|---|---|
| 316 | 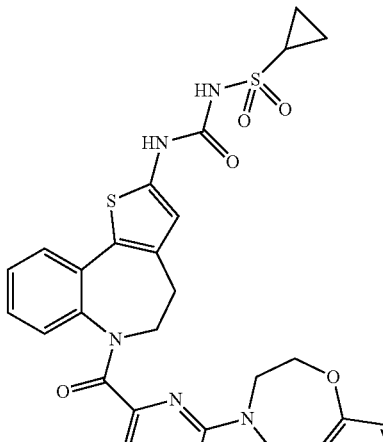 |
| 317 | |
| 318 | |
| Entry | Compound |
|---|---|
| 319 | 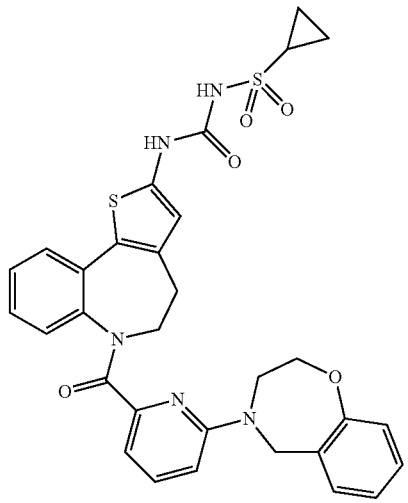 [SMILES: O=C(Nc1cc2c(s1)-c1ccccc1N(C(=O)c1cccc(N3CCOc4ccccc4C3)n1)CC2)NS(=O)(=O)C1CC1] |
| 320 | 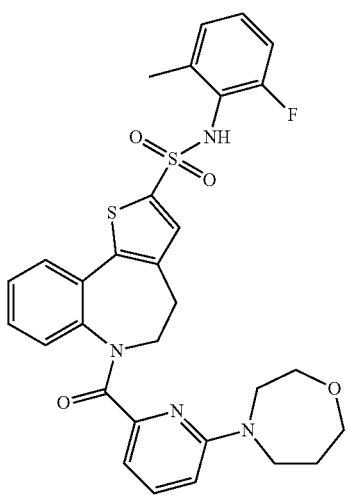 [SMILES: Cc1cccc(F)c1NS(=O)(=O)c1cc2c(s1)-c1ccccc1N(C(=O)c1cccc(N3CCCOCC3)n1)CC2] |
| 321 | 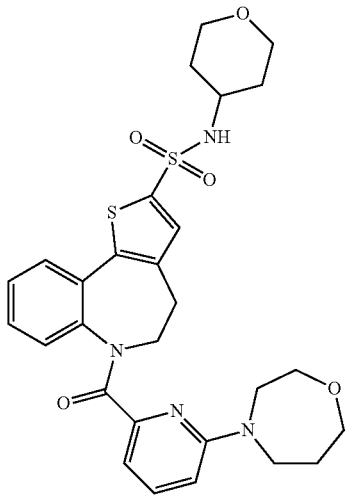 [SMILES: O=C(c1cccc(N2CCCOCC2)n1)N1CCc2cc(S(=O)(=O)NC3CCOCC3)sc2-c2ccccc21] |

| Entry | Compound |
|---|---|
| 322 | |
| 323 | |
| 324 | |
| 325 | |
| 326 | |
| 327 | |

| Entry | Compound |
|---|---|
| 328 | (structure) |
| 329 | (structure) |
| 330 | (structure) |
| 331 | (structure) |
| 332 | (structure) |
| 333 | (structure) |

609
-continued

| Entry | Compound |
|---|---|
| 334 | (structure) |
| 335 | (structure) |
| 336 | (structure) |

610
-continued

| Entry | Compound |
|---|---|
| 337 | (structure) |
| 338 | (structure) |
| 339 | (structure) |

611
-continued

| Entry | Compound |
|---|---|
| 340 | (structure) |
| 341 | (structure) |
| 342 | (structure) |

612
-continued

| Entry | Compound |
|---|---|
| 343 | (structure) |
| 344 | (structure) |
| 345 | (structure) |

| Entry | Compound |
|---|---|
| 346 | 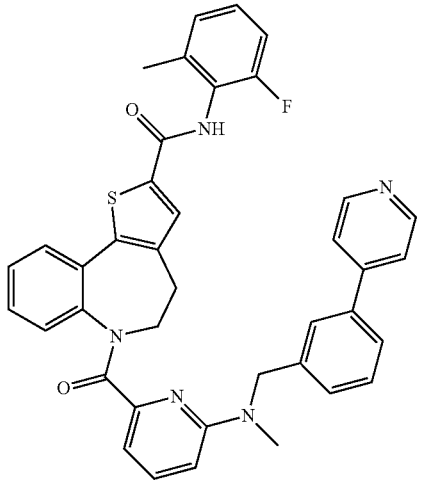 [SMILES: Cc1cccc(F)c1NC(=O)c1cc2c(s1)-c1ccccc1N(C(=O)c1cccc(N(C)Cc3cccc(-c4ccncc4)c3)n1)CC2] |
| 347 | 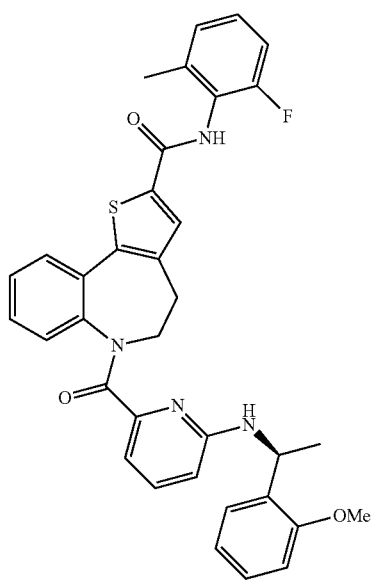 [SMILES: COc1ccccc1[C@H](C)Nc1cccc(C(=O)N2CCc3cc(C(=O)Nc4c(C)cccc4F)sc3-c3ccccc32)n1] |
| 348 | 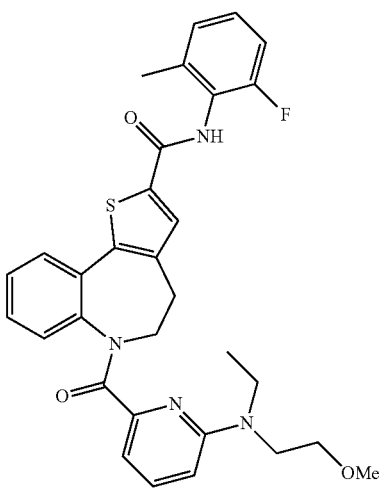 [SMILES: CCN(CCOC)c1cccc(C(=O)N2CCc3cc(C(=O)Nc4c(C)cccc4F)sc3-c3ccccc32)n1] |
| 349 | 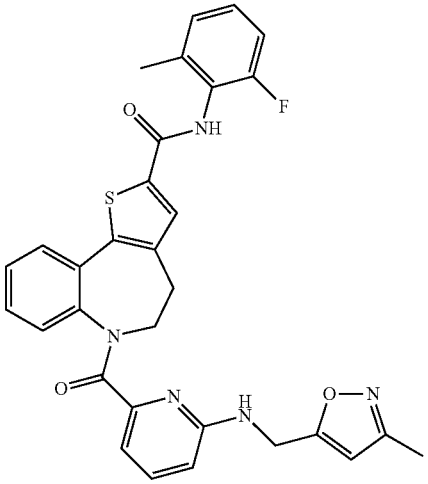 [SMILES: Cc1cc(CNc2cccc(C(=O)N3CCc4cc(C(=O)Nc5c(C)cccc5F)sc4-c4ccccc43)n2)on1] |
| 350 | 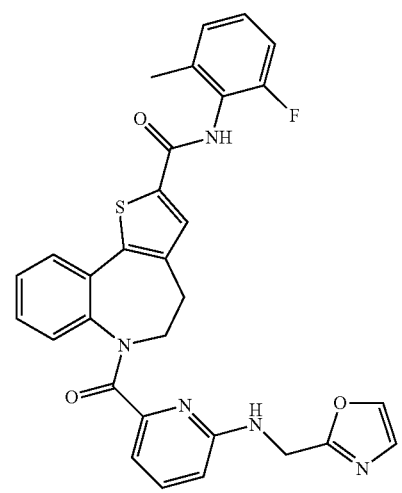 [SMILES: Cc1cccc(F)c1NC(=O)c1cc2c(s1)-c1ccccc1N(C(=O)c1cccc(NCc3ncco3)n1)CC2] |
| 351 | 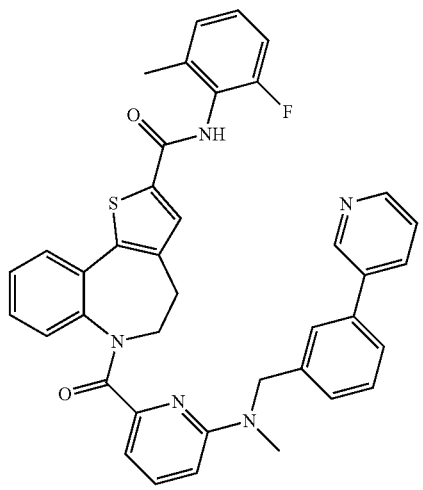 [SMILES: Cc1cccc(F)c1NC(=O)c1cc2c(s1)-c1ccccc1N(C(=O)c1cccc(N(C)Cc3cccc(-c4cccnc4)c3)n1)CC2] |

615
-continued

| Entry | Compound |
|---|---|
| 352 | |
| 353 | |
| 354 | |

616
-continued

| Entry | Compound |
|---|---|
| 355 | |
| 356 | |
| 357 | |

| Entry | Compound |
|---|---|
| 358 | |
| 359 | |
| 360 | |
| 361 | |
| 362 | |
| 363 | |

| Entry | Compound |
|---|---|
| 364 | 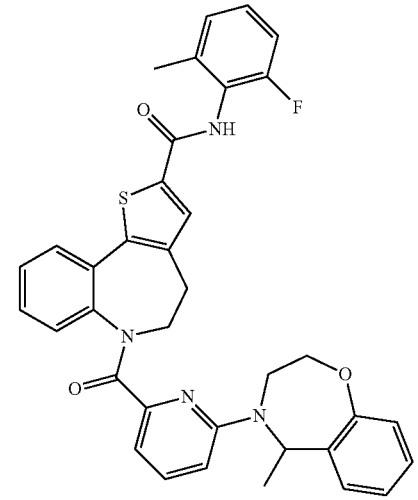 [SMILES: Cc1cccc(F)c1NC(=O)c1cc2c(s1)-c1ccccc1N(C(=O)c1cccc(N3CCOc4ccccc4C3C)n1)CC2] |
| 365 | 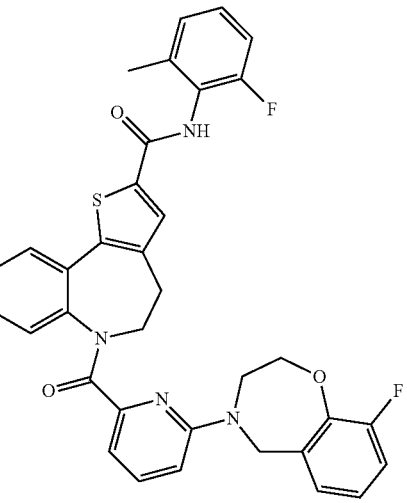 |
| 366 | 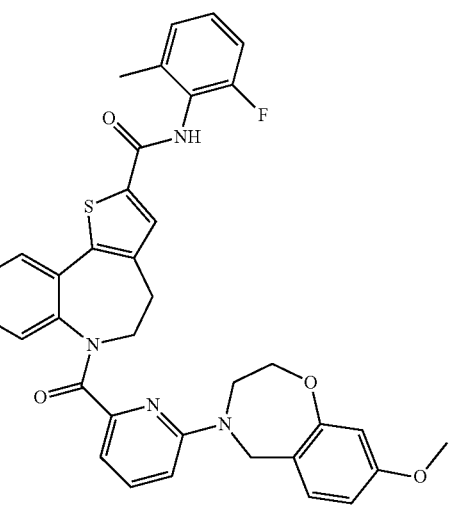 |
| 367 | 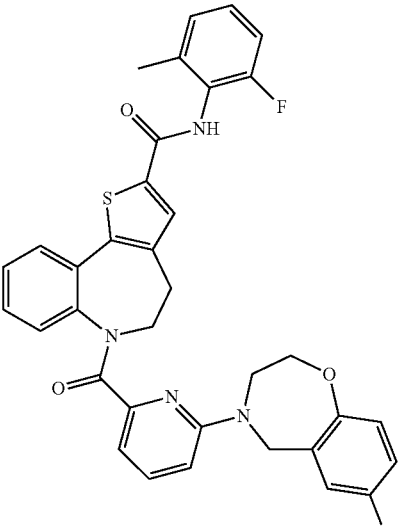 |
| 368 | |
| 369 | |

621
-continued
| Entry | Compound |
|---|---|
| 370 | 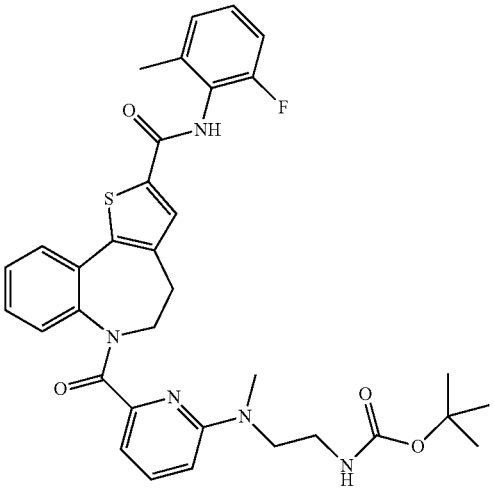 [SMILES: Cc1cccc(F)c1NC(=O)c1cc2c(s1)-c1ccccc1N(C(=O)c1cccc(N(C)CCNC(=O)OC(C)(C)C)n1)CC2] |
| 371 | 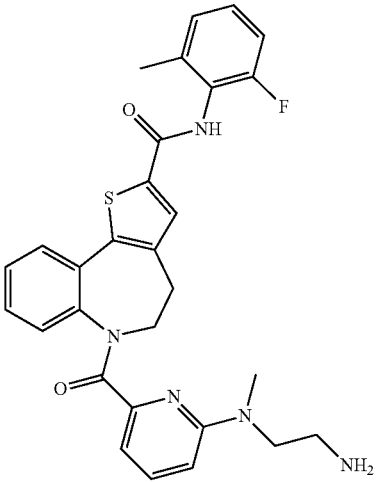 [SMILES: Cc1cccc(F)c1NC(=O)c1cc2c(s1)-c1ccccc1N(C(=O)c1cccc(N(C)CCN)n1)CC2] |
| 372 | 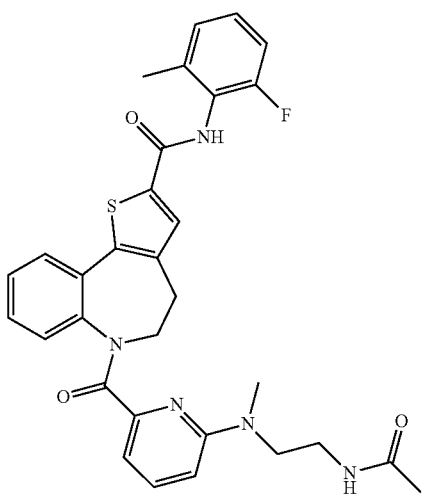 [SMILES: CC(=O)NCCN(C)c1cccc(C(=O)N2CCc3cc(C(=O)Nc4c(C)cccc4F)sc3-c3ccccc32)n1] |
622
-continued
| Entry | Compound |
|---|---|
| 373 | 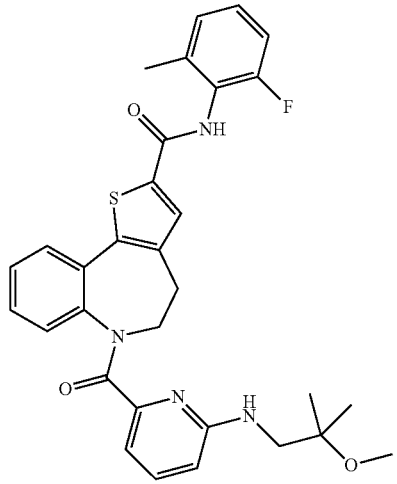 [SMILES: COC(C)(C)CNc1cccc(C(=O)N2CCc3cc(C(=O)Nc4c(C)cccc4F)sc3-c3ccccc32)n1] |
| 374 | 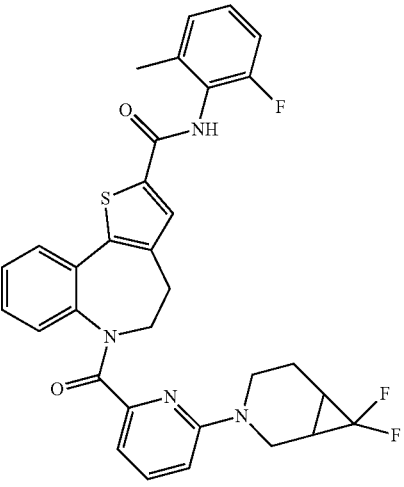 [SMILES: Cc1cccc(F)c1NC(=O)c1cc2c(s1)-c1ccccc1N(C(=O)c1cccc(N3CCC4C(C3)C4(F)F)n1)CC2] |
| 375 | 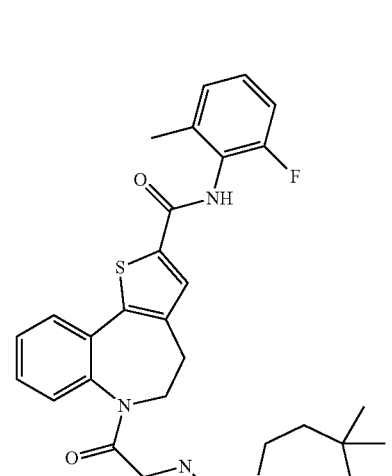 |

-continued

| Entry | Compound |
|---|---|
| 376 | |
| 377 | |
| 378 | |

-continued

| Entry | Compound |
|---|---|
| 379 | |
| 380 | |
| 381 | |

625
-continued

| Entry | Compound |
|---|---|
| 382 | |
| 383 | |
| 384 | |

626
-continued

| Entry | Compound |
|---|---|
| 385 | |
| 386 | |
| 387 | |

| Entry | Compound |
|---|---|
| 388 | 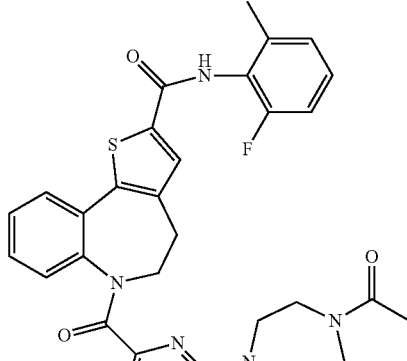 |
| 389 | |
| 390 | |
| 391 | |
| 392 | |
| 393 | |

629
-continued
| Entry | Compound |
|---|---|
| 394 | 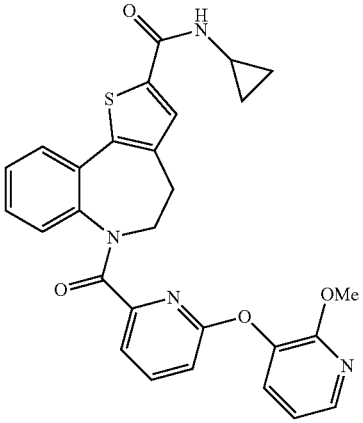 [SMILES: COc1ncccc1Oc1cccc(C(=O)N2CCc3cc(C(=O)NC4CC4)sc3-c3ccccc32)n1] |
| 395 | 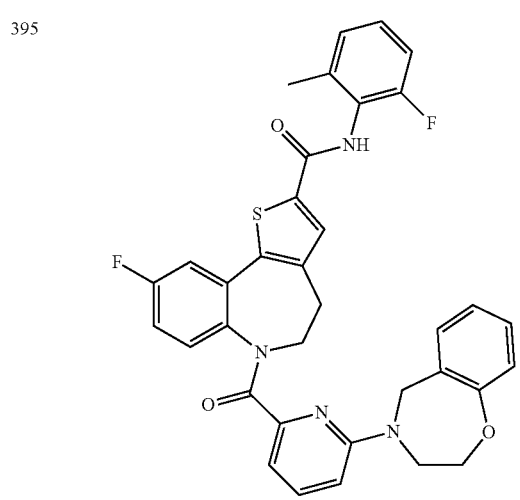 |
| 396 | 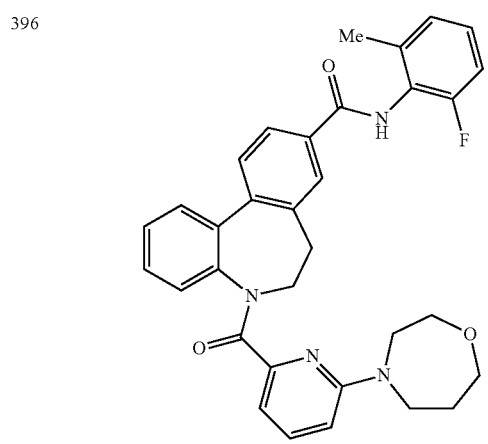 |
630
-continued
| Entry | Compound |
|---|---|
| 397 | 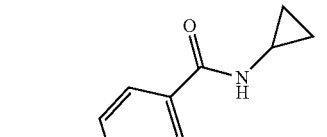 |
| 398 | 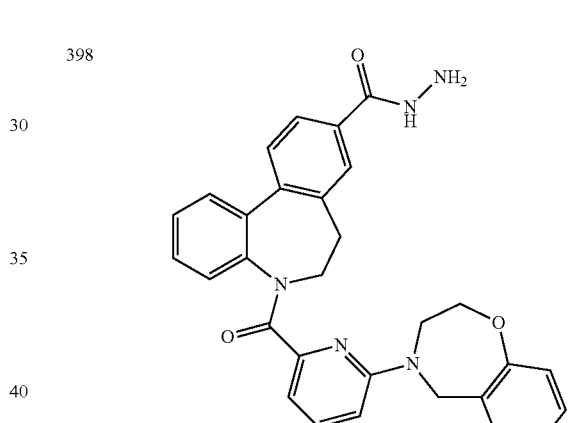 |
| 399 | 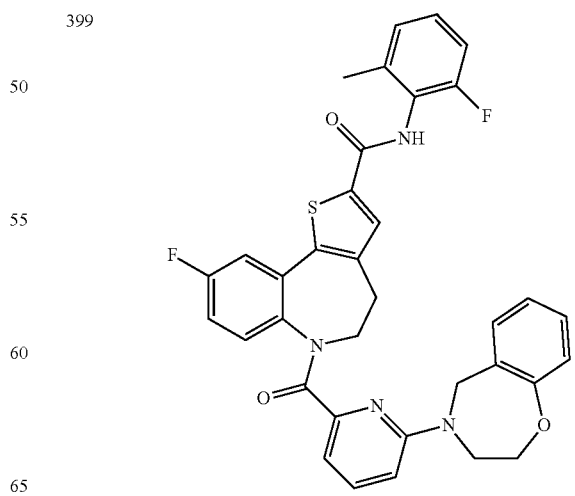 |

631
-continued
| Entry | Compound |
|---|---|
| 400 | 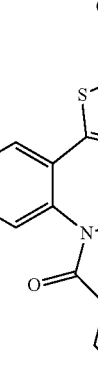 |
| 401 |  |
| 402 |  |
632
-continued
| Entry | Compound |
|---|---|
| 403 | 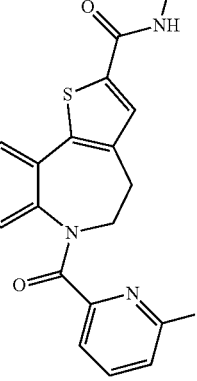 |
| 404 | 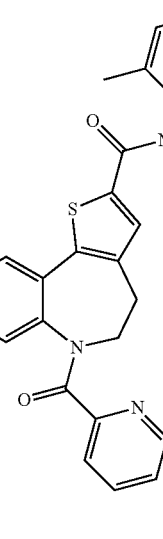 |
| 405 | 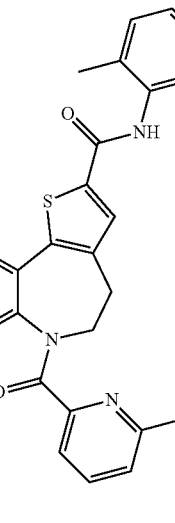 |

| Entry | Compound |
|---|---|
| 406 | |
| 407 | |
| 408 | |
| 409 | |
| 410 | |
| 411 | |

| Entry | Compound |
|---|---|
| 412 | |
| 413 | |
| 414 | |

| Entry | Compound |
|---|---|
| 415 | |
| 416 | |
| 417 | |

US 10,759,816 B2
637
-continued
| Entry | Compound |
|---|---|
| 418 | 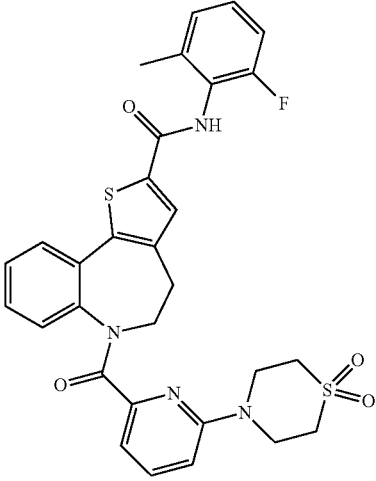 [SMILES: Cc1cccc(F)c1NC(=O)c1cc2c(s1)-c1ccccc1N(C(=O)c1cccc(N3CCS(=O)(=O)CC3)n1)CC2] |
| 419 | 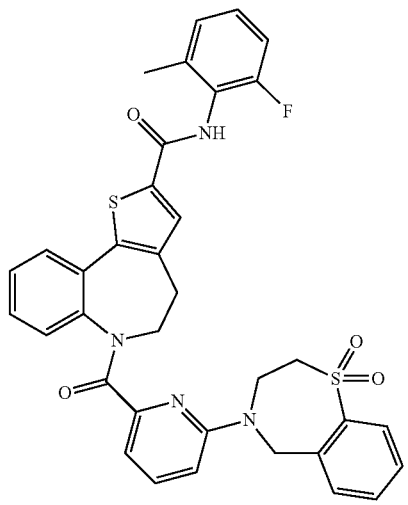 [SMILES: Cc1cccc(F)c1NC(=O)c1cc2c(s1)-c1ccccc1N(C(=O)c1cccc(N3CCS(=O)(=O)c4ccccc4C3)n1)CC2] |
| 420 | 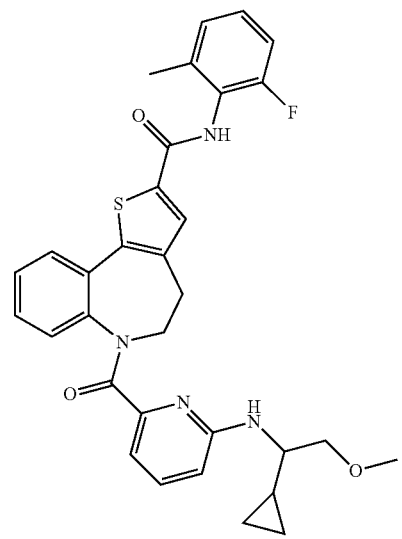 [SMILES: COCC(Nc1cccc(C(=O)N2CCc3cc(C(=O)Nc4c(C)cccc4F)sc3-c3ccccc32)n1)C1CC1] |
638
-continued
| Entry | Compound |
|---|---|
| 421 | 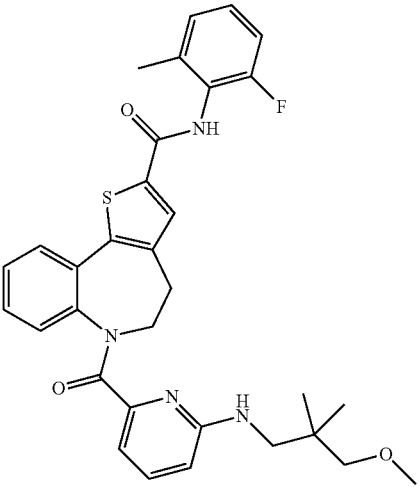 [SMILES: COCC(C)(C)CNc1cccc(C(=O)N2CCc3cc(C(=O)Nc4c(C)cccc4F)sc3-c3ccccc32)n1] |
| 422 | 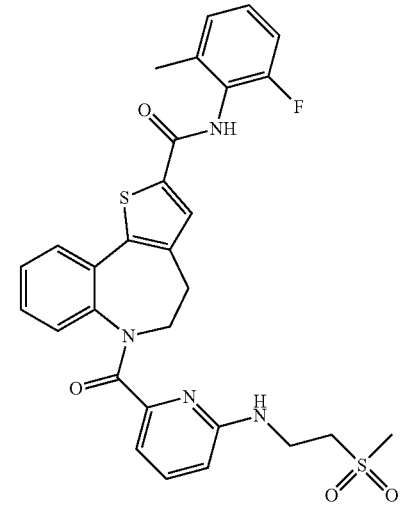 [SMILES: Cc1cccc(F)c1NC(=O)c1cc2c(s1)-c1ccccc1N(C(=O)c1cccc(NCCS(C)(=O)=O)n1)CC2] |
| 423 | 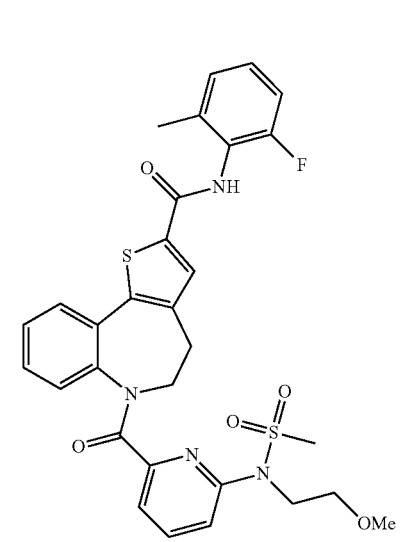 [SMILES: COCCN(c1cccc(C(=O)N2CCc3cc(C(=O)Nc4c(C)cccc4F)sc3-c3ccccc32)n1)S(C)(=O)=O] |

| Entry | Compound |
|---|---|
| 424 | 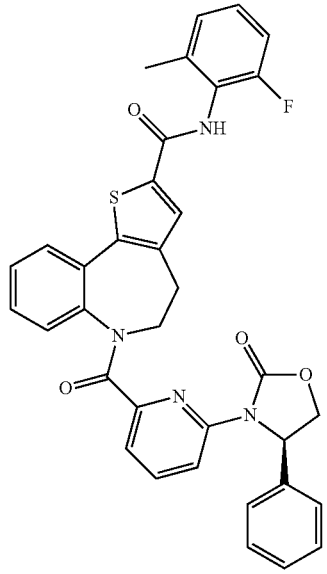 [SMILES: Cc1cccc(F)c1NC(=O)c1cc2c(s1)-c1ccccc1N(C(=O)c1cccc(N3C(=O)OC[C@H]3c3ccccc3)n1)CC2] |
| 425 | 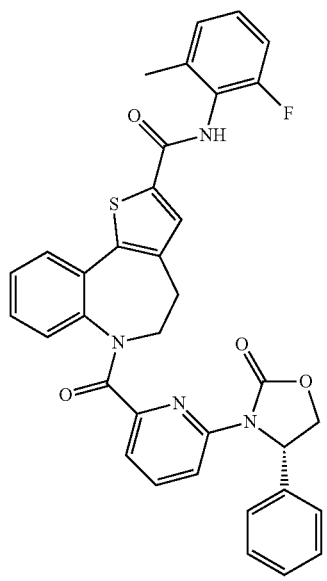 [SMILES: Cc1cccc(F)c1NC(=O)c1cc2c(s1)-c1ccccc1N(C(=O)c1cccc(N3C(=O)OC[C@@H]3c3ccccc3)n1)CC2] |
| Entry | Compound |
|---|---|
| 426 | |
| 427 | |
| 428 | |
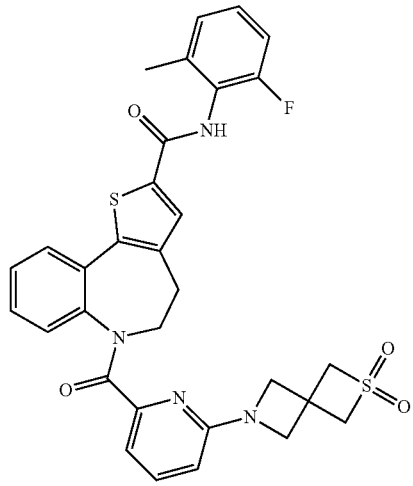 [SMILES: Cc1cccc(F)c1NC(=O)c1cc2c(s1)-c1ccccc1N(C(=O)c1cccc(N3CC4(C3)CS(=O)(=O)C4)n1)CC2]

| Entry | Compound |
|---|---|
| 429 | |
| 430 | |
| 431 | |
| 432 | |
| 433 | |
| 434 | |

| Entry | Compound |
|---|---|
| 435 | 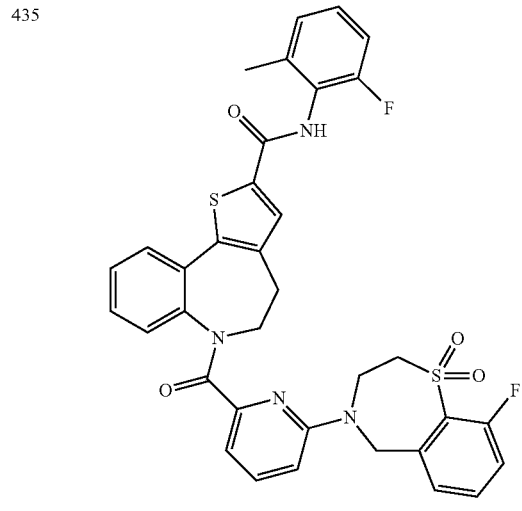 |
| 436 | 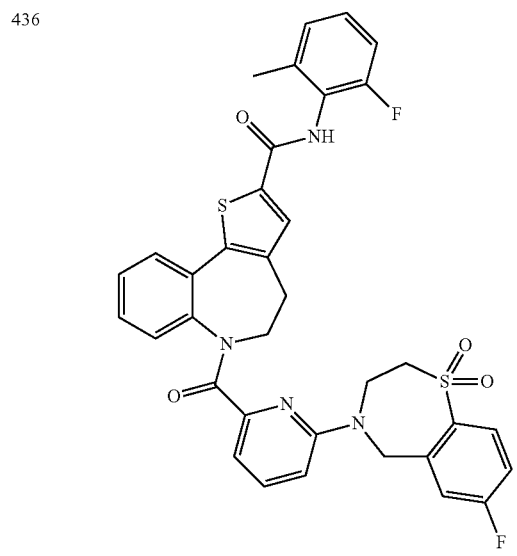 |
| 437 | 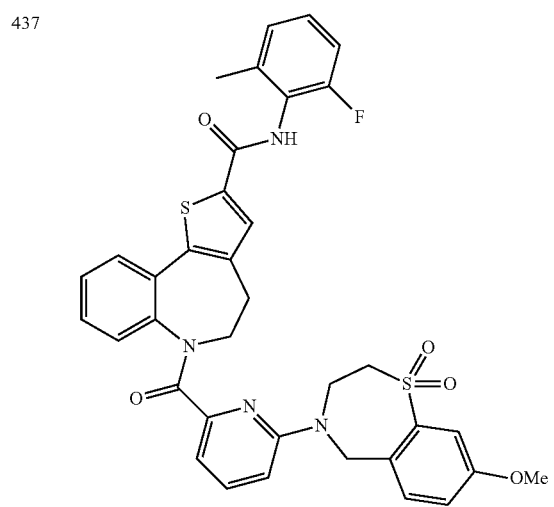 |
| Entry | Compound |
|---|---|
| 438 | 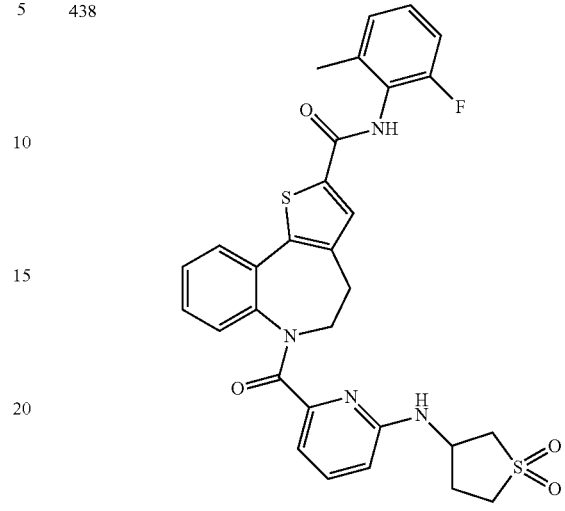 |
| 439 | 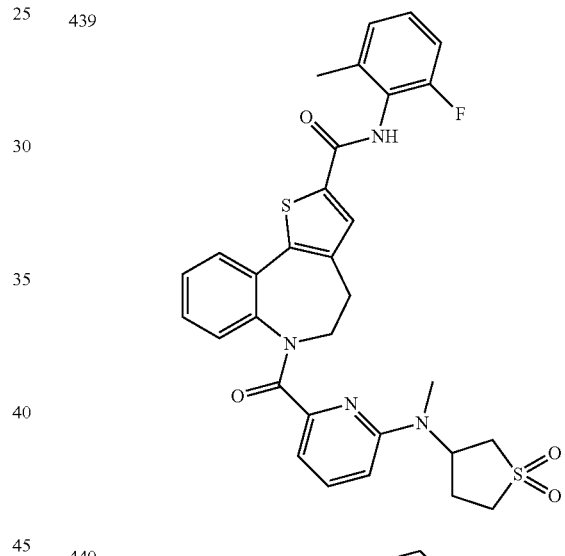 |
| 440 | 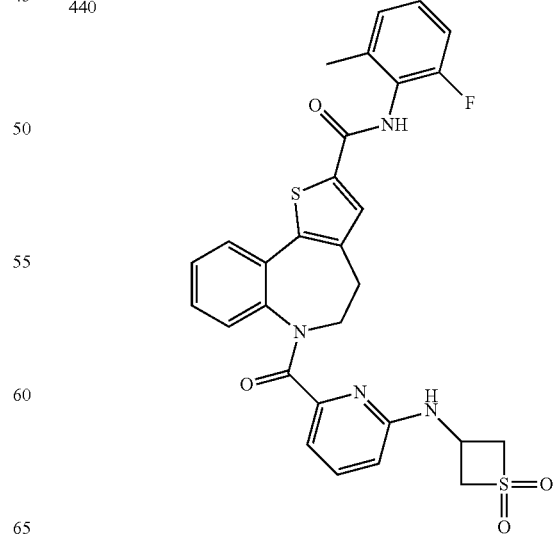 |

| Entry | Compound |
|---|---|
| 441 | (structure) |
| 442 | (structure) |
| 443 | (structure) |
| 444 | (structure) |
| 445 | (structure) |
| 446 | (structure) |

| Entry | Compound |
|---|---|
| 447 | 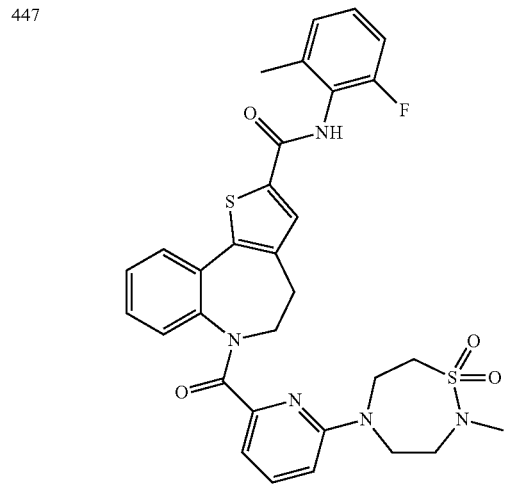 |
| 448 | 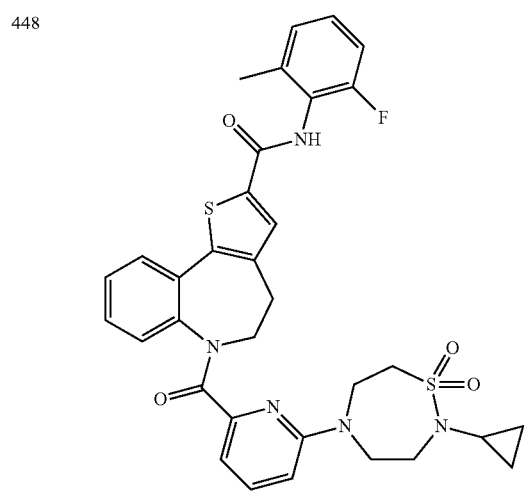 |
| 449 | 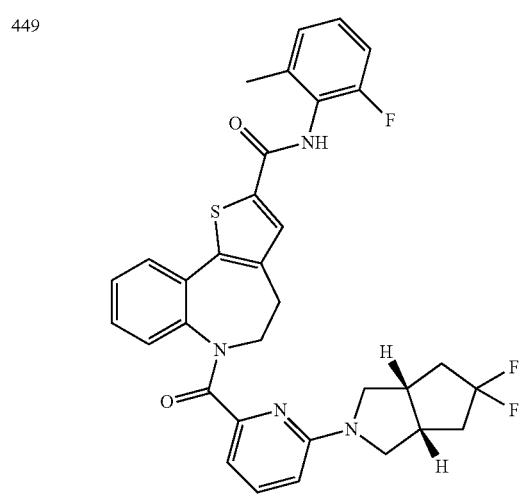 |
| 450 | 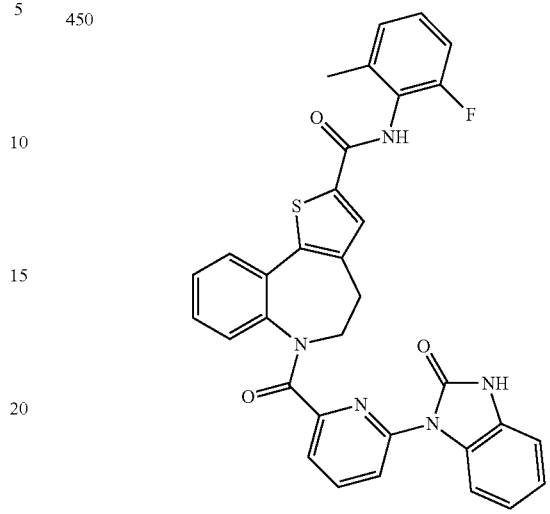 |
| 451 | 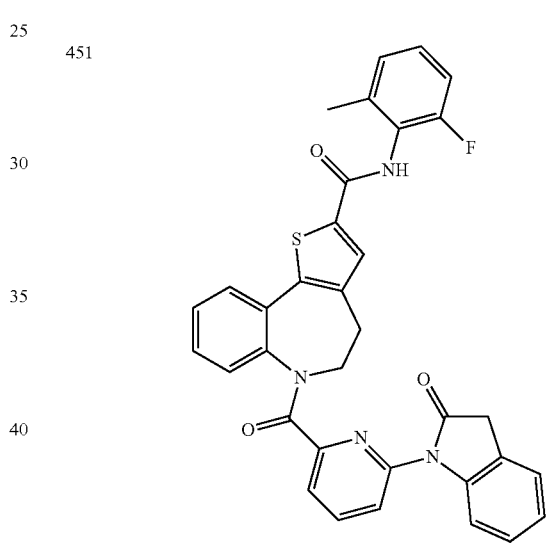 |
| 452 | 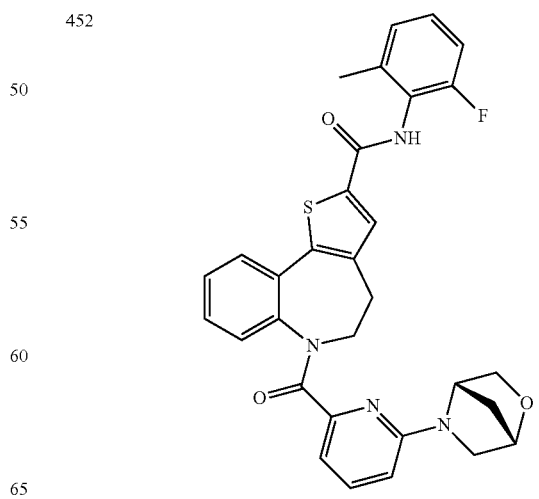 |

649
-continued
| Entry | Compound |
|---|---|
| 453 | 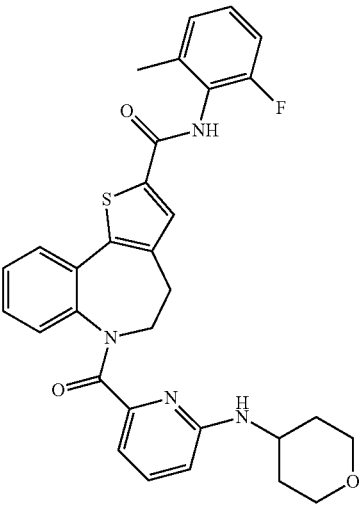 [SMILES: Cc1cccc(F)c1NC(=O)c1cc2c(s1)-c1ccccc1N(C(=O)c1cccc(NC3CCOCC3)n1)CC2] |
| 454 | 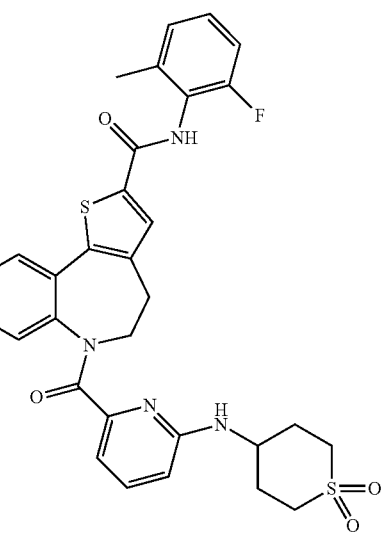 |
| 455 | 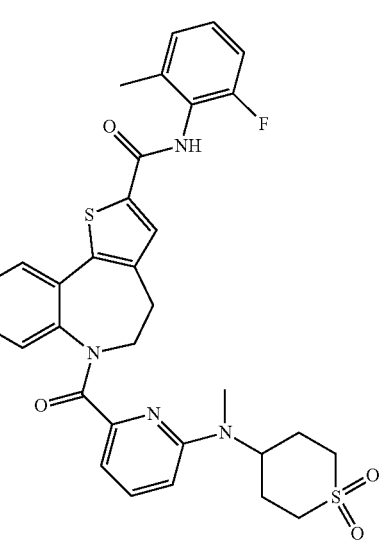 |
650
-continued
| Entry | Compound |
|---|---|
| 456 | 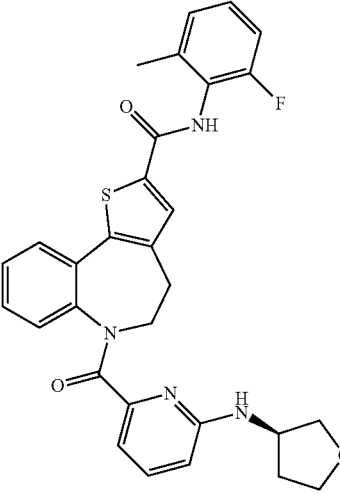 |
| 457 | 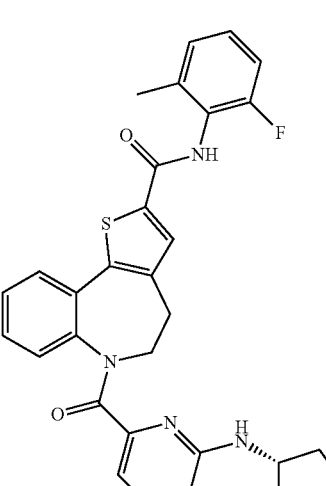 |
| 458 | 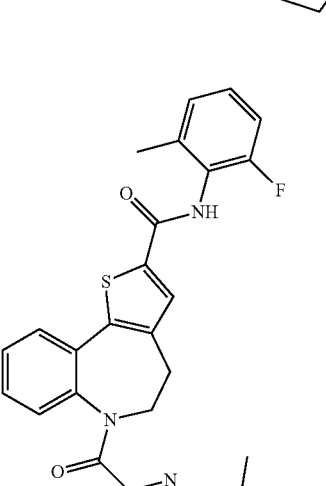 |

| Entry | Compound |
|---|---|
| 459 | 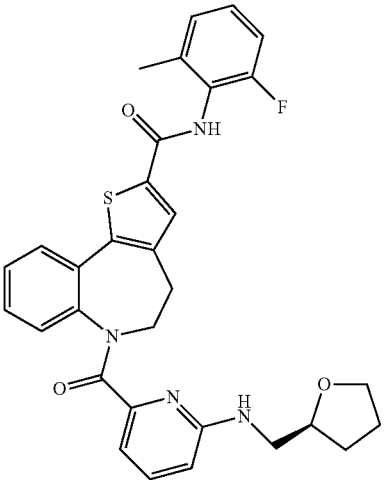 [SMILES: Cc1cccc(F)c1NC(=O)c1cc2c(s1)-c1ccccc1N(C(=O)c1cccc(NC[C@@H]3CCCO3)n1)CC2] |
| 460 | 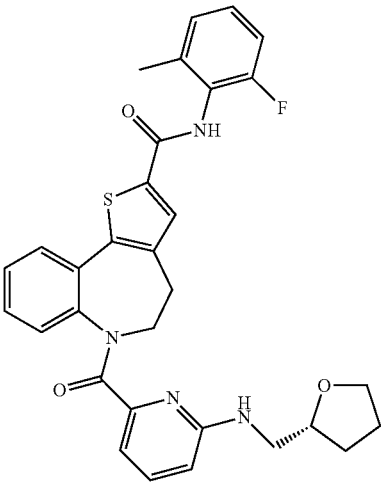 [SMILES: Cc1cccc(F)c1NC(=O)c1cc2c(s1)-c1ccccc1N(C(=O)c1cccc(NC[C@H]3CCCO3)n1)CC2] |
| 461 | 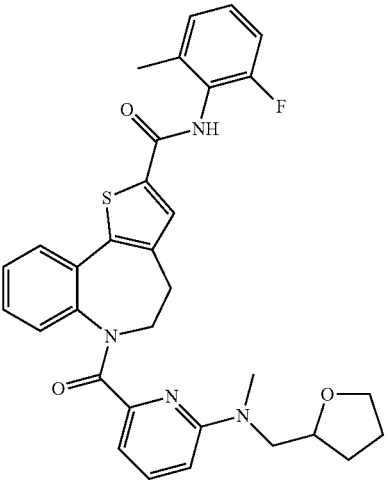 [SMILES: Cc1cccc(F)c1NC(=O)c1cc2c(s1)-c1ccccc1N(C(=O)c1cccc(N(C)CC3CCCO3)n1)CC2] |
| Entry | Compound |
|---|---|
| 462 | 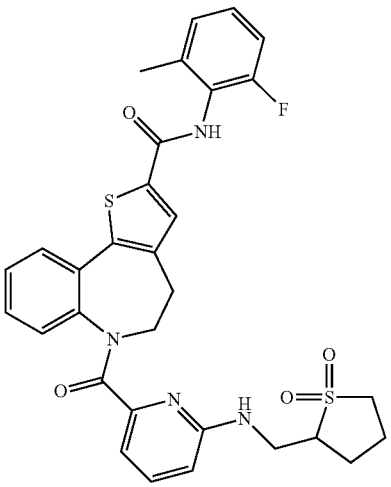 [SMILES: Cc1cccc(F)c1NC(=O)c1cc2c(s1)-c1ccccc1N(C(=O)c1cccc(NCC3CCCS3(=O)=O)n1)CC2] |
| 463 | 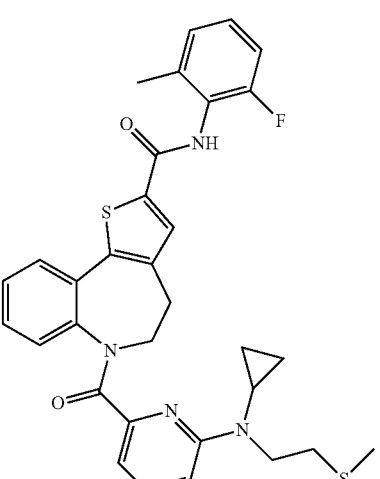 |
| 464 | 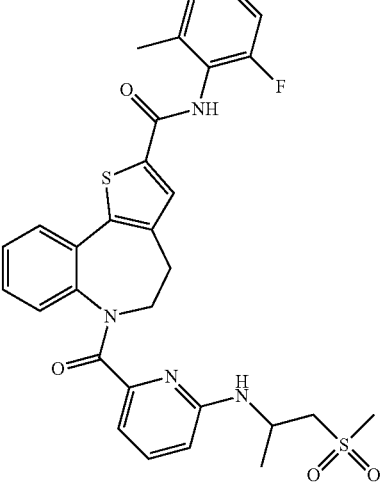 |

| Entry | Compound |
|---|---|
| 465 | |
| 466 | |
| 467 | |
| 468 | |
| 469 | |
| 470 | |

US 10,759,816 B2
655
-continued
| Entry | Compound |
|---|---|
| 471 | 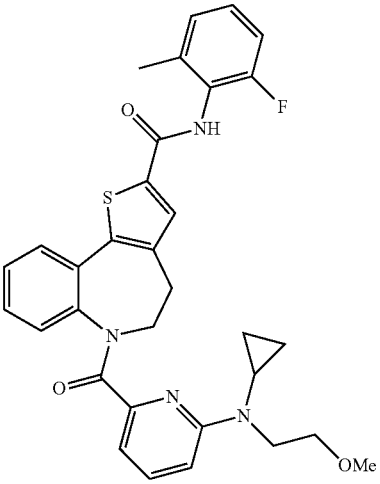 [SMILES: COCCN(c1cccc(C(=O)N2CCc3cc(C(=O)Nc4c(C)cccc4F)sc3-c3ccccc32)n1)C1CC1] |
| 472 | 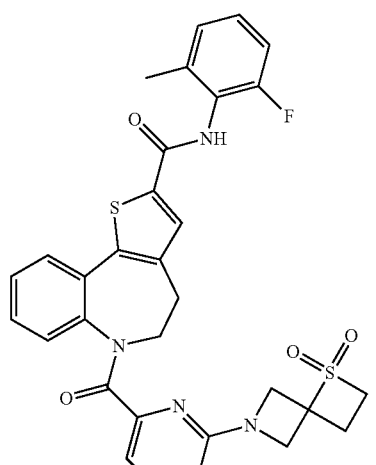 |
| 473 | 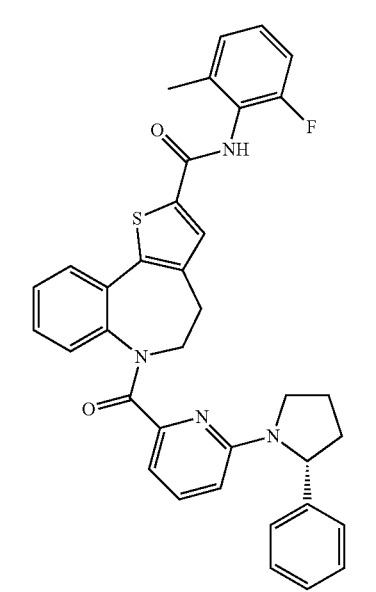 [SMILES: Cc1cccc(F)c1NC(=O)c1cc2c(s1)-c1ccccc1N(C(=O)c1cccc(N3CCC[C@@H]3c3ccccc3)n1)CC2] |
656
-continued
| Entry | Compound |
|---|---|
| 474 | 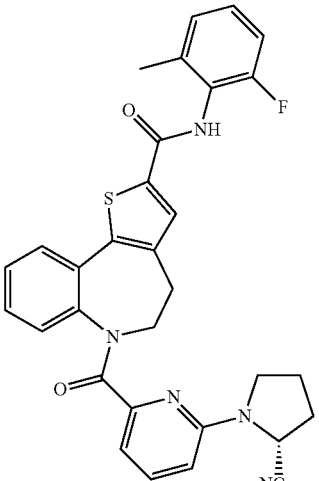 |
| 475 | 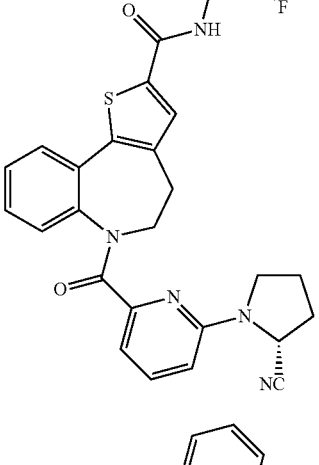 |
| 476 | 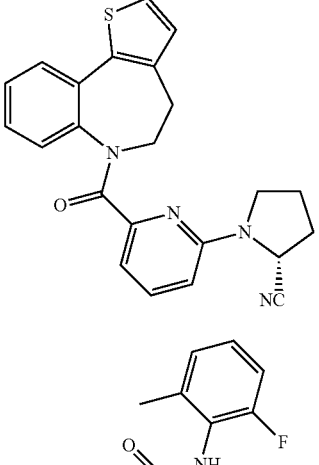 |

657
-continued

| Entry | Compound |
|---|---|
| 477 | (structure) |
| 478 | (structure) |
| 479 | (structure) |

658
-continued

| Entry | Compound |
|---|---|
| 480 | (structure) |
| 481 | (structure) |
| 482 | (structure) |

| Entry | Compound |
|---|---|
| 483 | 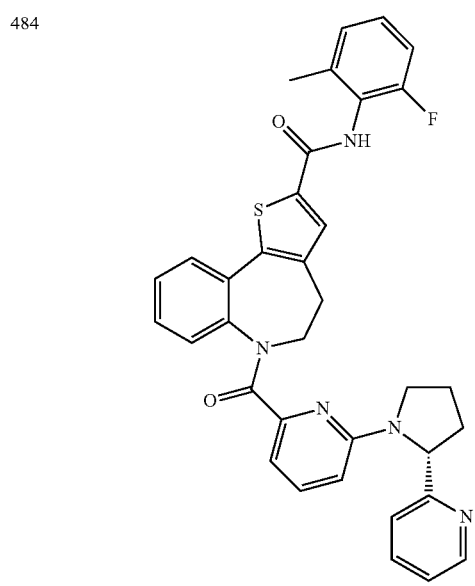 |
| 484 | |
| Entry | Compound |
|---|---|
| 485 | 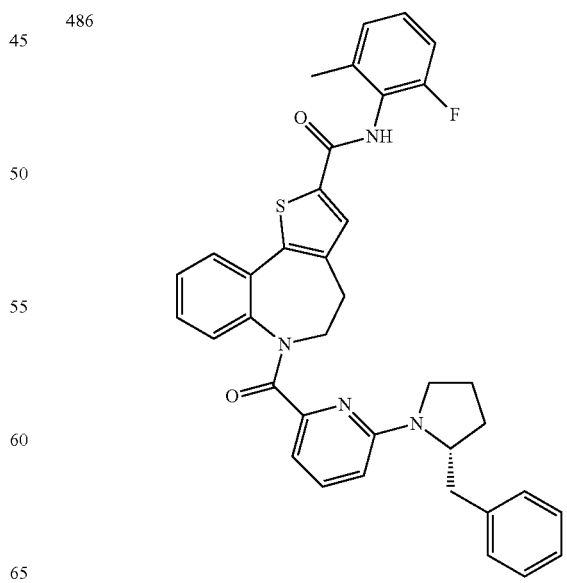 |
| 486 | |

| Entry | Compound |
|---|---|
| 487 | |
| 488 | |
| 489 | |
| 490 | |
| 491 | |
| 492 | |

663
-continued
| Entry | Compound |
|---|---|
| 493 | 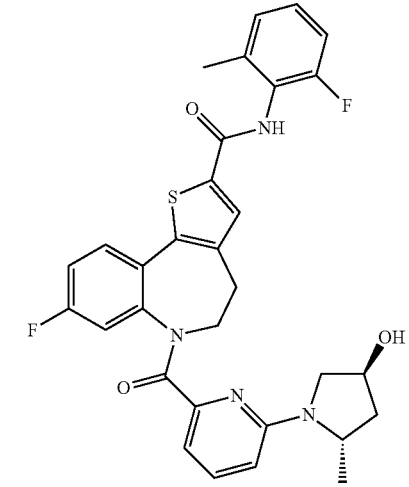 [SMILES: Cc1cccc(F)c1NC(=O)c1cc2c(s1)-c1ccc(F)cc1N(C(=O)c1cccc(N3C[C@@H](O)C[C@@H]3C)n1)CC2] |
| 494 | 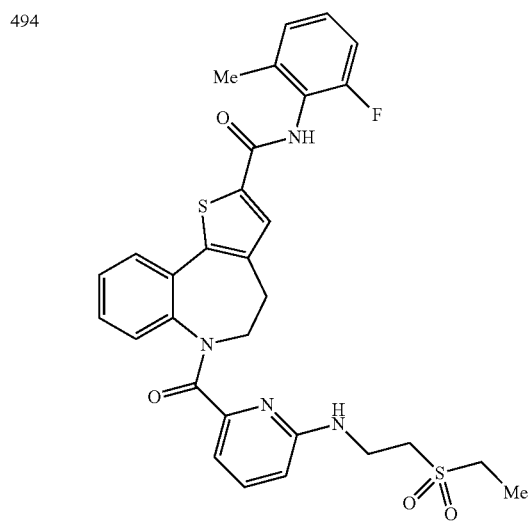 |
| 495 | 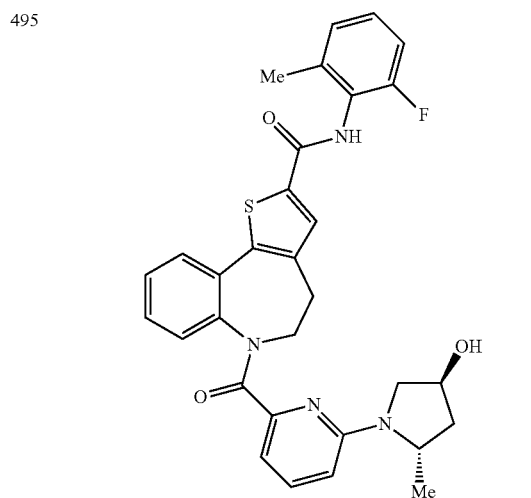 |
664
-continued
| Entry | Compound |
|---|---|
| 496 | 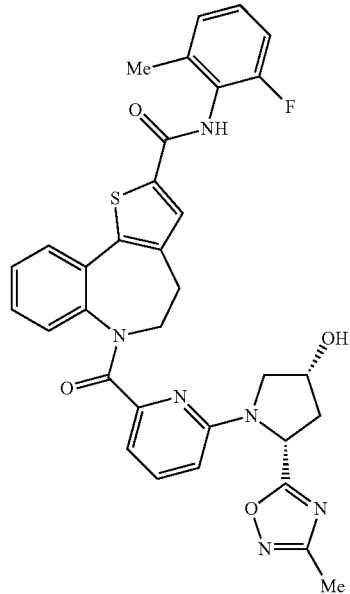 [SMILES: Cc1noc([C@H]2C[C@@H](O)CN2c2cccc(C(=O)N3CCc4cc(C(=O)Nc5c(C)cccc5F)sc4-c4ccccc43)n2)n1] |
| 497 | 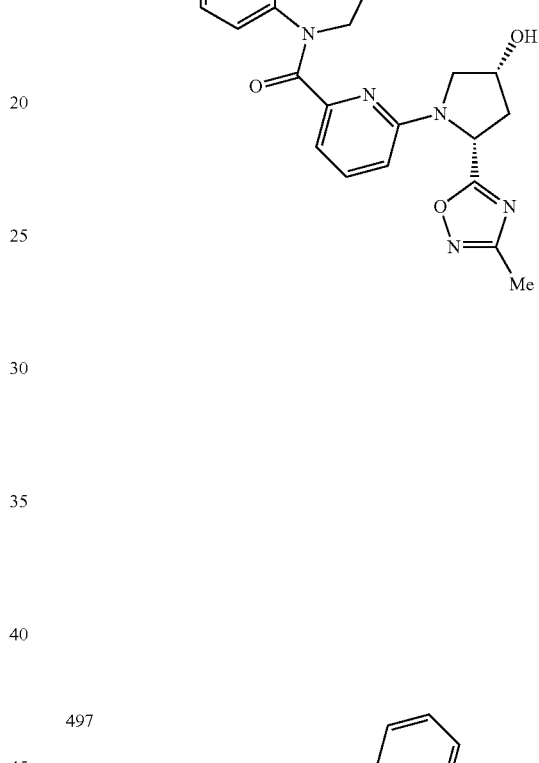 |
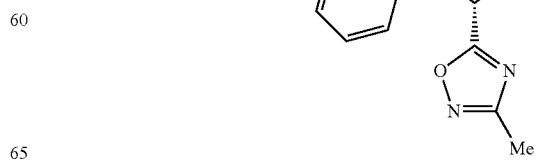

| Entry | Compound |
|---|---|
| 498 | (structure) |
| 499 | (structure) |
| 500 | (structure) |

| Entry | Compound |
|---|---|
| 501 | (structure) |
| 502 | (structure) |
| 503 | (structure) |

667
-continued

| Entry | Compound |
|---|---|
| 504 | |
| 505 | |
| 506 | |

668
-continued

| Entry | Compound |
|---|---|
| 507 | |
| 508 | |
| 509 | |

669
-continued
| Entry | Compound |
|---|---|
| 510 | 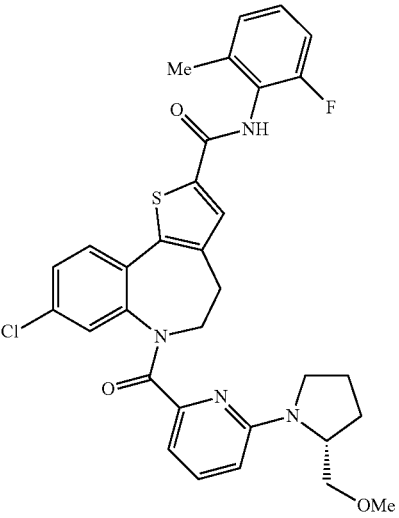 [SMILES: COC[C@H]1CCCN1c1cccc(C(=O)N2CCc3cc(C(=O)Nc4c(C)cccc4F)sc3-c3ccc(Cl)cc32)n1] |
| 511 | 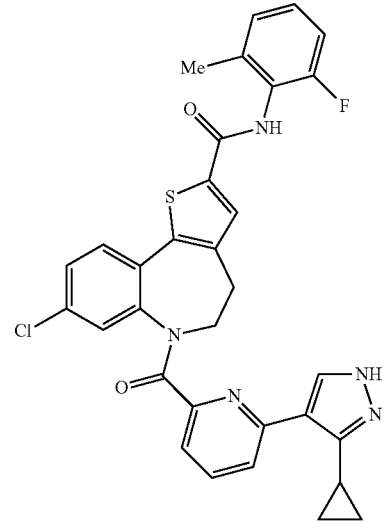 [SMILES: Cc1cccc(F)c1NC(=O)c1cc2c(s1)-c1ccc(Cl)cc1N(C(=O)c1cccc(-c3c[nH]nc3C3CC3)n1)CC2] |
| 512 | 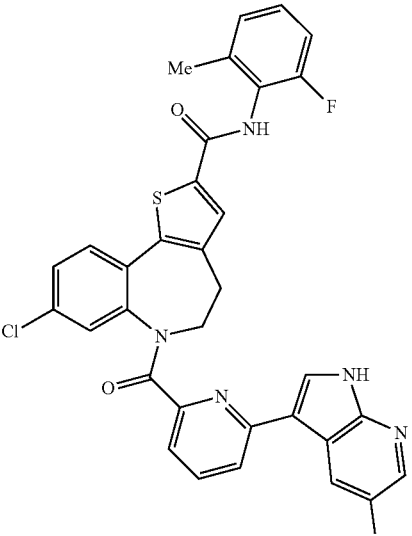 |
670
-continued
| Entry | Compound |
|---|---|
| 513 | 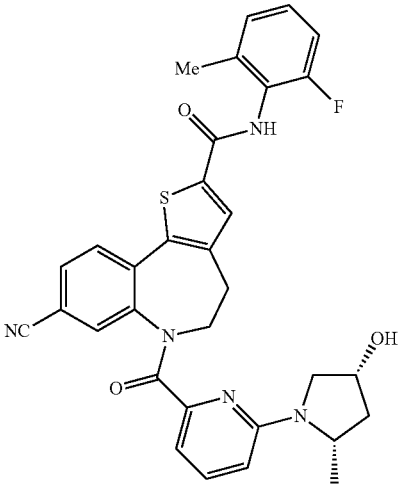 [SMILES: Cc1cccc(F)c1NC(=O)c1cc2c(s1)-c1ccc(C#N)cc1N(C(=O)c1cccc(N3C[C@H](O)C[C@@H]3C)n1)CC2] |
| 514 | 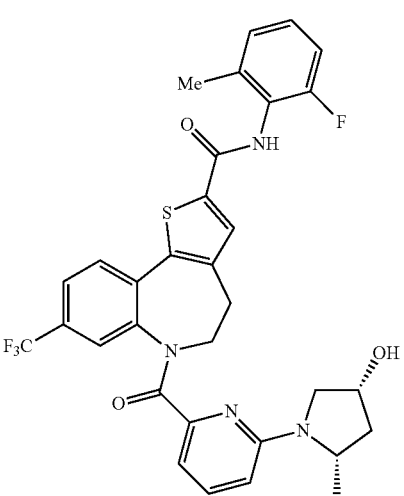 |
| 515 | 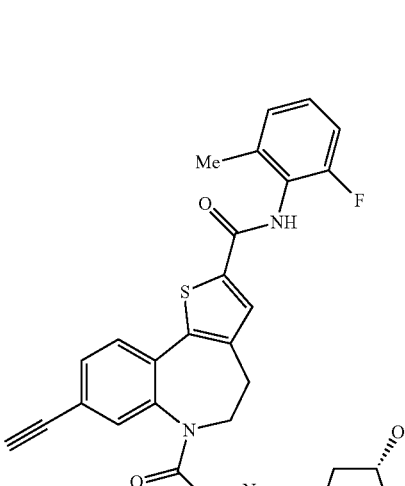 |

671
-continued
| Entry | Compound |
|---|---|
| 516 | 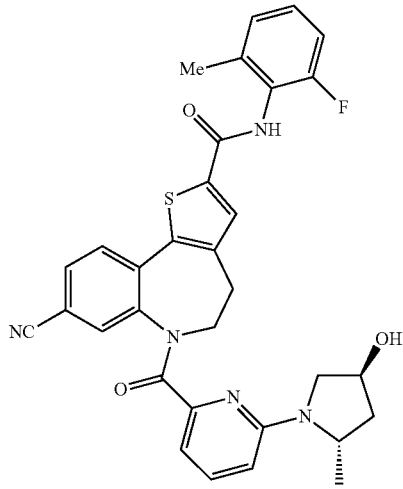 [SMILES: Cc1cccc(F)c1NC(=O)c1cc2c(s1)-c1ccc(C#N)cc1N(C(=O)c1cccc(N3C[C@@H](O)C[C@@H]3C)n1)CC2] |
| 517 | 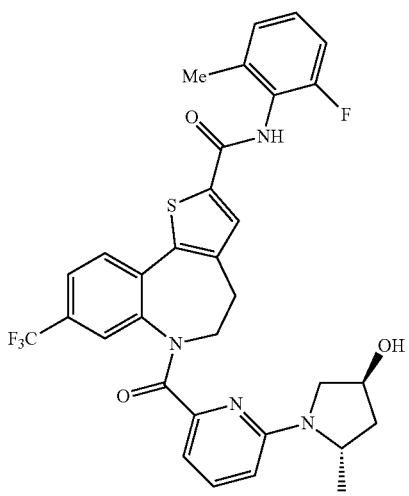 [SMILES: Cc1cccc(F)c1NC(=O)c1cc2c(s1)-c1ccc(C(F)(F)F)cc1N(C(=O)c1cccc(N3C[C@@H](O)C[C@@H]3C)n1)CC2] |
| 518 | 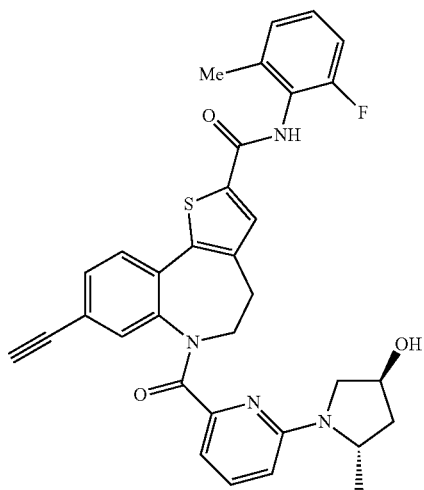 [SMILES: C#Cc1ccc2c(c1)N(C(=O)c1cccc(N3C[C@@H](O)C[C@@H]3C)n1)CCc1cc(C(=O)Nc3c(C)cccc3F)sc1-2] |
672
-continued
| Entry | Compound |
|---|---|
| 519 | 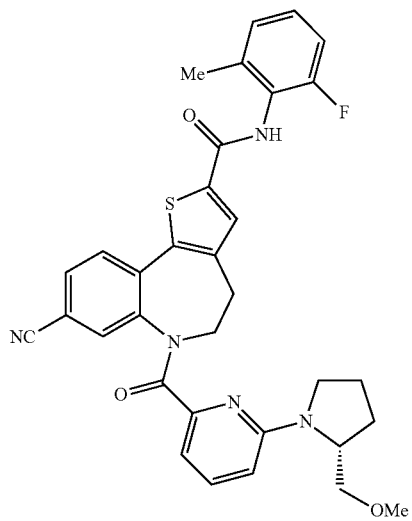 [SMILES: COC[C@H]1CCCN1c1cccc(C(=O)N2CCc3cc(C(=O)Nc4c(C)cccc4F)sc3-c3ccc(C#N)cc32)n1] |
| 520 | 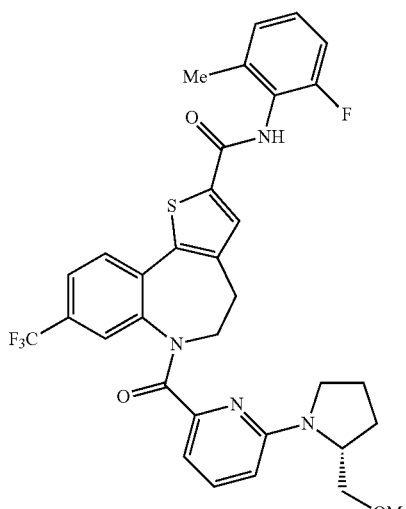 |
| 521 | 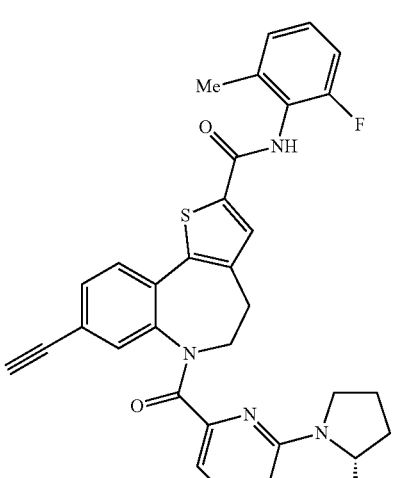 |

| Entry | Compound |
|---|---|
| 522 | |
| 523 | |
| 524 | |

| Entry | Compound |
|---|---|
| 525 | |
| 526 | |

| Entry | Compound |
|---|---|
| 527 | 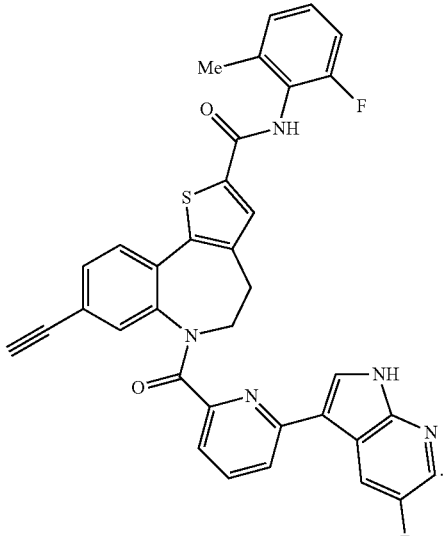 |

10. A pharmaceutical composition comprising a compound according to claim 1, in combination with a pharmaceutically acceptable carrier, diluent or excipient.

11. A method of treating an RSV infection in a subject in need thereof, comprising administering to the subject a therapeutically effective amount of a compound or a combination of compounds of claim 1.

12. The method of claim 11, further comprising the step of administering to the subject an additional anti-RSV agent.

13. The method of claim 11, further comprising administering to the individual a steroid anti-inflammatory compound.

14. A method of treating RSV and influenza in a subject in need thereof, comprising administering to the subject a therapeutically effective amount of a compound of claim 1 and a therapeutically effective amount of an anti-influenza agent.

15. The method of claim 12, wherein the compound and the additional anti-RSV agent are co-formulated.

16. The method of claim 12, wherein the compound and the additional anti-RSV agent are co-administered.

17. The compound of claim 1, wherein A is

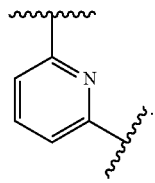 [SMILES: *c1cccc(*)n1]

18. The compound of claim 1, wherein $R_1$ is $-R_{13}R_{14}$.

19. The compound of claim 17, wherein $R_1$ is $-NR_{13}R_{14}$.

20. The compound of claim 18, wherein $R_{13}$ and $R_{14}$ are taken together with the nitrogen atom to which they are attached to form an optionally substituted 3- to 12-membered heterocyclic.

* * * * *

UNITED STATES PATENT AND TRADEMARK OFFICE
CERTIFICATE OF CORRECTION

Page 1 of 2

PATENT NO. : 10,759,816 B2
APPLICATION NO. : 16/100721
DATED : September 1, 2020
INVENTOR(S) : Jianming Yu et al.

It is certified that error appears in the above-identified patent and that said Letters Patent is hereby corrected as shown below:

In the Claims

<u>At Column 502</u>
In Claim 1, at Line 6 after substituted delete "–$C_1$-$C_5$-alkyl" and insert -- –$C_1$-$C_8$-alkyl --; and In Claim 4, Line 40 delete " 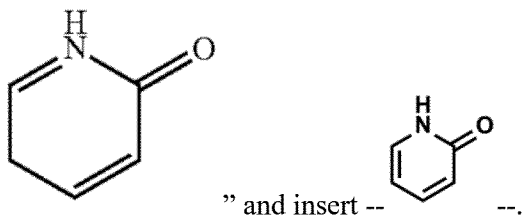 " and insert -- --.

<u>At Column 507</u>

In Claim 7, at Line 5 delete " 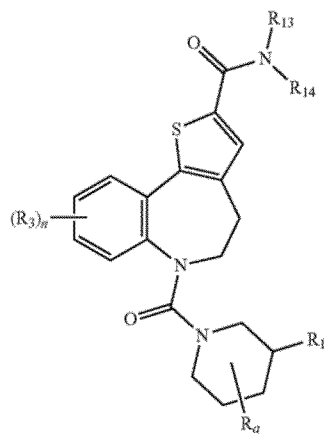 ".

Signed and Sealed this
Third Day of November, 2020

Andrei Iancu
*Director of the United States Patent and Trademark Office*

CERTIFICATE OF CORRECTION (continued)
U.S. Pat. No. 10,759,816 B2

At Column 516

In Claim 9, Line 55 delete " 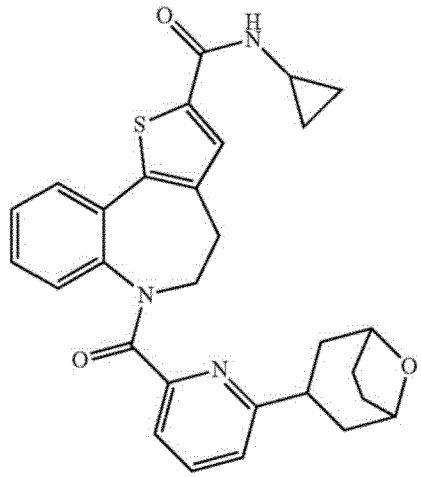 " and insert

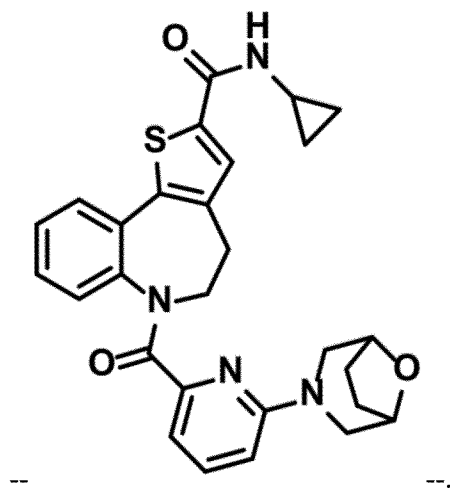

-- --.

At Column 676
In Claim 18, Line 26 after is delete "–$R_{13}R_{14}$" and insert -- –$NR_{13}R_{14}$ --.